United States Patent
Cha et al.

(10) Patent No.: US 11,081,650 B2
(45) Date of Patent: Aug. 3, 2021

(54) SPIRO COMPOUND AND ORGANIC LIGHT-EMITTING ELEMENT COMPRISING SAME

(71) Applicant: LG Chem, Ltd., Seoul (KR)

(72) Inventors: Yongbum Cha, Daejeon (KR); Jin Joo Kim, Daejeon (KR); Sung Kil Hong, Daejeon (KR); Sang Duk Suh, Daejeon (KR)

(73) Assignee: LG Chem, Ltd.

( * ) Notice: Subject to any disclaimer, the term of this patent is extended or adjusted under 35 U.S.C. 154(b) by 703 days.

(21) Appl. No.: 15/564,555

(22) PCT Filed: Nov. 17, 2016

(86) PCT No.: PCT/KR2016/013302
§ 371 (c)(1),
(2) Date: Oct. 5, 2017

(87) PCT Pub. No.: WO2017/086724
PCT Pub. Date: May 26, 2017

(65) Prior Publication Data
US 2018/0083198 A1    Mar. 22, 2018

(30) Foreign Application Priority Data

Nov. 17, 2015 (KR) .................. 10-2015-0161415

(51) Int. Cl.
*H01L 51/00* (2006.01)
*C07D 491/20* (2006.01)
(Continued)

(52) U.S. Cl.
CPC ........ *H01L 51/0071* (2013.01); *C07D 491/20* (2013.01); *C07D 491/22* (2013.01);
(Continued)

(58) Field of Classification Search
CPC . H01L 51/0071; C07D 491/20; C07D 491/22; C07D 495/20; C07D 495/22;
(Continued)

(56) References Cited

U.S. PATENT DOCUMENTS

2014/0316134 A1* 10/2014 Stoessel ............... C07D 221/20
                                                       544/180
2015/0144937 A1   5/2015 Park et al.
2015/0270506 A1   9/2015 Voges et al.

FOREIGN PATENT DOCUMENTS

KR   20000051826 A    8/2000
KR   20110113468 A   10/2011
(Continued)

OTHER PUBLICATIONS

Extended European Search Report including Written Opinion for Application No. EP16866676.6 dated Jun. 3, 2019.
(Continued)

*Primary Examiner* — Dylan C Kershner
*Assistant Examiner* — Elizabeth M. Dahlburg
(74) *Attorney, Agent, or Firm* — Lerner, David, Littenberg, Krumholz & Mentlik, LLP

(57) ABSTRACT

The present specification provides a compound having a spiro structure represented by the following Chemical Formula 1, and an organic light emitting device including the same:

(Continued)

[Chemical Formula 1]

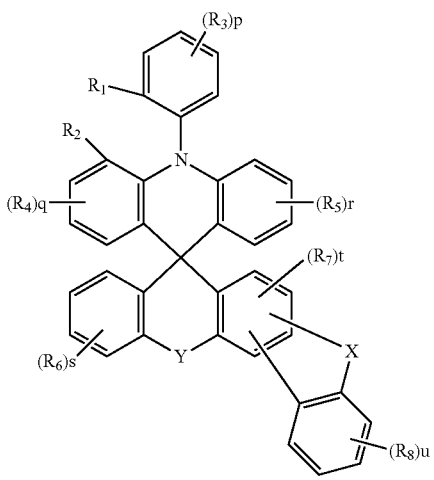

wherein R1 to R8, p, q, r, s, t, u, X and Y are defined therein.

12 Claims, 1 Drawing Sheet

(51) Int. Cl.
*C07D 491/22* (2006.01)
*C07D 495/20* (2006.01)
*C07D 495/22* (2006.01)
*C07F 7/08* (2006.01)
*C07F 9/6561* (2006.01)
*H01L 51/50* (2006.01)
*C09K 11/06* (2006.01)
*C09K 11/02* (2006.01)

(52) U.S. Cl.
CPC ......... *C07D 495/20* (2013.01); *C07D 495/22* (2013.01); *C07F 7/0816* (2013.01); *C07F 9/6561* (2013.01); *C09K 11/025* (2013.01); *C09K 11/06* (2013.01); *H01L 51/0072* (2013.01); *H01L 51/0073* (2013.01); *H01L 51/0074* (2013.01); *C09K 2211/1018* (2013.01); *H01L 51/006* (2013.01); *H01L 51/0052* (2013.01); *H01L 51/0061* (2013.01); *H01L 51/0067* (2013.01); *H01L 51/5012* (2013.01); *H01L 51/5016* (2013.01); *H01L 51/5056* (2013.01); *H01L 51/5088* (2013.01); *H01L 51/5096* (2013.01)

(58) Field of Classification Search
CPC ..... C07F 7/0816; C09K 11/06; C09K 11/025; C09K 2211/1018; C09K 2211/1011; C09K 2211/1033; C09K 2211/1037
See application file for complete search history.

(56) References Cited

FOREIGN PATENT DOCUMENTS

| KR | 20110113469 A | 10/2011 | |
|---|---|---|---|
| KR | 20110113470 A | 10/2011 | |
| KR | 20140096372 A | 8/2014 | |
| KR | 20150010016 A | 1/2015 | |
| WO | 2014056565 A1 | 4/2014 | |
| WO | 2015009076 A1 | 1/2015 | |
| WO | WO-2015009076 A1 * | 1/2015 | ......... H01L 51/0058 |

OTHER PUBLICATIONS

Search report from International Application No. PCT/KR2016/013302, dated Feb. 22, 2017.

* cited by examiner

[Figure 1]
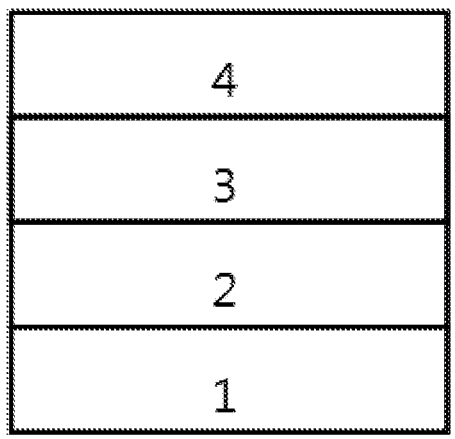
[Figure 2]
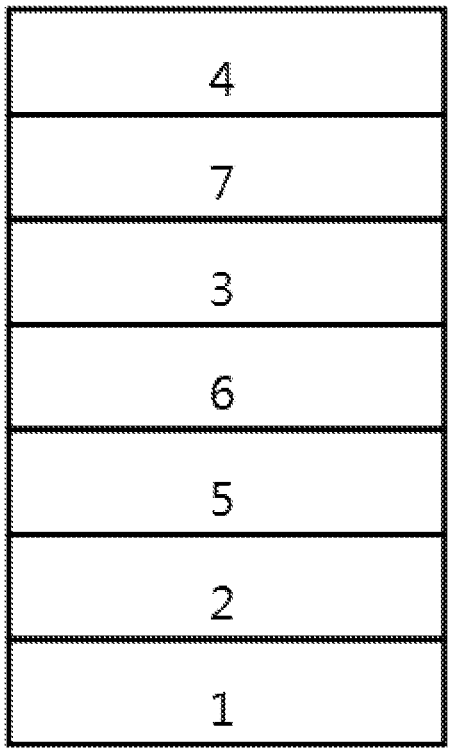

SPIRO COMPOUND AND ORGANIC LIGHT-EMITTING ELEMENT COMPRISING SAME

TECHNICAL FIELD

The present application is a national phase entry under 35 U.S.C. § 371 of International Application No. PCT/KR2016/013302, filed Nov. 17, 2016, published in Korean, which claims priority from Korean Patent Application No. 10-2015-0161415 filed in the Korean Intellectual Property Office on Nov. 17, 2015, the disclosures of which are incorporated herein by reference.

The present specification relates to a compound having a spiro structure and an organic light emitting device including the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

[Patent Document]

Official Gazette of Korean Patent Application Laid-Open No. 2000-0051826

DETAILED DESCRIPTION OF THE INVENTION

Technical Problem

The present specification describes a compound having a spiro structure and an organic light emitting device including the same.

Technical Solution

An exemplary embodiment of the present specification provides a compound represented by the following Chemical Formula 1:

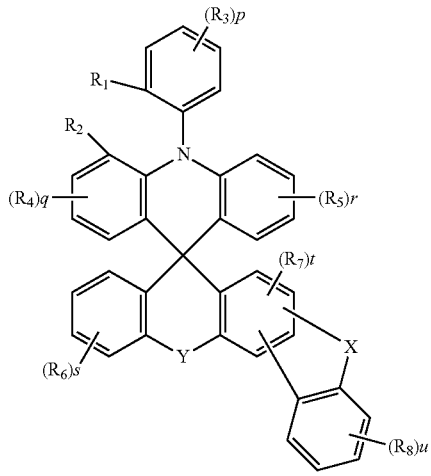

[Chemical Formula 1]

In Chemical Formula 1,
Y is O, S, or $SiR_{11}R_{12}$,
X is NAr, O, or S, and
$R_1$ to $R_8$ and Ar are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or may be bonded to an adjacent group to form a ring, $R_{11}$ and $R_{12}$ are the same as or different from each other, and are each independently hydrogen; deuterium; a substituted or unsubstituted alkyl group; or a substituted or unsubstituted aryl group, p, s, r, and u are each an integer from 0 to 4, q is an integer from 0 to 3, t is an integer from 0 to 2, and when p, q, r, s, t, and u are each 2 or more, groups in the parenthesis are the same as or different from each other.

Further, an exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the compound of Chemical Formula 1.

Advantageous Effects

The compound described in the present specification may be used as a material for an organic material layer of an organic light emitting device. The compound according to at least one exemplary embodiment of the present specification may improve the efficiency, achieve low driving voltage and/or improve service life characteristics in the organic light emitting device. In particular, the compound described in the present specification may be used as a material for hole injection, hole transport, hole injection and hole transport, light emission, electron transport, electron blocking, or electron injection. In addition, the compound described in the present specification may be used as a material for an organic solar cell or an organic transistor in addition to an organic light emitting device.

BRIEF DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 3, an electron transporting layer 7, and a negative electrode 4.

MODE FOR INVENTION

Hereinafter, the present specification will be described in more detail.

Examples of the substituents will be described below, but are not limited thereto.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamino group; an aralkylamino group; a heteroarylamino group; an arylamino group; an arylphosphine group; and a heterocyclic group, or being unsubstituted or substituted with a substituent to which two or more substituents among the substituents exemplified above are linked. For example, "the substituent to which two or more substituents are linked" may be an aryl group substituted with a heteroaryl group.

In the present specification, the number of carbon atoms of a carbonyl group is not particularly limited, but is preferably 1 to 40. Specifically, the carbonyl group may be a compound having the following structures, but is not limited thereto.

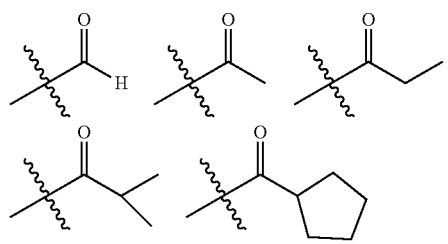

-continued

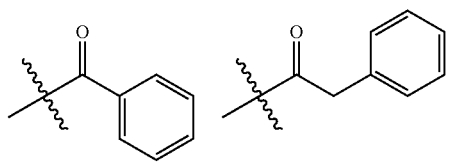

In the present specification, for an ester group, the oxygen of the ester group may be substituted with a straight, branched, or cyclic alkyl group having 1 to 25 carbon atoms, or an aryl group having 6 to 25 carbon atoms. Specifically, the ester group may be a compound having the following structural formulae, but is not limited thereto.

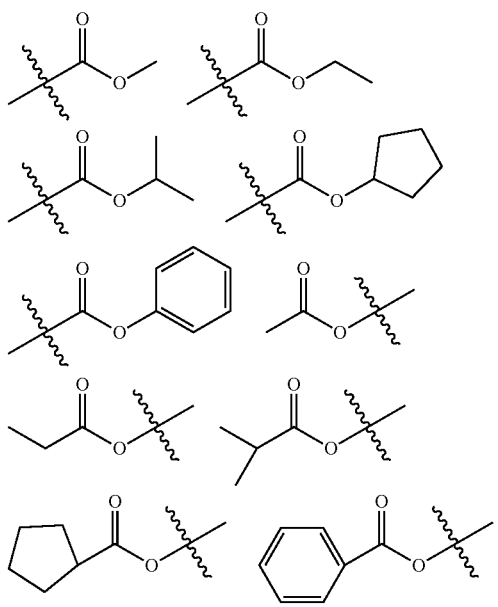

In the present specification, the number of carbon atoms of an imide group is not particularly limited, but is preferably 1 to 25. Specifically, the imide group may be a compound having the following structures, but is not limited thereto.

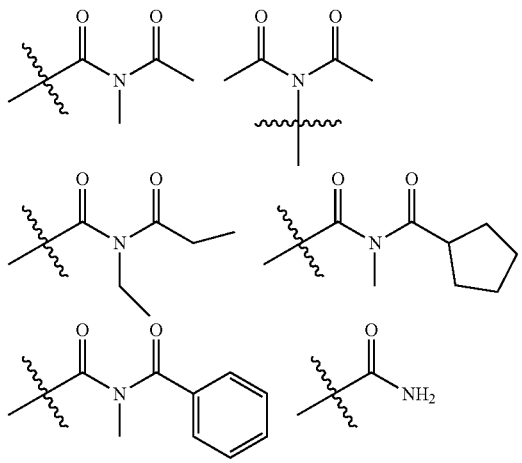

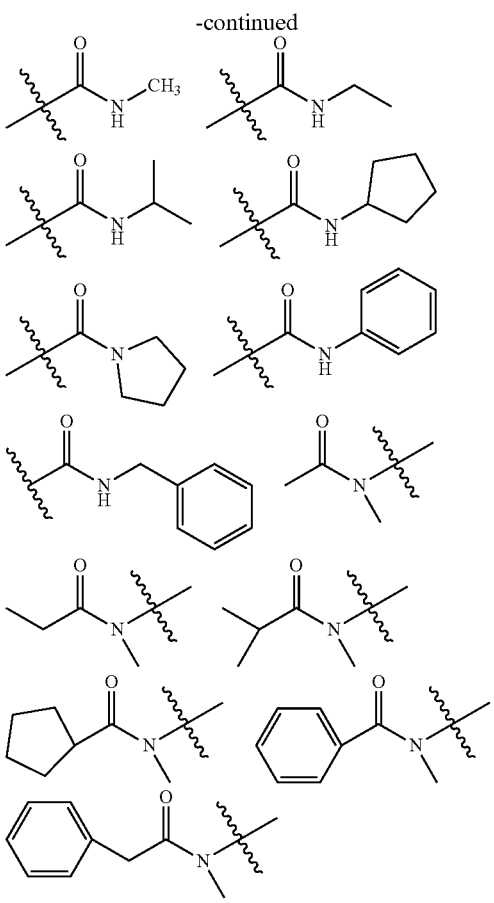

In the present specification, a silyl group may be represented by a chemical formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a formula of —BRR', and R and R' may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, examples of a halogen group include fluorine, chlorine, bromine or iodine.

In the present specification, the alkyl group may be straight or branched, and the number of carbon atoms thereof is not particularly limited, but is preferably 1 to 40. According to an exemplary embodiment, the number of carbon atoms of the alkyl group is 1 to 20. According to another exemplary embodiment, the number of carbon atoms of the alkyl group is 1 to 10. According to still another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to still another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an alkoxy group is not particularly limited, but has preferably 1 to 40 carbon atoms. According to an exemplary embodiment, the number of carbon atoms of the alkoxy group is 1 to 10. According to another exemplary embodiment, the number of carbon atoms of the alkoxy group is 1 to 6. Specific examples of the alkoxy group include a methoxy group, an ethoxy group, a propoxy group, an isobutyloxy group, a sec-butyloxy group, a pentyloxy group, an iso-amyloxy group, a hexyloxy group, and the like, but are not limited thereto.

In the present specification, the number of carbon atoms of an amino group is not particularly limited, but is preferably 1 to 30. Specific examples of the amino group include a methylamino group, a dimethylamino group, an ethylamino group, a diethylamino group, a phenylamino group, a naphthylamino group, a biphenylamino group, an anthracenylamino group, a 9-methyl-anthracenylamino group, a diphenylamino group, a phenylnaphthylamino group, a ditolylamino group, a phenyltolylamino group, a triphenylamino group, and the like, but are not limited thereto.

In the present specification, examples of an arylamino group include a substituted or unsubstituted monoarylamino group, a substituted or unsubstituted diarylamino group, or a substituted or unsubstituted triarylamino group. The aryl group in the arylamino group may be a monocyclic aryl group, and may be a polycyclic aryl group. The arylamino group including two or more aryl groups may include a monocyclic aryl group, a polycyclic aryl group, or both a monocyclic aryl group and a polycyclic aryl group. Specific examples of the arylamino group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamino group, a phenylnaphthylamino group, a ditolylamino group, a phenyltolylamino group, carbazole, a triphenylamino group, and the like, but are not limited thereto.

In the present specification, examples of a heteroarylamino group include a substituted or unsubstituted monoheteroarylamino group, a substituted or unsubstituted diheteroarylamino group, or a substituted or unsubstituted triheteroarylamino group. The heteroaryl group in the heteroarylamino group may be a monocyclic heterocyclic group, and may be a polycyclic heterocyclic group. The heteroarylamino group including two or more heterocyclic groups may include a monocyclic heterocyclic group, a polycyclic heterocyclic group, or both a monocyclic heterocyclic group and a polycyclic heterocyclic group.

In the present specification, an arylheteroarylamino group means an amino group substituted with an aryl group and a heterocyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a triphenylene group, and the like, but are not limited thereto.

In the present specification, a fluorenyl group may be substituted, and two substituents may be bonded to each other to form a spiro structure.

When the fluorenyl group is substituted, the fluorenyl group may be

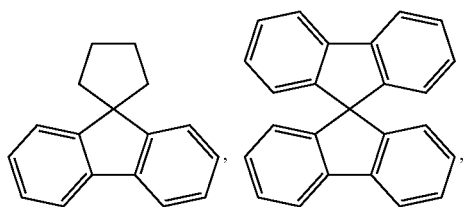

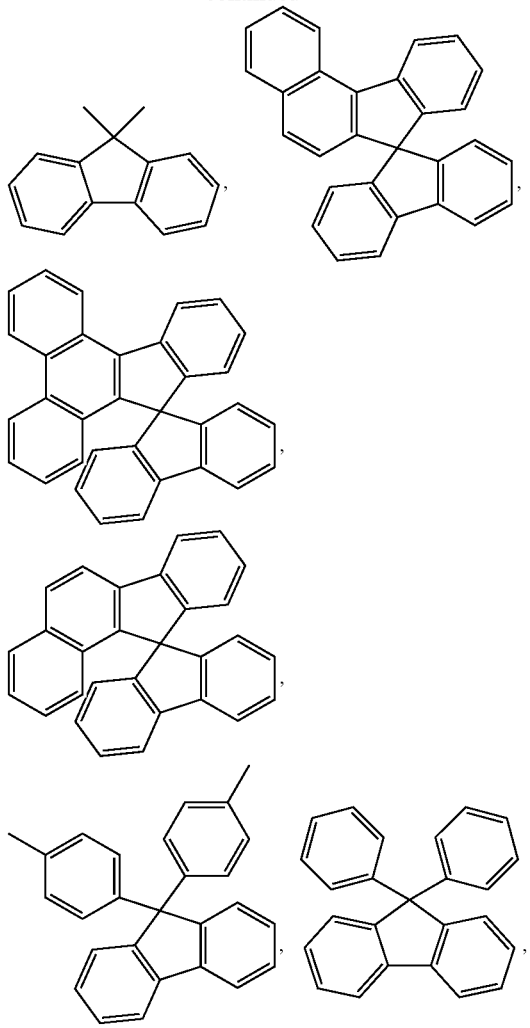

and the like. However, the fluorenyl group is not limited thereto.

In the present specification, a heterocyclic group is a heterocyclic group including one or more of N, O, S, Si, and Se as a heteroatom, and the number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the above-described description on the heterocyclic group may be applied to a heteroaryl group except for an aromatic heteroaryl group.

In the present specification, the above-described description on the aryl group may be applied to an aryl group in an aryloxy group, an arylthioxy group, an arylsulfoxy group, an arylphosphine group, an aralkyl group, an aralkylamino group, an aralkenyl group, an alkylaryl group, an arylamino group, and an arylheteroarylamino group.

In the present specification, the above-described description on the alkyl group may be applied to an alkyl group in an alkylthioxy group, an alkylsulfoxy group, an aralkyl group, an aralkylamino group, an alkylaryl group, and an alkylamino group.

In the present specification, the above-described description on the heterocyclic group may be applied to a heteroaryl group in a heteroaryl group, a heteroarylamino group, and an arylheteroarylamino group.

In the present specification, the above-described description on the alkenyl group may be applied to an alkenyl group in an aralkenyl group.

In the present specification, the above-described description on the aryl group may be applied to an arylene except for a divalent arylene group.

In the present specification, the above-described description on the heterocyclic group may be applied to a heteroarylene except for a divalent heteroarylene group.

In the present specification, being bonded to an adjacent group to form a ring means being bonded to an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a fused ring thereof. The aliphatic hydrocarbon ring is a ring which is not an aromatic ring, and is a ring composed of only carbon and hydrogen atoms. Examples of the aromatic hydrocarbon ring include benzene, naphthalene, anthracene, and the like, but are not limited thereto. The aliphatic hetero ring is an aliphatic ring including one or more heteroatoms. The aromatic hetero ring is an aromatic ring including one or more heteroatoms. The hetero ring may include O, S, Se, N, or Si as a heteroatom. The aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by the following Chemical Formula 2 or 3.

[Chemical Formula 2]

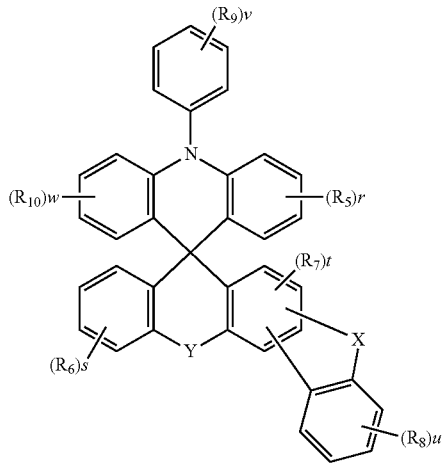

In Chemical Formula 2, Y, X, $R_5$ to $R_8$, r, s, t, and u are the same as those defined in Chemical Formula 1, $R_9$ and $R_{10}$ are the same as or different from each other, and are the same as the definitions of $R_1$ to $R_8$ of Chemical Formula 1, v is an integer from 0 to 5, w is an integer from 0 to 4, and when v and w are each 2 or more, groups in the parenthesis are the same as or different from each other.

[Chemical Formula 3]

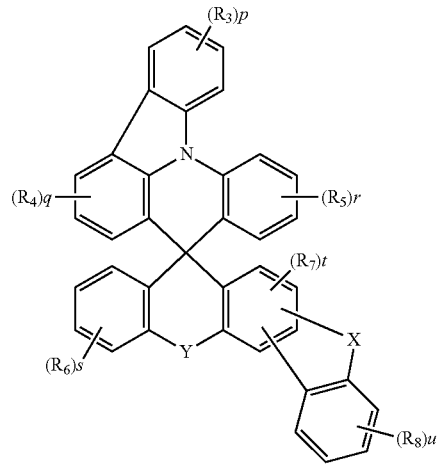

In Chemical Formula 3, Y, X, $R_3$ to $R_8$, p, q, r, s, t, and u are the same as those defined in Chemical Formula 1. According to an exemplary embodiment of the present specification, Chemical Formula 1 may be represented by any one of the following Chemical Formulae 4 to 7.

[Chemical Formula 4]

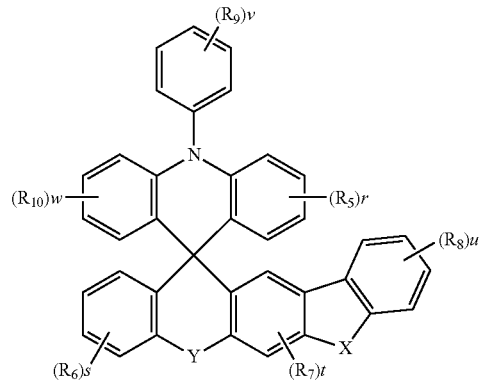

[Chemical Formula 5]

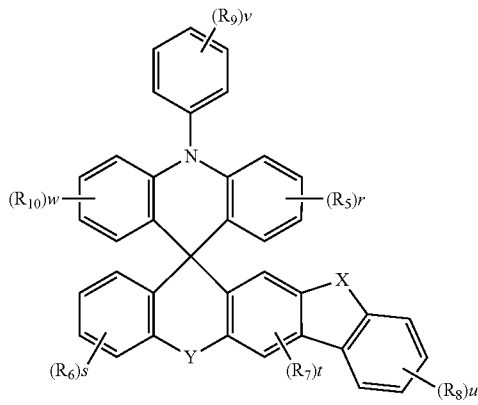

[Chemical Formula 6]

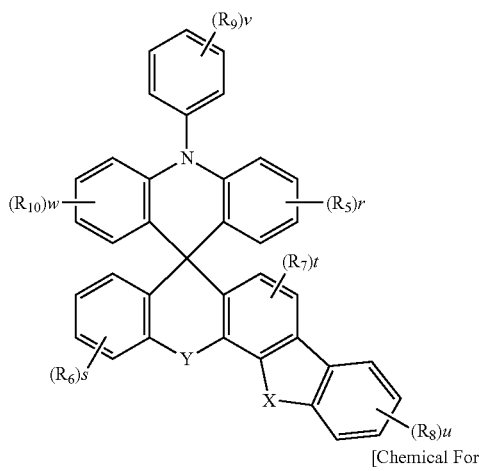

[Chemical Formula 7]

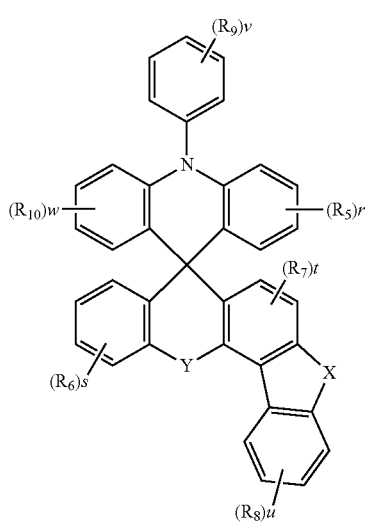

In Chemical Formulae 4 and 7, the definitions of the substituents are the same as those in Chemical Formula 2.

According to an exemplary embodiment of the present specification, Chemical Formula 1 may be represented by any one of the following Chemical Formulae 8 to 11.

[Chemical Formula 8]

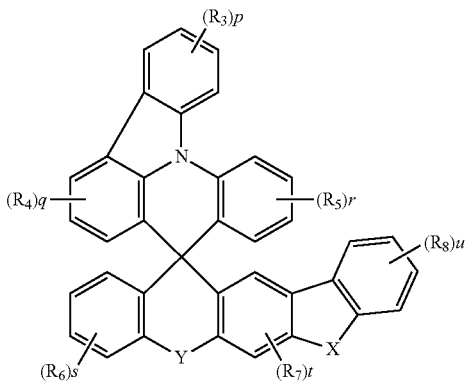

[Chemical Formula 9]

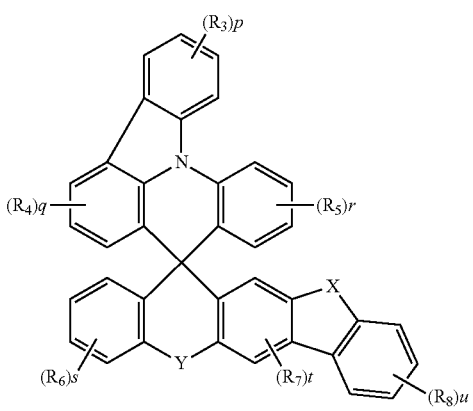

[Chemical Formula 10]

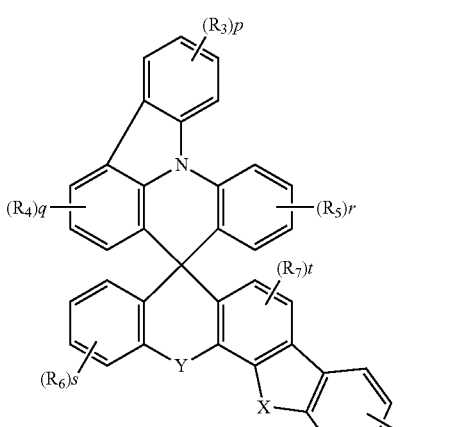

[Chemical Formula 11]

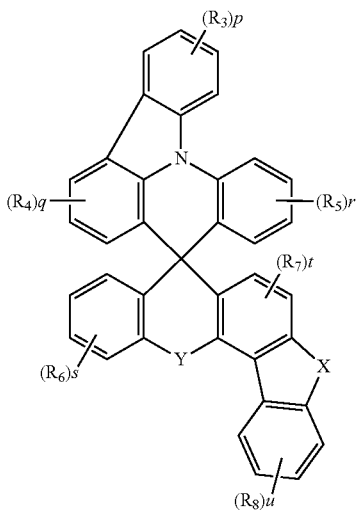

In Chemical Formulae 8 to 11, the definitions of the substituents are the same as those in Chemical Formula 1.

According to an exemplary embodiment of the present invention, X is NAr and Ar is represented by —($L_1$)n-$Ar_1$, $L_1$ is a direct bond; a substituted or unsubstituted arylene group; or a substituted or unsubstituted heteroarylene, n is an integer from 0 to 2, and when n is 2, $L_1$'s are the same as or different from each other, and $Ar_1$ is hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group.

According to an exemplary embodiment of the present invention, $Ar_1$ is a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or is bonded to an adjacent group to form a ring, and the others are hydrogen or deuterium.

According to an exemplary embodiment of the present invention, $Ar_1$ is a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or is bonded to an adjacent group to form a ring, and when these groups are substituted, the substituent is deuterium, a halogen group, a nitrile group, a silyl group, an alkyl group, an alkylamino group, an aralkylamino group, a heteroarylamino group, an arylamino group, an arylheteroarylamino group, an arylphosphine group, a phosphine oxide group, an aryl group, or a heterocyclic group.

According to an exemplary embodiment of the present invention, $Ar_1$ is a substituted or unsubstituted aryl group; a substituted or unsubstituted heterocyclic group; a substituted or unsubstituted arylamino group; or a substituted or unsubstituted arylphosphine group.

According to an exemplary embodiment of the present invention, $Ar_1$ is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylphosphine group which is unsubstituted or substituted with a group to which one or two or more groups of a halogen group, a nitrile group, an alkyl group, a silyl group, an arylamino group, an arylphosphine group, an aryl group, and a heteroaryl group is or are bonded. The group to which two or more groups are bonded may be a group to which two or more substituents exemplified above are bonded, for example, a heteroaryl group substituted with an aryl group, an aryl group substituted with a heteroaryl group, an aryl group substituted with an arylamino group, an aryl group substituted with an arylphosphine group, and the like, and are not limited to these examples.

According to an exemplary embodiment of the present invention, $Ar_1$ is an aryl group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; a heterocyclic group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; an arylamino group which is unsubstituted or substituted with a group to which one or two or more groups of a halogen group, a nitrile group, an alkyl group, a silyl group, an arylamino group, an arylphosphine group, an aryl group, and a heteroaryl group is or are bonded; or an arylphosphine group which is unsubstituted or substituted with a group to which one or two or more groups of a halogen group, a nitrile group, an alkyl group, a silyl group, an arylphosphine group, an arylamino group, an aryl group, and a heteroaryl group is or are bonded, here, the halogen group is a fluorine group, the alkyl group is a straight or branched alkyl group having 1 to 20 carbon atoms, for example, 1 to 6 carbon atoms, the silyl group is trialkylsilyl, for example, a trimethylsilyl group or a triphenylsilyl, the aryl group and aryl are phenyl, biphenylyl, terphenylyl, naphthyl, phenanthrenyl, a triphenylene group, fluorenyl, and a spirobifluorene group, and the heteroaryl group may be pyridyl, pyrimidyl, triazinyl, carbazolyl, benzocarbazolyl, quinazolyl, quinolyl, isoquinolyl, thienyl, benzoquinolyl, phenanthrolinyl, benzimidazolyl, benzoxazolyl, benzothiazolyl, a dibenzofuran group, a dibenzothiophene group, a benzo naphtho furan group, a benzo naphtho thiophene group, a phenoxazine group, a phenothiazine group, or a substituent of Group A.

[Group A]

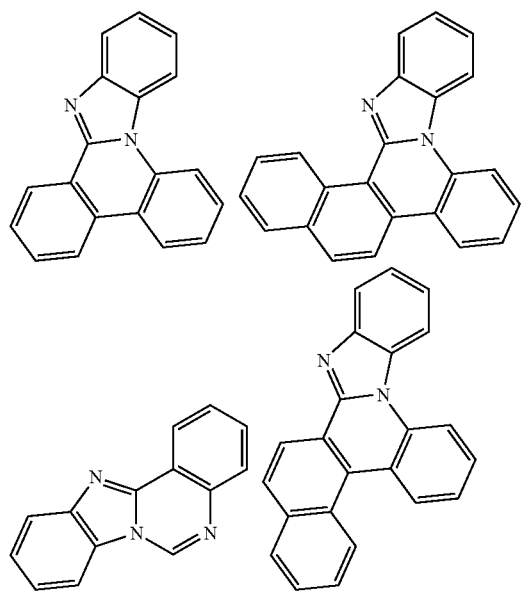

In the structural formulae, any one carbon is a linking moiety for forming a monovalent group, and the other carbons are a group to which one or two or more groups of hydrogen or a substituent, for example, a halogen group, a nitrile group, an alkyl group, a silyl group, an arylamino group, an arylphosphine group, an aryl group, and a heteroaryl group is or are bonded.

According to an exemplary embodiment of the present invention, Ar$_1$ is selected from the following structural formulae.

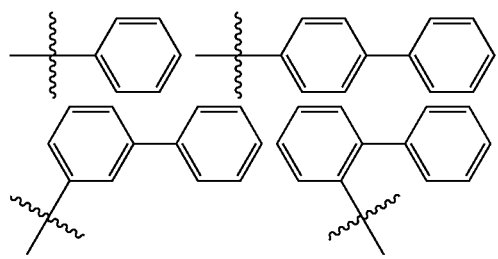

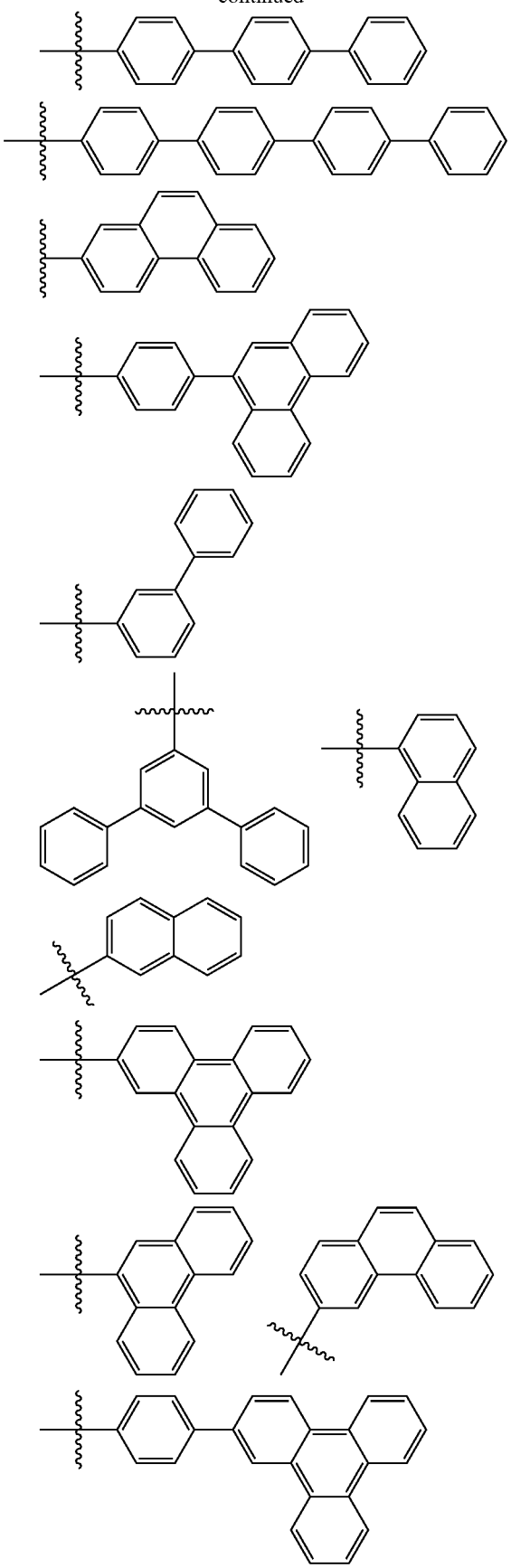

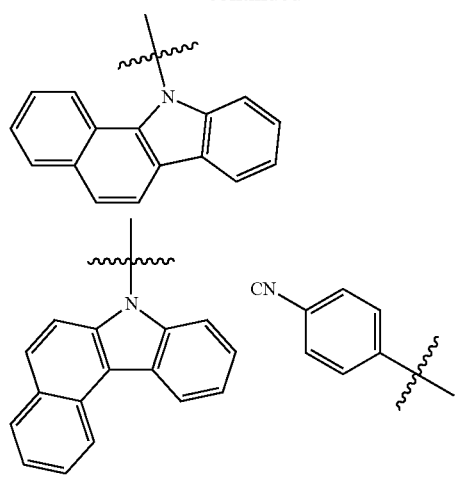
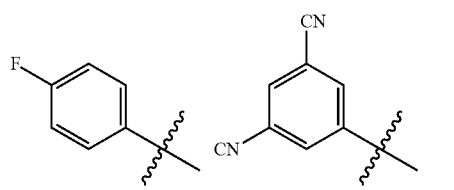
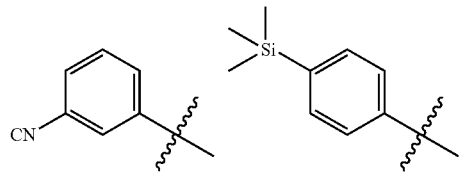
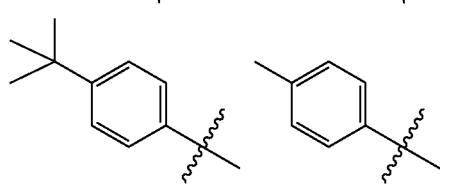
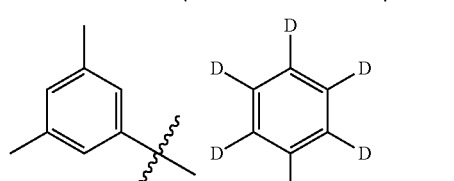
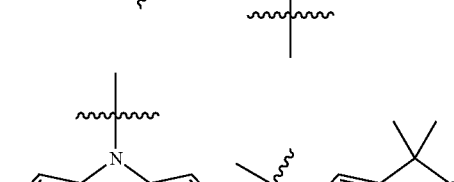
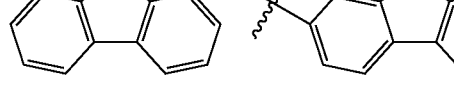
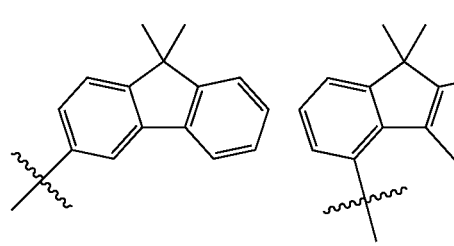
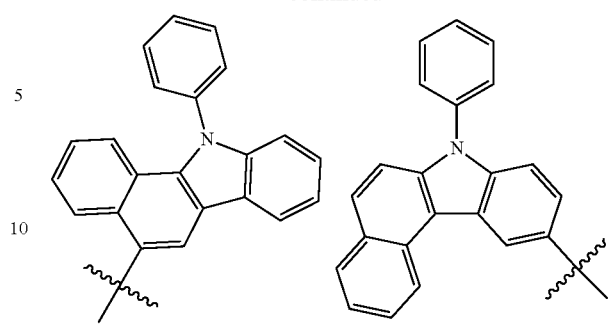
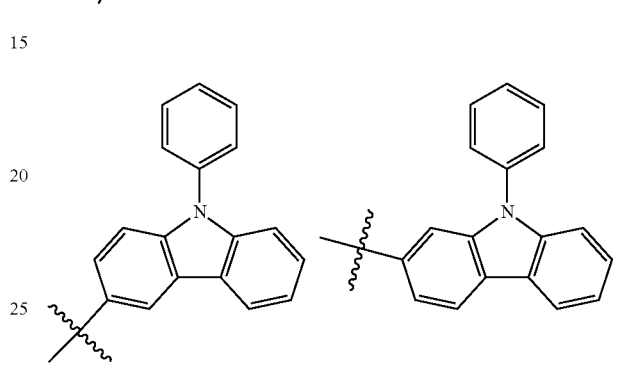
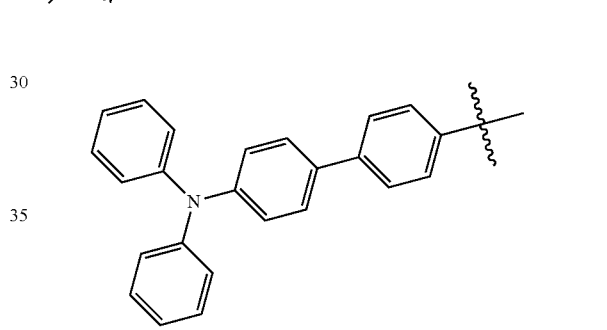
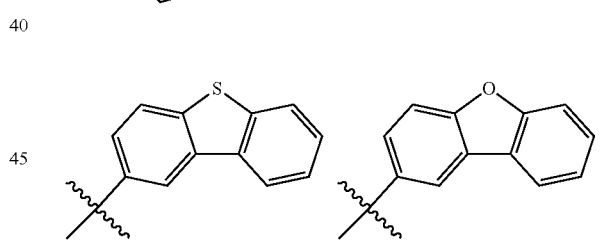
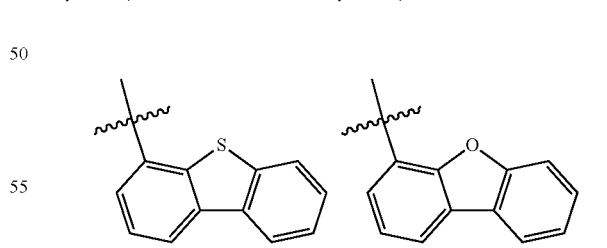
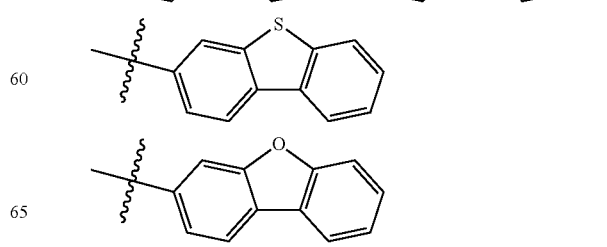

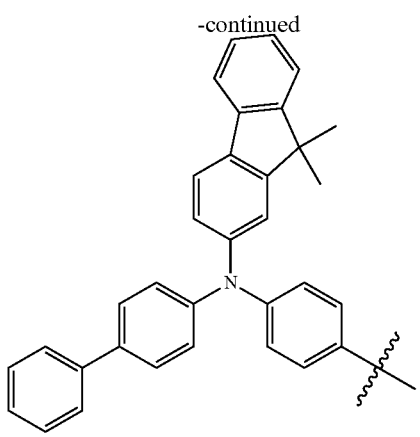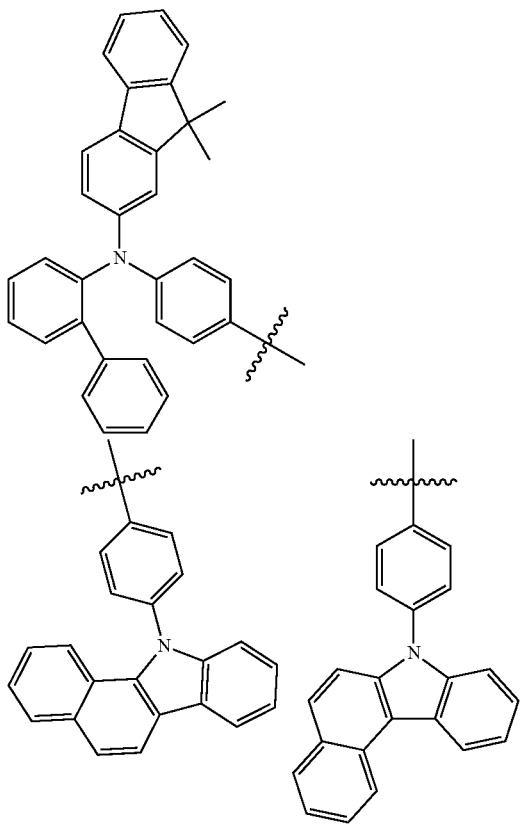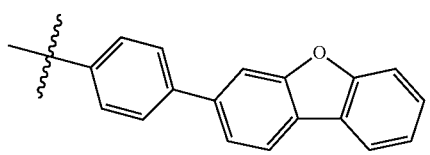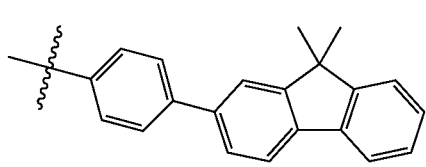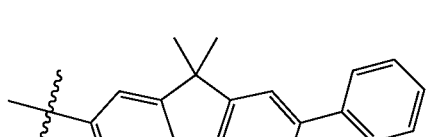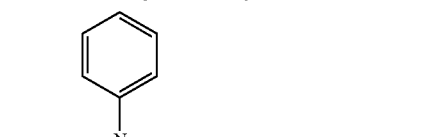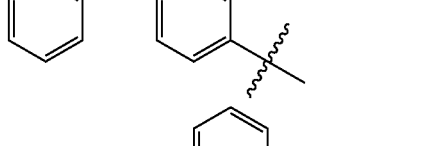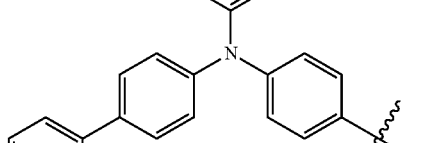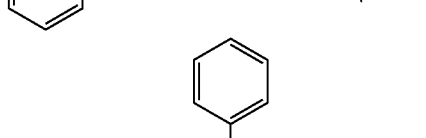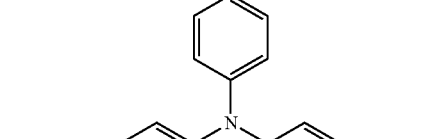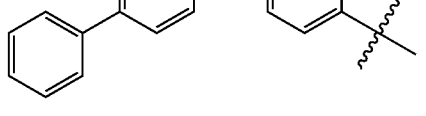

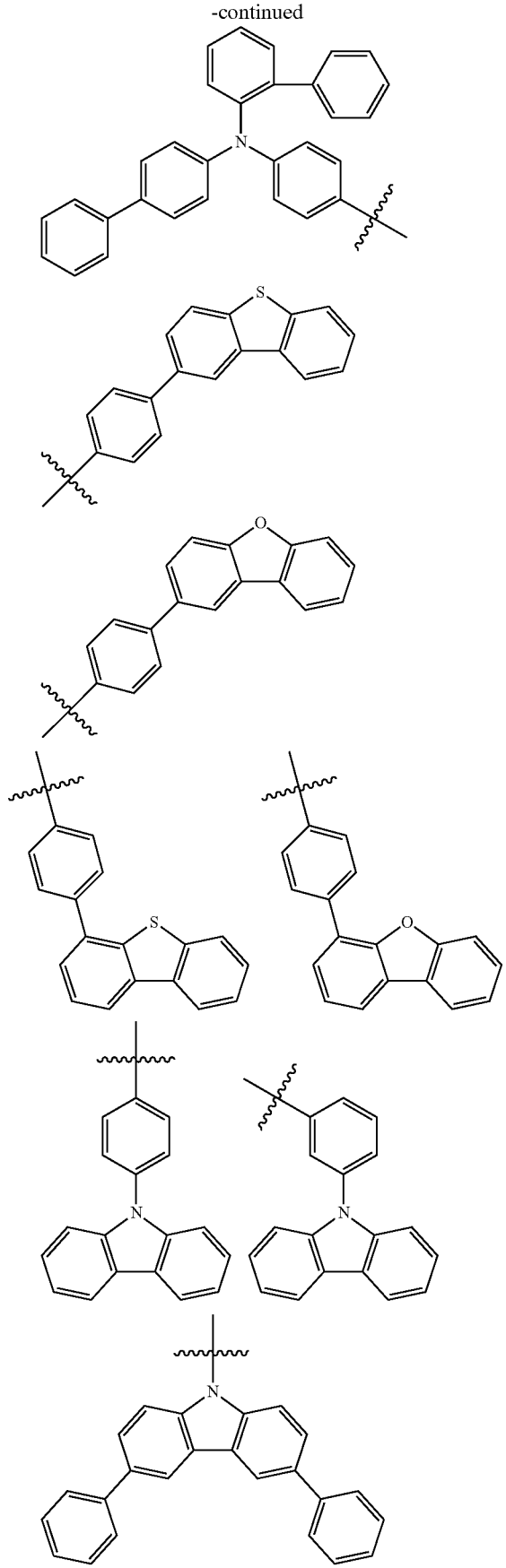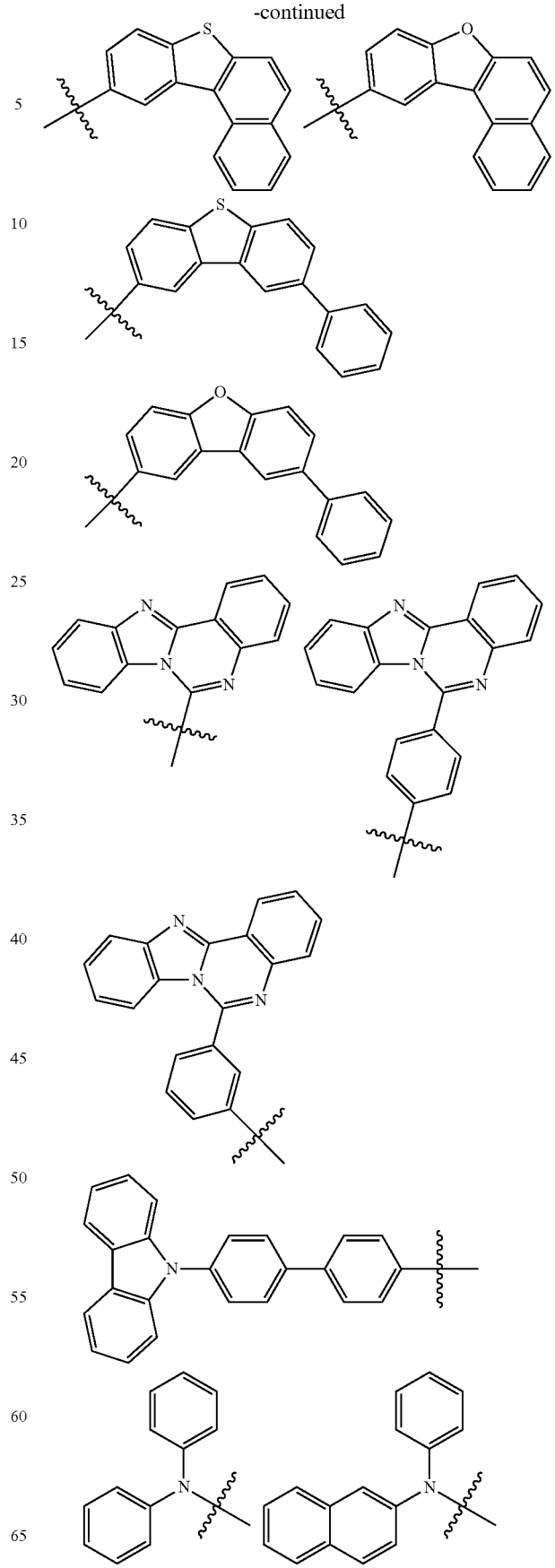

-continued
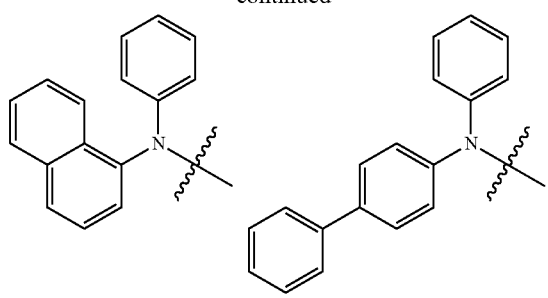
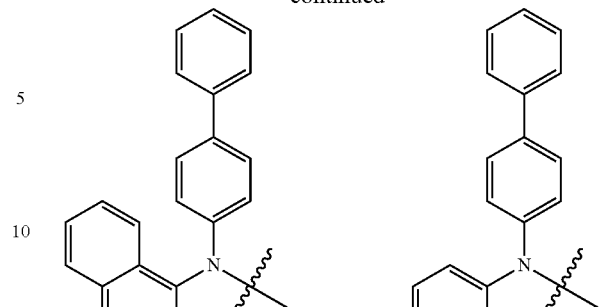
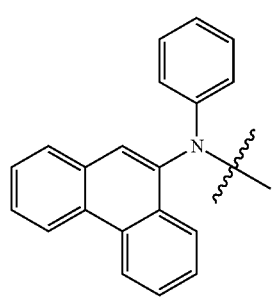
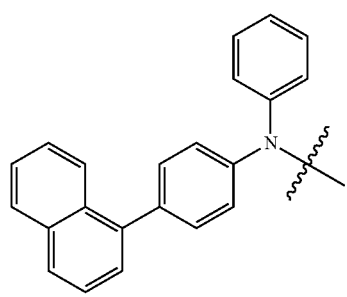
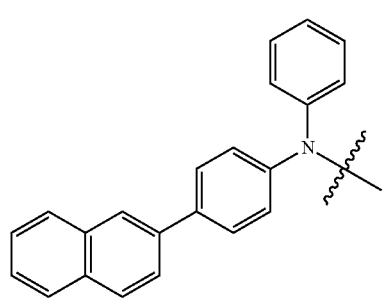
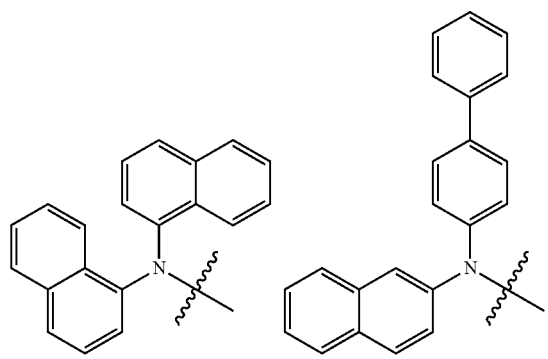

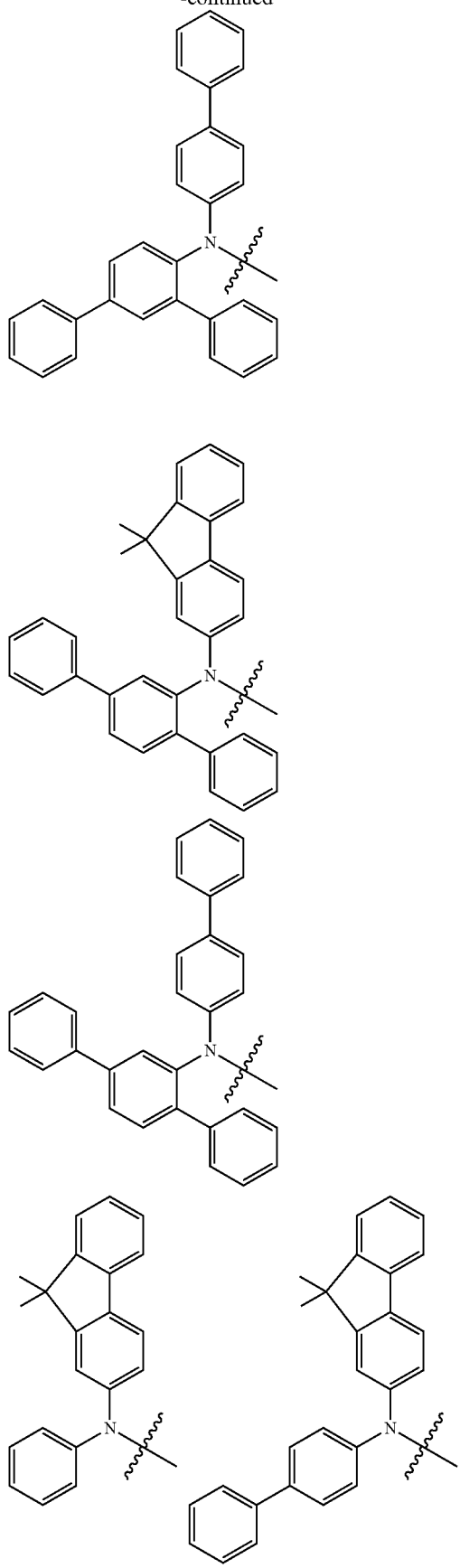
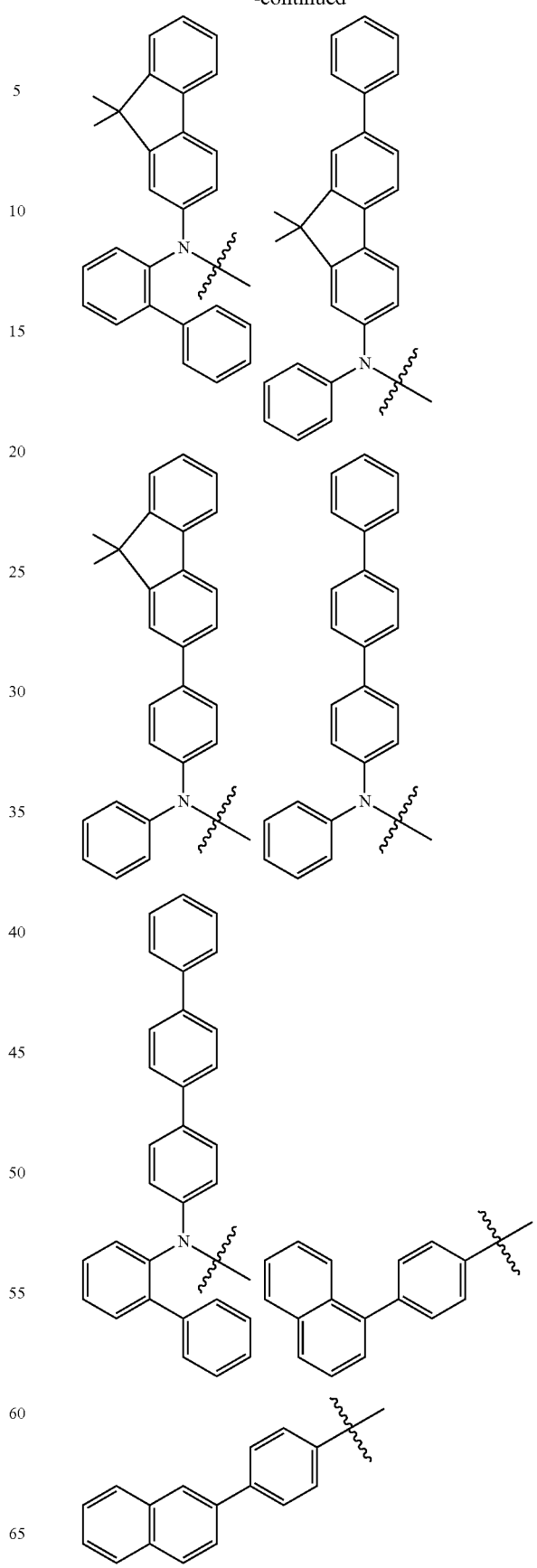

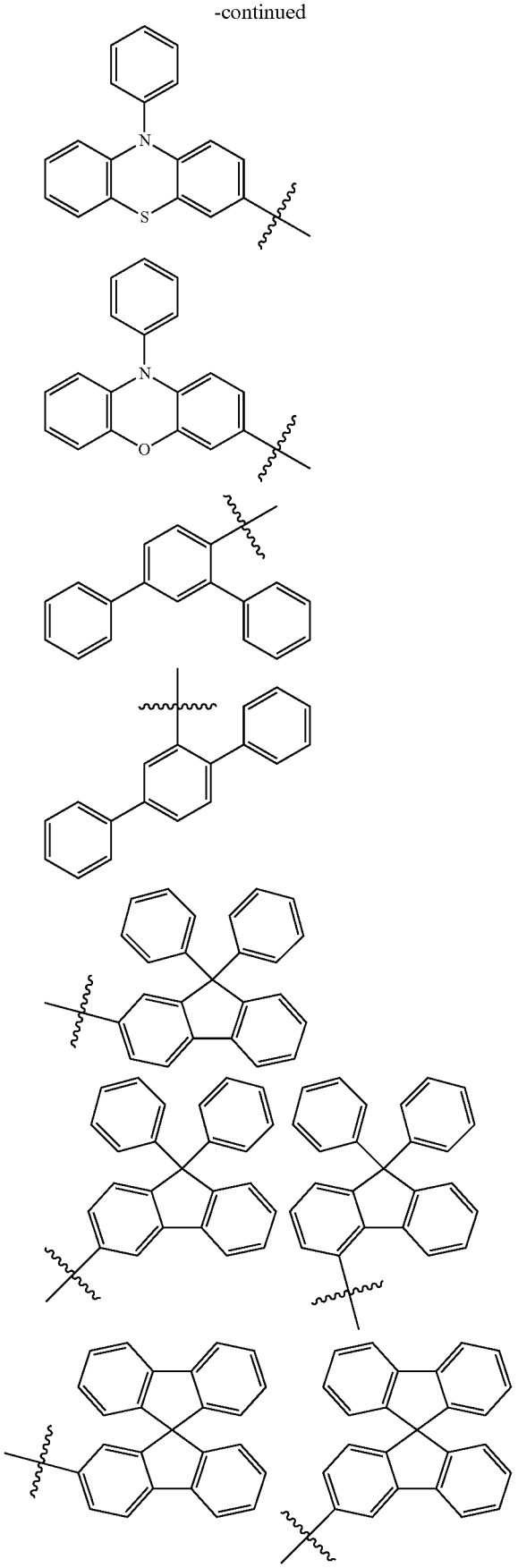
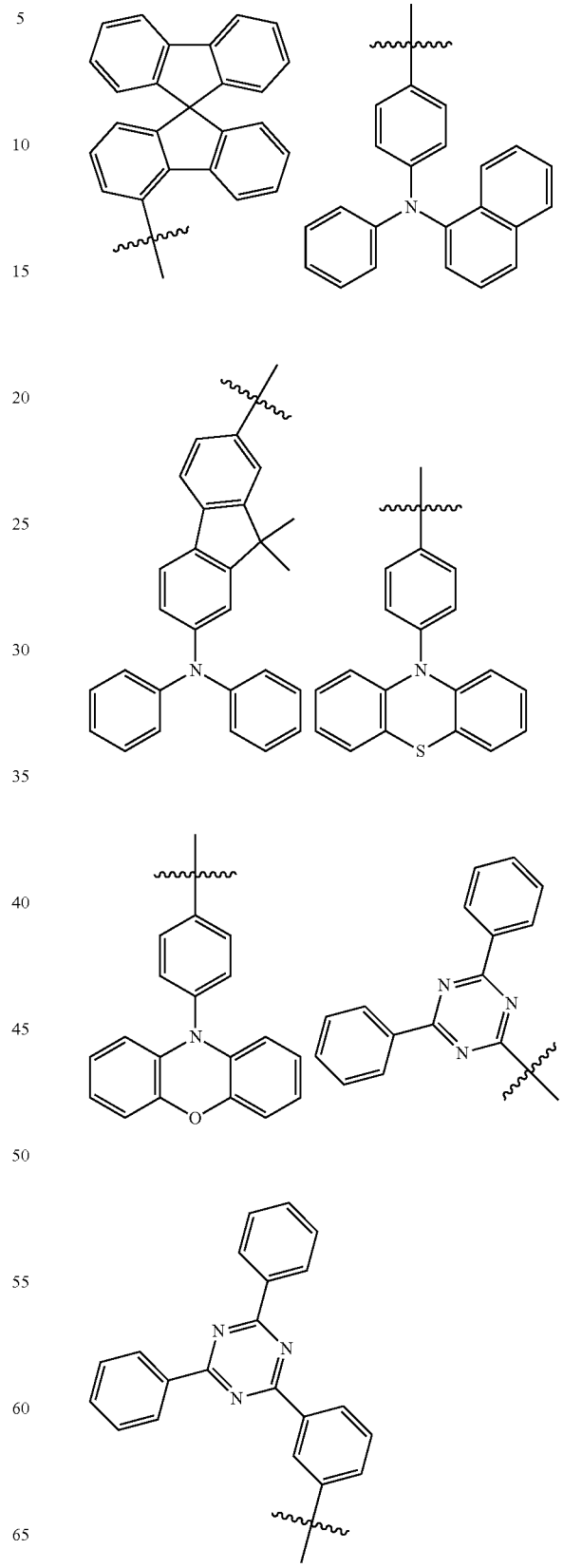

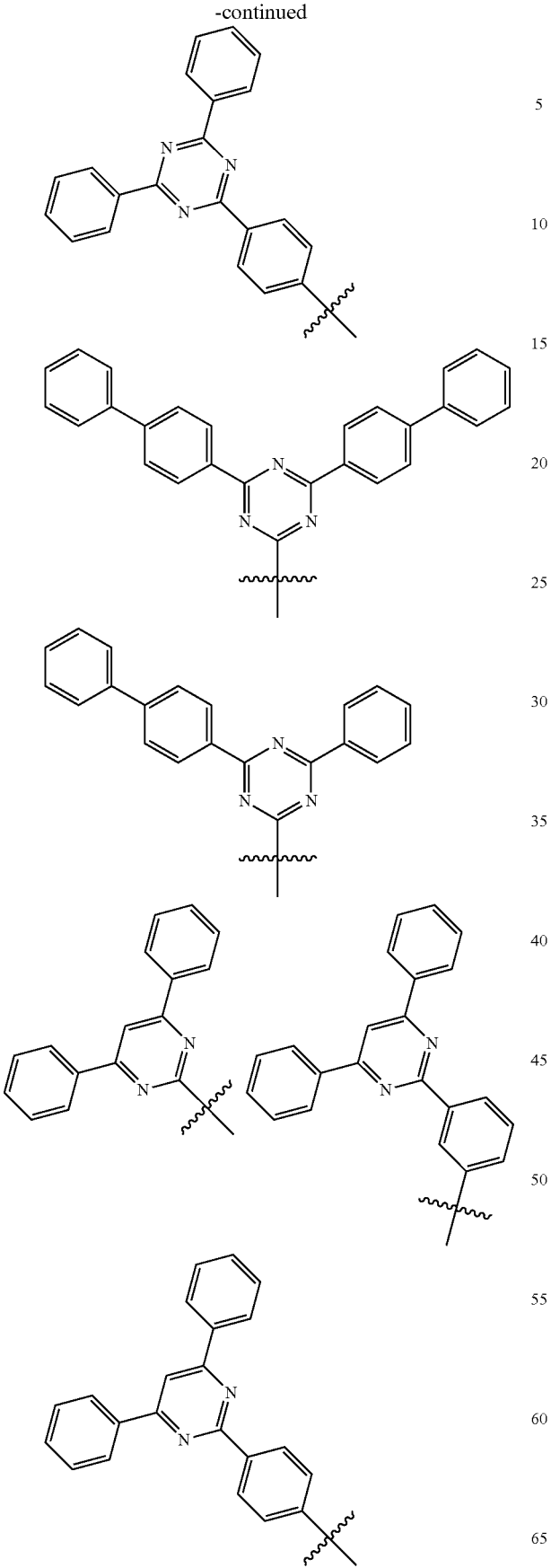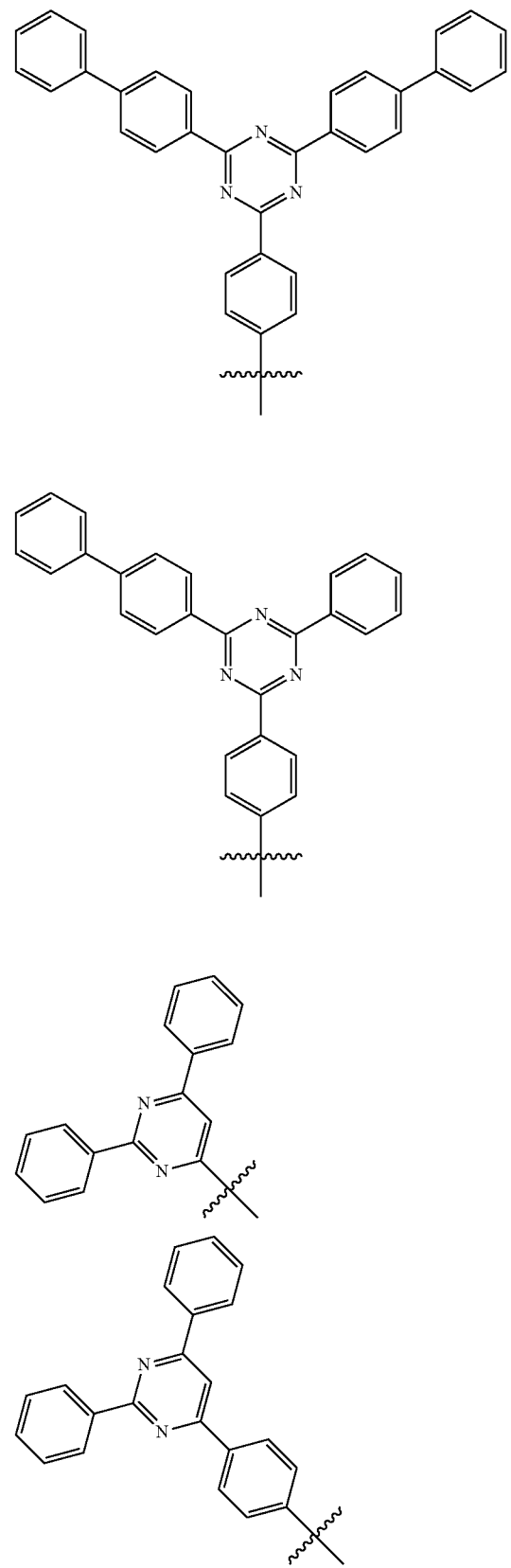

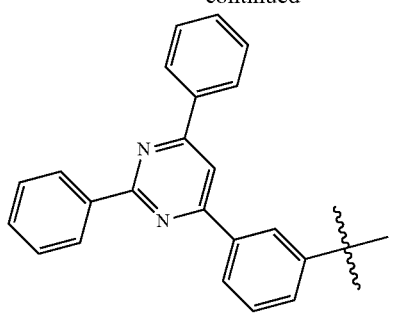
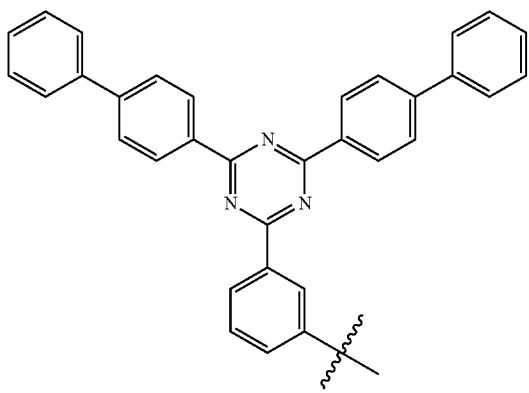
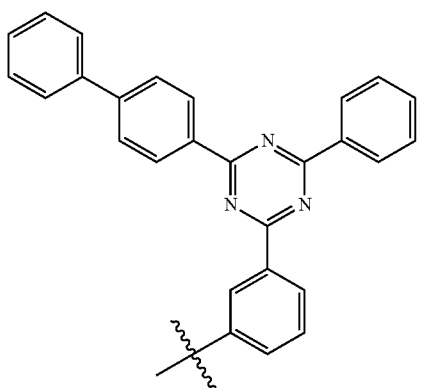
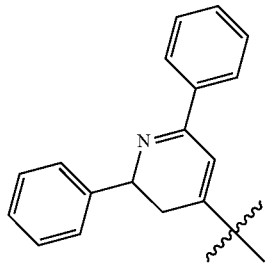
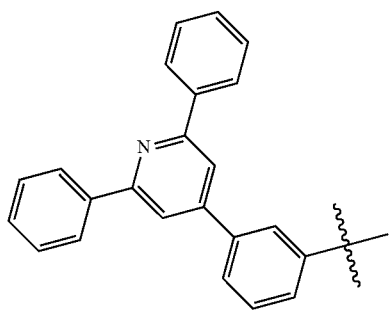
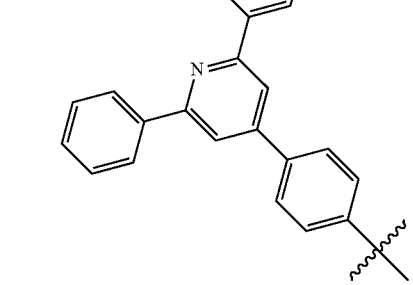
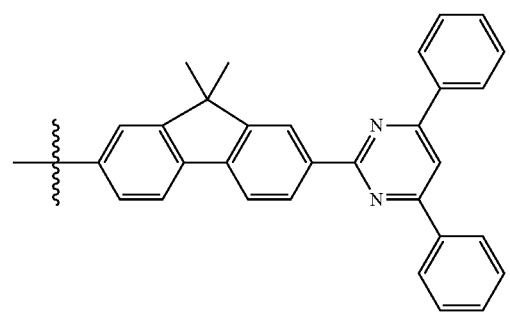
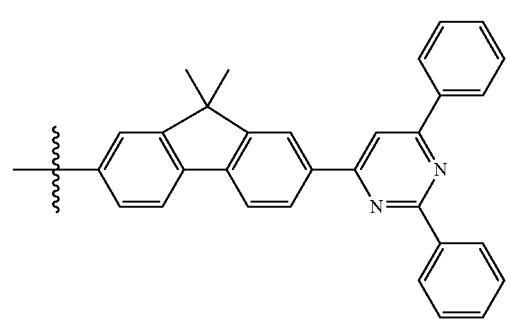
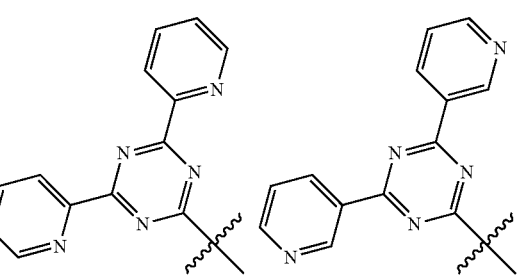
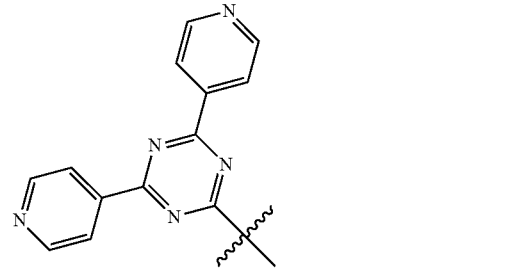

33
-continued
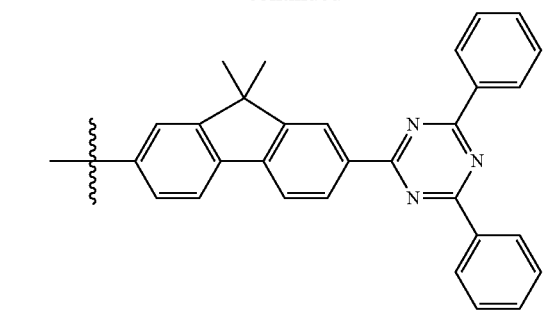
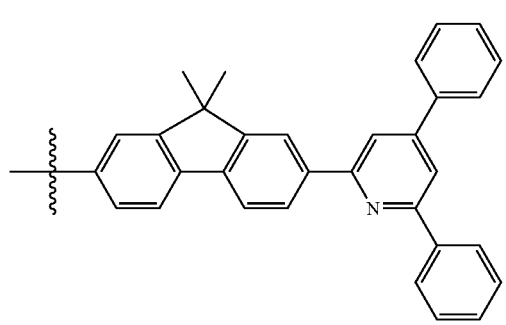
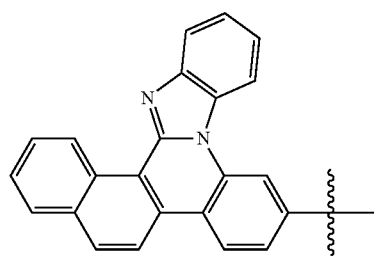
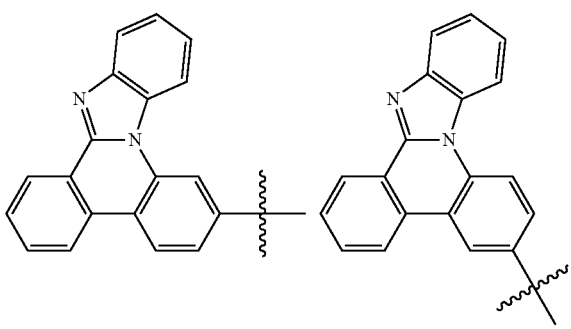
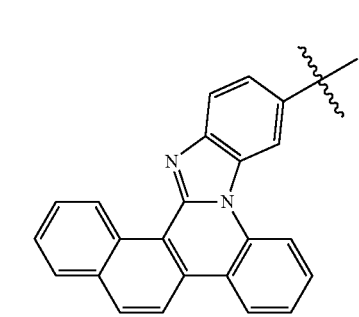
34
-continued
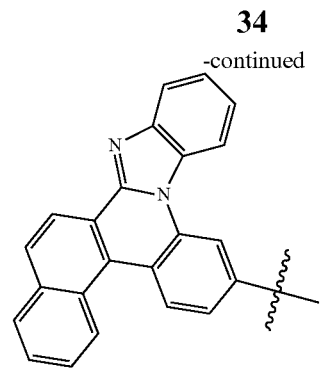
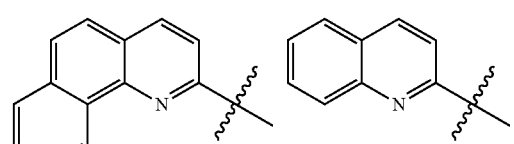
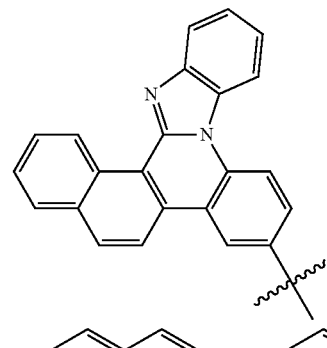
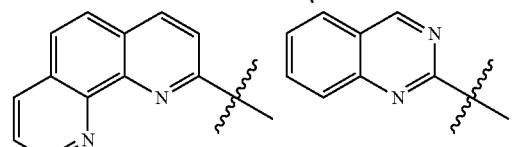
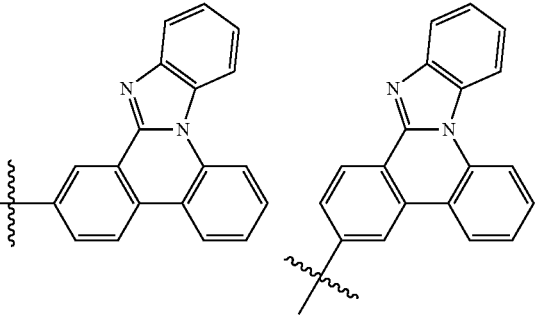
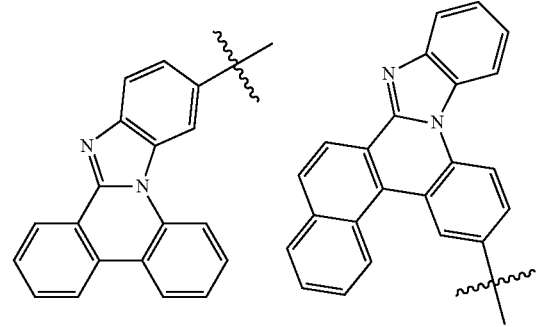

35
-continued
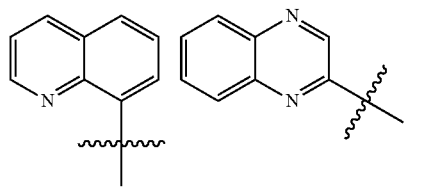
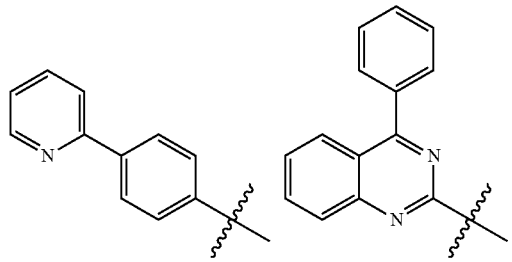
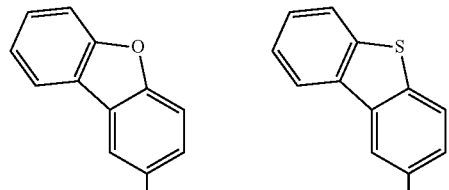
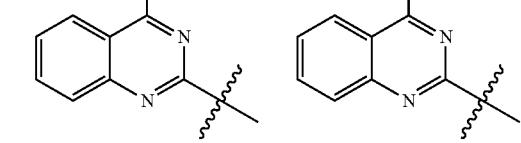
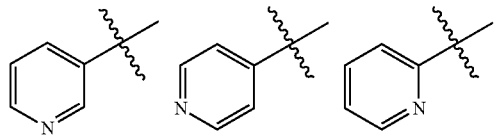
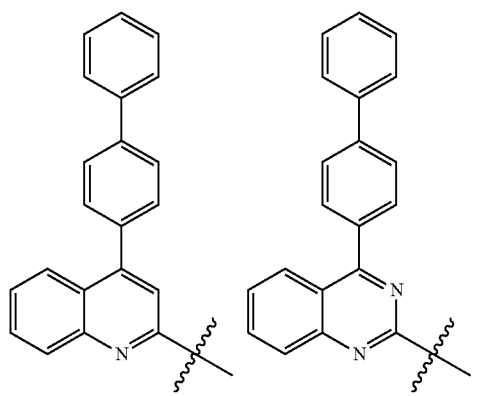
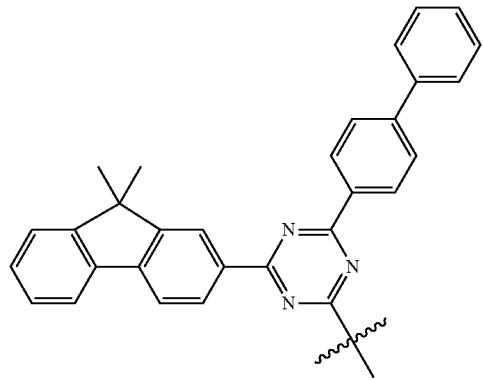
36
-continued
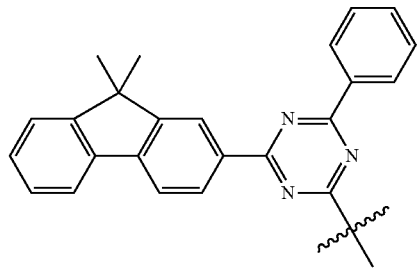
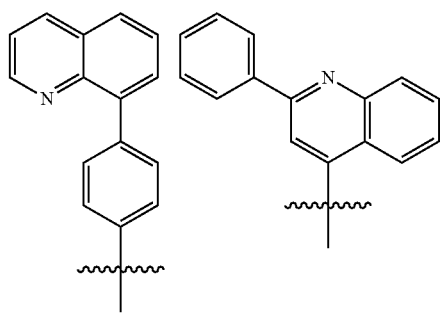
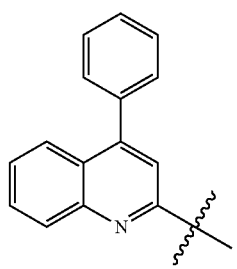
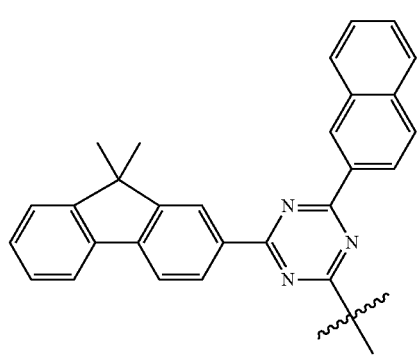
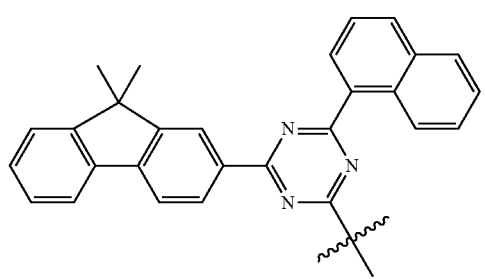

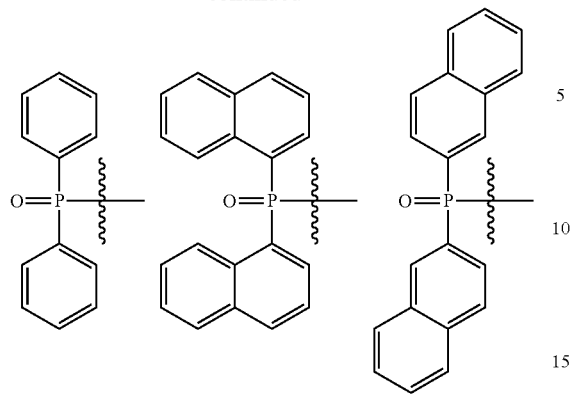
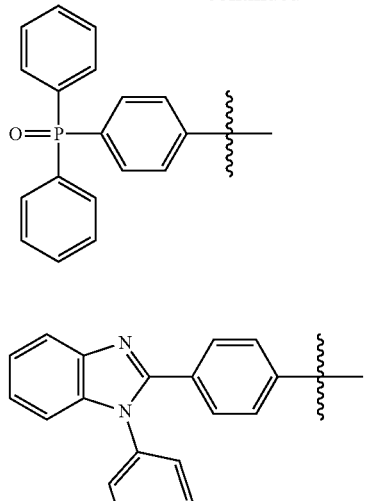
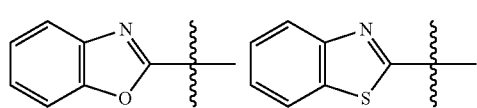
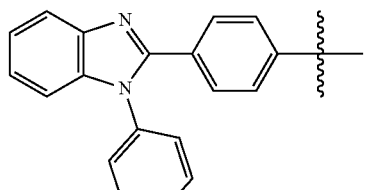
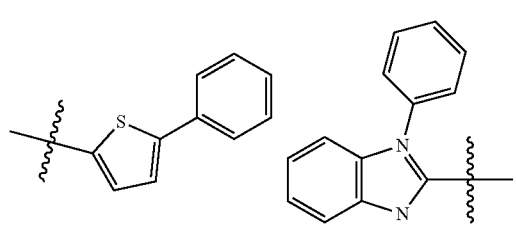
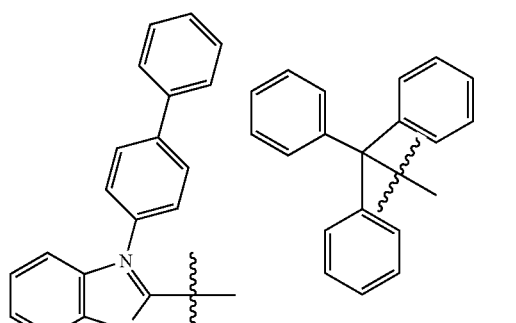
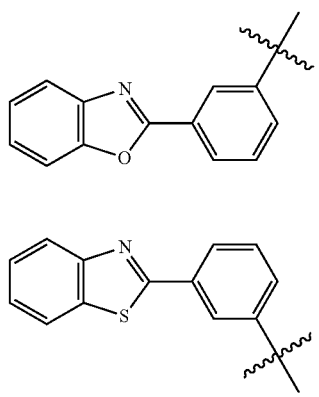
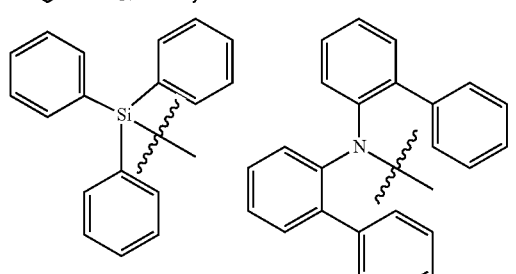
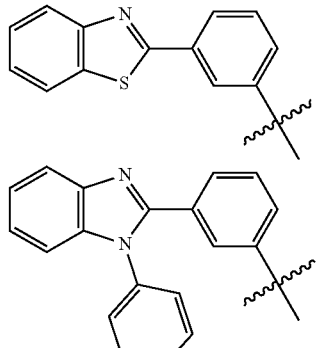
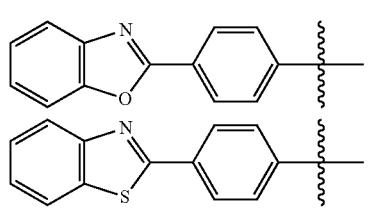
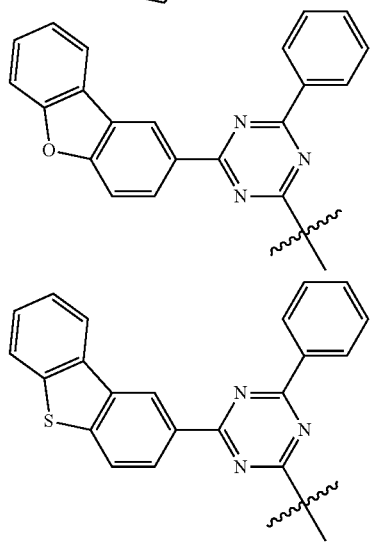

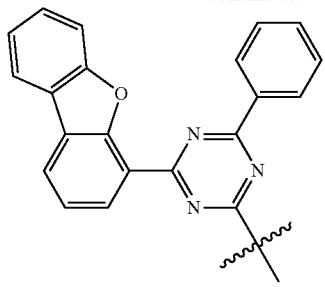
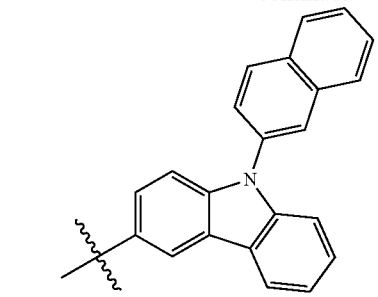 [SMILES: *c1ccc2c(c1)c1ccccc1n2-c1ccc2ccccc2c1]
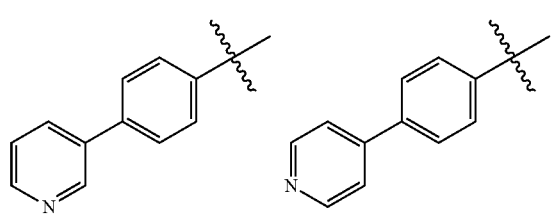

According to an exemplary embodiment of the present invention, $L_1$ is a direct bond; or a substituted or unsubstituted arylene.

According to an exemplary embodiment of the present invention, $L_1$ is a direct bond, a substituted or unsubstituted phenylene, a substituted or unsubstituted biphenylylene, a substituted or unsubstituted terphenylylene, a substituted or unsubstituted quarterphenylylene, a substituted or unsubstituted naphthylene, a substituted or unsubstituted anthrylene, a substituted or unsubstituted fluorene, a substituted or unsubstituted phenanthrene, a substituted or unsubstituted pyrene, or a substituted or unsubstituted triphenylene.

According to an exemplary embodiment of the present invention, $L_1$ is a direct bond, phenylene, biphenylylene, terphenylylene, quarterphenylylene, naphthylene, anthrylene, fluorene, phenanthrene, pyrene, or triphenylene.

According to an exemplary embodiment of the present invention, $L_1$ may be a direct bond, or may be selected from the following structural formulae.

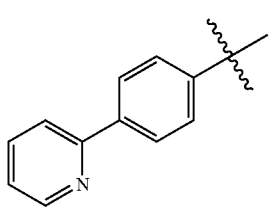
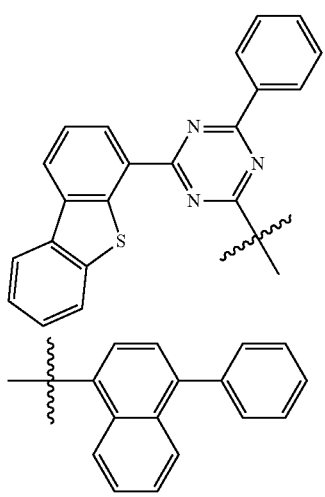
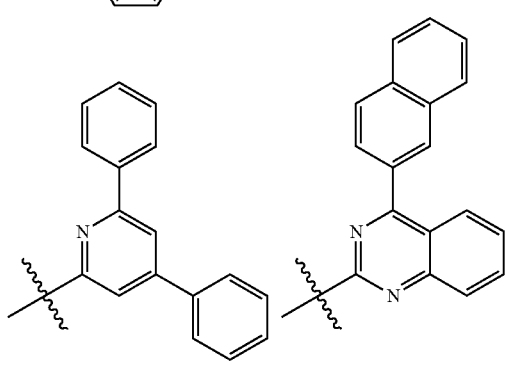
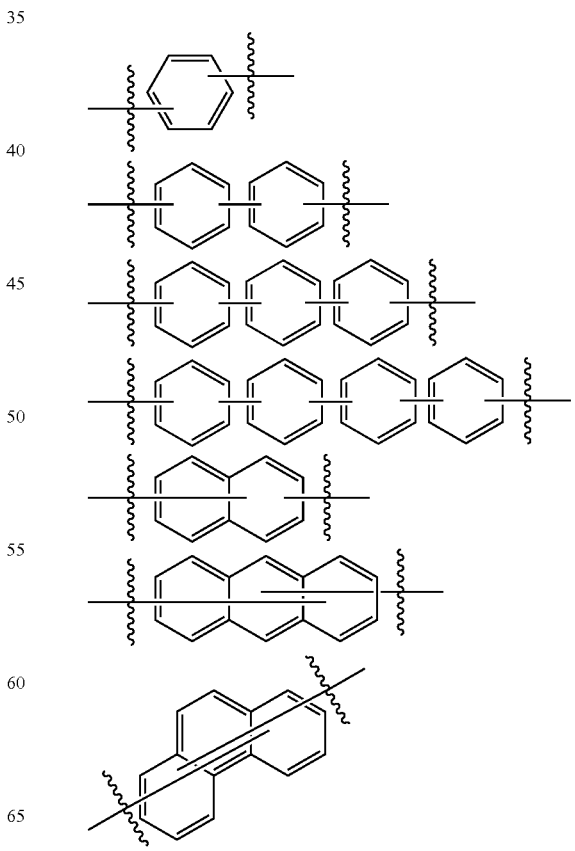

-continued

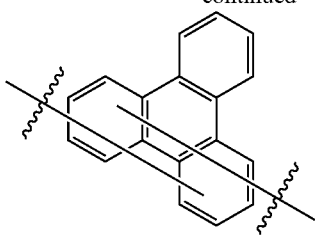

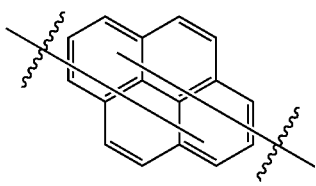

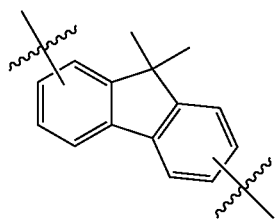

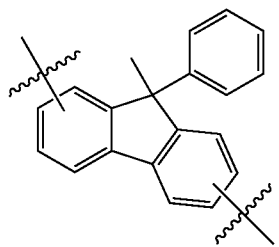

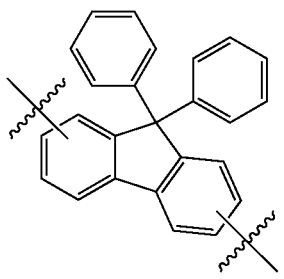

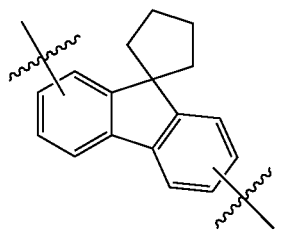

According to an exemplary embodiment of the present invention, $L_1$ is a direct bond, or phenylene.

According to an exemplary embodiment of the present invention, n is 0 or 1.

According to an exemplary embodiment of the present invention, $R_1$ to $R_8$ are hydrogen or deuterium.

According to an exemplary embodiment of the present invention, $R_{11}$ and $R_{12}$ are each independently hydrogen; deuterium; a substituted or unsubstituted alkyl group; or a substituted or unsubstituted aryl group.

According to an exemplary embodiment of the present invention, $R_{11}$ and $R_{12}$ are each independently a substituted or unsubstituted alkyl group.

According to an exemplary embodiment of the present invention, $R_{11}$ and $R_{12}$ are each independently an alkyl group having 1 to 6 carbon atoms.

$R_{11}$ and $R_{12}$ are each independently a methyl group.

According to an exemplary embodiment of the present invention, the compound of Chemical Formula 1 may be any one selected from the following compounds.

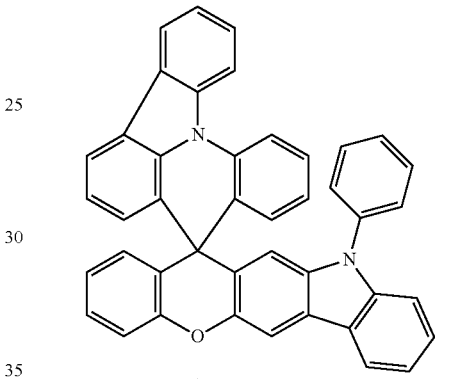

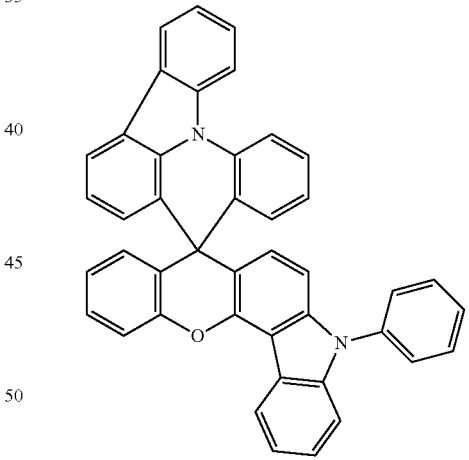

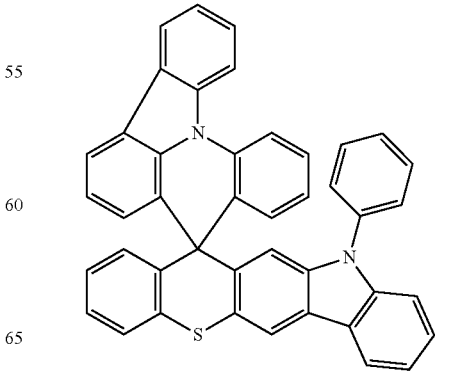

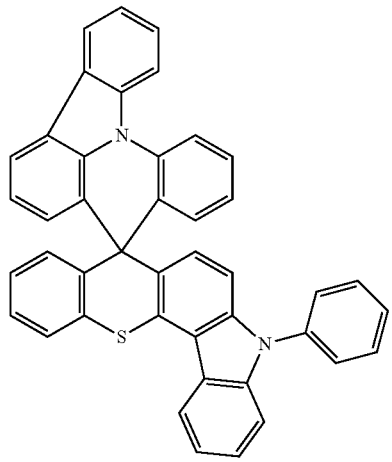
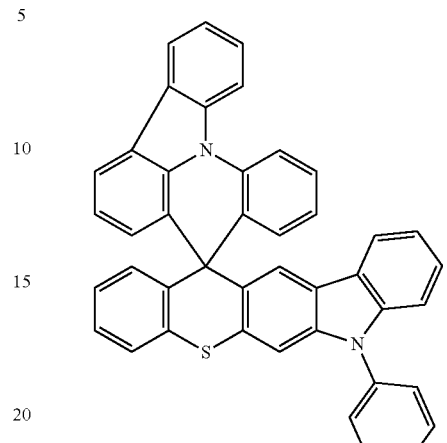
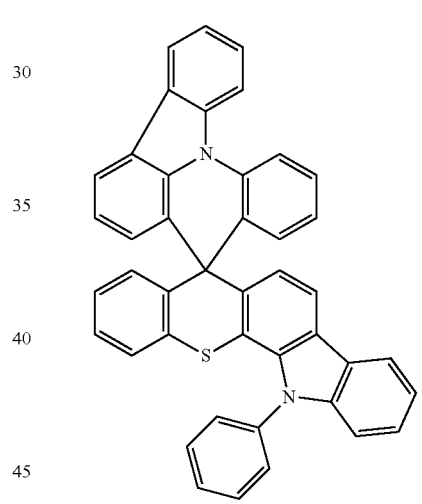
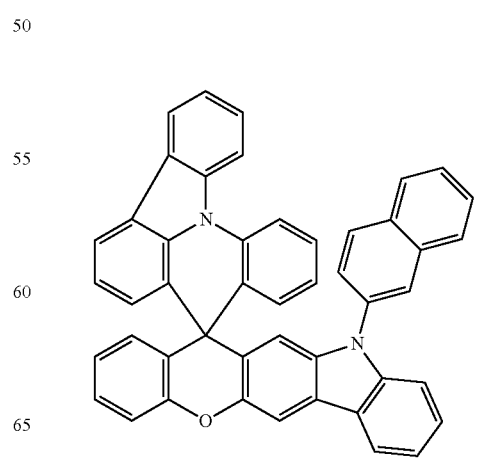
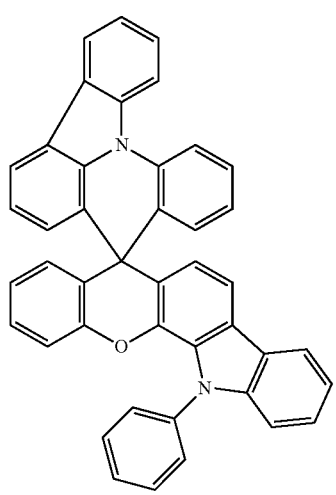

45
-continued
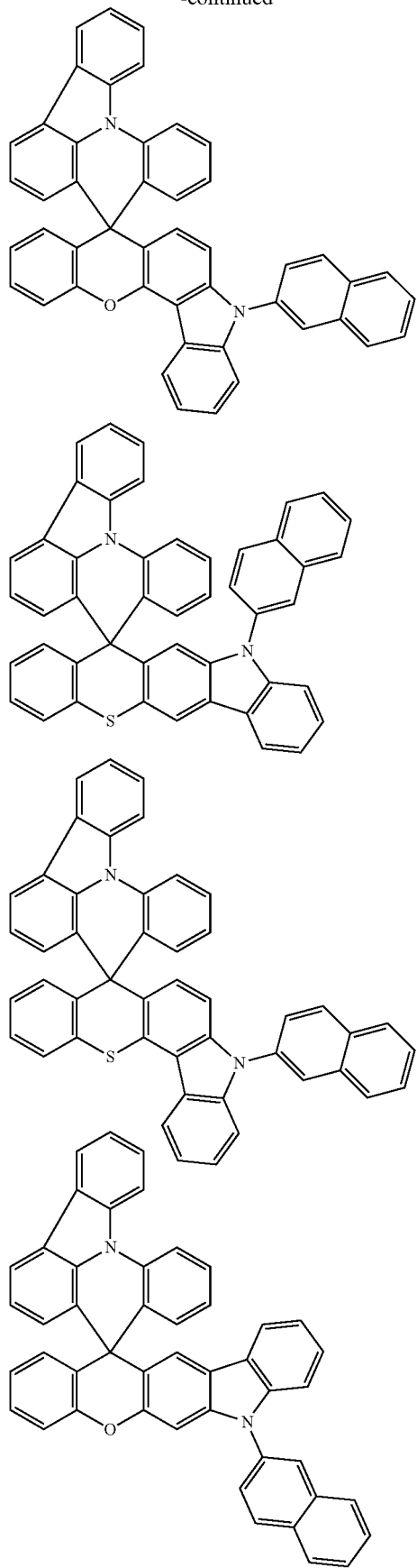
46
-continued
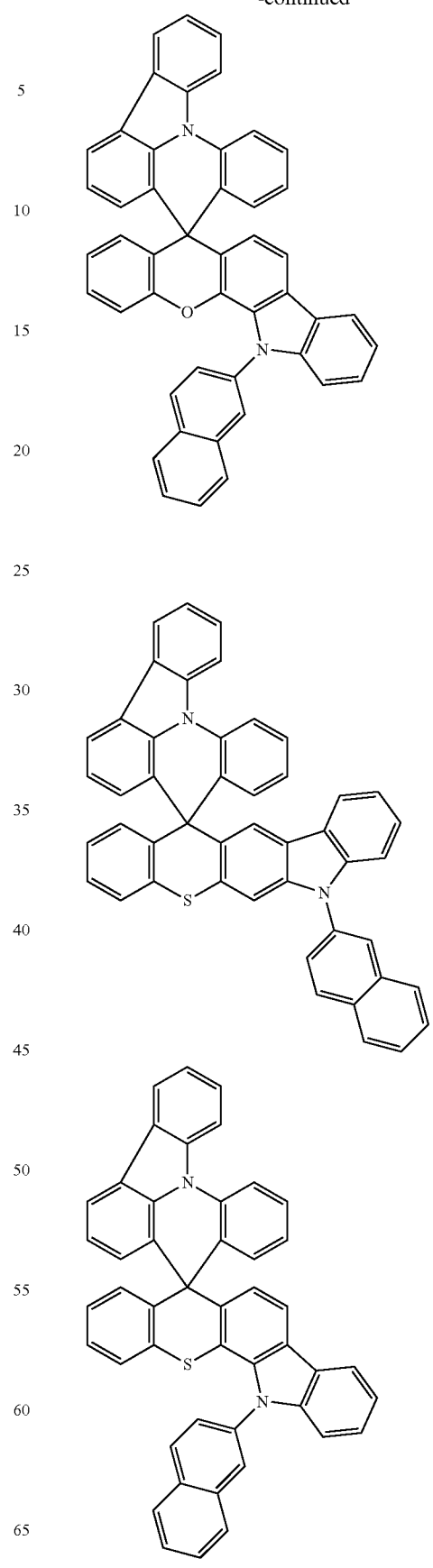

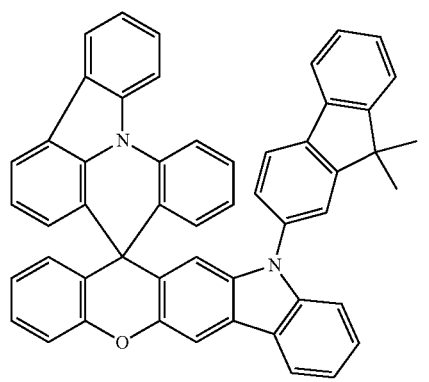
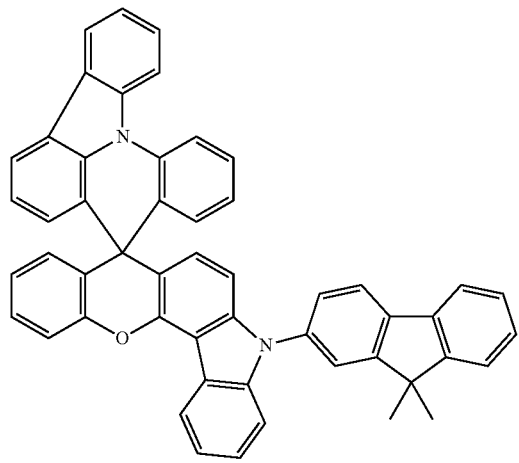
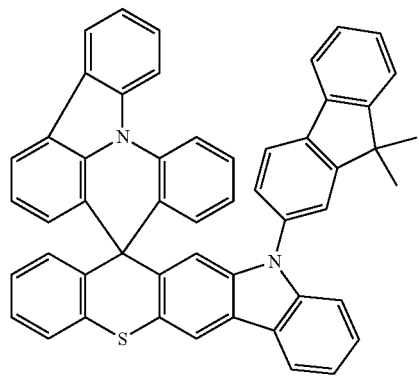
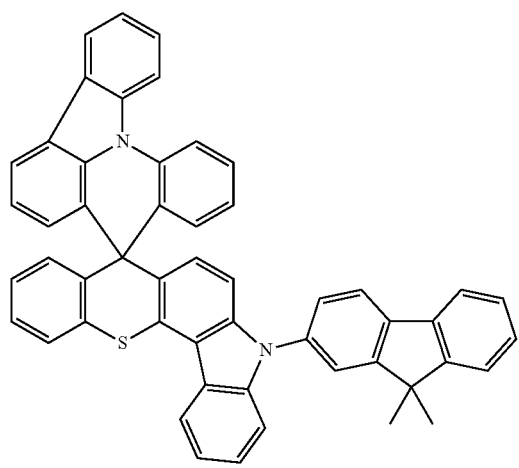
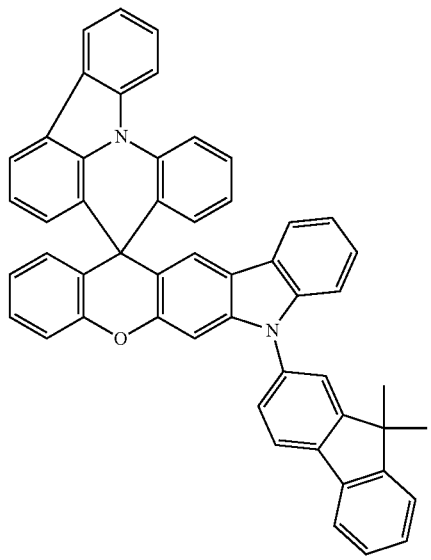
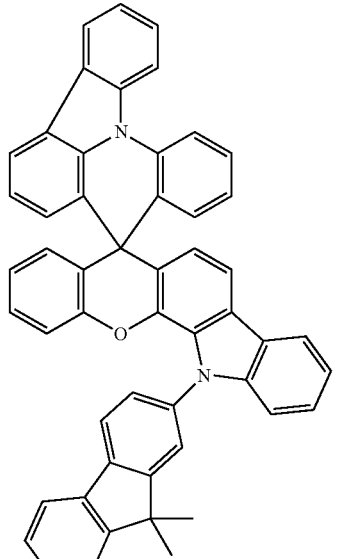
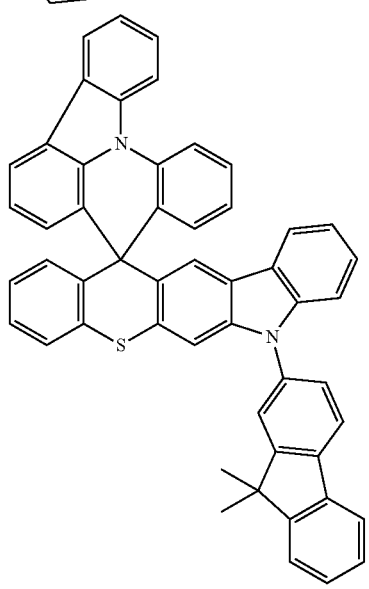

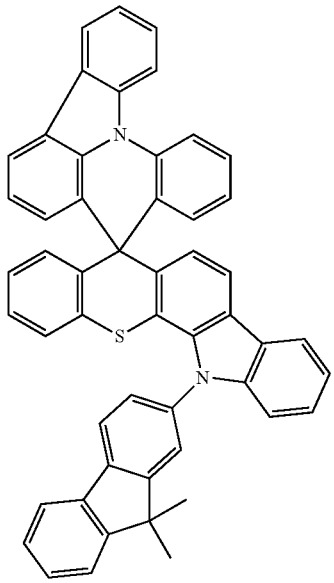
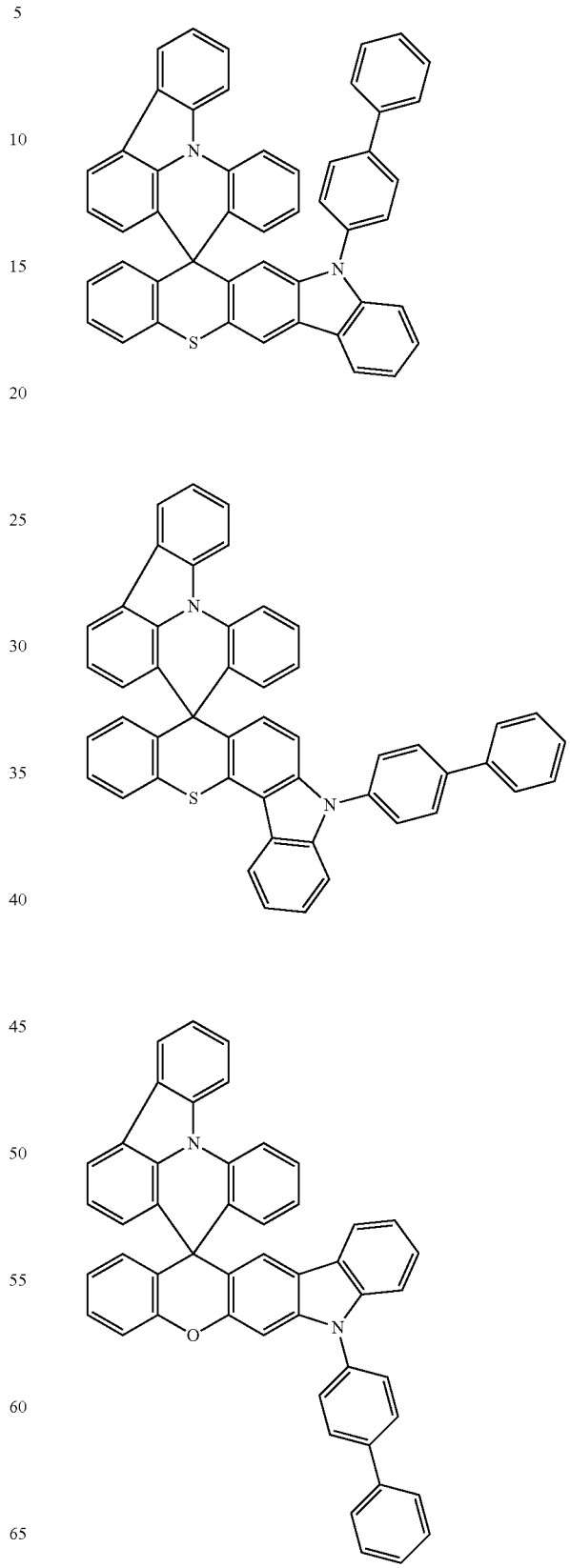

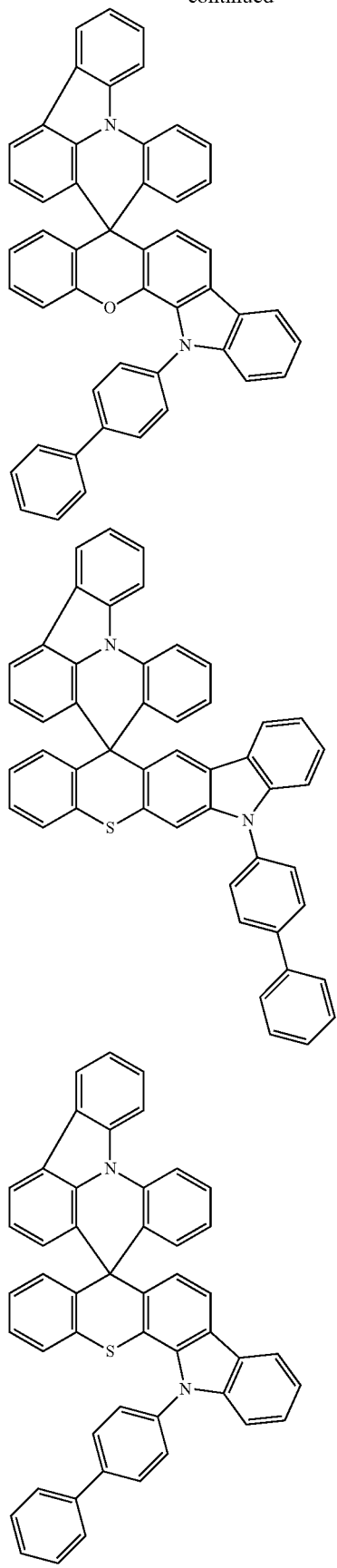
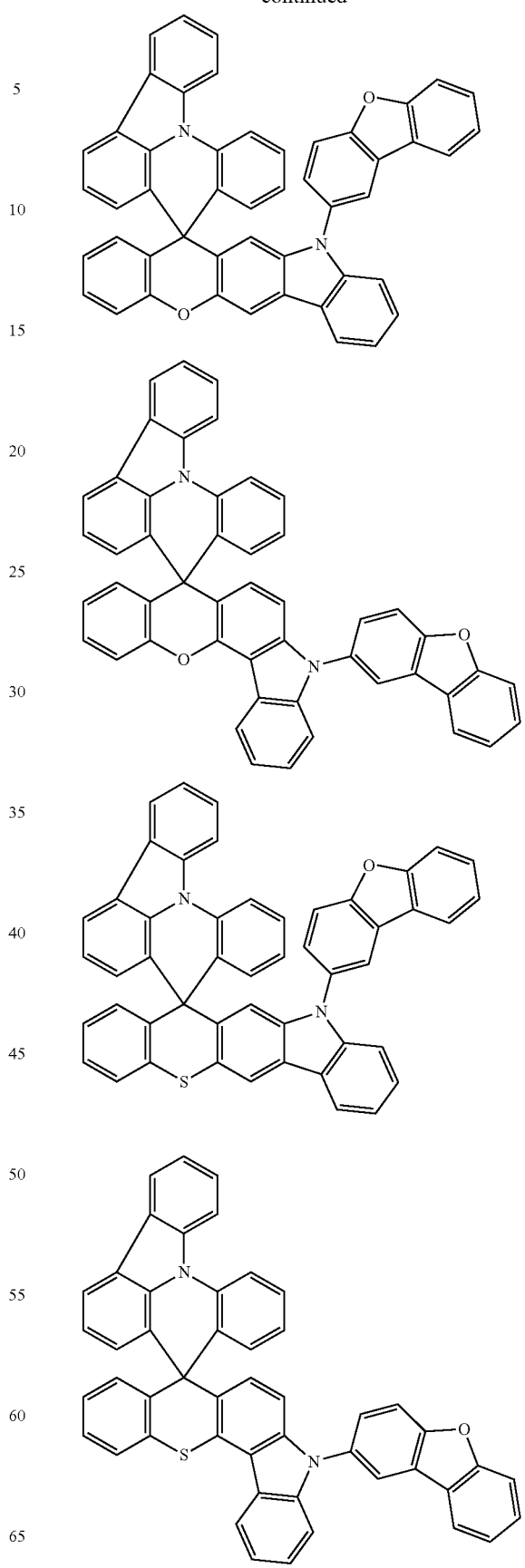

53
-continued
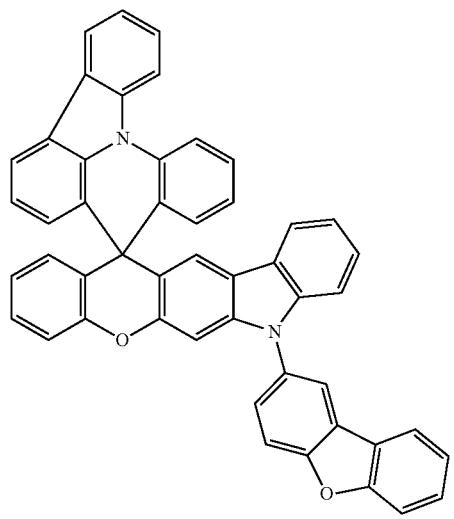
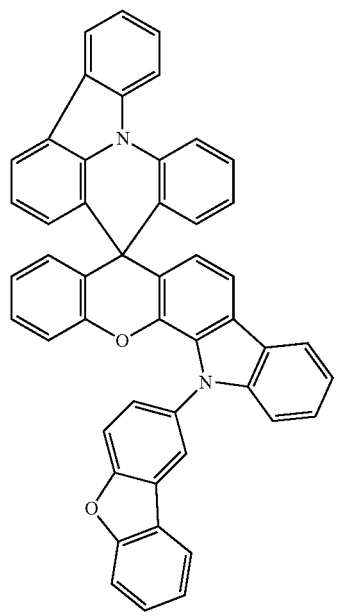
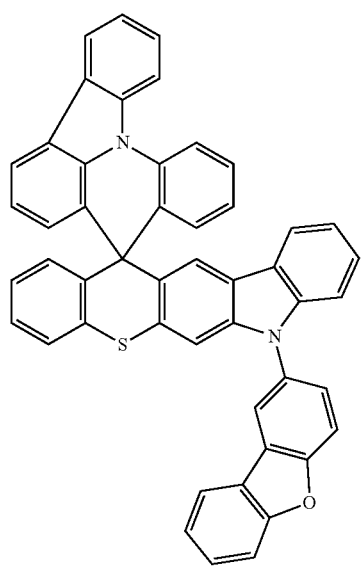
54
-continued
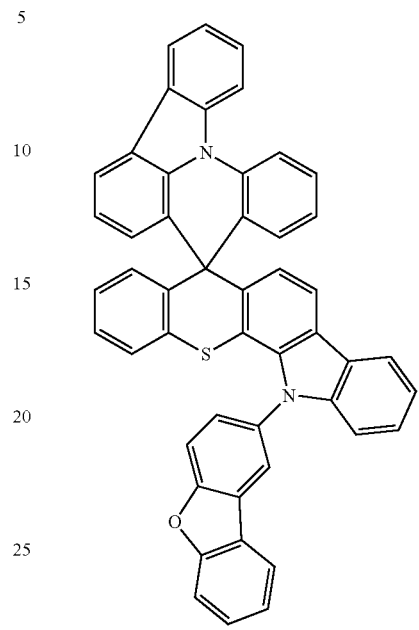
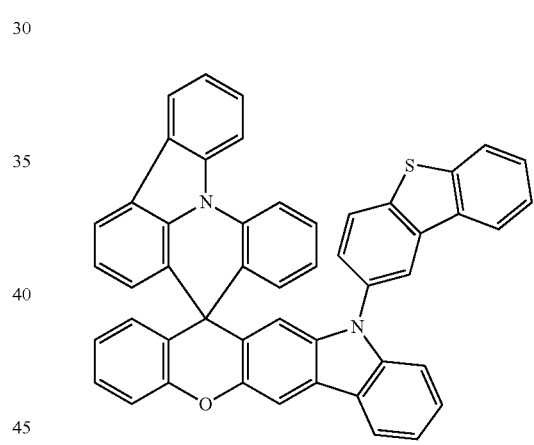
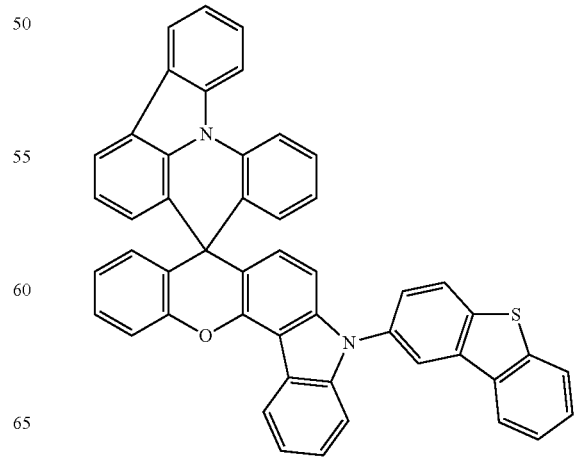

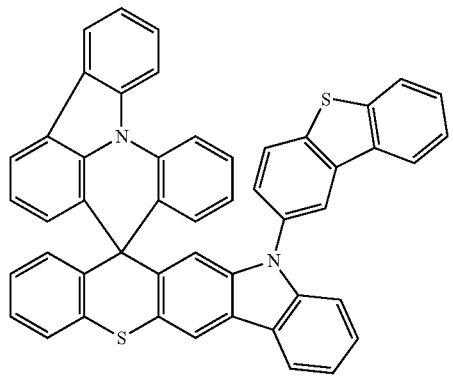
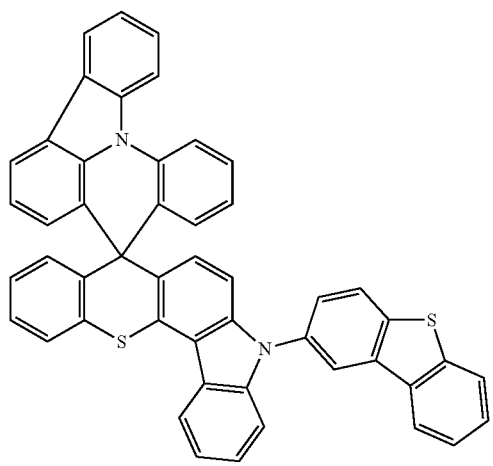
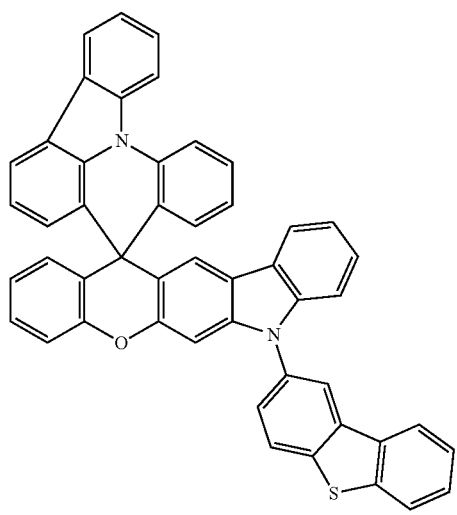
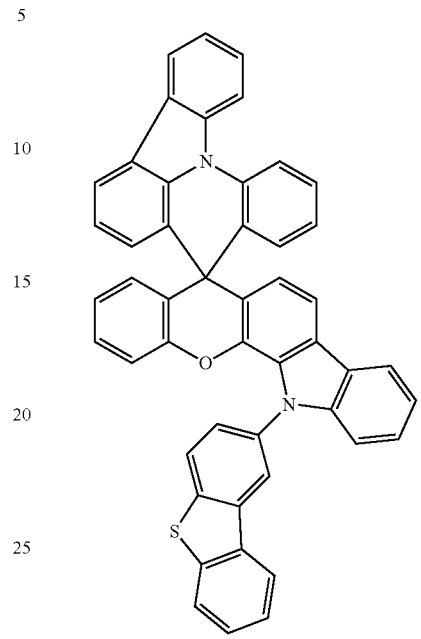
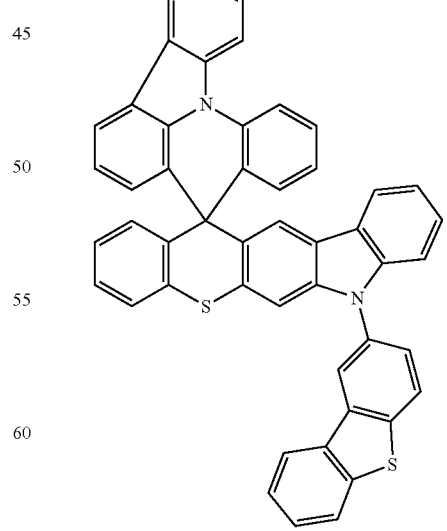

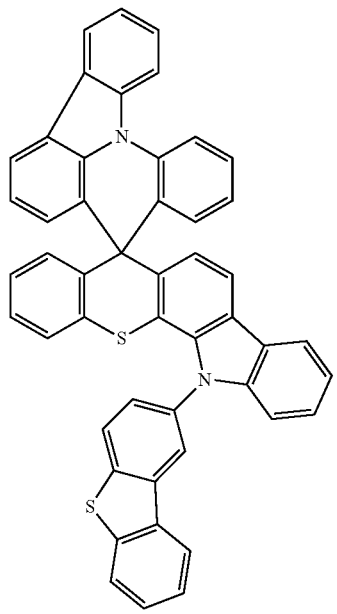
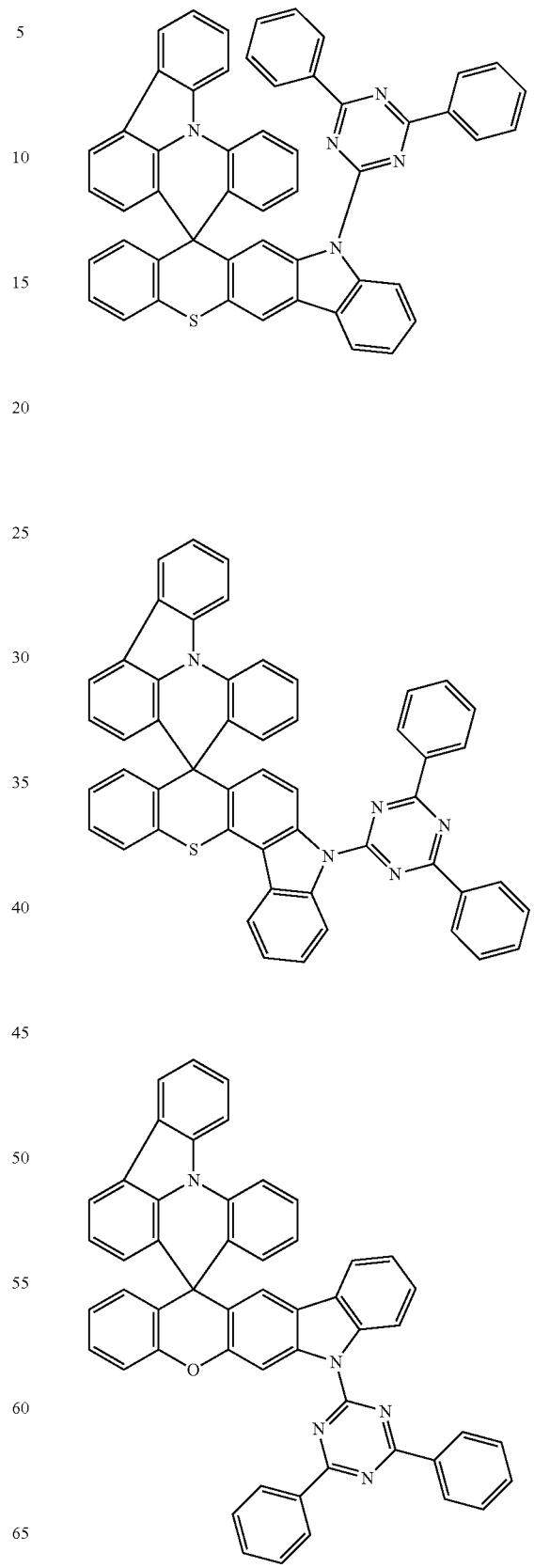

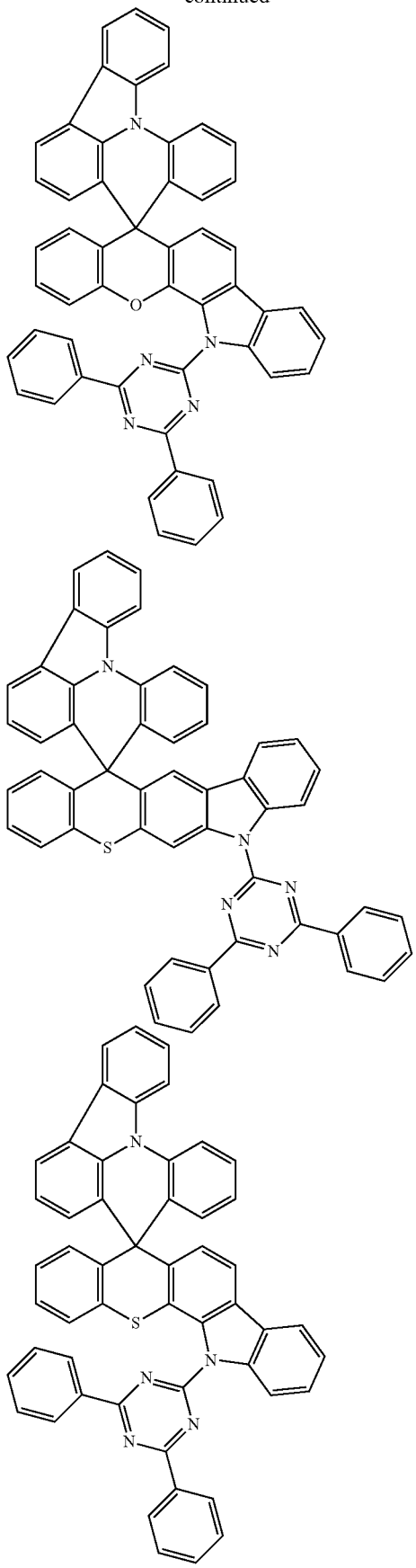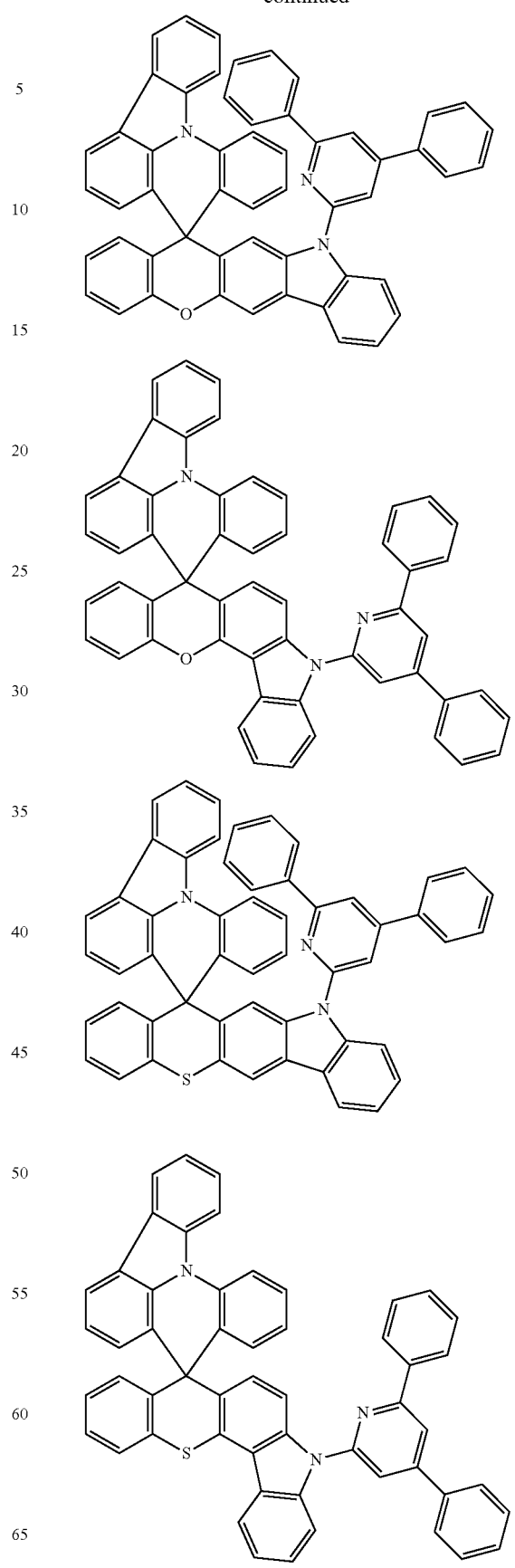

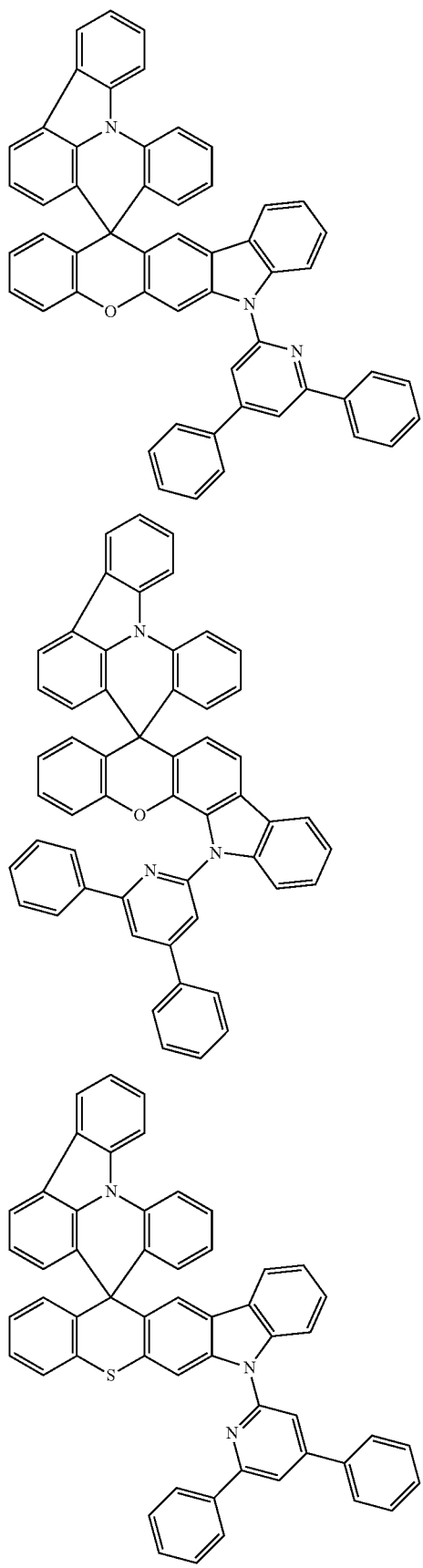
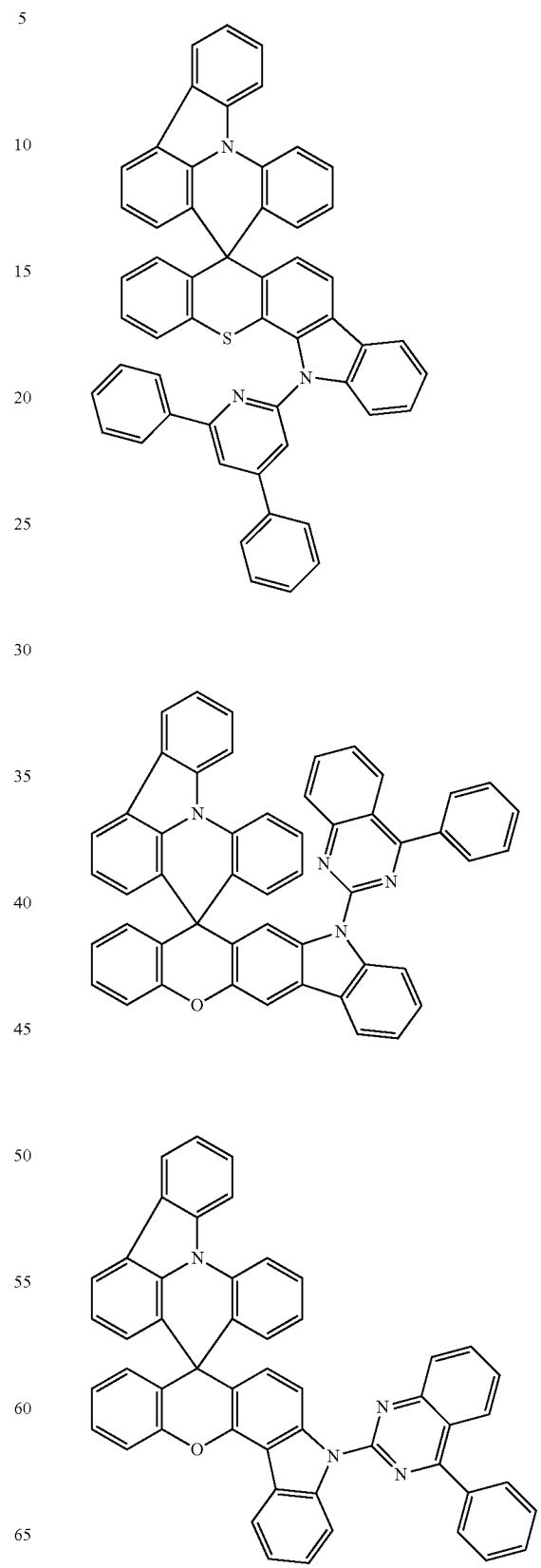

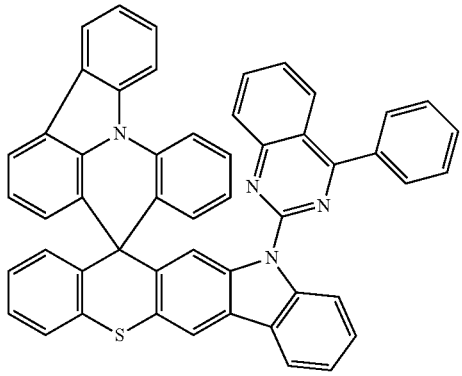
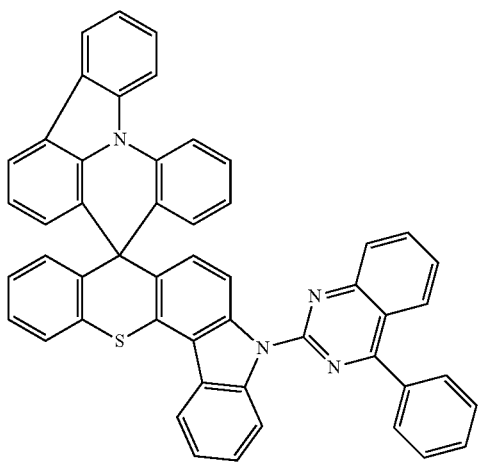
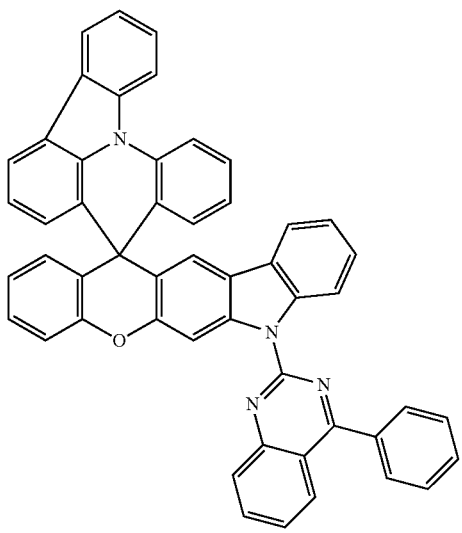
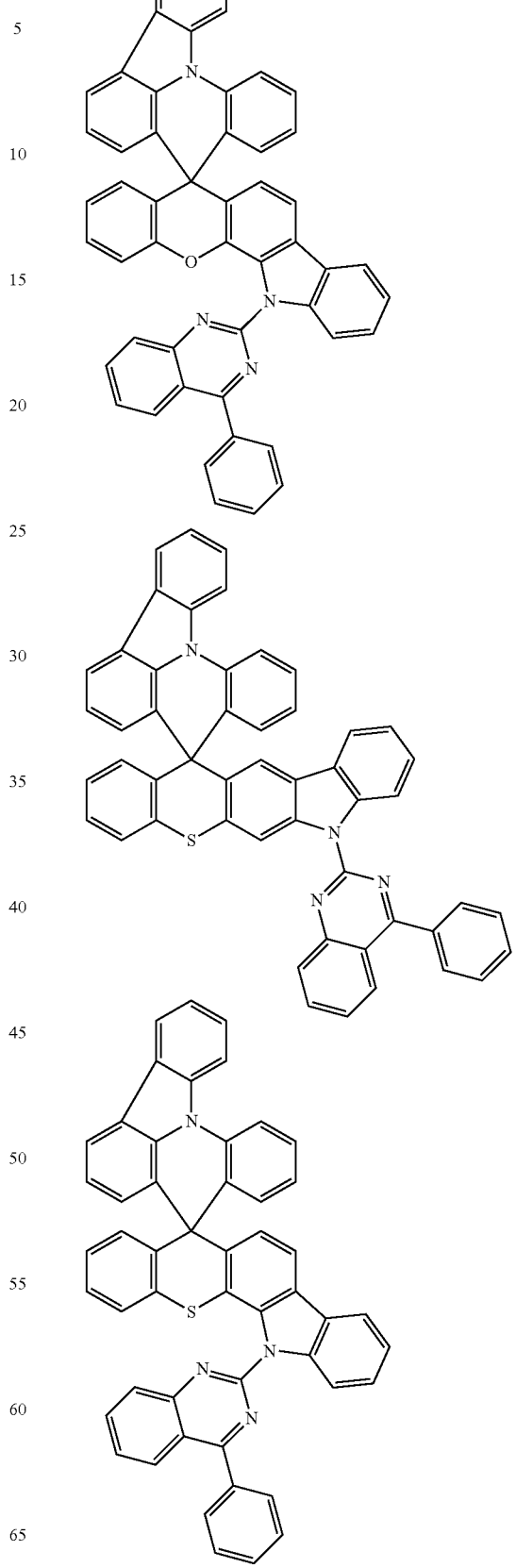

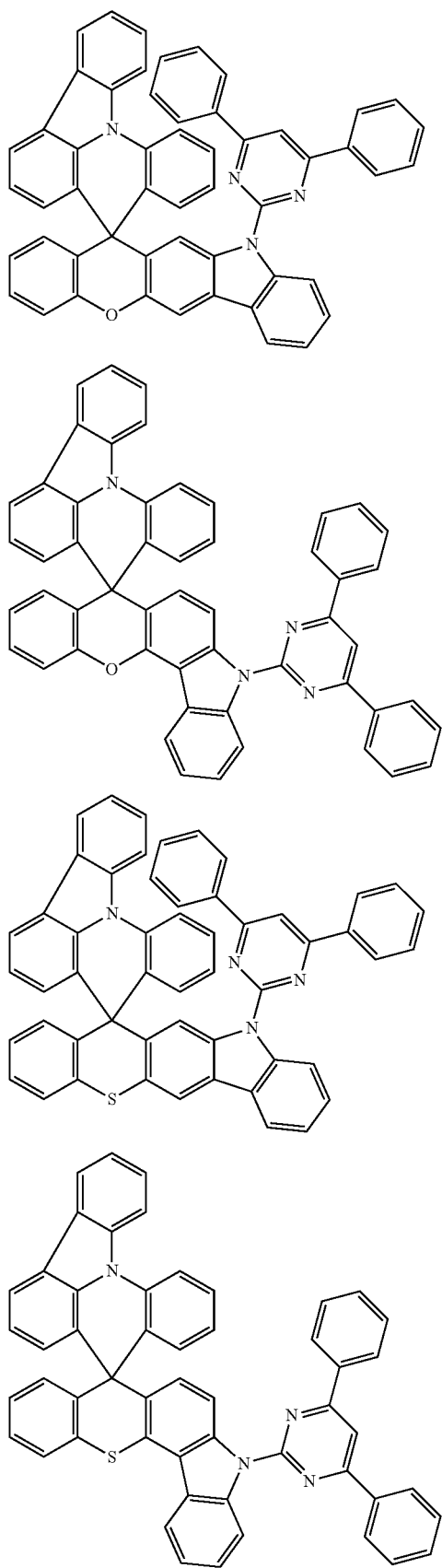 [SMILES: c1ccc(-c2cc(-n3c4ccccc4c4cc5c(cc43)C3(c4ccccc4O5)c4ccccc4-n4c5ccccc5c5cccc3c54)cc(-c3ccccc3)n2)cc1 ; c1ccc(-c2cc(-n3c4ccccc4c4c5c(ccc43)C3(c4ccccc4O5)c4ccccc4-n4c5ccccc5c5cccc3c54)cc(-c3ccccc3)n2)cc1 ; c1ccc(-c2cc(-n3c4ccccc4c4cc5c(cc43)C3(c4ccccc4S5)c4ccccc4-n4c5ccccc5c5cccc3c54)cc(-c3ccccc3)n2)cc1 ; c1ccc(-c2cc(-n3c4ccccc4c4c5c(ccc43)C3(c4ccccc4S5)c4ccccc4-n4c5ccccc5c5cccc3c54)cc(-c3ccccc3)n2)cc1]
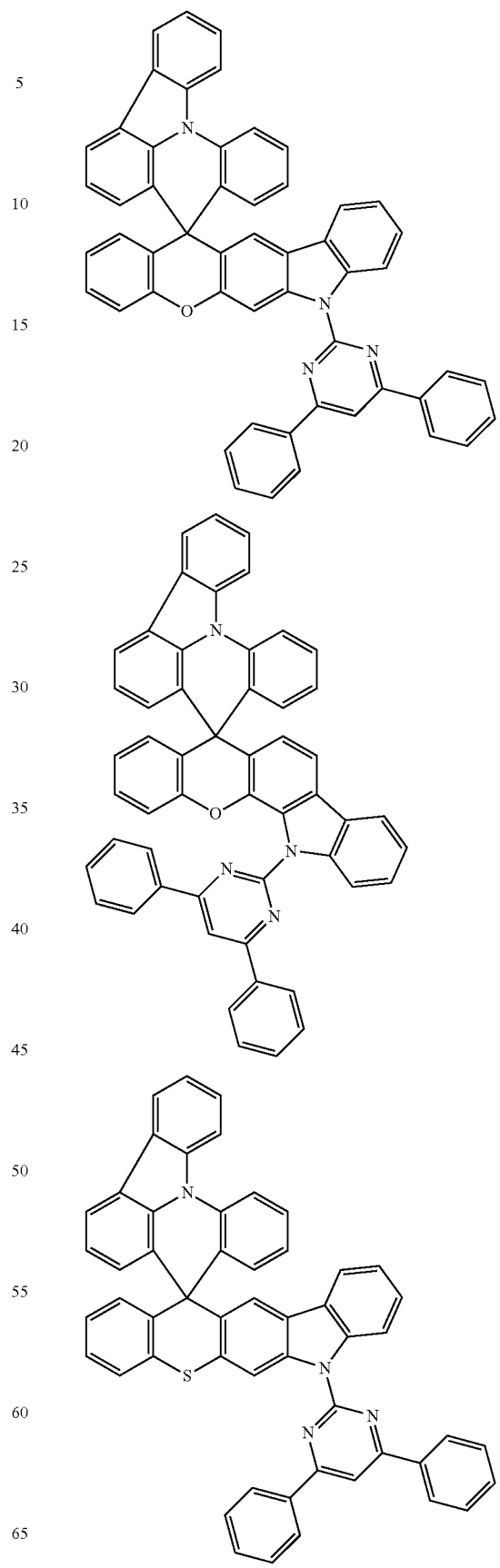

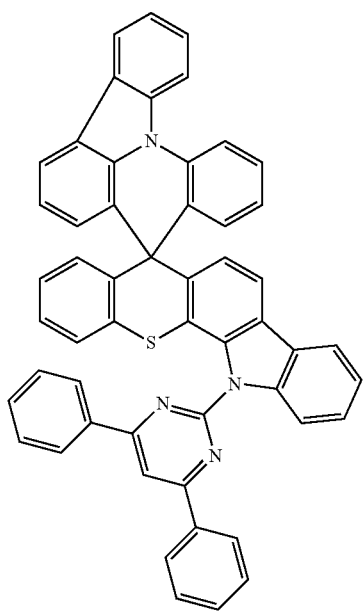
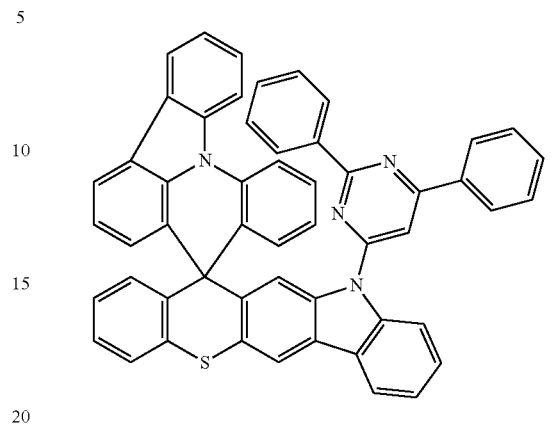
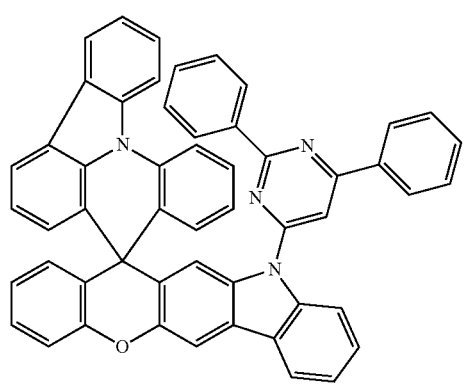
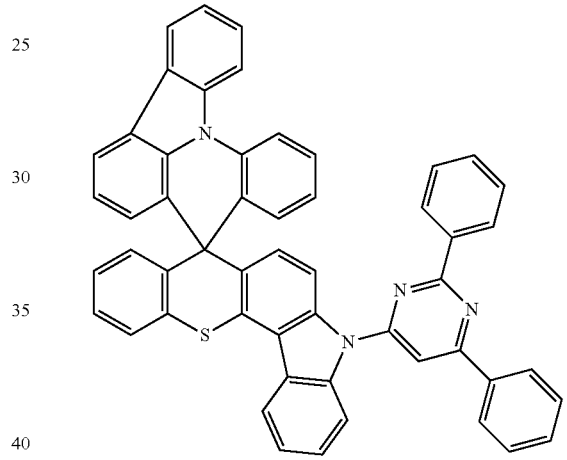
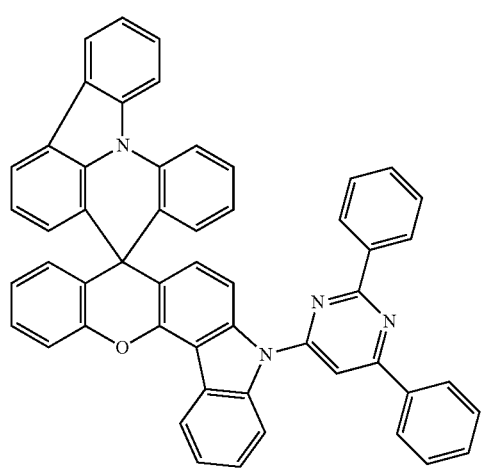
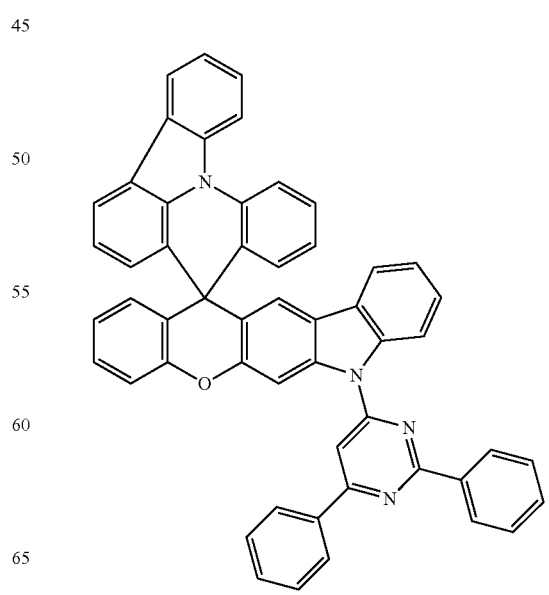

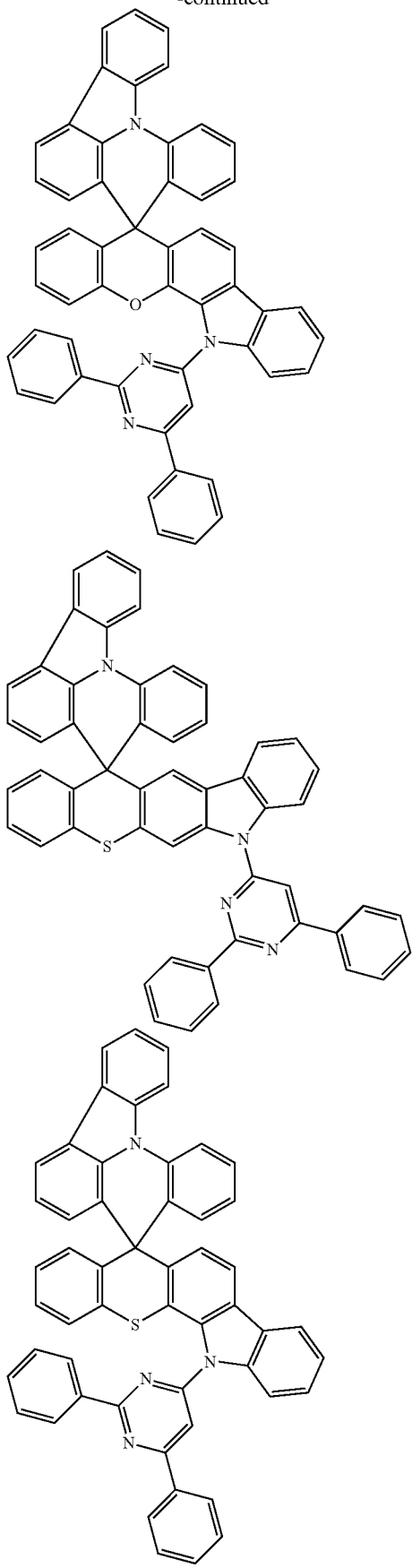
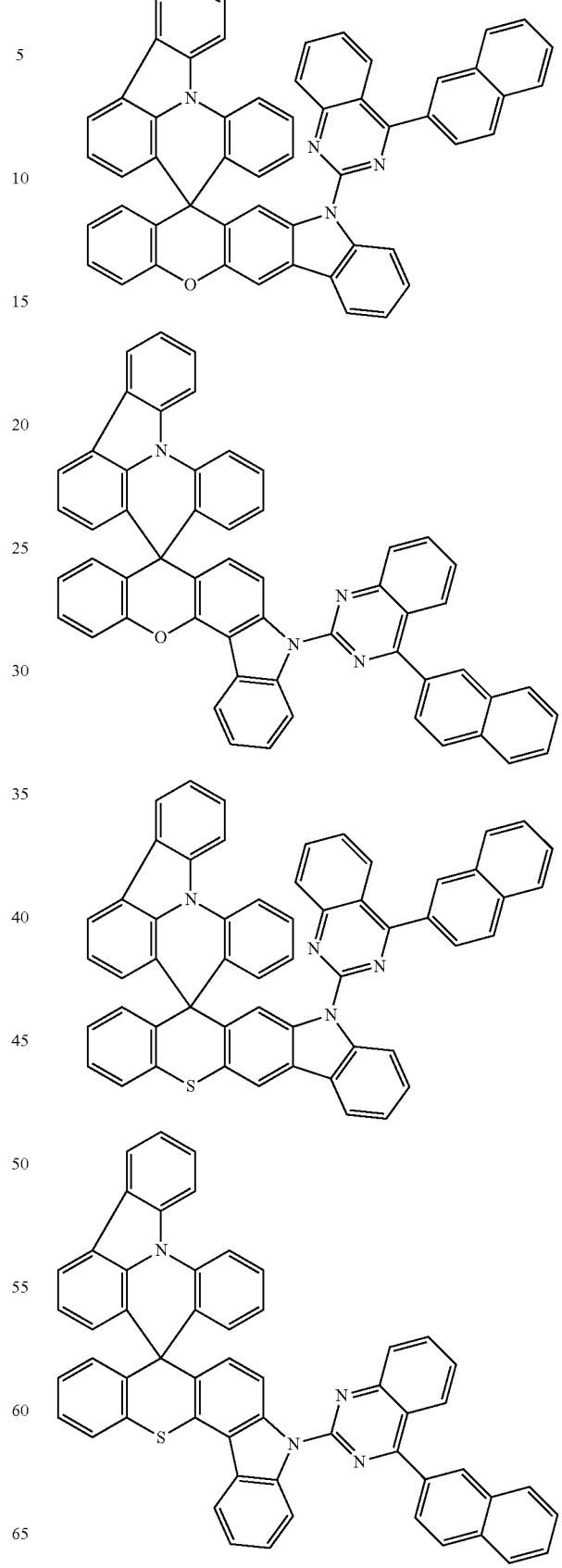

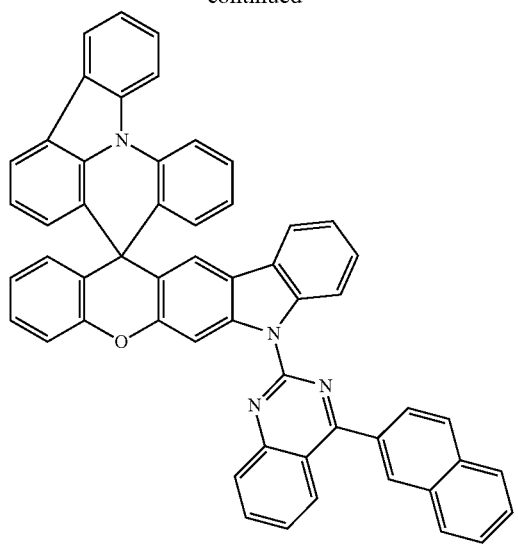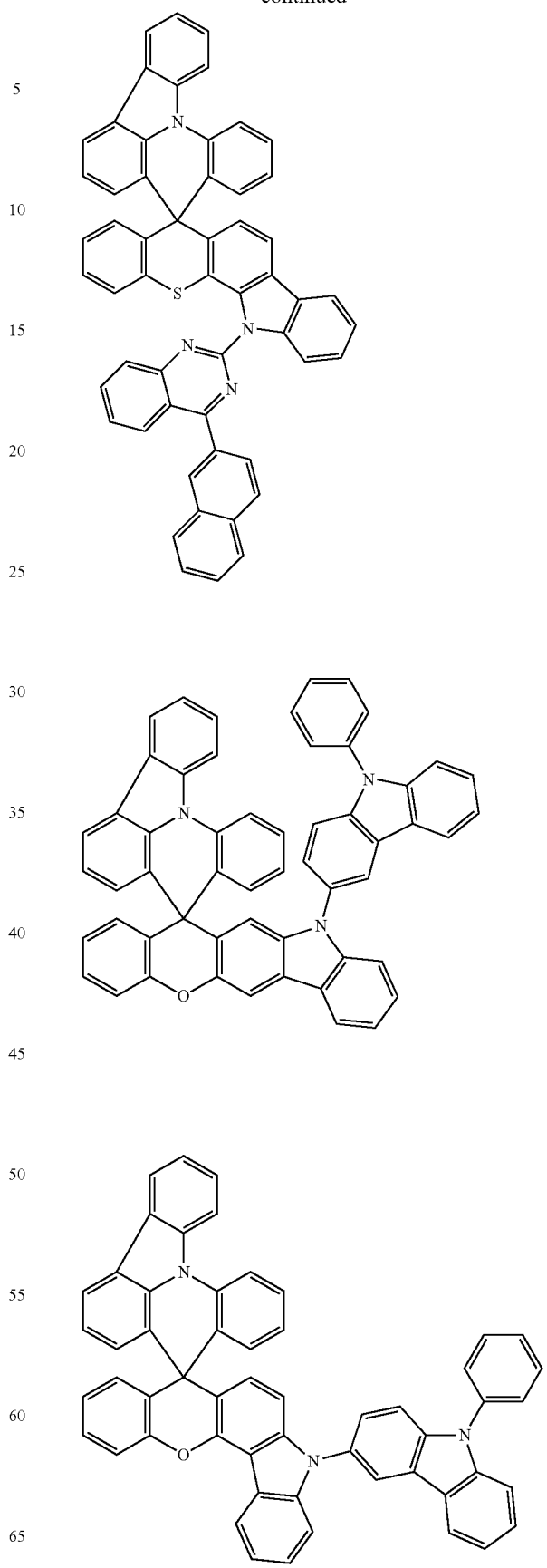

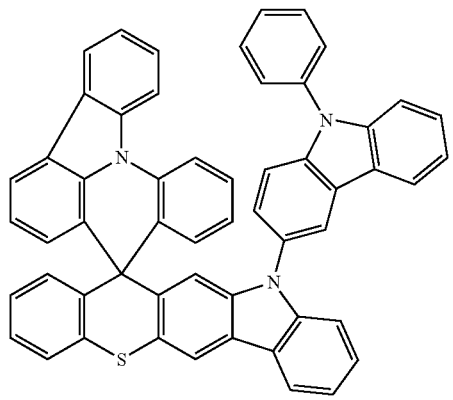
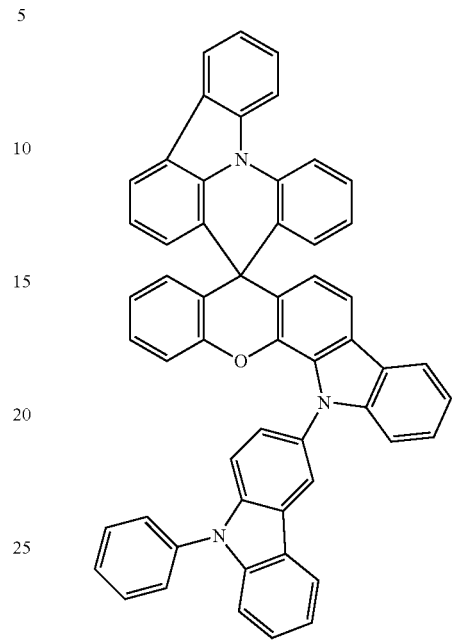
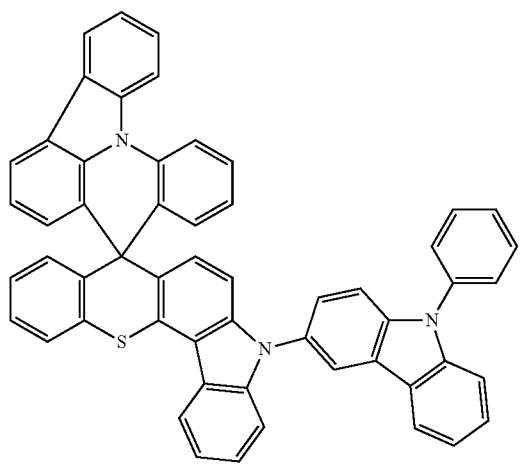
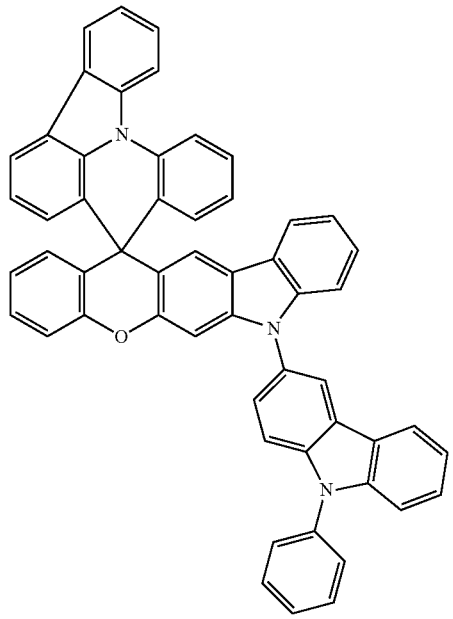
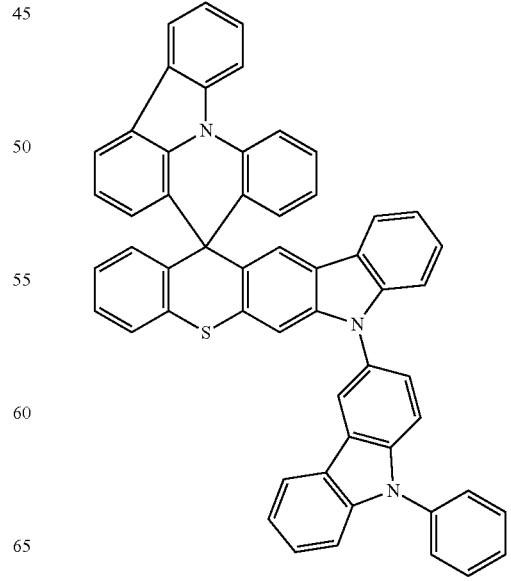

75
-continued
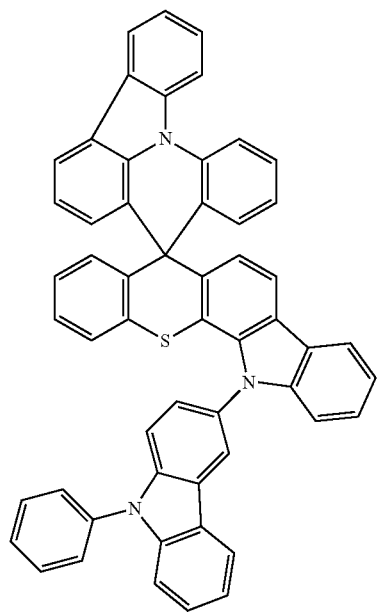
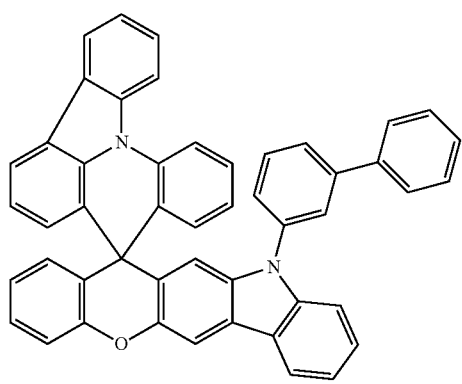
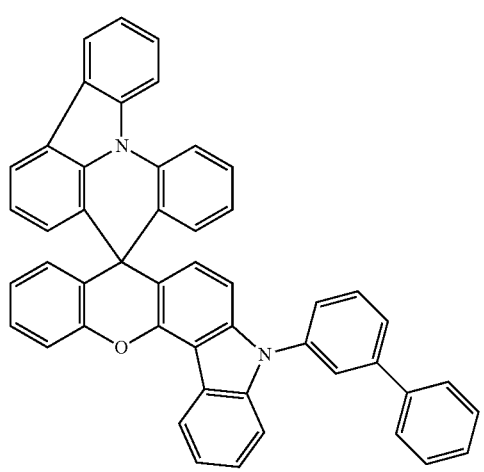
76
-continued
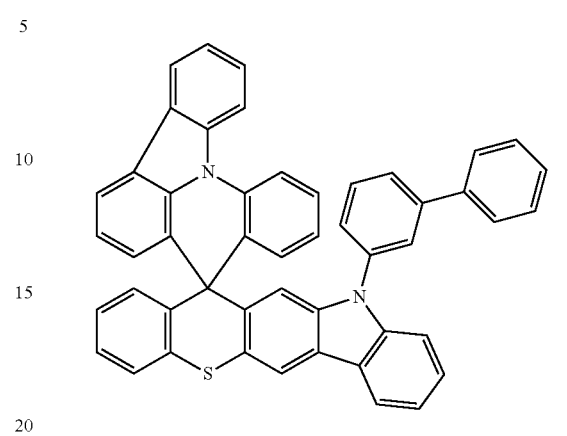

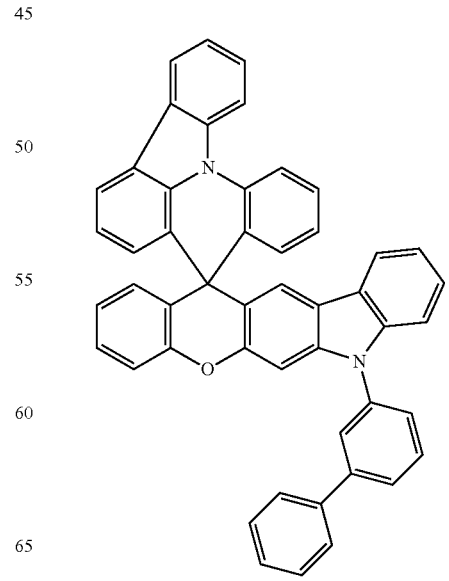

77
-continued
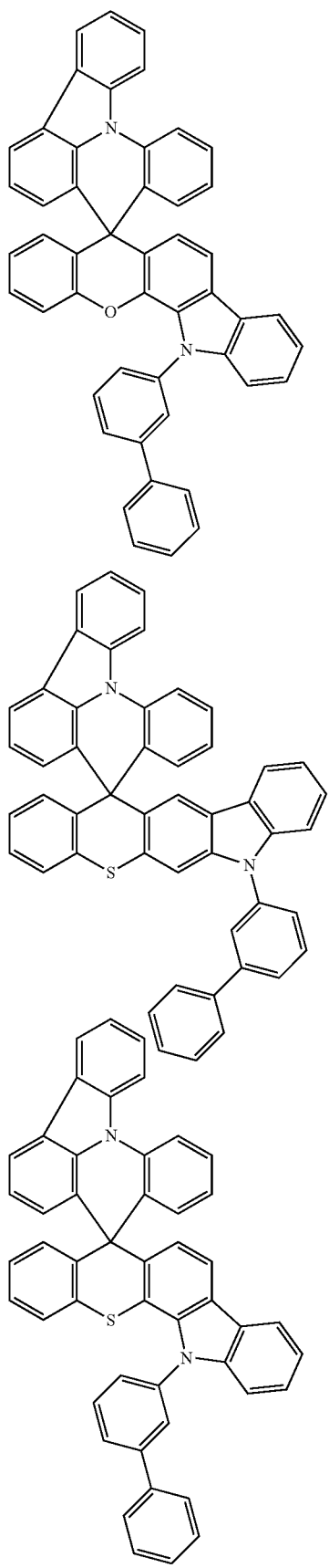
78
-continued
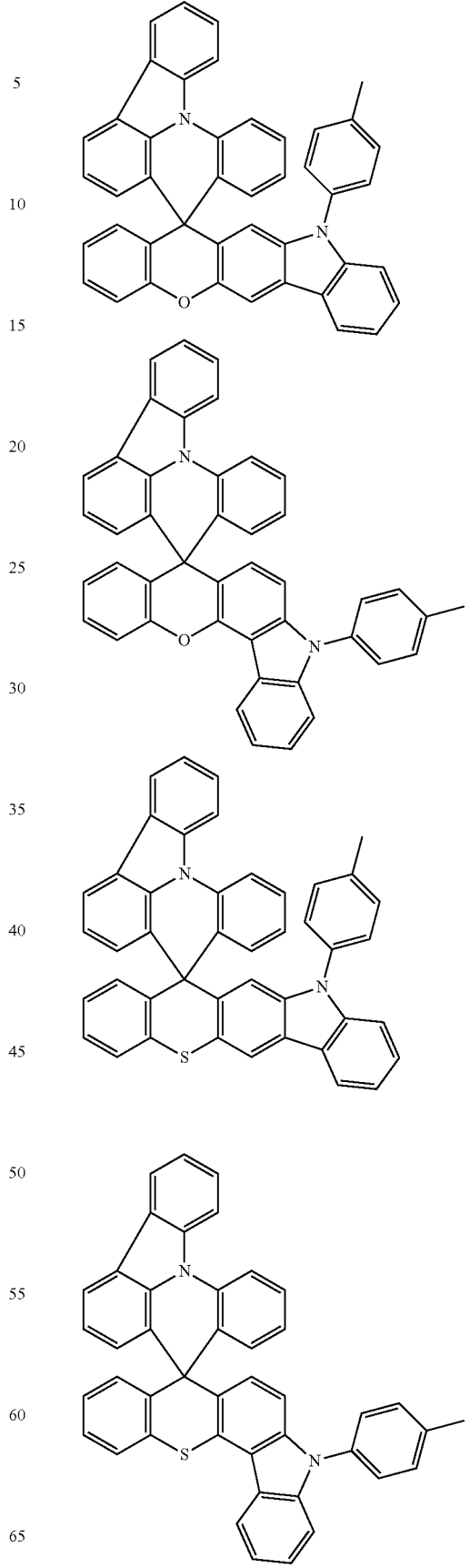

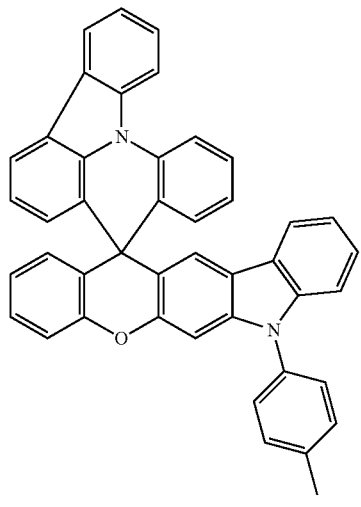
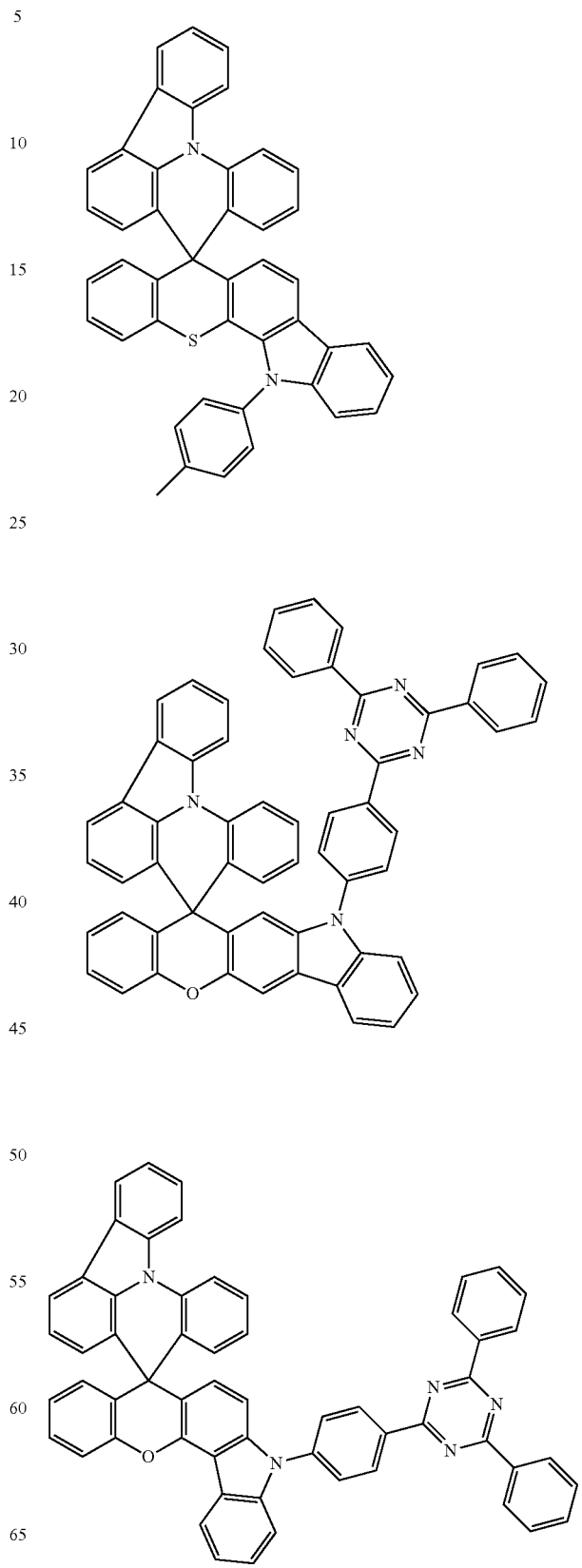

81
-continued
82
-continued
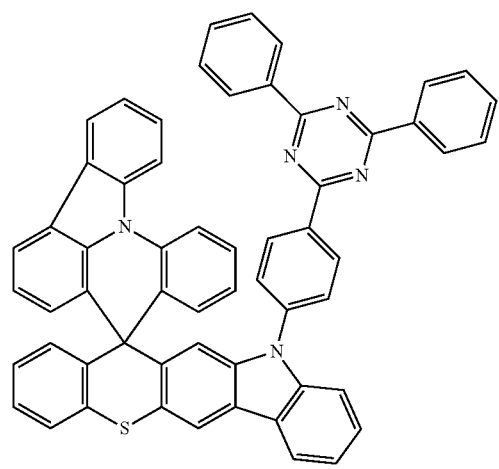
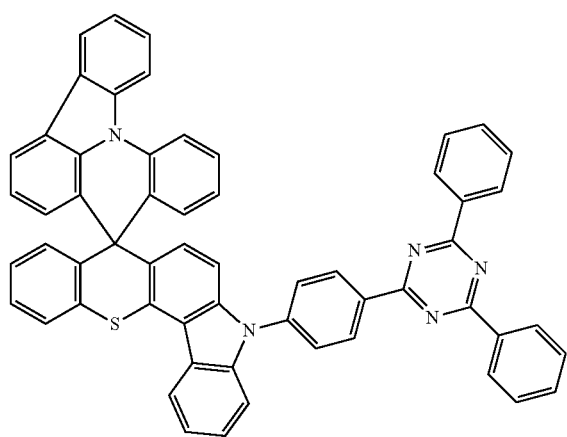
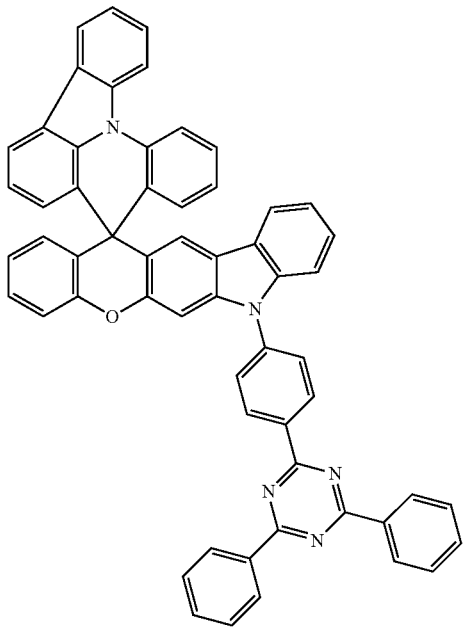
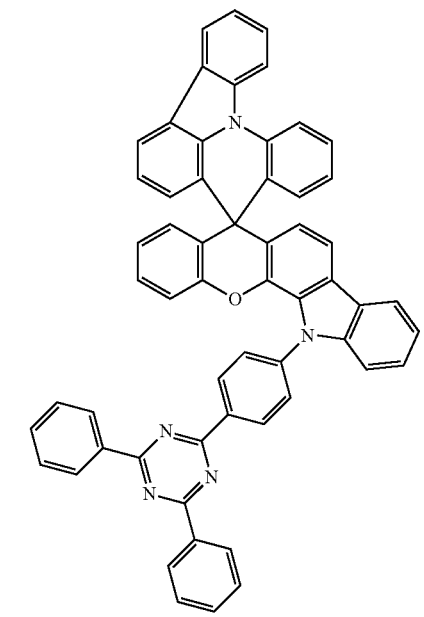
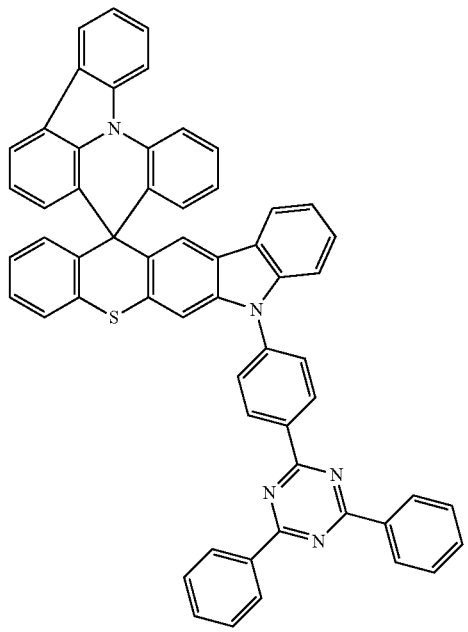

-continued
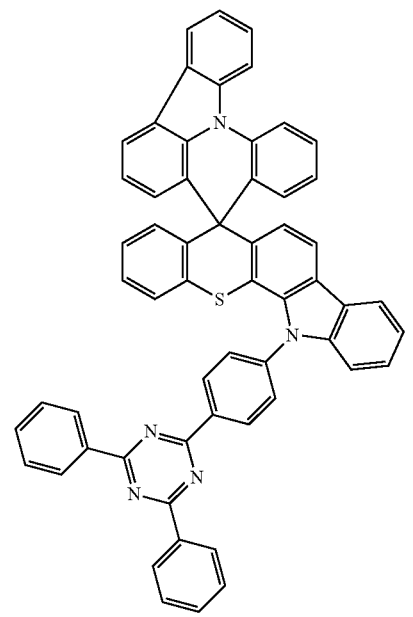
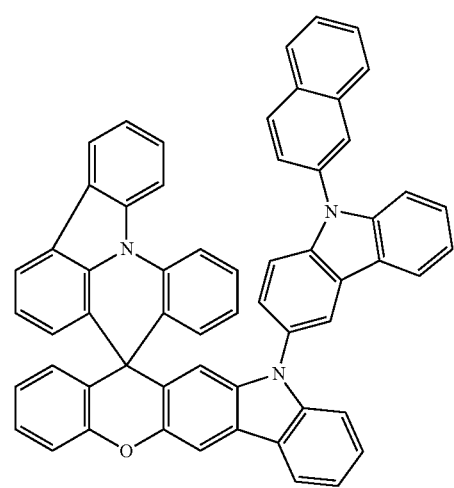
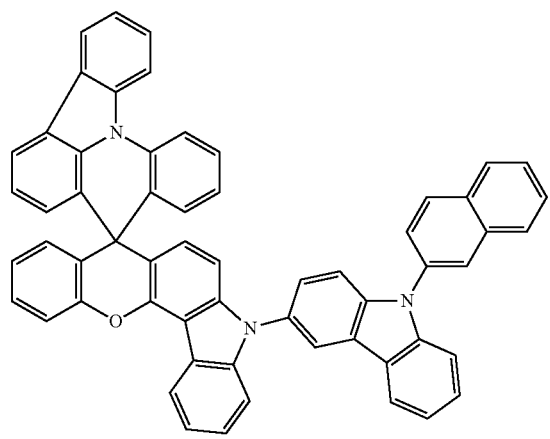
-continued
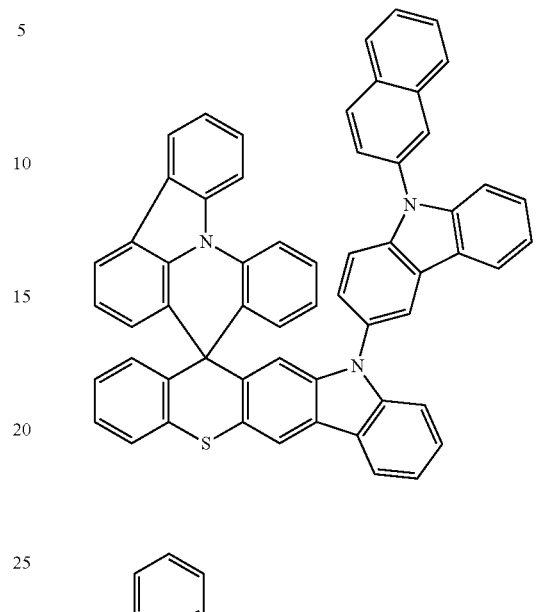
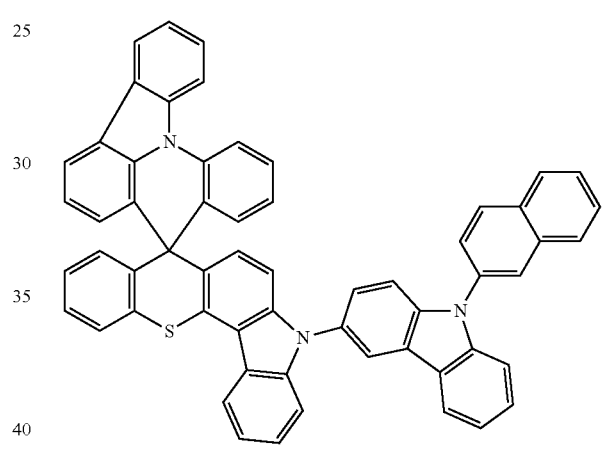
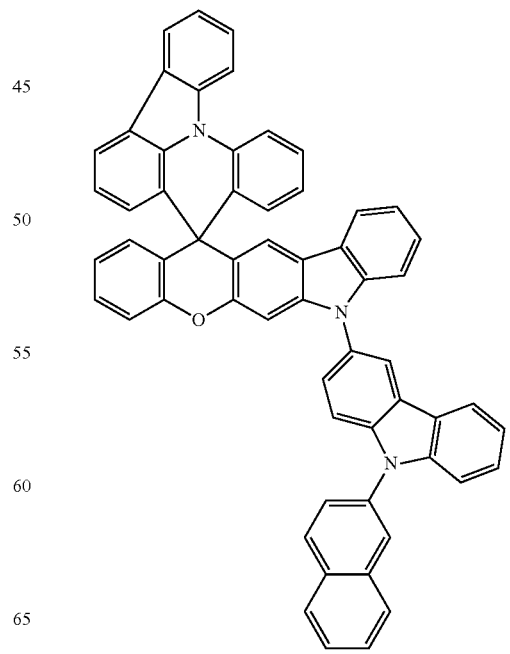

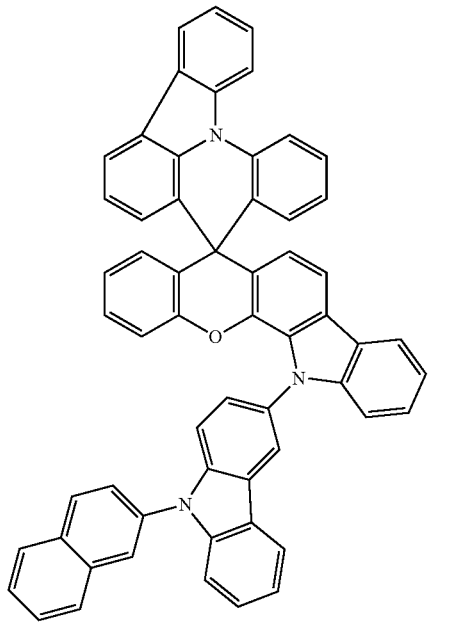
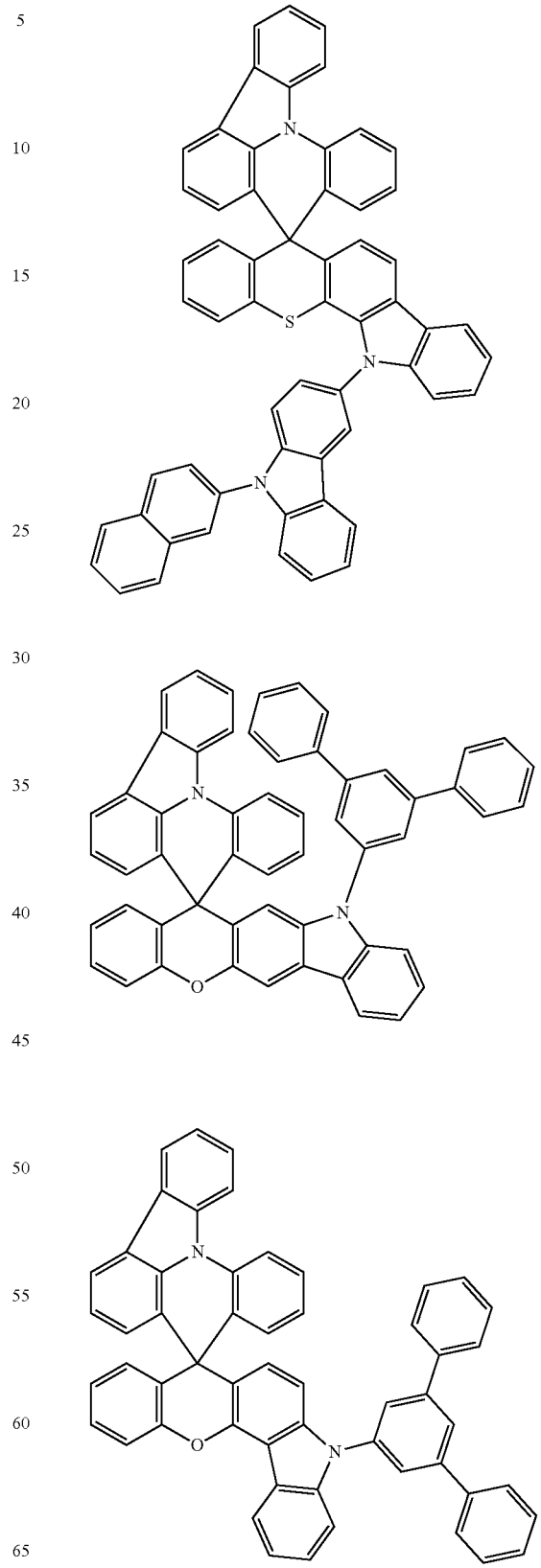

87
-continued
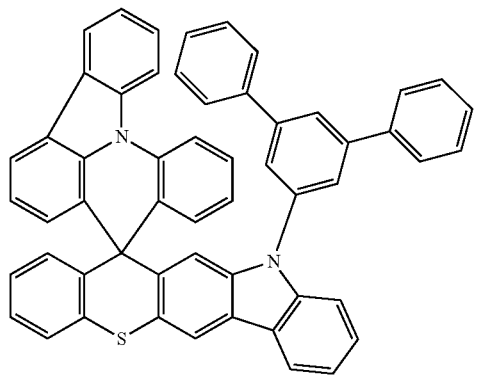
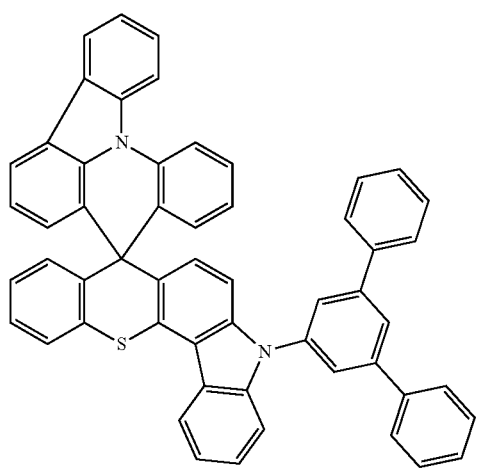
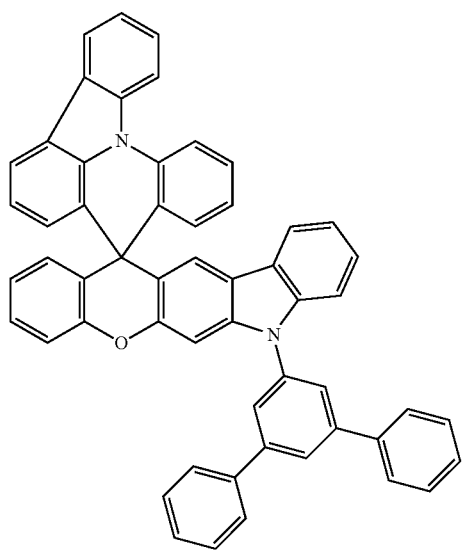
88
-continued
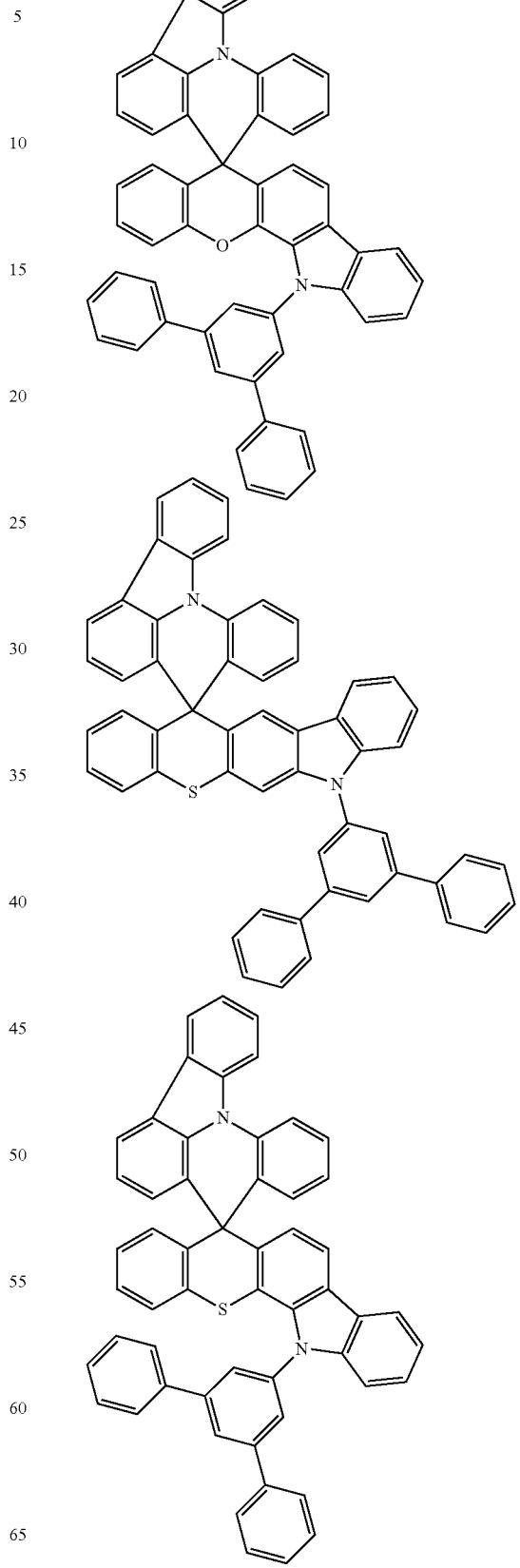

89
-continued
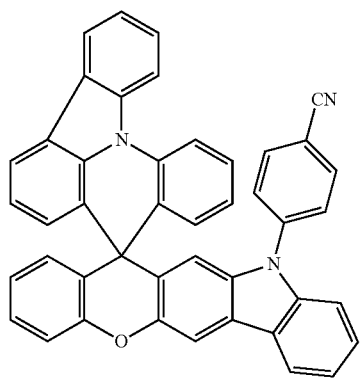
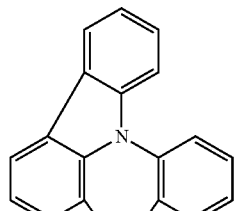
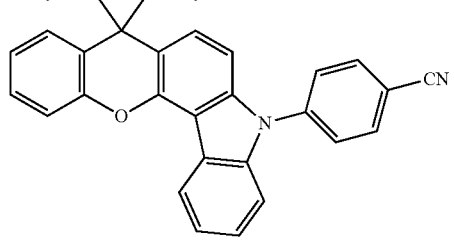
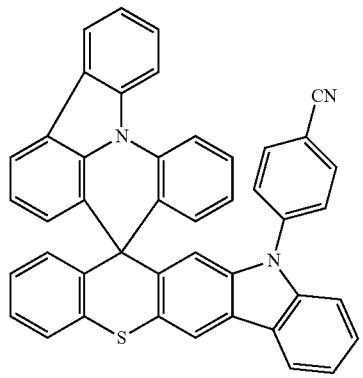
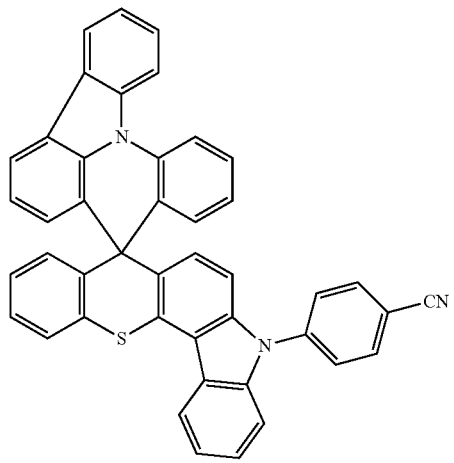
90
-continued
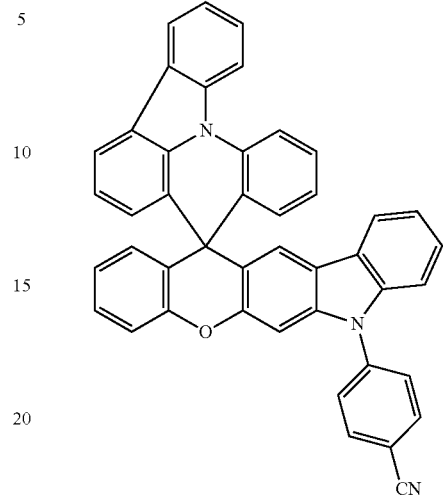
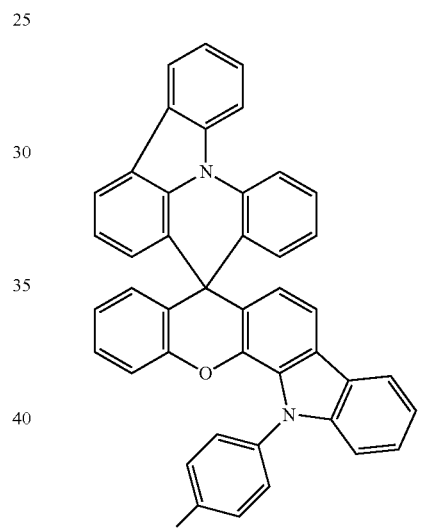
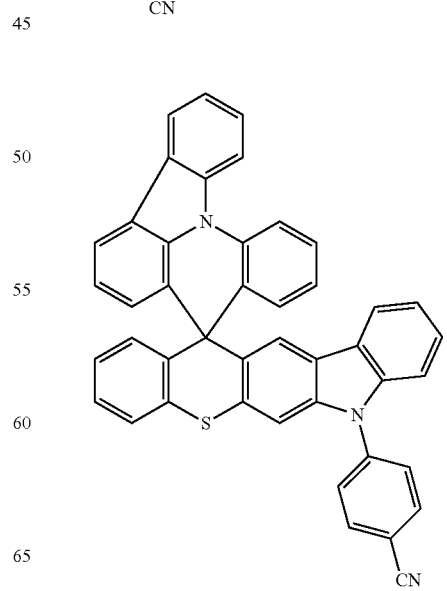

91
-continued
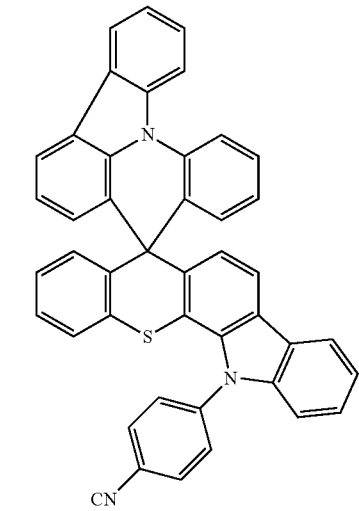
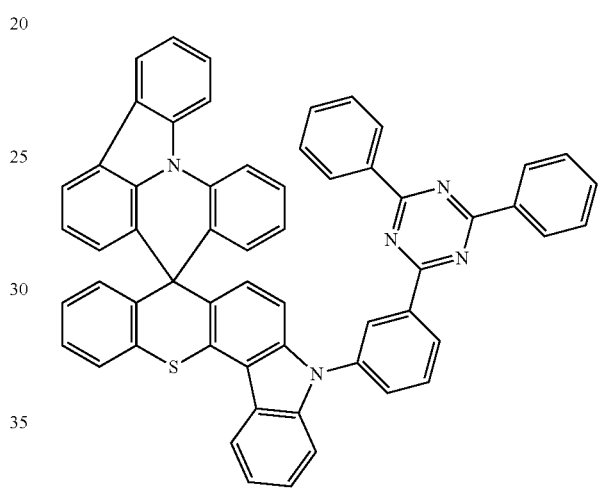
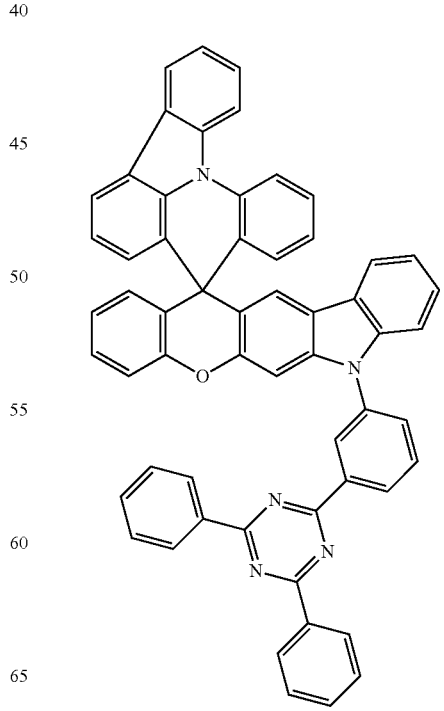
92
-continued
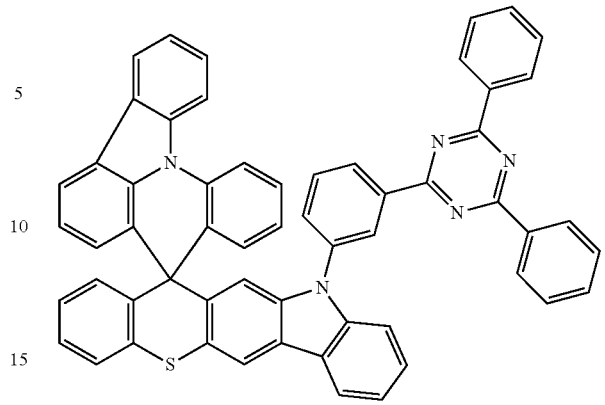

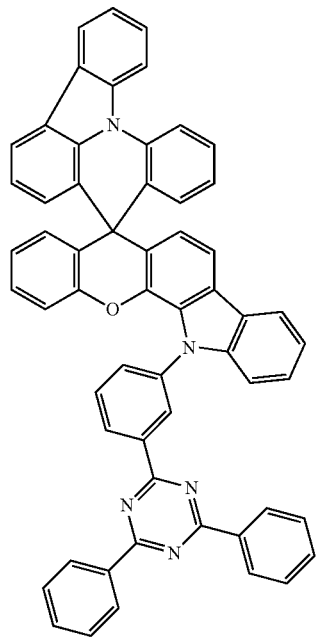
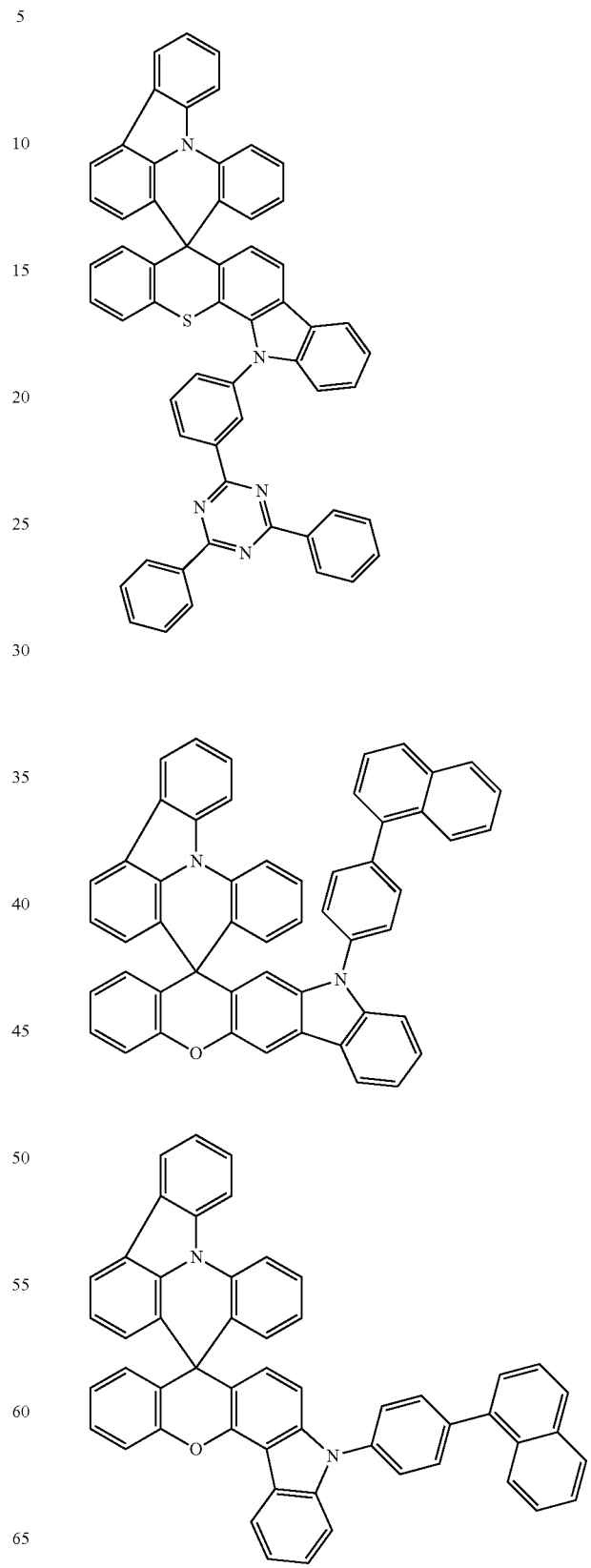

95
-continued
96
-continued
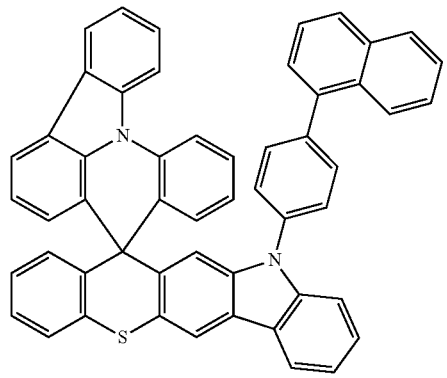
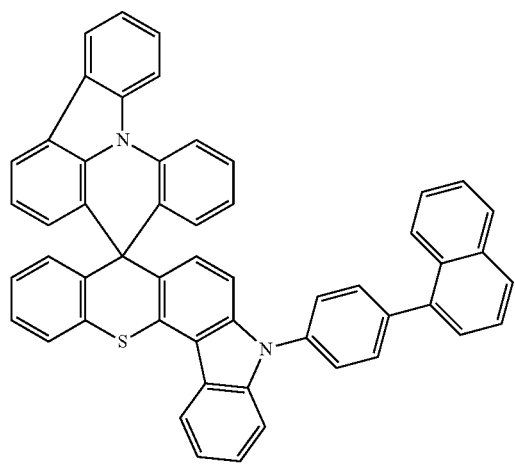
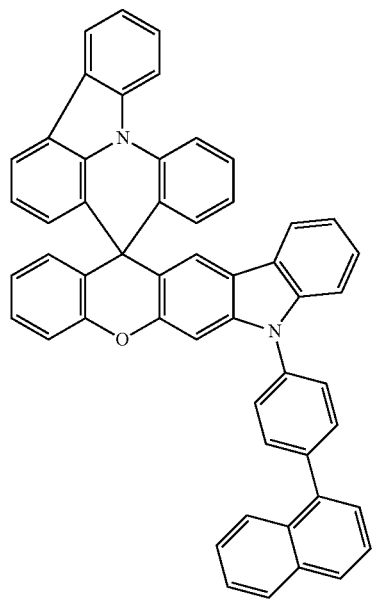
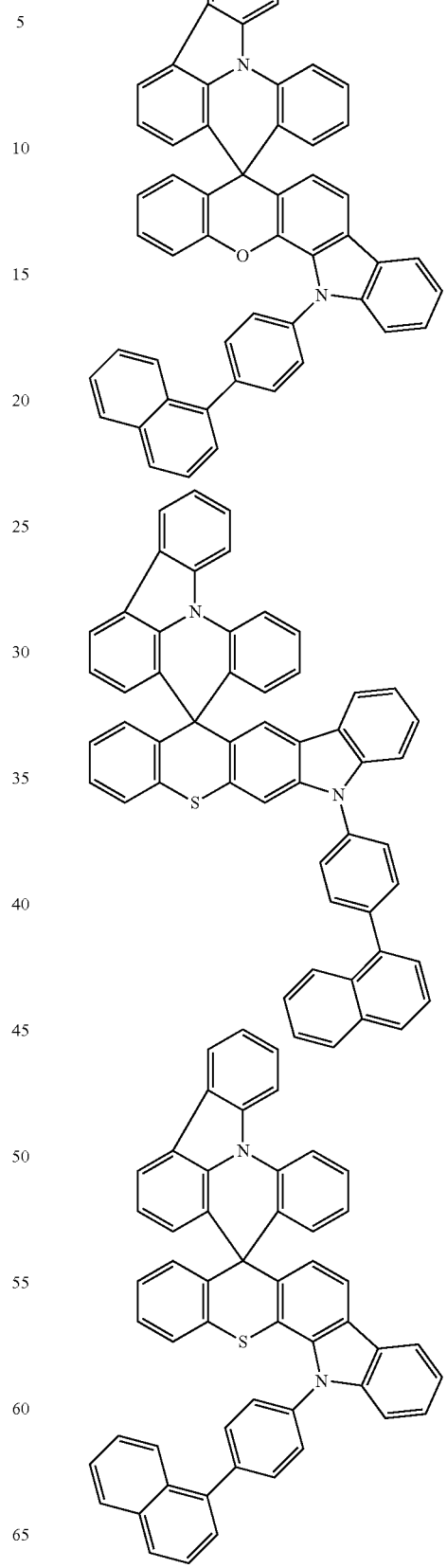

97
-continued
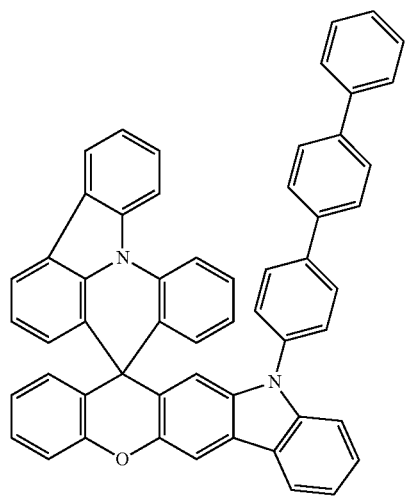
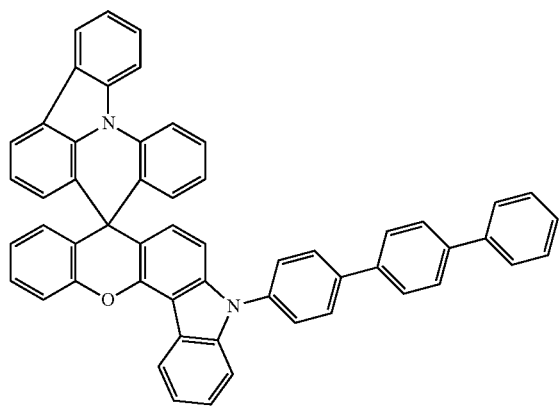
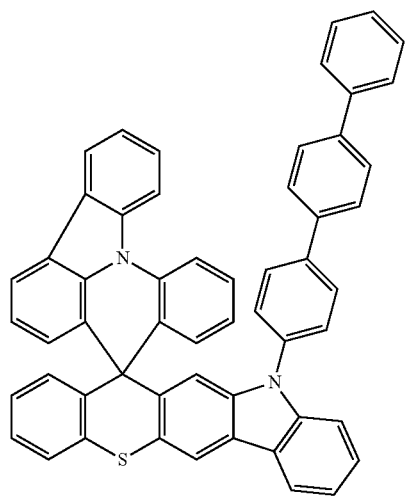
98
-continued
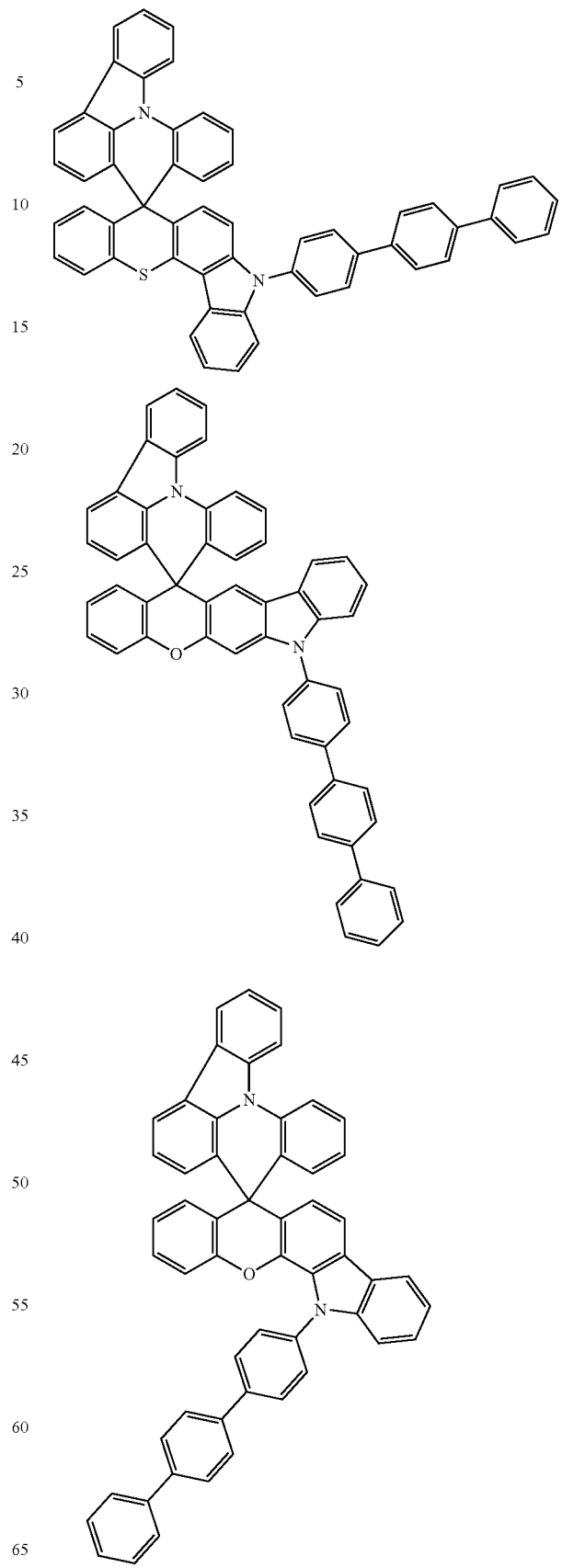

99
-continued
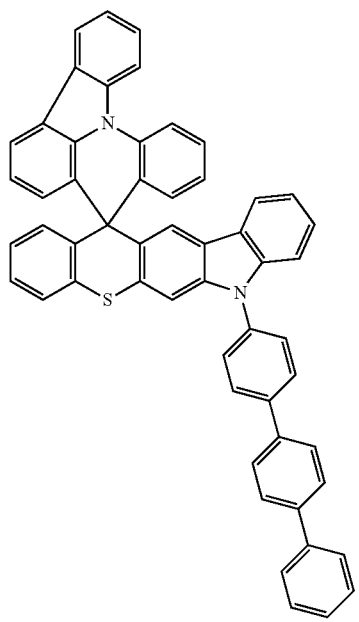
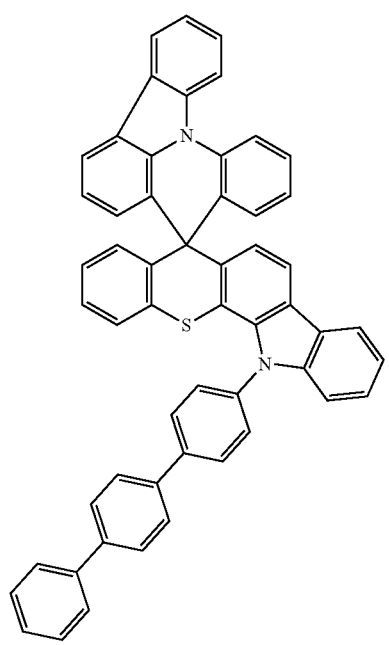
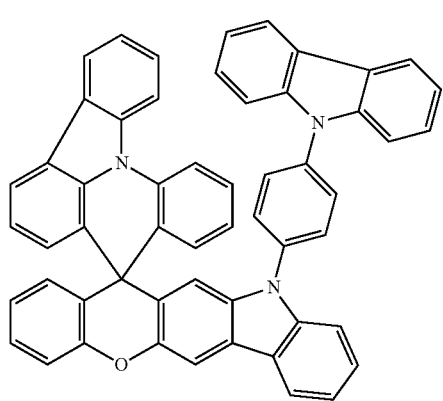
100
-continued
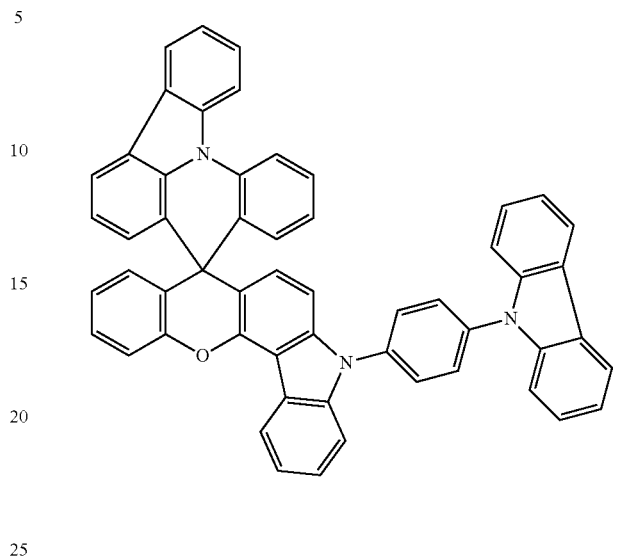
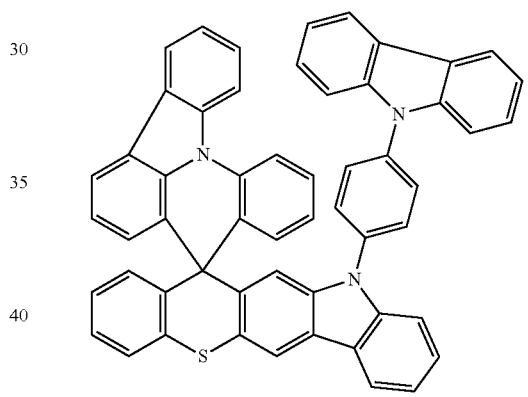
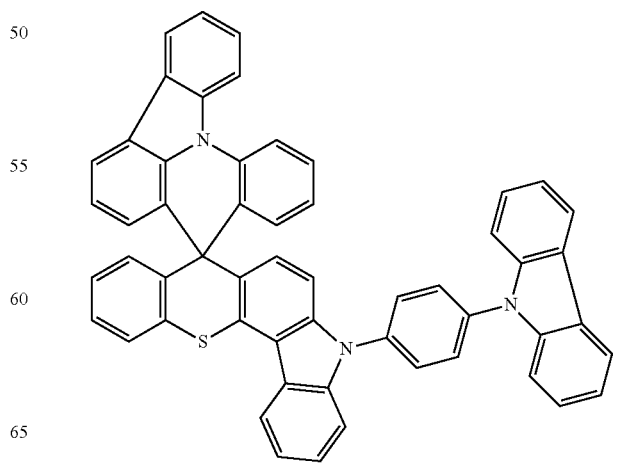

101
-continued
102
-continued
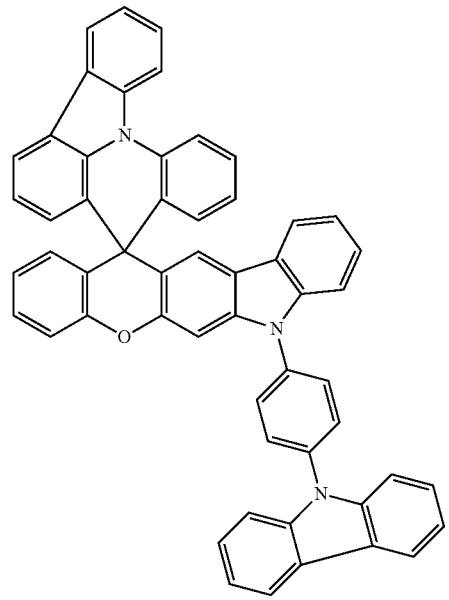
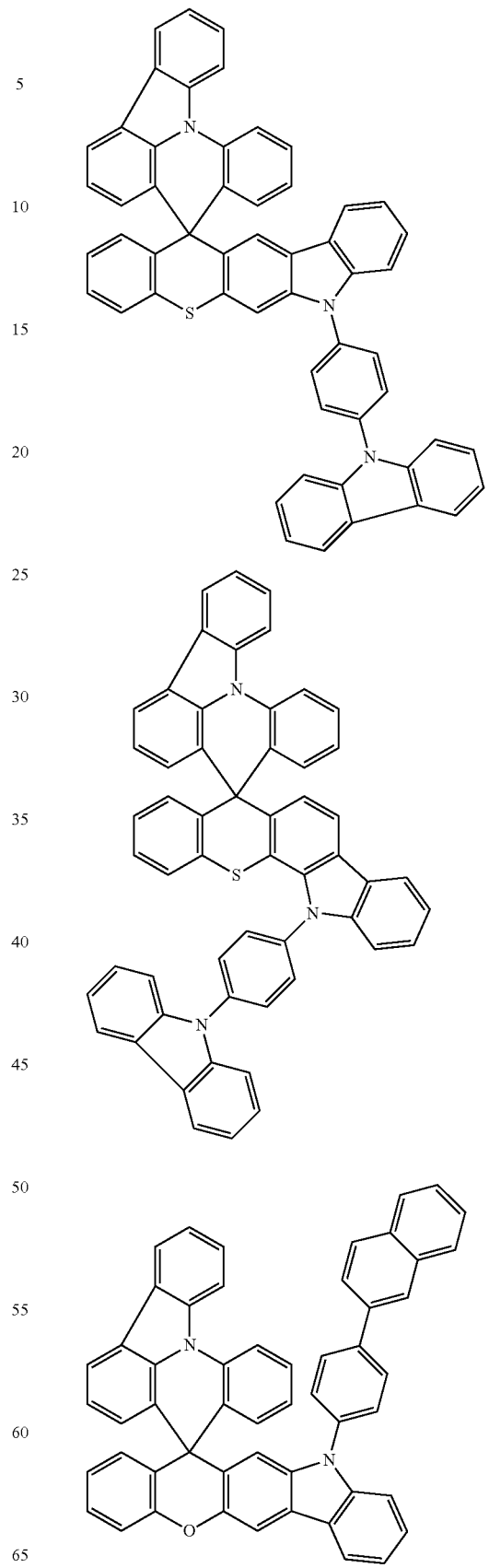

103
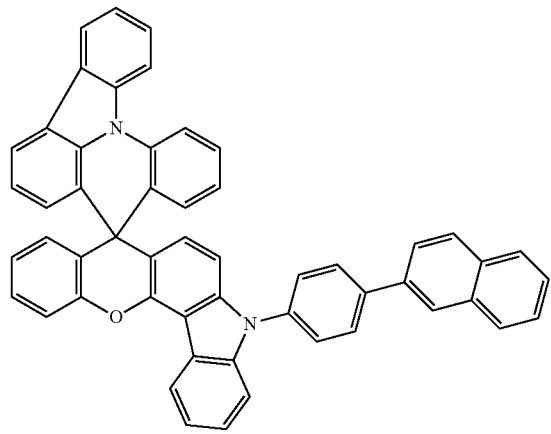
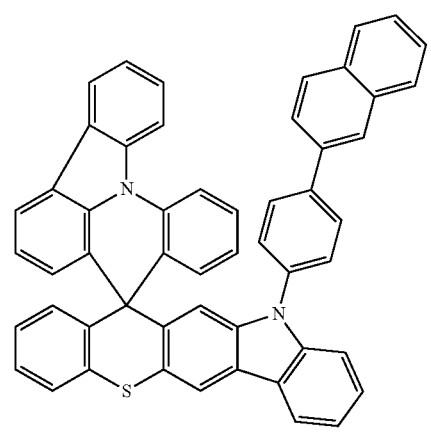
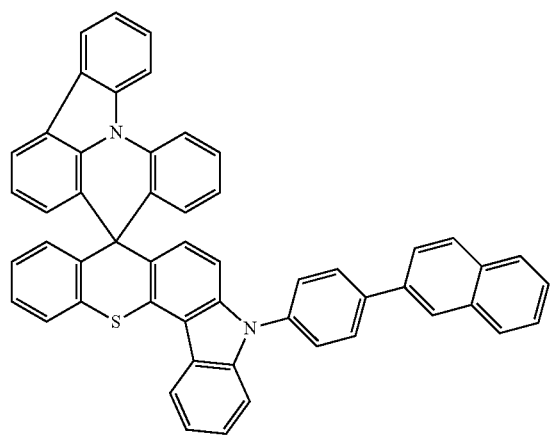
104
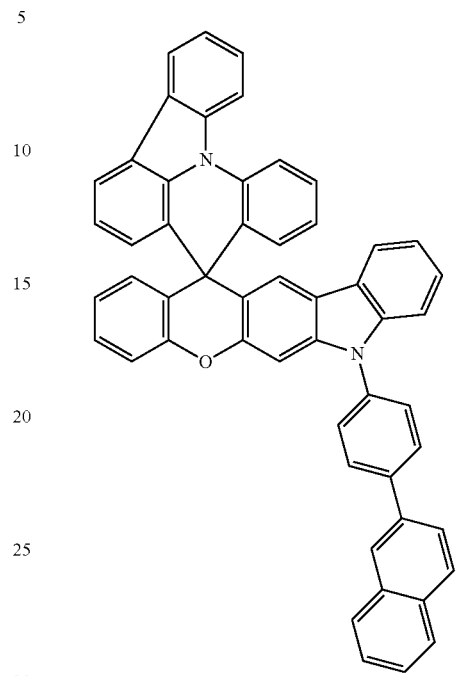
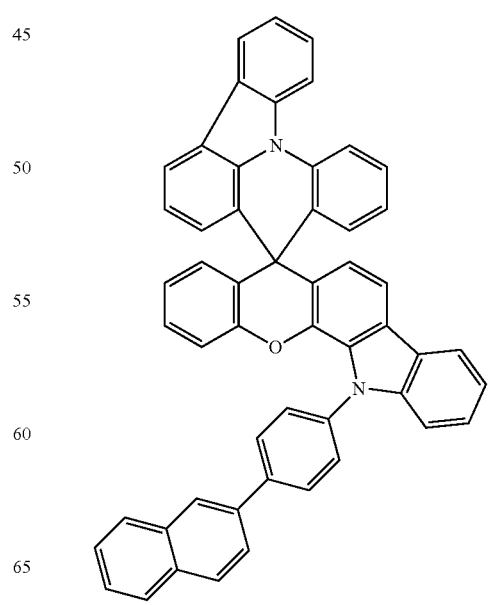

105
-continued
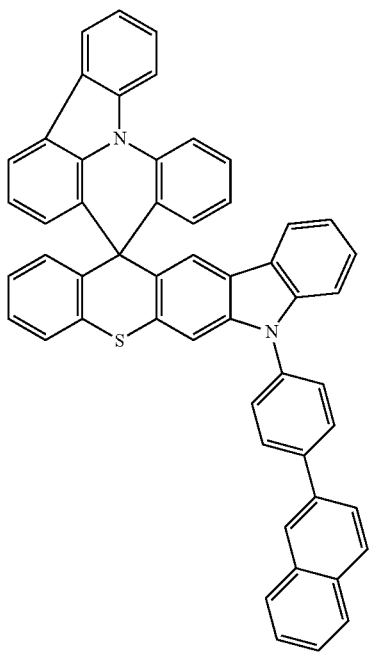
106
-continued
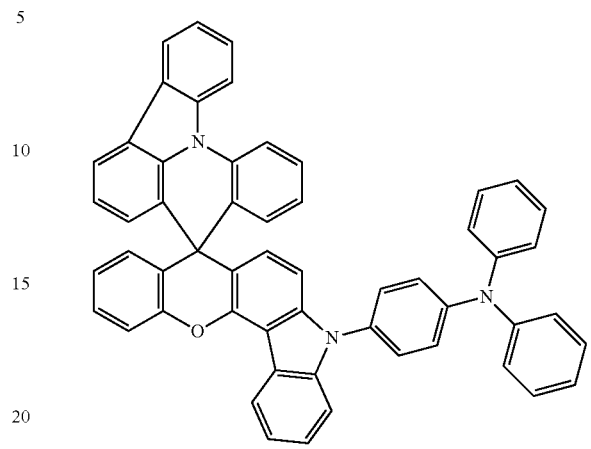
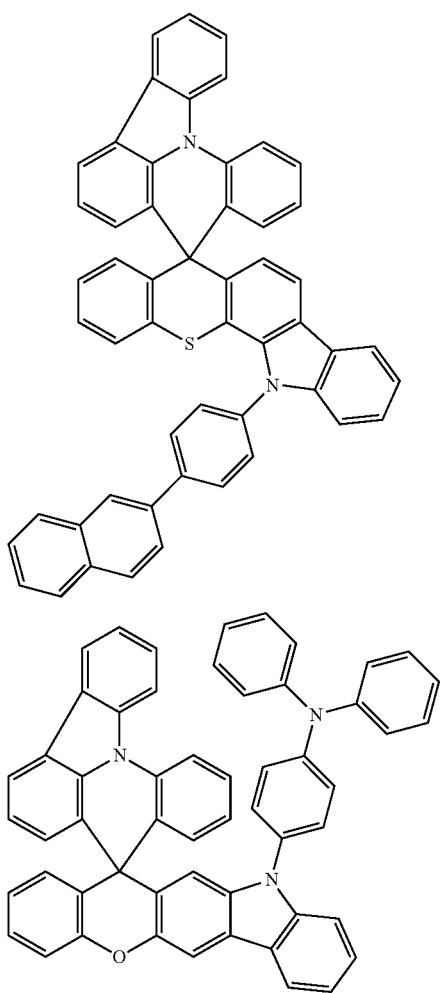
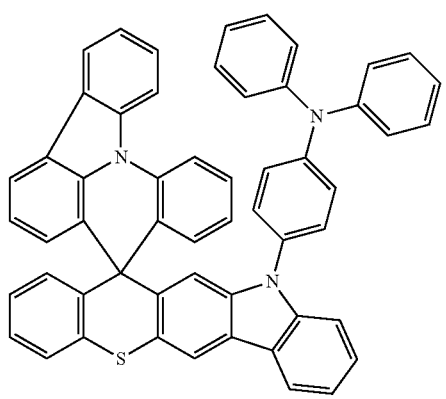
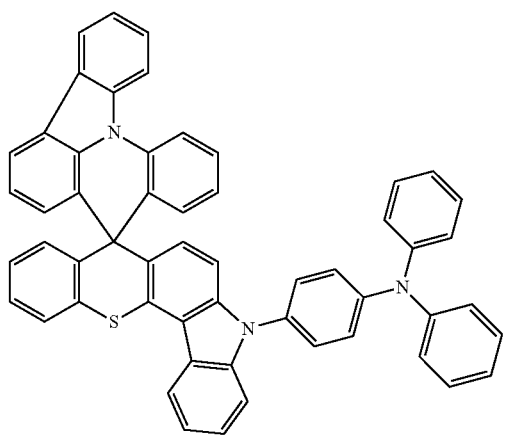

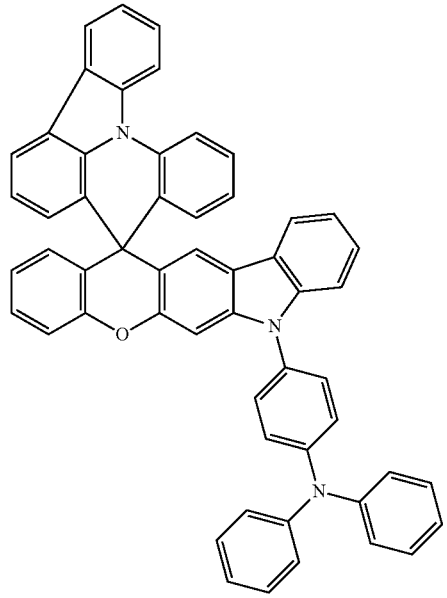
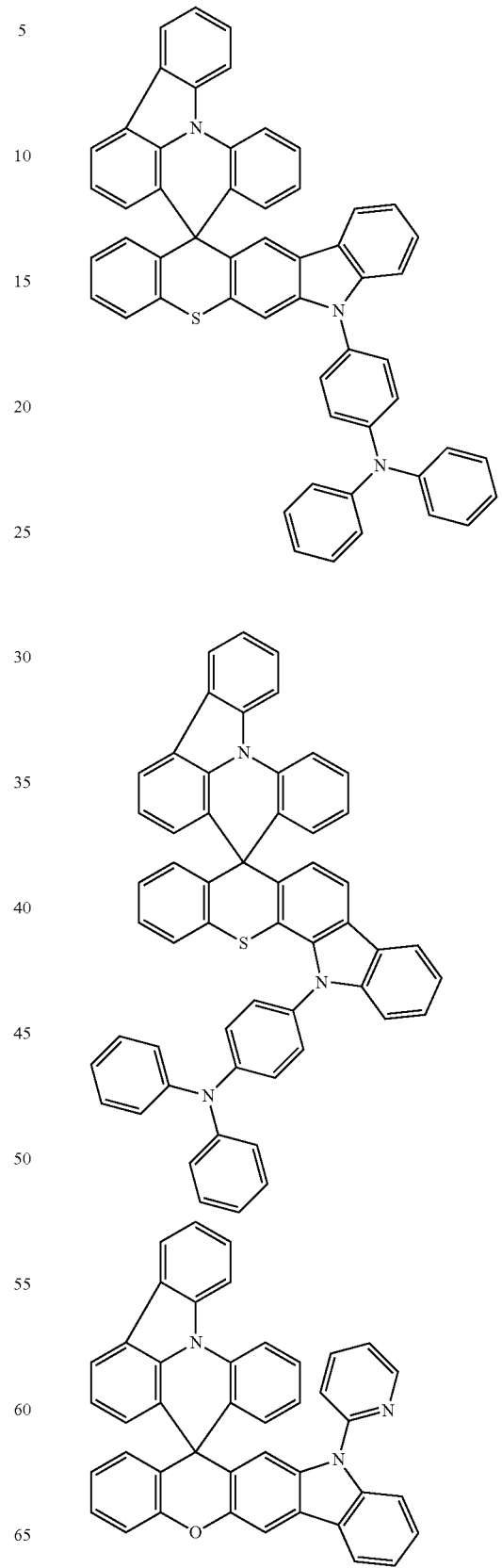

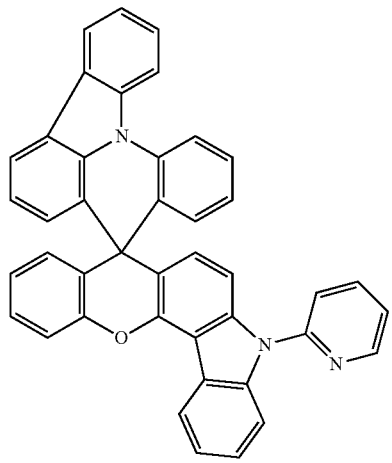
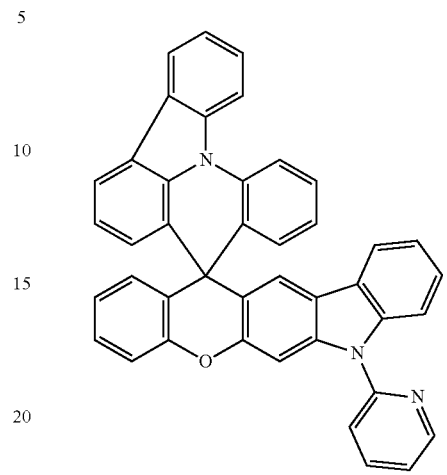
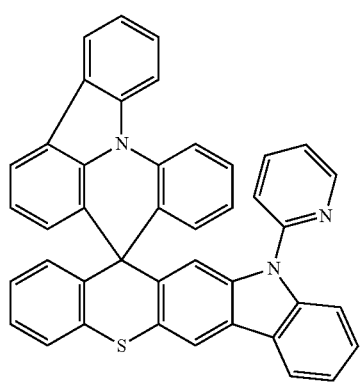
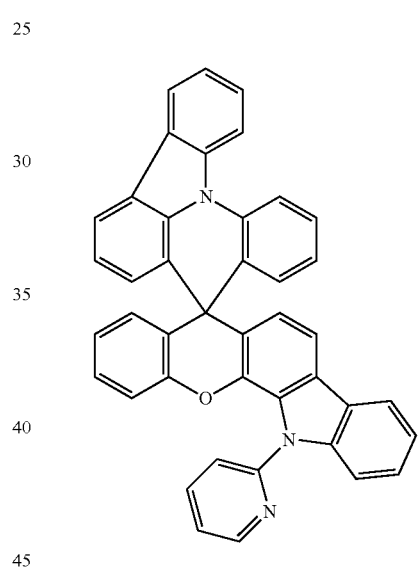
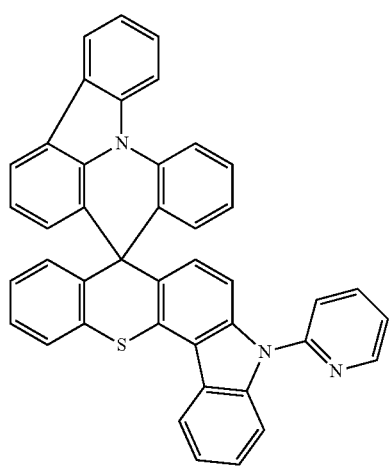
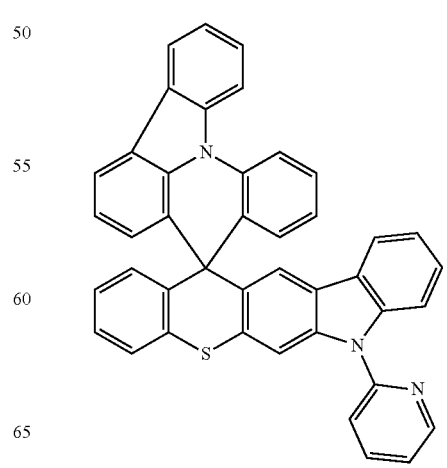

111
-continued
112
-continued
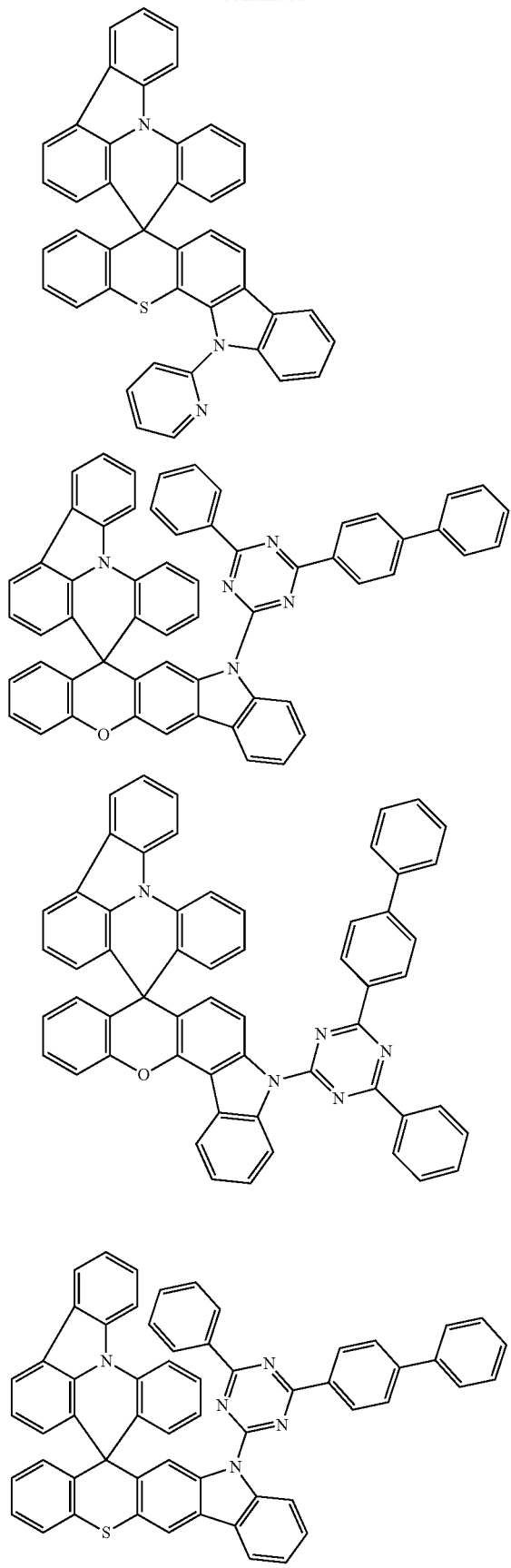
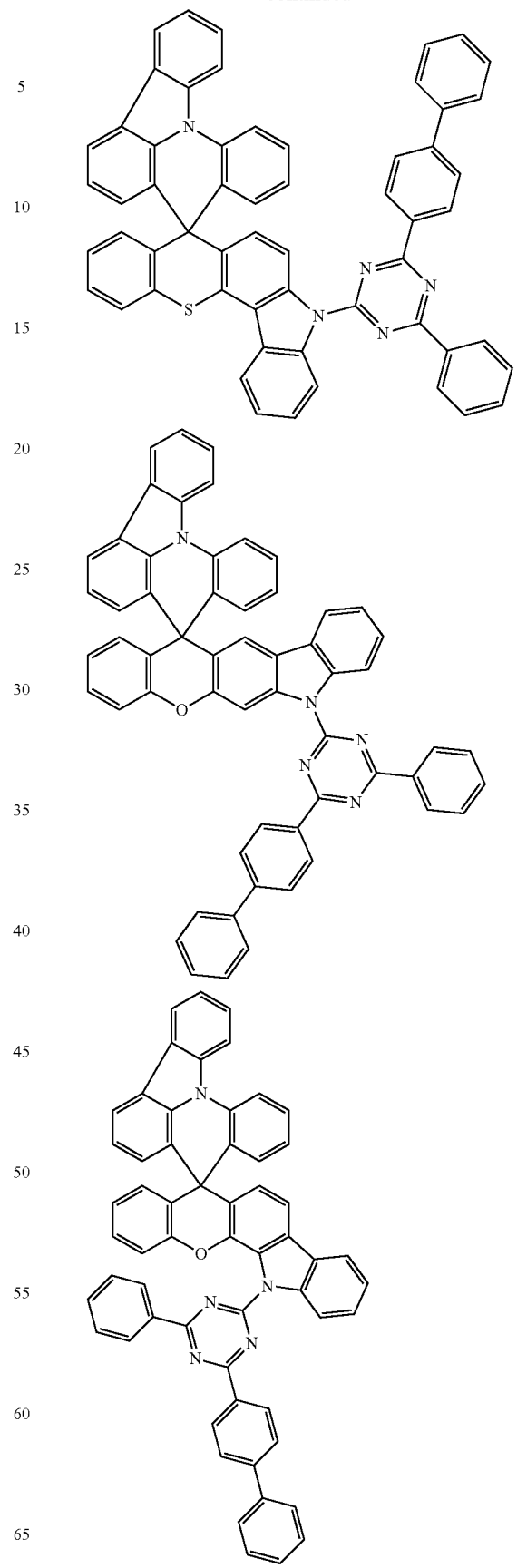

113
-continued
114
-continued
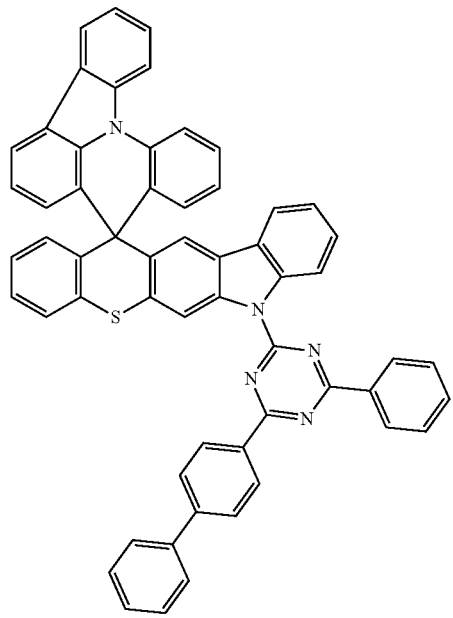
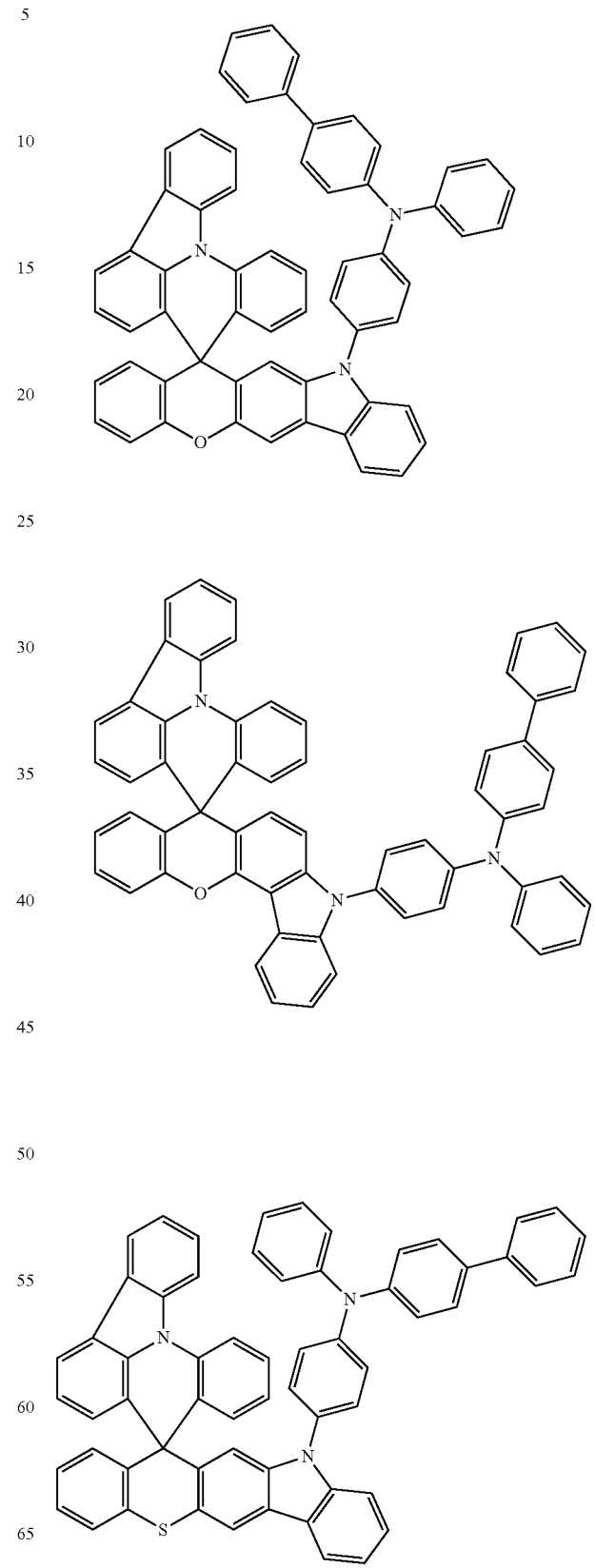

115
-continued
116
-continued
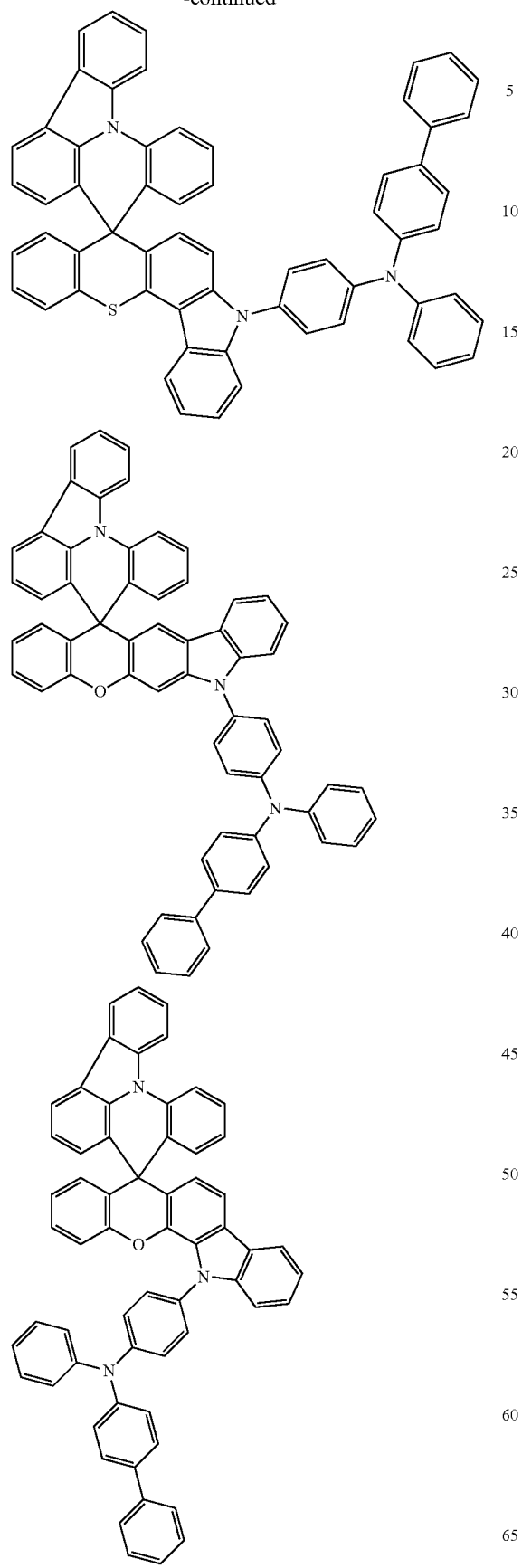
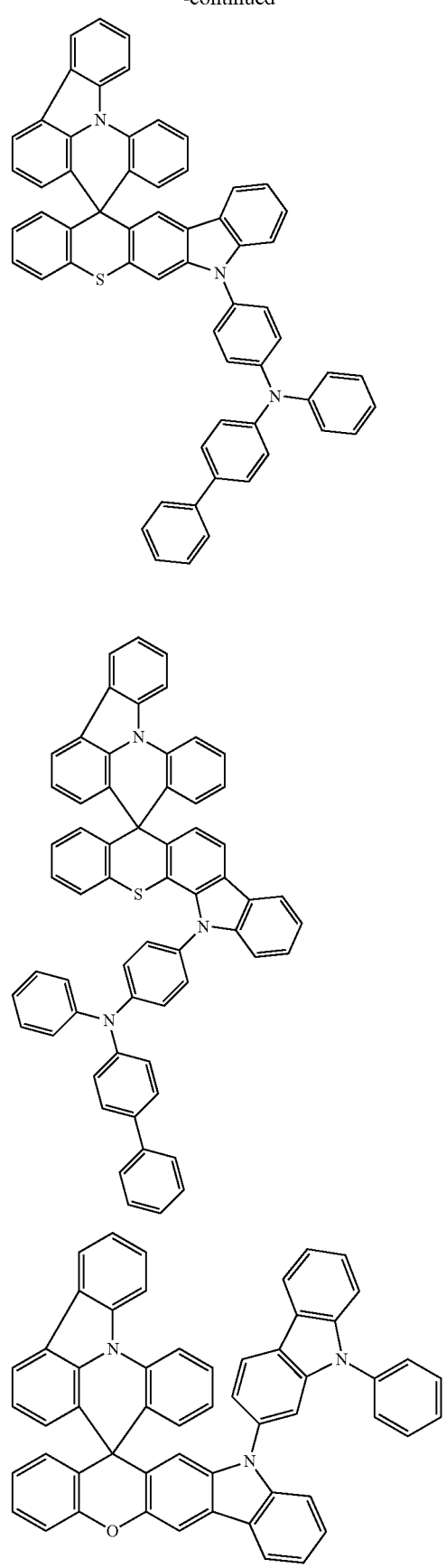

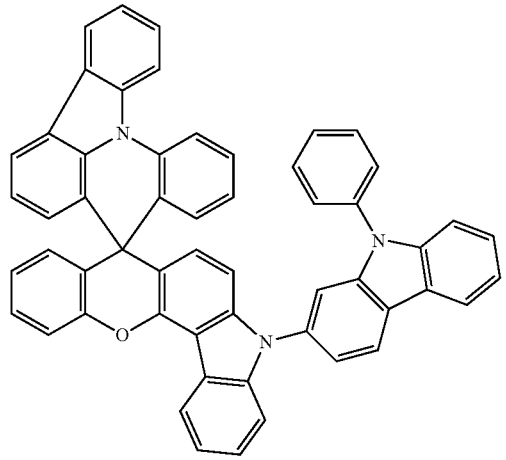
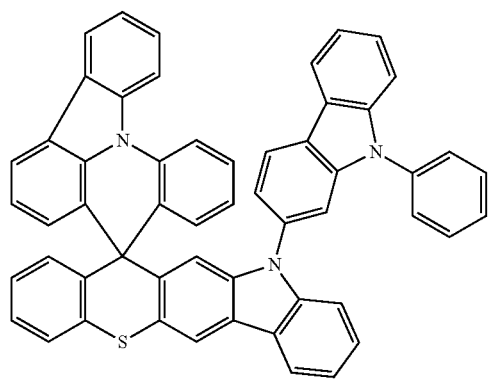
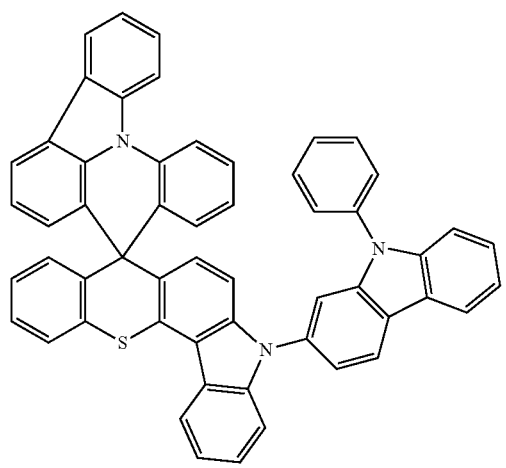
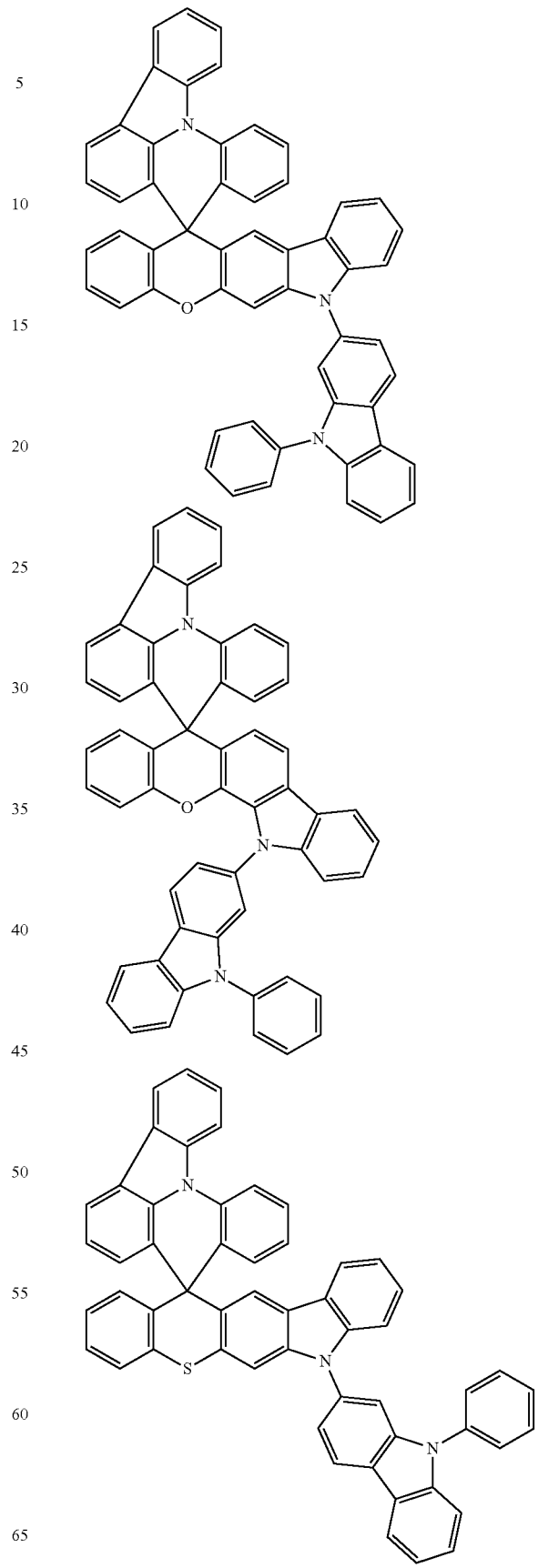

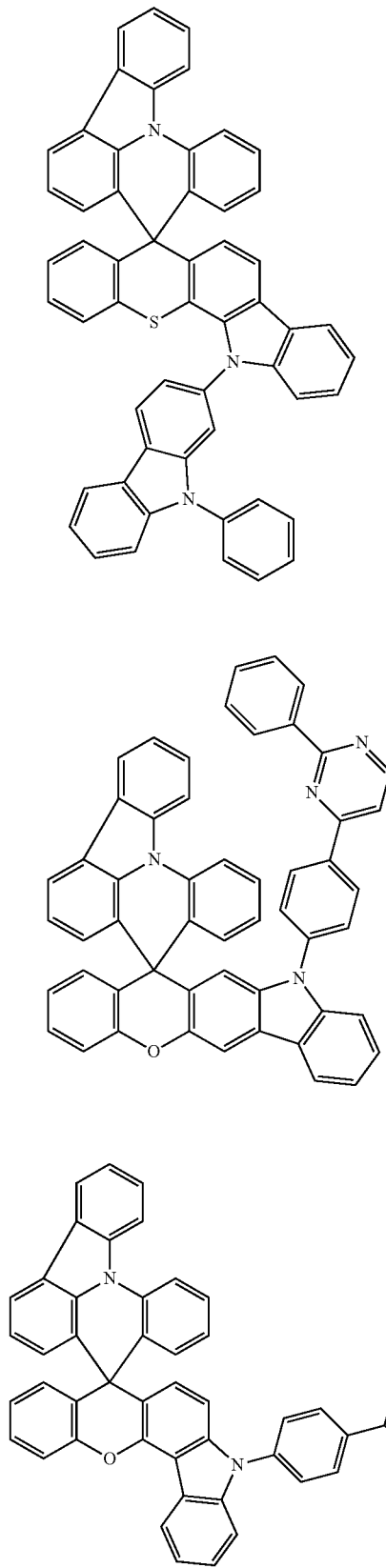
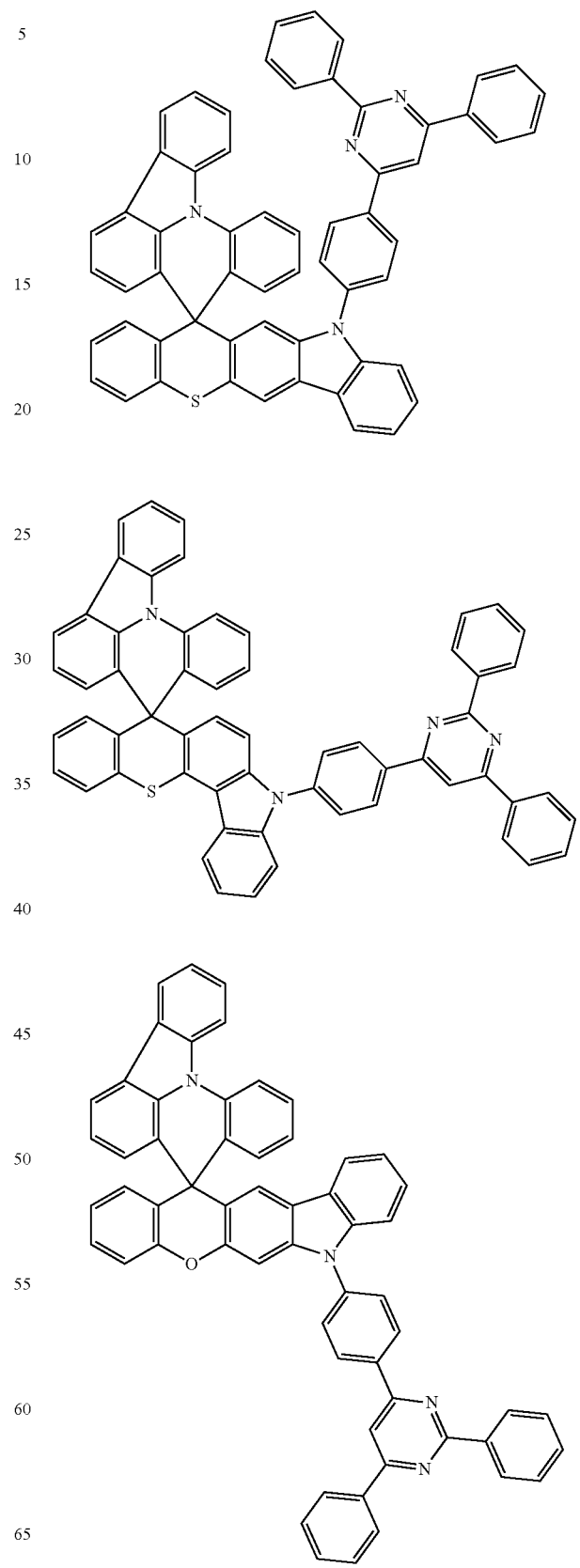

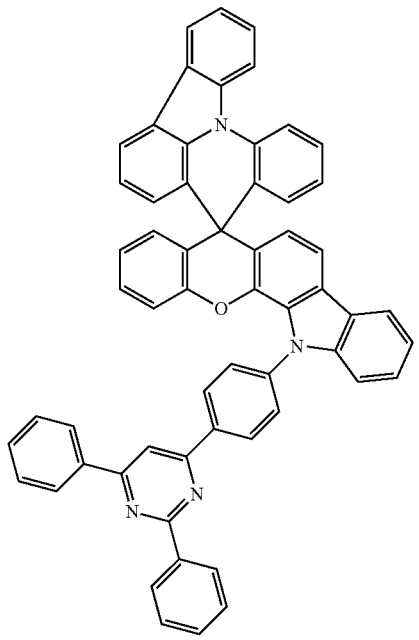
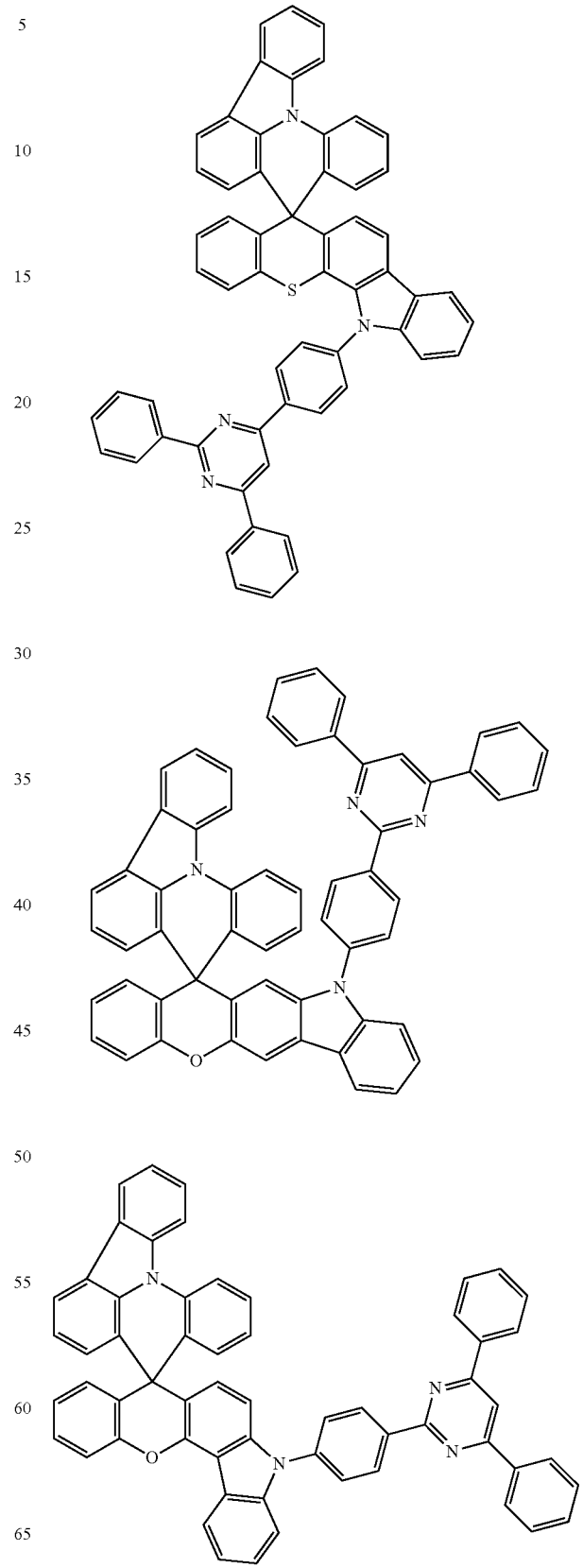

123
-continued
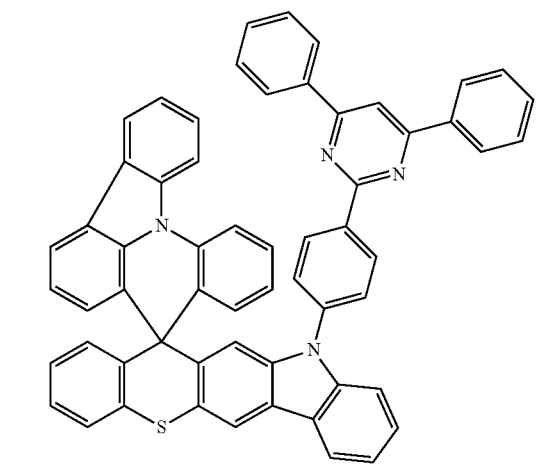
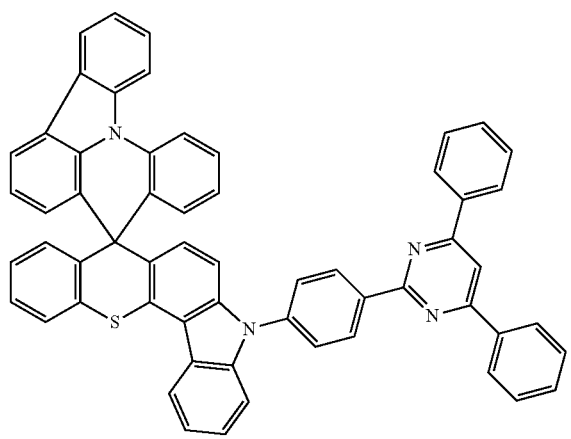
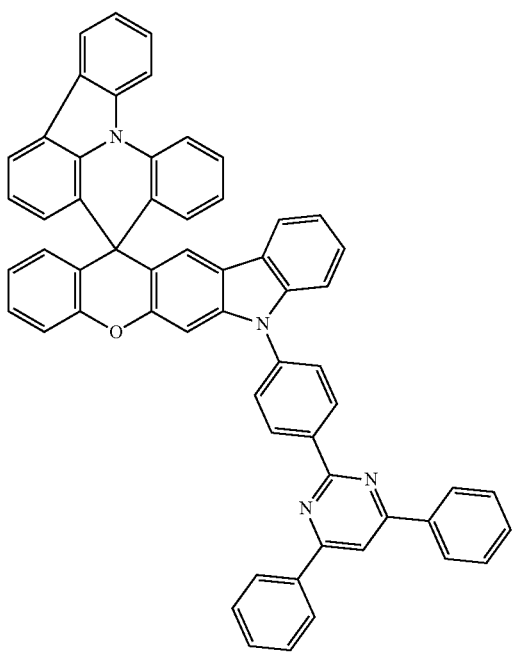
124
-continued
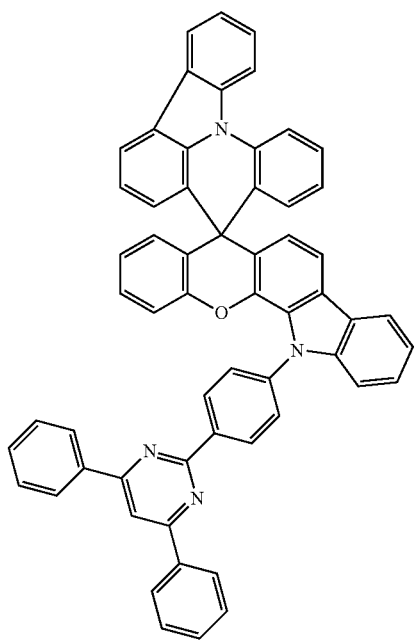
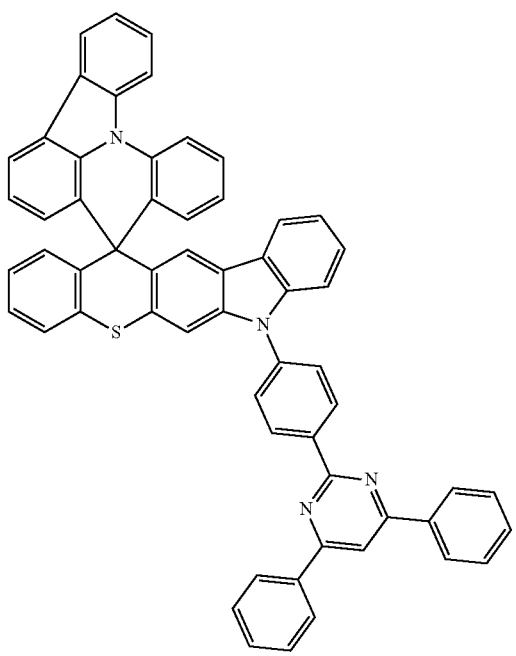

125
-continued
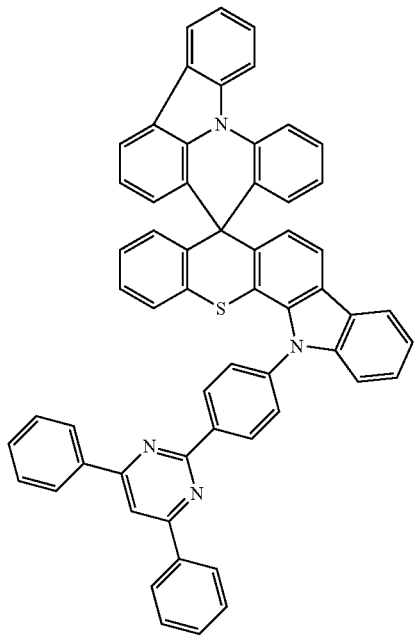
126
-continued
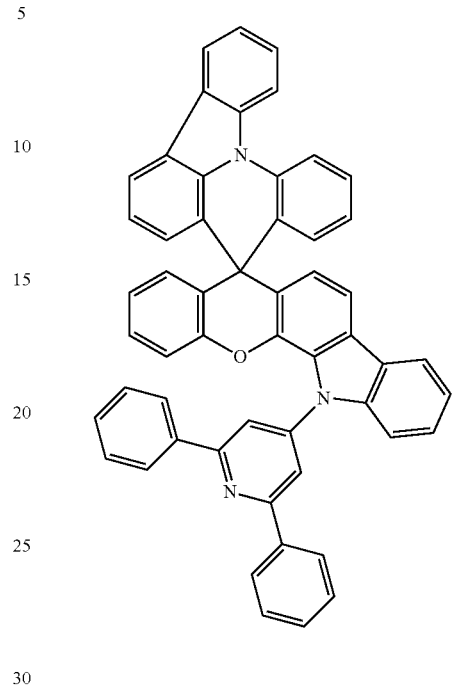
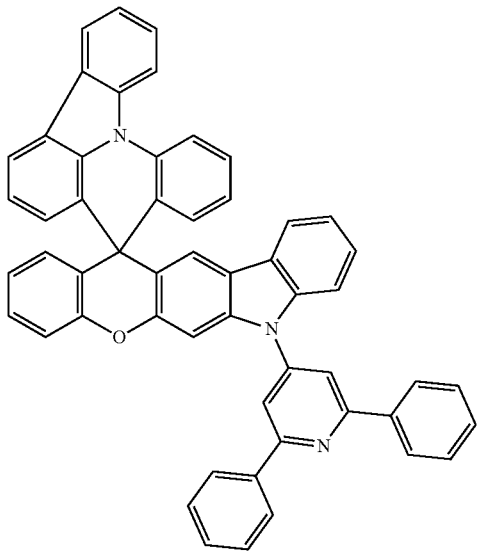

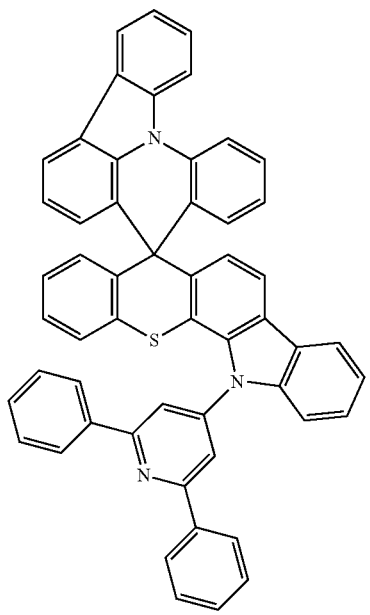
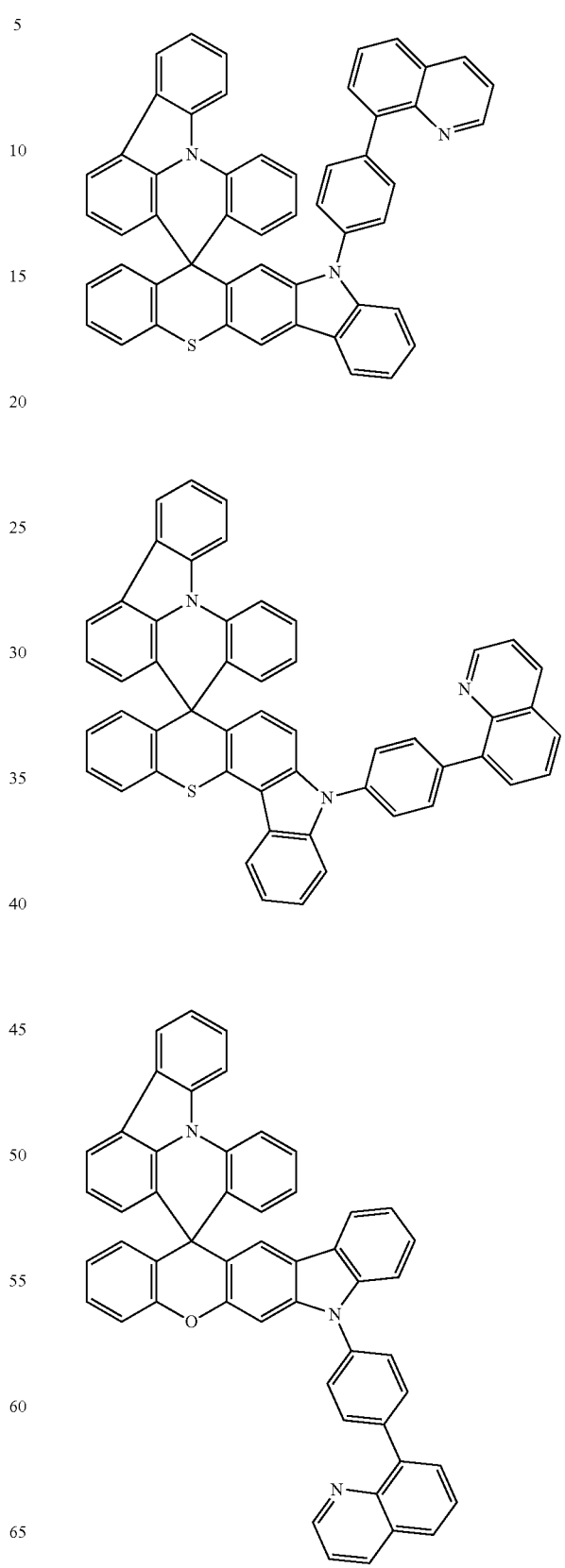

129
-continued
130
-continued
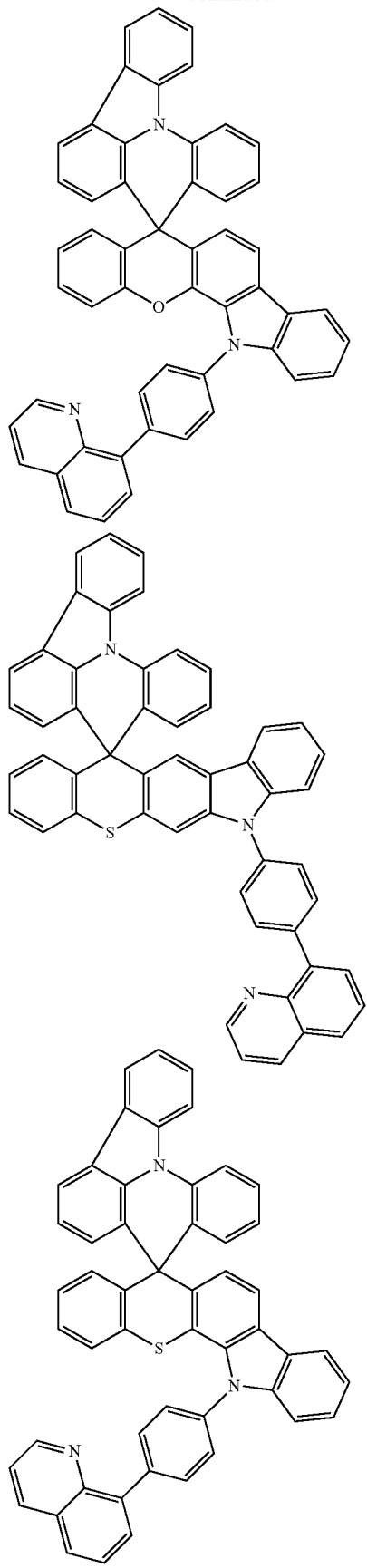
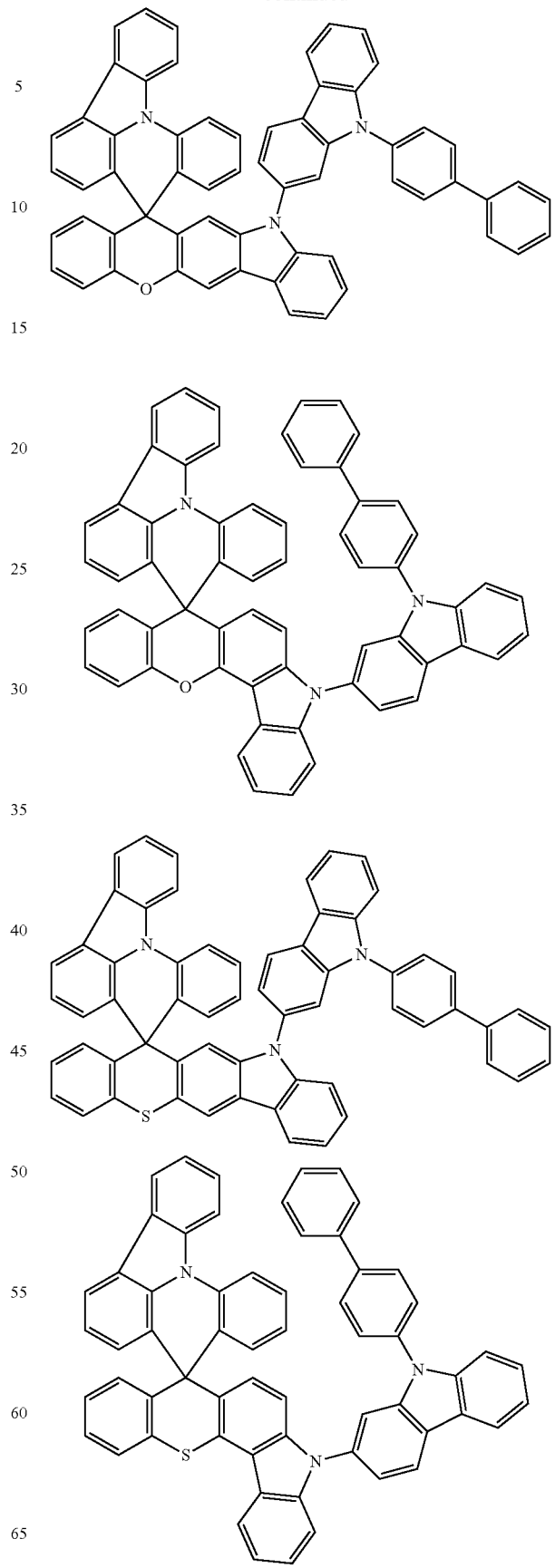

131
-continued
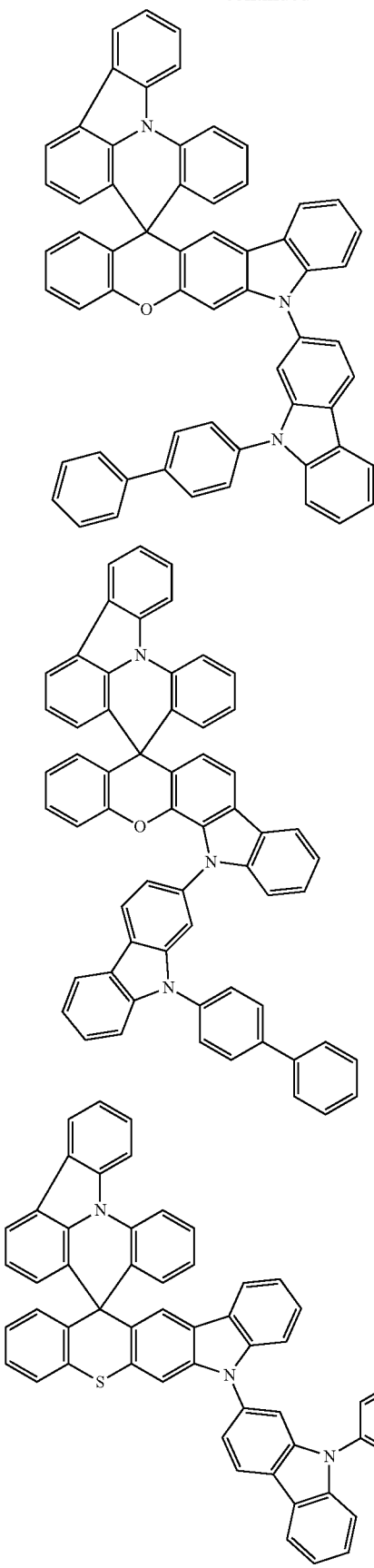
132
-continued
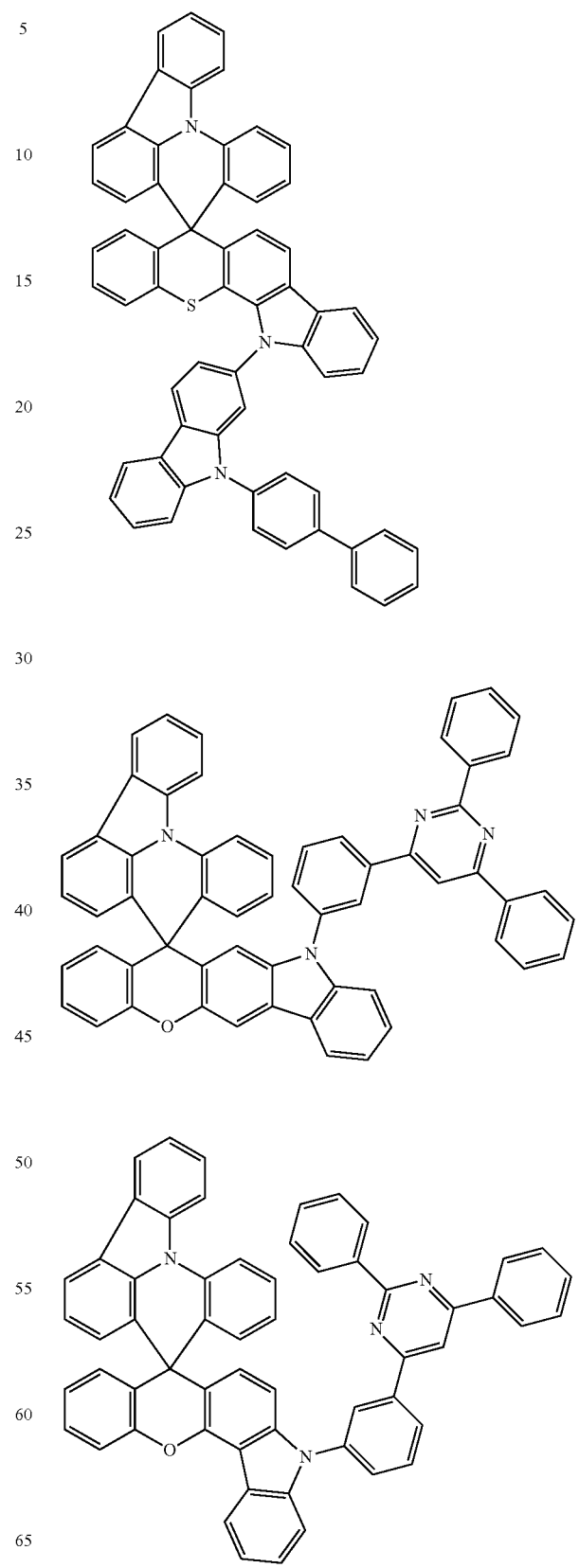

133
-continued
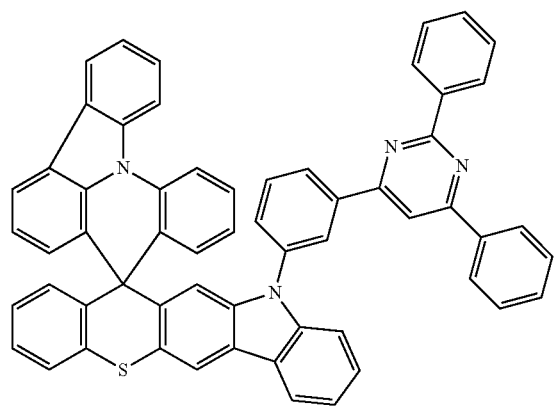
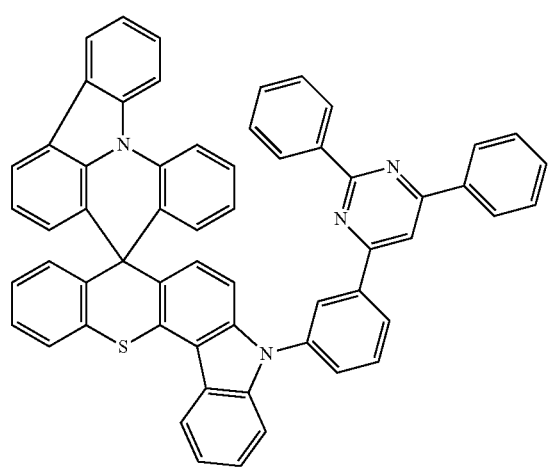
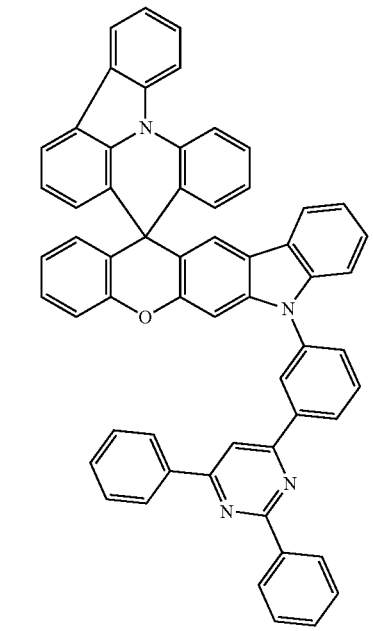
134
-continued
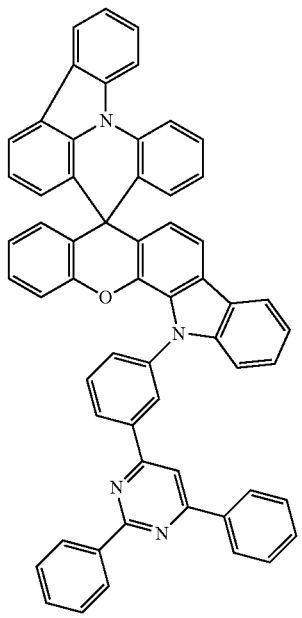
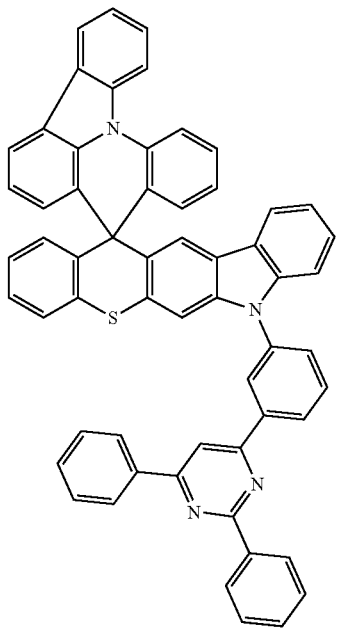

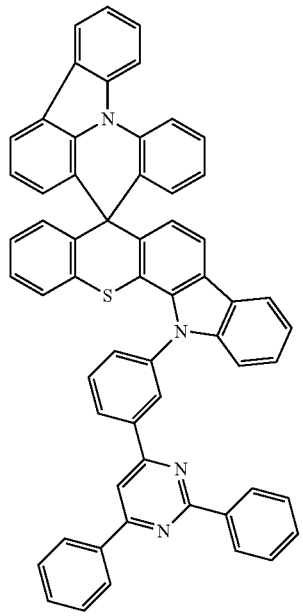
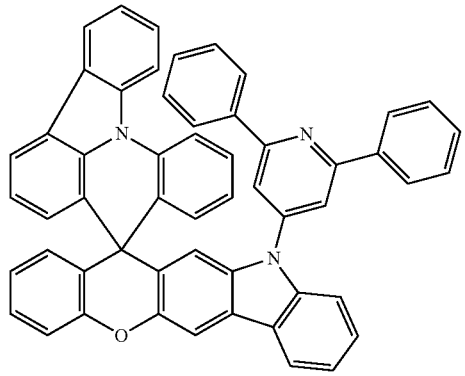
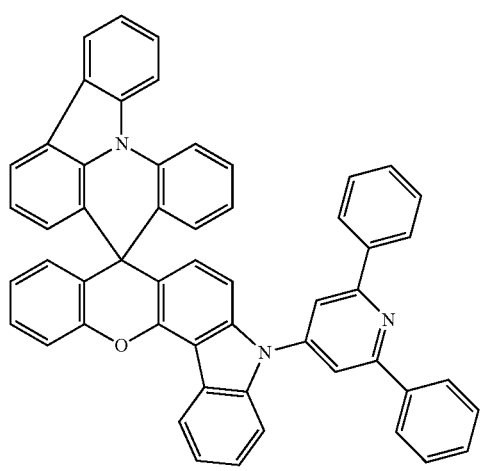
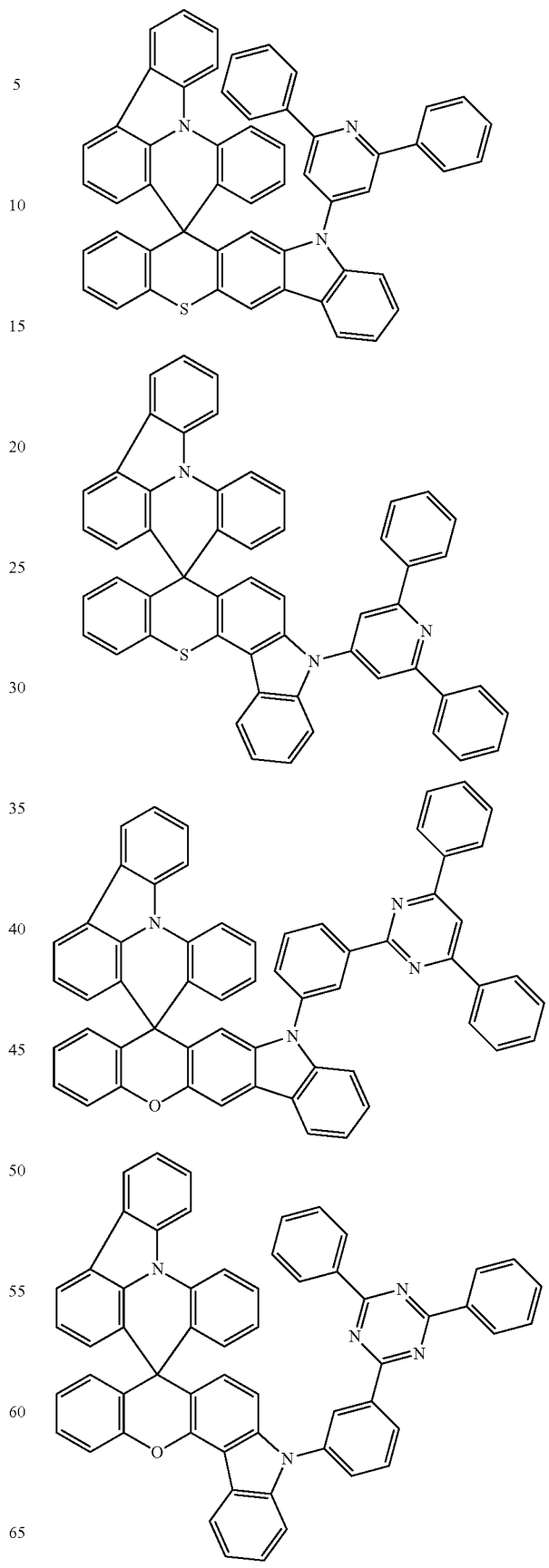

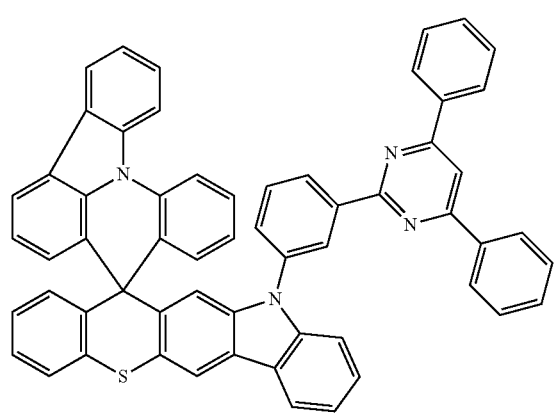
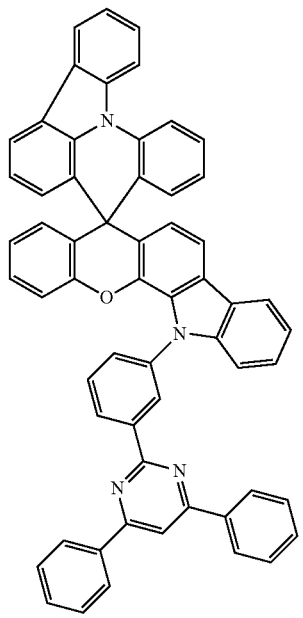
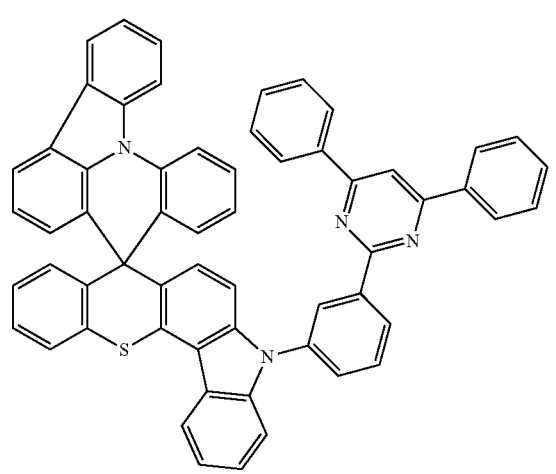
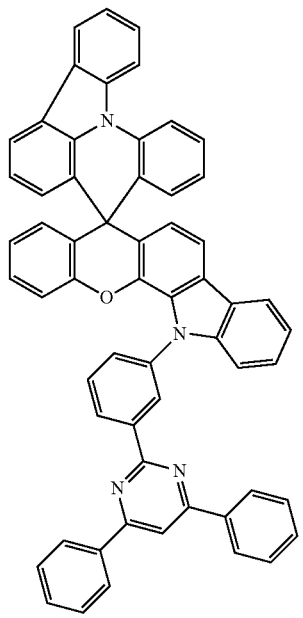
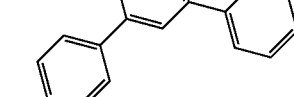
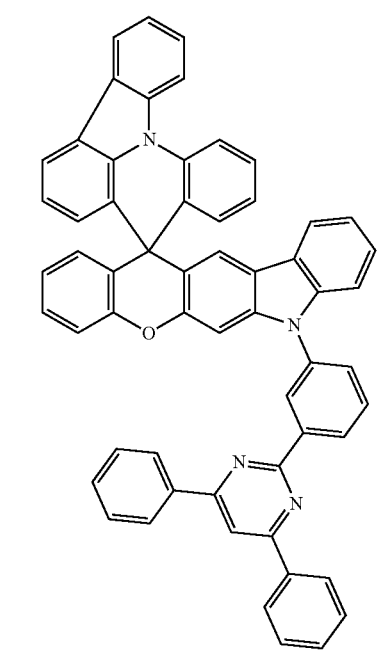
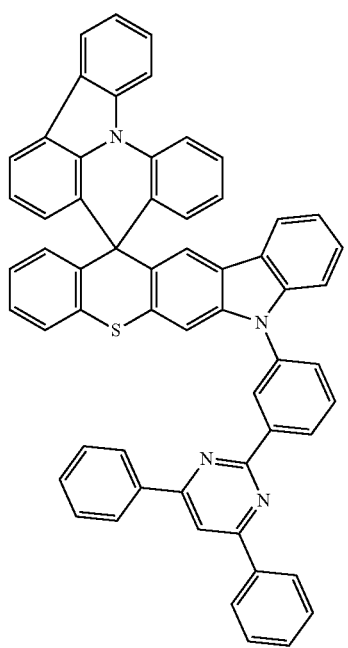

139
-continued
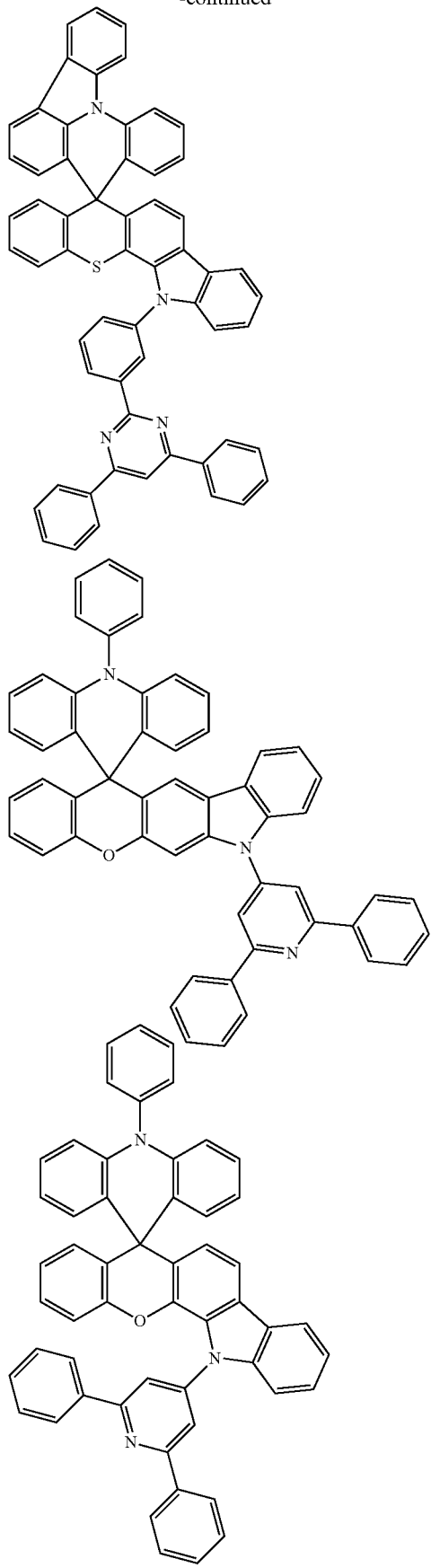
140
-continued
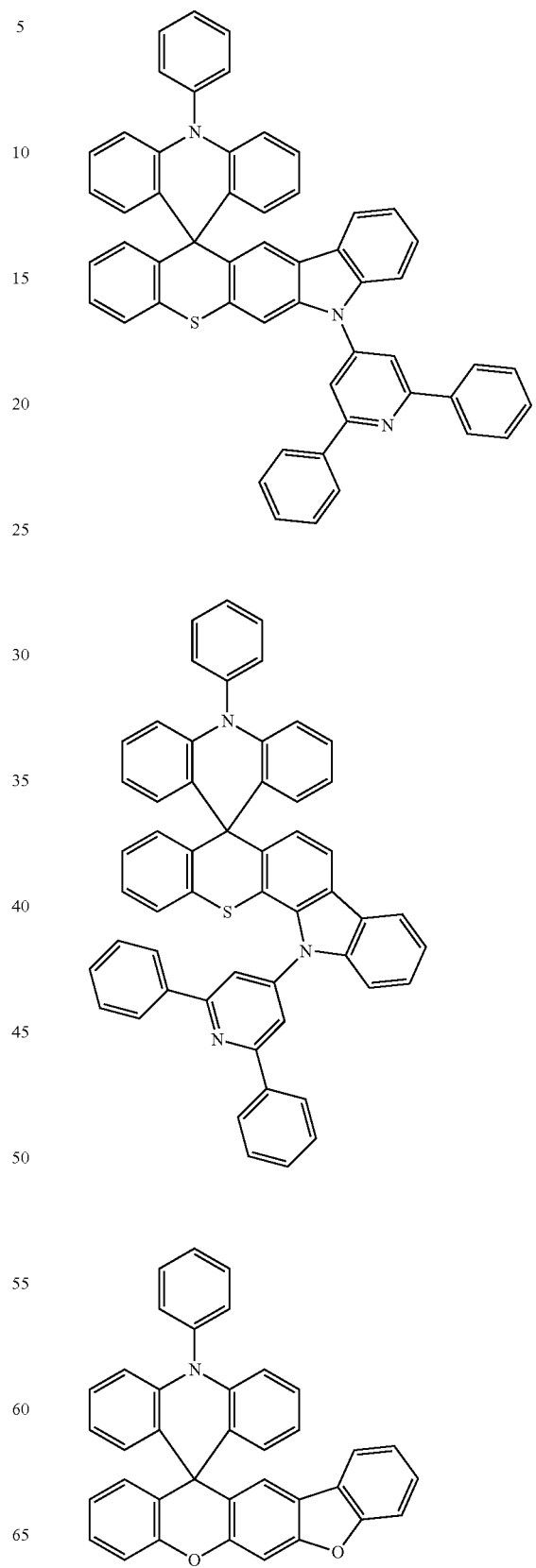

141
-continued
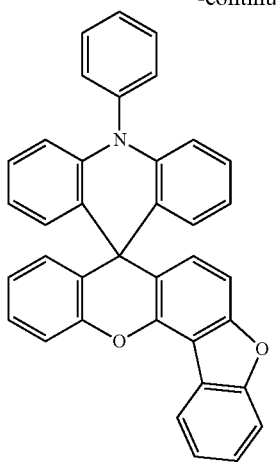
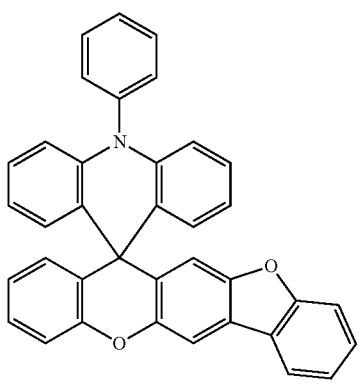
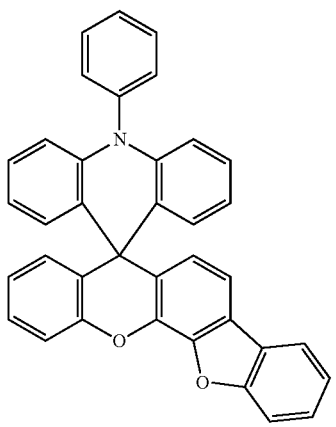
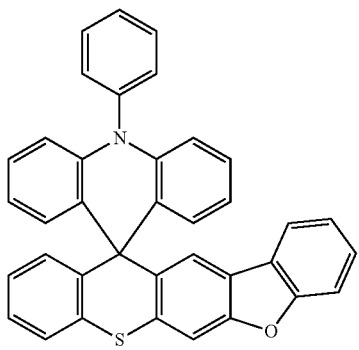
142
-continued
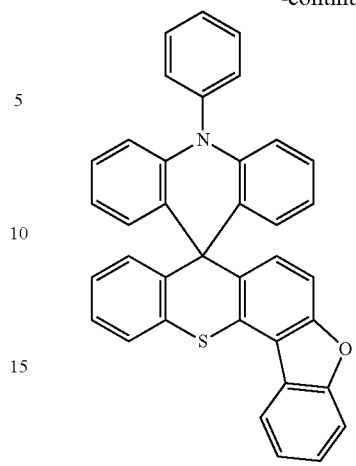
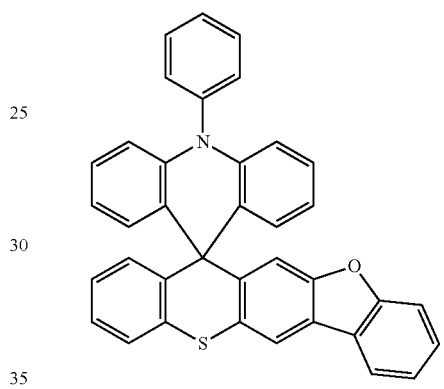
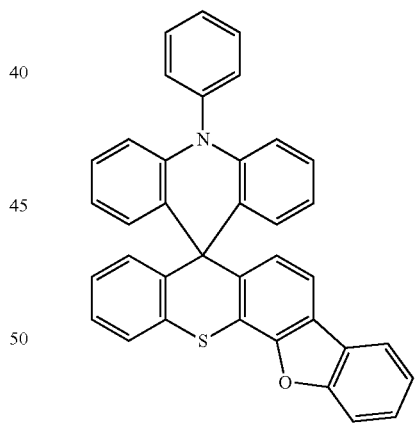
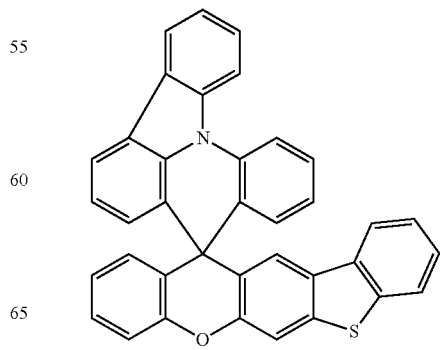

143
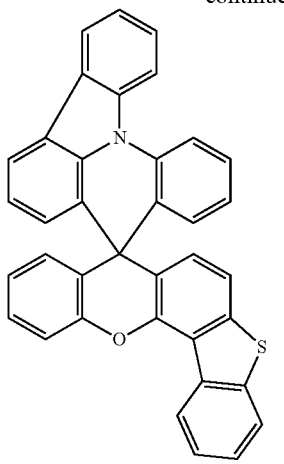
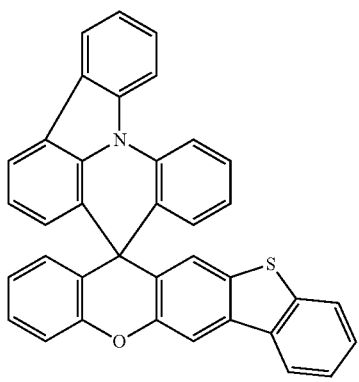
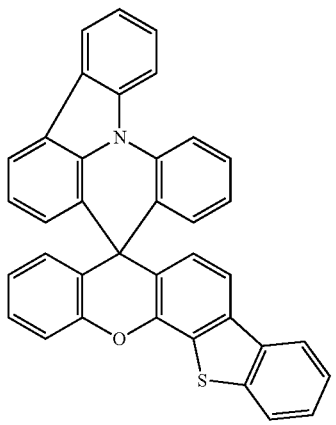
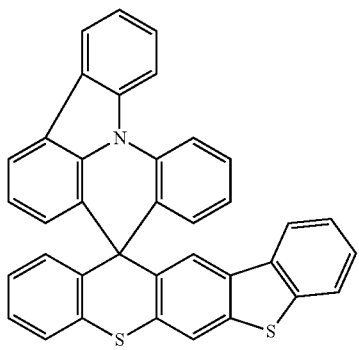
144
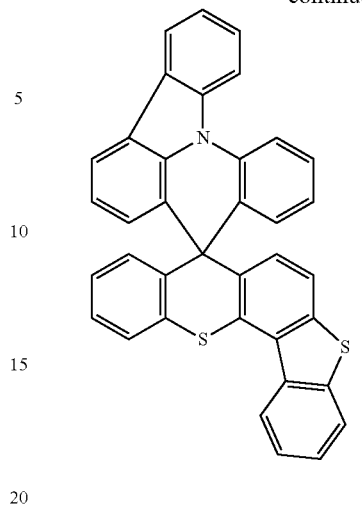
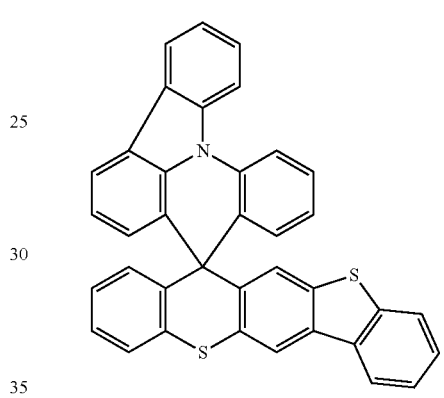
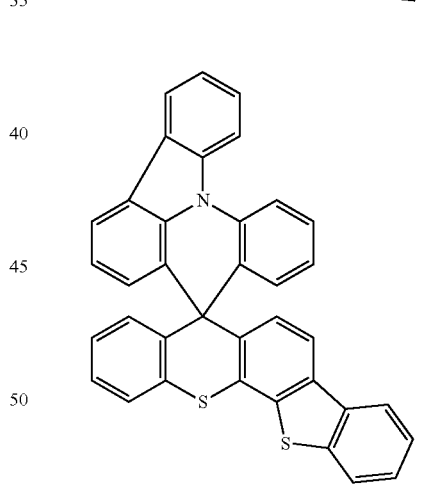
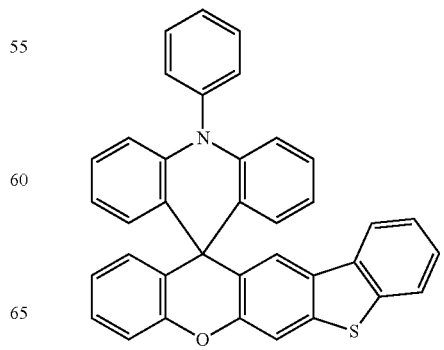

145
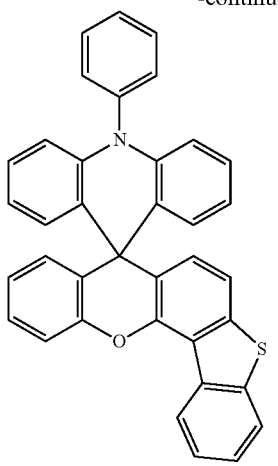
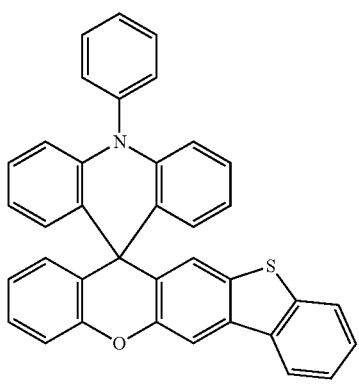
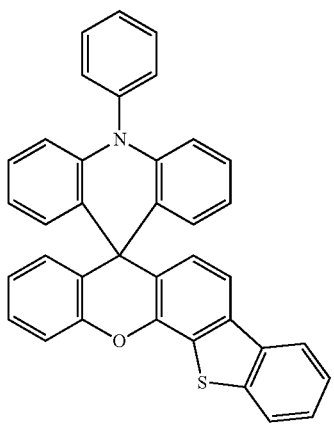
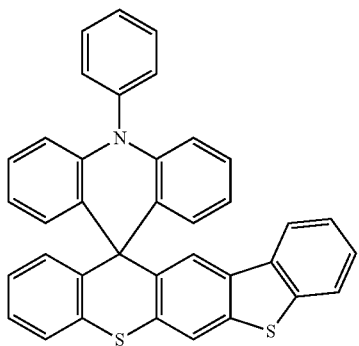
146
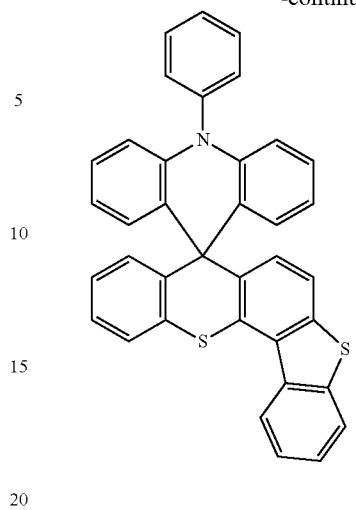
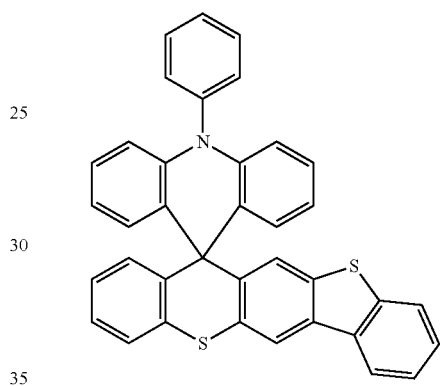
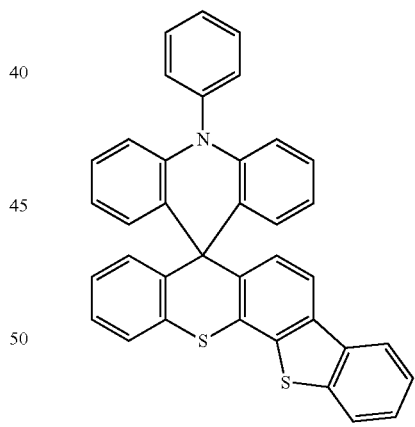
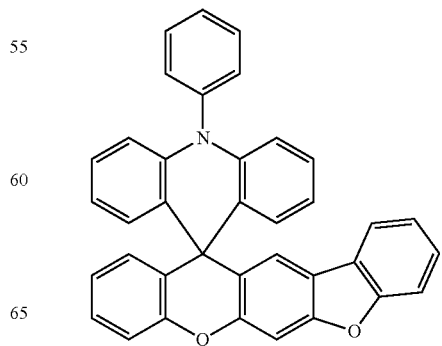

147
-continued
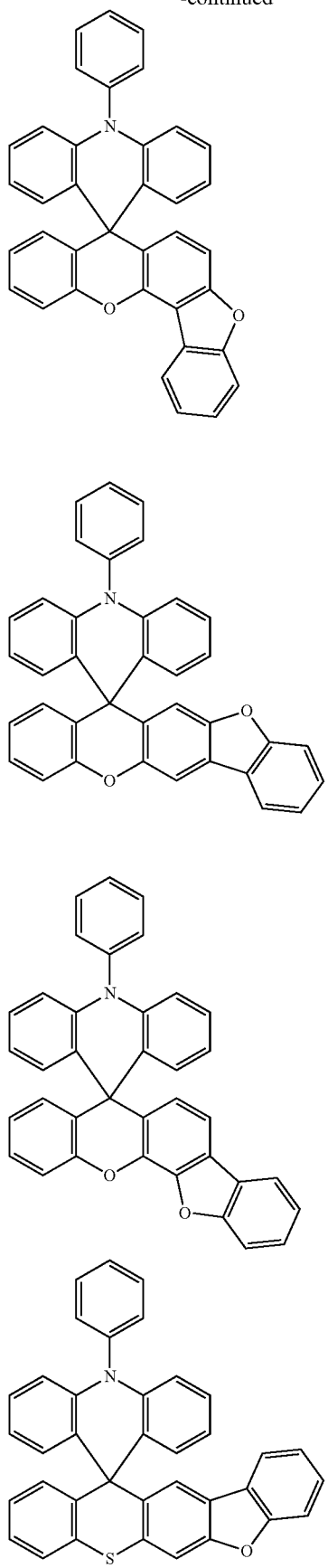
148
-continued
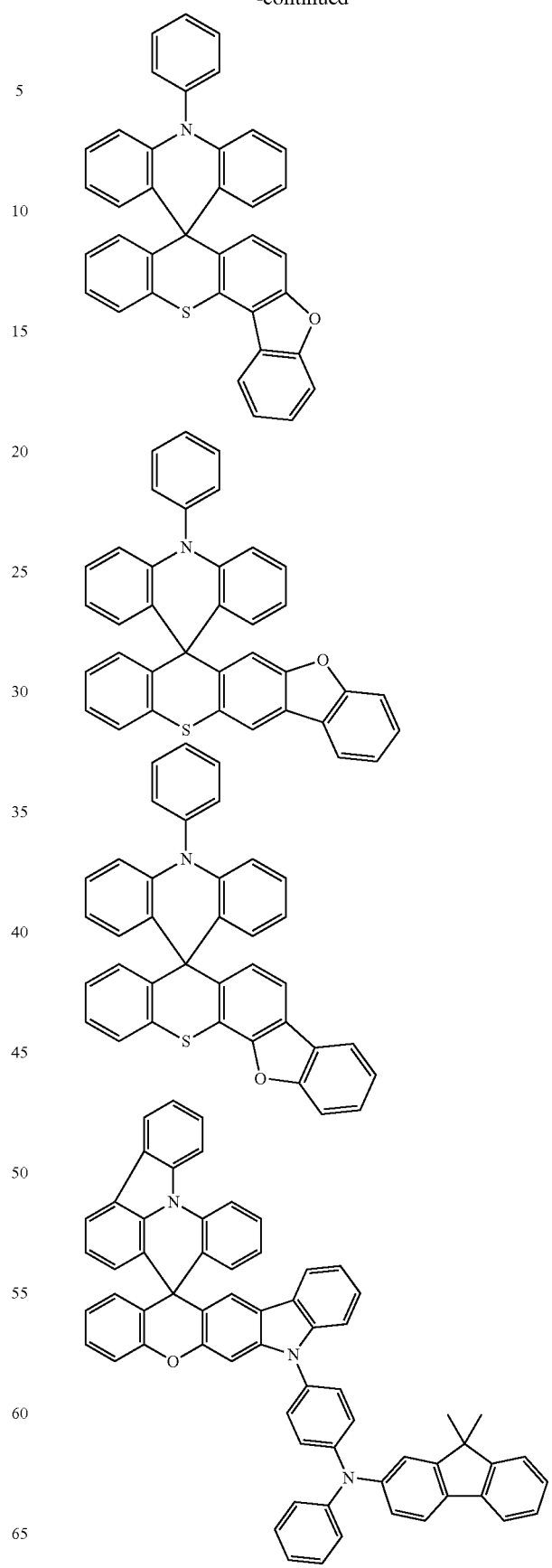

149
-continued
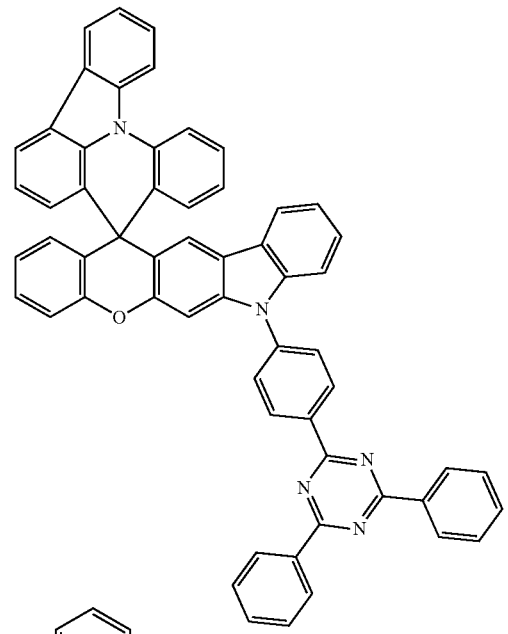
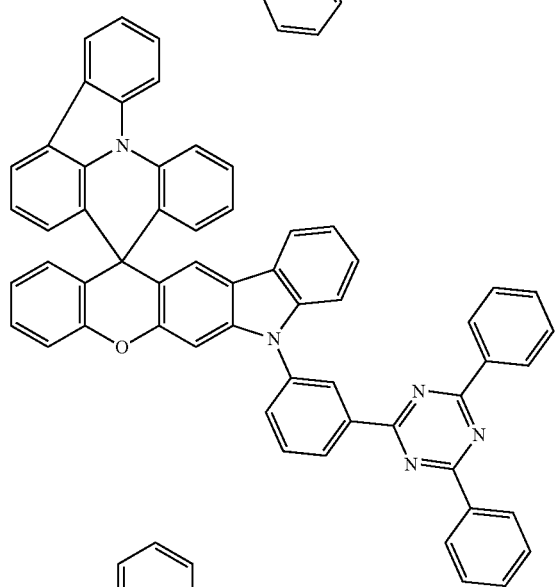
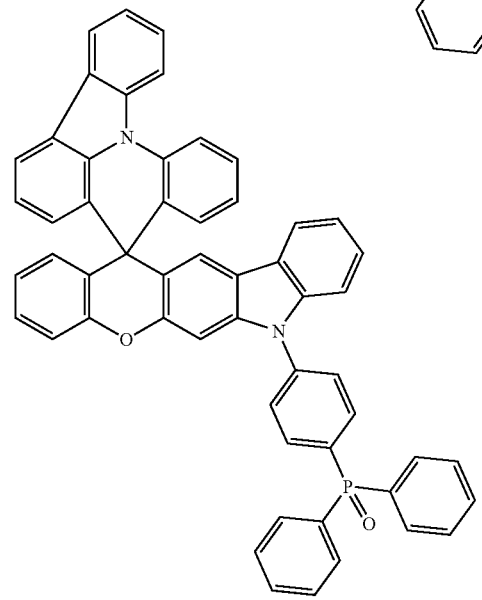
150
-continued
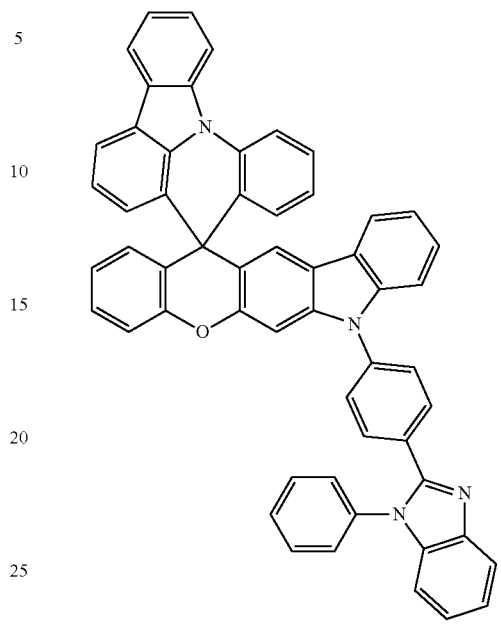
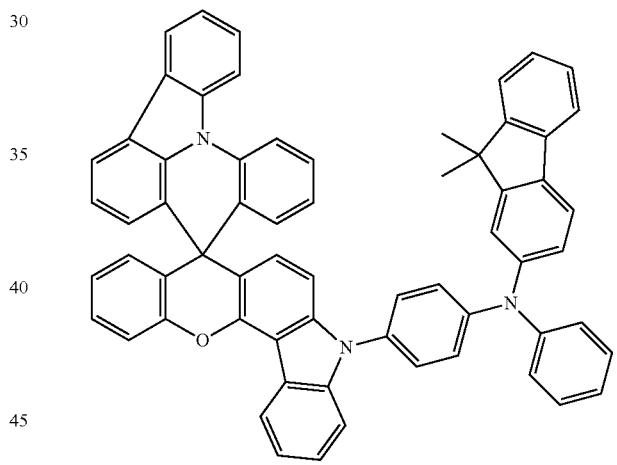
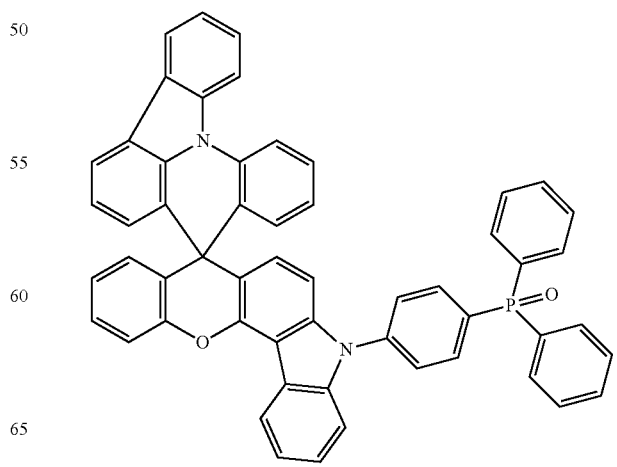

151
-continued
152
-continued
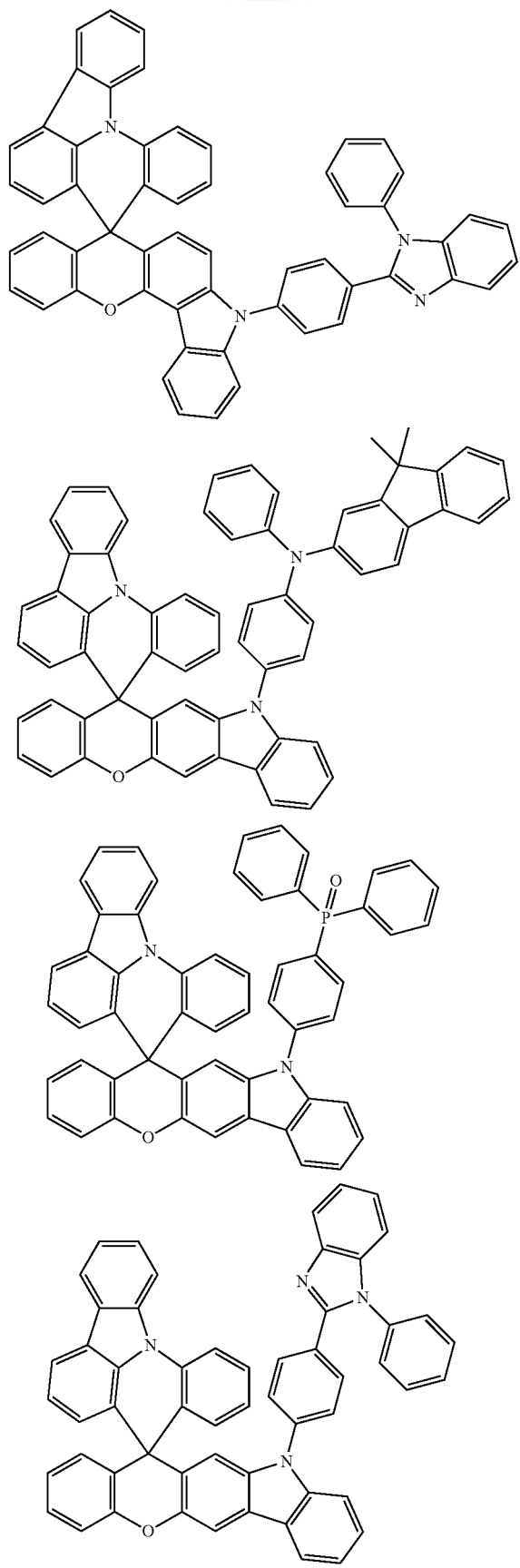
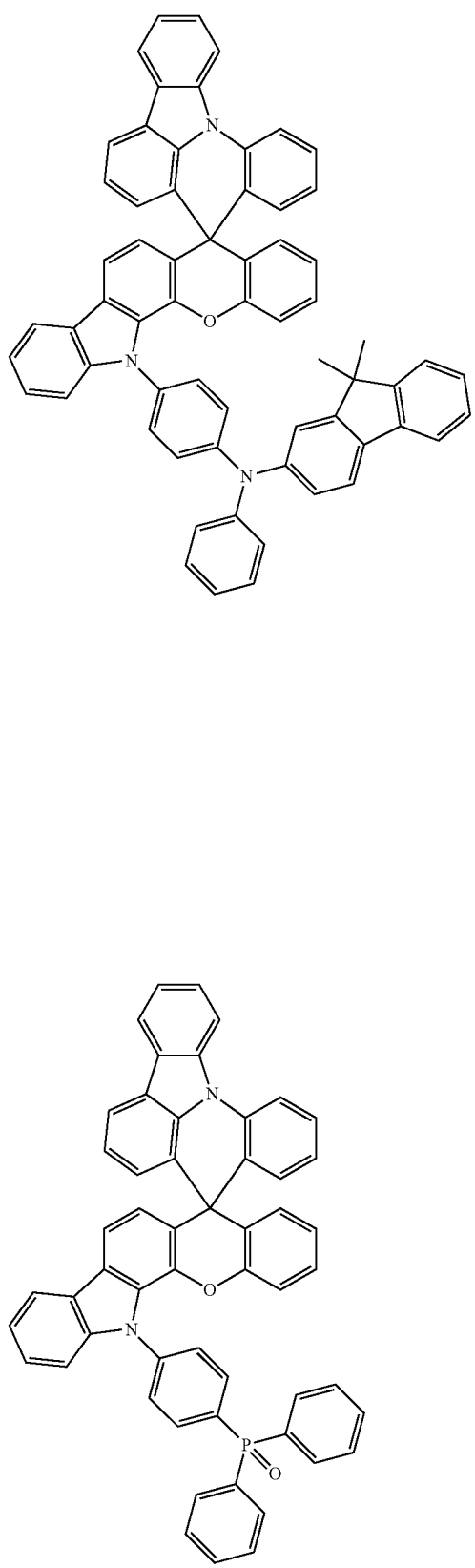

153
-continued
154
-continued
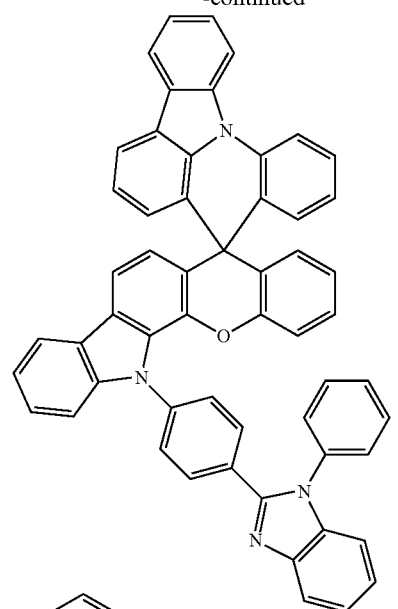
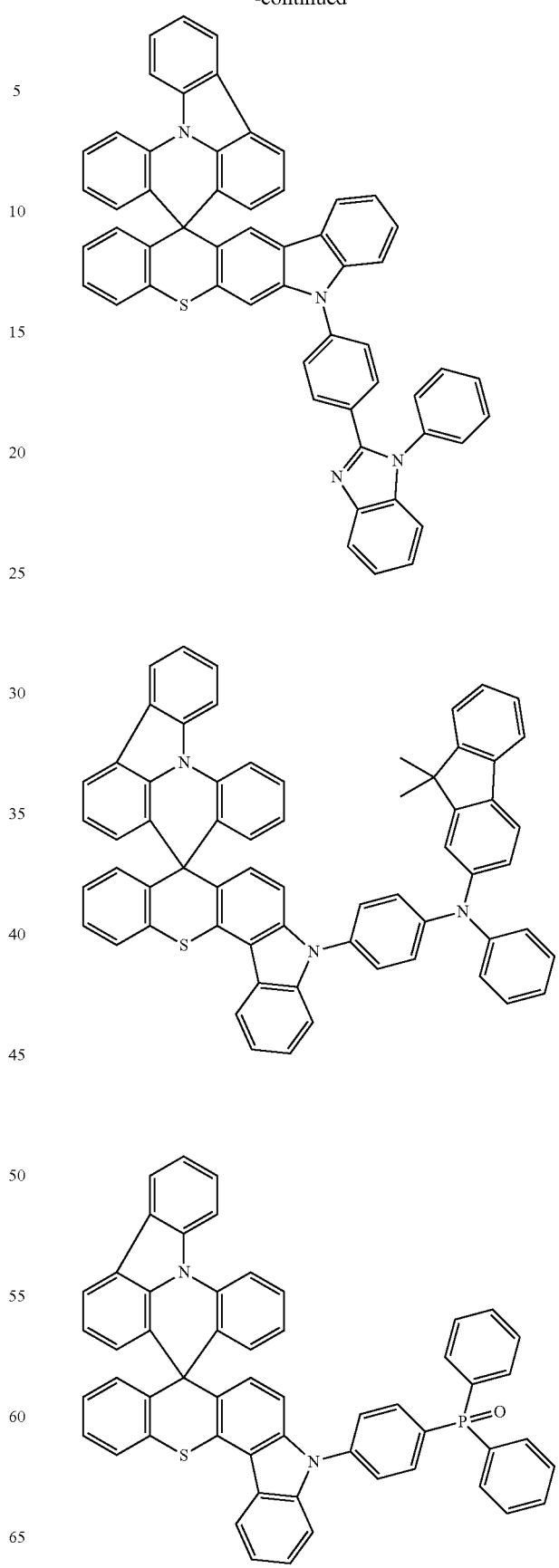

155
-continued
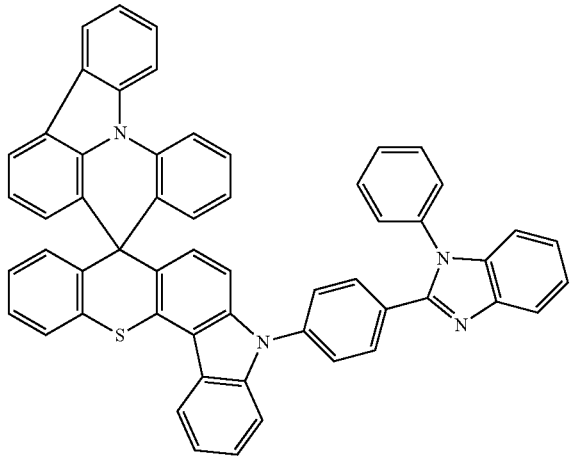
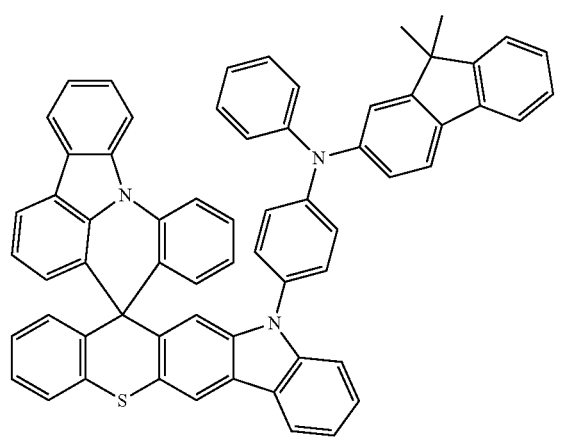
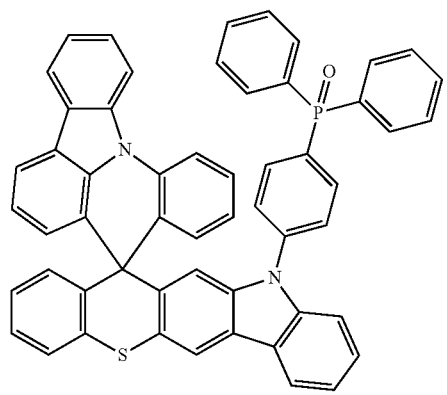
156
-continued
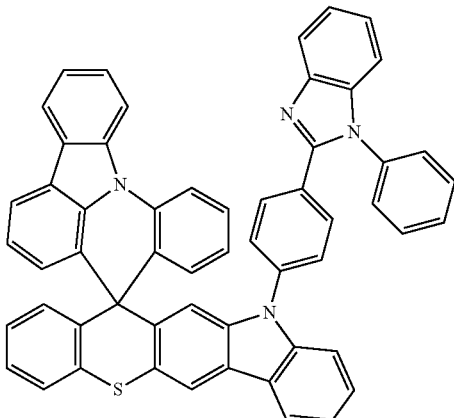
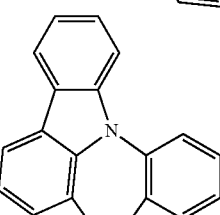
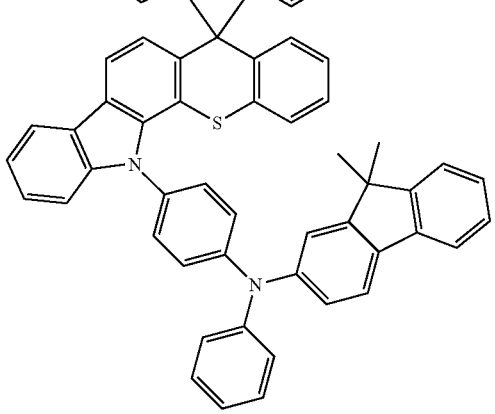
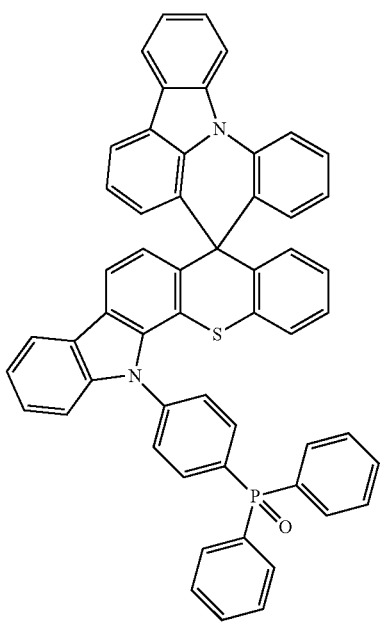

157
-continued
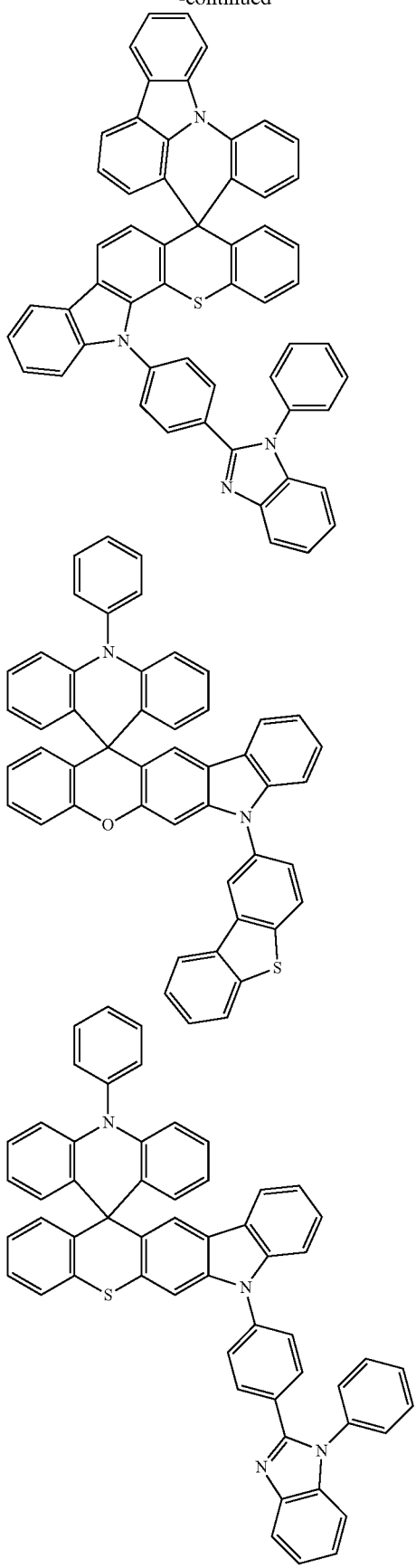
158
-continued
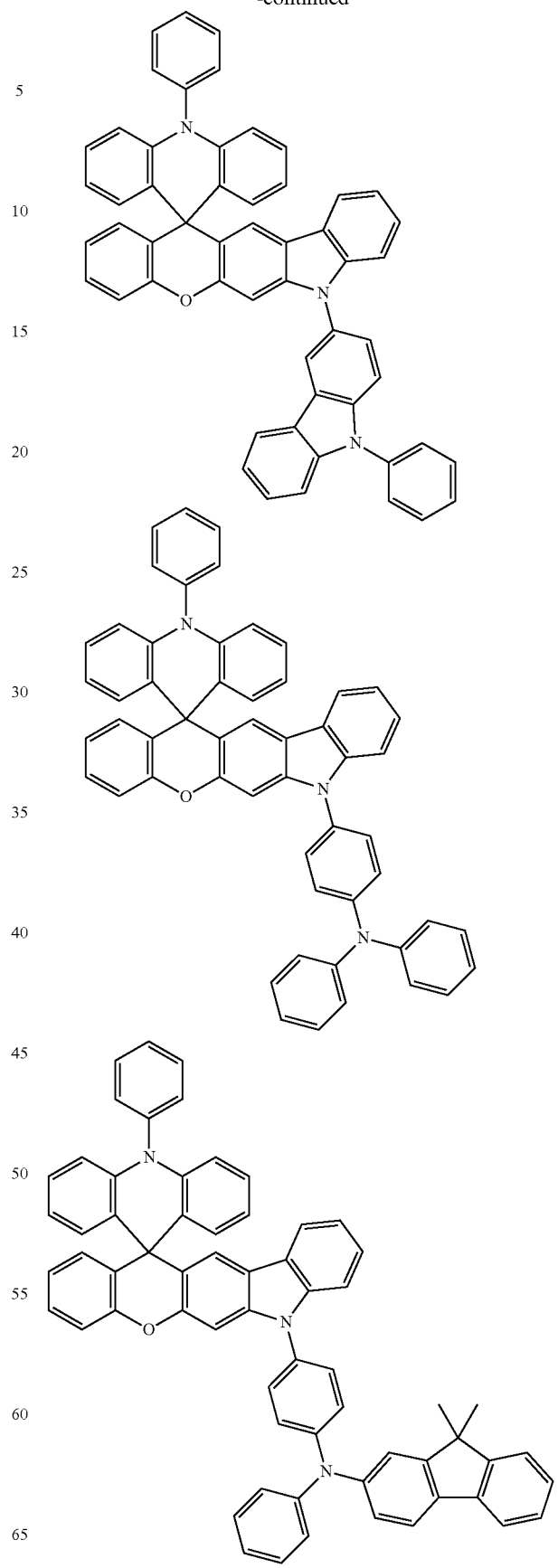

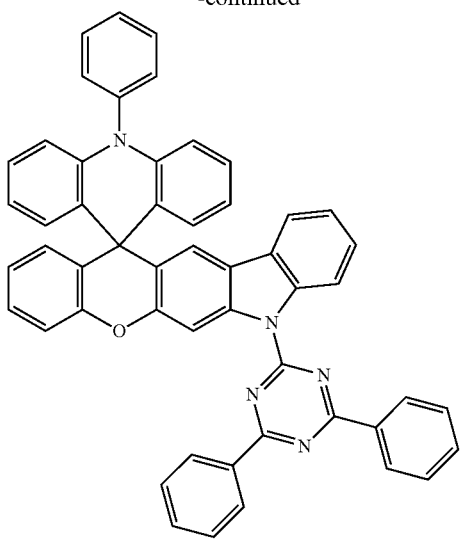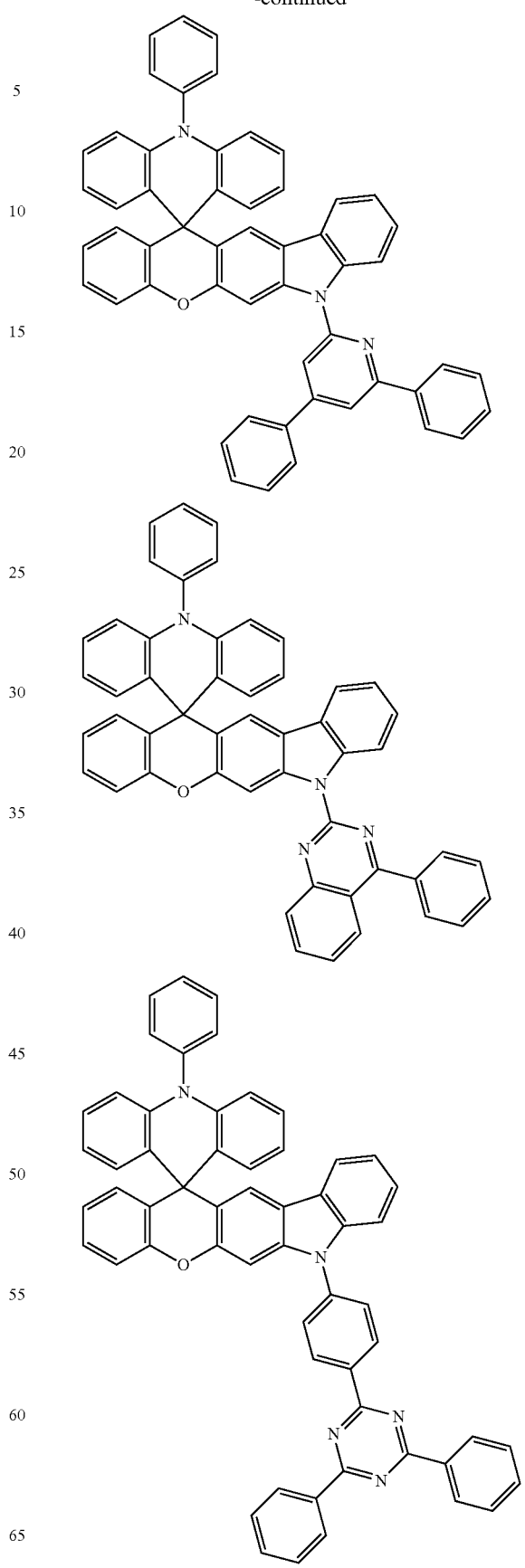

161
-continued
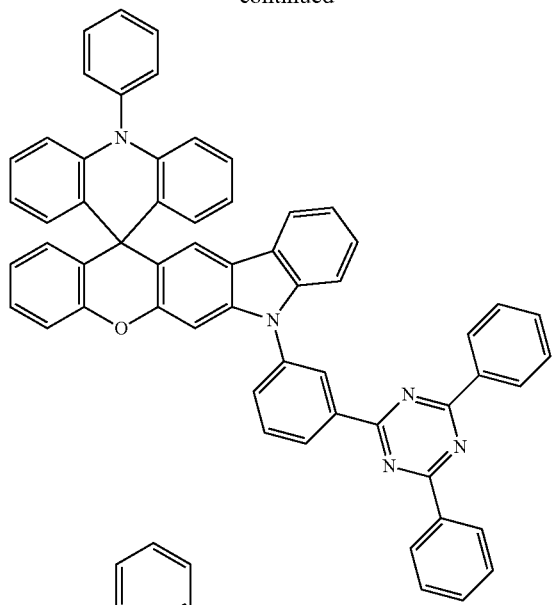
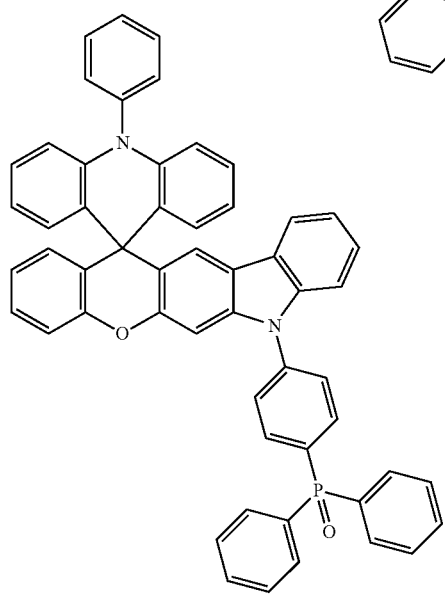
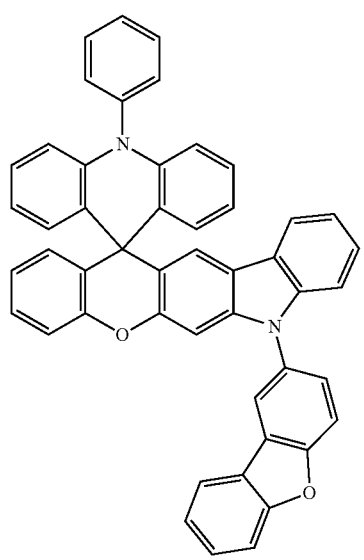
162
-continued
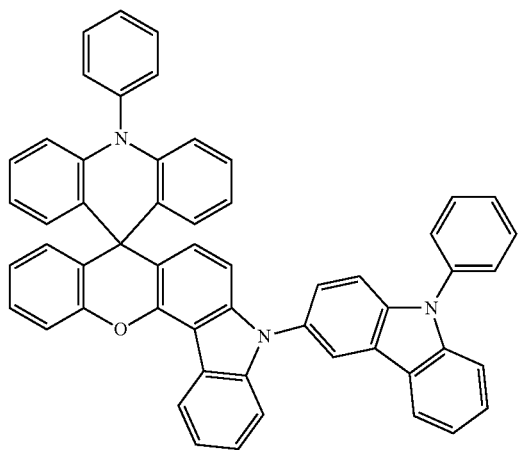
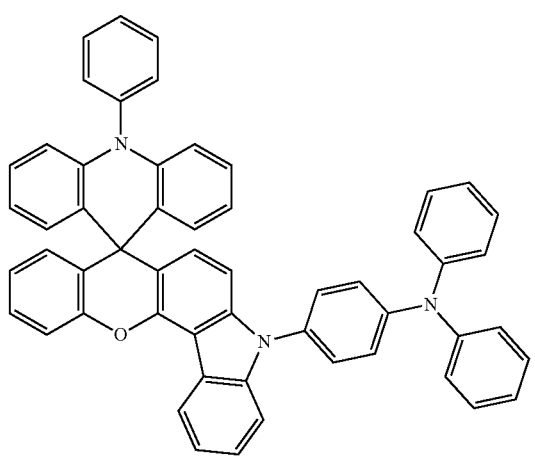
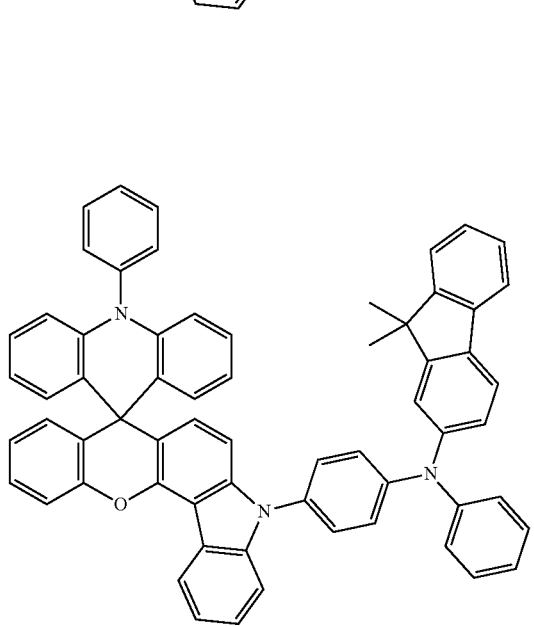

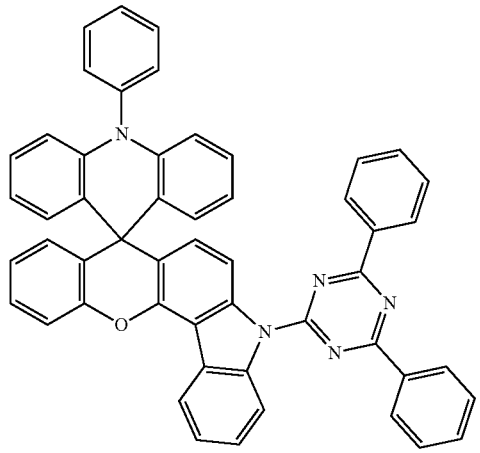
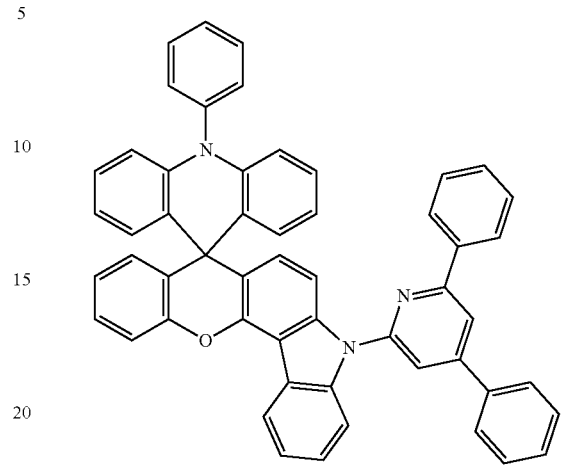
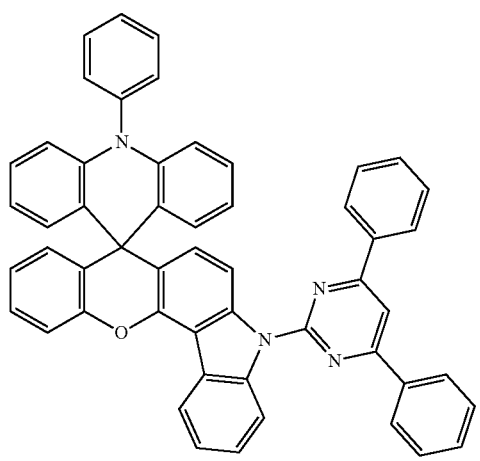
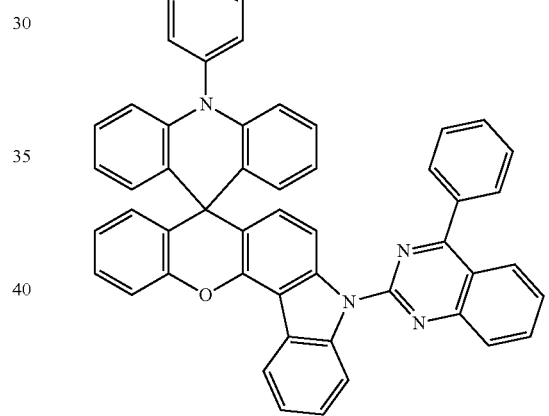
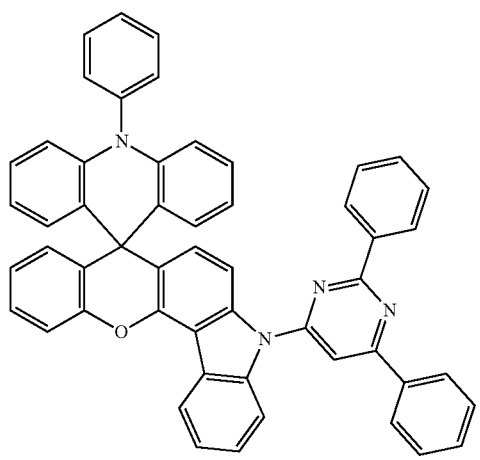
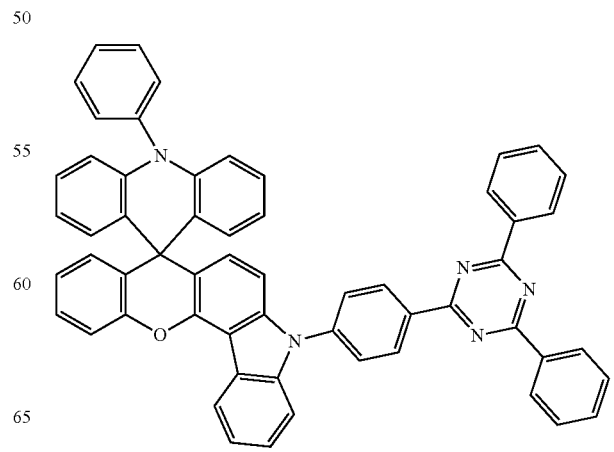

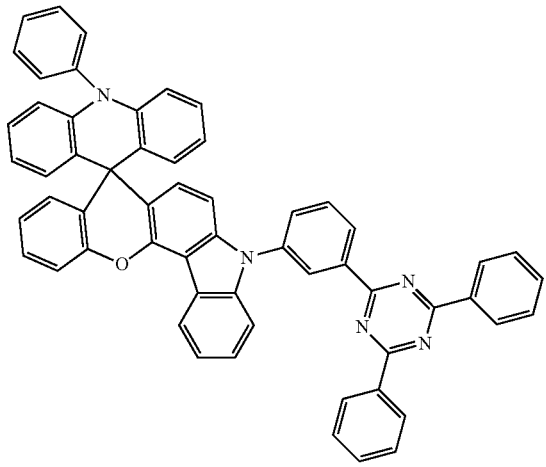
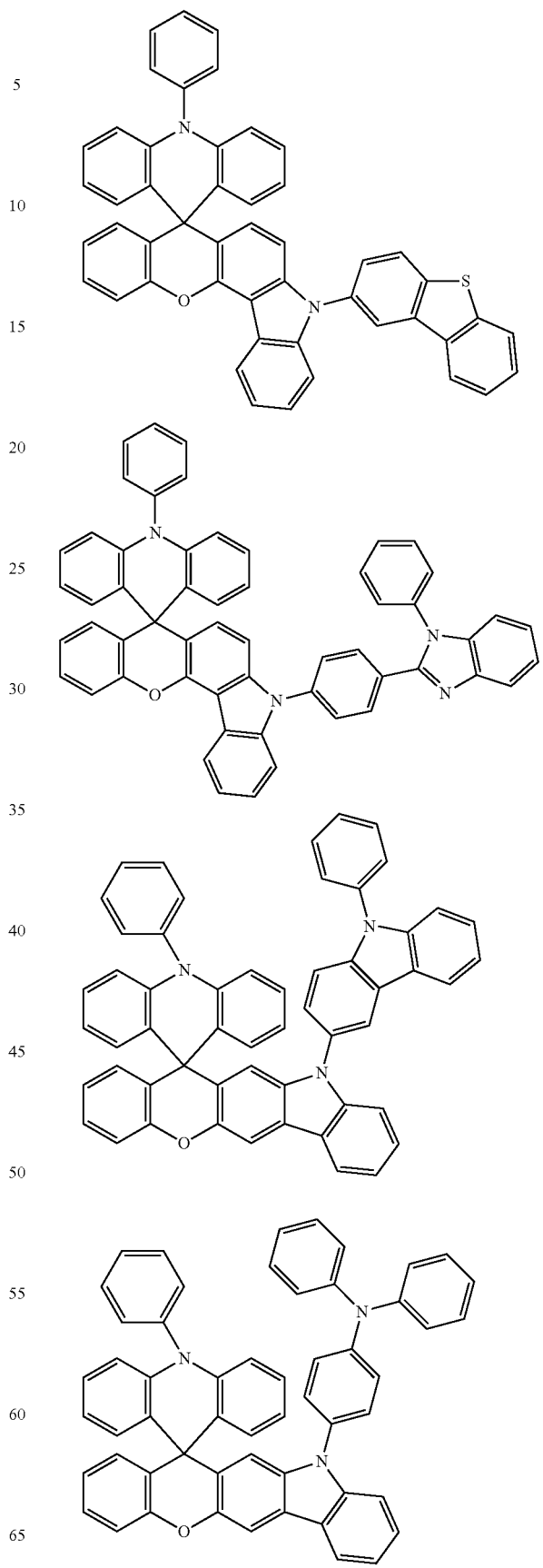

167
-continued
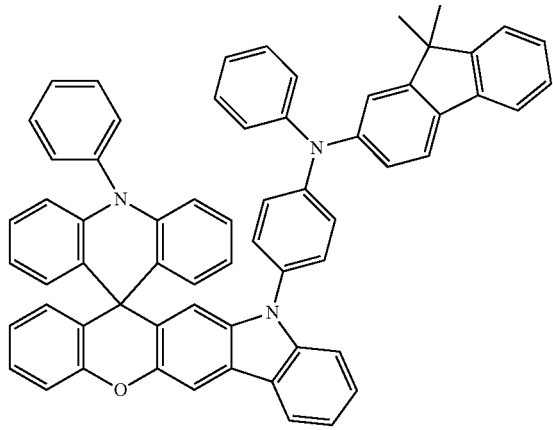
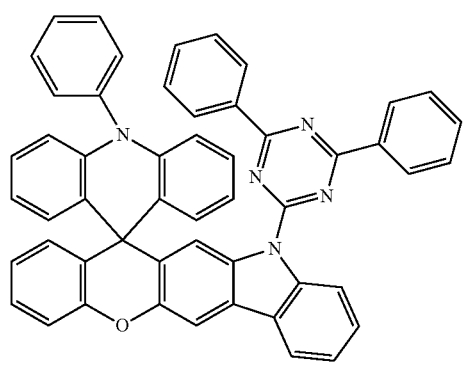
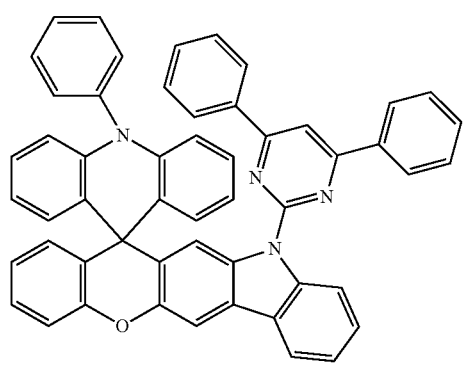
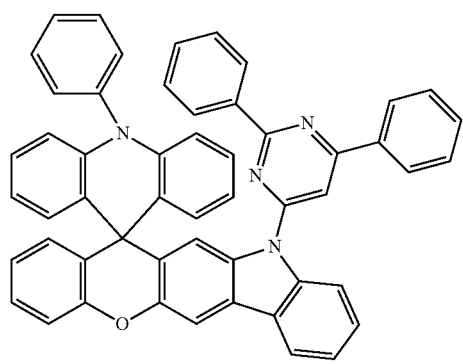
168
-continued
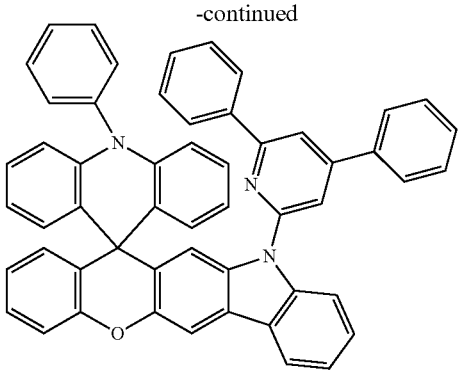
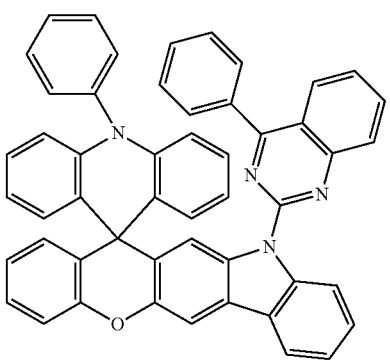
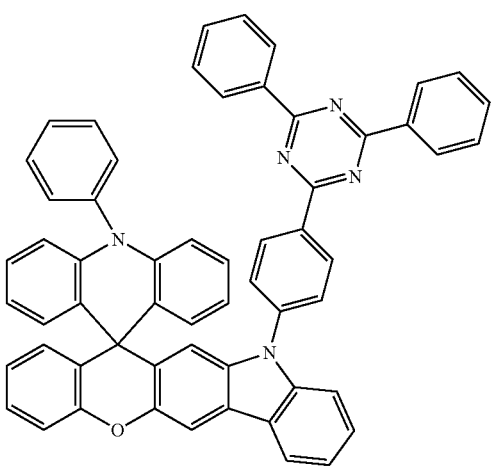
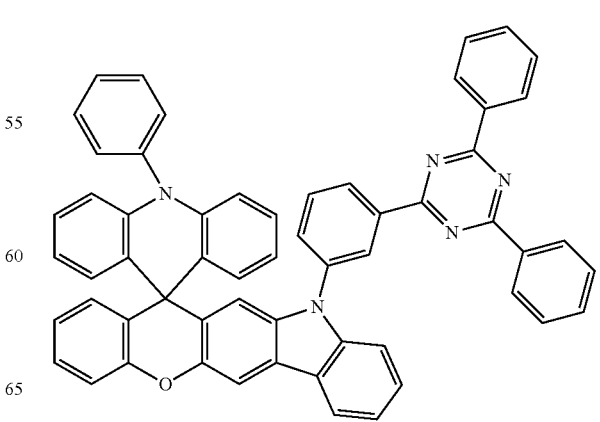

169
-continued
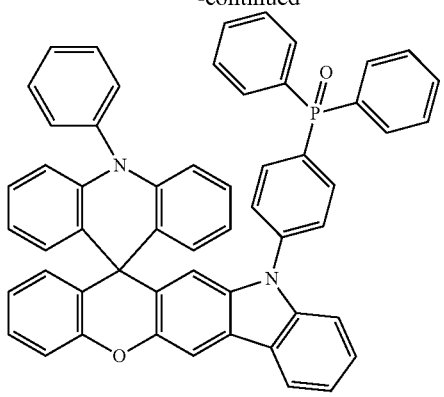
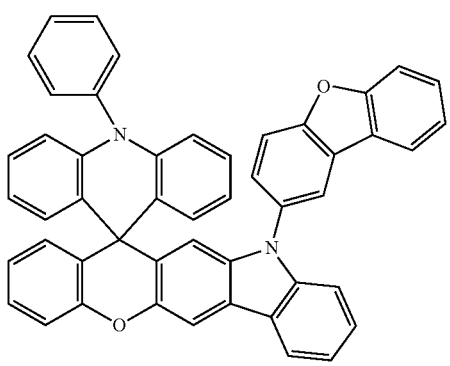
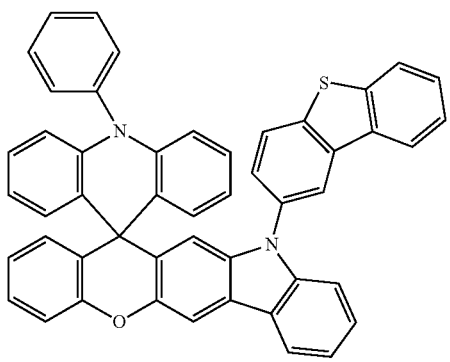
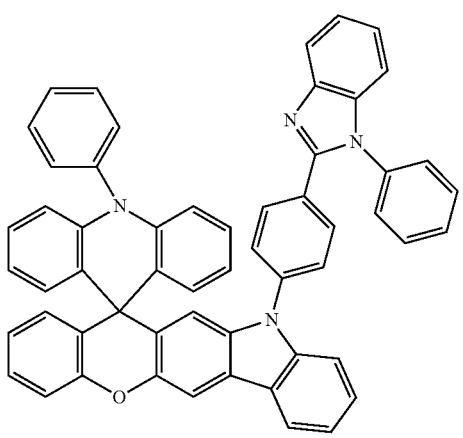
170
-continued
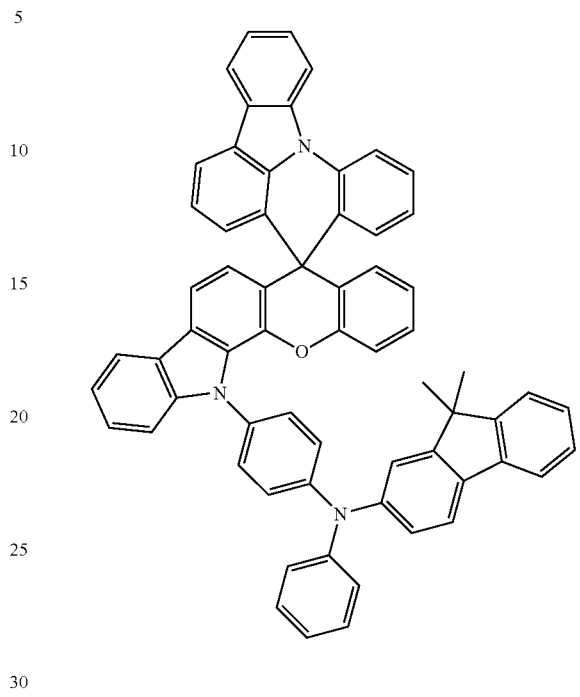
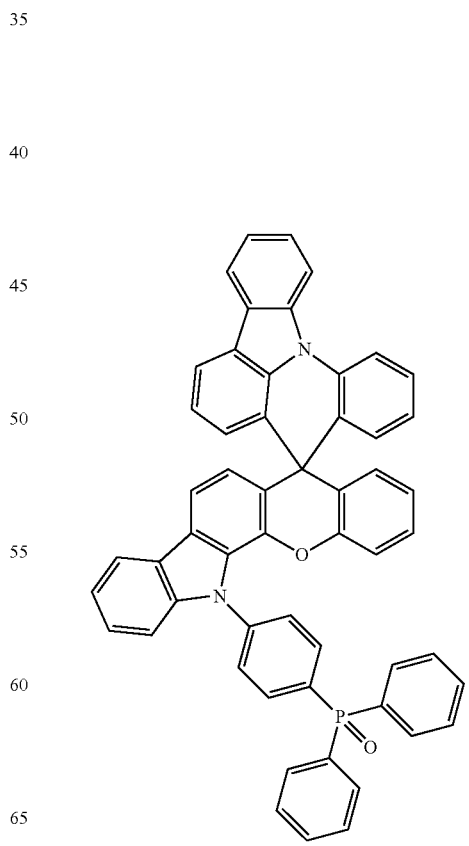

171
-continued
172
-continued
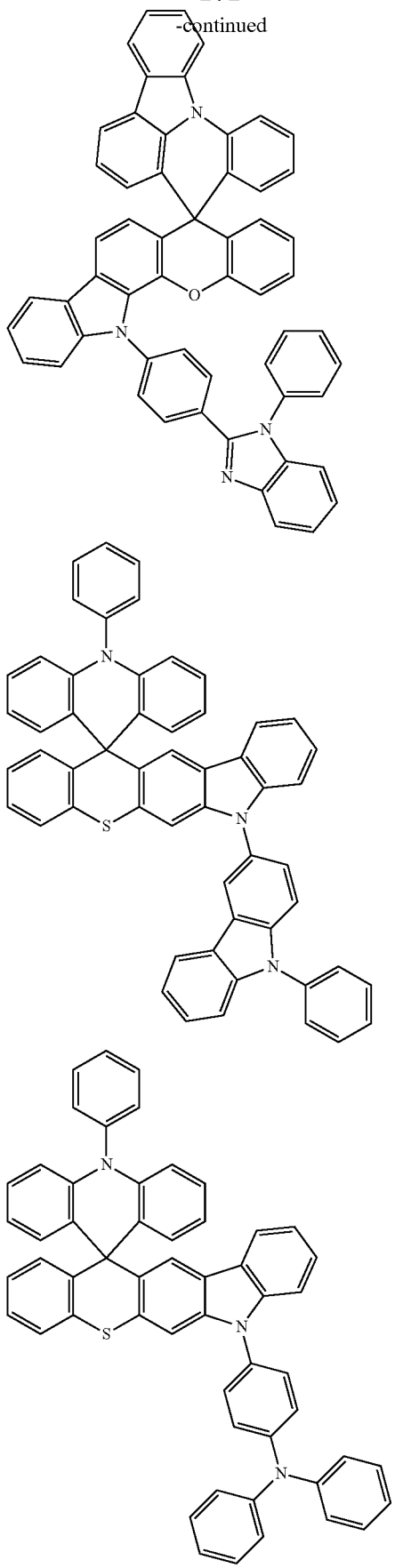
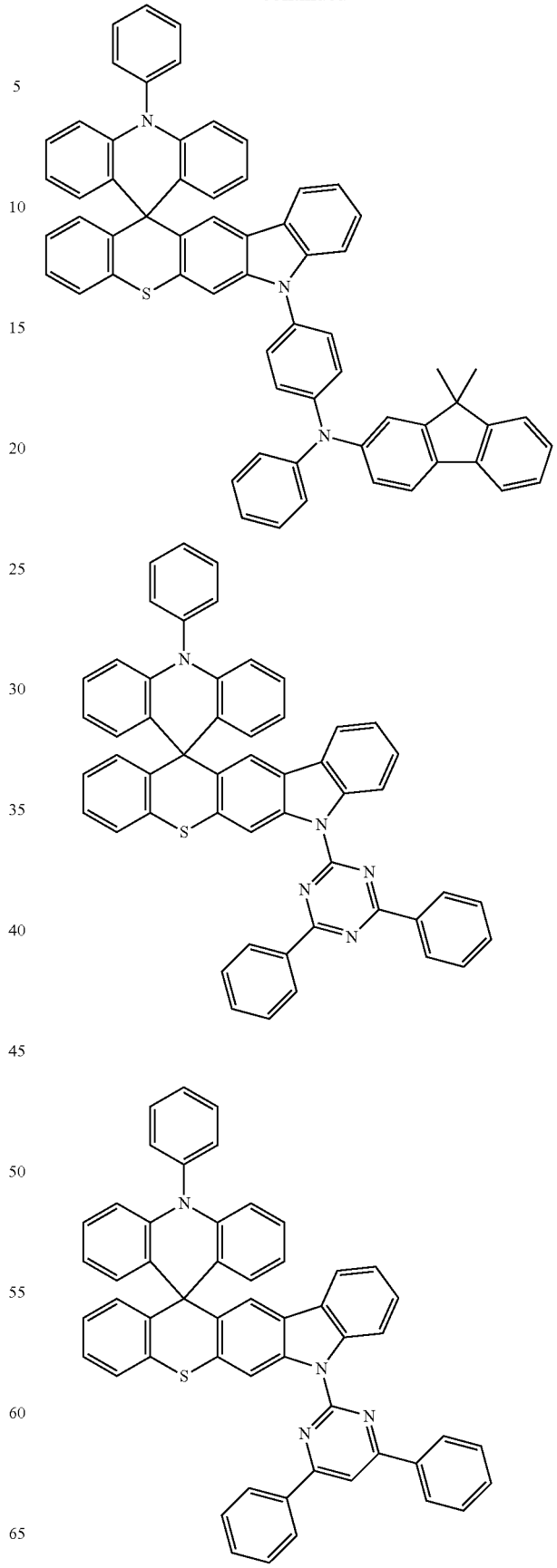

173
-continued
174
-continued
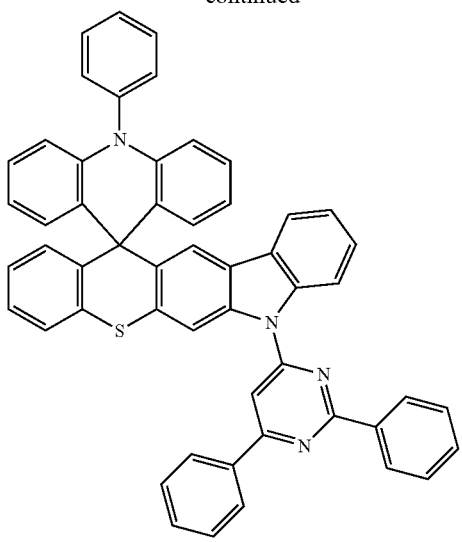
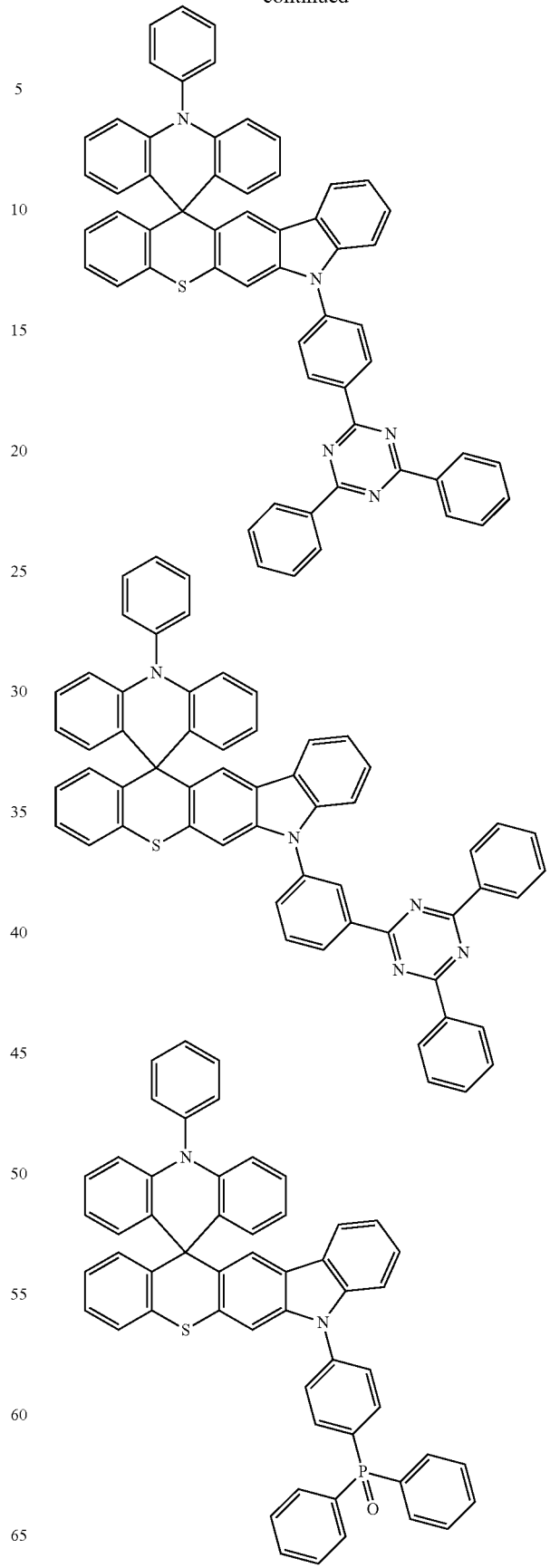

175
-continued
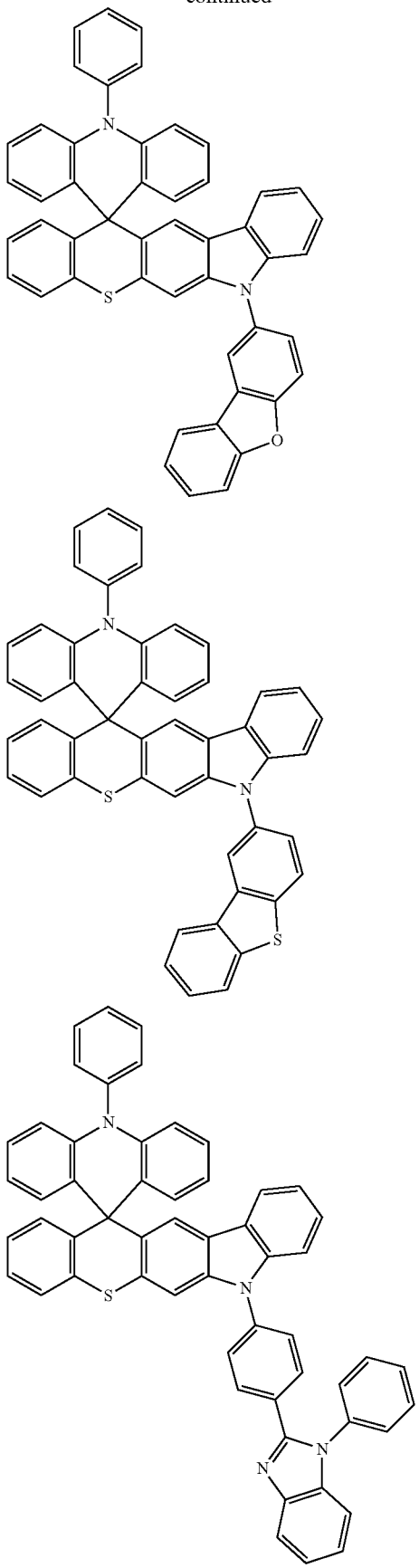
176
-continued
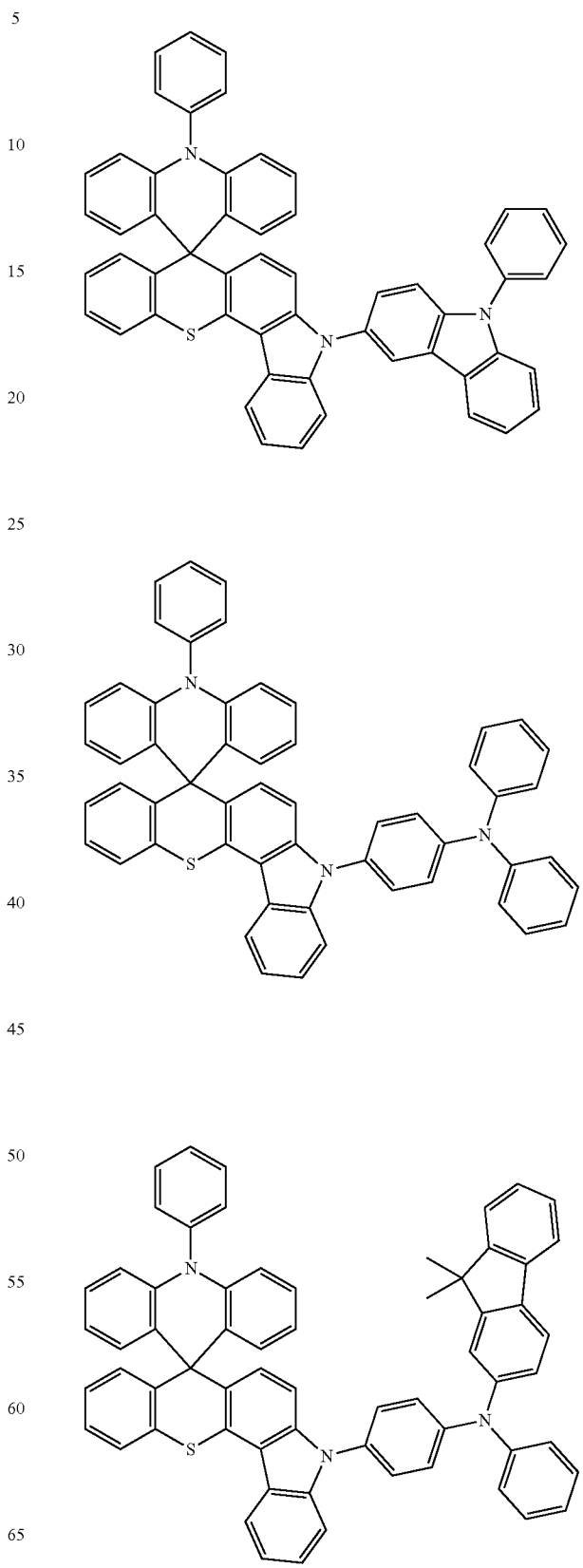

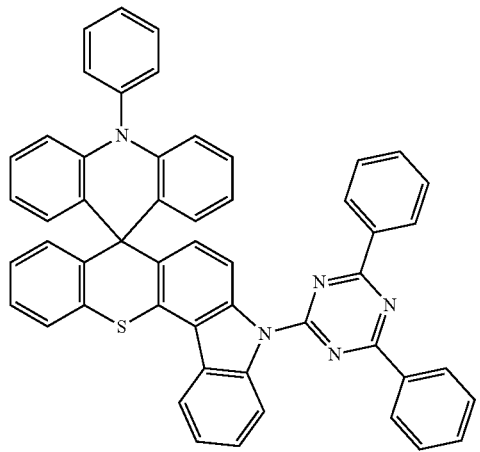
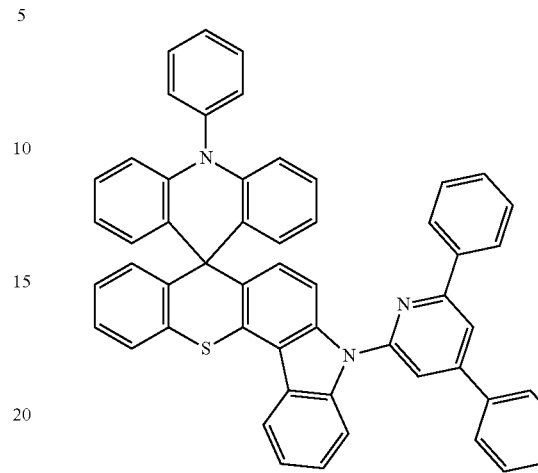
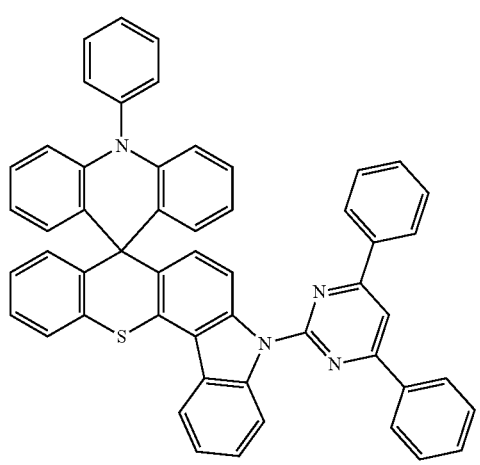
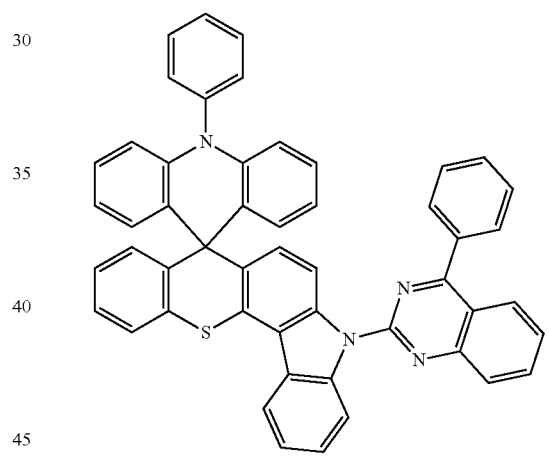
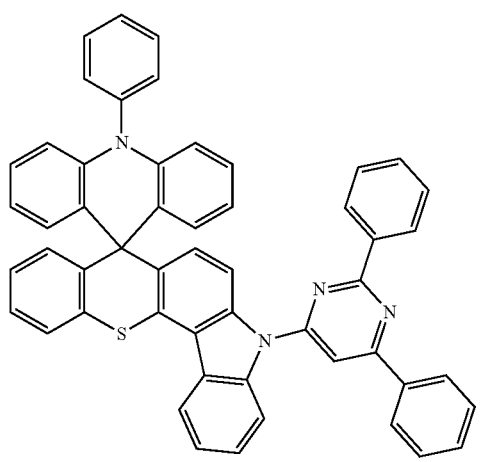
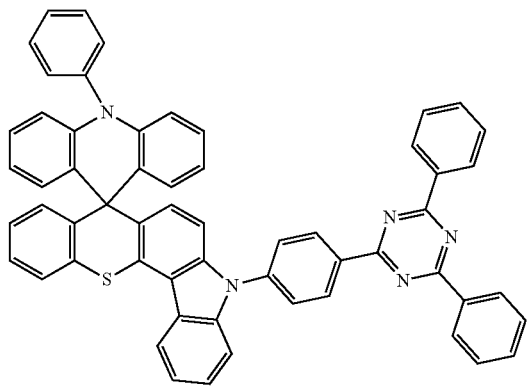

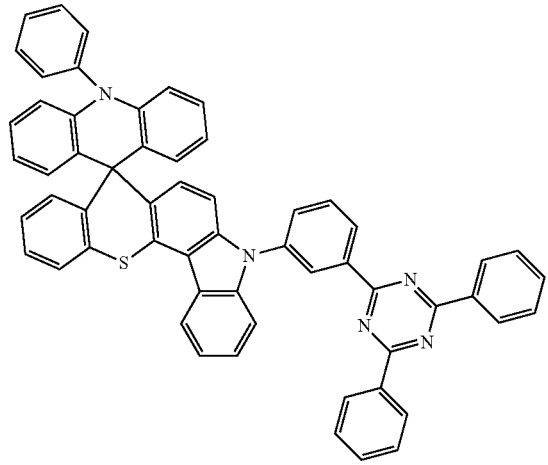
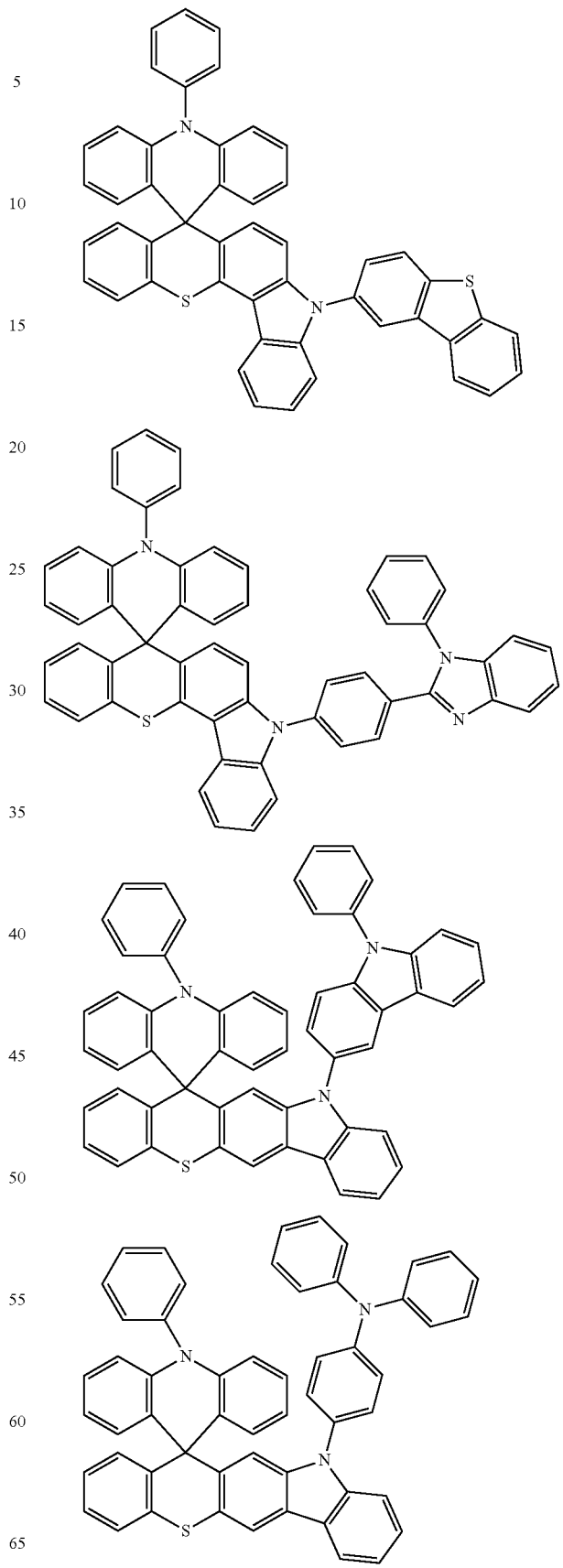

181
-continued
182
-continued
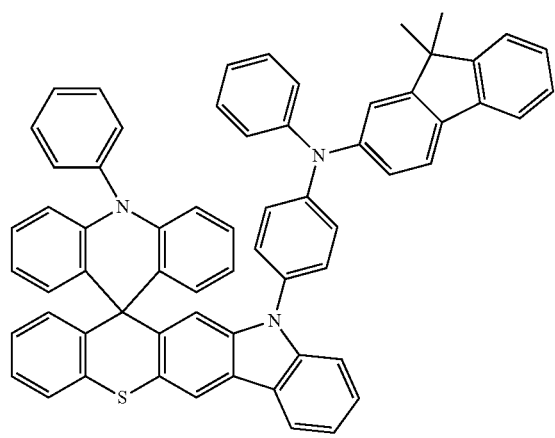
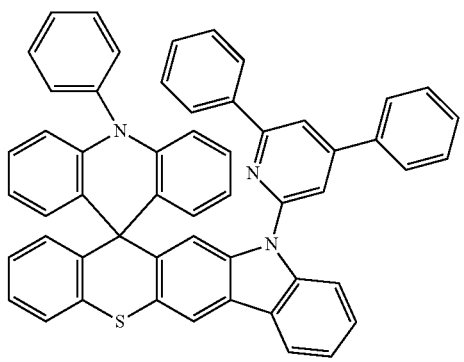
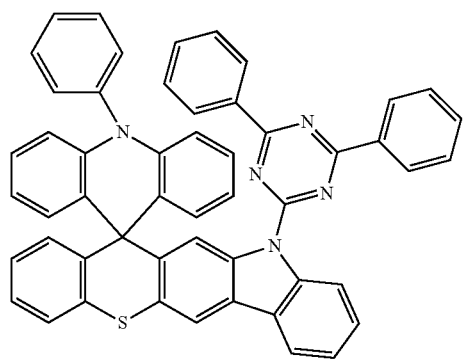
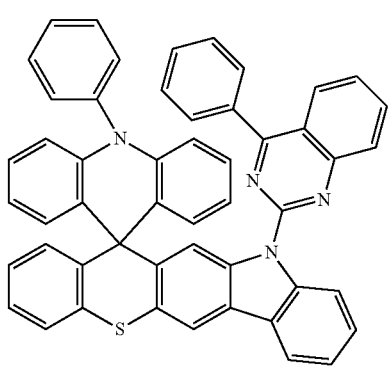
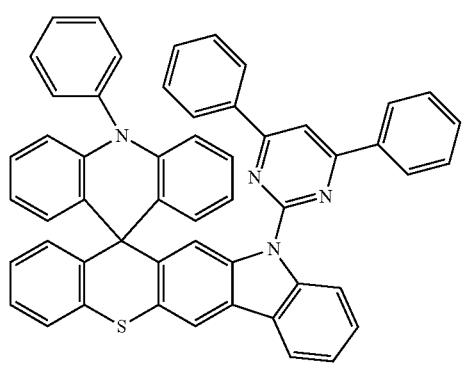
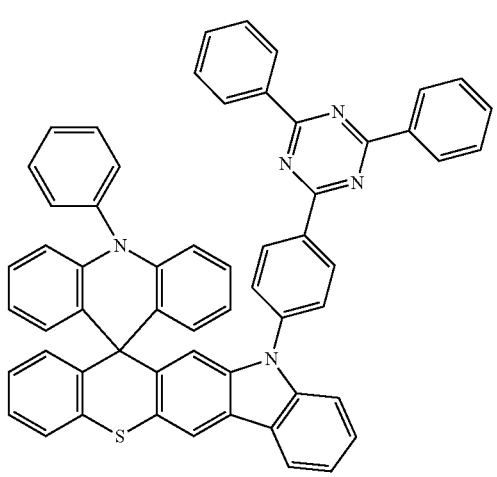
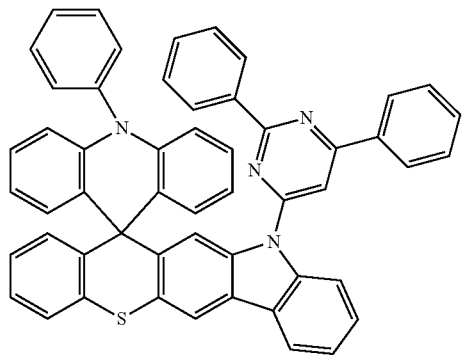
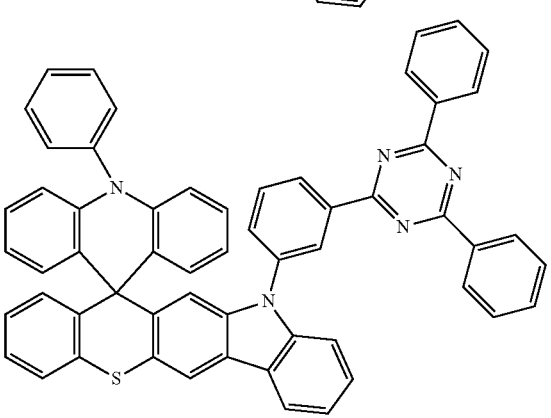

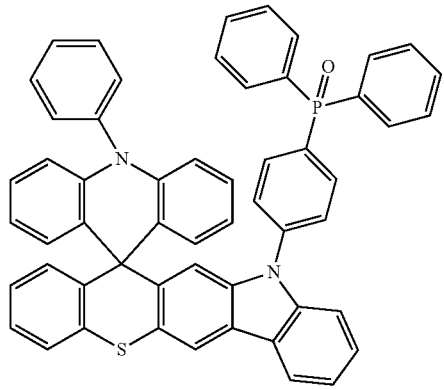
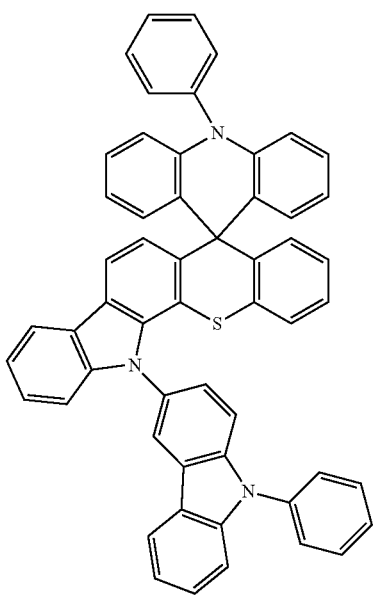
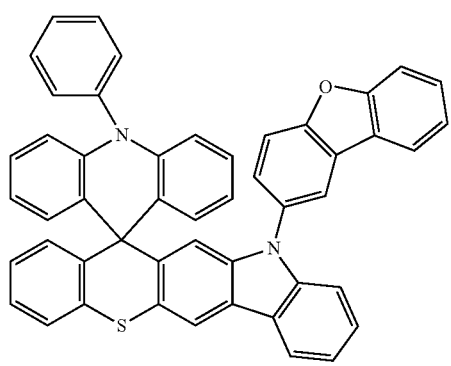
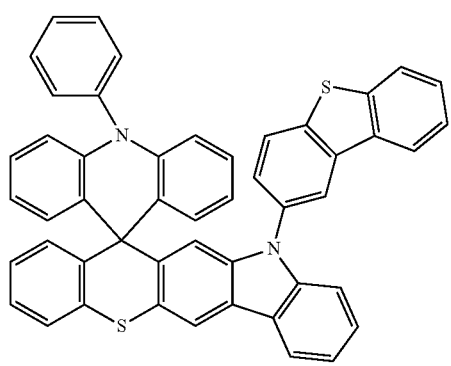
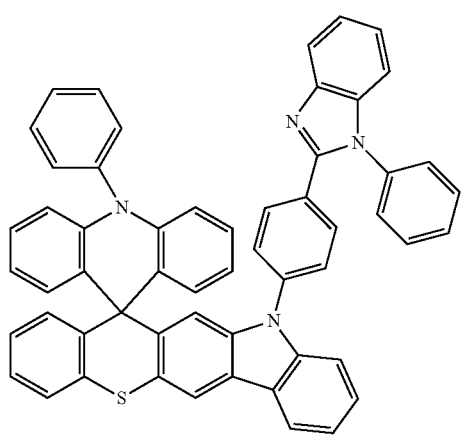
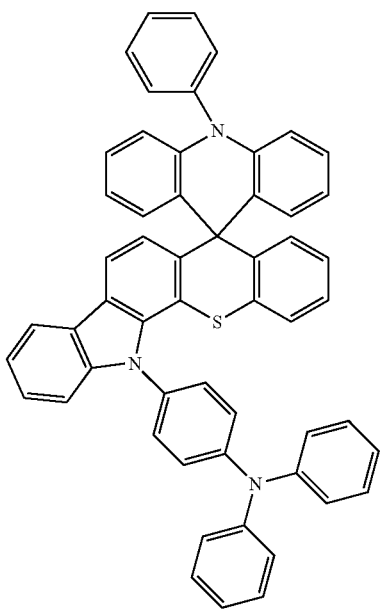

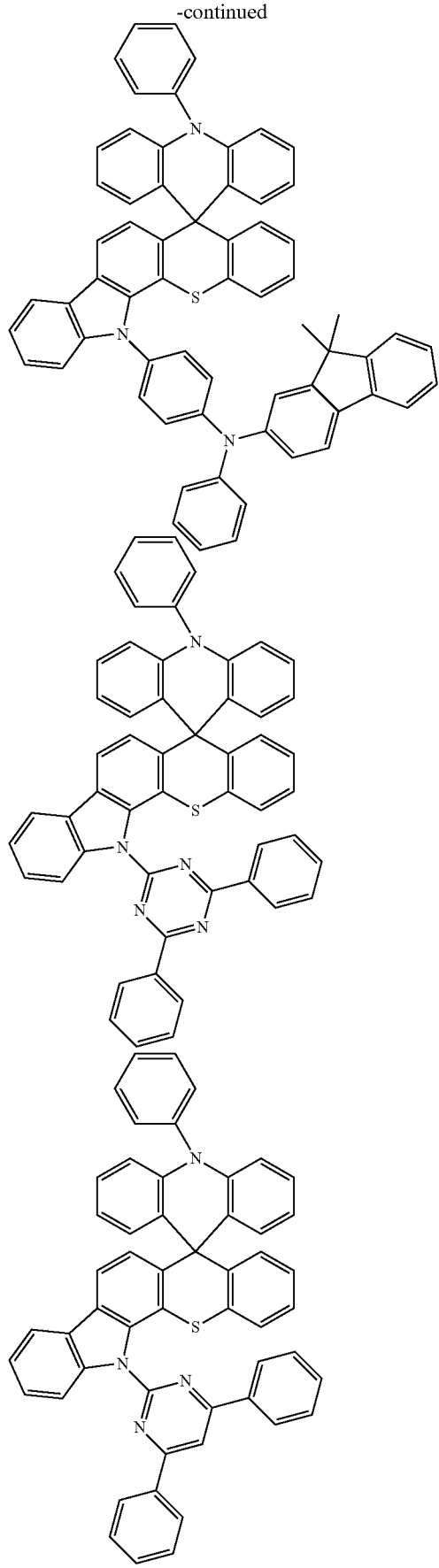
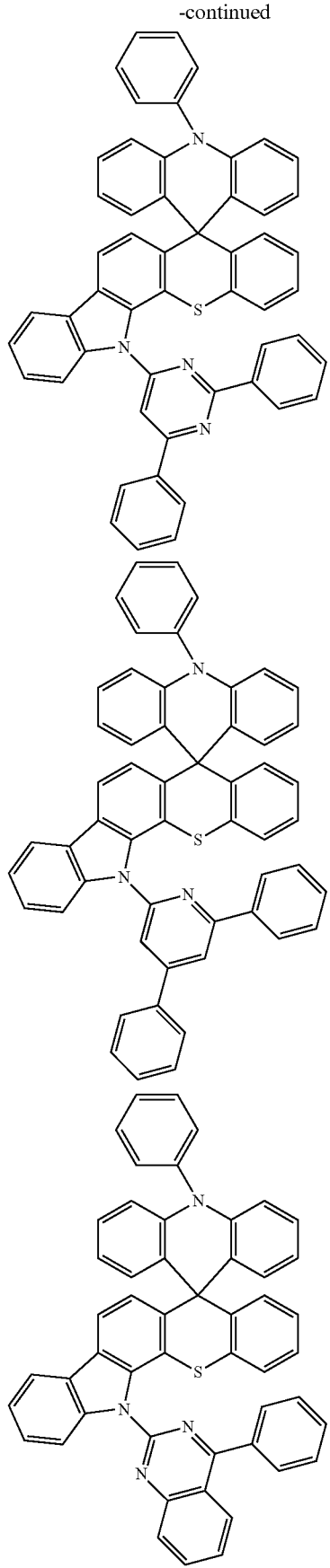

187
-continued
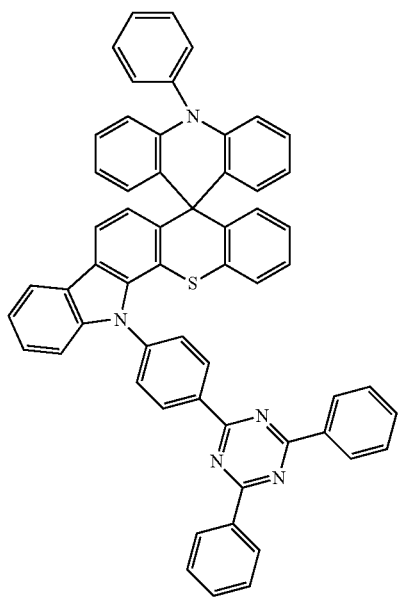
188
-continued
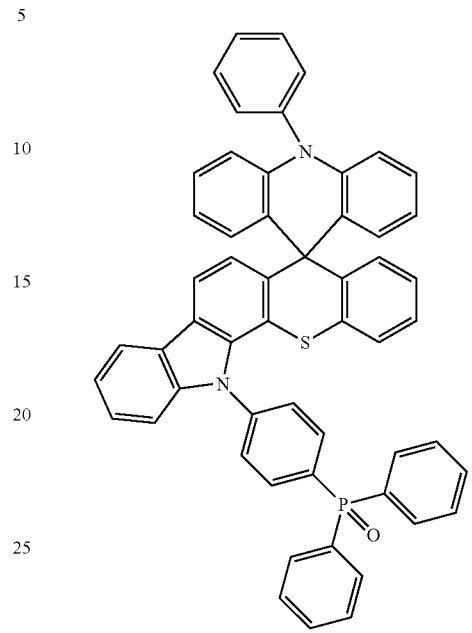
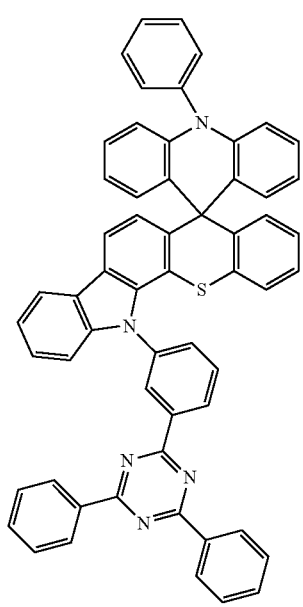
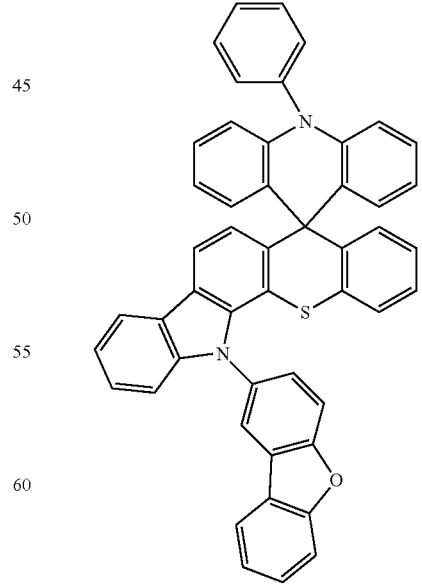

189
-continued
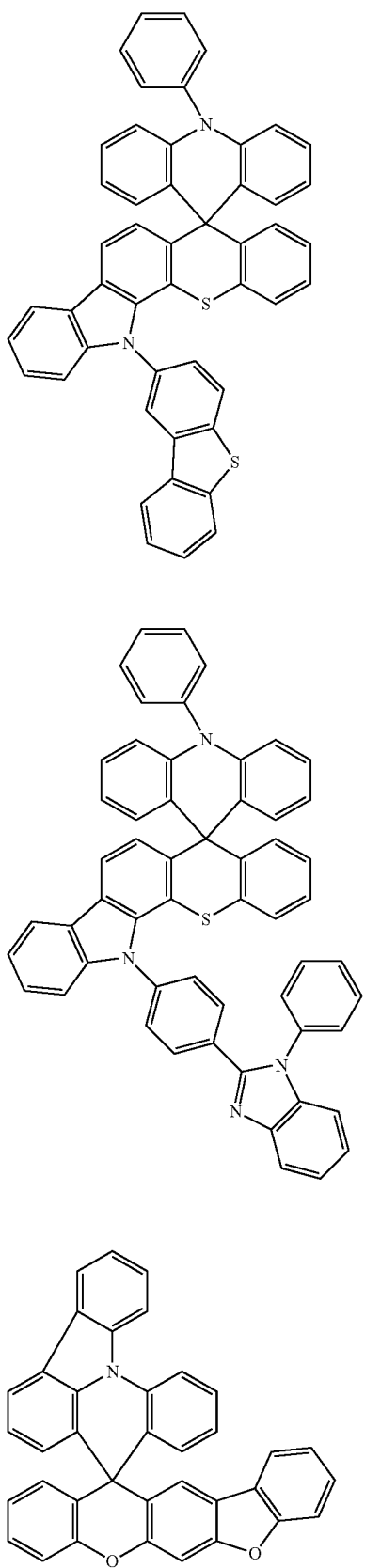
190
-continued
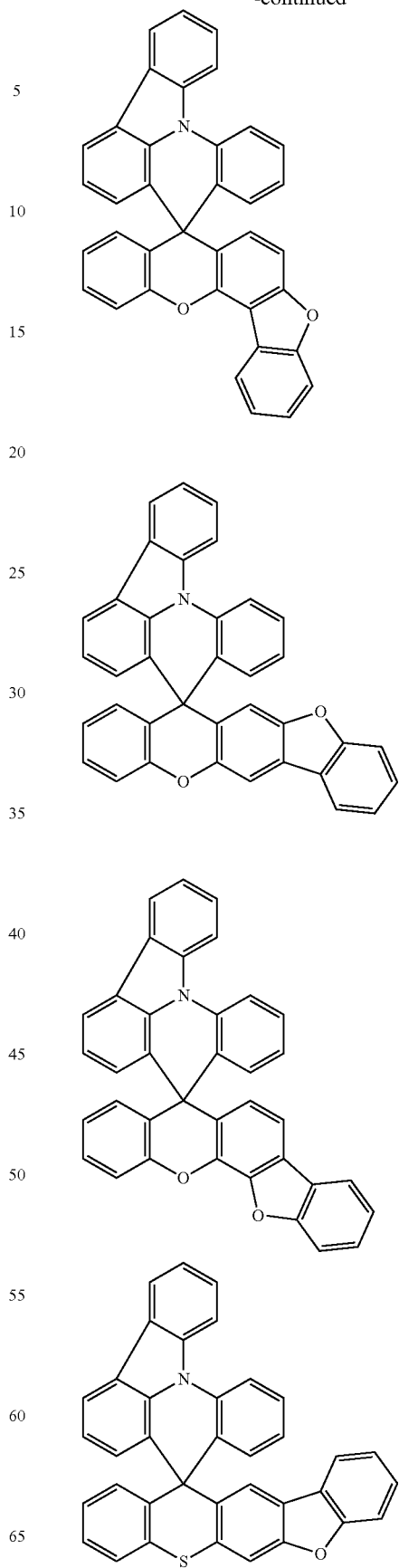

191
-continued
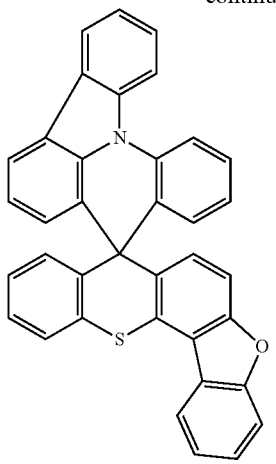
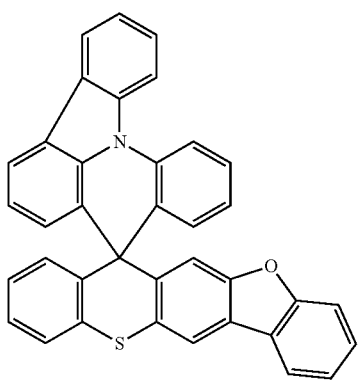
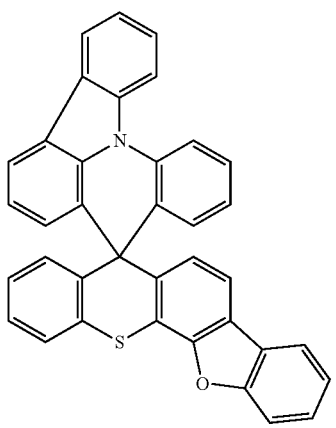
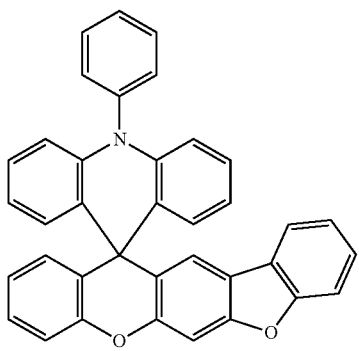
192
-continued
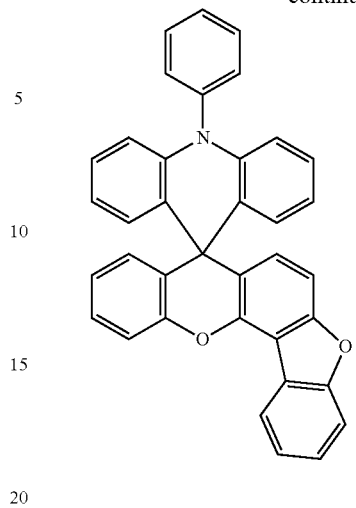
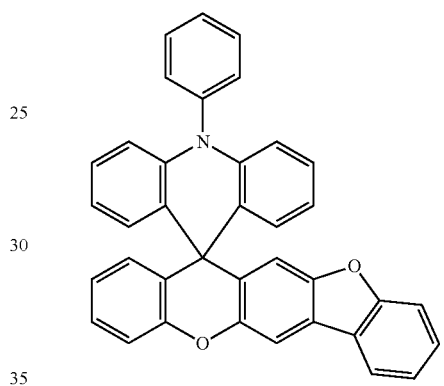
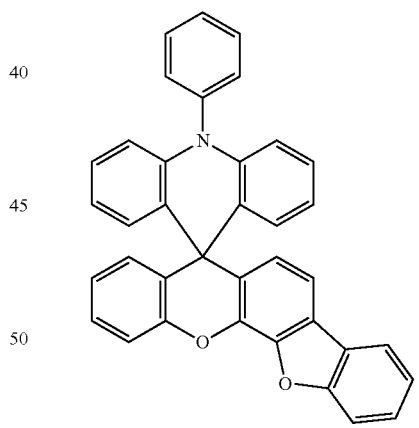
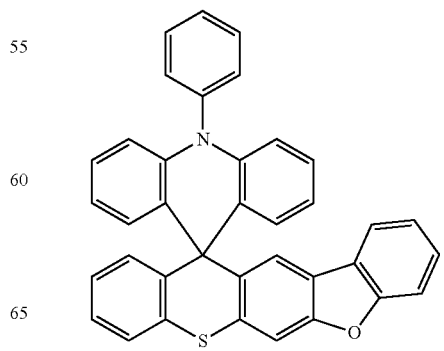

193 194
-continued -continued
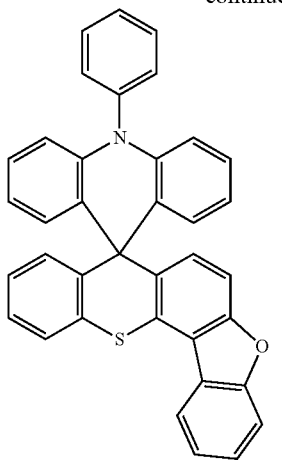
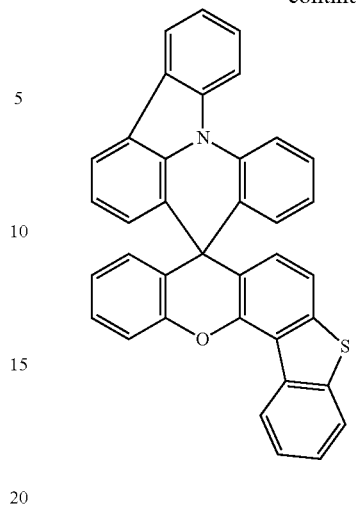
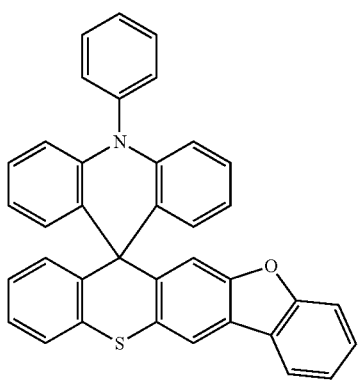
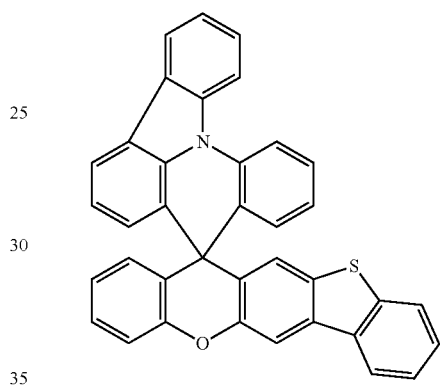
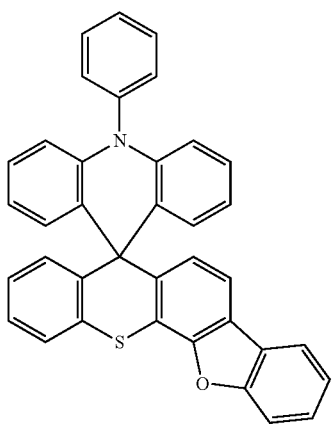
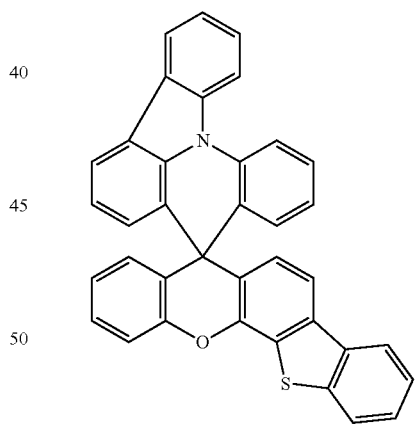
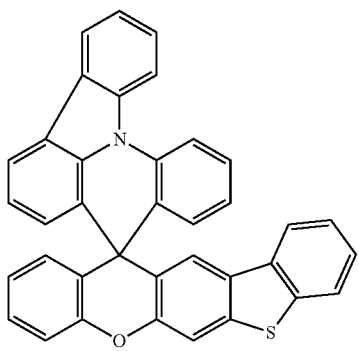
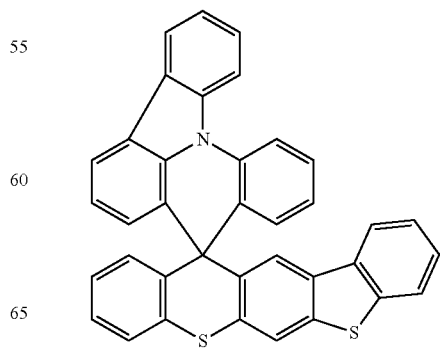

195
-continued
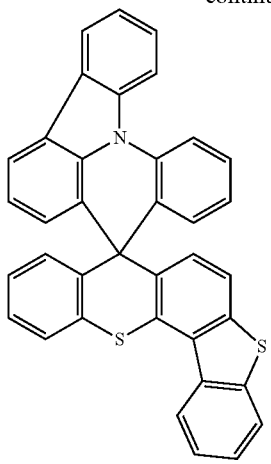
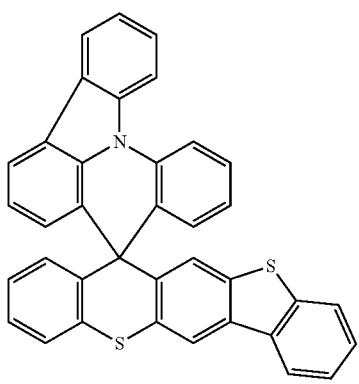
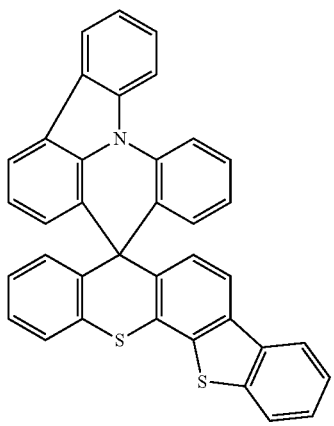
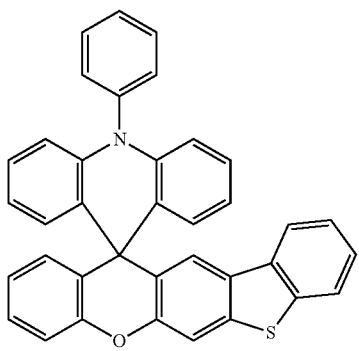
196
-continued
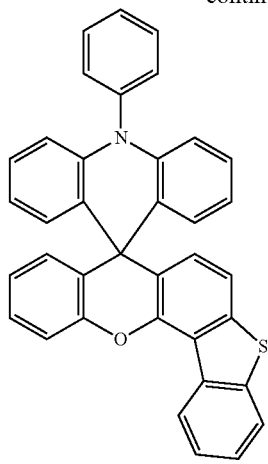
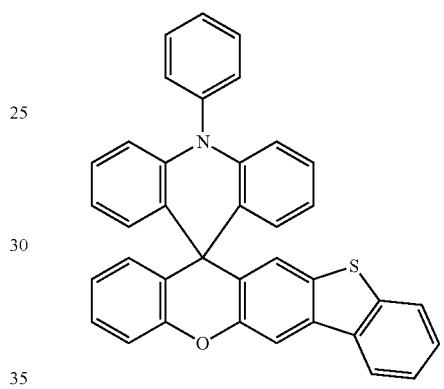
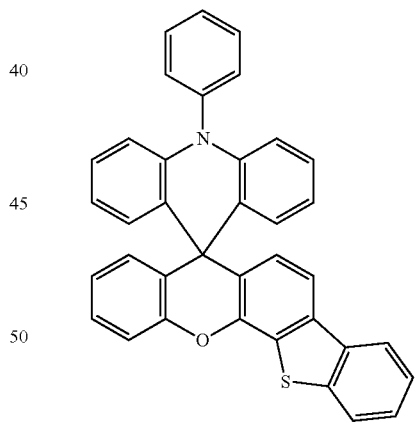
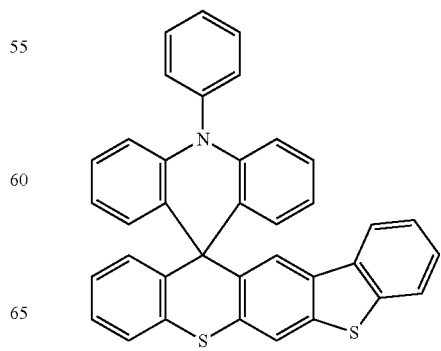

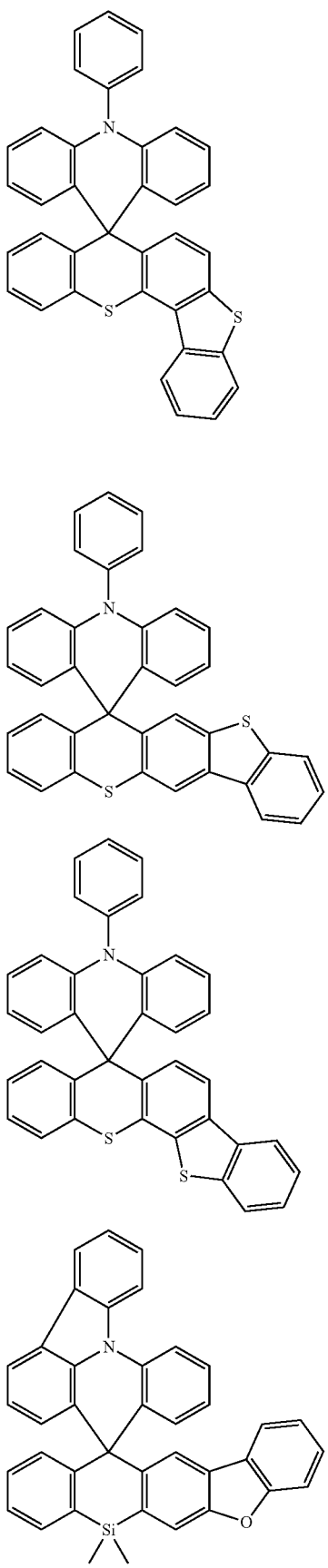
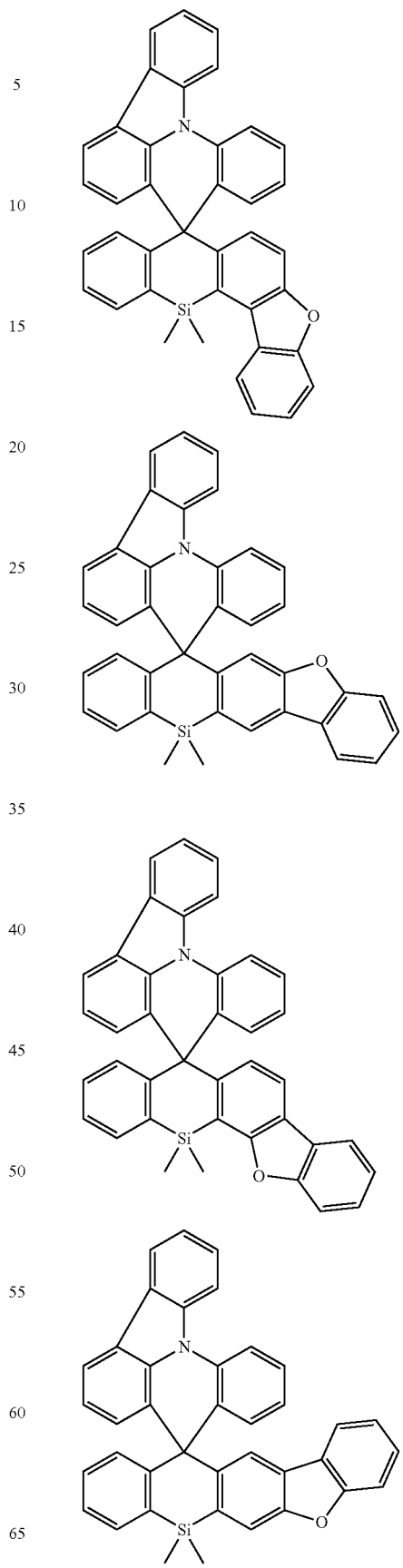

199
-continued
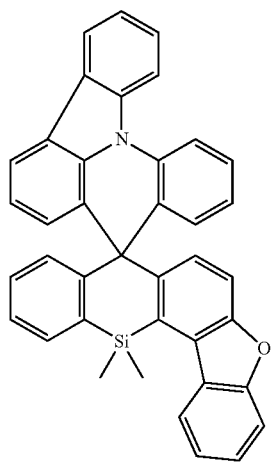
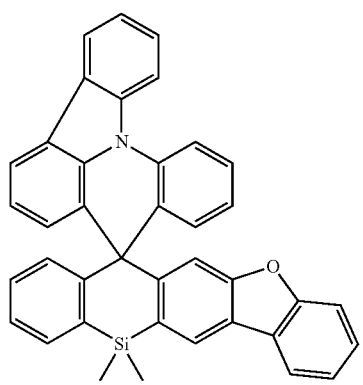
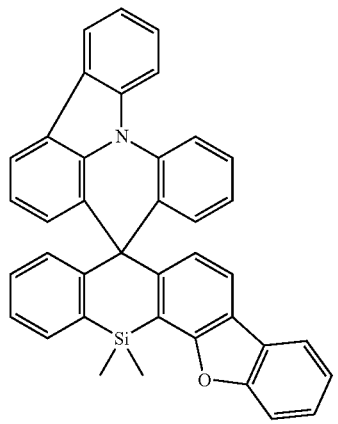
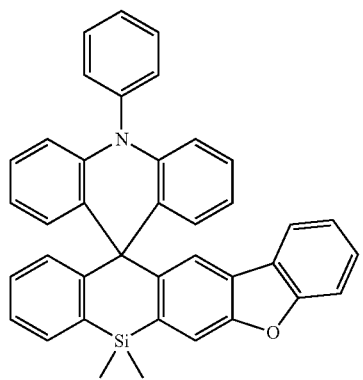
200
-continued
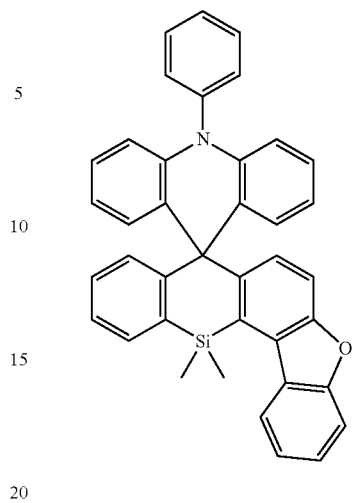
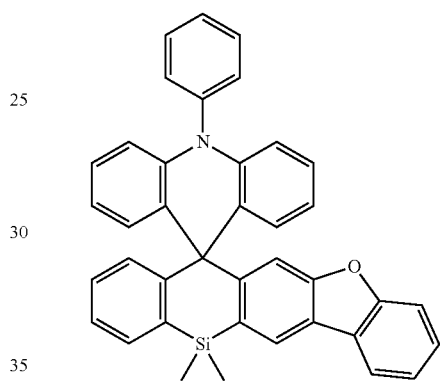
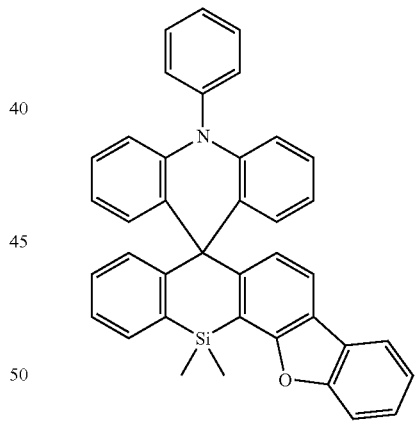
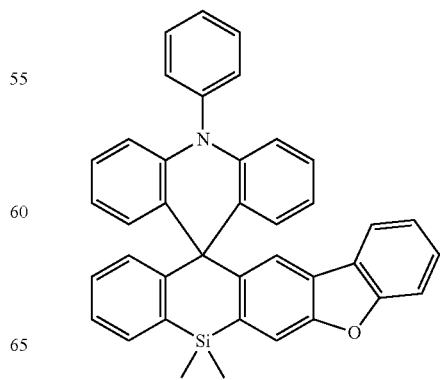

201
-continued
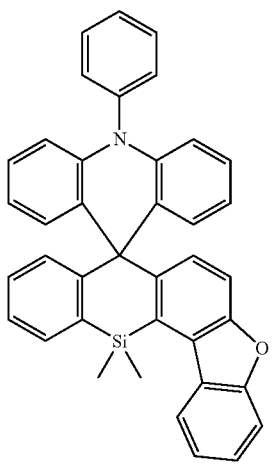
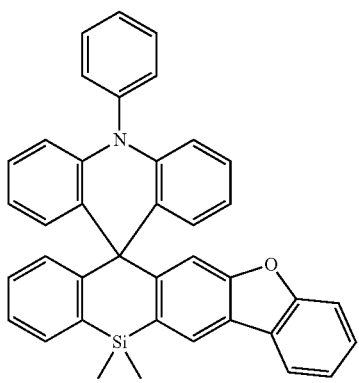
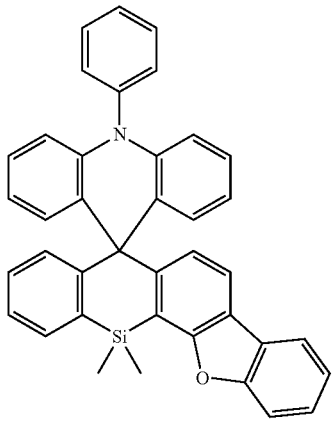
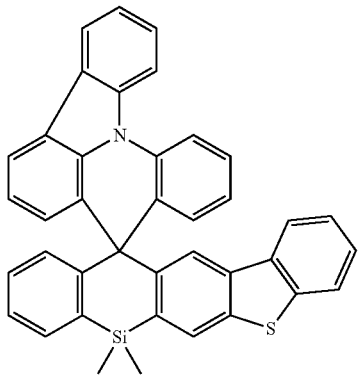
202
-continued
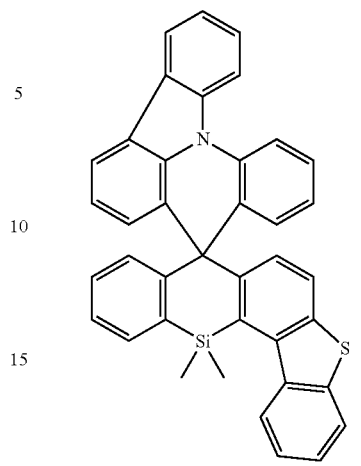
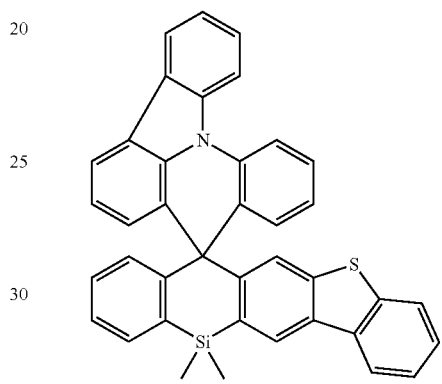
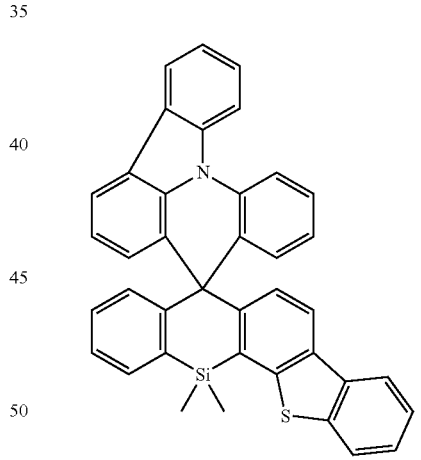
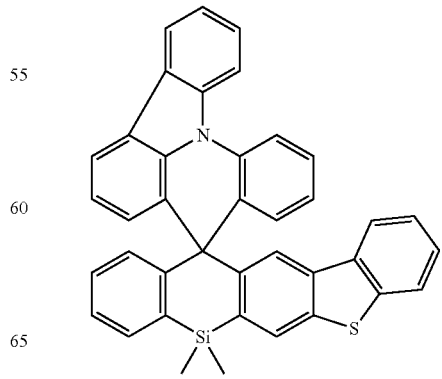

203
-continued
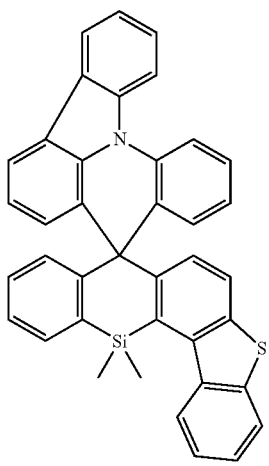
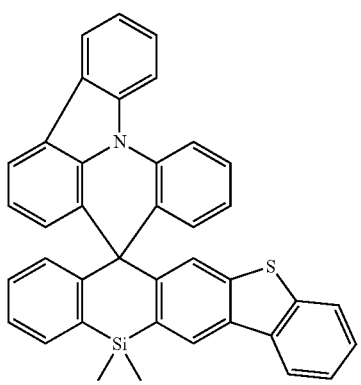
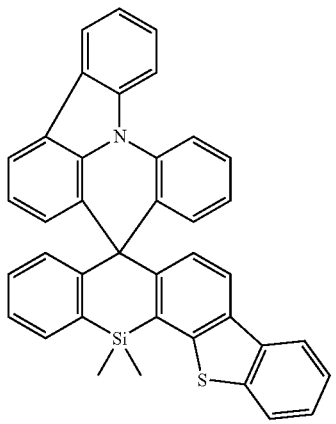
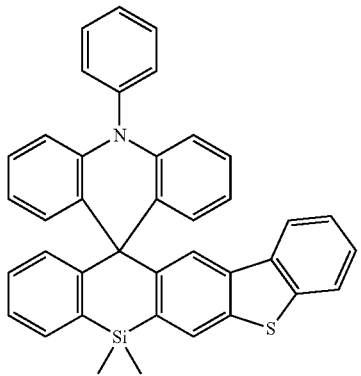
204
-continued
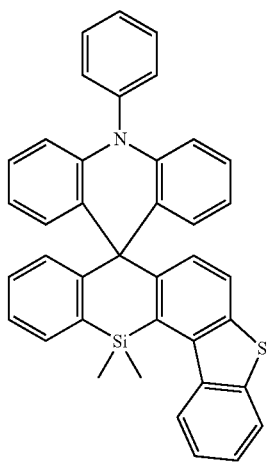
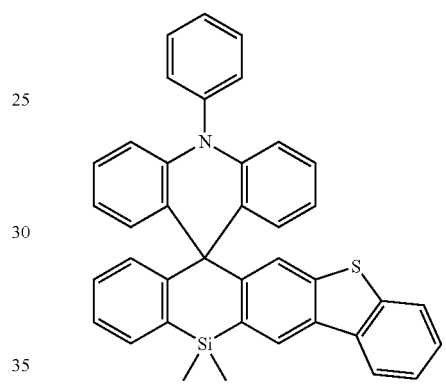
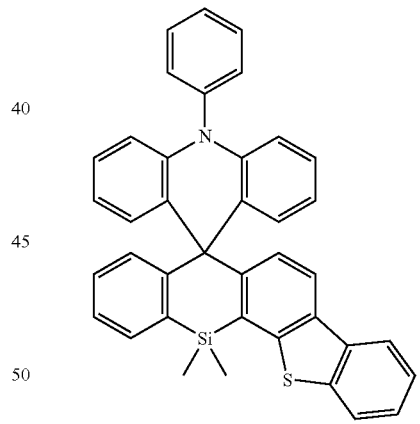
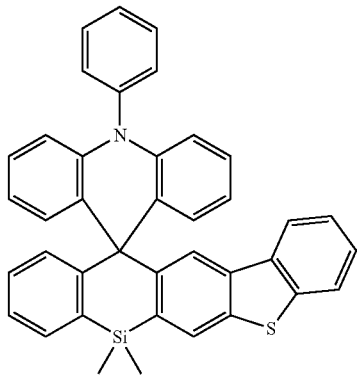

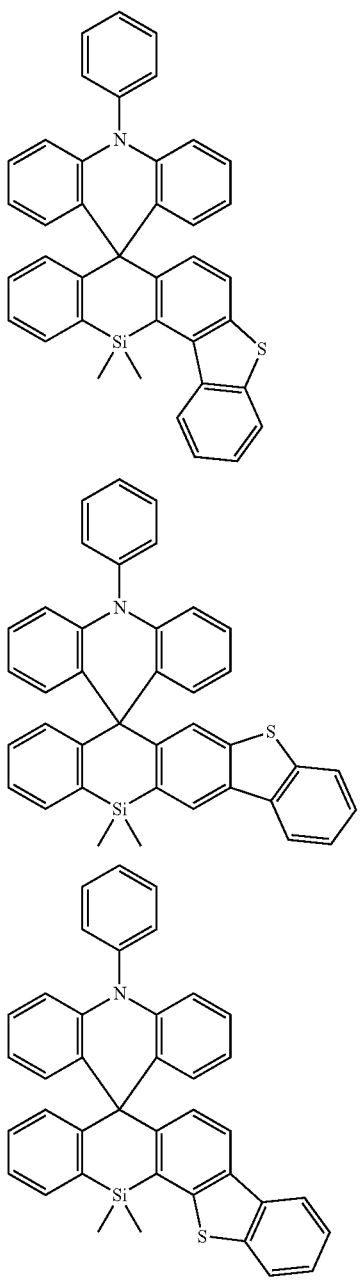
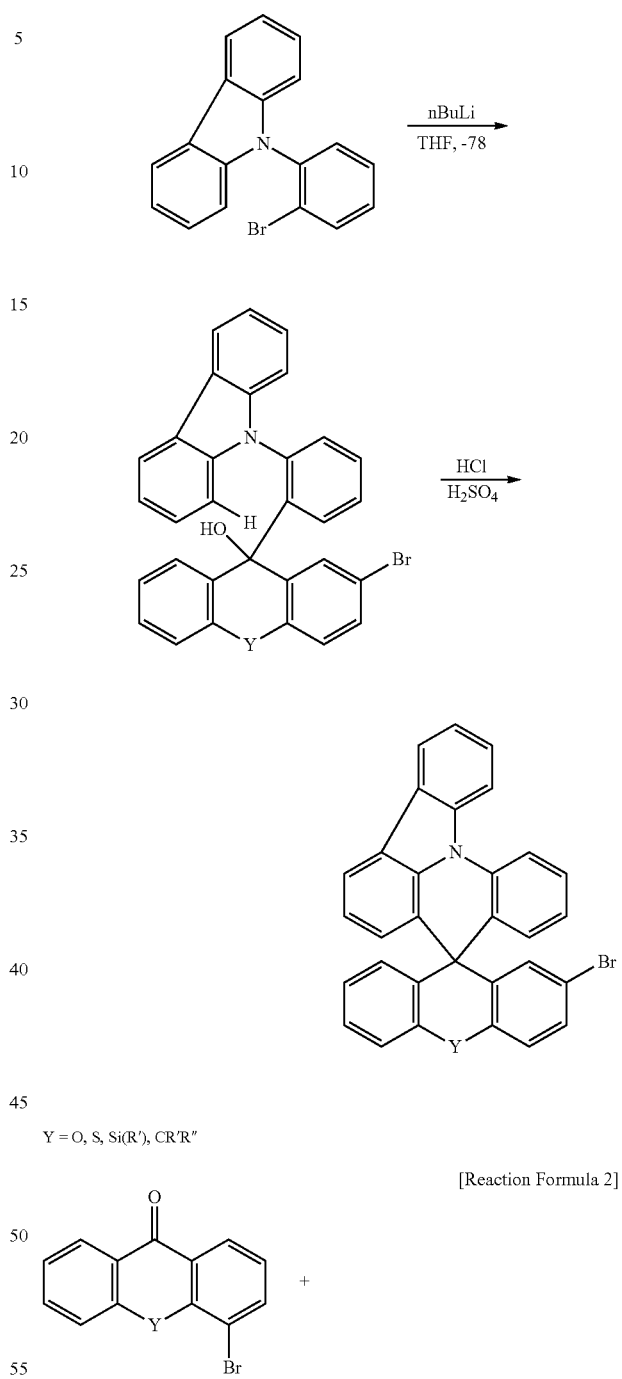
Y = O, S, Si(R'), CR'R''
The compound represented by Chemical Formula 1 may be prepared based on the Preparation Examples to be described below.
As an example, an intermediate is prepared as in the following Reaction Formulae 1 and 2.
[Reaction Formula 1]
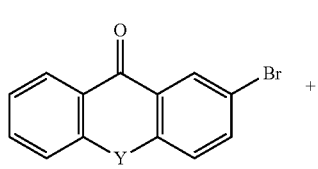
[Reaction Formula 2]
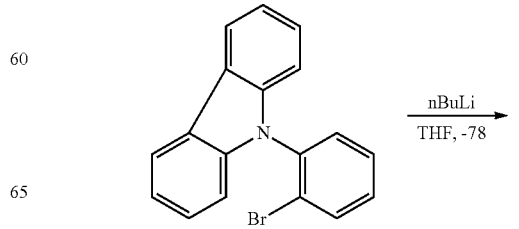

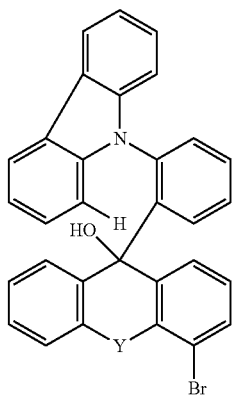
Y = O, S, Si(R'), CR'R''
Subsequently, a core structure of Chemical Formula 1 may be prepared in the same manner as in the following Reaction Formulae 3 to 6.
[Reaction Formula 3]
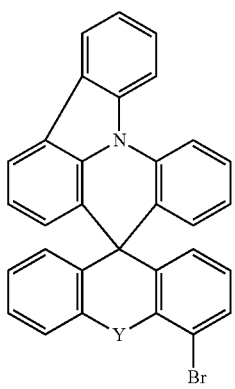
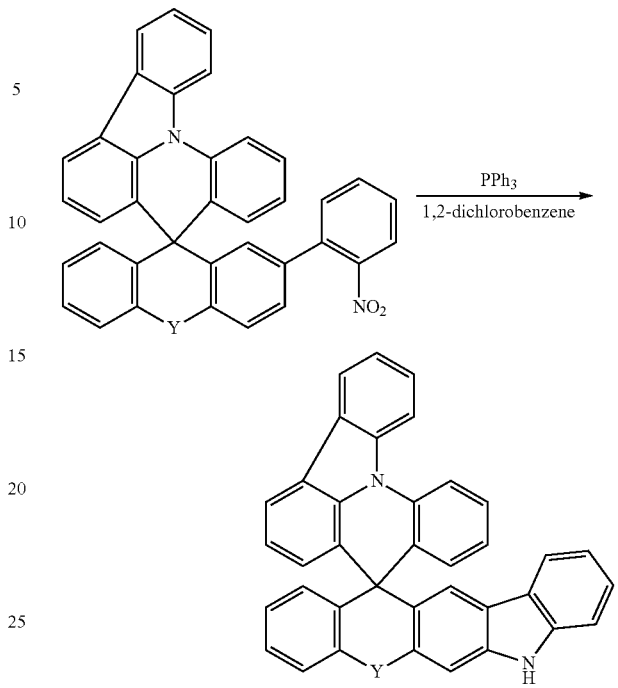
[Reaction Formula 4]
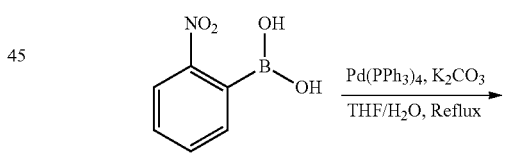
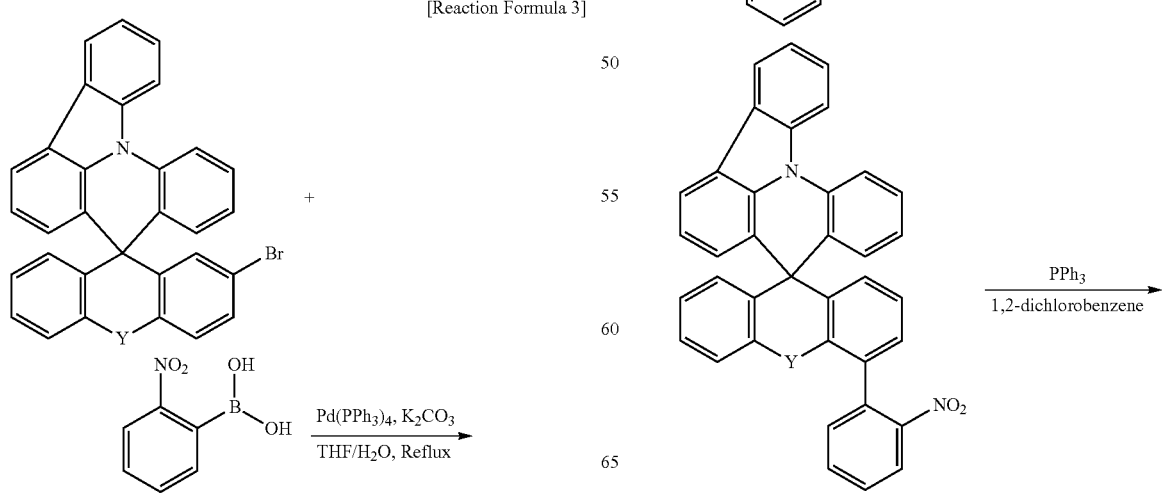

209
-continued
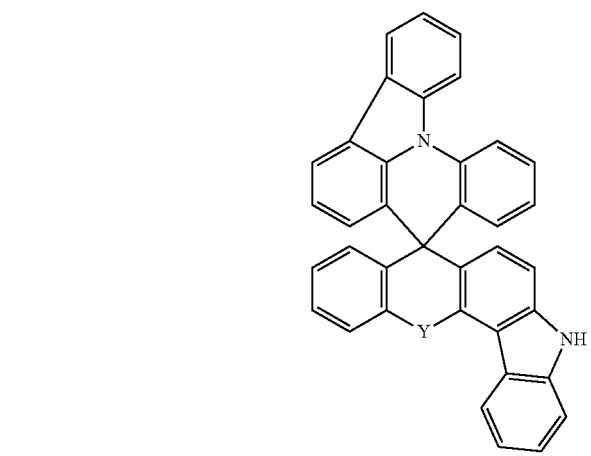
[Reaction Formula 5]
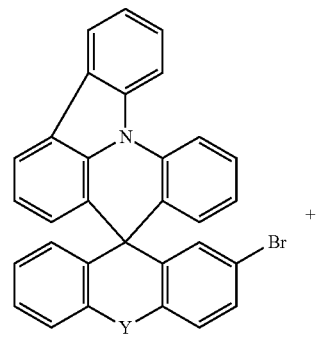
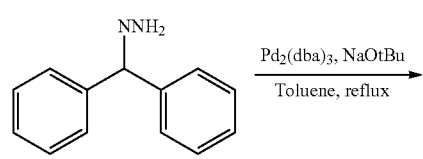
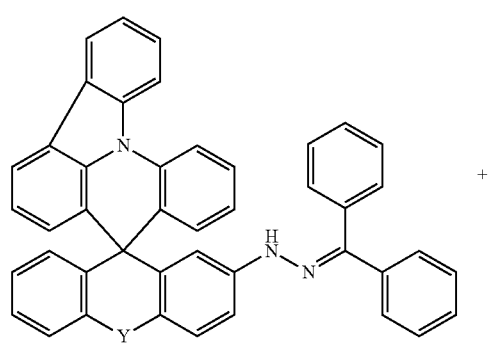
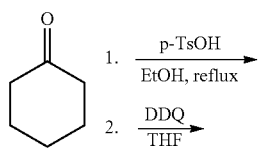
210
-continued
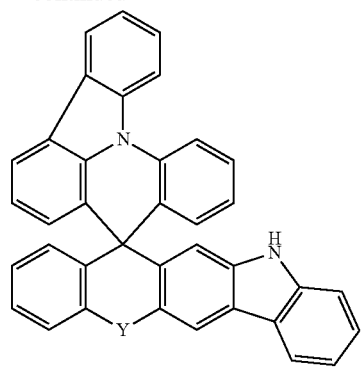
[Reaction Formula 6]
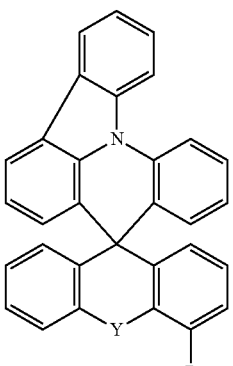
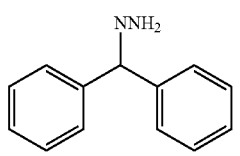
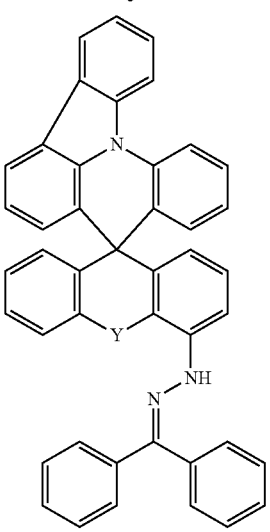
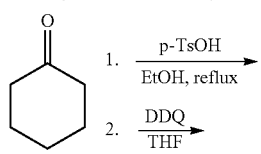

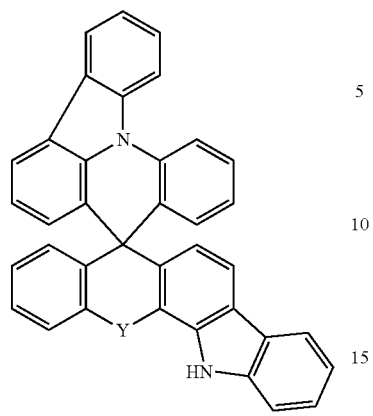
As another example, an intermediate is prepared as in the following Reaction Formulae 7 and 8.
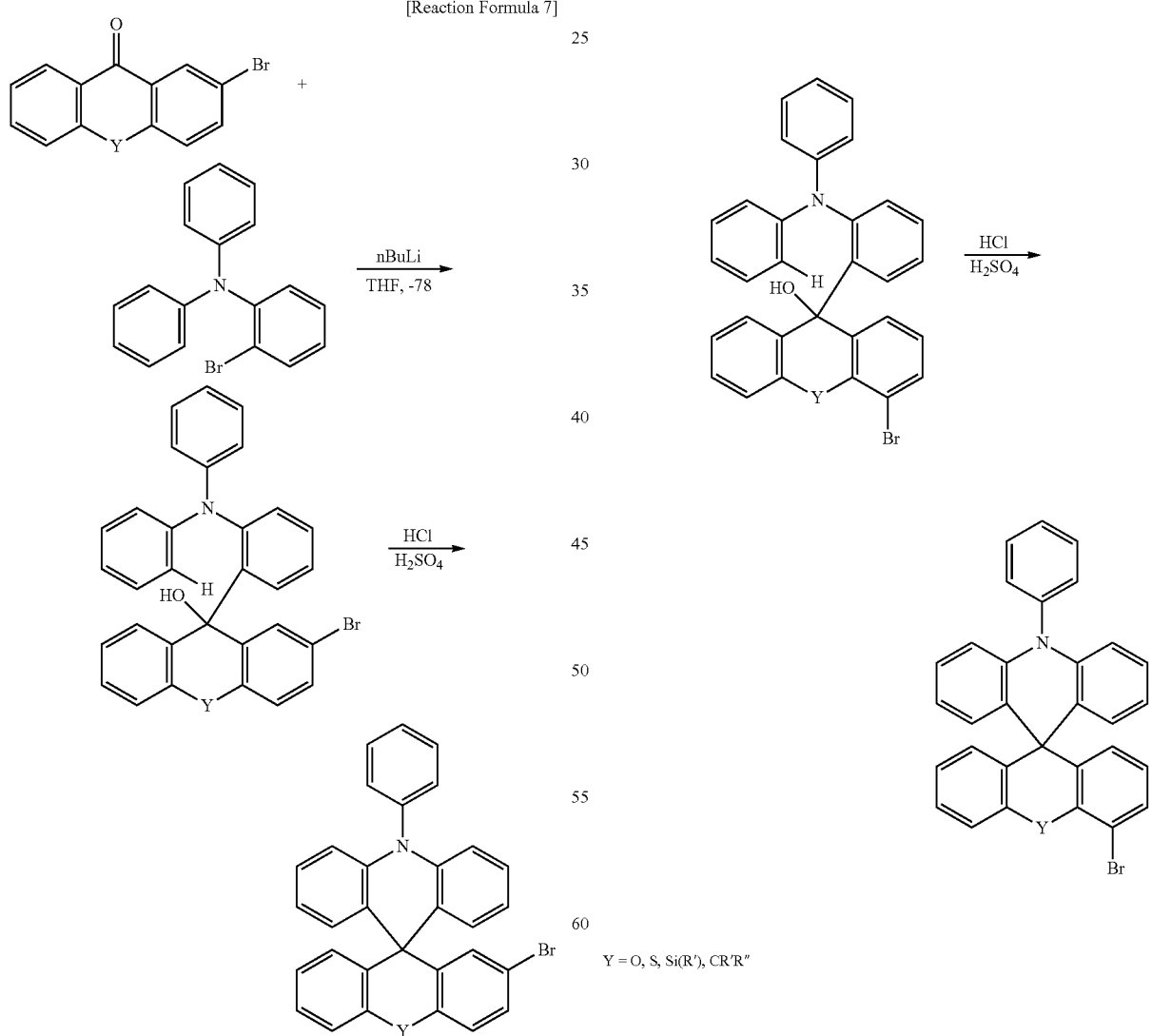
Subsequently, a core structure of Chemical Formula 1 may be prepared in the same manner as in the following Reaction Formulae 9 to 12.

213
[Reaction Formula 9]
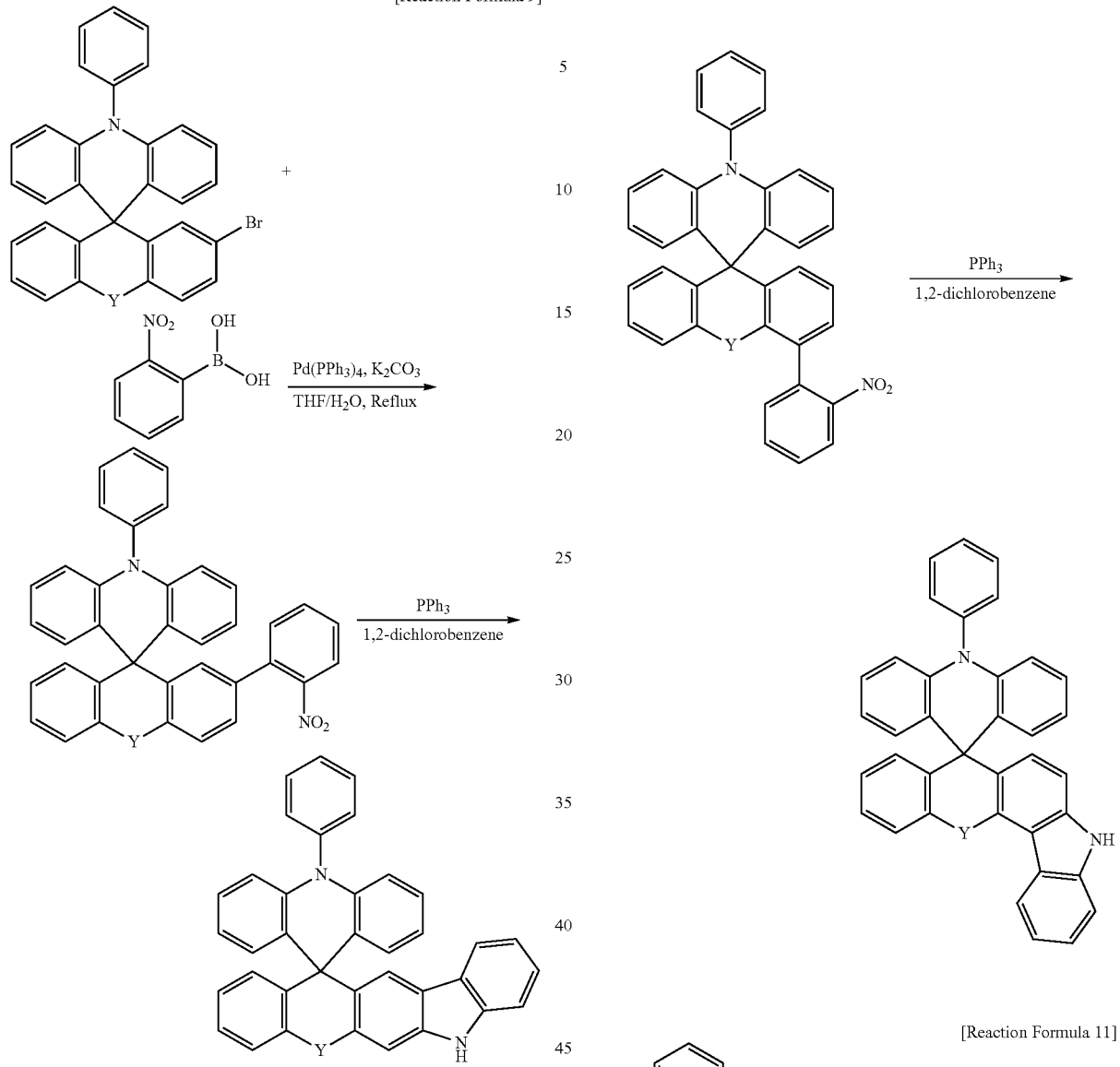
[Reaction Formula 10]
214
-continued
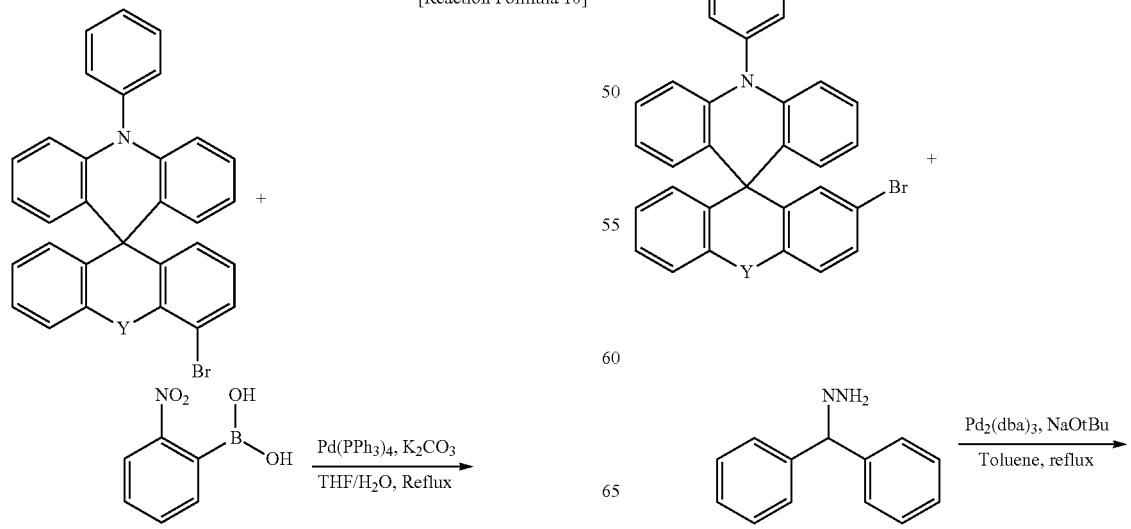
[Reaction Formula 11]

215
-continued

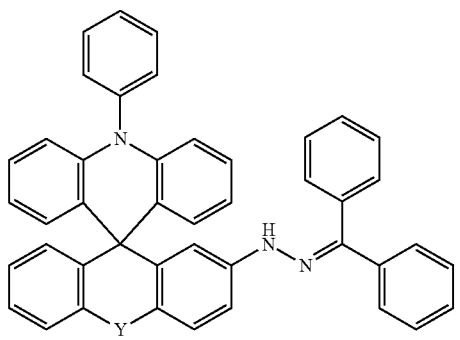

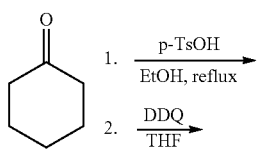

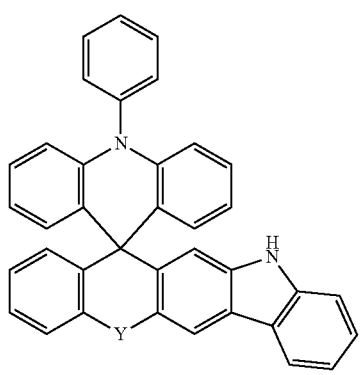

[Reaction Formula 12]

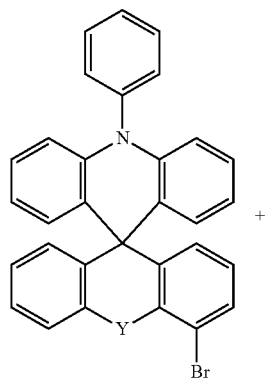

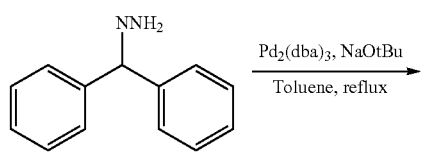

216
-continued

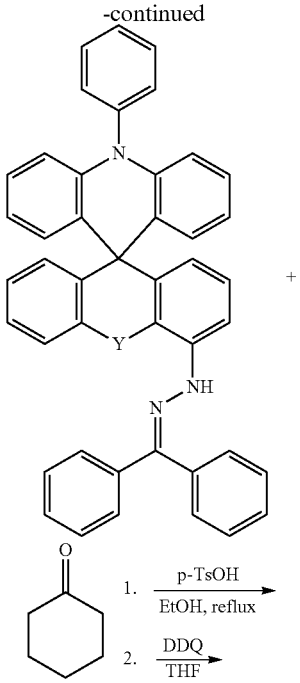

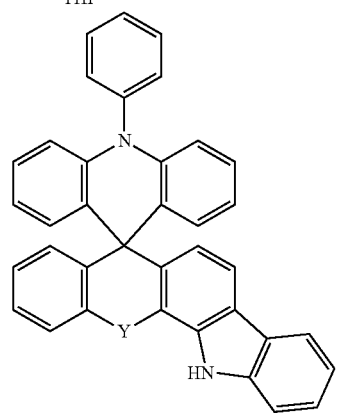

Subsequently, a substituent may be additionally introduced by using the technology known in the art. The reaction formulae relate to a method for preparing a compound in which X is NAr, but the person skilled in the art may prepare a compound in which X is O or S by using the technology known in the art or may introduce a substituent, if necessary, and may also prepare various compounds by changing the kind or number of substituent. Further, the person skilled in the art may perform the introduction by changing samples, reaction conditions, or starting materials of the reaction formulae using the technology known in the art.

Furthermore, the present specification provides an organic light emitting device including the compound represented by Chemical Formula 1.

An exemplary embodiment of the present specification provides an organic light emitting device including: a first electrode; a second electrode disposed to face the first electrode; and an organic material layer having one or more layers disposed between the first electrode and the second electrode, in which one or more layers of the organic material layer include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

In an exemplary embodiment of the present specification, the organic material layer includes a hole injection layer, a hole transporting layer, or a layer which injects and transports holes simultaneously, and the hole injection layer, the hole transporting layer, or the layer which injects and transports holes simultaneously includes the compound of Chemical Formula 1.

In another exemplary embodiment, the organic material layer includes a light emitting layer, and the light emitting layer includes the compound of Chemical Formula 1.

In an exemplary embodiment of the present specification, the light emitting layer includes the compound of Chemical Formula 1 and further includes a light emitting dopant.

In another exemplary embodiment, the light emitting dopant includes a fluorescent dopant or a phosphorescent dopant.

In still another exemplary embodiment, the phosphorescent dopant includes an iridium-based phosphorescent dopant.

In yet another exemplary embodiment, the phosphorescent dopant material includes Ir(ppy)$_3$ or (piq)$_2$Ir(acac).

In an exemplary embodiment of the present specification, the organic material layer includes an electron transporting layer or an electron injection layer, and the electron transporting layer or the electron injection layer includes the compound of Chemical Formula 1.

In an exemplary embodiment of the present specification, the organic material layer includes an electron blocking layer, and the electron blocking layer includes the compound of Chemical Formula 1.

In an exemplary embodiment of the present specification, the electron transporting layer, the electron injection layer, or the layer which transports and injects electrons simultaneously includes the compound of Chemical Formula 1.

In another exemplary embodiment, the organic material layer includes a light emitting layer and an electron transporting layer, and the electron transporting layer includes the compound of Chemical Formula 1.

One exemplary embodiment of the present specification is an organic light emitting device including: a first electrode; a second electrode disposed to face the first electrode; a light emitting layer disposed between the first electrode and the second electrode; and an organic material layer having two or more layers disposed between the light emitting layer and the first electrode, or between the light emitting layer and the second electrode, in which at least one of the organic material layer having two or more layers includes the heterocyclic compound. In one exemplary embodiment, as the organic material layer having two or more layers, two or more may be selected from the group consisting of an electron transporting layer, an electron injection layer, a layer which transports and injects electrons simultaneously, and a hole blocking layer.

In an exemplary embodiment of the present specification, the organic material layer includes two or more electron transporting layers, and at least one of the electron transporting layer having two or more layers includes the heterocyclic compound. Specifically, in an exemplary embodiment of the present specification, the heterocyclic compound may also be included in one layer of the electron transporting layer having two or more layers, and may be included in each of the electron transporting layer having two or more layers.

Further, in an exemplary embodiment of the present specification, when the heterocyclic compound is included in each of the electron transporting layer having two or more layers, the other materials except for the heterocyclic compound may be the same as or different from each other.

In another exemplary embodiment, the organic light emitting device may be an organic light emitting device having a structure (normal type) in which a positive electrode, an organic material layer having one or more layers, and a negative electrode are sequentially stacked on a substrate.

In still another exemplary embodiment, the organic light emitting device may be an organic light emitting device having a reverse-direction structure (inverted type) in which a negative electrode, an organic material layer having one or more layers, and a positive electrode are sequentially stacked on a substrate.

For example, the structure of the organic light emitting device according to an exemplary embodiment of the present specification is exemplified in FIGS. 1 and 2.

FIG. 1 illustrates an example of an organic light emitting device composed of a substrate 1, a positive electrode 2, a light emitting layer 3, and a negative electrode 4. In the structure as described above, the compound may be included in the light emitting layer.

FIG. 2 illustrates an example of an organic light emitting device composed of a substrate 1, a positive electrode 2, a hole injection layer 5, a hole transporting layer 6, a light emitting layer 3, an electron transporting layer 7, and a negative electrode 4. In the structure as described above, the compound may be included in one or more layers of the hole injection layer, the hole transporting layer, the light emitting layer, and the electron transporting layer.

According to an exemplary embodiment of the present specification, the organic material layer includes the light emitting layer, and the light emitting layer includes a compound represented by the following Chemical Formula 1-A.

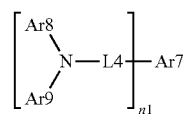

[Chemical Formula 1-A]

In Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Arg are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may be bonded to each other to form a substituted or unsubstituted ring, and when n1 is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, L4 is a direct bond.

According to an exemplary embodiment of the present specification, n1 is 2.

In an exemplary embodiment of the present specification, Ar7 is a divalent pyrene group which is unsubstituted or substituted with deuterium, a methyl group, an ethyl group, or a tert-butyl group.

According to an exemplary embodiment of the present specification, Ar8 and Arg are the same as or different from each other, and are each independently a substituted or unsubstituted aryl group having 6 to 30 carbon atoms.

According to an exemplary embodiment of the present specification, Ar8 and Ar9 are the same as or different from each other, and are each independently an aryl group which is unsubstituted or substituted with a germanium group substituted with an alkyl group.

According to an exemplary embodiment of the present specification, Ar8 and Ar9 are the same as or different from each other, and are each independently an aryl group which is unsubstituted or substituted with a trimethylgermanium group.

According to an exemplary embodiment of the present specification, Ar8 and Ar9 are the same as or different from each other, and are each independently a substituted or unsubstituted phenyl group.

According to an exemplary embodiment of the present specification, Ar8 and Ar9 are a phenyl group which is unsubstituted or substituted with a trimethylgermanium group.

According to an exemplary embodiment of the present specification, Chemical Formula 1-A is represented by the following compound.

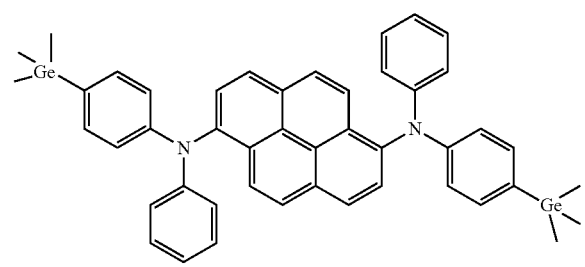

According to an exemplary embodiment of the present specification, the organic material layer includes a light emitting layer, and the light emitting layer includes a compound represented by the following Chemical Formula 2-A.

[Chemical Formula 2-A]

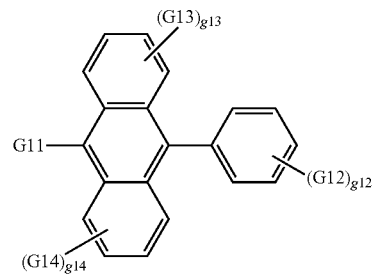

In Chemical Formula 2-A,

G11 is a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

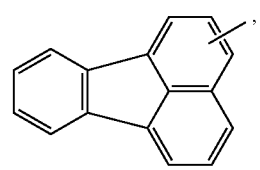

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, G11 is a 1-naphthyl group.

According to an exemplary embodiment of the present specification, G12 is a 2-naphthyl group.

According to an exemplary embodiment of the present specification, G13 and G14 are hydrogen.

According to an exemplary embodiment of the present specification, Chemical Formula 2-A is represented by the following compound.

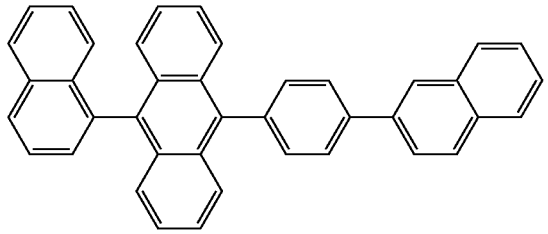 [SMILES: c1ccc2cc(-c3ccc(-c4c5ccccc5c(-c5cccc6ccccc56)c5ccccc45)cc3)ccc2c1]

The organic light emitting device of the present specification may be manufactured by the materials and methods known in the art, except that one or more layers of the organic material layer include the compound of the present specification, that is, the compound of Chemical Formula 1.

When the organic light emitting device includes a plurality of organic material layers, the organic material layers may be formed of the same material or different materials.

The organic light emitting device of the present specification may be manufactured by the materials and methods known in the art, except that one or more layers of the organic material layer include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, materials having a large work function are usually preferred so as to facilitate the injection of holes into an organic material layer. Specific examples of the positive electrode material which may be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline, and the like, but are not limited thereto.

As the negative electrode material, materials having a small work function are usually preferred so as to facilitate the injection of electrons into an organic material layer. Specific examples of the negative electrode material include: a metal such as magnesium, calcium, sodium, potassium, titanium, indium, yttrium, lithium, gadolinium, aluminum, silver, tin, and lead, or an alloy thereof; a multi-layer structured material such as LiF/Al or $LiO_2$/Al; and the like, but are not limited thereto.

The hole injection layer is a layer which injects holes from an electrode, and a hole injection material is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is a value between the work function of the positive electrode material and the HOMO of the neighboring organic material layer. Specific examples of the hole injection material include metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based conductive polymers, and the like, but are not limited thereto.

The hole transporting layer is a layer which accepts holes from a hole injection layer and transports the holes to a light emitting layer, and a hole transporting material is suitably a material having high hole mobility which may accept holes from a positive electrode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The light emitting material is preferably a material which may receive holes and electrons transported from a hole transporting layer and an electron transporting layer, respectively, and combine the holes and the electrons to emit light in a visible ray region, and has good quantum efficiency to fluorescence or phosphorescence. Specific examples thereof include: 8-hydroxy-quinoline-aluminum complex ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer may include a host material and a dopant material. Examples of the host material include a fused aromatic ring derivative, or a hetero ring-containing compound, and the like. Specific examples of the fused aromatic ring derivative include an anthracene derivative, a pyrene derivative, a naphthalene derivative, a pentacene derivative, a phenanthrene compound, a fluoranthene compound, and the like, and specific examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting layer is a layer which accepts electrons from an electron injection layer and transports the electrons to a light emitting layer, and an electron transporting material is suitably a material having high electron mobility which may proficiently accept electrons from a negative electrode and transfer the electrons to a light emitting layer. Specific examples thereof include: Al complexes of 8-hydroxyquinoline; complexes including Alq$_3$; organic radical compounds; hydroxyflavone-metal complexes, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato)(o-cresolato) gallium, bis(2-methyl-8-quinolinato)(1-naphtholato) aluminum, bis(2-methyl-8-quinolinato)(2-naphtholato) gallium, and the like, but are not limited thereto.

The organic light emitting device according to the present specification may be a top emission type, a bottom emission type, or a dual emission type according to the materials to be used.

In an exemplary embodiment of the present specification, the compound of Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present specification, and the scope of the present specification is not limited thereby.

Synthesis Example 1

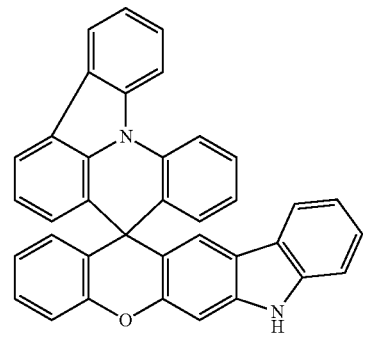

A

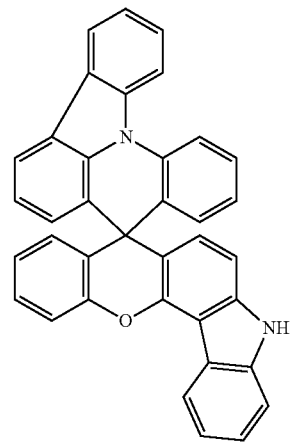

B

225
-continued
C
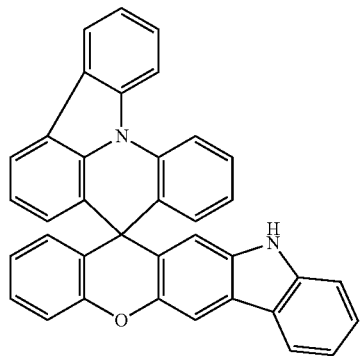
D
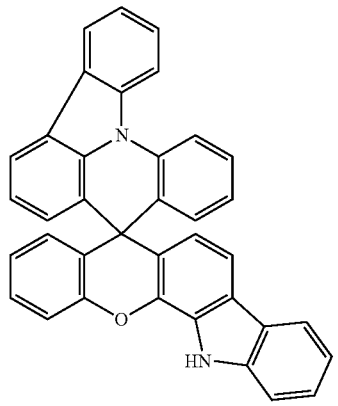
E
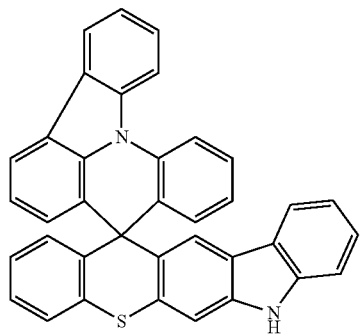
F
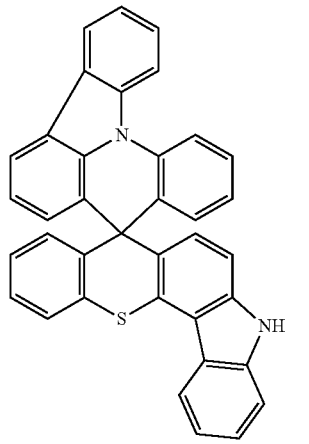
226
-continued
G
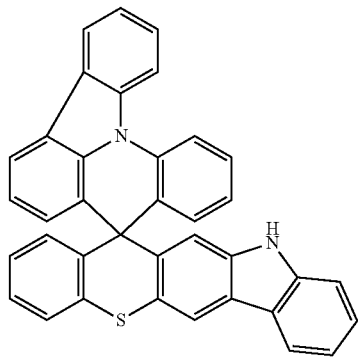
H
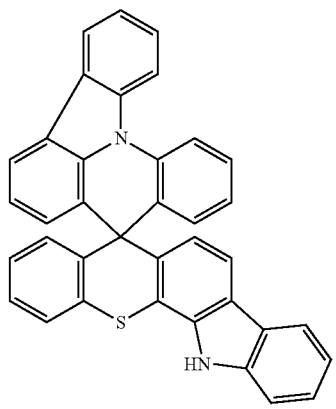
I
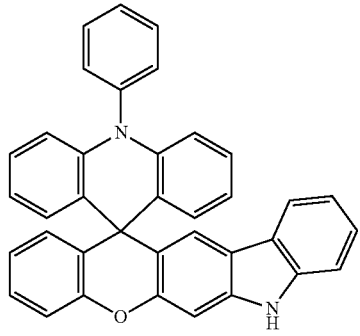
J K
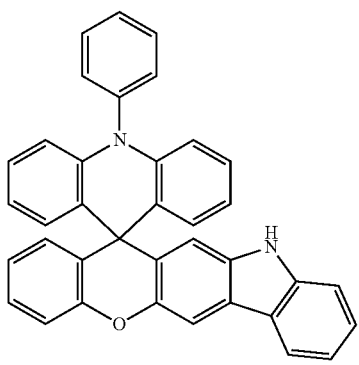
L
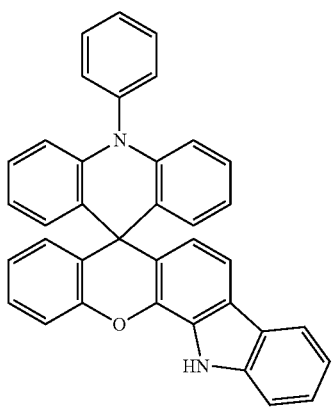
M
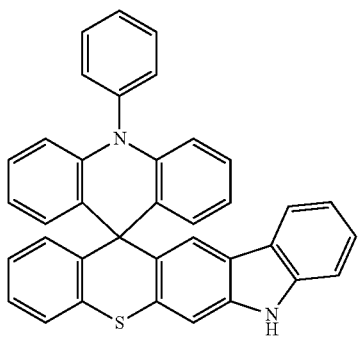
N
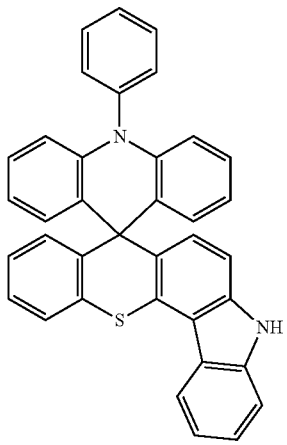
O
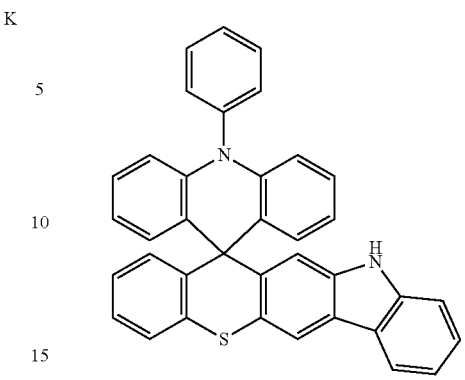
P
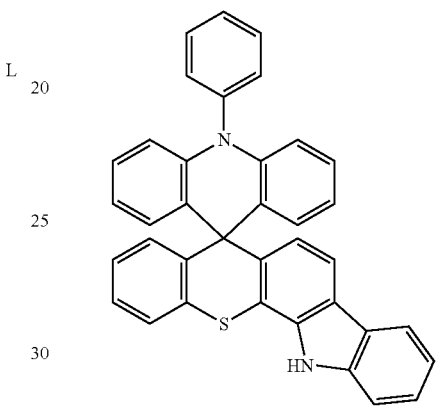
<Preparation Example 1> Synthesis of Compound of the Following Compound 1
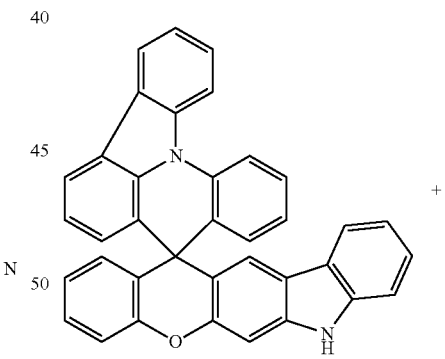
Compound A
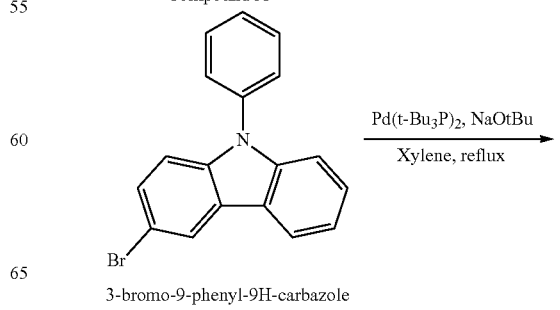
3-bromo-9-phenyl-9H-carbazole

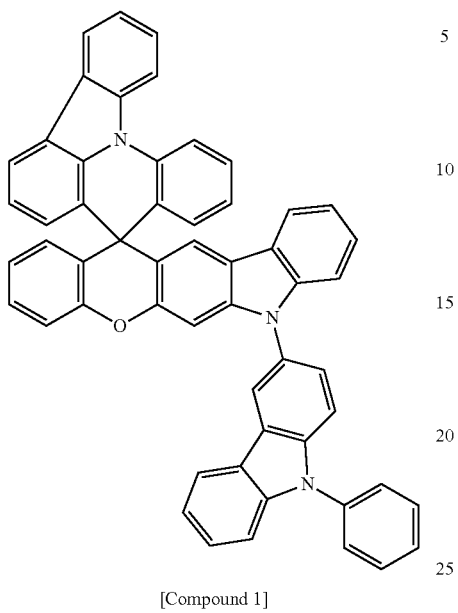

[Compound 1]

Compound A (10.0 g, 19.61 mmol) and 3-bromo-9-phenyl-9H-carbazole (6.92 g, 21.57 mmol) were completely dissolved in 240 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 300 ml of ethyl acetate to prepare Compound 1 (12.45 g, yield: 85%).

MS[M+H]$^+$=752

<Preparation Example 2> Synthesis of Compound of the Following Compound 2

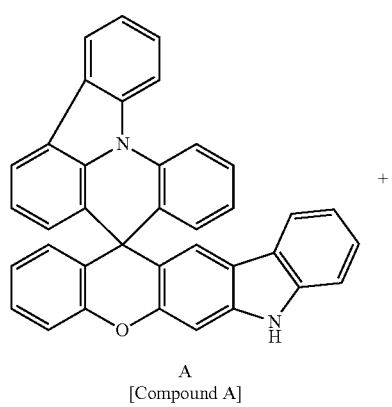

A
[Compound A]

+

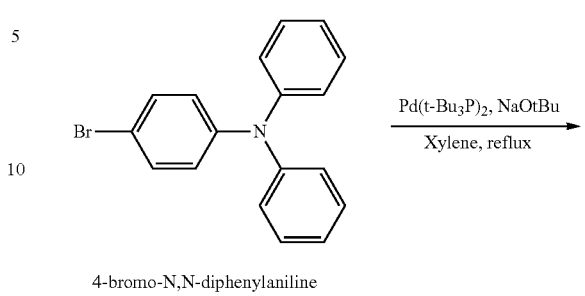

4-bromo-N,N-diphenylaniline

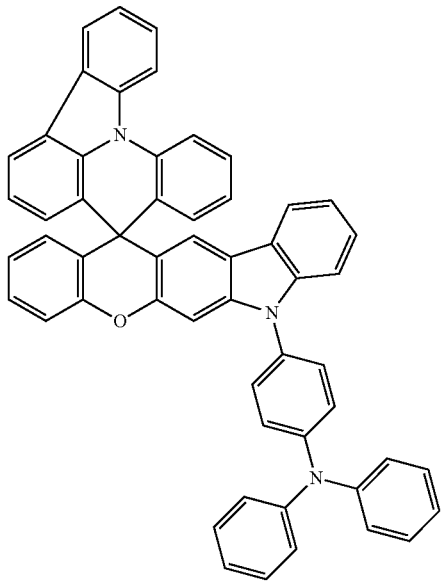

[Compound 2]

Compound A (10.0 g, 19.61 mmol) and 4-bromo-N,N-diphenylaniline (6.97 g, 21.57 mmol) were completely dissolved in 210 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 2 hours. The temperature was lowered to normal temperature, the mixture was filtered to remove the base, and then xylene was concentrated under reduced pressure, and the residue was recrystallized with 210 ml of ethyl acetate to prepare Compound 2 (9.95 g, yield: 67%).

MS[M+H]$^+$=754

<Preparation Example 3> Synthesis of Compound of the Following Compound 3

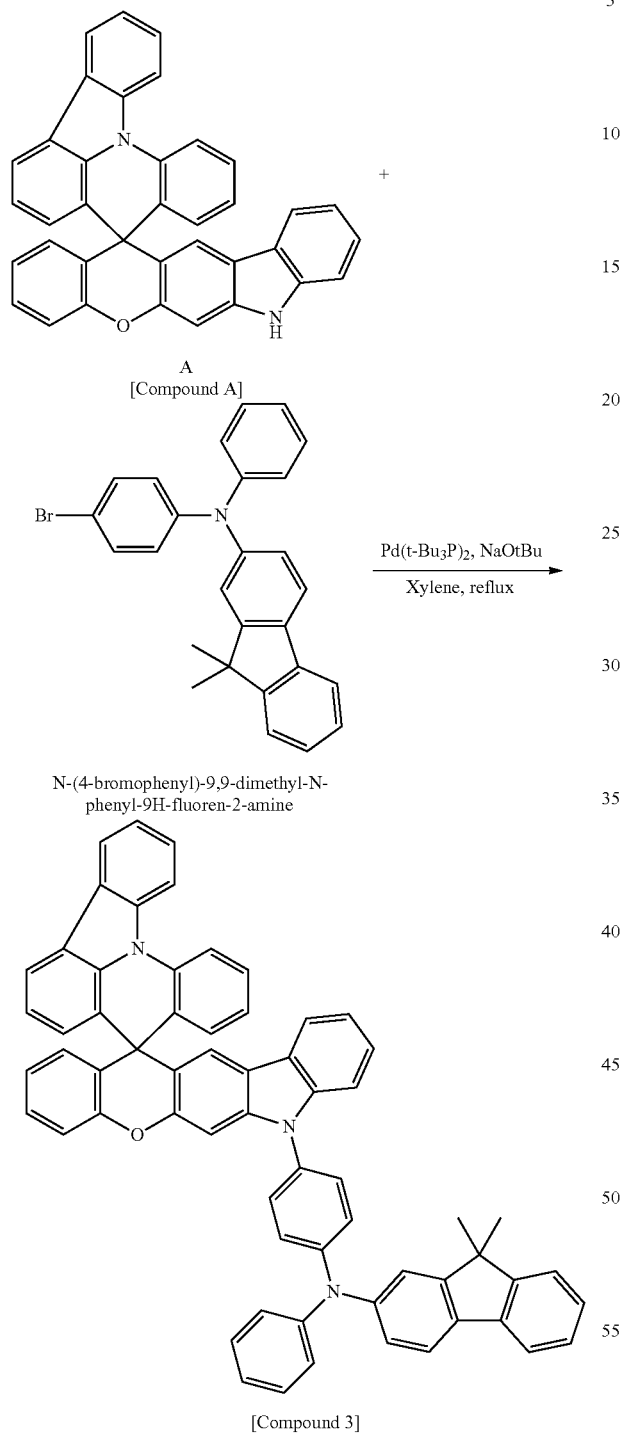

[Compound 3]

Compound A (10.0 g, 19.61 mmol) and N-(4-bromophenyl)-9,9-dimethyl-N-phenyl-9H-fluoren-2-amine (9.49 g, 21.57 mmol) were completely dissolved in 260 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 6 hours. The temperature was lowered to normal temperature, the mixture was filtered to remove the base, and then xylene was concentrated under reduced pressure, and the residue was recrystallized with 310 ml of ethyl acetate to prepare Compound 3 (14.33 g, yield: 84%).

MS[M+H]$^+$=871

<Preparation Example 4> Synthesis of Compound of the Following Compound 4

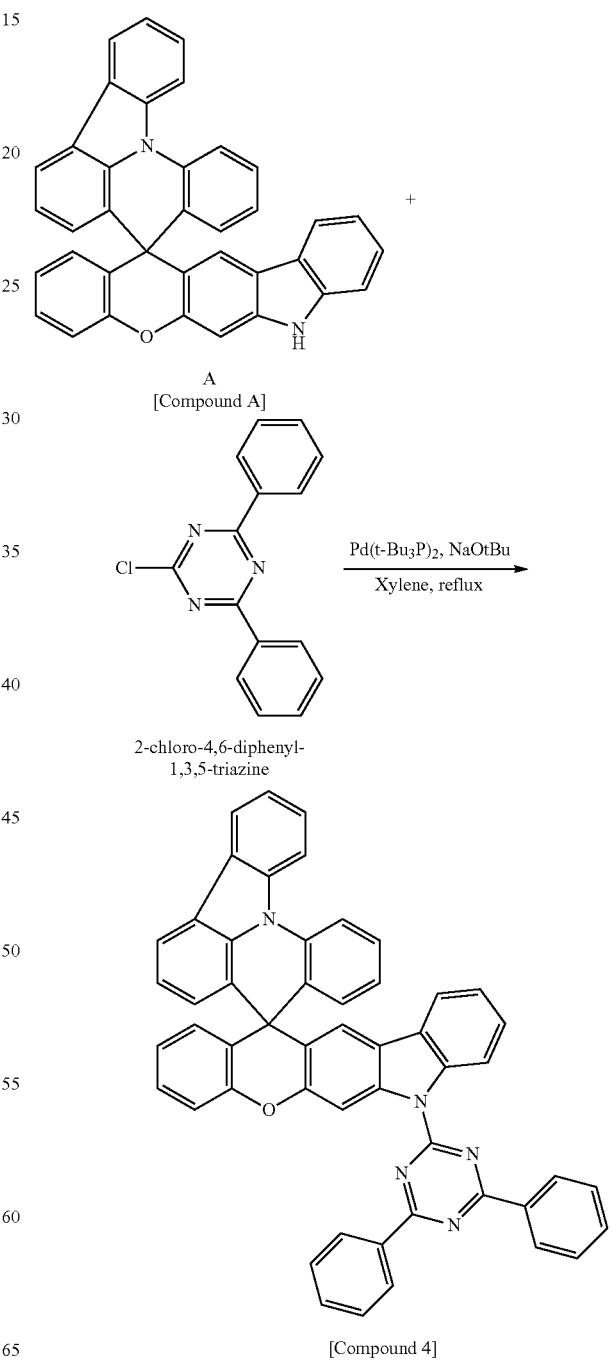

[Compound 4]

Compound A (10.0 g, 27.25 mmol) and 2-chloro-4,6-diphenyl-1,3,5-triazine (5.76 g, 29.97 mmol) were completely dissolved in 320 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 450 ml of ethyl acetate to prepare Compound 4 (12.98 g, yield: 89%).

MS[M+H]$^+$=742

<Preparation Example 5> Synthesis of Compound of the Following Compound 5

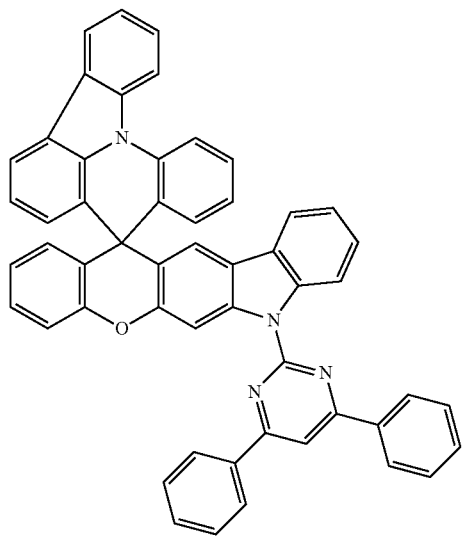

[Compound 5]

Compound A (10.0 g, 27.25 mmol) and 2-chloro-4,6-diphenylpyrimidine (5.71 g, 29.97 mmol) were completely dissolved in 320 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 380 ml of ethyl acetate to prepare Compound 5 (10.44 g, yield: 72%).

MS[M+H]$^+$=741

<Preparation Example 6> Synthesis of Compound of the Following Compound 6

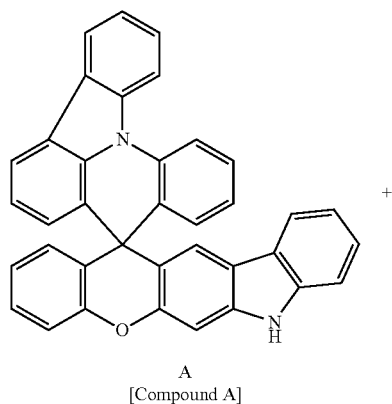

A
[Compound A]

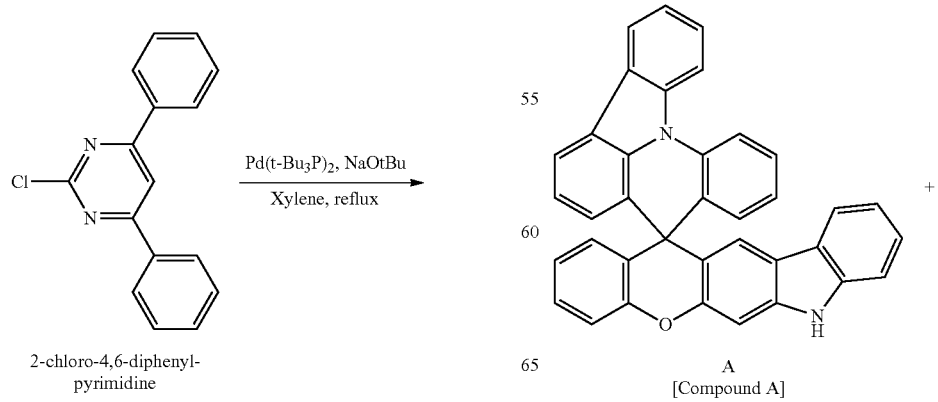

2-chloro-4,6-diphenyl-pyrimidine

A
[Compound A]

<Preparation Example 7> Synthesis of Compound of the Following Compound 7

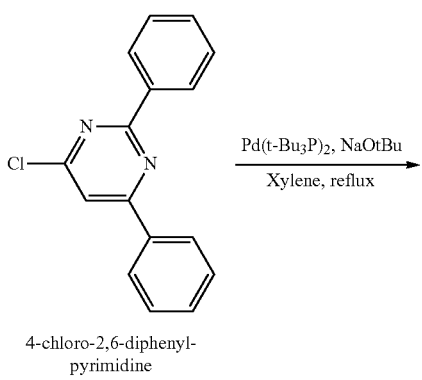

4-chloro-2,6-diphenyl-pyrimidine

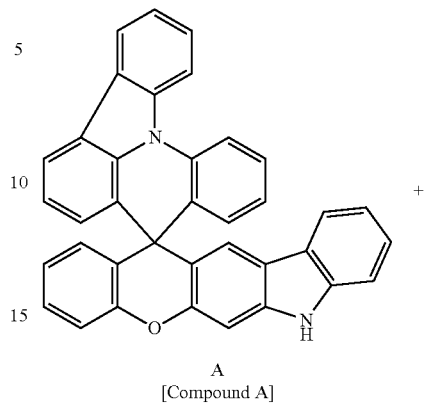

[Compound A]

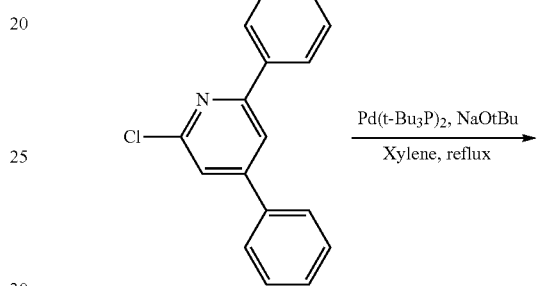

2-chloro-4,6-diphenyl-pyridine

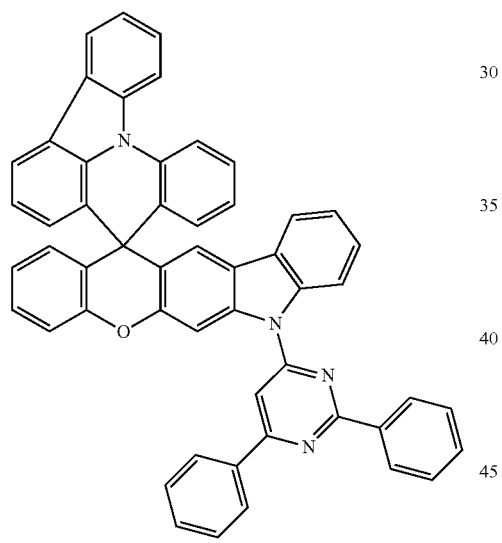

[Compound 6]

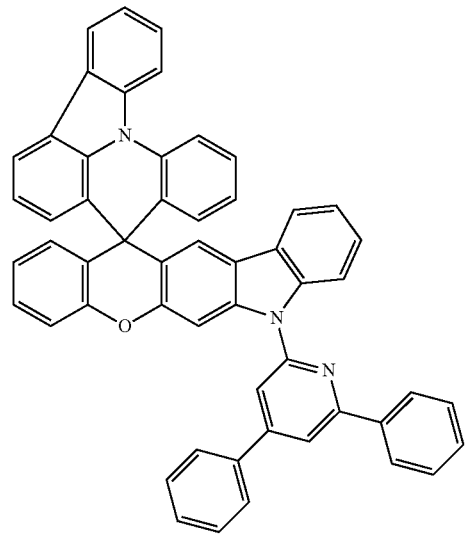

[Compound 7]

Compound A (10.0 g, 27.25 mmol) and 4-chloro-2,6-diphenylpyrimidine (5.71 g, 29.97 mmol) were completely dissolved in 280 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 380 ml of ethyl acetate to prepare Compound 6 (9.66 g, yield: 66%).

MS[M+H]$^+$=741

Compound A (10.0 g, 27.25 mmol) and 2-chloro-4,6-diphenylpyridine (5.66 g, 29.97 mmol) were completely dissolved in 280 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 8 hours. The temperature was lowered to normal temperature, the mixture was filtered to remove the base, and then xylene was concentrated under reduced pressure, and the residue was recrystallized with 310 ml of ethyl acetate to prepare Compound 7 (11.35 g, yield: 78%).
MS[M+H]⁺=740

<Preparation Example 8> Synthesis of Compound of the Following Compound 8

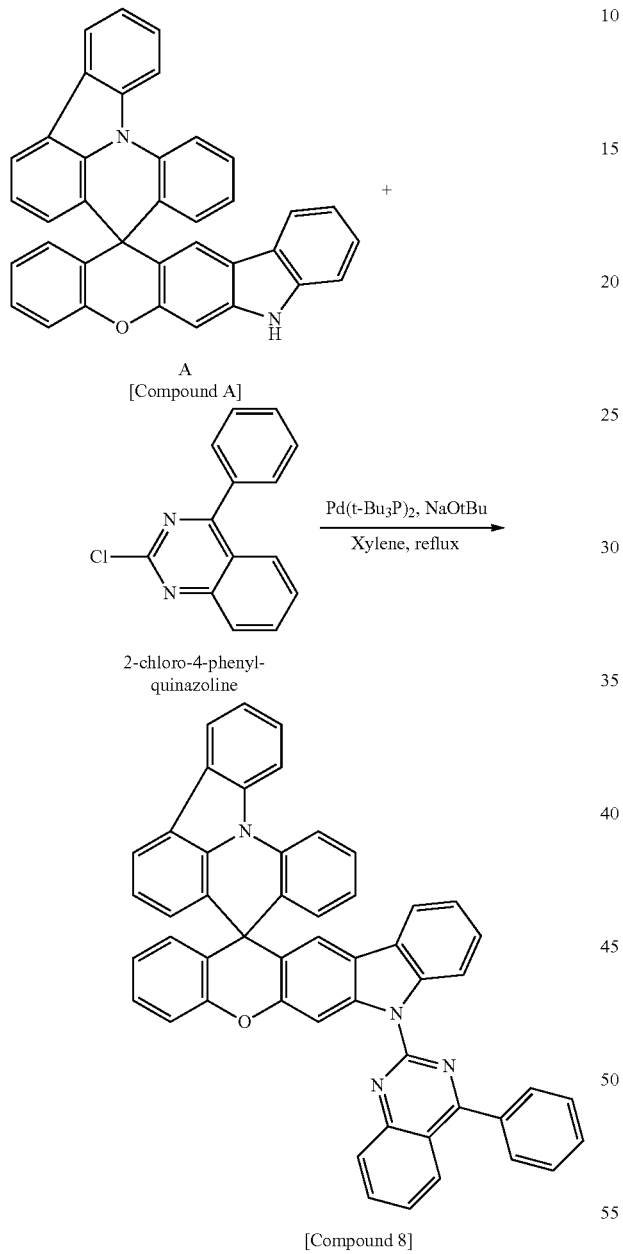

[Compound 8]

Compound A (10.0 g, 27.25 mmol) and 2-chloro-4-phenylquinazoline (5.18 g, 29.97 mmol) were completely dissolved in 250 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 2 hours. The temperature was lowered to normal temperature, the mixture was filtered to remove the base, and then xylene was concentrated under reduced pressure, and the residue was recrystallized with 310 ml of ethyl acetate to prepare Compound 8 (11.35 g, yield: 78%).
MS[M+H]⁺=715

<Preparation Example 9> Synthesis of Compound of the Following Compound 9

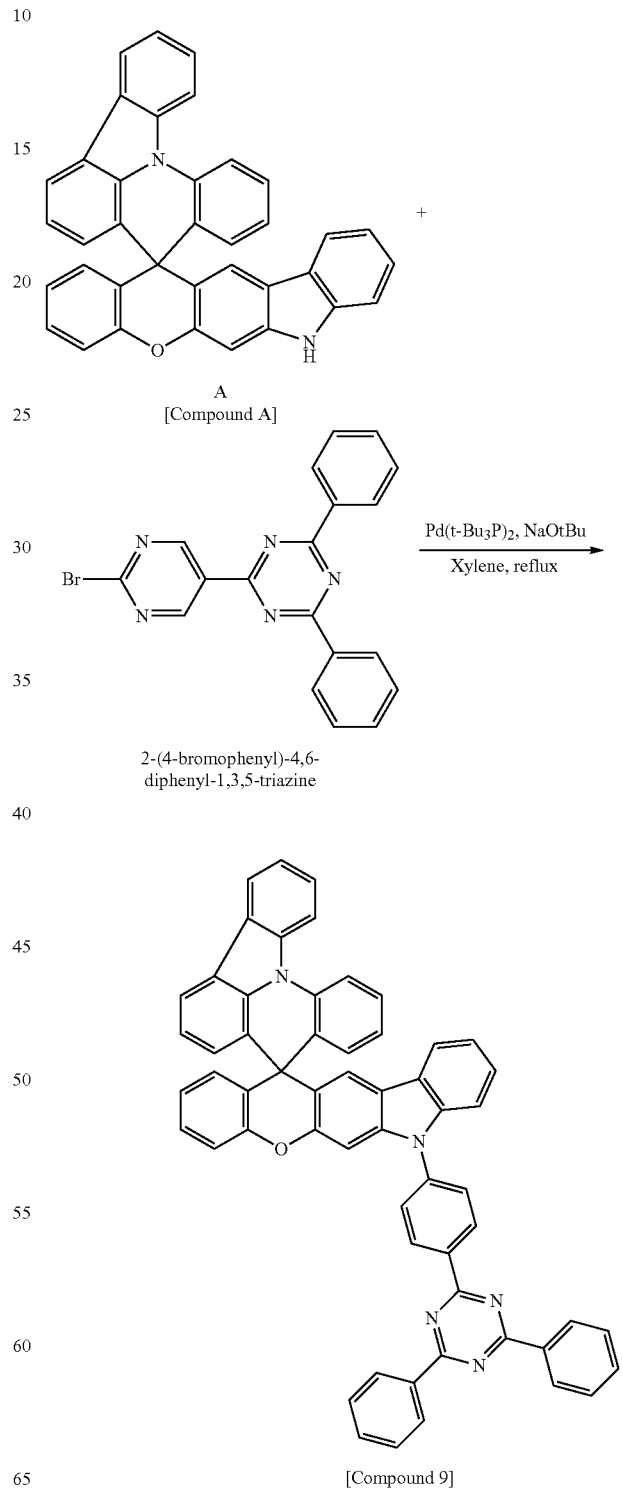

[Compound 9]

Compound A (10.0 g, 27.25 mmol) and 2-(4-chlorophenyl)-4,6-diphenyl-1,3,5-triazine (8.37 g, 29.97 mmol) were completely dissolved in 420 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 250 ml of tetrahydrofuran to prepare Compound 9 (14.88 g, yield: 92%).

MS[M+H]$^+$=818

<Preparation Example 10> Synthesis of Compound of the Following Compound 10

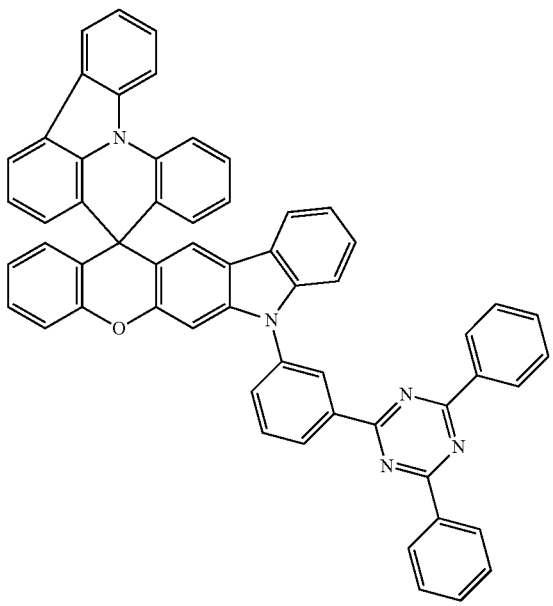

[Compound 10]

Compound A (10.0 g, 27.25 mmol) and 2-(3-chlorophenyl)-4,6-diphenyl-1,3,5-triazine (8.37 g, 29.97 mmol) were completely dissolved in 420 ml of xylene in a 500-ml round bottom flask under a nitrogen atmosphere, and then sodium tert-butoxide (3.41 g, 35.43 mol) was added thereto, bis(tri-tert-butylphosphine) palladium(0) (0.14 g, 0.27 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 210 ml of tetrahydrofuran to prepare Compound 10 (13.11 g, yield: 82%).

MS[M+H]$^+$=818

<Preparation Example 11> Synthesis of Compound of the Following Compound 11

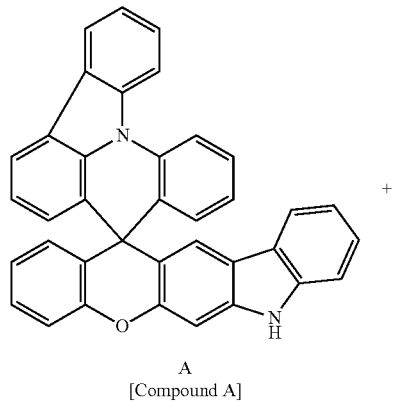

[Compound A]

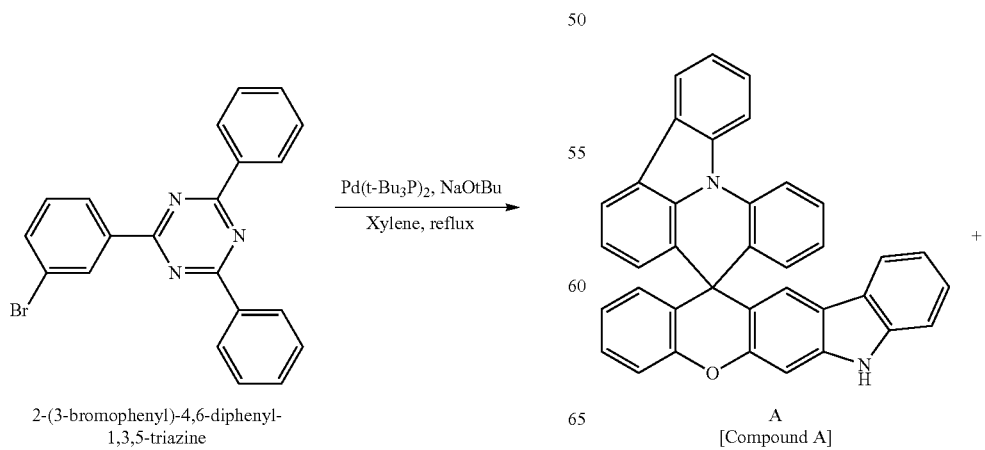

Preparation Example 12> Synthesis of Compound of the Following Compound 12

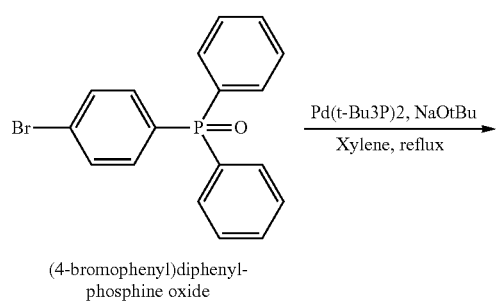

(4-bromophenyl)diphenyl-phosphine oxide

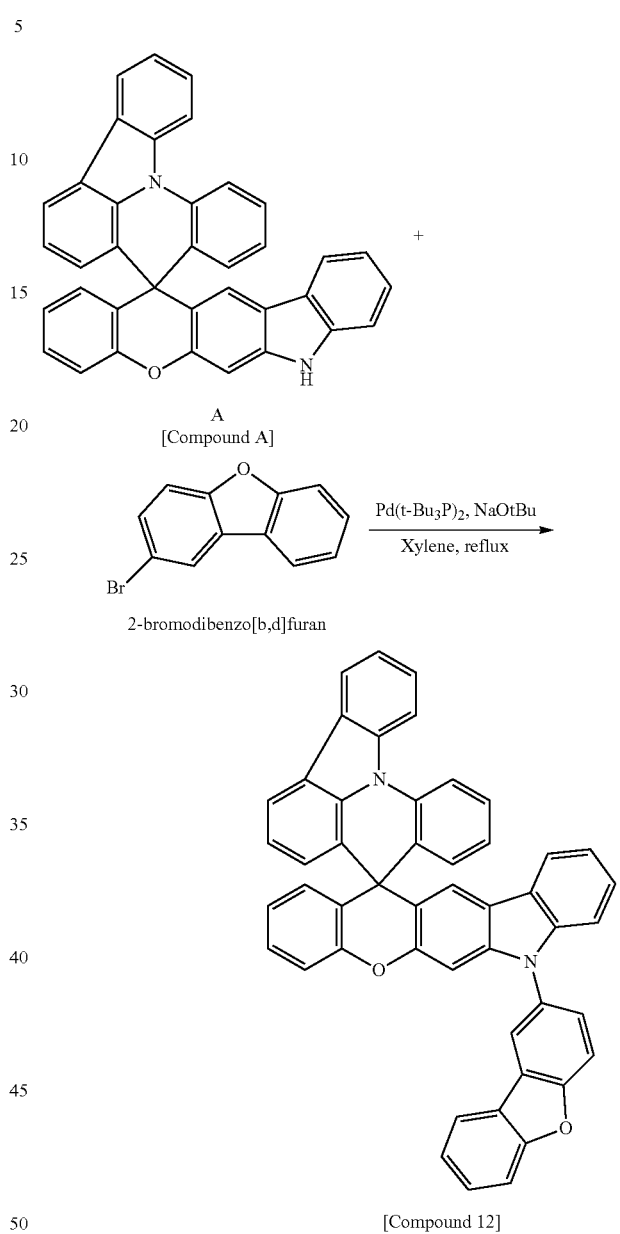

[Compound 11]

Compound A (10.0 g, 19.61 mmol) and (4-bromophenyl)diphenylphosphine oxide (7.70 g, 21.57 mmol) were completely dissolved in 230 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 210 ml of ethyl acetate to prepare Compound 11 (12.85 g, yield: 83%).

MS[M+H]$^+$=787

Compound A (10.0 g, 19.61 mmol) and 2-bromodibenzo[b,d]furan (5.33 g, 21.57 mmol) were completely dissolved in 240 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 3 hours. The temperature was lowered to normal temperature, the mixture was filtered to remove the base, and then xylene was concentrated under reduced pressure, and the residue was recrystallized with 300 ml of ethyl acetate to prepare Compound 12 (8.76 g, yield: 66%).

MS[M+H]$^+$=677

243
<Preparation Example 13> Synthesis of Compound of the Following Compound 13

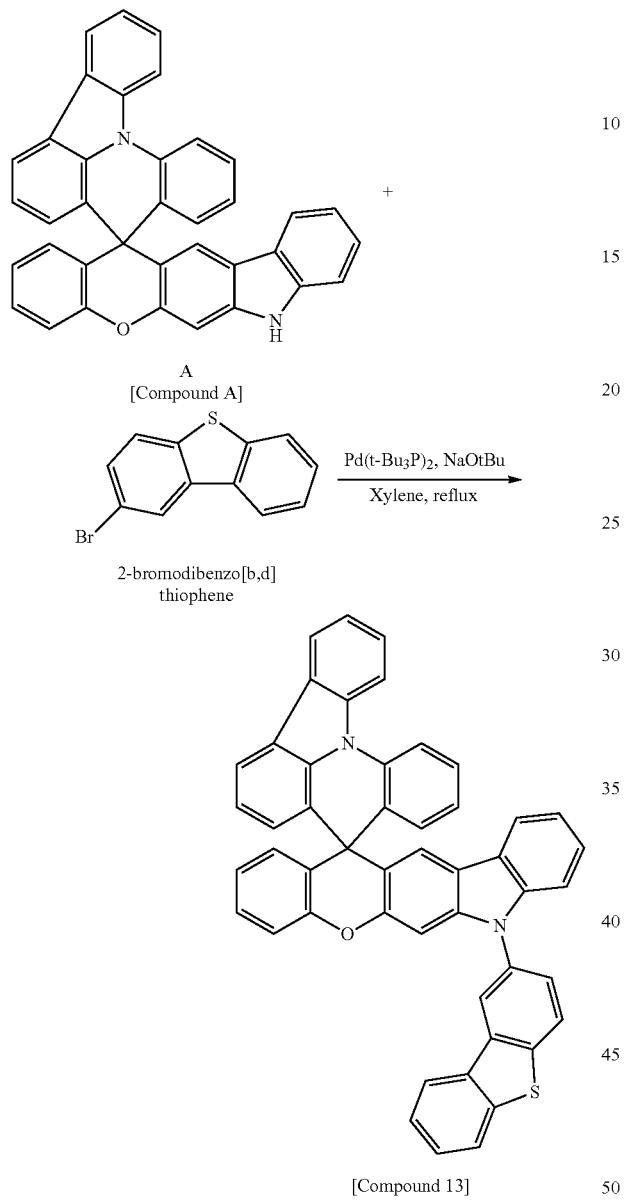

Compound A (10.0 g, 19.61 mmol) and 2-bromodibenzo[b,d]thiophene (5.67 g, 21.57 mmol) were completely dissolved in 220 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 5 hours. The temperature was lowered to normal temperature, the mixture was filtered to remove the base, and then xylene was concentrated under reduced pressure, and the residue was recrystallized with 300 ml of ethyl acetate to prepare Compound 13 (9.06 g, yield: 67%).

MS[M+H]$^+$=693

244
<Preparation Example 14> Synthesis of Compound of the Following Compound 14

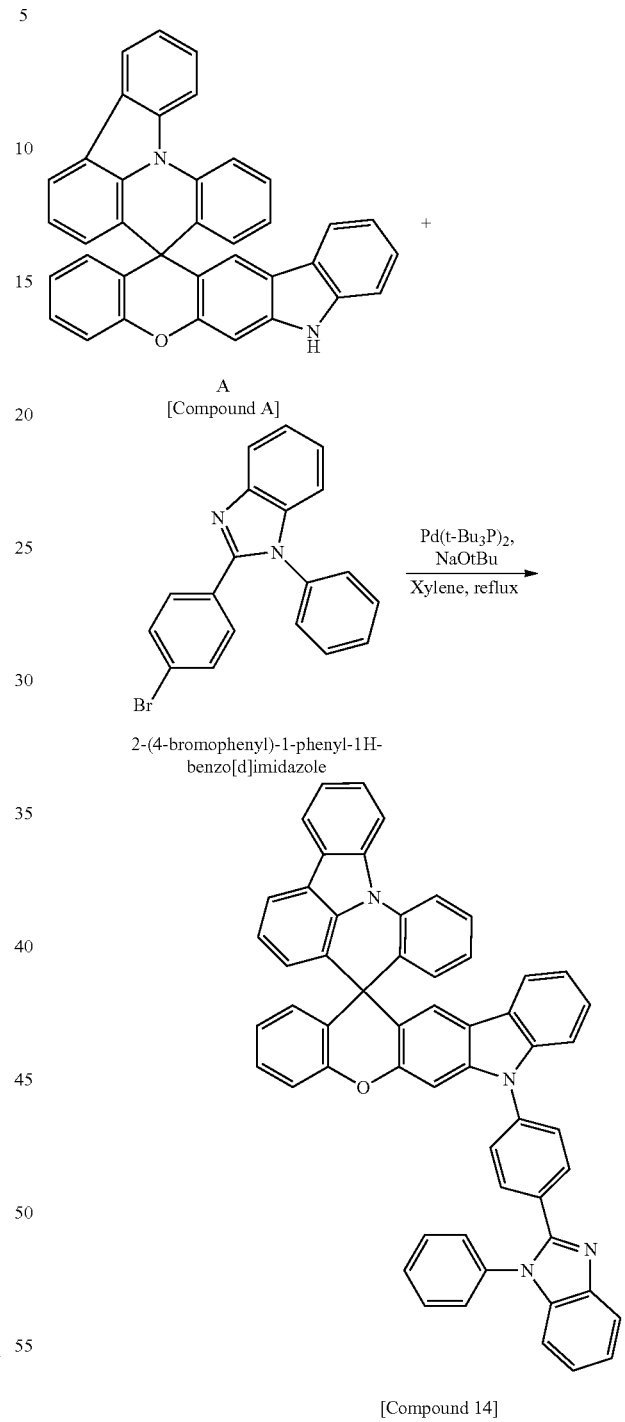

Compound A (10.0 g, 19.61 mmol) and 2-(4-bromophenyl)-1-phenyl-1H-benzo[d]imidazole (7.53 g, 21.57 mmol) were completely dissolved in 290 ml of xylene in a 500-ml round bottom flask under a nitrogen atmosphere, and then sodium tert-butoxide (2.26 g, 23.53 mol) was added thereto, bis(tri-tert-butylphosphine) palladium(0) (0.10 g, 0.20 mmol) was put thereinto, and then the resulting mixture was heated and stirred for 4 hours. The temperature was lowered to normal temperature, the mixture was filtered to remove the base, and then xylene was concentrated under reduced pressure, and the residue was recrystallized with 280 ml of ethyl acetate to prepare Compound 14 (12.23 g, yield: 80%).
<Preparation Example 15> Synthesis of Compounds of the Following Compounds 15 to 28
15
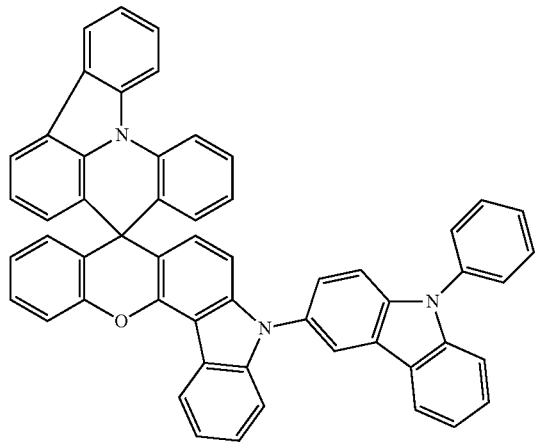
16
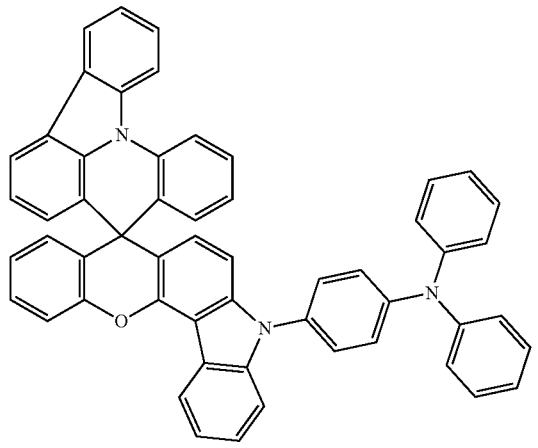
17
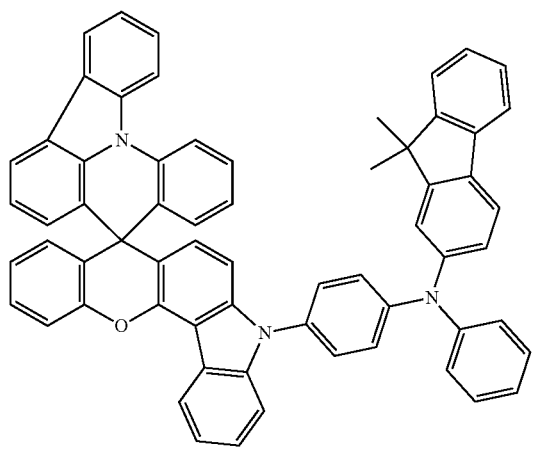
-continued
18
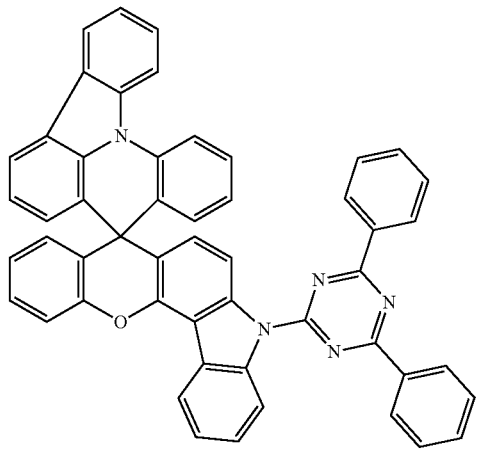
19
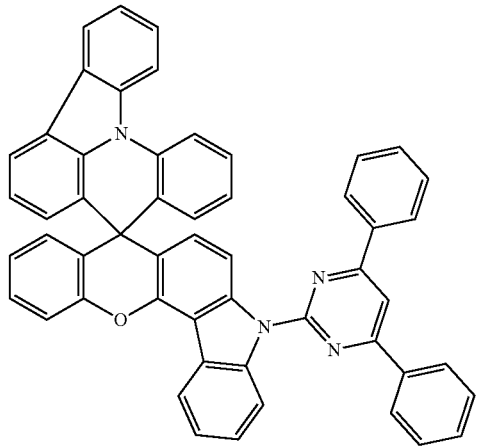
20
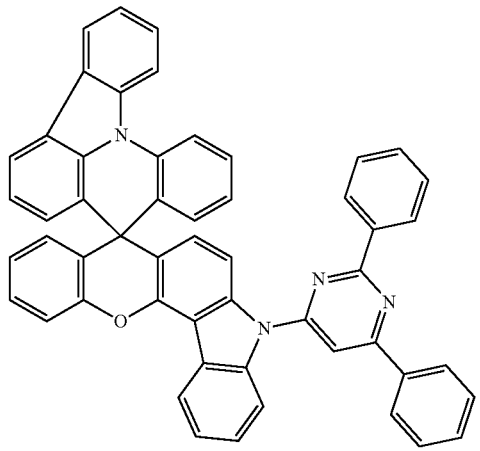

21
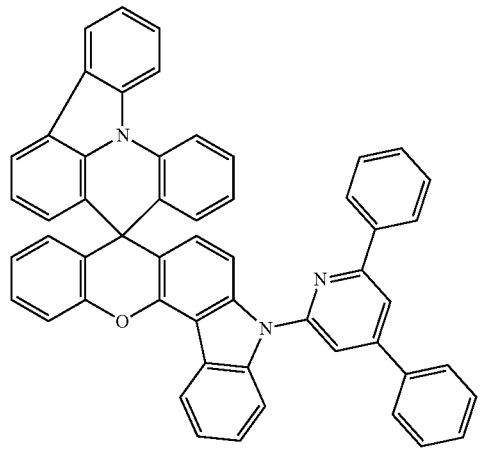
22
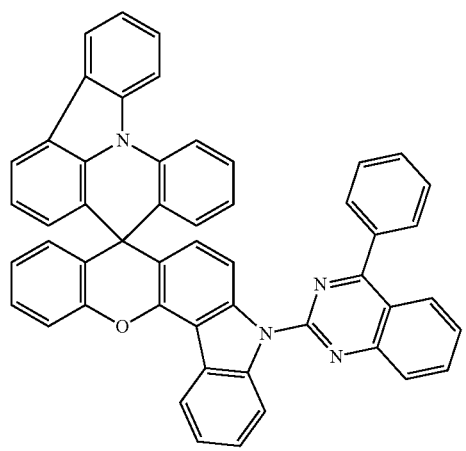
23
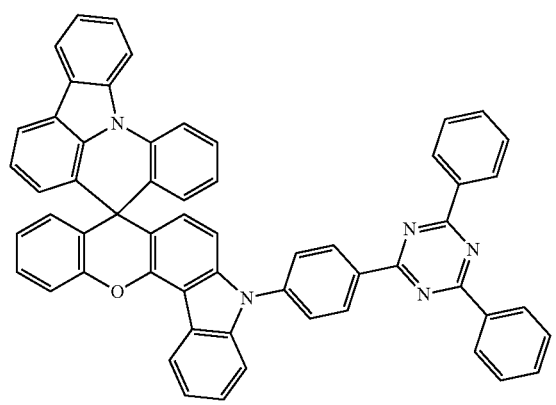
24
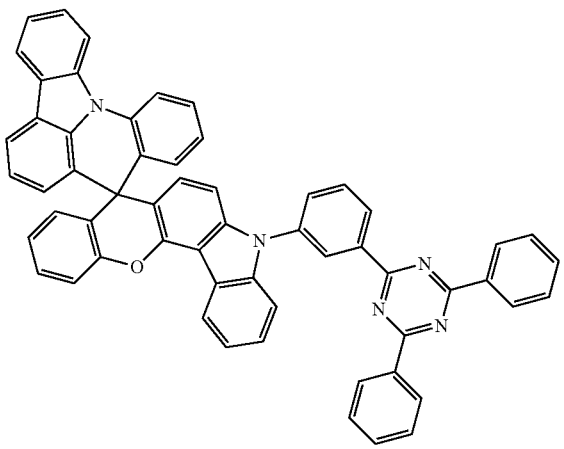
25
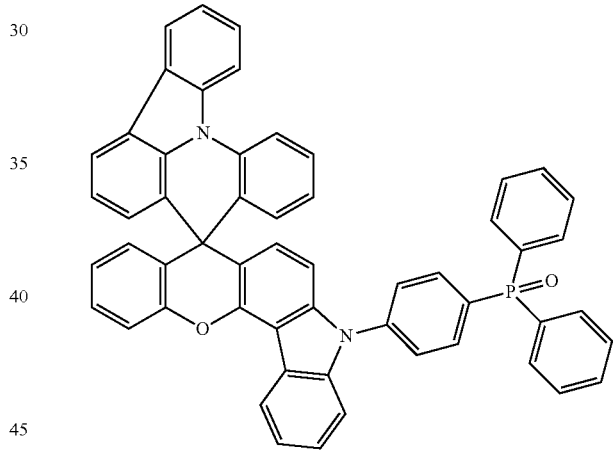
26
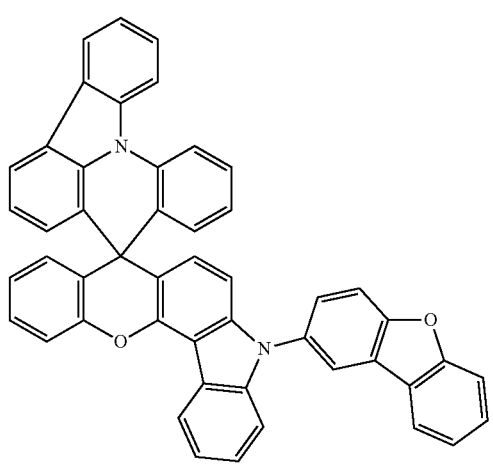

Preparation Example 16> Synthesis of Compounds of the Following Compounds 29 to 42

27
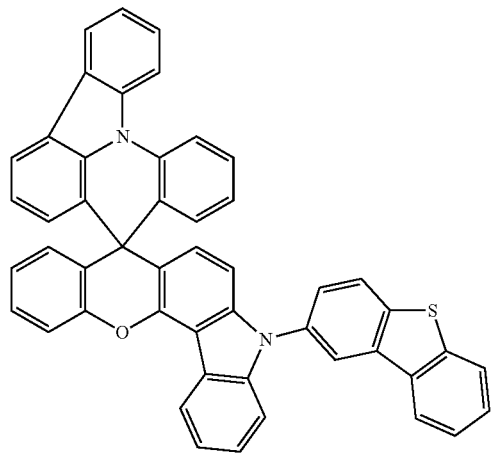

29
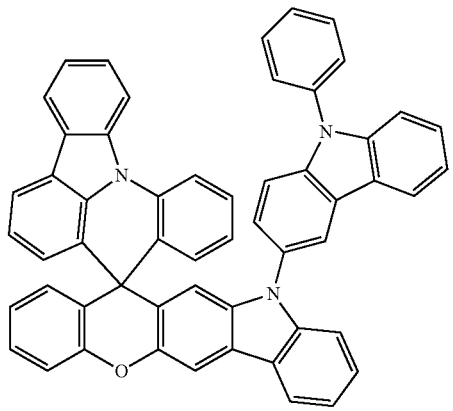

28
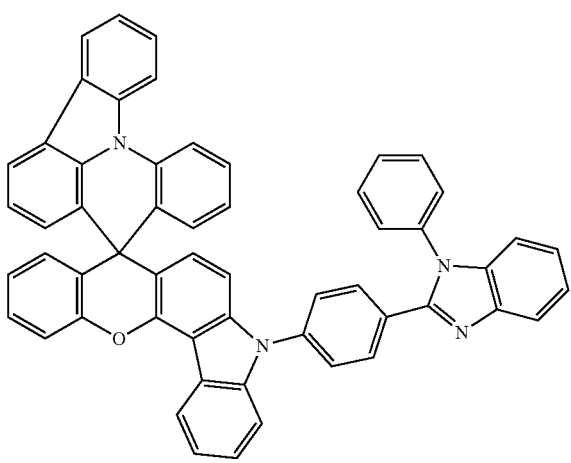

30
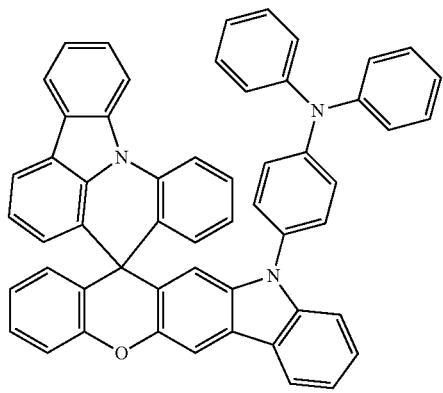

Compounds 15 to 28 were prepared in the same manner as in the method of preparing Compounds 1 to 14, except that a material which is Compound B was used instead of Compound A as a starting material in Preparation Examples 1 to 14. The MS[M+H]$^+$ values of Compounds 15 to 28 are shown in the following Table 1.

TABLE 1

| Compound No. | MS[M + H]$^+$ | Compound No. | MS[M + H] |
|---|---|---|---|
| 15 | 752 | 22 | 715 |
| 16 | 754 | 23 | 818 |
| 17 | 871 | 24 | 818 |
| 18 | 742 | 25 | 787 |
| 19 | 741 | 26 | 677 |
| 20 | 741 | 27 | 693 |
| 21 | 740 | 28 | 779 |

31
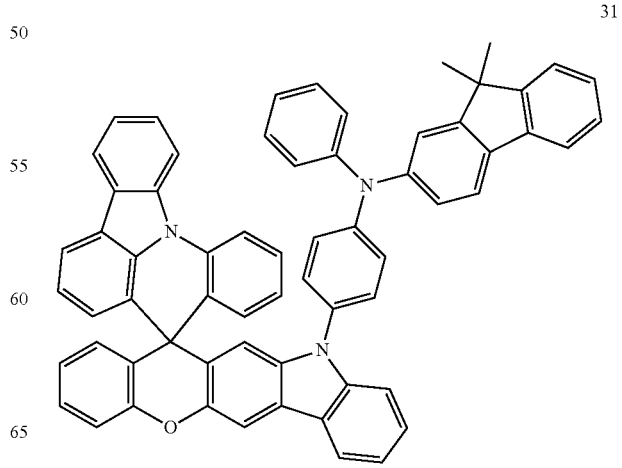

251
-continued
32
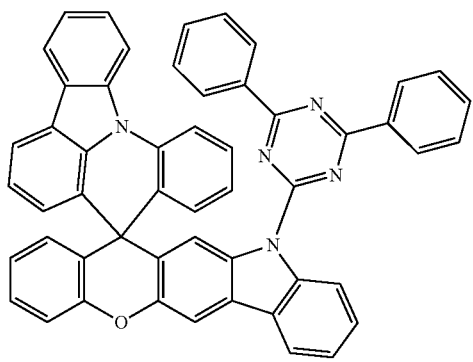
33
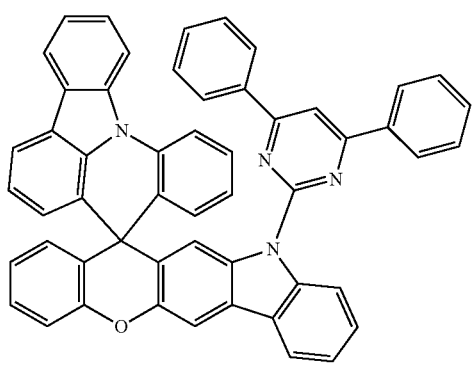
34
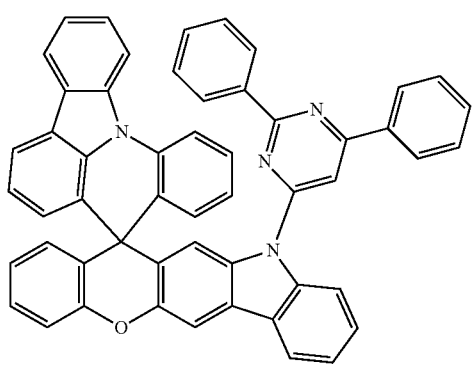
35
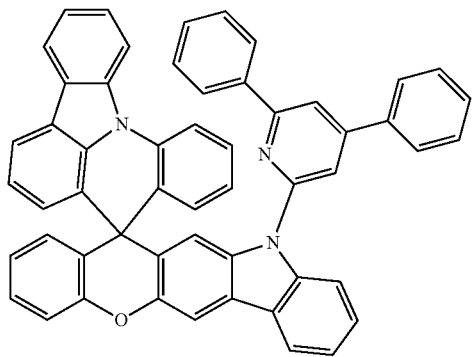
252
-continued
36
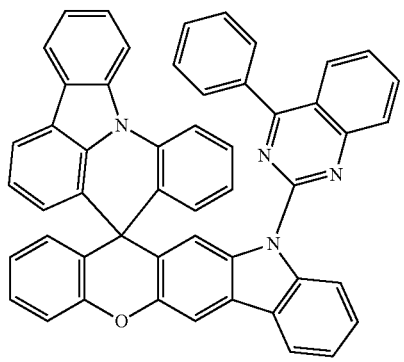
37
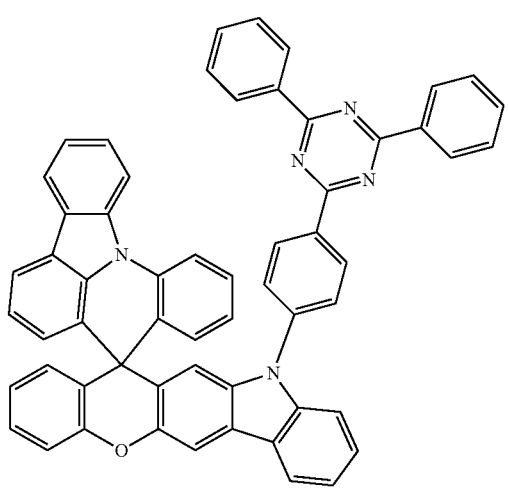
38
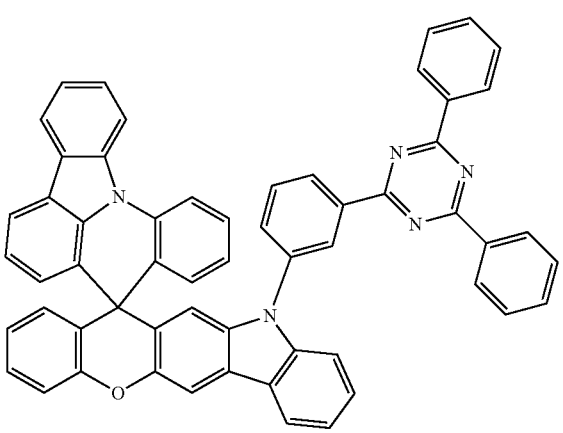

-continued

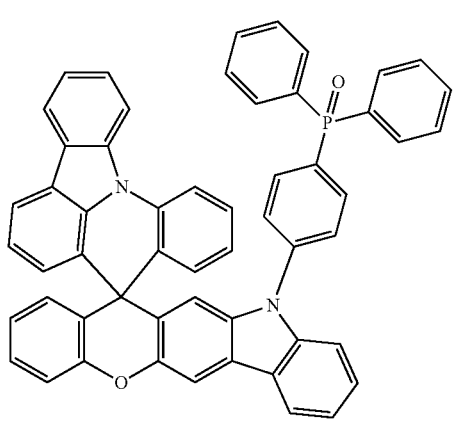

39

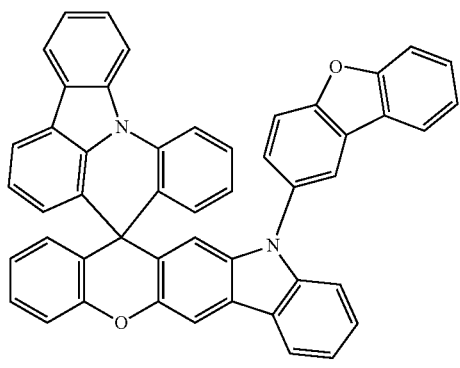

40

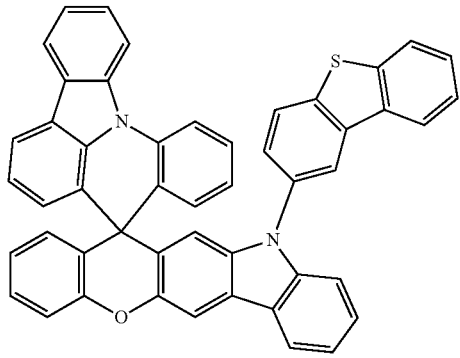

41

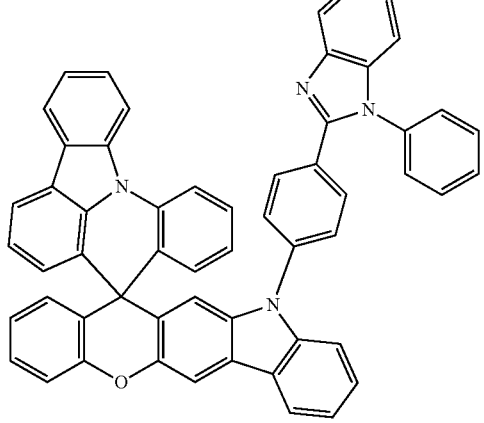

42

Compounds 29 to 42 were prepared in the same manner as in the method of preparing Compounds 1 to 16, except that a material which is Compound C was used instead of Compound A as a starting material in Preparation Examples 1 to 16. The MS[M+H]$^+$ values of Compounds 29 to 42 are shown in the following Table 2.

TABLE 2

| Compound No. | MS[M + H]$^+$ | Compound No. | MS[M + H] |
|---|---|---|---|
| 29 | 752 | 36 | 715 |
| 30 | 754 | 37 | 818 |
| 31 | 871 | 38 | 818 |
| 32 | 742 | 39 | 787 |
| 33 | 741 | 40 | 677 |
| 34 | 741 | 41 | 693 |
| 35 | 740 | 42 | 779 |

<Preparation Example 17> Synthesis of Compounds of the Following Compounds 43 to 56

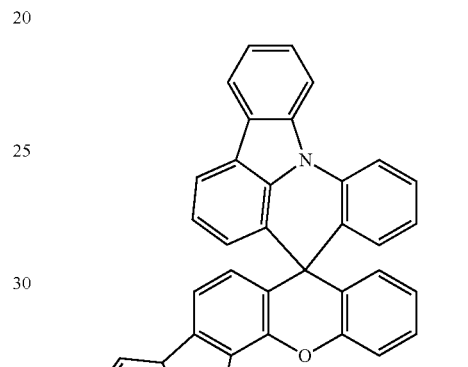

43

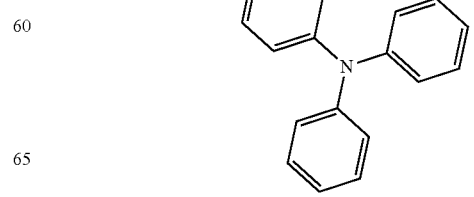

44

255
-continued
45
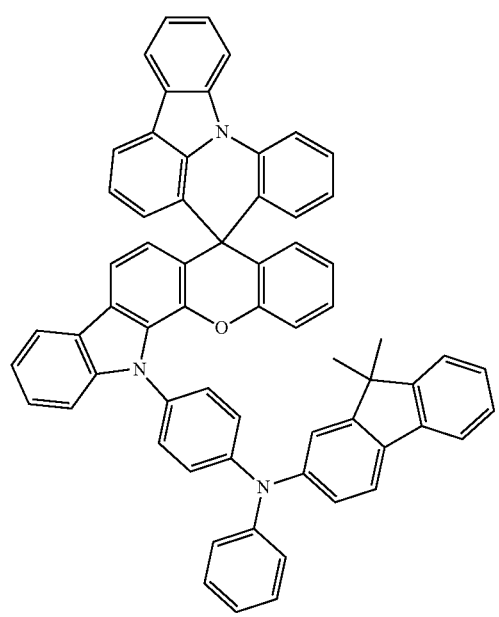
46
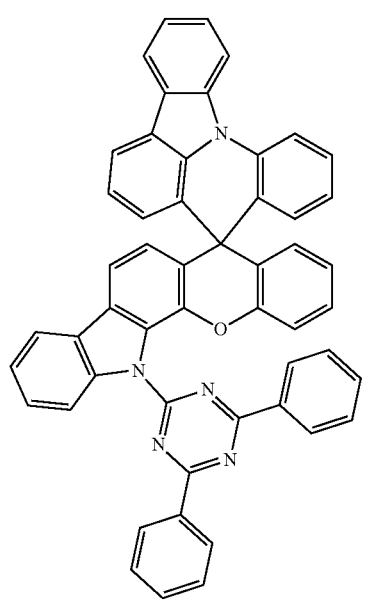
256
-continued
47
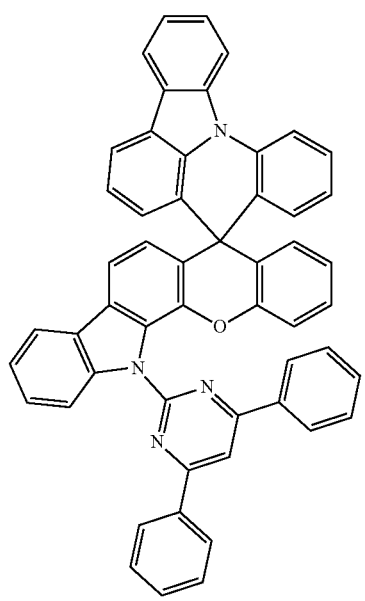
48
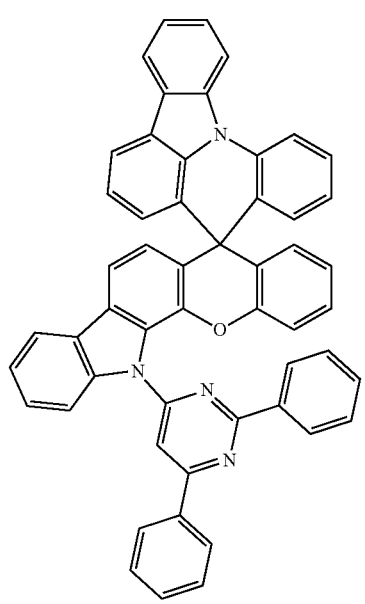

257
-continued
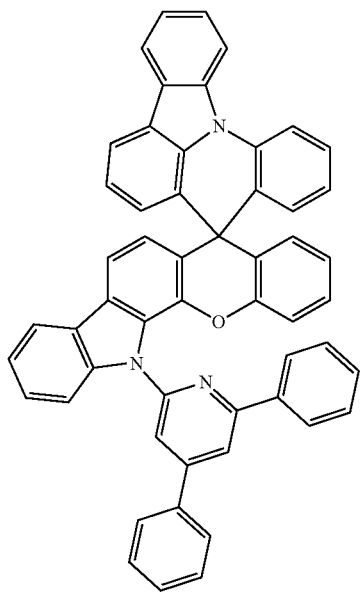
49
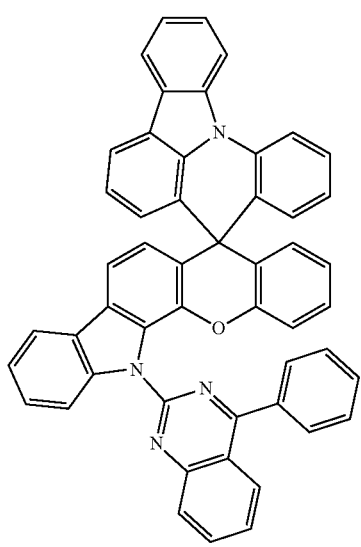
50
258
-continued
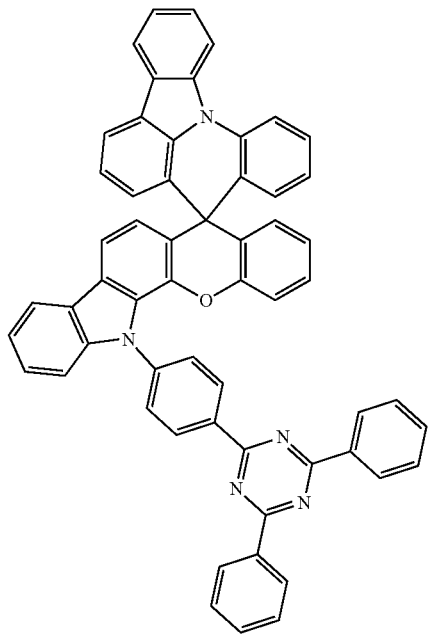
51
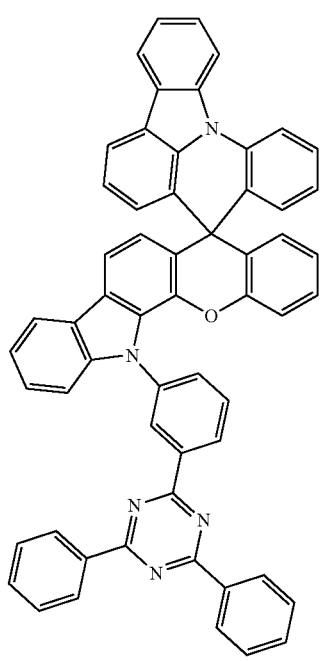
52

53
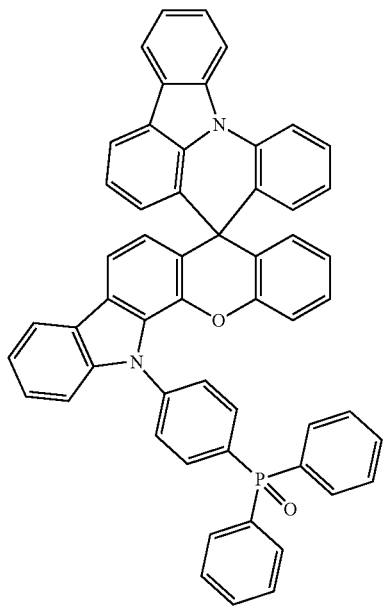
5
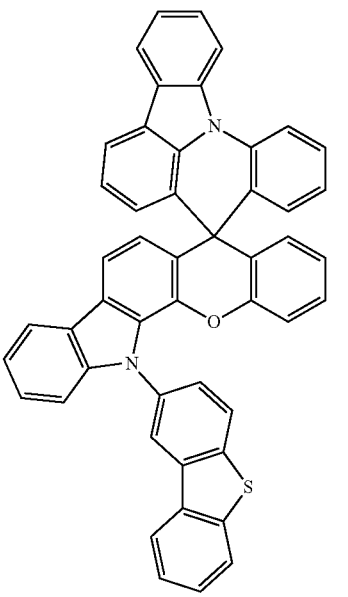
56
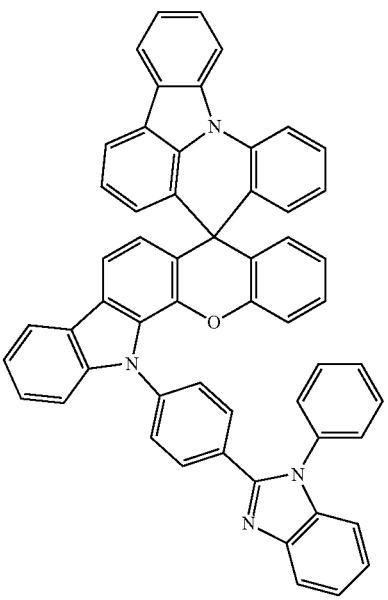
54
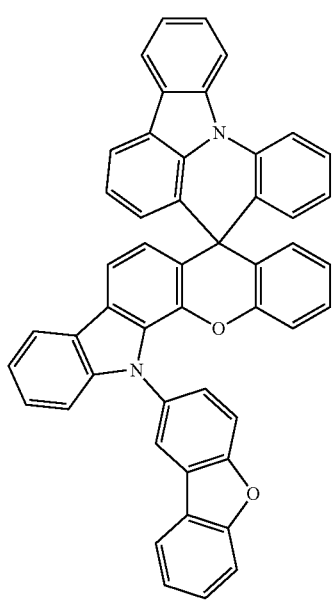
Compounds 43 to 56 were prepared in the same manner as in the method of preparing Compounds 1 to 16, except that a material which is Compound D was used instead of Compound A as a starting material in Preparation Examples 1 to 16. The MS[M+H]$^+$ values of Compounds 43 to 56 are shown in the following Table 3.
TABLE 3
| Compound No. | MS[M + H]$^+$ | Compound No. | MS[M + H] |
|---|---|---|---|
| 43 | 752 | 50 | 715 |
| 44 | 754 | 51 | 818 |
| 45 | 871 | 52 | 818 |
| 46 | 742 | 53 | 787 |
| 47 | 741 | 54 | 677 |
| 48 | 741 | 55 | 693 |
| 49 | 740 | 56 | 779 |

<Preparation Example 18> Synthesis of Compounds of the Following Compounds 57 to 70
57
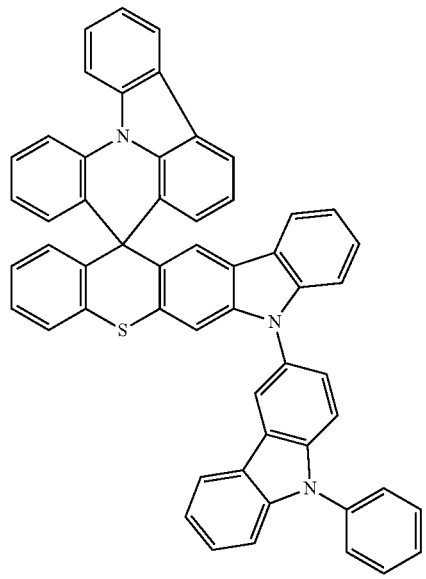
58
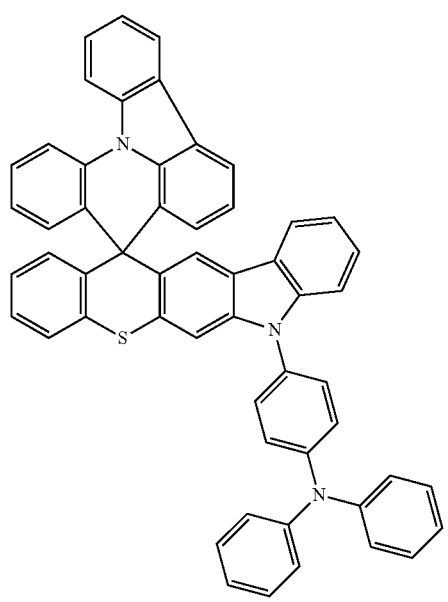
59
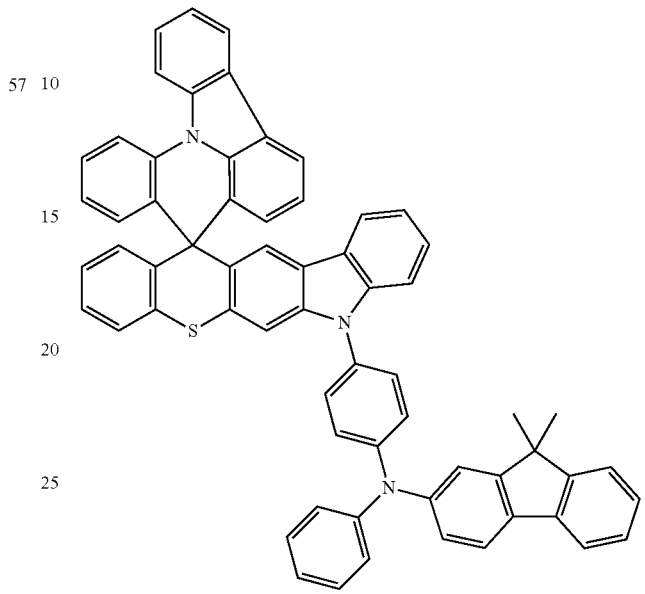
60
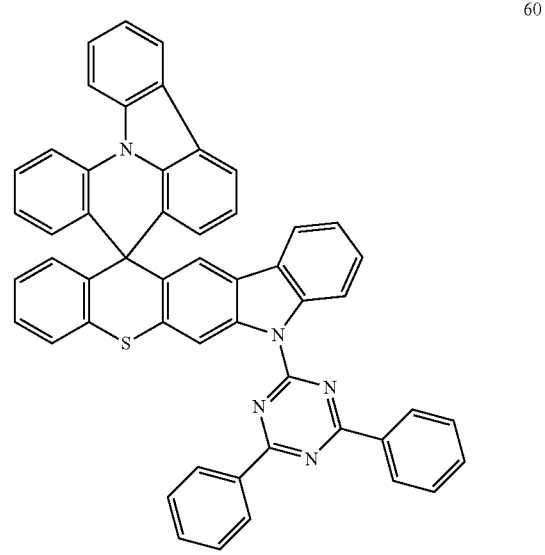

61
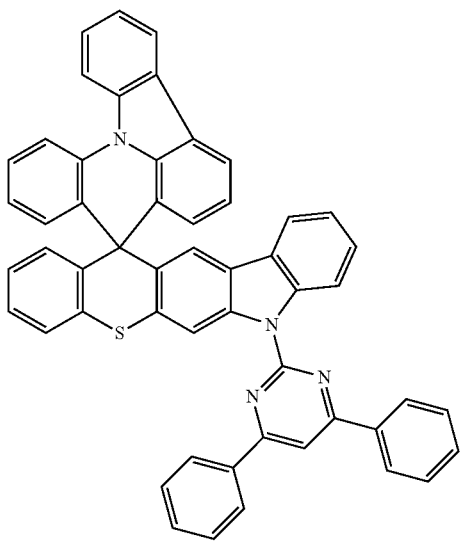
62
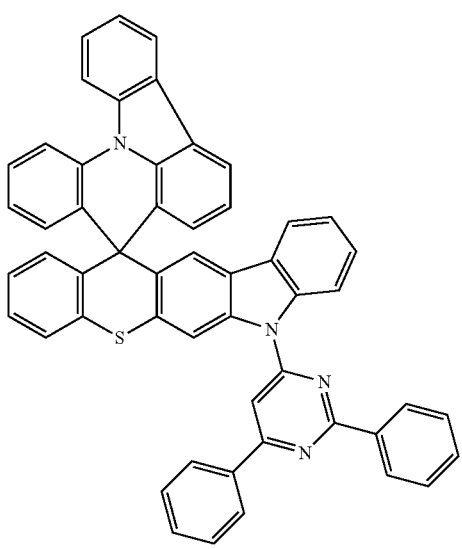
63
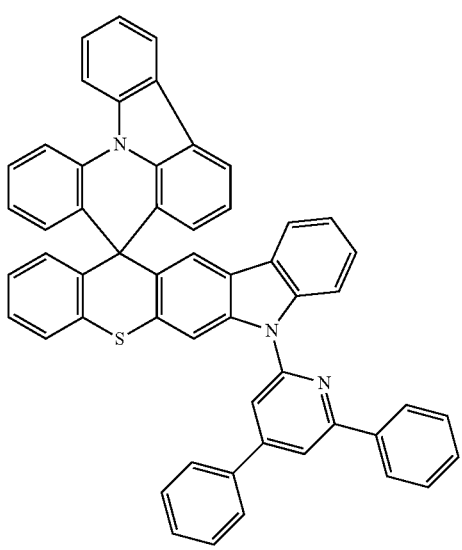
64
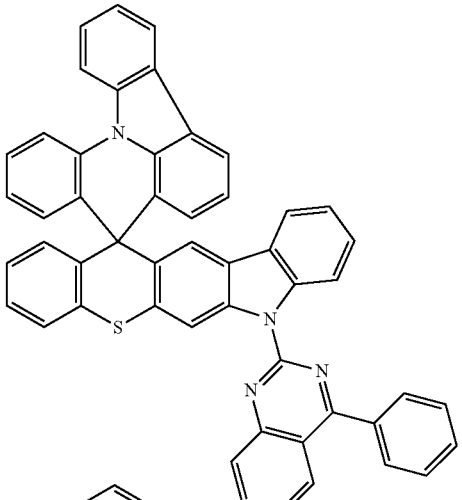
65
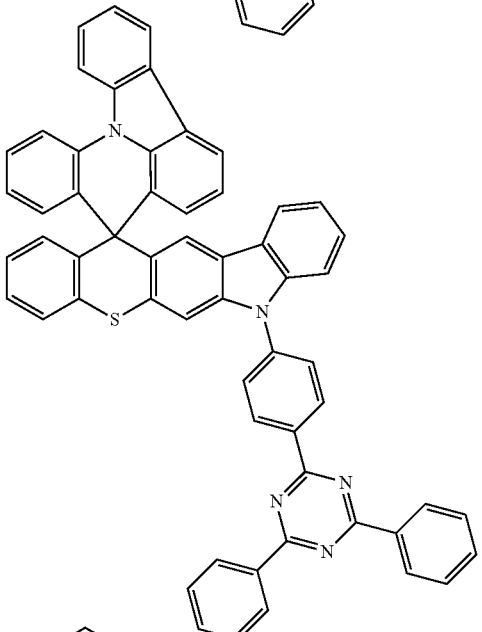
66
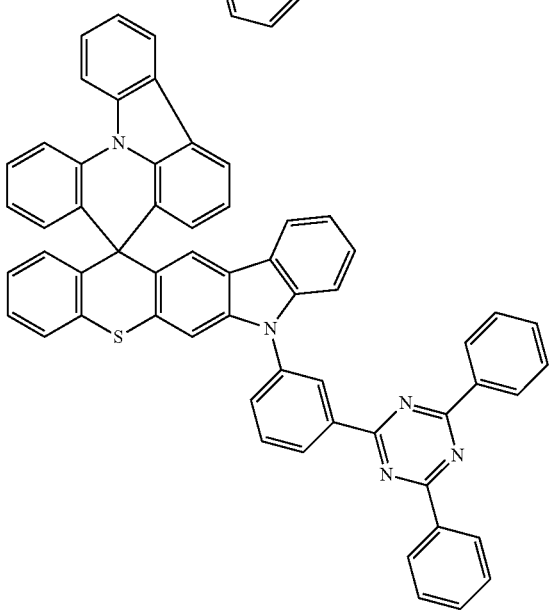

67

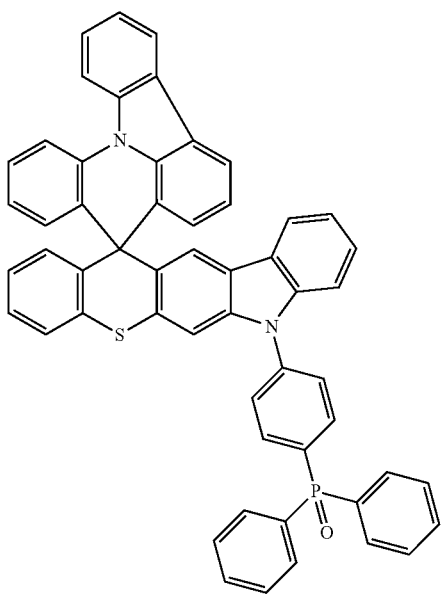

68

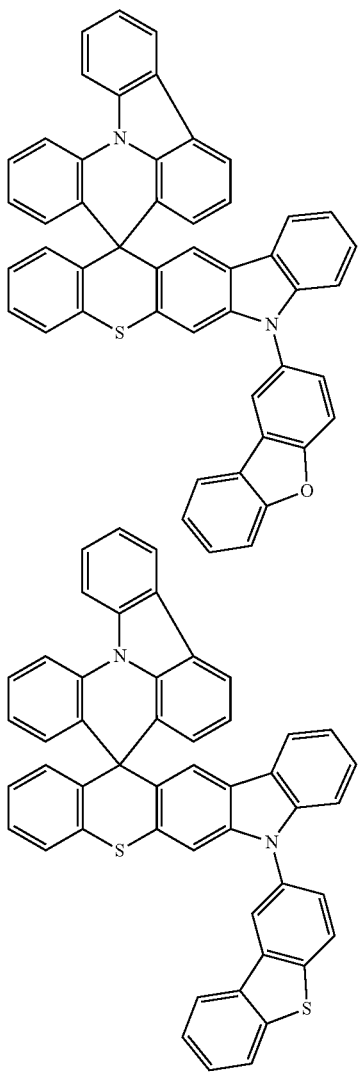

70

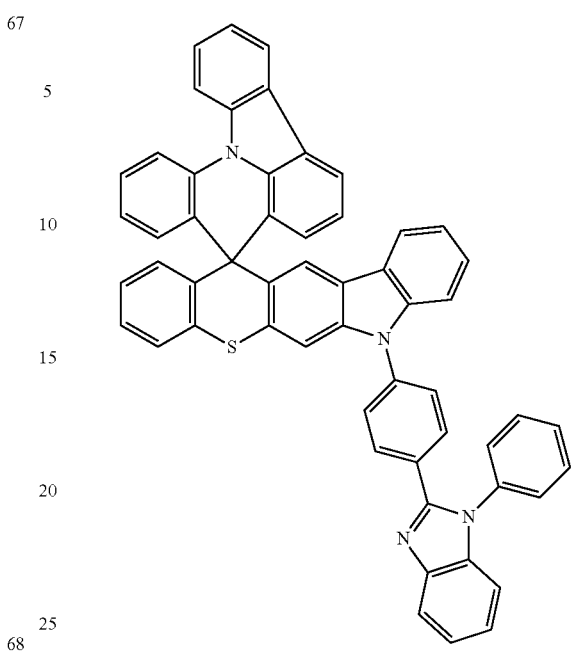

Compounds 57 to 70 were prepared in the same manner as in the method of preparing Compounds 1 to 16, except that a material which is Compound E was used instead of Compound A as a starting material in Preparation Examples 1 to 16. The MS[M+H]$^+$ values of Compounds 57 to 70 are shown in the following Table 4.

TABLE 4

| Compound No. | MS[M + H]$^+$ | Compound No. | MS[M + H] |
|---|---|---|---|
| 57 | 768 | 64 | 731 |
| 58 | 770 | 65 | 834 |
| 59 | 887 | 66 | 834 |
| 60 | 758 | 67 | 803 |
| 61 | 757 | 68 | 693 |
| 62 | 757 | 69 | 709 |
| 63 | 756 | 70 | 795 |

<Preparation Example 19> Synthesis of Compounds of the Following Compounds 71 to 84

71

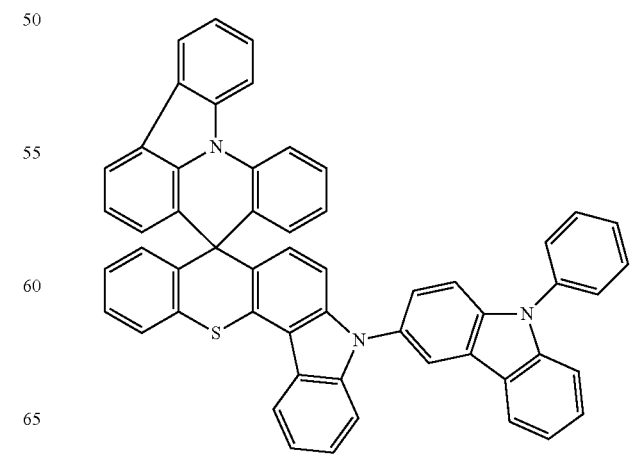

72
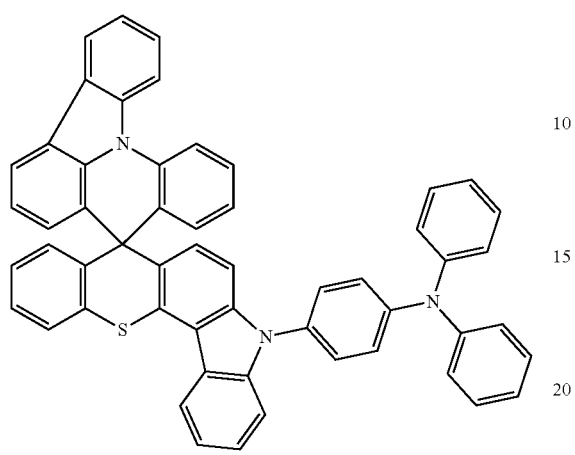
73
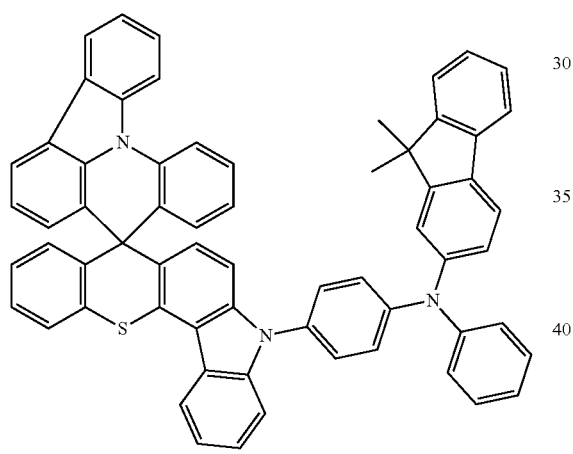
74
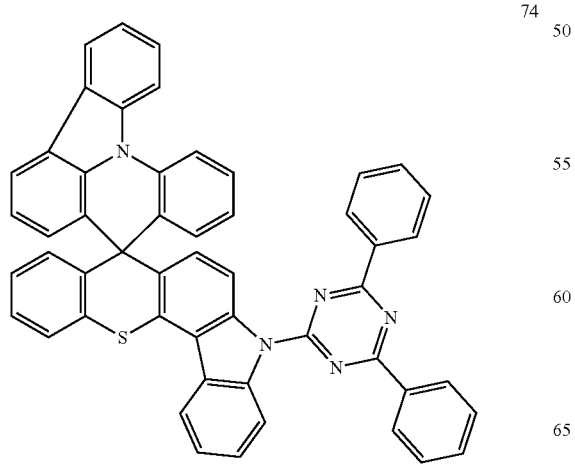
75
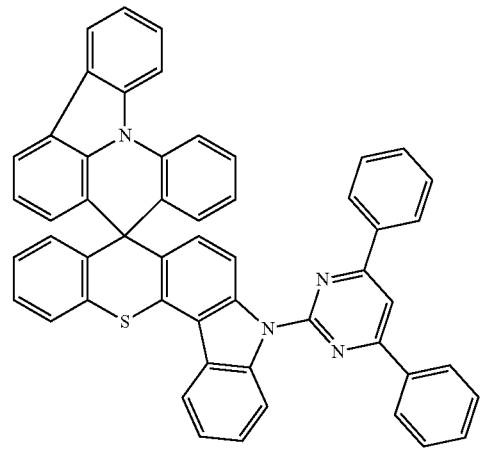
76
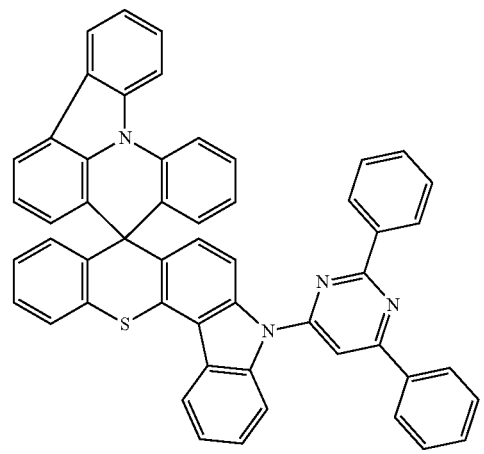
77
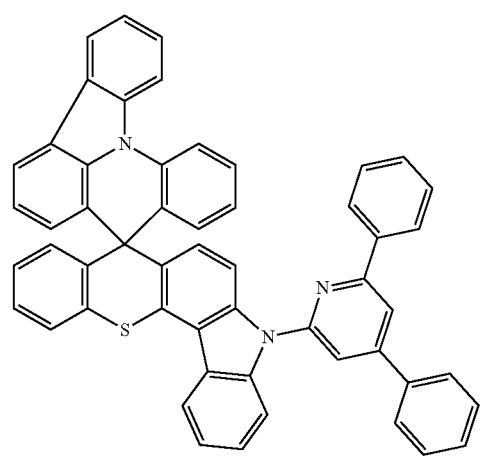

269
-continued
78
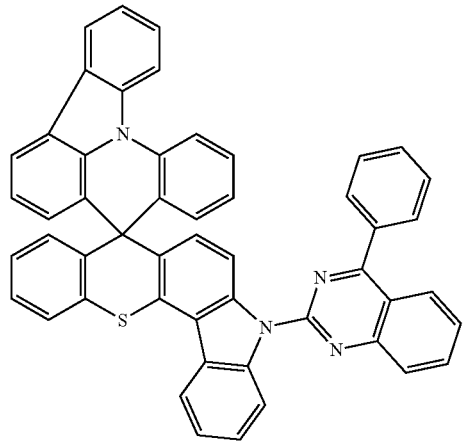
79
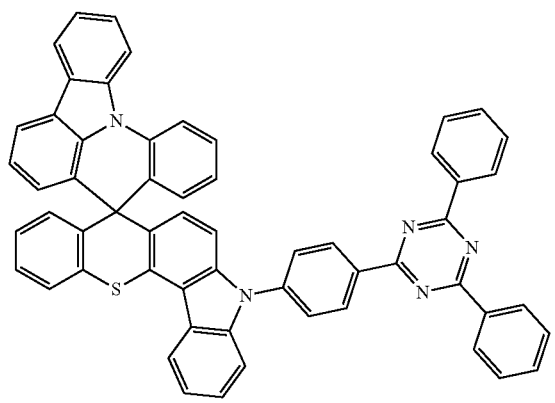
80
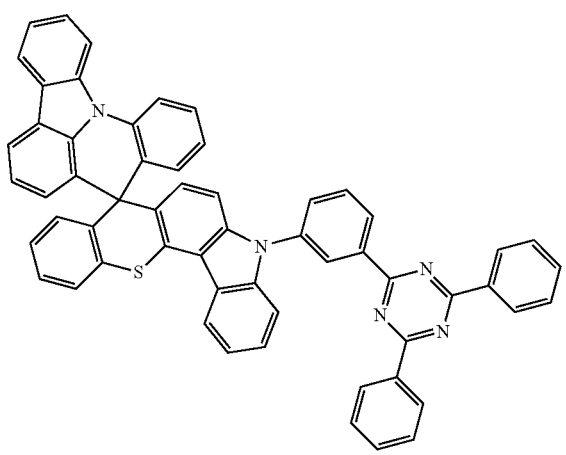
270
-continued
81
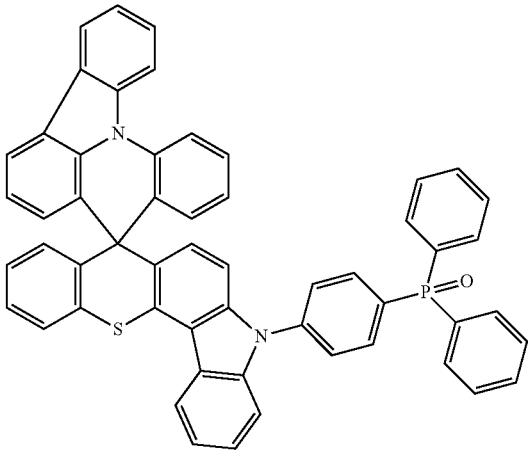
82
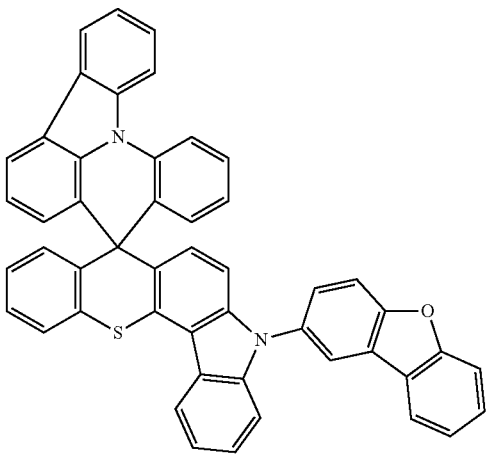
83
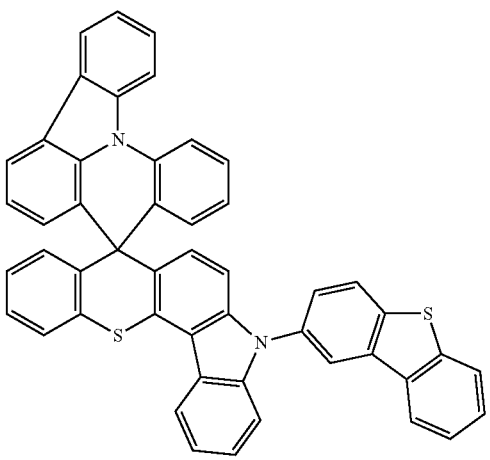

84

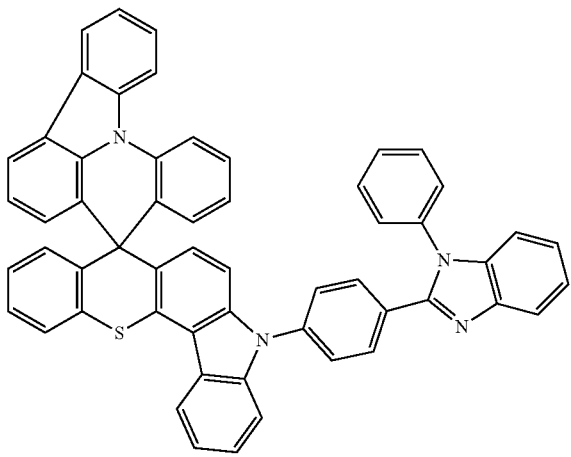

86

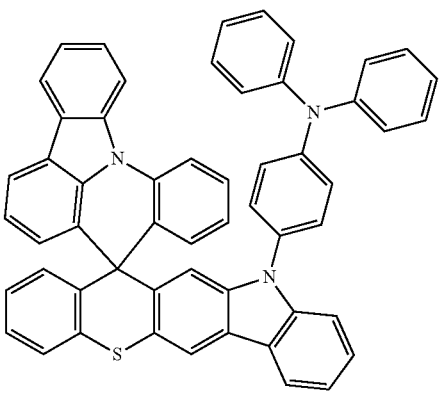

Compounds 71 to 84 were prepared in the same manner as in the method of preparing Compounds 1 to 16, except that a material which is Compound F was used instead of Compound A as a starting material in Preparation Examples 1 to 16. The MS[M+H]⁺ values of Compounds 71 to 84 are shown in the following Table 5.

TABLE 5

| Compound No. | MS[M + H]⁺ | Compound No. | MS[M + H] |
| --- | --- | --- | --- |
| 71 | 768 | 78 | 731 |
| 72 | 770 | 79 | 834 |
| 73 | 887 | 80 | 834 |
| 74 | 758 | 81 | 803 |
| 75 | 757 | 82 | 693 |
| 76 | 757 | 83 | 709 |
| 77 | 756 | 84 | 795 |

<Preparation Example 20> Synthesis of Compounds of the Following Compounds 85 to 98

87

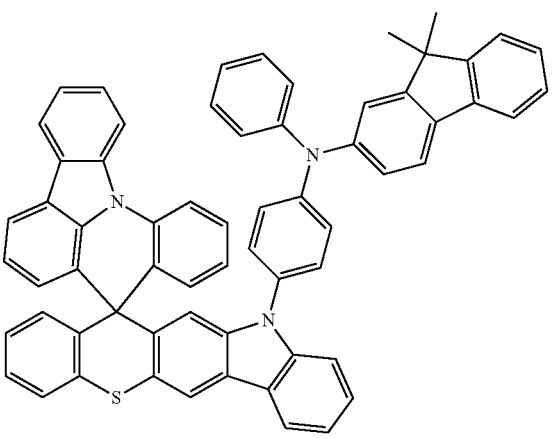

85

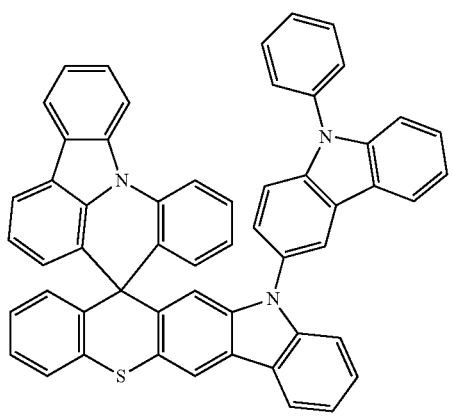

88

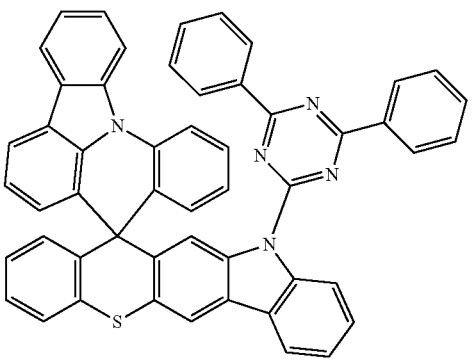

89

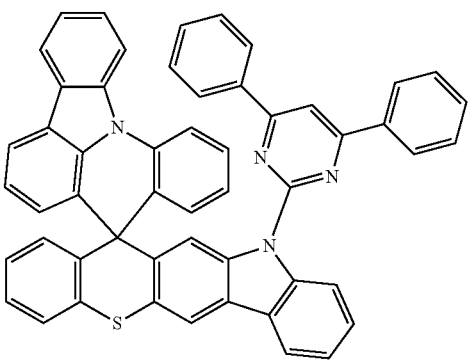

90
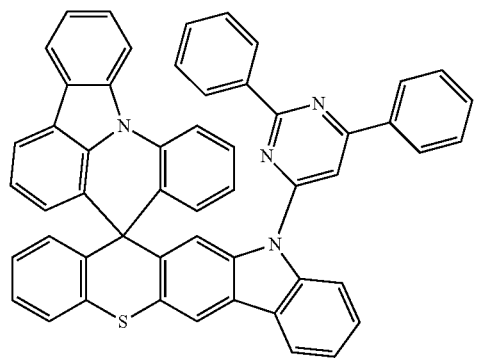
91
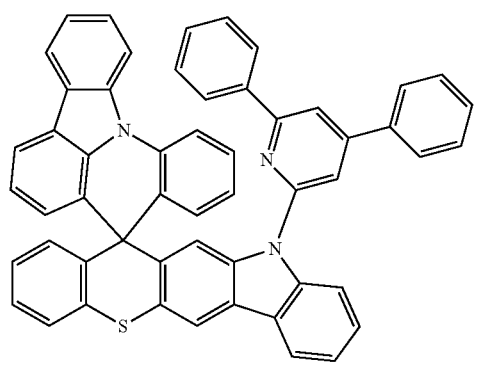
92
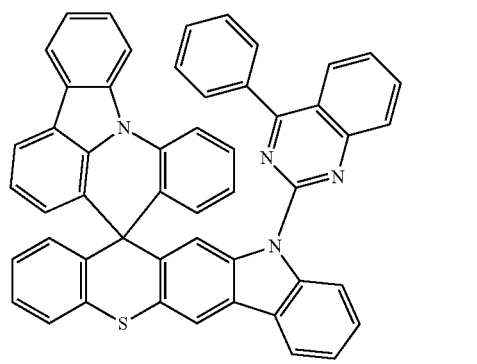
93
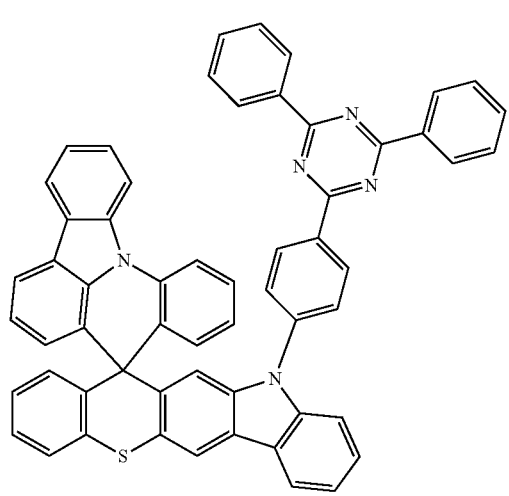
94
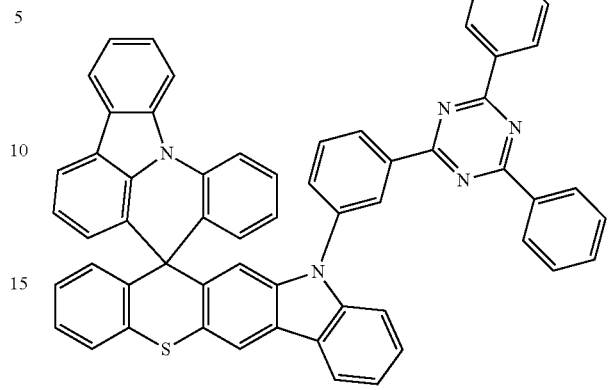
95
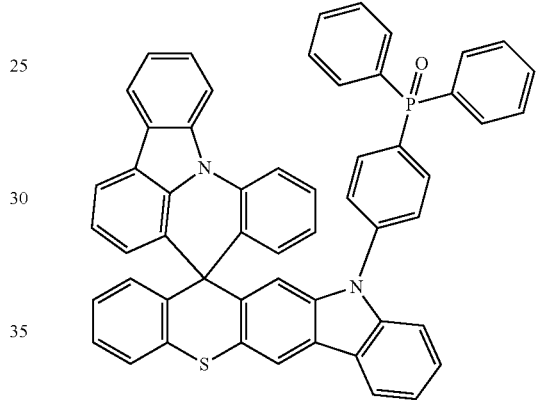
96
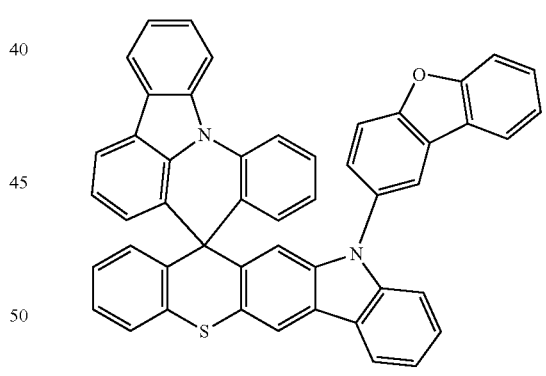
97
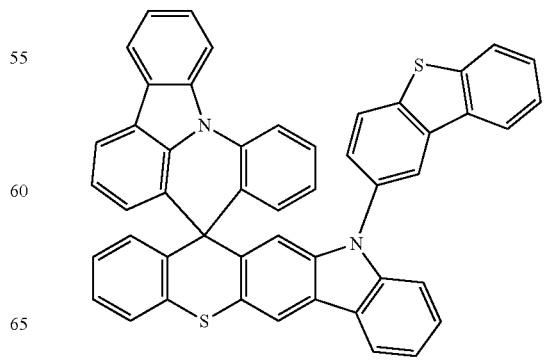

98

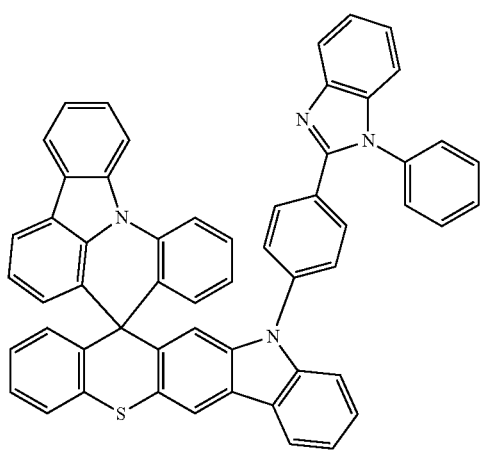

Compounds 85 to 98 were prepared in the same manner as in the method of preparing Compounds 1 to 16, except that a material which is Compound G was used instead of Compound A as a starting material in Preparation Examples 1 to 16. The MS[M+H]$^+$ values of Compounds 85 to 98 are shown in the following Table 6.

TABLE 6

| Compound No. | MS[M + H]$^+$ | Compound No. | MS[M + H] |
|---|---|---|---|
| 85 | 768 | 92 | 731 |
| 86 | 770 | 93 | 834 |
| 87 | 887 | 94 | 834 |
| 88 | 758 | 95 | 803 |
| 89 | 757 | 96 | 693 |
| 90 | 757 | 97 | 709 |
| 91 | 756 | 98 | 795 |

<Preparation Example 21> Synthesis of Compounds of the Following Compounds 99 to 112

99

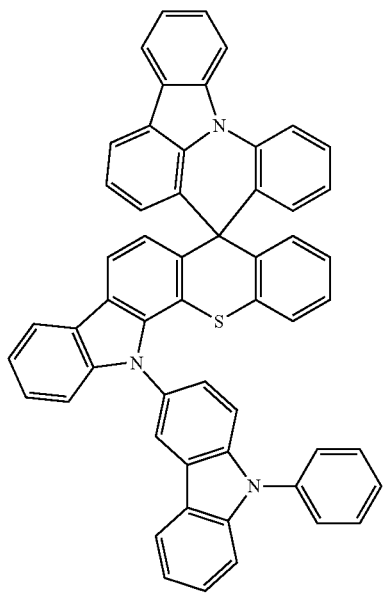

100

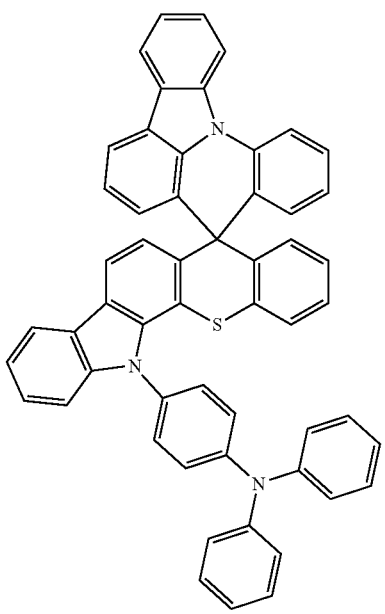

101

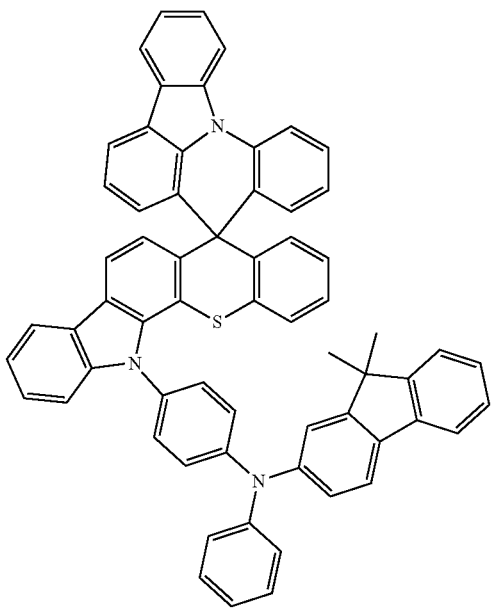

277
-continued
102
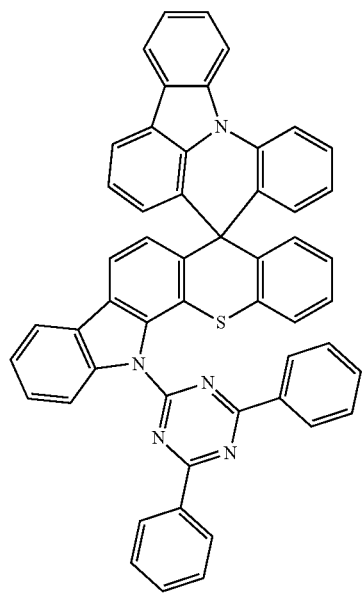
103
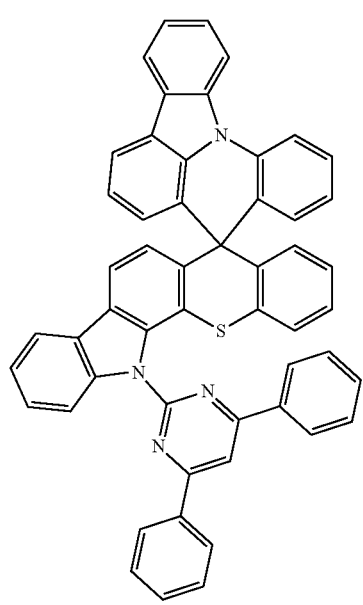
278
-continued
104
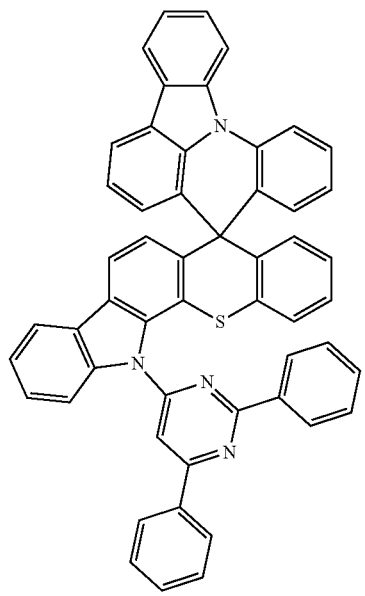
105
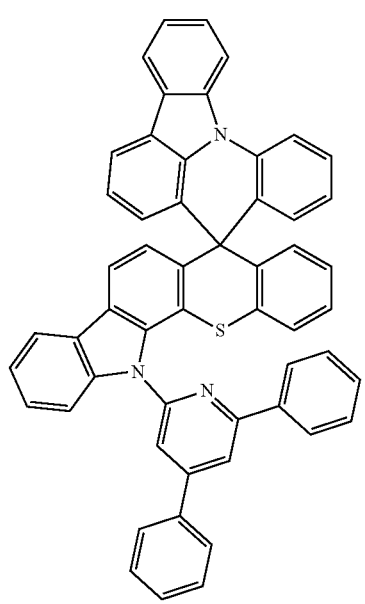

279
-continued
106
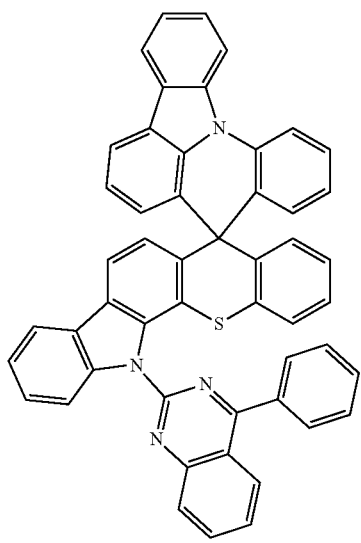
107
280
-continued
108
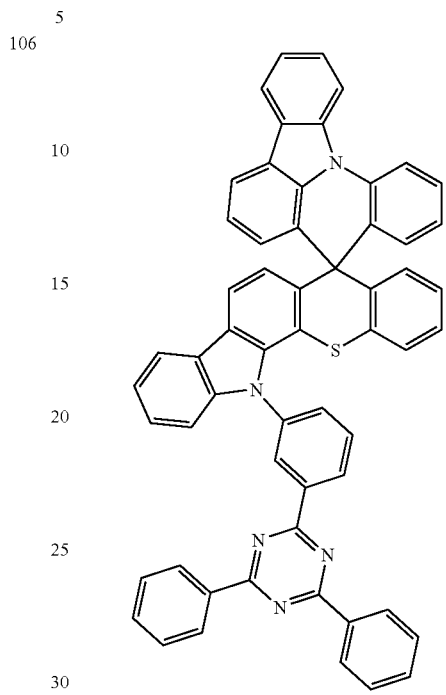
109

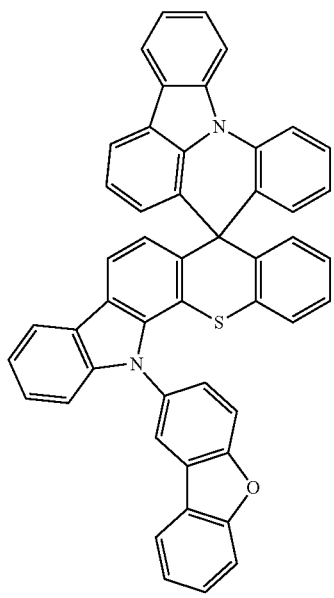
110
111
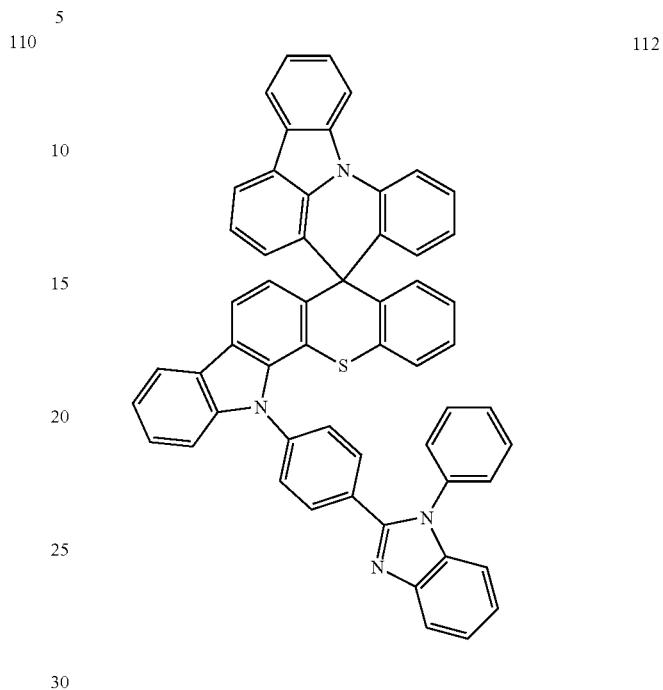
112
Compounds 99 to 112 were prepared in the same manner as in the method of preparing Compounds 1 to 16, except that a material which is Compound H was used instead of Compound A as a starting material in Preparation Examples 1 to 16. The MS[M+H]$^+$ values of Compounds 99 to 112 are shown in the following Table 7.
TABLE 7
| Compound No. | MS[M + H]$^+$ | Compound No. | MS[M + H] |
|---|---|---|---|
| 99 | 768 | 106 | 731 |
| 100 | 770 | 107 | 834 |
| 101 | 887 | 108 | 834 |
| 102 | 758 | 109 | 803 |
| 103 | 757 | 110 | 693 |
| 104 | 757 | 111 | 709 |
| 105 | 756 | 112 | 795 |

<Preparation Example 22> Synthesis of Compounds of the Following Compounds 113 to 224
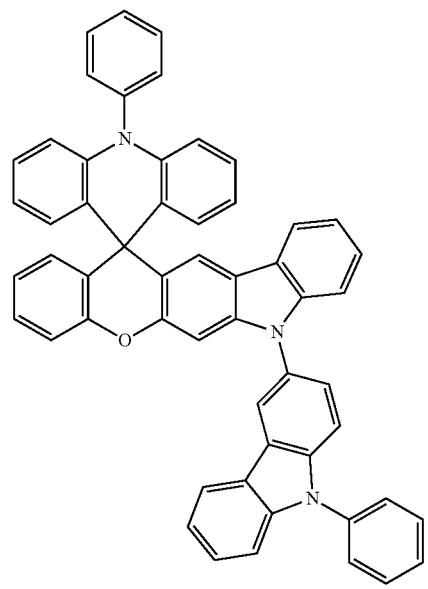
113
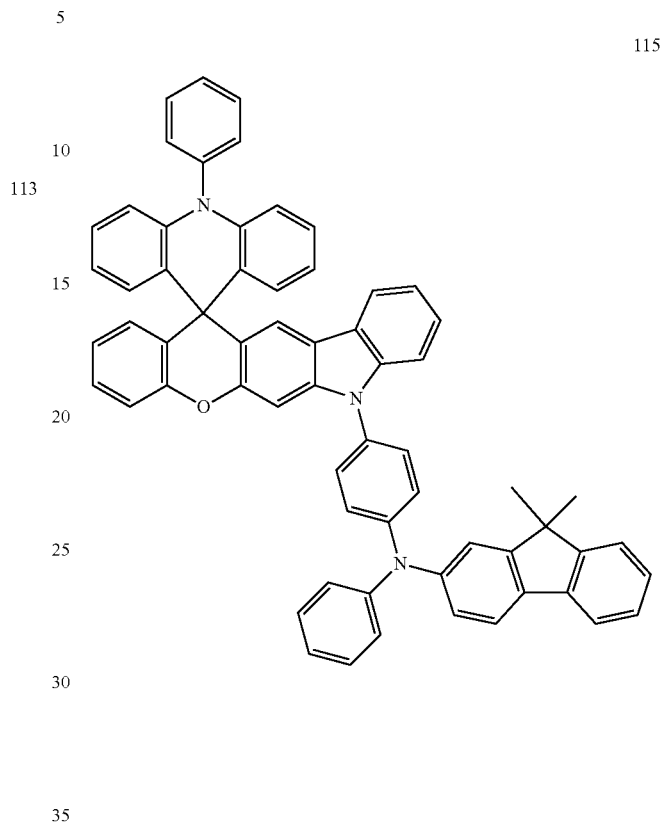
115
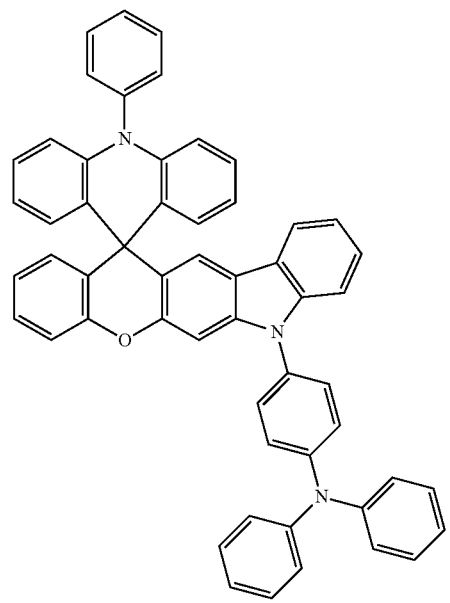
114
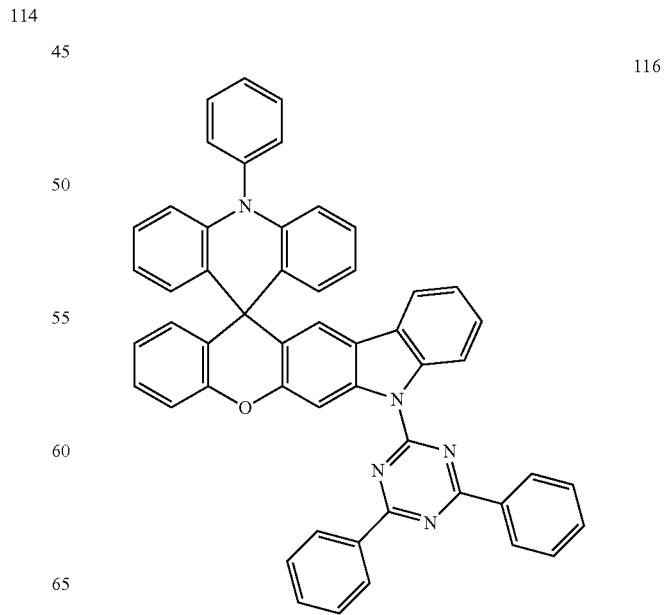
116

-continued
117
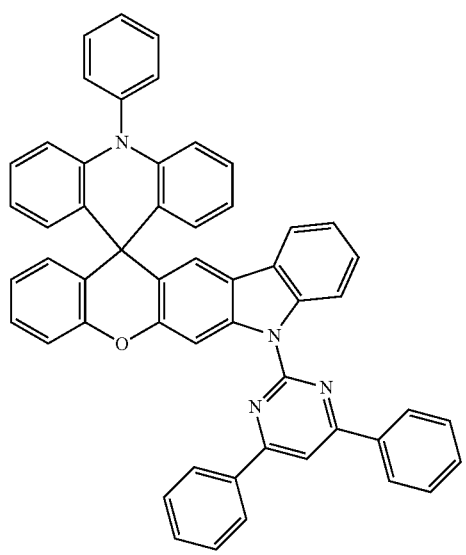
118
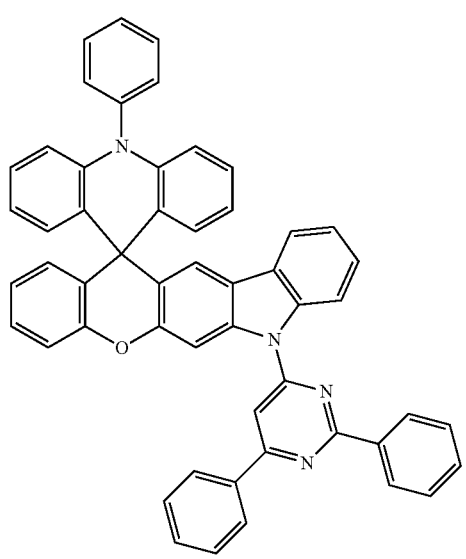
119
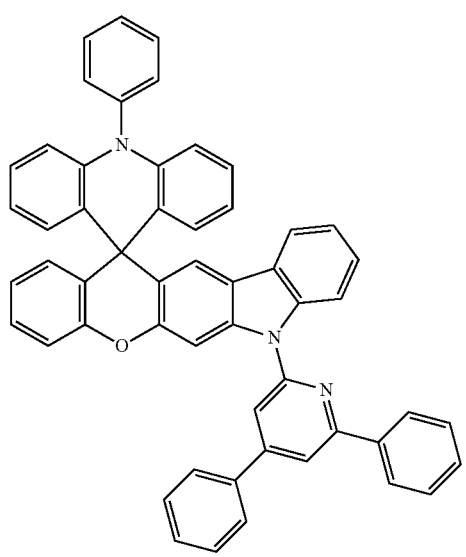
-continued
120
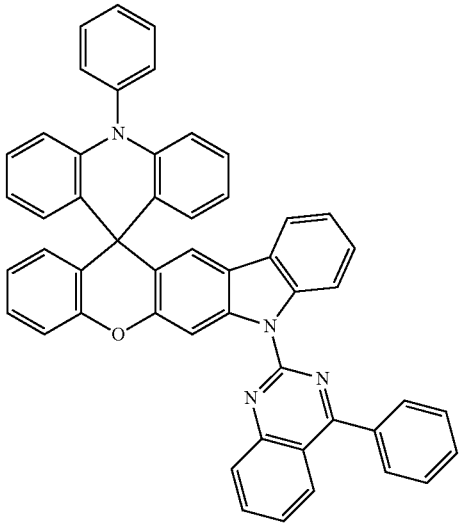
121
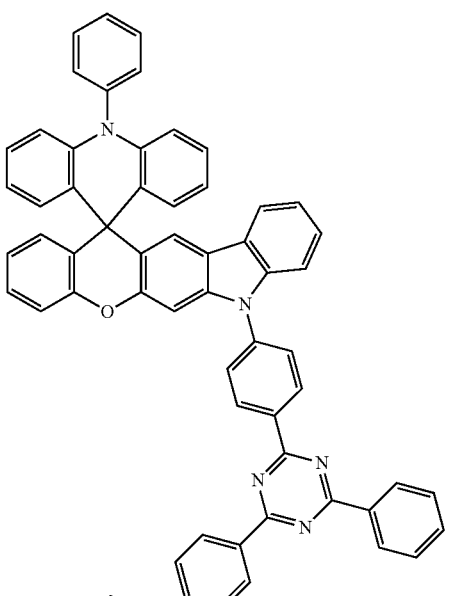
122
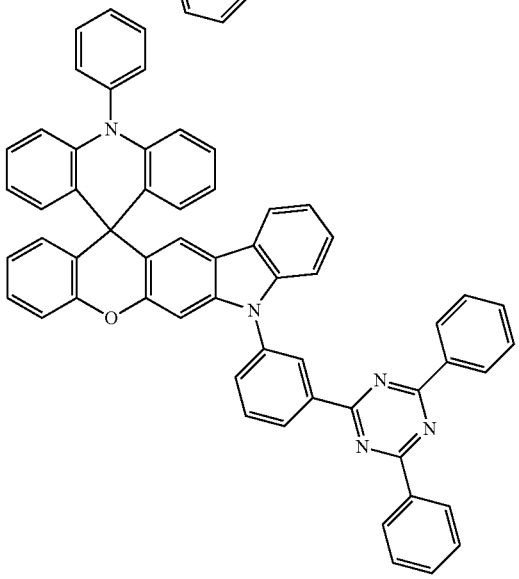

287
-continued
123
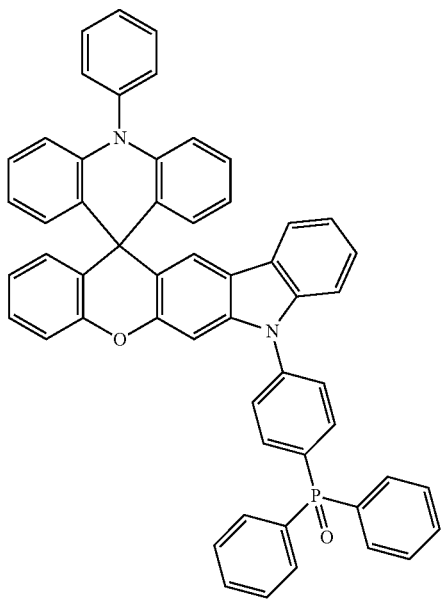
124
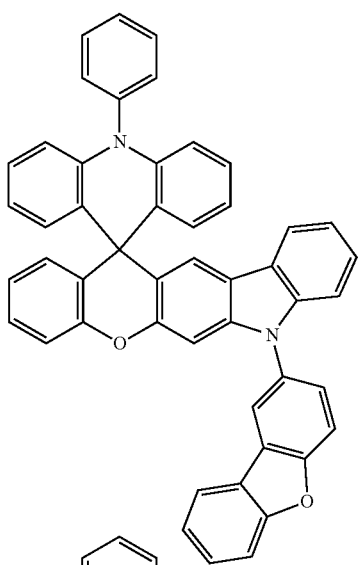
125
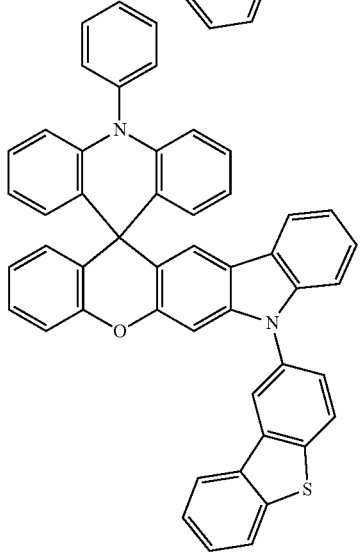
288
-continued
126
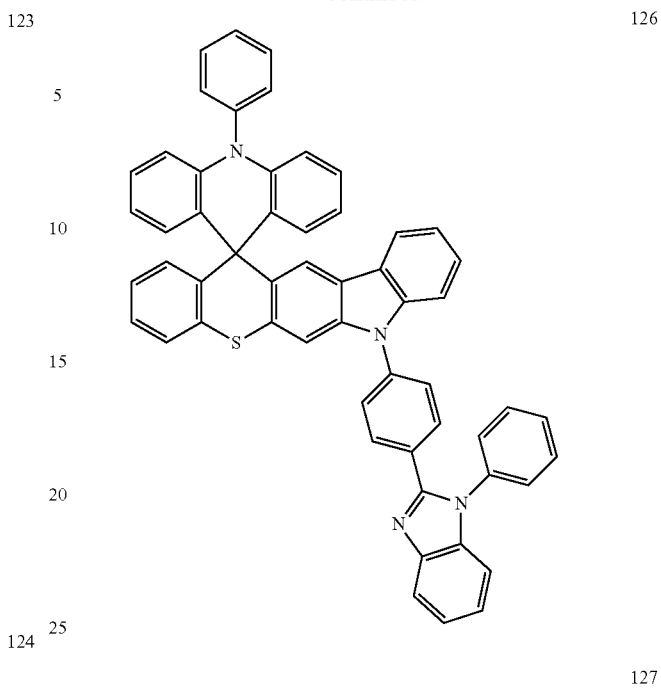
127
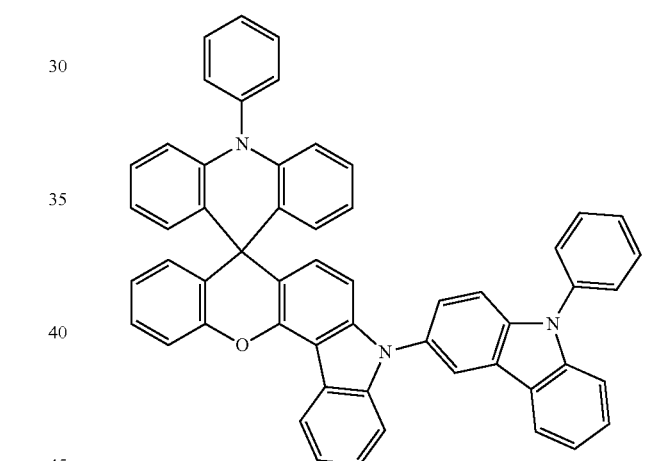
128
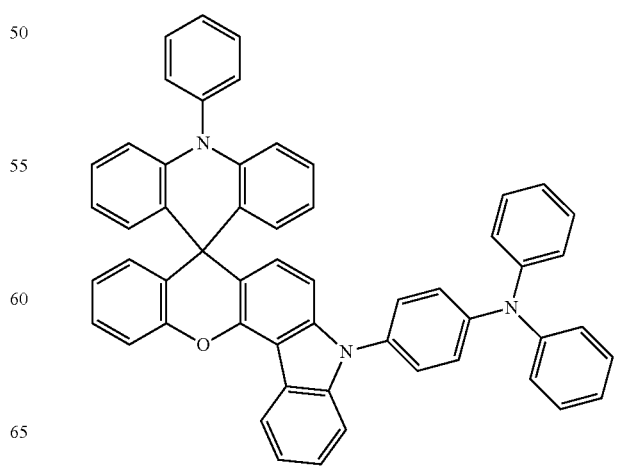

289
-continued
129
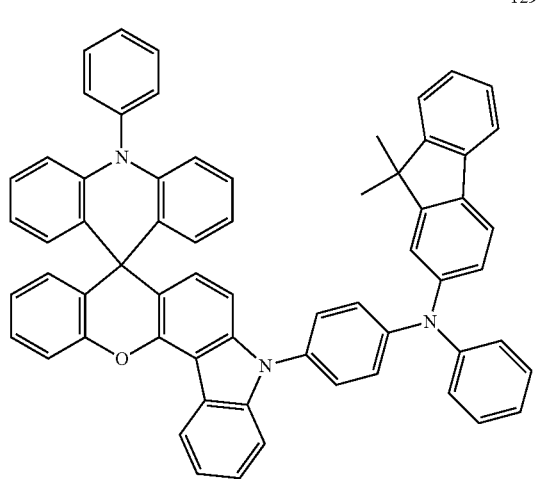
130
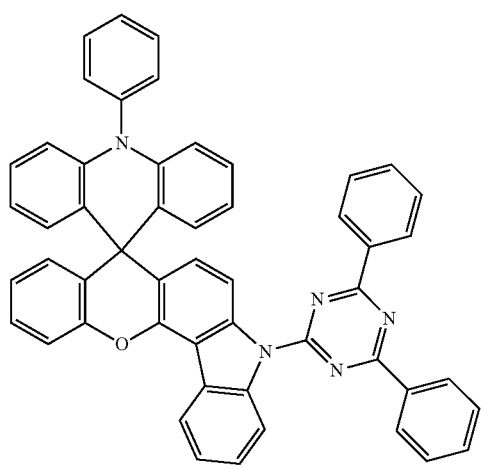
131
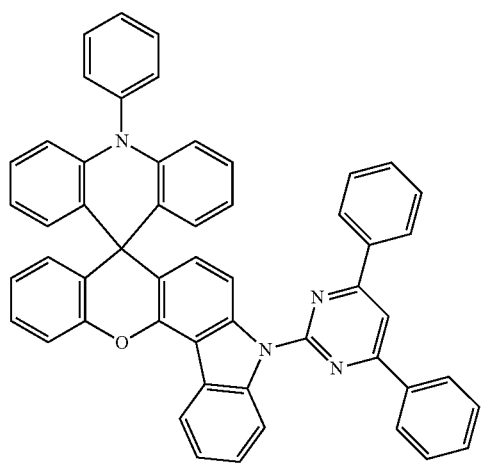
290
-continued
132
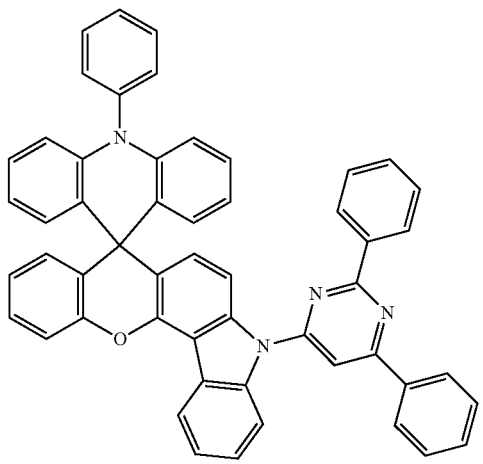
133
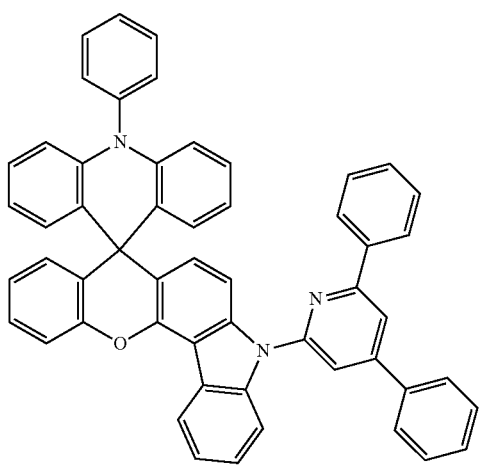
134
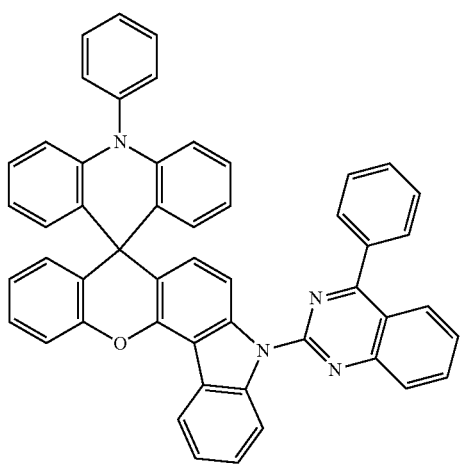

291
-continued
135
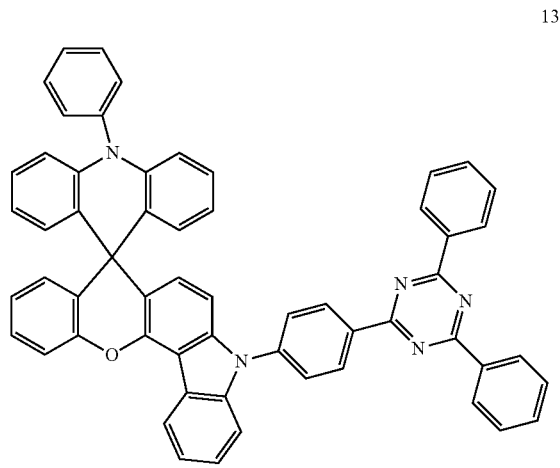
136
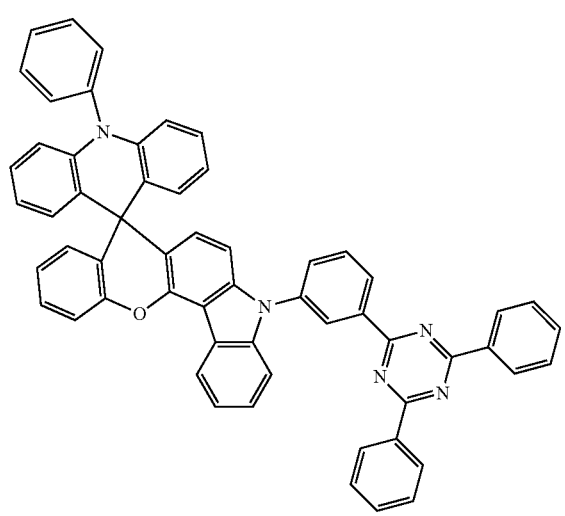
137
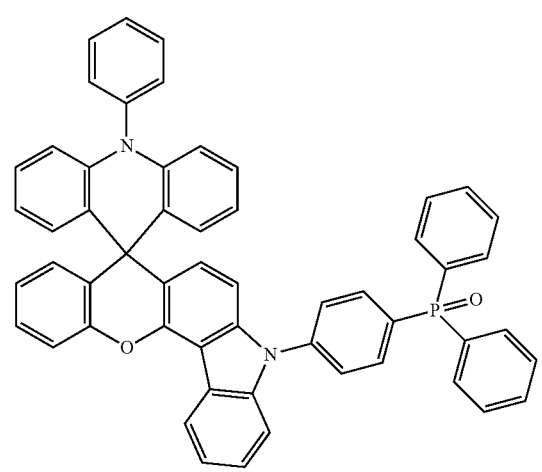
292
-continued
138
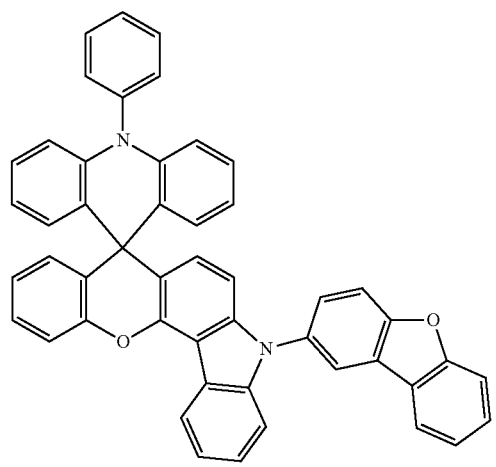
139
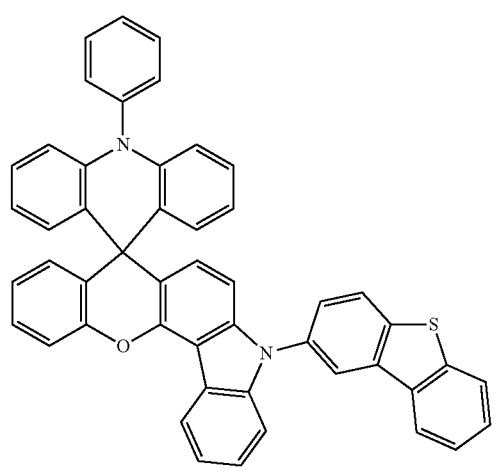
140
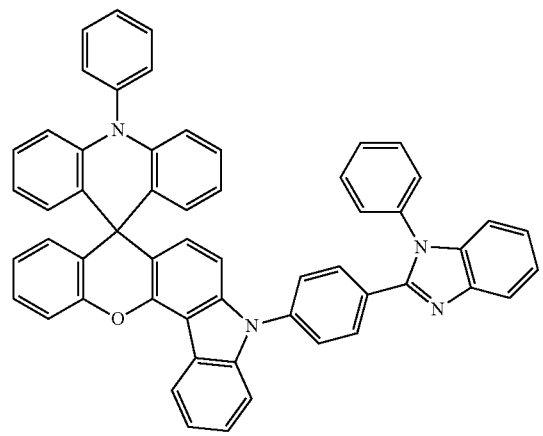

141
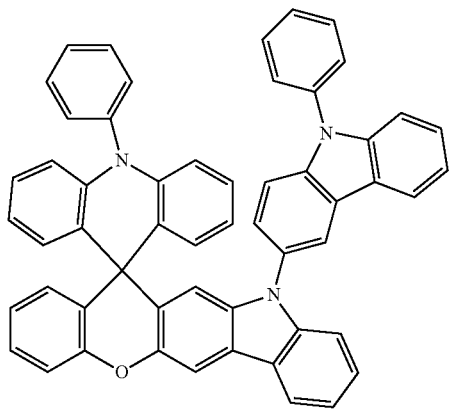
142
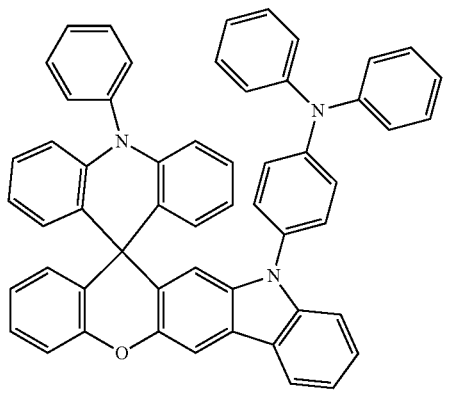
143
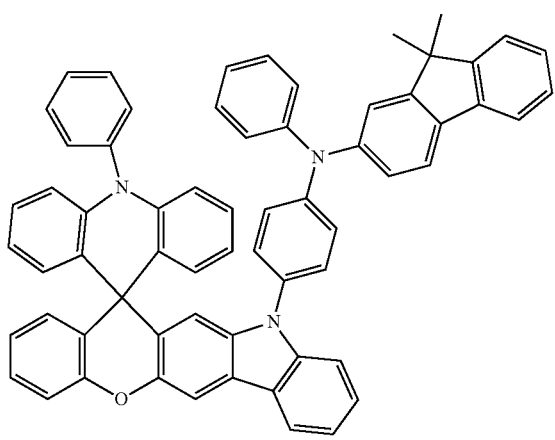
144
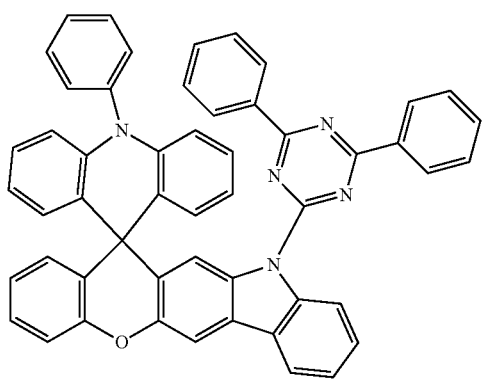
145
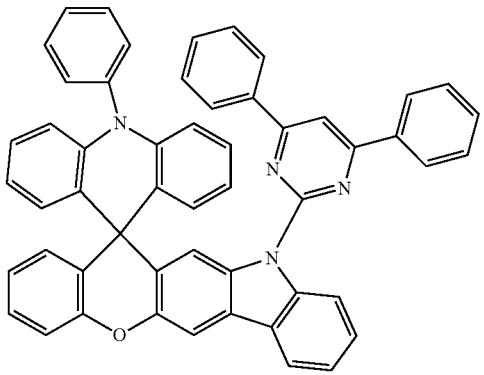
146
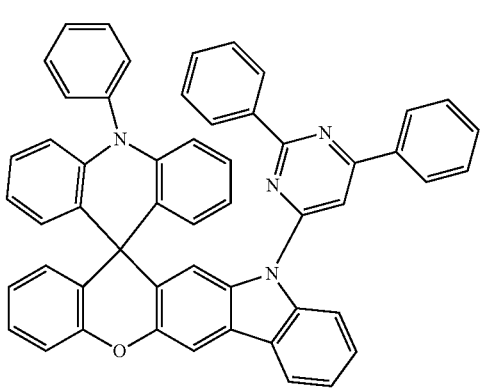
147
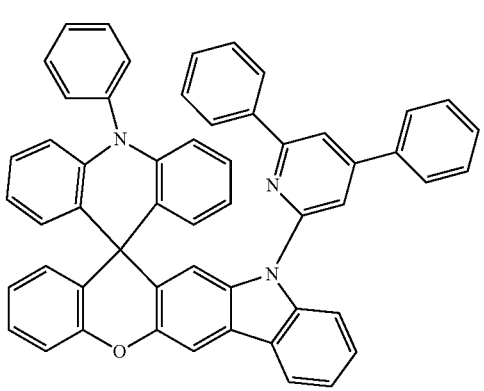
148
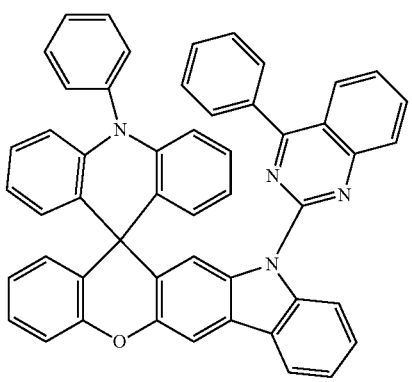

149
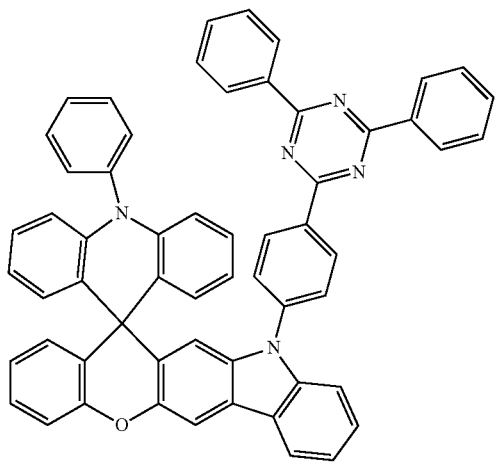
150
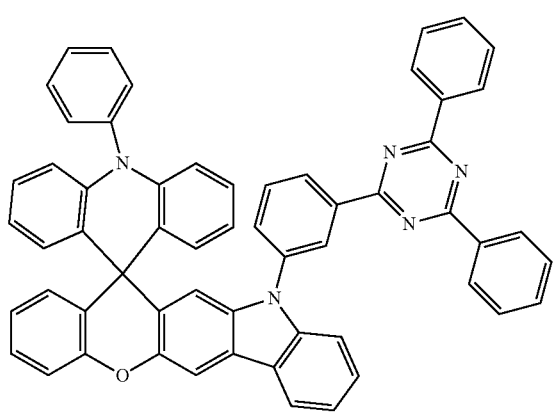
151
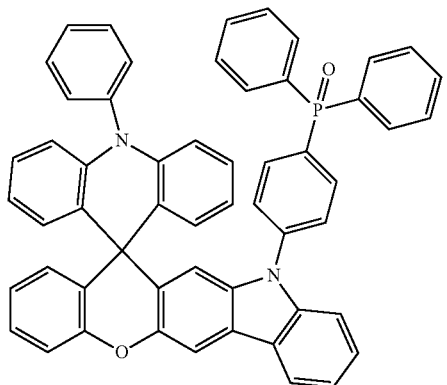
152
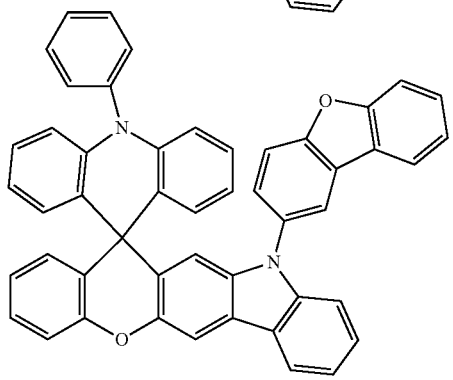
153
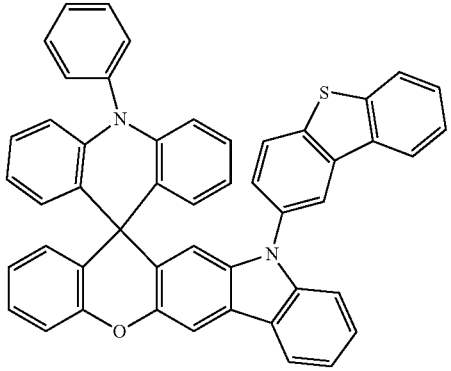
154
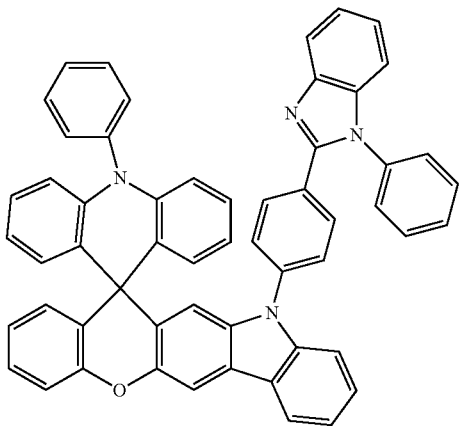
155
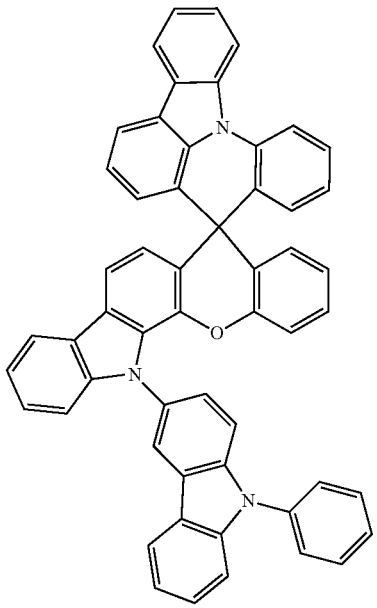

297
-continued
156
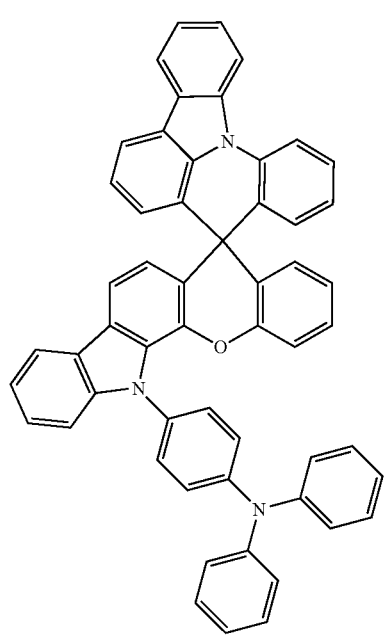
157
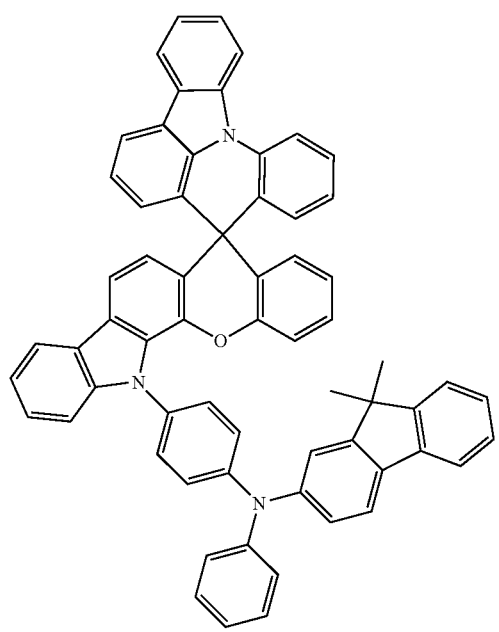
298
-continued
158
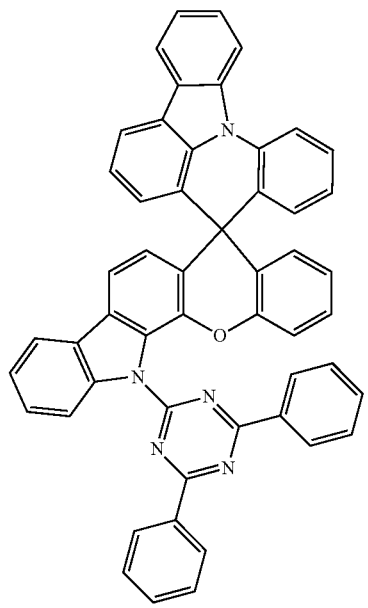
159
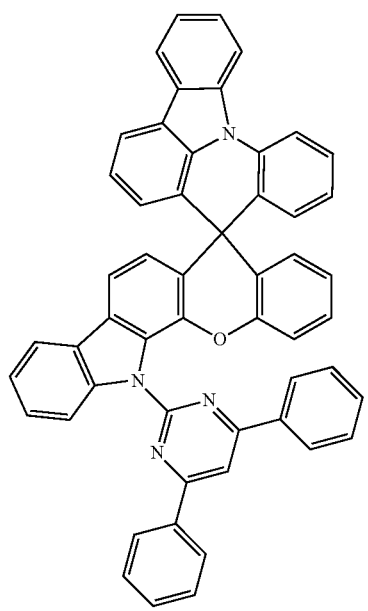

299
-continued
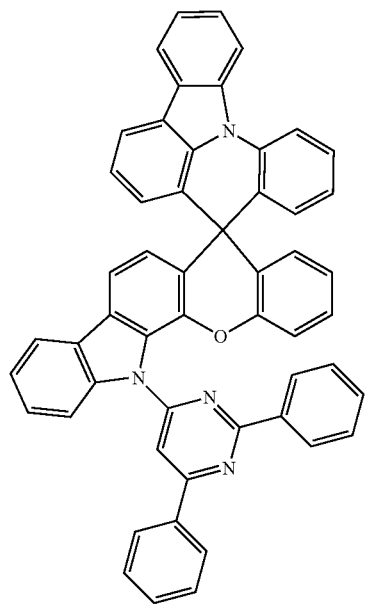
160
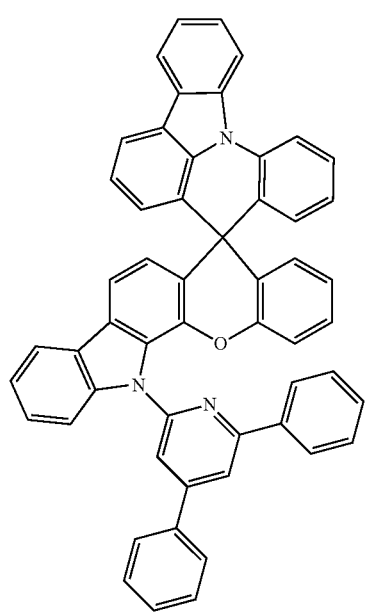
161
300
-continued
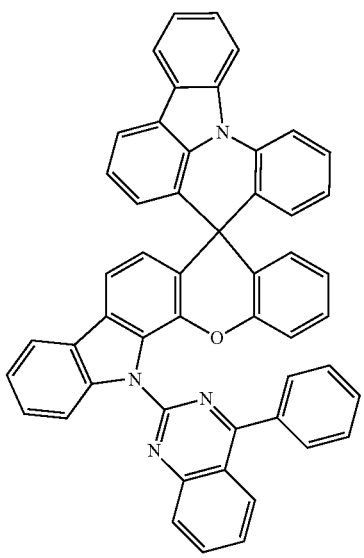
162
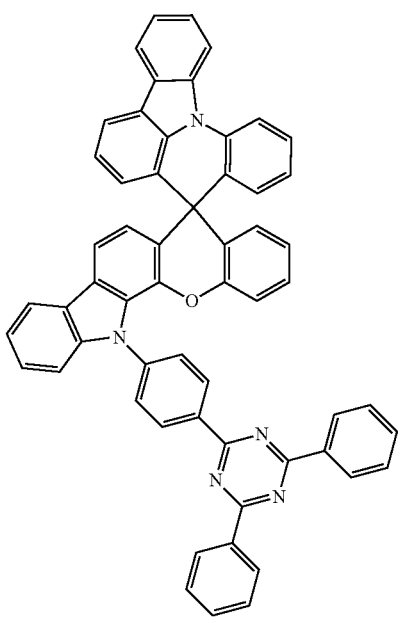
163

301
-continued
164
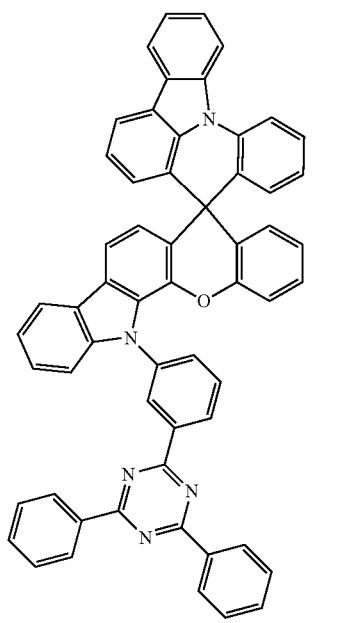
165
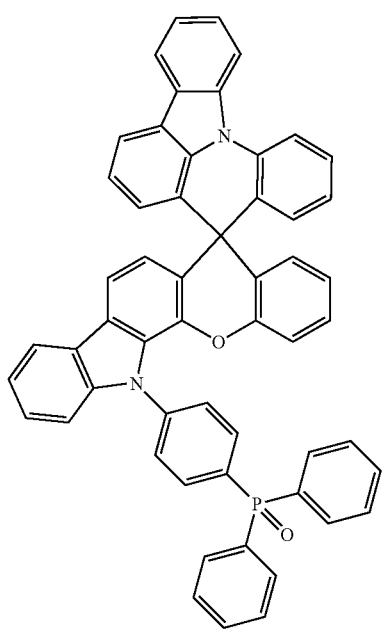
302
-continued
166
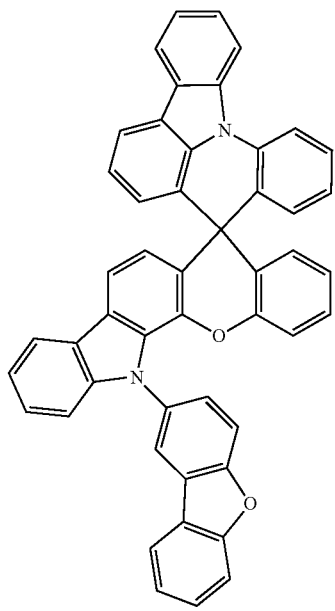
167
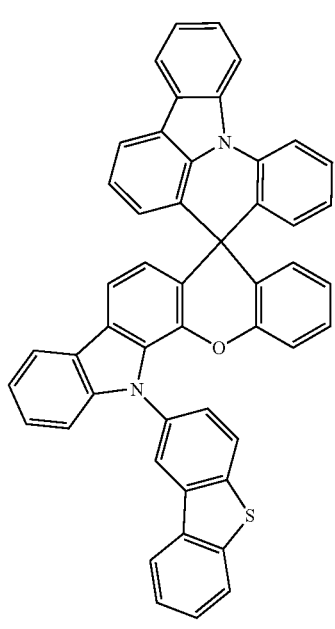

303
-continued
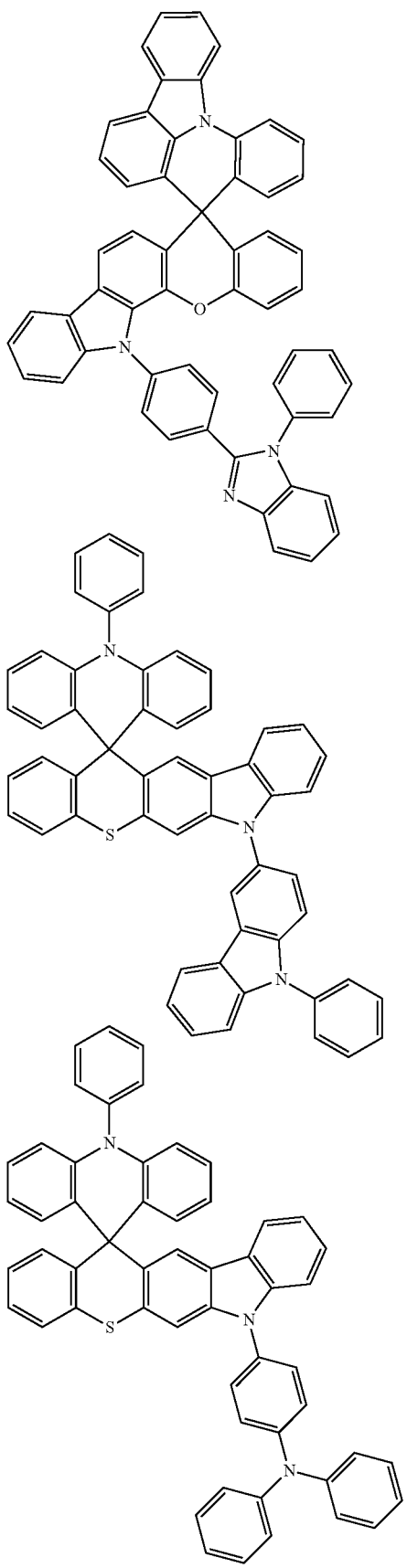
304
-continued
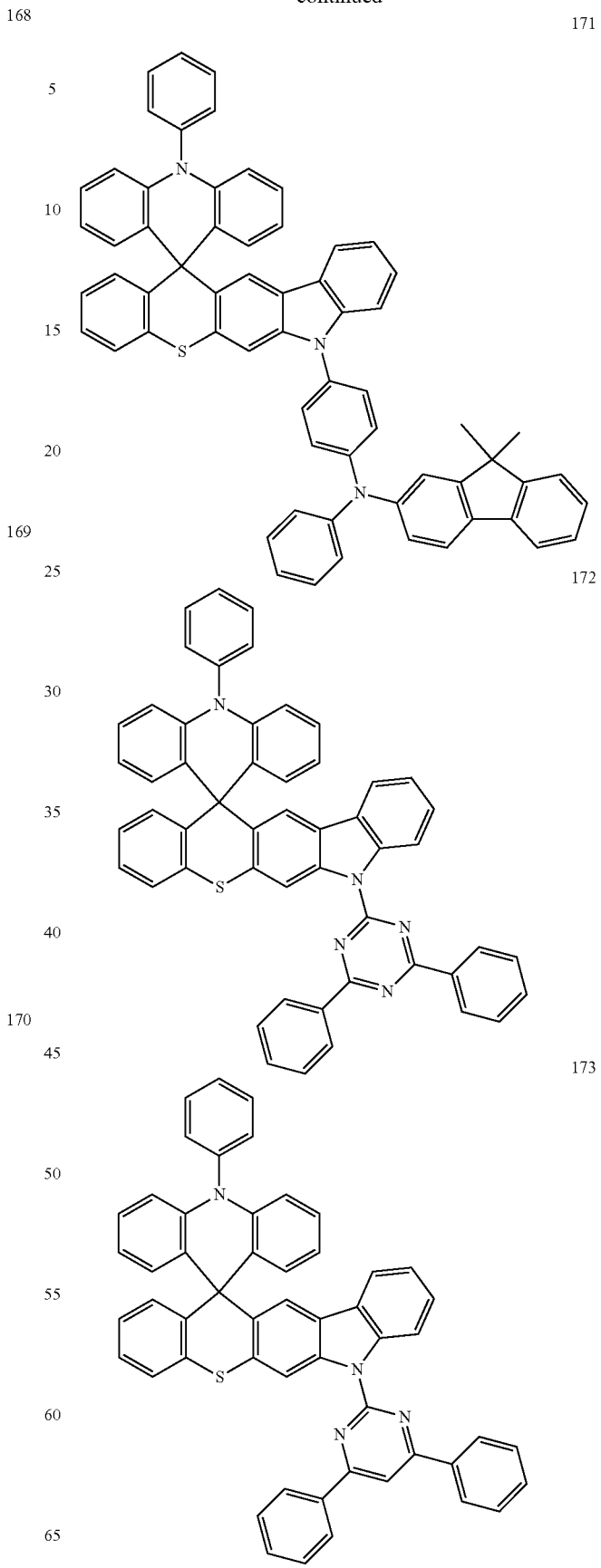

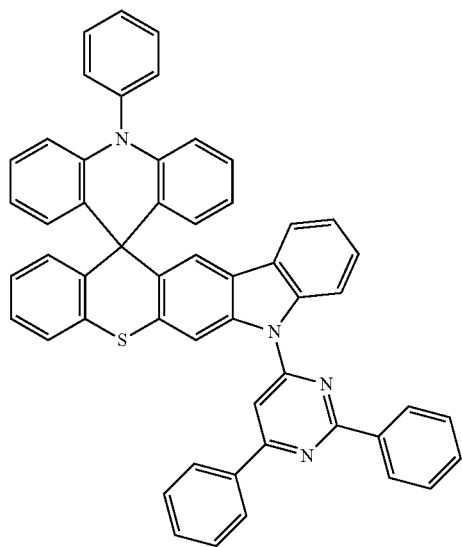
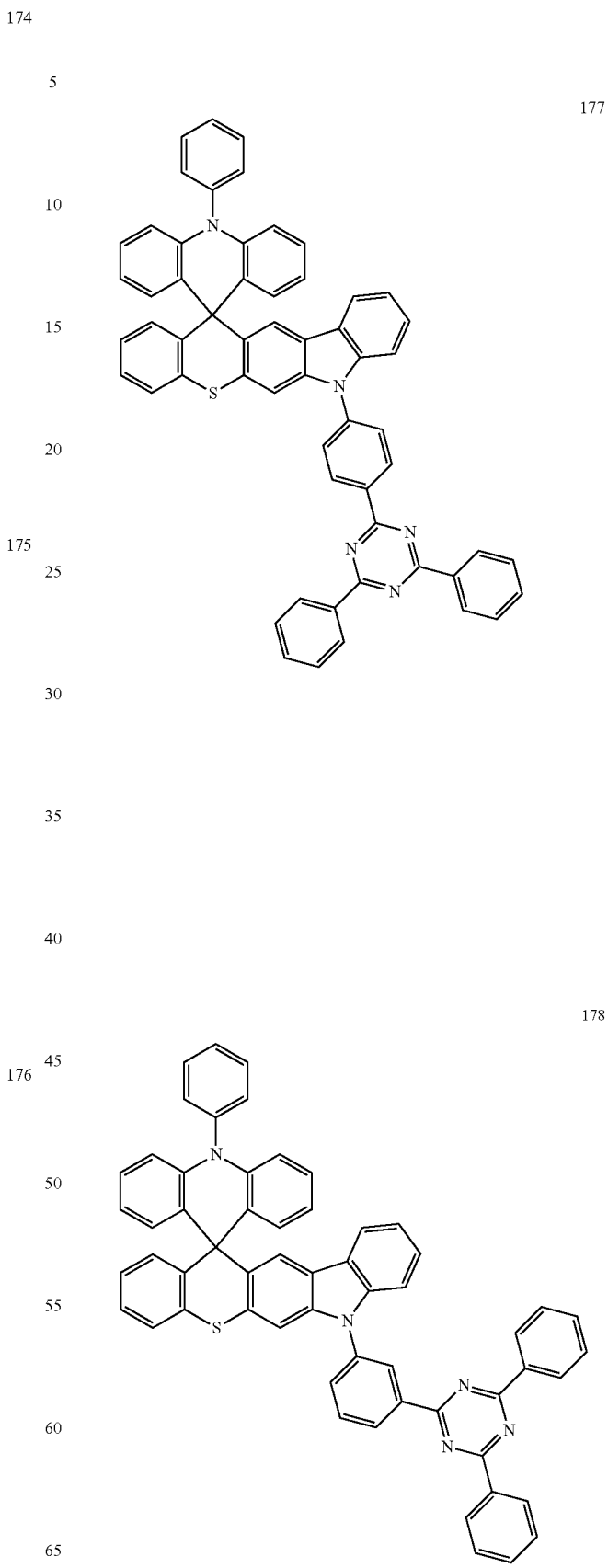

307
-continued
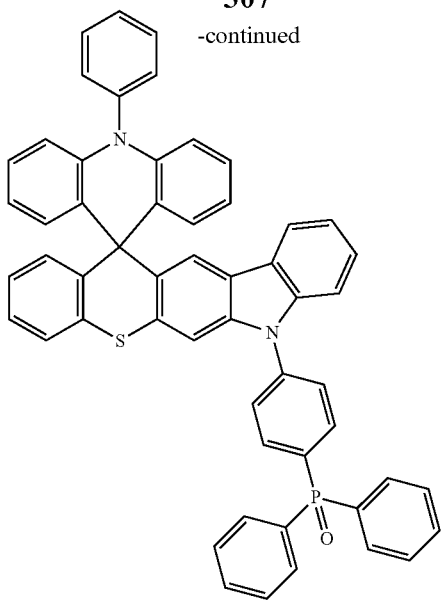
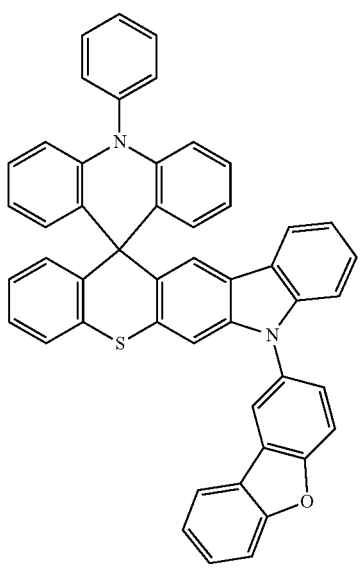
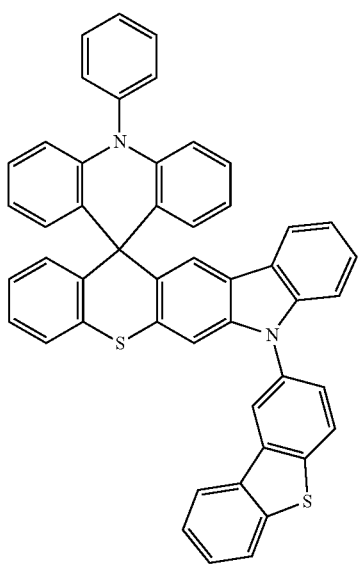
308
-continued
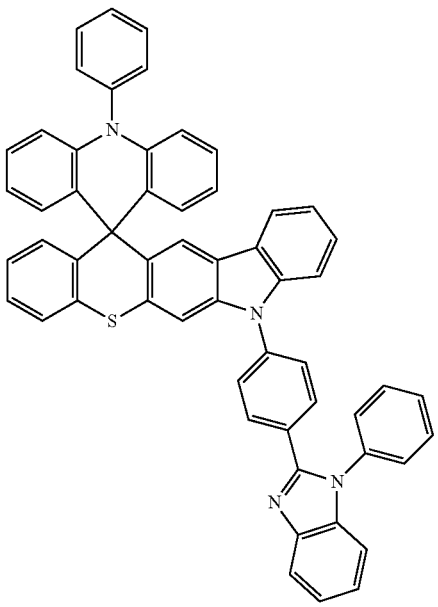
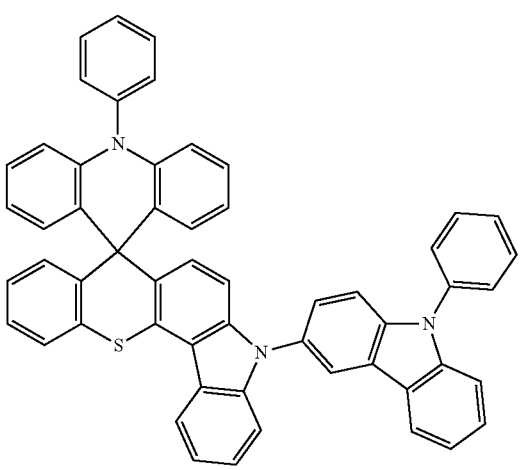
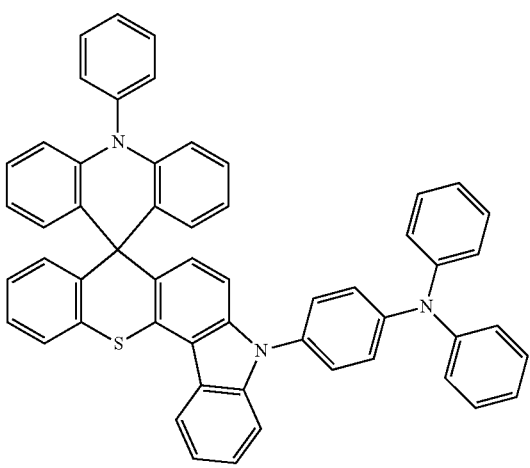

309
-continued
185
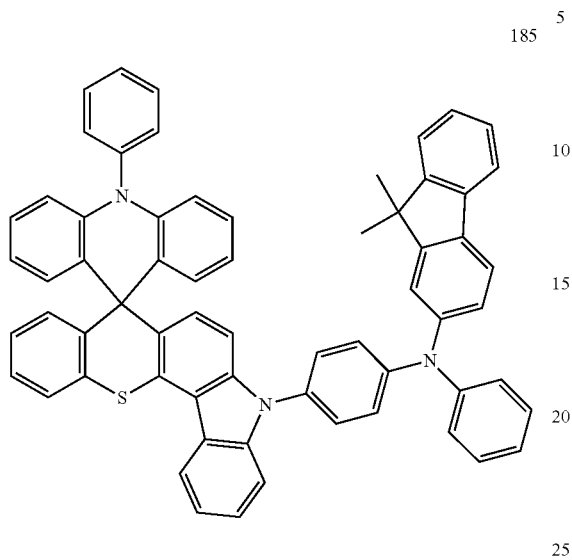
186
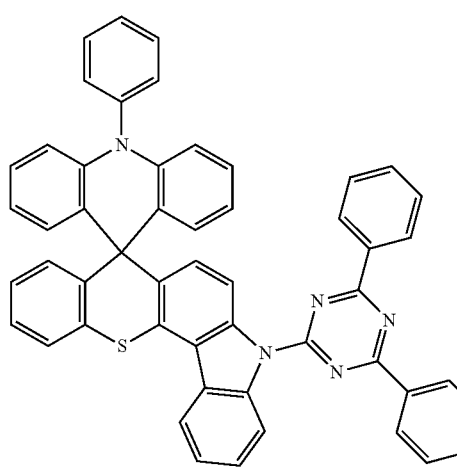
187
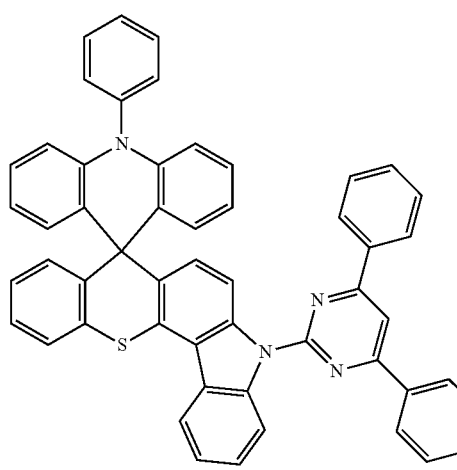
310
-continued
188
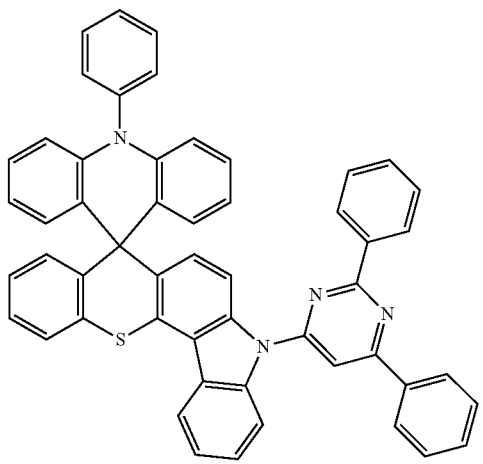
189
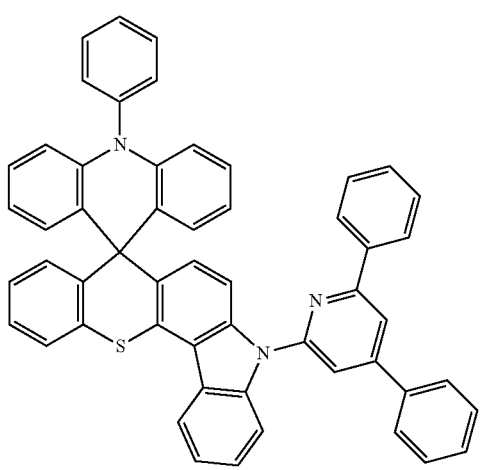
190
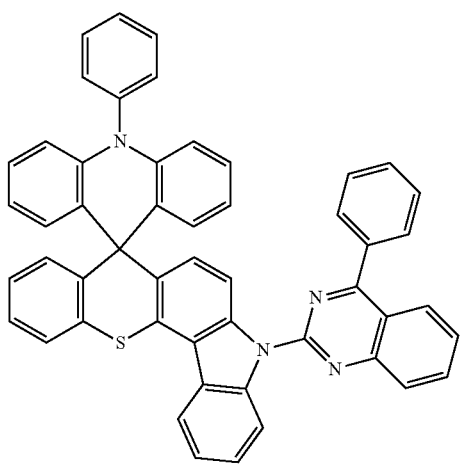

-continued
191
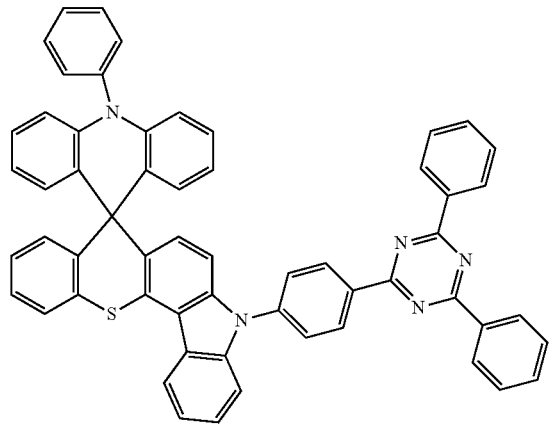
192
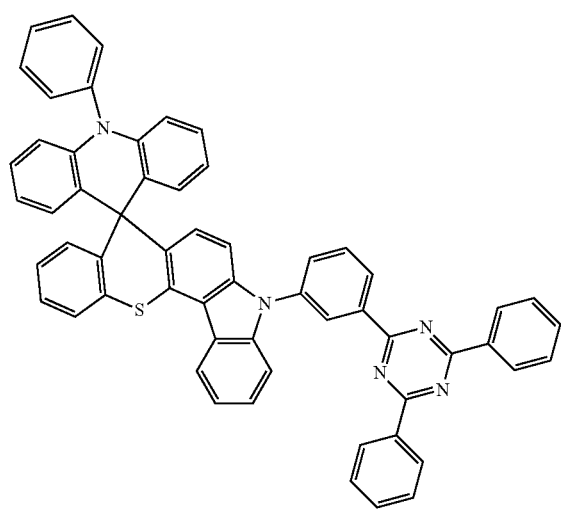
193
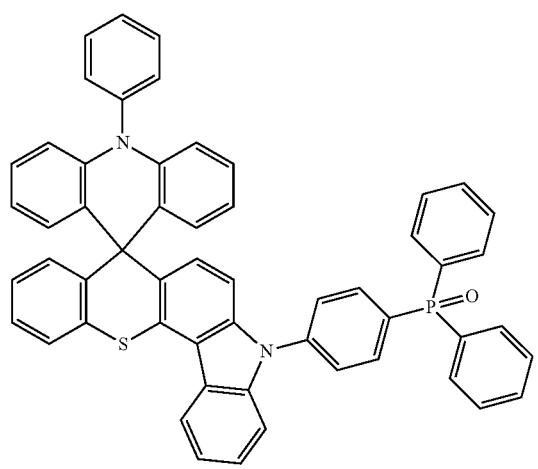
-continued
194
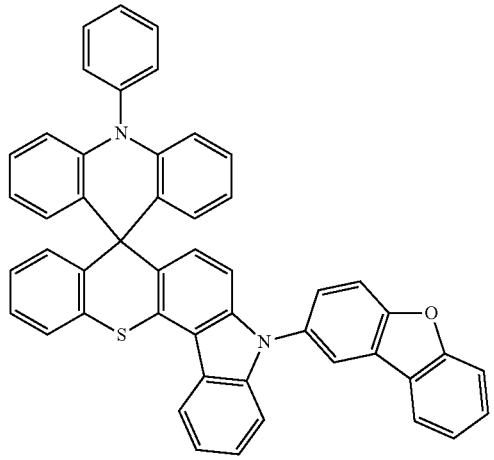
195
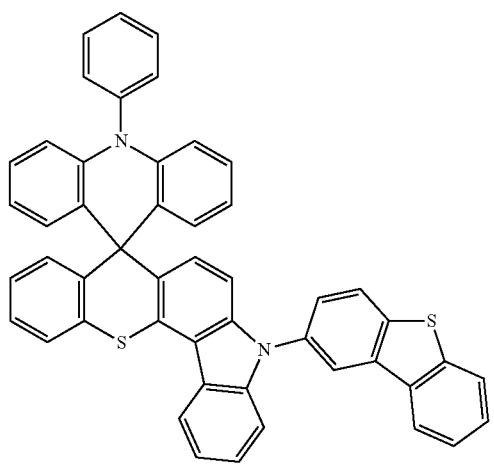
196
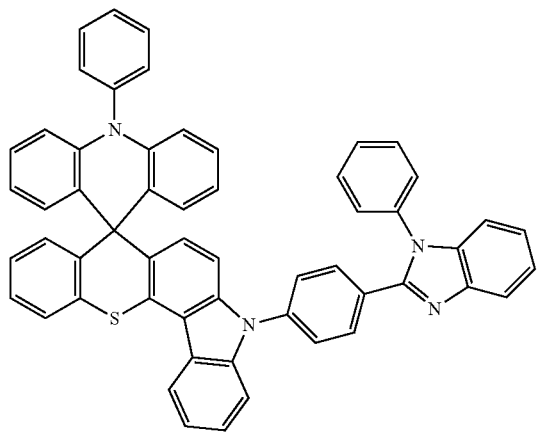

-continued
197
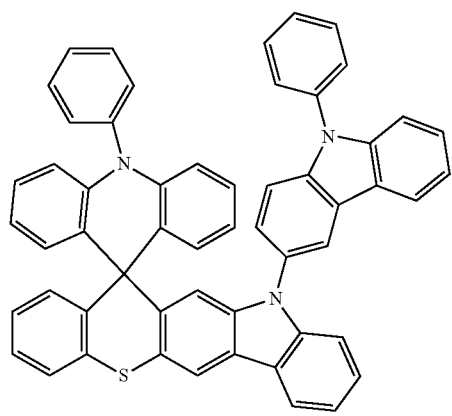
198
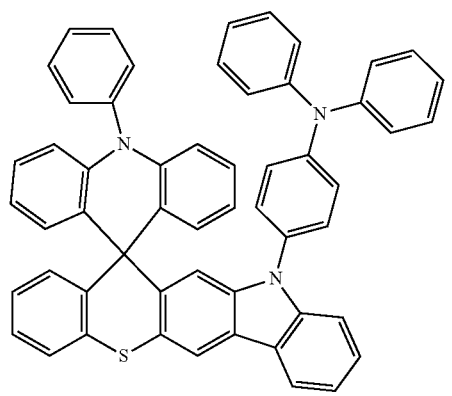
199
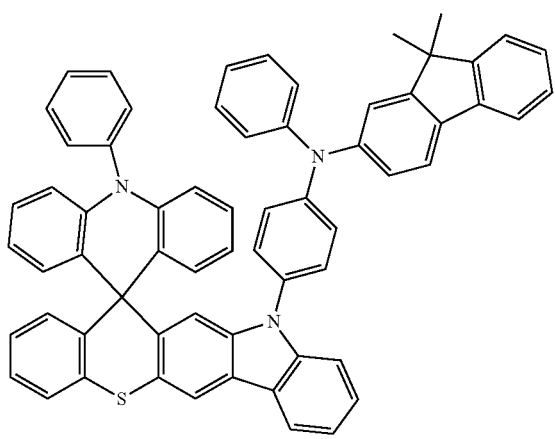
200
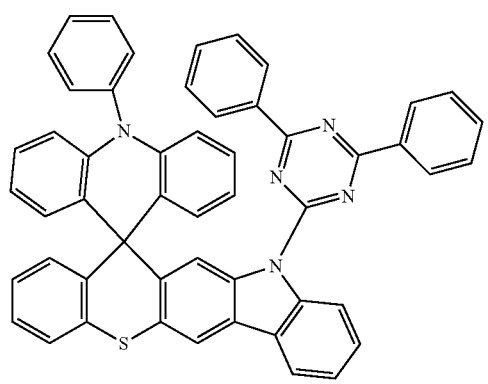
-continued
201
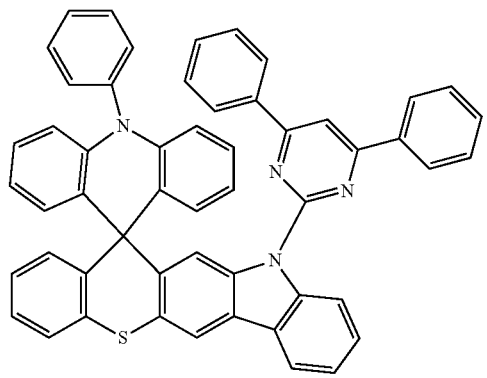
202
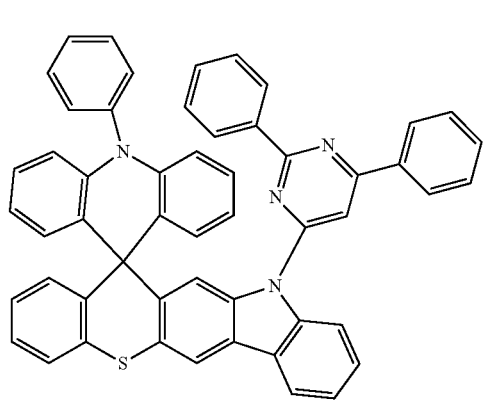
203
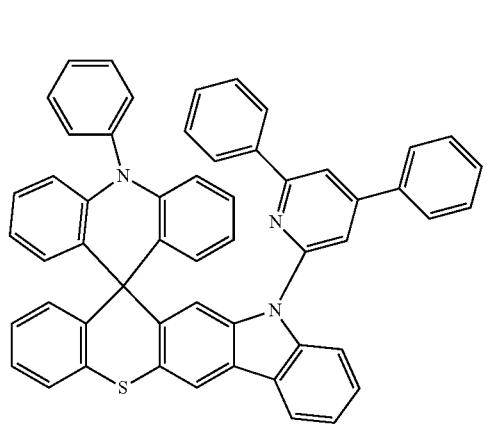
204
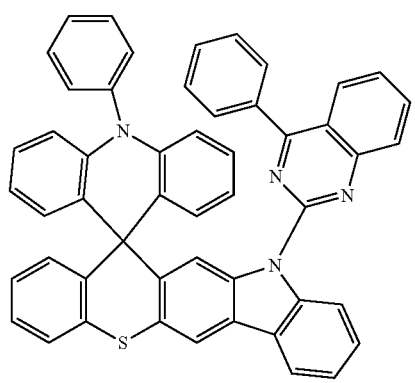

315
-continued
205
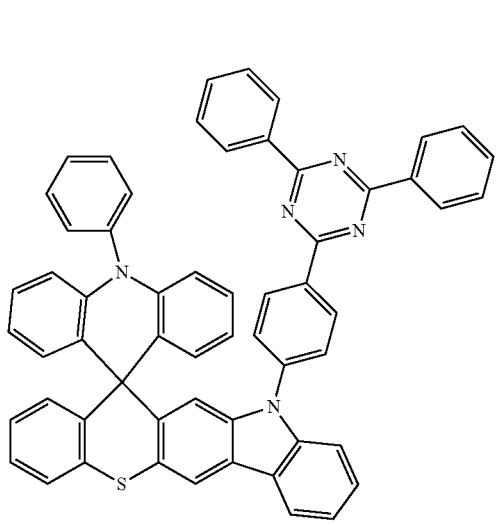
206
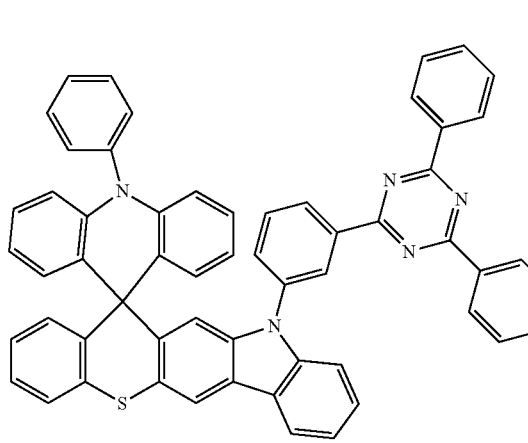
207
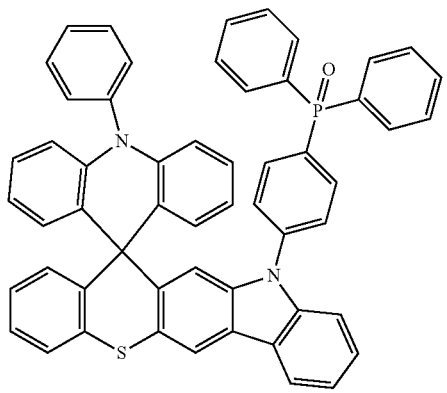
316
-continued
208
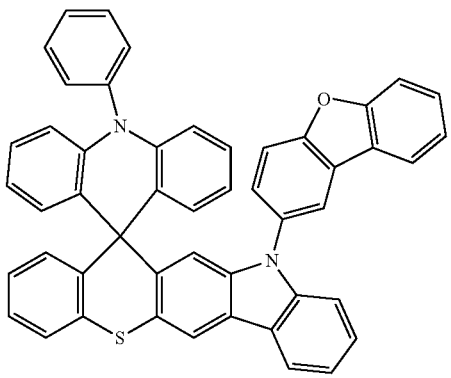
209
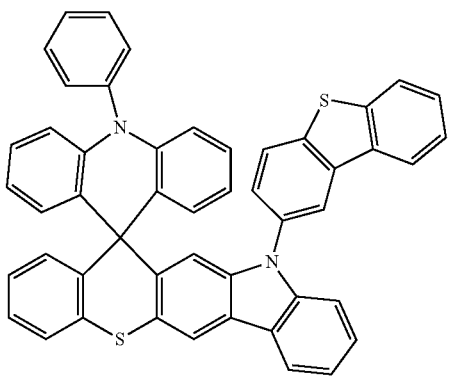
210
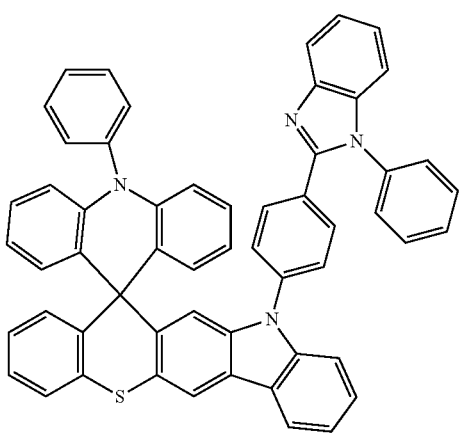

317
-continued
211
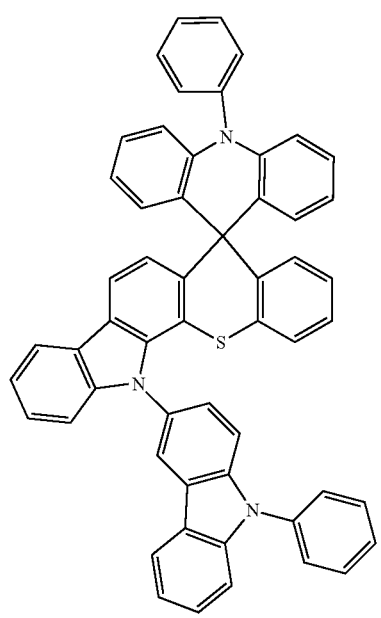
212
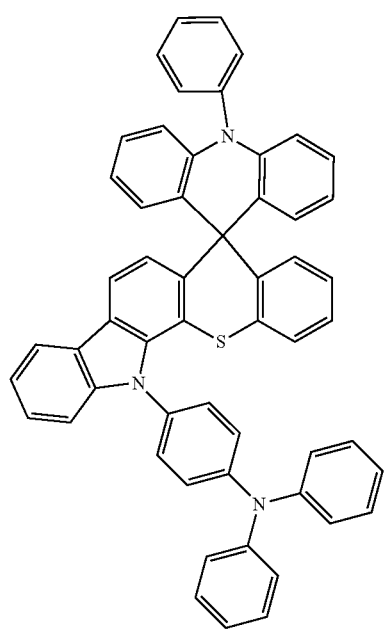
318
-continued
213
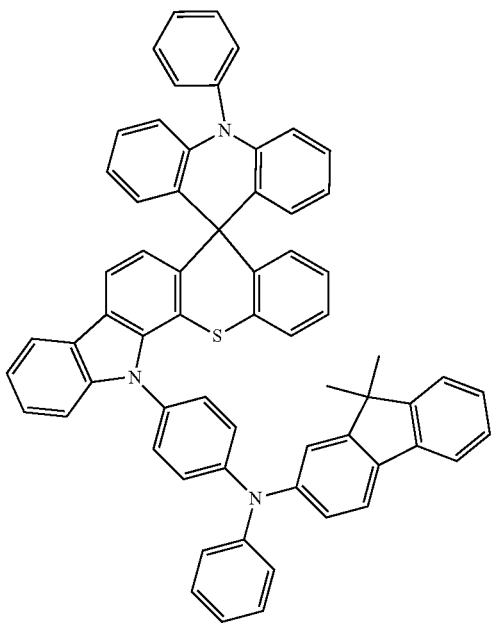
214
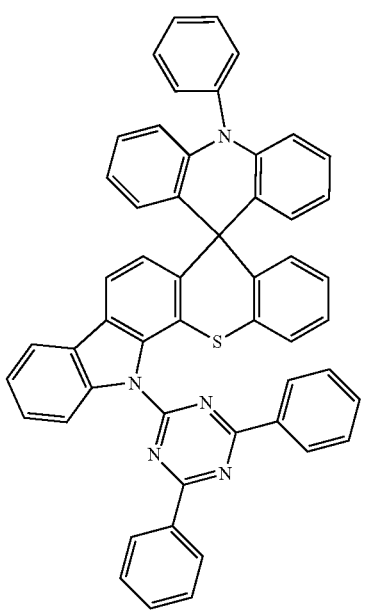

319
-continued
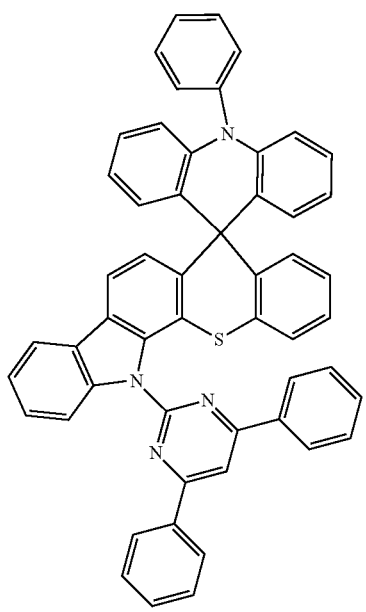
215
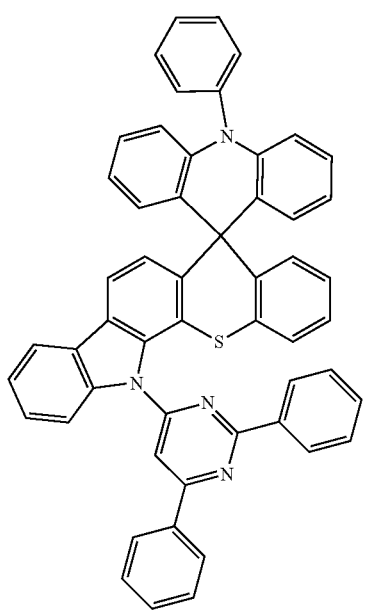
216
320
-continued
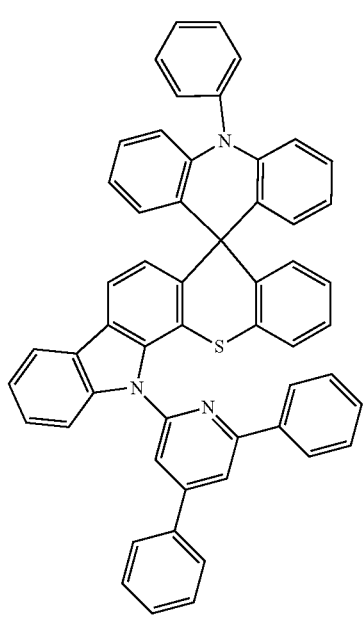
217
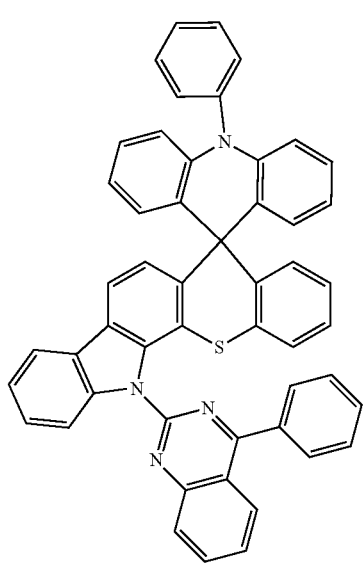
218

321
-continued
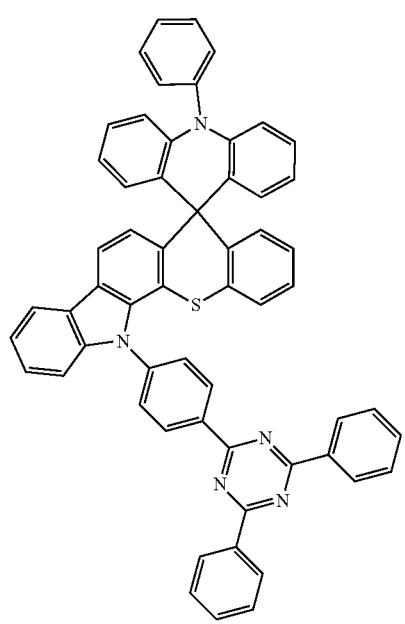
322
-continued
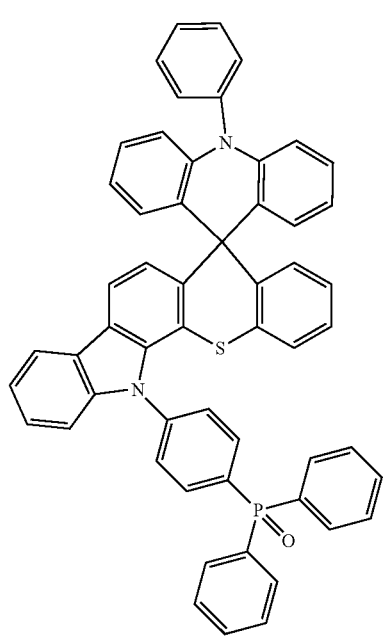
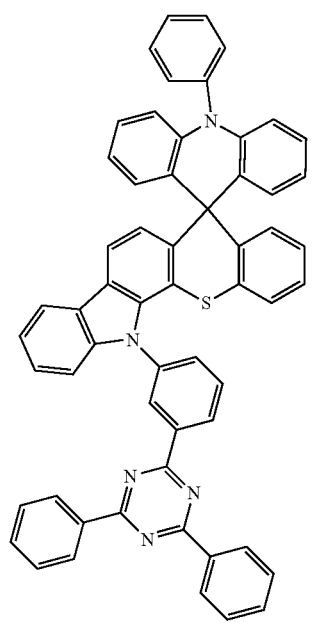
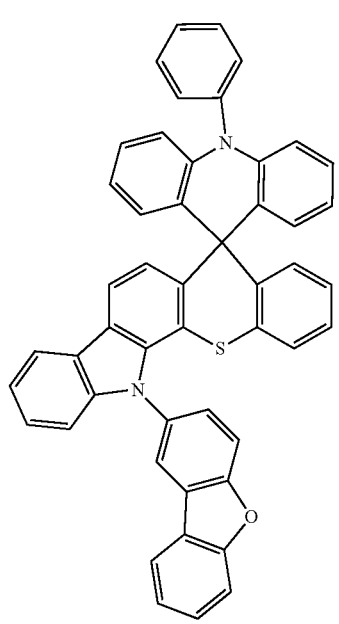

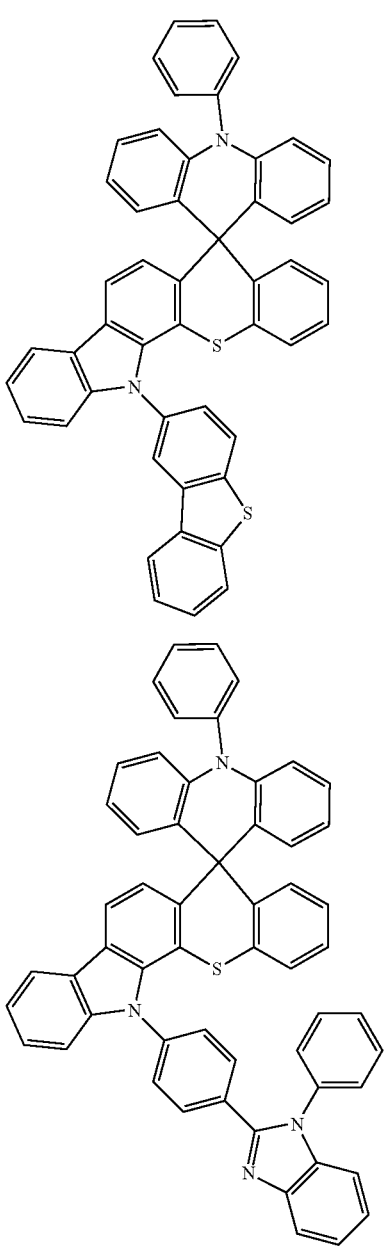

Compounds 113 to 224 were prepared in the same manner as in the method of preparing Compounds 1 to 112, except that materials which are Compounds I to P were used instead of Compounds A to H as a starting material in Preparation Examples 1 to 21. The MS[M+H]⁺ values of Compounds 113 to 224 are shown in the following Table 8.

TABLE 8

| Compound No. | MS[M + H]⁺ | Compound No. | MS[M + H] |
|---|---|---|---|
| 113 | 770 | 169 | 770 |
| 114 | 772 | 170 | 772 |
| 115 | 889 | 171 | 889 |
| 116 | 760 | 172 | 760 |
| 117 | 759 | 173 | 759 |
| 118 | 759 | 174 | 759 |
| 119 | 758 | 175 | 758 |

TABLE 8-continued

| Compound No. | MS[M + H]⁺ | Compound No. | MS[M + H] |
|---|---|---|---|
| 120 | 733 | 176 | 733 |
| 121 | 837 | 177 | 837 |
| 122 | 837 | 178 | 837 |
| 123 | 805 | 179 | 805 |
| 124 | 695 | 180 | 695 |
| 125 | 711 | 181 | 711 |
| 126 | 797 | 182 | 797 |
| 127 | 770 | 183 | 770 |
| 128 | 772 | 184 | 772 |
| 129 | 889 | 185 | 889 |
| 130 | 760 | 186 | 760 |
| 131 | 759 | 187 | 759 |
| 132 | 759 | 188 | 759 |
| 133 | 758 | 189 | 758 |
| 134 | 733 | 190 | 733 |
| 135 | 837 | 191 | 837 |
| 136 | 837 | 192 | 837 |
| 137 | 805 | 193 | 805 |
| 138 | 695 | 194 | 695 |
| 139 | 711 | 195 | 711 |
| 140 | 797 | 196 | 797 |
| 141 | 770 | 197 | 770 |
| 142 | 772 | 198 | 772 |
| 143 | 889 | 199 | 889 |
| 144 | 760 | 200 | 760 |
| 145 | 759 | 201 | 759 |
| 146 | 759 | 202 | 759 |
| 147 | 758 | 203 | 758 |
| 148 | 733 | 204 | 733 |
| 149 | 837 | 205 | 837 |
| 150 | 837 | 206 | 837 |
| 151 | 805 | 207 | 805 |
| 152 | 695 | 208 | 695 |
| 153 | 711 | 209 | 711 |
| 154 | 797 | 210 | 797 |
| 155 | 770 | 211 | 770 |
| 156 | 772 | 212 | 772 |
| 157 | 889 | 213 | 889 |
| 158 | 760 | 214 | 760 |
| 159 | 759 | 215 | 759 |
| 160 | 759 | 216 | 759 |
| 161 | 758 | 217 | 758 |
| 162 | 733 | 218 | 733 |
| 163 | 837 | 219 | 837 |
| 164 | 837 | 220 | 837 |
| 165 | 805 | 221 | 805 |
| 166 | 695 | 222 | 695 |
| 167 | 711 | 223 | 711 |
| 168 | 797 | 224 | 797 |

Experimental Example 1-1

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine. Hexanitrile hexaazatriphenylene (HAT) of the following Chemical Formula was thermally vacuum deposited to have a thickness of 500 Å on the transparent ITO electrode, which was thus prepared, thereby forming a hole injection layer.

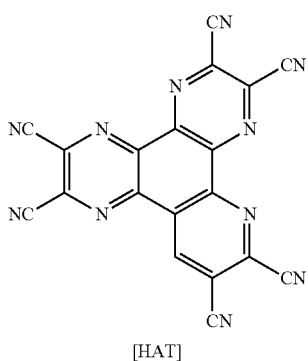

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transporting layer.

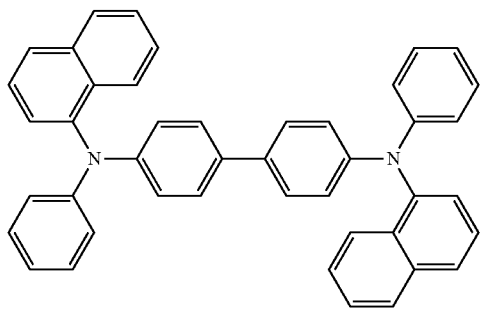

[NPB]

Subsequently, the following Compound 1 was vacuum deposited to have a film thickness of 100 Å on the hole transporting layer, thereby forming an electron blocking layer.

[Compound 1]

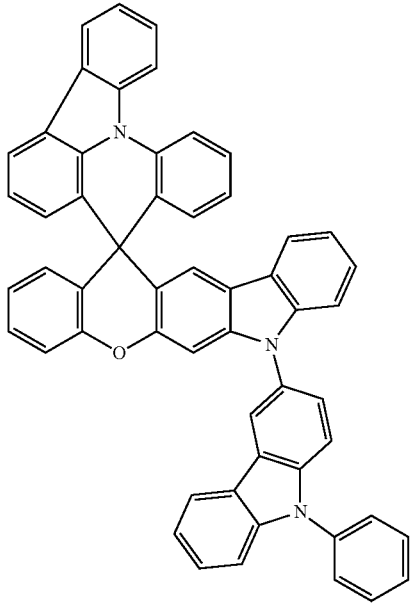

Subsequently, the following BH and BD were vacuum deposited at a weight ratio of 25:1 to have a film thickness of 300 Å on the electron blocking layer, thereby forming a light emitting layer.

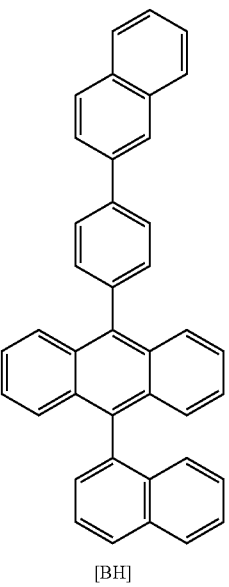

[BH]

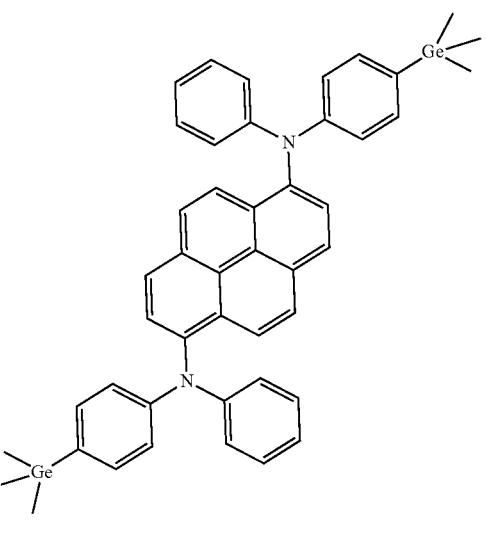

[BD]

-continued

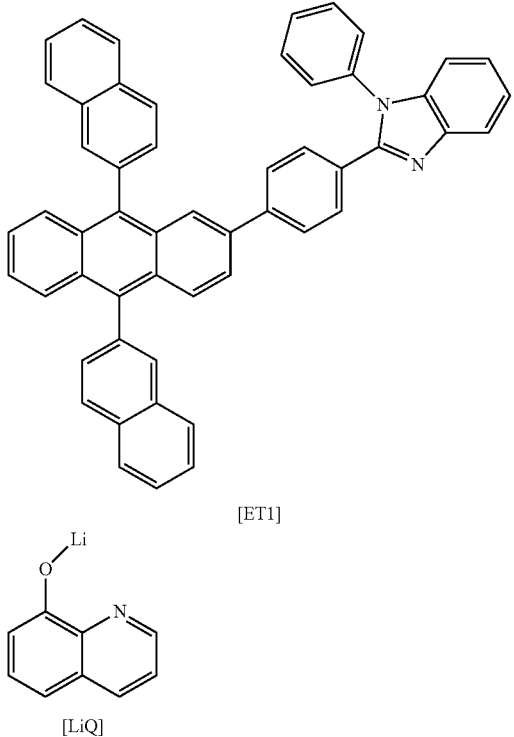

[ET1]

[LiQ]

Compound ET1 and Compound LiQ (lithium quinolate) were vacuum deposited at a weight ratio of 1:1 on the light emitting layer, thereby forming an electron injection and transporting layer having a thickness of 300 Å. Lithium fluoride (LiF) and aluminum were sequentially deposited on the electron injection and transporting layer to have a thickness of 12 Å and 2,000 Å, respectively, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2\times10^{-7}$ to $5\times10^{-6}$ torr, thereby manufacturing an organic light emitting device.

Experimental Example 1-2

An organic light emitting device was manufactured in the same manner as in Experimental Example 1-1, except that Compound 2 was used instead of Compound 1 in Experimental Example 1-1.

Experimental Example 1-3

An organic light emitting device was manufactured in the same manner as in Experimental Example 1-1, except that Compound 3 was used instead of Compound 1 in Experimental Example 1-1.

Experimental Example 1-4

An organic light emitting device was manufactured in the same manner as in Experimental Example 1-1, except that Compound 15 was used instead of Compound 1 in Experimental Example 1-1.

Experimental Example 1-5

An organic light emitting device was manufactured in the same manner as in Experimental Example 1-1, except that Compound 16 was used instead of Compound 1 in Experimental Example 1-1.

Experimental Example 1-6

An organic light emitting device was manufactured in the same manner as in Experimental Example 1-1, except that Compound 17 was used instead of Compound 1 in Experimental Example 1-1.

Experimental Example 1-7

An organic light emitting device was manufactured in the same manner as in Experimental Example 1-1, except that Compound 29 was used instead of Compound 1 in Experimental Example 1-1.

Experimental Example 1-8

An organic light emitting device was manufactured in the same manner as in Experimental Example 1-1, except that Compound 30 was used instead of Compound 1 in Experimental Example 1-1.

Experimental Example 1-9

An organic light emitting device was manufactured in the same manner as in Experimental Example 1-1, except that Compound 31 was used instead of Compound 1 in Experimental Example 1-1.

Experimental Example 1-10

An organic light emitting device was manufactured in the same manner as in Experimental Example 1-1, except that Compound 43 was used instead of Compound 1 in Experimental Example 1-1.

Experimental Example 1-11

An organic light emitting device was manufactured in the same manner as in Experimental Example 1-1, except that Compound 58 was used instead of Compound 1 in Experimental Example 1-1.

Experimental Example 1-12

An organic light emitting device was manufactured in the same manner as in Experimental Example 1-1, except that Compound 73 was used instead of Compound 1 in Experimental Example 1-1.

Experimental Example 1-13

An organic light emitting device was manufactured in the same manner as in Experimental Example 1-1, except that Compound 85 was used instead of Compound 1 in Experimental Example 1-1.

Experimental Example 1-14

An organic light emitting device was manufactured in the same manner as in Experimental Example 1-1, except that Compound 100 was used instead of Compound 1 in Experimental Example 1-1.

Experimental Example 1-15

An organic light emitting device was manufactured in the same manner as in Experimental Example 1-1, except that Compound 115 was used instead of Compound 1 in Experimental Example 1-1.

Experimental Example 1-16

An organic light emitting device was manufactured in the same manner as in Experimental Example 1-1, except that Compound 127 was used instead of Compound 1 in Experimental Example 1-1.

Experimental Example 1-17

An organic light emitting device was manufactured in the same manner as in Experimental Example 1-1, except that Compound 142 was used instead of Compound 1 in Experimental Example 1-1.

Experimental Example 1-18

An organic light emitting device was manufactured in the same manner as in Experimental Example 1-1, except that Compound 157 was used instead of Compound 1 in Experimental Example 1-1.

Experimental Example 1-19

An organic light emitting device was manufactured in the same manner as in Experimental Example 1-1, except that Compound 169 was used instead of Compound 1 in Experimental Example 1-1.

Experimental Example 1-20

An organic light emitting device was manufactured in the same manner as in Experimental Example 1-1, except that Compound 184 was used instead of Compound 1 in Experimental Example 1-1.

Experimental Example 1-21

An organic light emitting device was manufactured in the same manner as in Experimental Example 1-1, except that Compound 199 was used instead of Compound 1 in Experimental Example 1-1.

Experimental Example 1-22

An organic light emitting device was manufactured in the same manner as in Experimental Example 1-1, except that Compound 211 was used instead of Compound 1 in Experimental Example 1-1.

Comparative Example 1-1

An organic light emitting device was manufactured in the same manner as in Experimental Example 1-1, except that EB 1 was used instead of Compound 1 in Experimental Example

[EB 1]

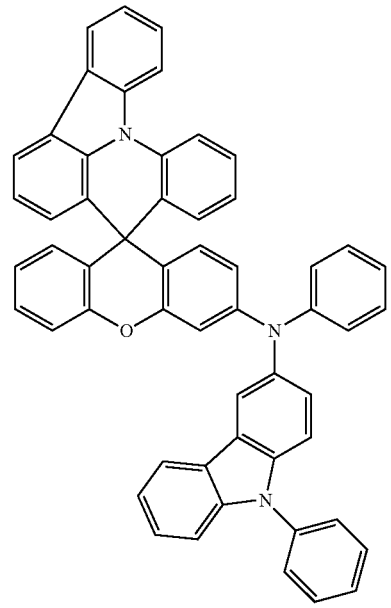

Comparative Example 1-2

An organic light emitting device was manufactured in the same manner as in Experimental Example 1-1, except that EB 2 was used instead of Compound 1 in Experimental Example 1-1.

[EB 2]

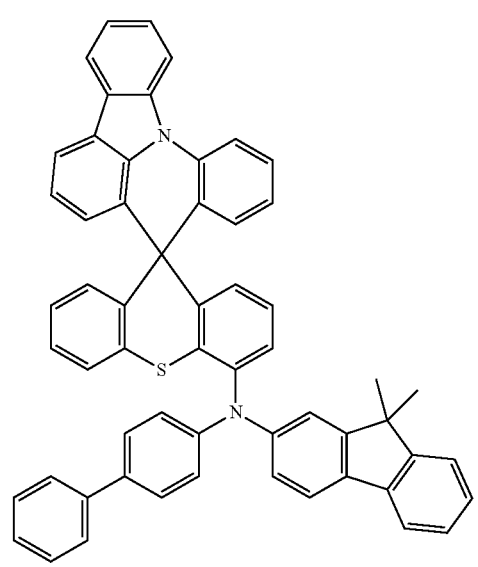

When current was applied to the organic light emitting devices manufactured in Experimental Examples 1-1 to 22 and Comparative Examples 1-1 and 1-2, the results of Table 1 were obtained.

TABLE 9

| | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1 | 3.75 | 5.40 | (0.139, 0.125) |
| Experimental Example 1-2 | Compound 2 | 3.62 | 5.55 | (0.138, 0.126) |
| Experimental Example 1-3 | Compound 3 | 3.47 | 5.89 | (0.138, 0.127) |
| Experimental Example 1-4 | Compound 15 | 3.48 | 5.77 | (0.137, 0.125) |
| Experimental Example 1-5 | Compound 16 | 3.49 | 5.88 | (0.136, 0.125) |
| Experimental Example 1-6 | Compound 17 | 3.44 | 5.71 | (0.136, 0.127) |
| Experimental Example 1-7 | Compound 29 | 3.43 | 5.83 | (0.136, 0.125) |
| Experimental Example 1-8 | Compound 30 | 3.44 | 5.75 | (0.137, 0.125) |
| Experimental Example 1-9 | Compound 31 | 3.53 | 5.60 | (0.138, 0.125) |
| Experimental Example 1-10 | Compound 43 | 3.58 | 5.53 | (0.136, 0.125) |
| Experimental Example 1-11 | Compound 58 | 3.53 | 5.62 | (0.137, 0.125) |
| Experimental Example 1-12 | Compound 73 | 3.55 | 5.51 | (0.136, 0.125) |
| Experimental Example 1-13 | Compound 85 | 3.64 | 5.60 | (0.138, 0.126) |
| Experimental Example 1-14 | Compound 100 | 3.60 | 5.69 | (0.137, 0.125) |
| Experimental Example 1-15 | Compound 115 | 3.65 | 5.57 | (0.136, 0.127) |
| Experimental Example 1-16 | Compound 127 | 3.65 | 5.66 | (0.135, 0.127) |
| Experimental Example 1-17 | Compound 142 | 3.58 | 5.64 | (0.137, 0.125) |
| Experimental Example 1-18 | Compound 157 | 3.44 | 5.85 | (0.136, 0.125) |
| Experimental Example 1-19 | Compound 169 | 3.48 | 5.70 | (0.138, 0.126) |
| Experimental Example 1-20 | Compound 184 | 3.46 | 5.88 | (0.137, 0.125) |
| Experimental Example 1-21 | Compound 199 | 3.45 | 5.71 | (0.136, 0.127) |
| Experimental Example 1-22 | Compound 211 | 3.60 | 5.68 | (0.135, 0.127) |
| Comparative Example 1-1 | EB 1 | 4.16 | 4.72 | (0.138, 0.127) |
| Comparative Example 1-2 | EB 2 | 4.35 | 4.58 | (0.139, 0.125) |

As observed in Table 1, it can be seen that the compounds in Experimental Examples 1-1 to 1-22 exhibit lower voltage and higher efficiency characteristics than those in Comparative Examples 1-1 and 1-2, in which there is no fused carbazole ring at the core of Chemical Formula 1 of the present invention as an electron blocking layer in the organic light emitting device.

It could be confirmed that the compound derivatives of the Chemical Formulae according to the present invention have excellent electron blocking capability and thus exhibit low voltage and high efficiency characteristics, and may be applied to an organic light emitting device.

Experimental Example 2-1

The compounds synthesized in the Synthesis Examples were subjected to high-purity sublimation purification by a typically known method, and then green organic light emitting devices were manufactured by the following method.

A glass substrate on which a thin film of indium tin oxide (ITO) was coated to have a thickness of 1,000 Å was placed into distilled water in which a detergent was dissolved, and washed using ultrasonic waves. In this case, a product manufactured by Fischer Co., was used as the detergent, and distilled water twice filtered using a filter manufactured by Millipore Co., was used as the distilled water. After the ITO was washed for 30 minutes, ultrasonic washing was repeated twice using distilled water for 10 minutes. After the washing using distilled water was completed, ultrasonic washing was conducted using a solvent of isopropyl alcohol, acetone, and methanol, and the resultant product was dried and then transported to a plasma washing machine. Furthermore, the substrate was washed by using an oxygen plasma for 5 minutes, and then was transported to a vacuum deposition machine.

An organic light emitting device was manufactured by configuring a light emitting device in the order of m-MTDATA (60 nm)/TCTA (80 nm)/Compound 4+10% Ir(ppy)$_3$ (300 nm)/BCP (10 nm)/Alq$_3$ (30 nm)/LiF (1 nm)/Al (200 nm) on the thus prepared ITO transparent electrode by using Compound 4 as a host.

The structures of m-MTDATA, TCTA, Ir(ppy)$_3$, and BCP are as follows.

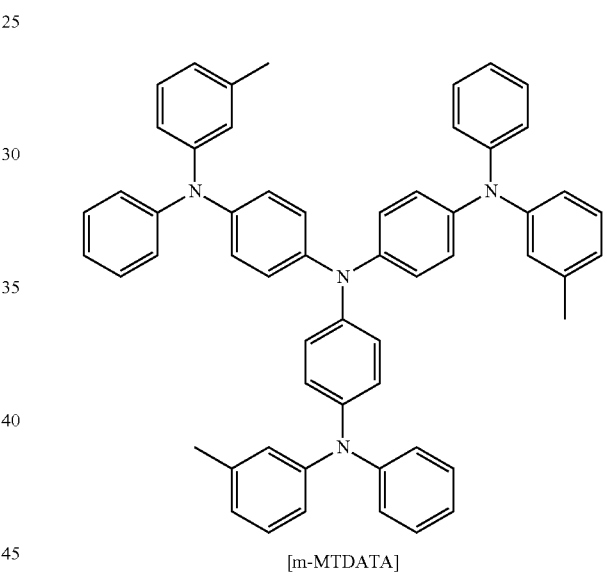

[m-MTDATA]

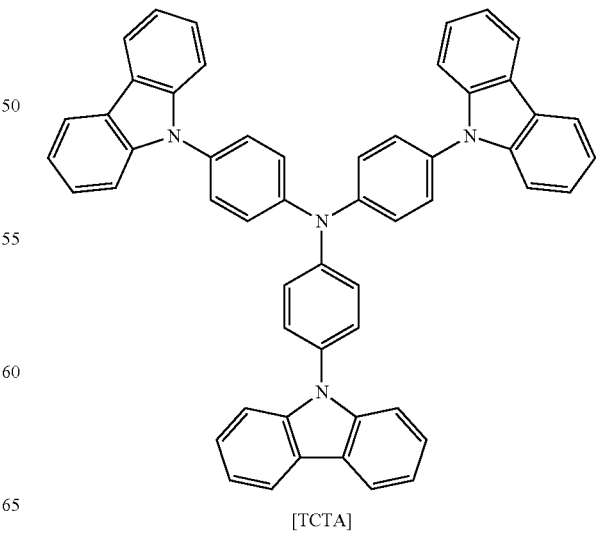

[TCTA]

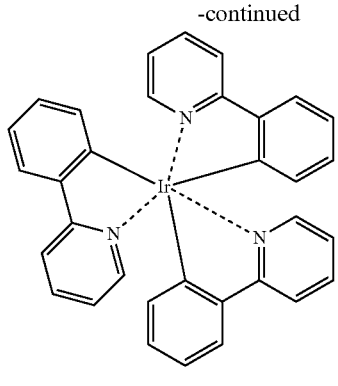

[Ir(ppy)₃]

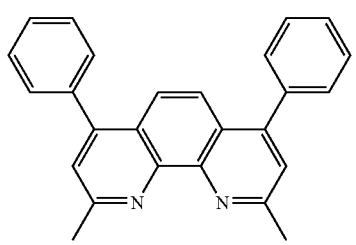

[BCP]

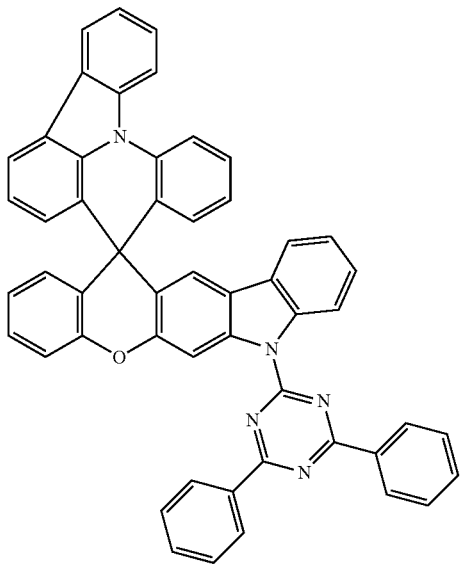

[Compound 4]

Experimental Example 2-2

An organic light emitting device was manufactured in the same manner as in Experimental Example 2-1, except that Compound 5 was used instead of Compound 4 in Experimental Example 2-1.

Experimental Example 2-3

An organic light emitting device was manufactured in the same manner as in Experimental Example 2-1, except that Compound 6 was used instead of Compound 4 in Experimental Example 2-1.

Experimental Example 2-4

An organic light emitting device was manufactured in the same manner as in Experimental Example 2-1, except that Compound 7 was used instead of Compound 4 in Experimental Example 2-1.

Experimental Example 2-5

An organic light emitting device was manufactured in the same manner as in Experimental Example 2-1, except that Compound 9 was used instead of Compound 4 in Experimental Example 2-1.

Experimental Example 2-6

An organic light emitting device was manufactured in the same manner as in Experimental Example 2-1, except that Compound 10 was used instead of Compound 4 in Experimental Example 2-1.

Experimental Example 2-7

An organic light emitting device was manufactured in the same manner as in Experimental Example 2-1, except that Compound 18 was used instead of Compound 4 in Experimental Example 2-1.

Experimental Example 2-8

An organic light emitting device was manufactured in the same manner as in Experimental Example 2-1, except that Compound 19 was used instead of Compound 4 in Experimental Example 2-1.

Experimental Example 2-9

An organic light emitting device was manufactured in the same manner as in Experimental Example 2-1, except that Compound 20 was used instead of Compound 4 in Experimental Example 2-1.

Experimental Example 2-10

An organic light emitting device was manufactured in the same manner as in Experimental Example 2-1, except that Compound 21 was used instead of Compound 4 in Experimental Example 2-1.

Experimental Example 2-11

An organic light emitting device was manufactured in the same manner as in Experimental Example 2-1, except that Compound 23 was used instead of Compound 4 in Experimental Example 2-1.

Experimental Example 2-12

An organic light emitting device was manufactured in the same manner as in Experimental Example 2-1, except that Compound 24 was used instead of Compound 4 in Experimental Example 2-1.

Experimental Example 2-13

An organic light emitting device was manufactured in the same manner as in Experimental Example 2-1, except that Compound 32 was used instead of Compound 4 in Experimental Example 2-1.

Comparative Example 2-1

An organic light emitting device was manufactured in the same manner as in Experimental Example 2-1, except that GH 1 was used instead of Compound 4 in Experimental Example 2-1.

[GH 1]

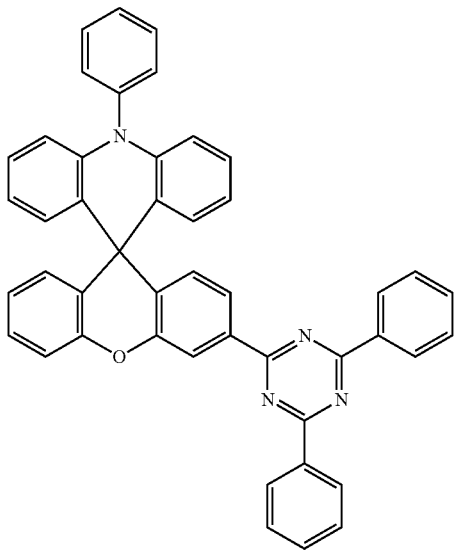

Comparative Example 2-2

An organic light emitting device was manufactured in the same manner as in Experimental Example 2-1, except that GH 2 was used instead of Compound 4 in Experimental Example 2-1.

[GH 2]

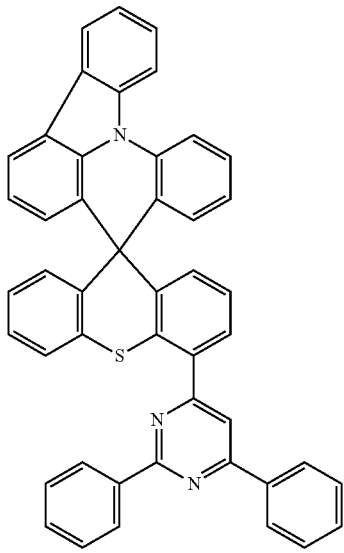

When current was applied to the organic light emitting devices manufactured in Experimental Examples 2-1 to 2-13 and Comparative Examples 2-1 and 2-2, the results of Table 2 were obtained.

TABLE 10

| | Compound (Host) | Voltage (V@10 mA/cm$^2$) | Efficiency (cd/A@10 mA/cm$^2$) | EL peak (nm) |
|---|---|---|---|---|
| Experimental Example 2-1 | Compound 4 | 5.28 | 46.93 | 517 |
| Experimental Example 2-2 | Compound 5 | 5.36 | 45.22 | 516 |
| Experimental Example 2-3 | Compound 6 | 5.25 | 46.98 | 518 |
| Experimental Example 2-4 | Compound 7 | 5.39 | 45.16 | 517 |
| Experimental Example 2-5 | Compound 9 | 5.38 | 45.30 | 515 |
| Experimental Example 2-6 | Compound 10 | 5.23 | 46.61 | 516 |
| Experimental Example 2-7 | Compound 18 | 5.39 | 45.43 | 516 |
| Experimental Example 2-8 | Compound 19 | 5.37 | 45.54 | 517 |
| Experimental Example 2-9 | Compound 20 | 5.33 | 45.67 | 518 |
| Experimental Example 2-10 | Compound 21 | 5.40 | 44.28 | 517 |
| Experimental Example 2-11 | Compound 23 | 5.47 | 44.31 | 517 |
| Experimental Example 2-12 | Compound 24 | 5.39 | 45.70 | 517 |
| Experimental Example 2-13 | Compound 32 | 5.45 | 44.61 | 517 |
| Comparative Example 2-1 | GH 1 | 6.51 | 35.72 | 517 |
| Comparative Example 2-2 | GH 2 | 6.25 | 38.45 | 517 |

As a result of the experiment, it could be confirmed that the green organic light emitting devices of Experimental Examples 2-1 to 2-13 in which the compound represented by Chemical Formula 1 according to the present invention was used as a host material of the green light emitting layer exhibited better performances in terms of current efficiency and driving voltage than the green organic light emitting devices of Comparative Examples 2-1 and 2-2, in which a material having no fused carbazole ring at the core of Chemical Formula 1 of the present invention was used.

Experimental Example 3-1

The compounds synthesized in the Synthesis Examples were subjected to high-purity sublimation purification in a typically known method, and then red organic light emitting devices were manufactured by the following method. An ITO glass was patterned and then washed, such that the light emitting area of the ITO glass became 2 mm×2 mm. After the substrate was mounted in a vacuum chamber, the base pressure was set to 1×10$^{-6}$ torr, and then layers were sequentially formed on the ITO by using DNTPD (700 Å) and a-NPB (300 Å). Subsequently, a light emitting layer was formed by using Compound 8 as a host (90 wt %) and co-depositing the following (piq)$_2$Ir(acac) (10 wt %) (300 Å) as a dopant, films were additionally formed in the order of Alq$_3$ (350 Å), LiF (5 Å), and Al (1,000 Å), and measurements were made at 0.4 mA.

The structures of DNTPD, α-NPB, (piq)$_2$Ir(acac), and Alq$_3$ are as follows.

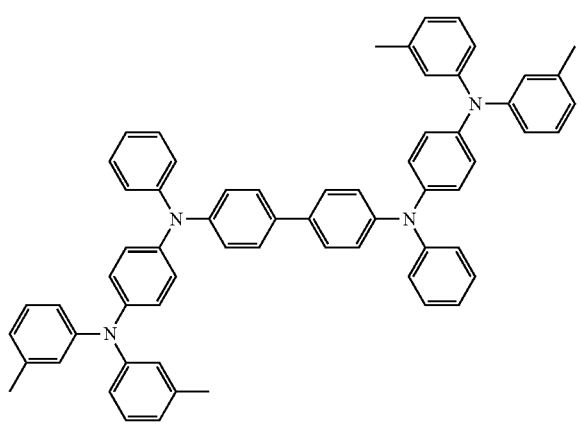

[DNTPD]

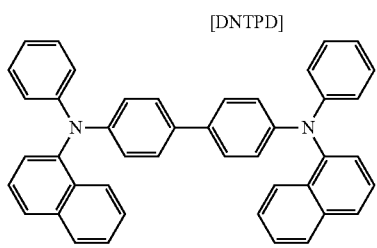

[α-NPB]

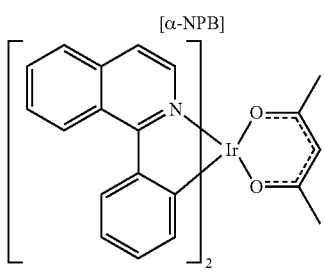

[(piq)₂Ir(acac)]

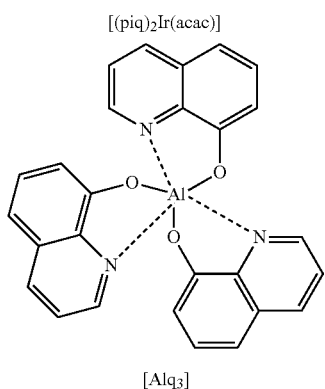

[Alq₃]

Experimental Example 3-2

An organic light emitting device was manufactured in the same manner as in Experimental Example 3-1, except that Compound 22 was used instead of Compound 8 in Experimental Example 3-1.

Experimental Example 3-3

An organic light emitting device was manufactured in the same manner as in Experimental Example 3-1, except that Compound 36 was used instead of Compound 8 in Experimental Example 3-1.

Experimental Example 3-4

An organic light emitting device was manufactured in the same manner as in Experimental Example 3-1, except that Compound 50 was used instead of Compound 8 in Experimental Example 3-1.

Experimental Example 3-5

An organic light emitting device was manufactured in the same manner as in Experimental Example 3-1, except that Compound 64 was used instead of Compound 8 in Experimental Example 3-1.

Experimental Example 3-6

An organic light emitting device was manufactured in the same manner as in Experimental Example 3-1, except that Compound 78 was used instead of Compound 8 in Experimental Example 3-1.

Experimental Example 3-7

An organic light emitting device was manufactured in the same manner as in Experimental Example 3-1, except that Compound 92 was used instead of Compound 8 in Experimental Example 3-1.

Experimental Example 3-8

An organic light emitting device was manufactured in the same manner as in Experimental Example 3-1, except that Compound 106 was used instead of Compound 8 in Experimental Example 3-1.

Experimental Example 3-9

An organic light emitting device was manufactured in the same manner as in Experimental Example 3-1, except that Compound 120 was used instead of Compound 8 in Experimental Example 3-1.

Experimental Example 3-10

An organic light emitting device was manufactured in the same manner as in Experimental Example 3-1, except that Compound 134 was used instead of Compound 8 in Experimental Example 3-1.

Experimental Example 3-11

An organic light emitting device was manufactured in the same manner as in Experimental Example 3-1, except that Compound 148 was used instead of Compound 8 in Experimental Example 3-1.

Experimental Example 3-12

An organic light emitting device was manufactured in the same manner as in Experimental Example 3-1, except that Compound 162 was used instead of Compound 8 in Experimental Example 3-1.

Experimental Example 3-13

An organic light emitting device was manufactured in the same manner as in Experimental Example 3-1, except that Compound 176 was used instead of Compound 8 in Experimental Example 3-1.

Experimental Example 3-14

An organic light emitting device was manufactured in the same manner as in Experimental Example 3-1, except that Compound 190 was used instead of Compound 8 in Experimental Example 3-1.

Experimental Example 3-15

An organic light emitting device was manufactured in the same manner as in Experimental Example 3-1, except that Compound 204 was used instead of Compound 8 in Experimental Example 3-1.

Comparative Example 3-1

An organic light emitting device for Comparative Example 3-1 was manufactured equally, except that the following compound CBP frequently used as a general phosphorescent host material was used instead of the organic light emitting compound prepared by the present invention as a host of the light emitting layer in the device structures of the Examples.

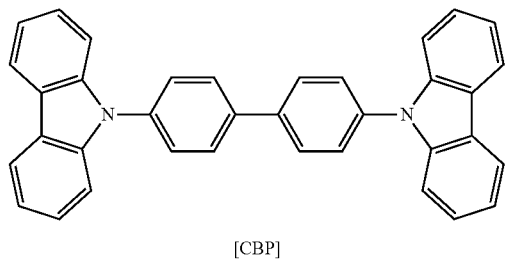

[CBP]

For the organic light emitting devices manufactured according to Experimental Examples 3-1 to 3-15 and Comparative Example 3-1, the voltages, current densities, luminances, color coordinates, and service lives were measured, and the results are shown in the following [Table 3]. T95 means the time taken for the luminance to be reduced to 95% of the initial luminance (5,000 nit).

TABLE 11

| Classification | Host | Dopant | Voltage | Luminance (V) | CIEx (cd/m$^2$) | CIEy | T95(hr) |
|---|---|---|---|---|---|---|---|
| Experimental Example 3-1 | 8 | [(piq)$_2$Ir(acac)] | 4.4 | 1690 | 0.672 | 0.328 | 475 |
| Experimental Example 3-2 | 22 | [(piq)$_2$Ir(acac)] | 4.2 | 1840 | 0.673 | 0.327 | 455 |
| Experimental Example 3-3 | 36 | [(piq)$_2$Ir(acac)] | 4.1 | 1930 | 0.672 | 0.326 | 450 |
| Experimental Example 3-4 | 50 | [(piq)$_2$Ir(acac)] | 4.3 | 1870 | 0.673 | 0.336 | 445 |
| Experimental Example 3-5 | 64 | [(piq)$_2$Ir(acac)] | 4.4 | 1680 | 0.672 | 0.329 | 475 |
| Experimental Example 3-6 | 78 | [(piq)$_2$Ir(acac)] | 4.2 | 1810 | 0.674 | 0.326 | 455 |
| Experimental Example 3-7 | 92 | [(piq)$_2$Ir(acac)] | 4.1 | 1960 | 0.672 | 0.328 | 450 |
| Experimental Example 3-8 | 106 | [(piq)$_2$Ir(acac)] | 4.3 | 1740 | 0.673 | 0.335 | 445 |
| Experimental Example 3-9 | 120 | [(piq)$_2$Ir(acac)] | 4.4 | 1690 | 0.671 | 0.326 | 475 |
| Experimental Example 3-10 | 134 | [(piq)$_2$Ir(acac)] | 4.2 | 1870 | 0.673 | 0.326 | 455 |
| Experimental Example 3-11 | 148 | [(piq)$_2$Ir(acac)] | 4.1 | 1920 | 0.672 | 0.327 | 450 |
| Experimental Example 3-12 | 162 | [(piq)$_2$Ir(acac)] | 4.3 | 1750 | 0.671 | 0.336 | 445 |
| Experimental Example 3-13 | 176 | [(piq)$_2$Ir(acac)] | 4.4 | 1680 | 0.671 | 0.328 | 455 |
| Experimental Example 3-14 | 190 | [(piq)$_2$Ir(acac)] | 4.2 | 1840 | 0.672 | 0.326 | 455 |
| Experimental Example 3-15 | 204 | [(piq)$_2$Ir(acac)] | 4.1 | 1920 | 0.672 | 0.327 | 450 |
| Comparative Example 3-1 | CBP | [(piq)$_2$Ir(acac)] | 6.8 | 1220 | 0.679 | 0.339 | 290 |

As a result of the experiments, it could be confirmed that the red organic light emitting devices of Experimental Examples 3-1 to 3-15 in which Compounds 8, 22, 36, 50, 64, 78, 92, 106, 120, 134, 148, 162, 176, 190, and 204 prepared according to the present invention was used as a host material of the light emitting layer exhibited better performances, in terms of current efficiency, driving voltage, and service life, than the red organic light emitting device of Comparative Example 3-1 in which CBP in the related art was used. It can be seen that the compounds having quinazoline as the substituent are suitable as a red organic light emitting device.

Although the preferred exemplary embodiments (an electron blocking layer, a green light emitting layer, and a red light emitting layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Electron transporting layer

The invention claimed is:

1. An organic light emitting device comprising:
a first electrode;
a second electrode disposed to face the first electrode; and
an organic material layer having one or more layers disposed between the first electrode and the second electrode,
wherein the organic material layer comprises an electron blocking layer, and the electron blocking layer comprises a compound represented by the following Chemical Formula 1:

[Chemical Formula 1]

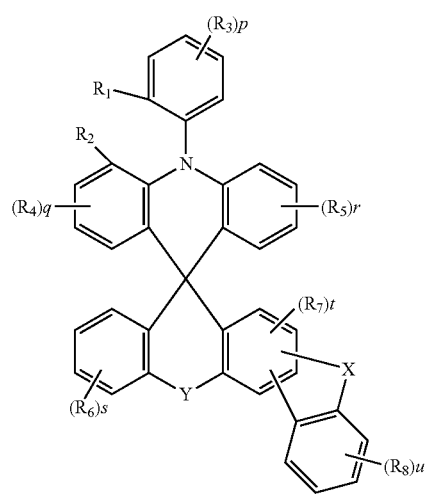

in Chemical Formula 1,
Y is O, S, or $SiR_{11}R_{12}$,
X is NAr,
Ar is represented by $(L1)n\text{-}Ar1$,
L1 is a direct bond; a substituted or unsubstituted arylene group; or a substituted or unsubstituted heteroarylene, n is an integer from 0 to 2, and when n is 2, L1's are the same as or different from each other,
Ar1 is a substituted or unsubstituted heterocyclic group; a substituted or unsubstituted arylamino group; or a substituted or unsubstituted arylphosphine group, and
$R_1$ to $R_8$ are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamino group; a substituted or unsubstituted aralkylamino group; a substituted or unsubstituted heteroarylamino group; a substituted or unsubstituted arylamino group; a substituted or unsubstituted arylheteroarylamino group; a substituted or unsubstituted arylphosphine group; a substituted or unsubstituted phosphine oxide group; a substituted or unsubstituted aryl group; or a substituted or unsubstituted heterocyclic group, or are optionally bonded to an adjacent group to form a ring,
$R_{11}$ and $R_{12}$ are the same as or different from each other, and are each independently hydrogen; a substituted or unsubstituted alkyl group; or a substituted or unsubstituted aryl group,
p, s, r, and u are each an integer from 0 to 4, q is an integer from 0 to 3, t is an integer from 0 to 2, and when p, q, r, s, t, and u are each 2 or more, each of $R_3$ to $R_8$ is the same as or different from each other.

2. The organic light emitting device of claim 1, wherein Chemical Formula 1 is represented by the following Chemical Formula 2 or 3:

[Chemical Formula 2]

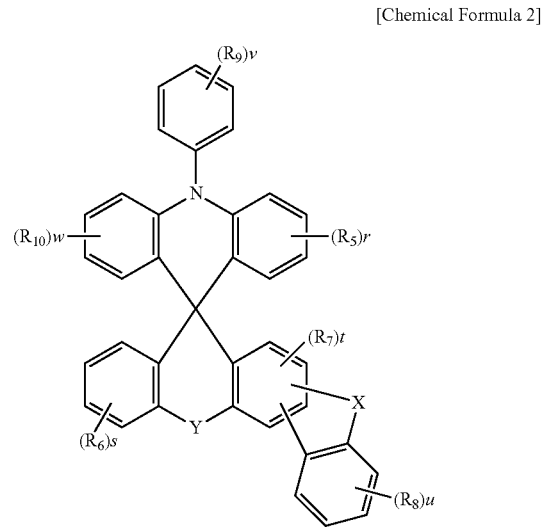

in Chemical Formula 2, Y, X, $R_5$ to $R_8$, r, s, t, and u are the same as those defined in Chemical Formula 1, $R_9$ and $R_{10}$ are the same as or different from each other, and are the same as the definitions of $R_1$ to $R_8$ of Chemical Formula 1, v is an integer from 0 to 5, w is an integer from 0 to 4, and when v and w are each 2 or more, each of $R_9$ and $R_{10}$ is the same as or different from each other, and

[Chemical Formula 3]

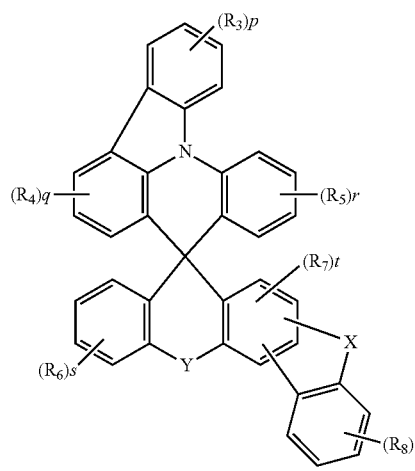

in Chemical Formula 3, Y, X, $R_3$ to $R_8$, p, q, r, s, t, and u are the same as those defined in Chemical Formula 1.

3. The organic light emitting device of claim 2, wherein Chemical Formula 1 is represented by one of the following Chemical Formulae 4 to 7:

[Chemical Formula 4]

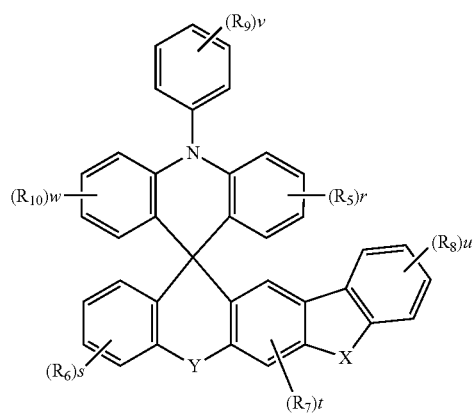

[Chemical Formula 5]

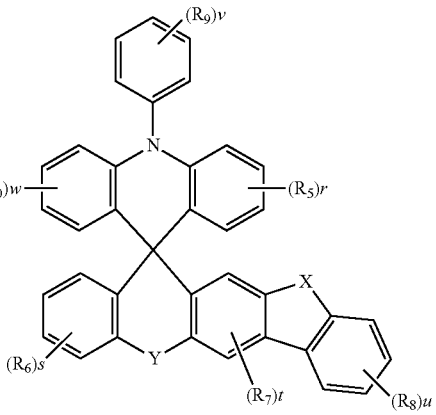

[Chemical Formula 6]

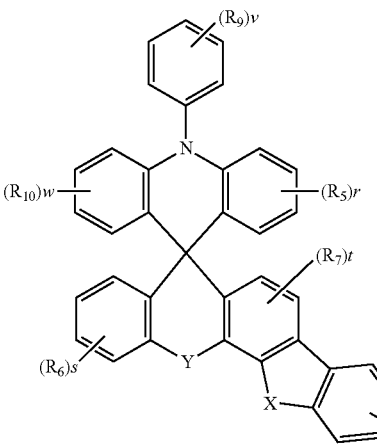

[Chemical Formula 7]

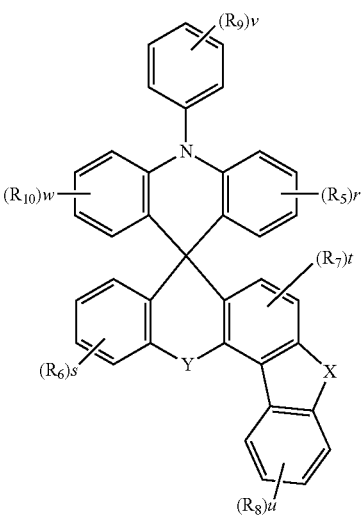

in Chemical Formulae 4 to 7, the definitions of the substituents are the same as those in Chemical Formula 2.

4. The organic light emitting device of claim 2, wherein Chemical Formula 1 is represented by one of the following Chemical Formulae 8 to 11:

[Chemical Formula 8]

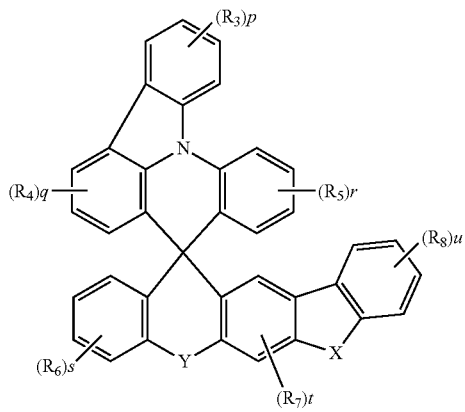

[Chemical Formula 9]

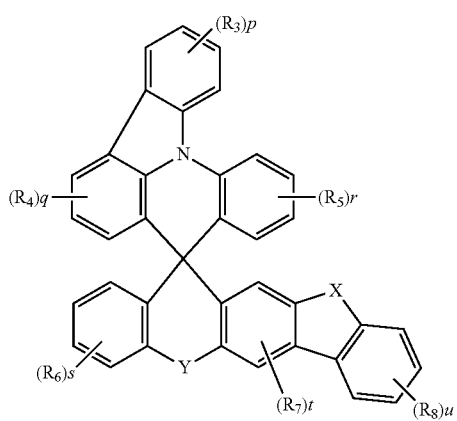

[Chemical Formula 10]

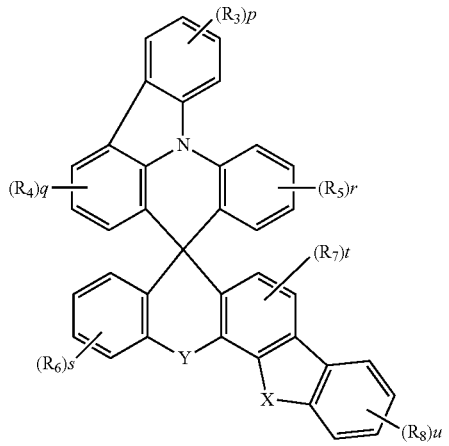

[Chemical Formula 11]

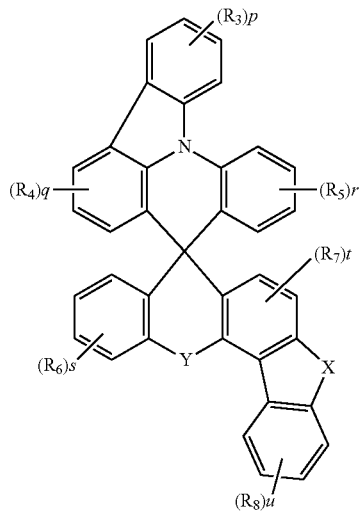

in Chemical Formulae 8 to 11, the definitions of the substituents are the same as those in Chemical Formula 1.

5. The organic light emitting device of claim 1, wherein $L_1$ is a direct bond or a substituted or unsubstituted arylene.

6. The organic light emitting device of claim 1, wherein $L_1$ is a direct bond, phenylene, biphenylylene, terphenylylene, quarterphenylylene, naphthylene, anthrylene, fluorene, phenanthrene, pyrene, or triphenylene.

7. The organic light emitting device of claim 1, wherein the compound of Chemical Formula 1 is any one selected from the following structural formulae:

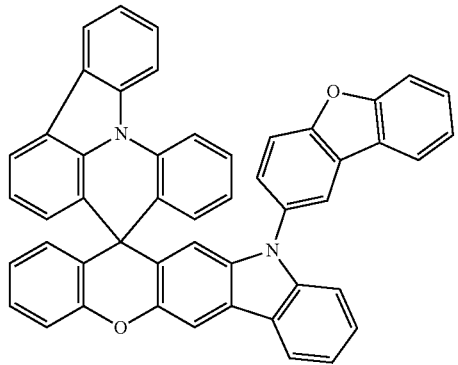

347
-continued
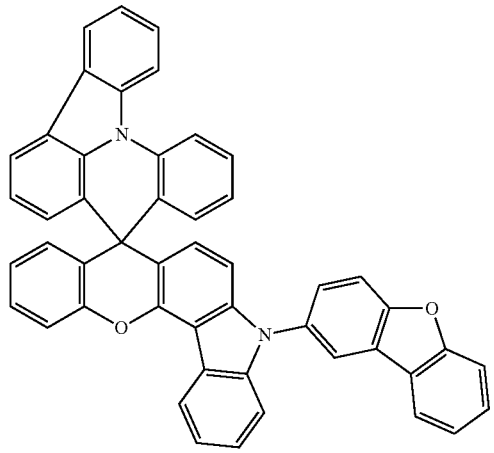
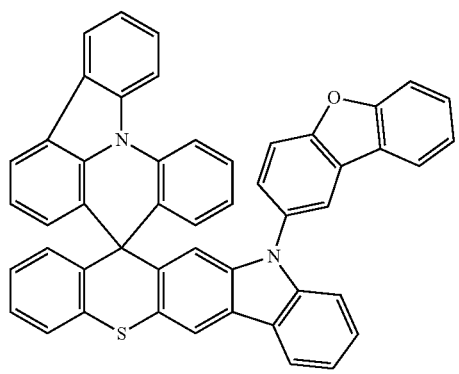
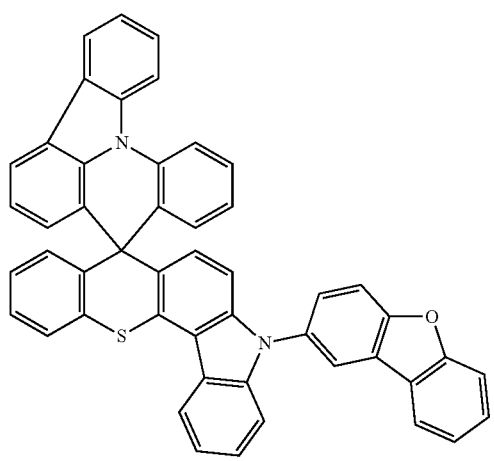
348
-continued
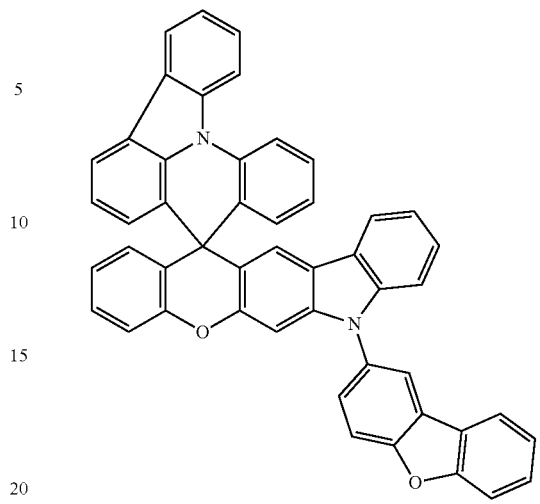
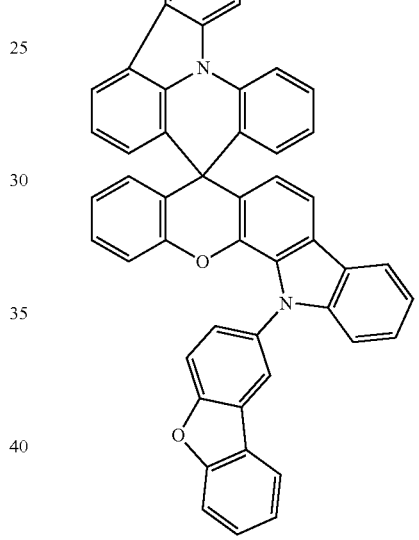
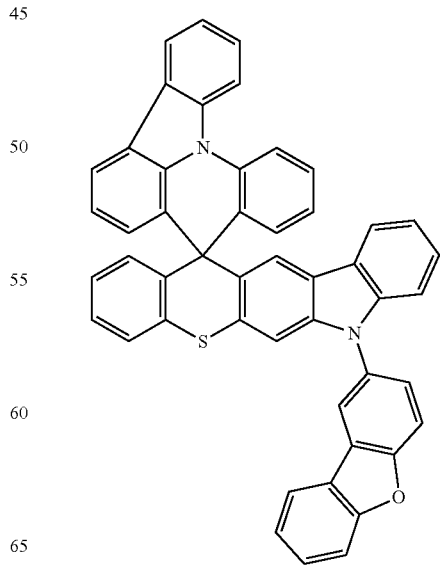

349
-continued
350
-continued
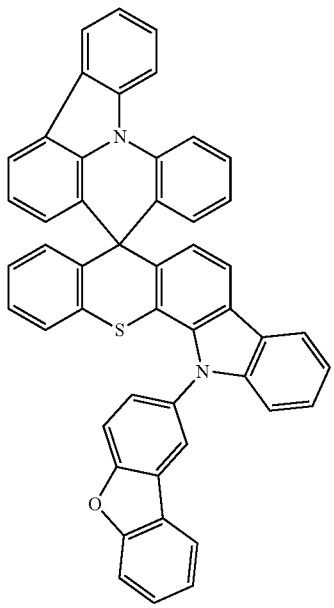
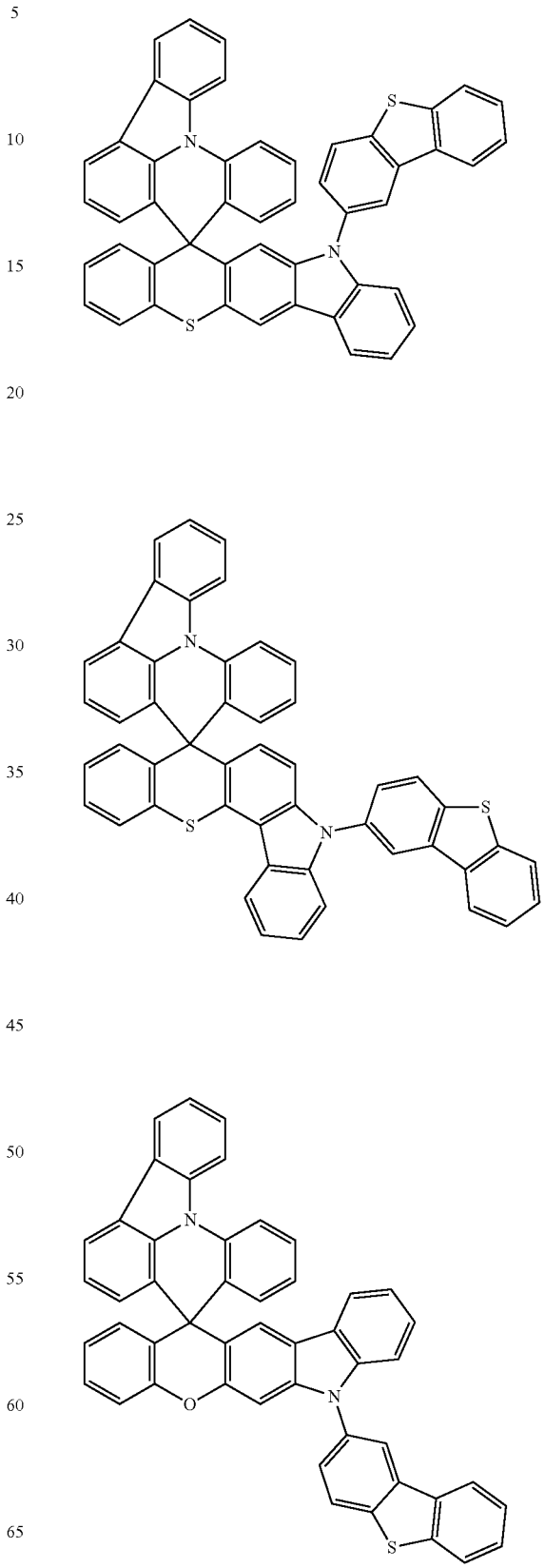

351
-continued
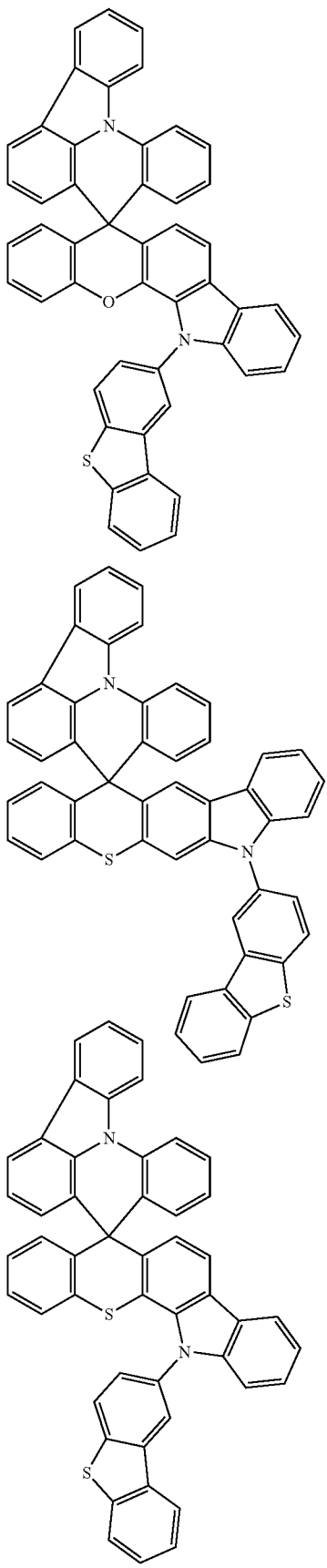
352
-continued
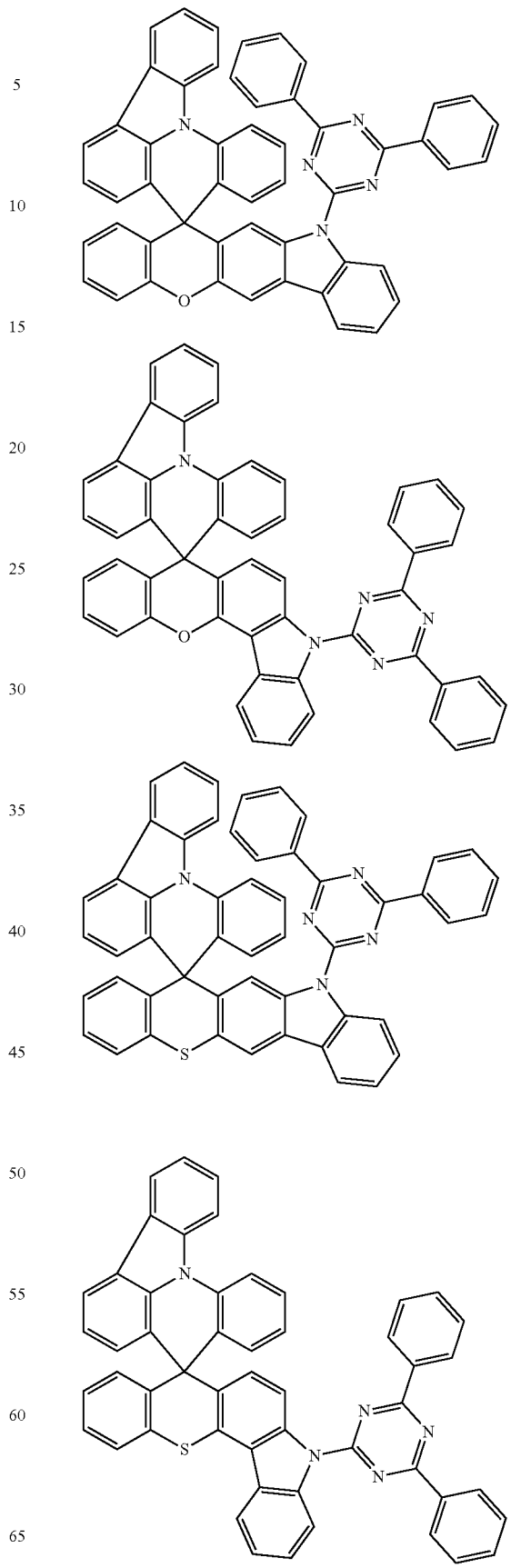

353
-continued
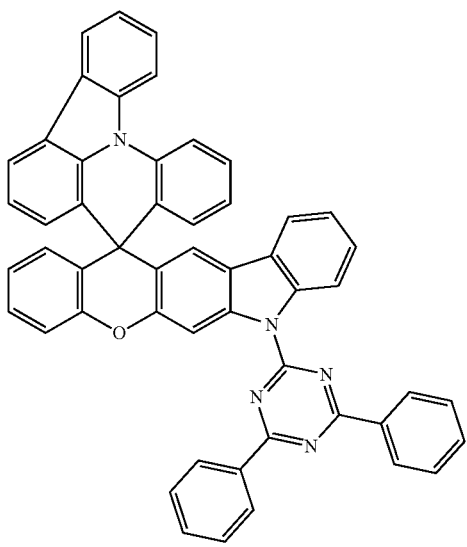
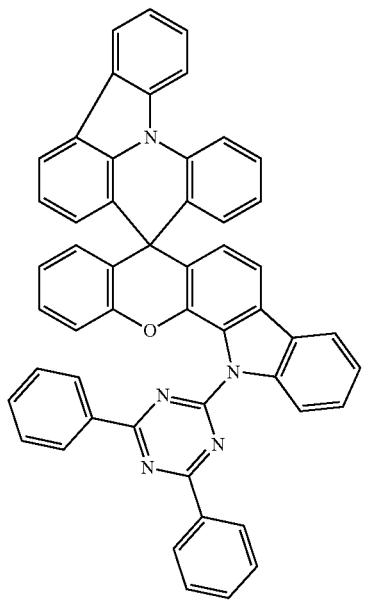
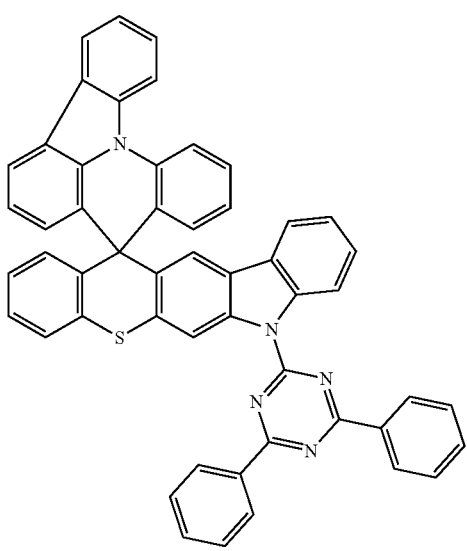
354
-continued
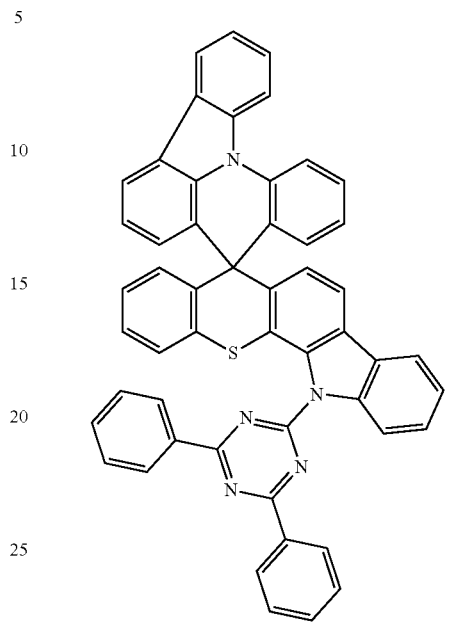
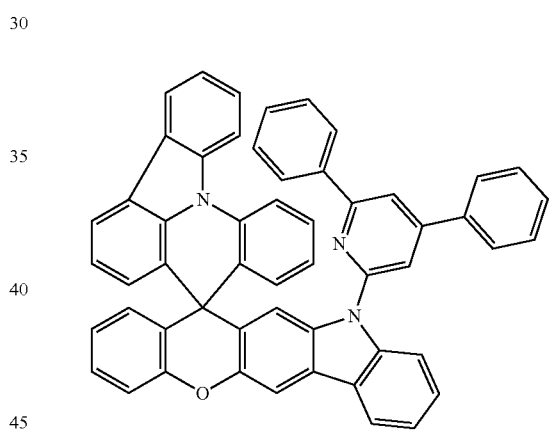
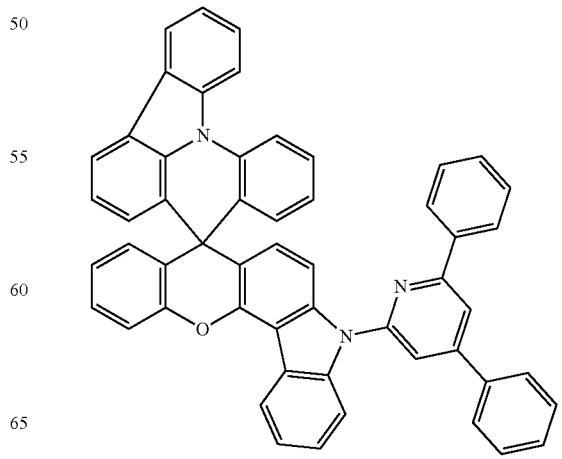

355
-continued
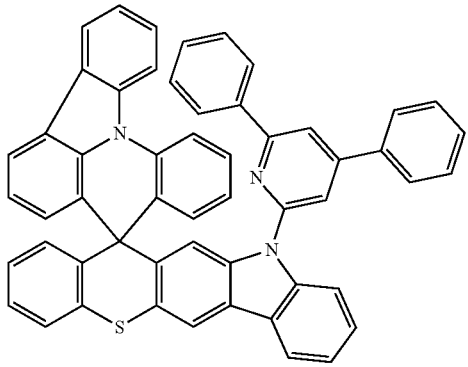
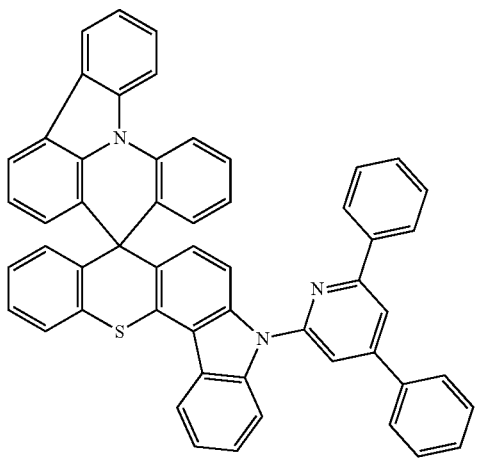
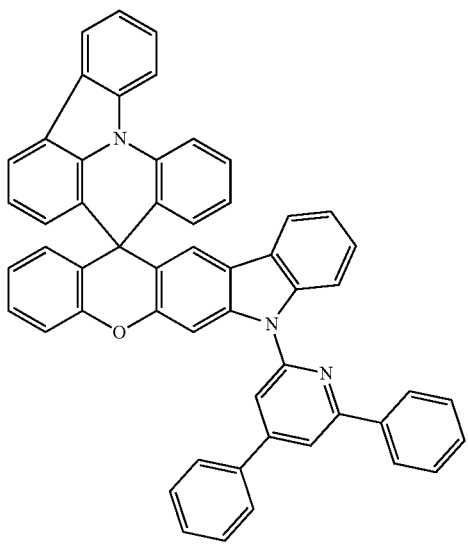
356
-continued
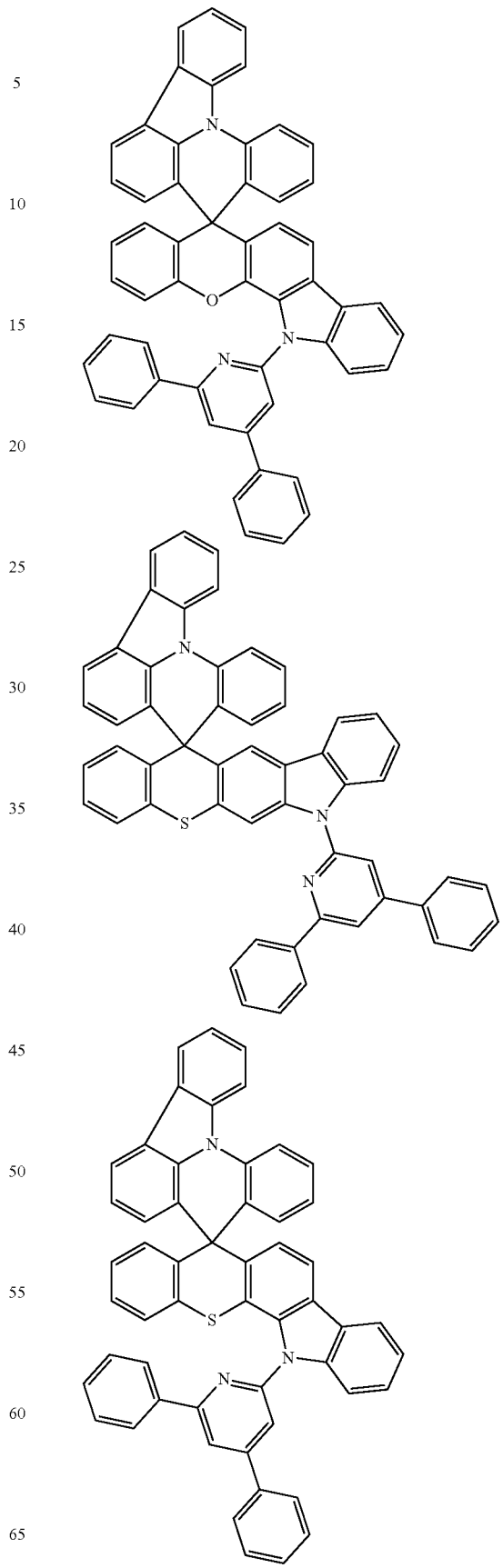

357
-continued
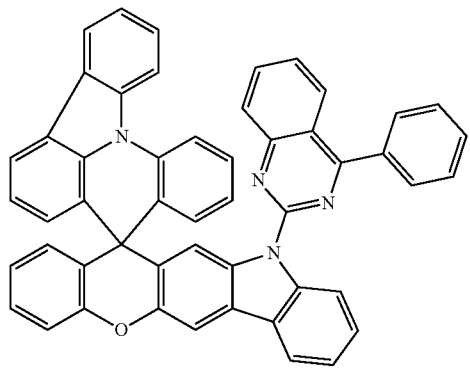
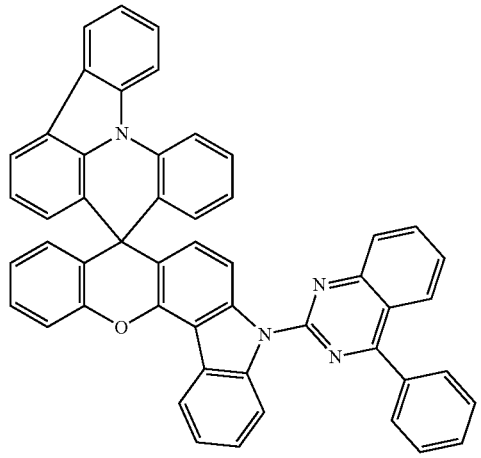
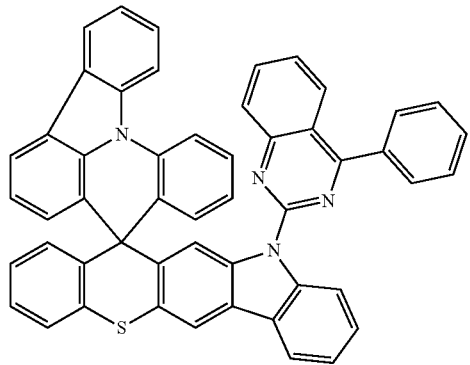
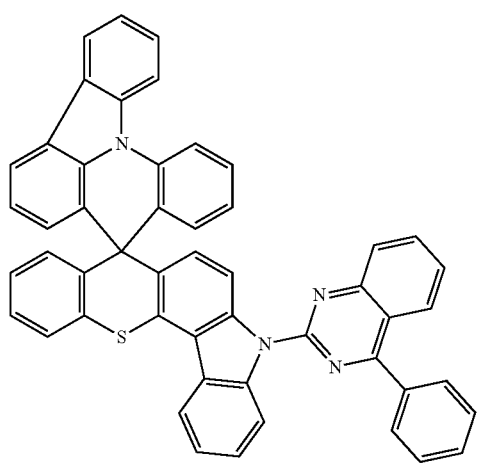
358
-continued
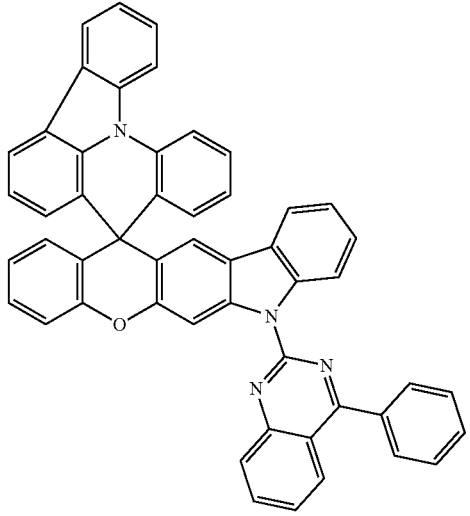
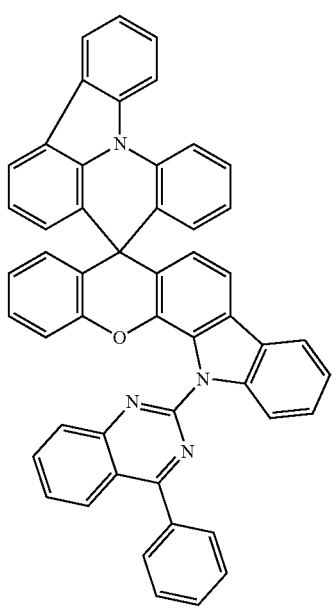
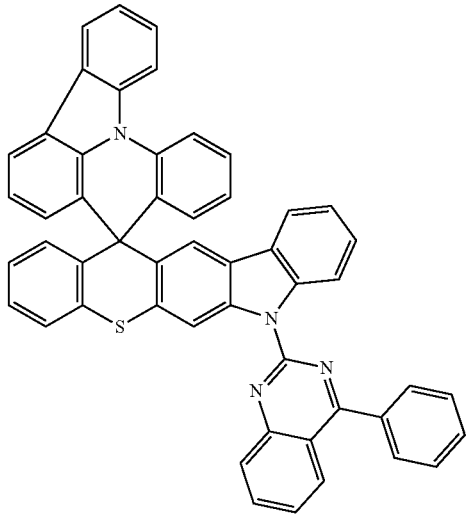

359
-continued
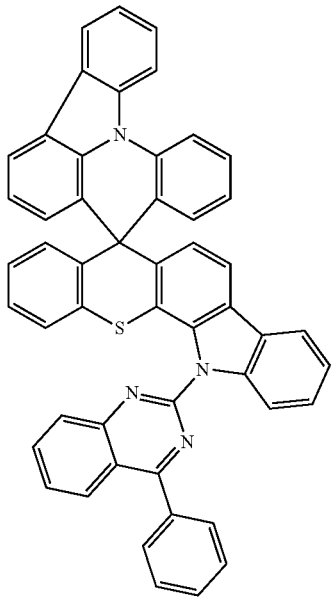
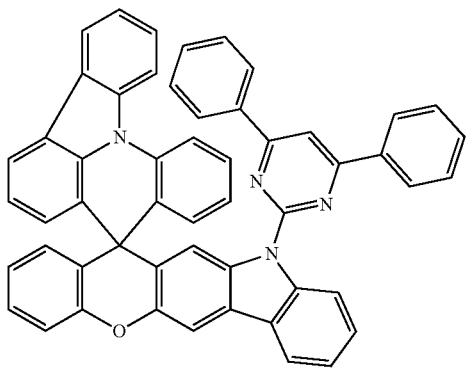
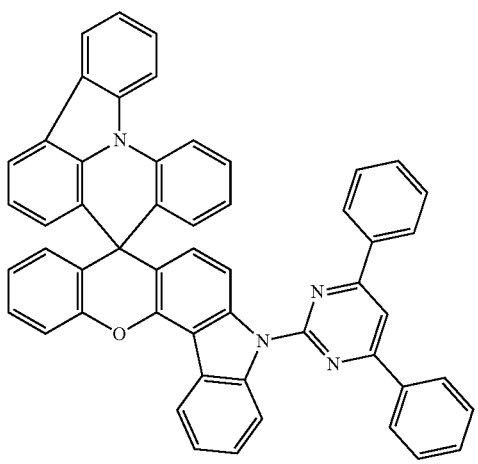
360
-continued
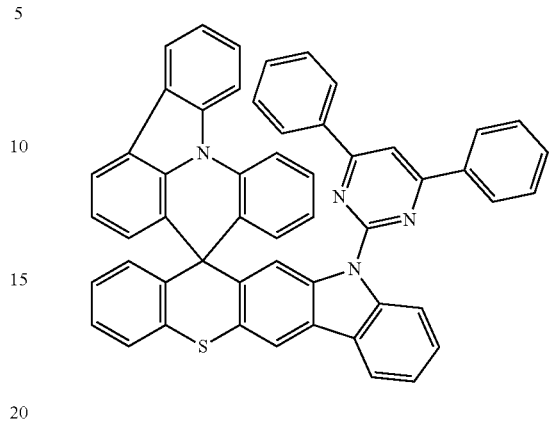
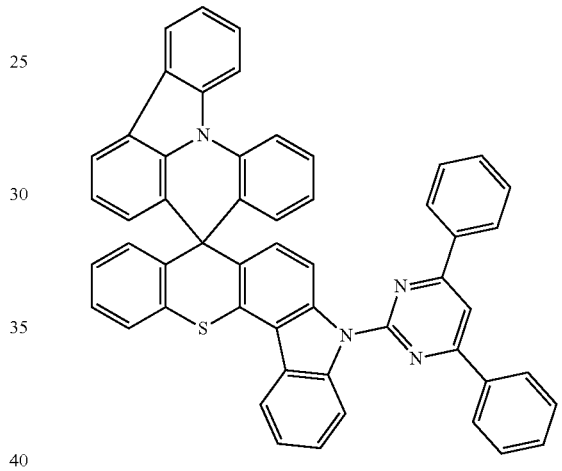
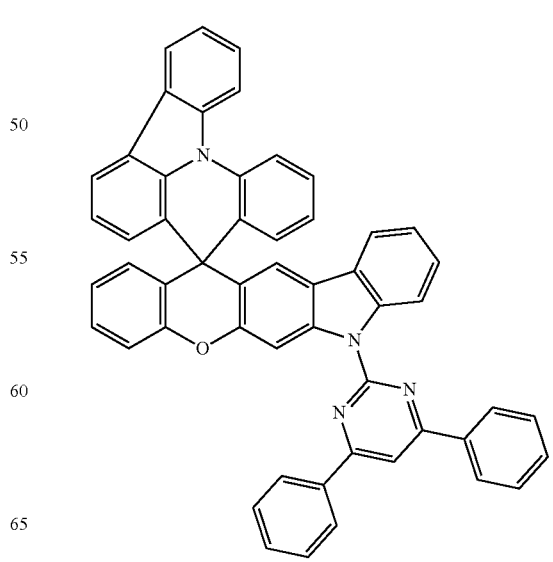

361
-continued
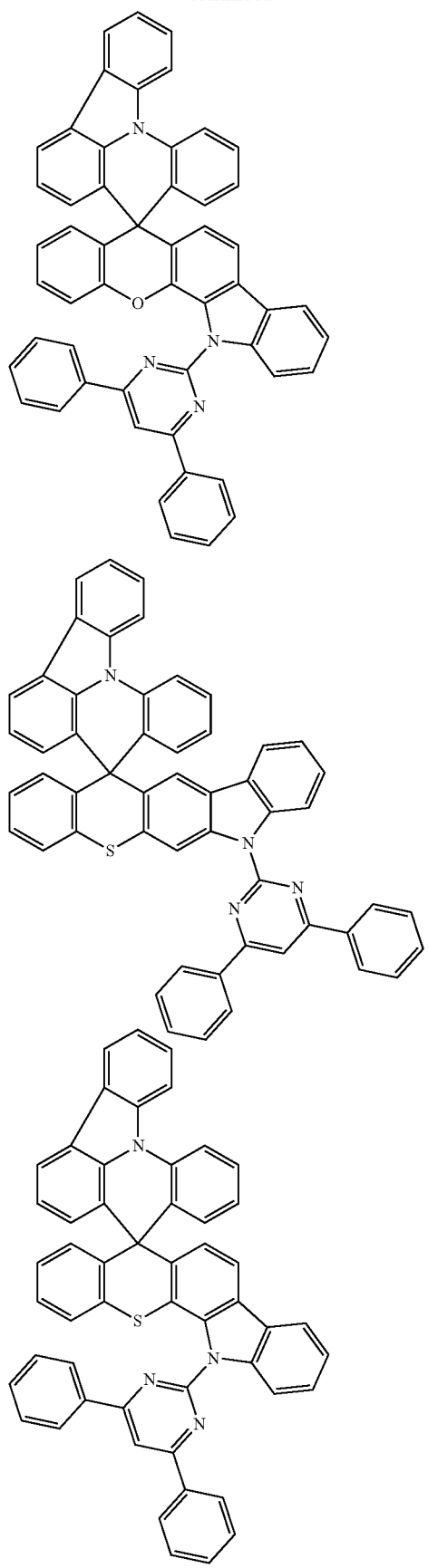
362
-continued
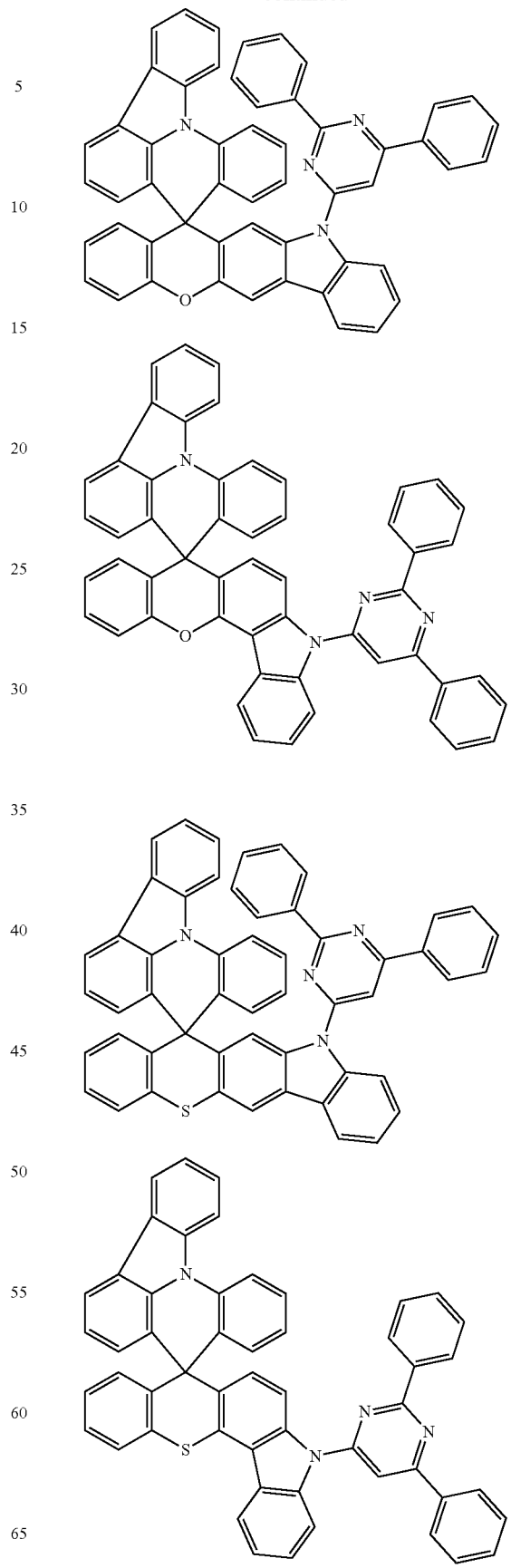

363
-continued
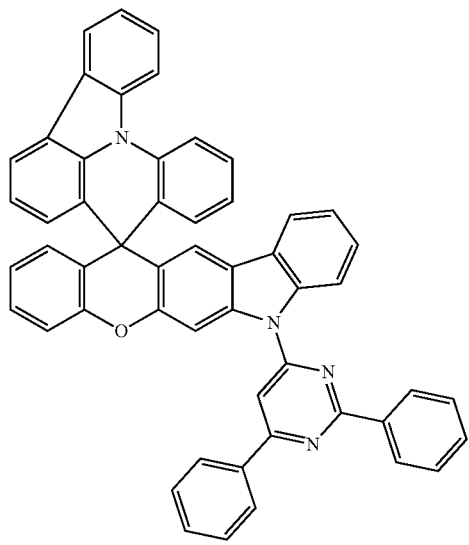
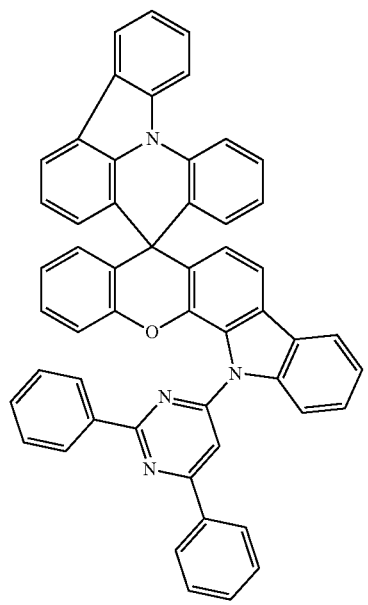
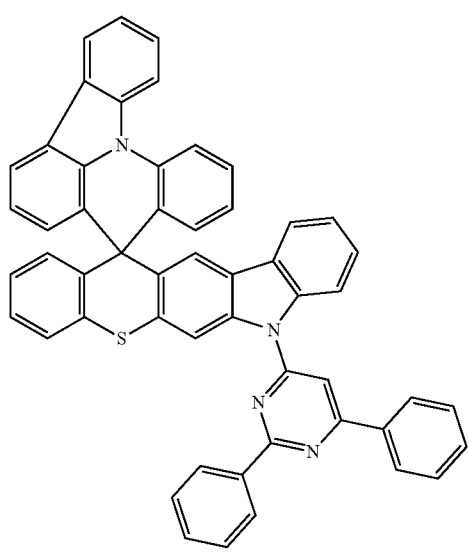
364
-continued
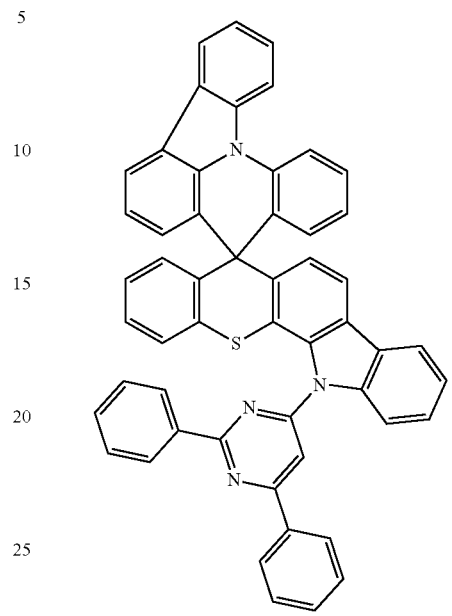
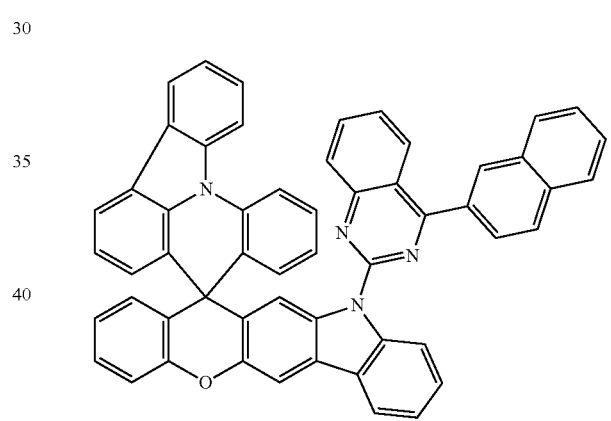
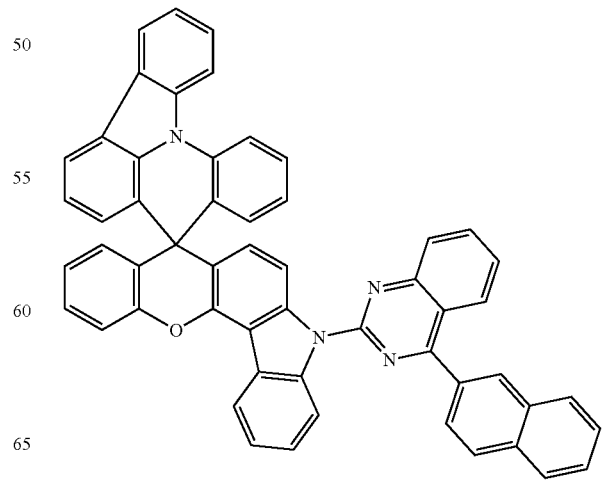

365
-continued
366
-continued
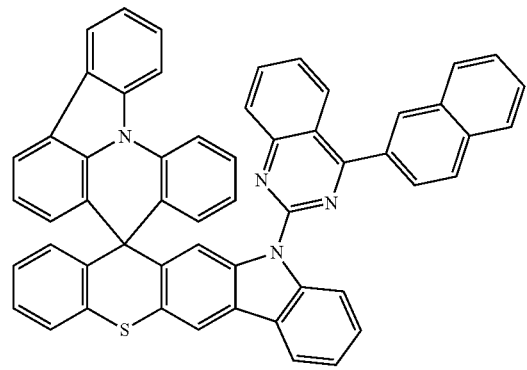
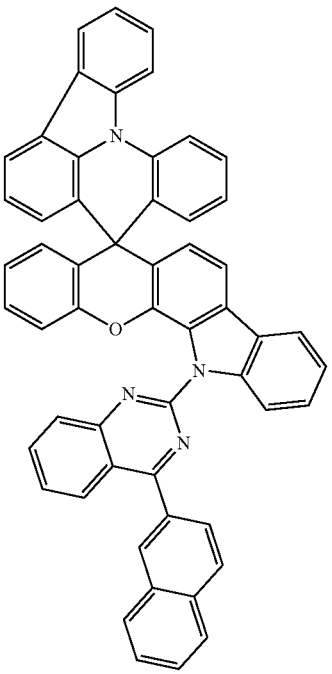
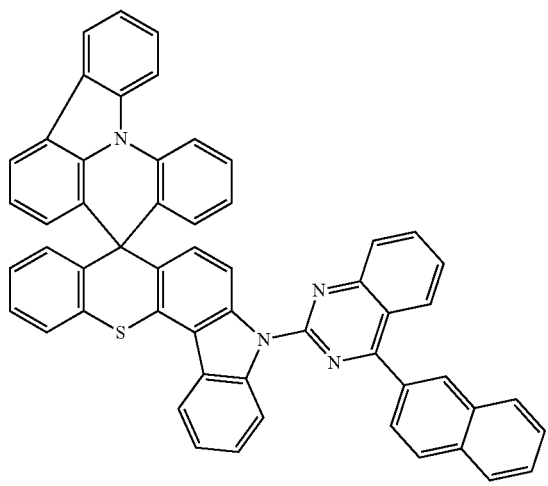
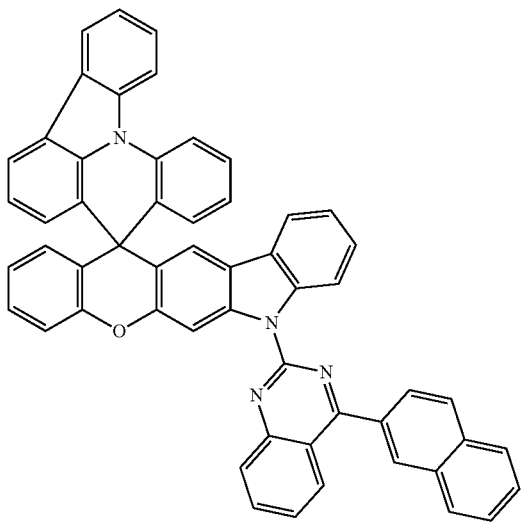
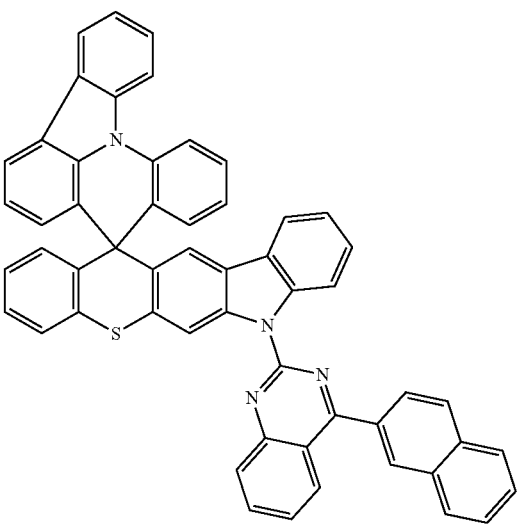

367
-continued
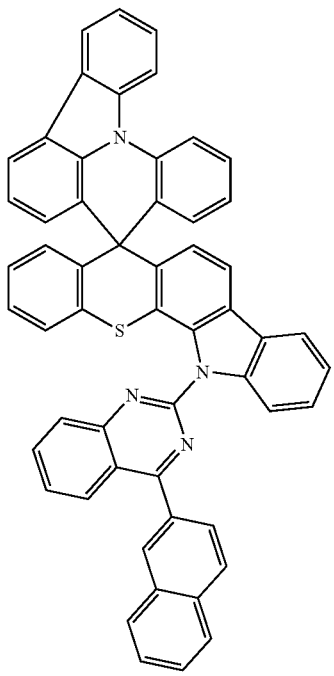
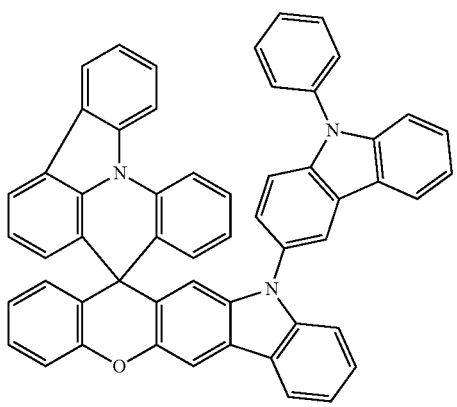
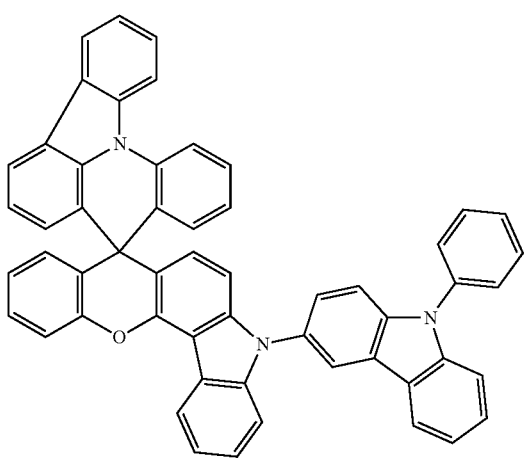
368
-continued
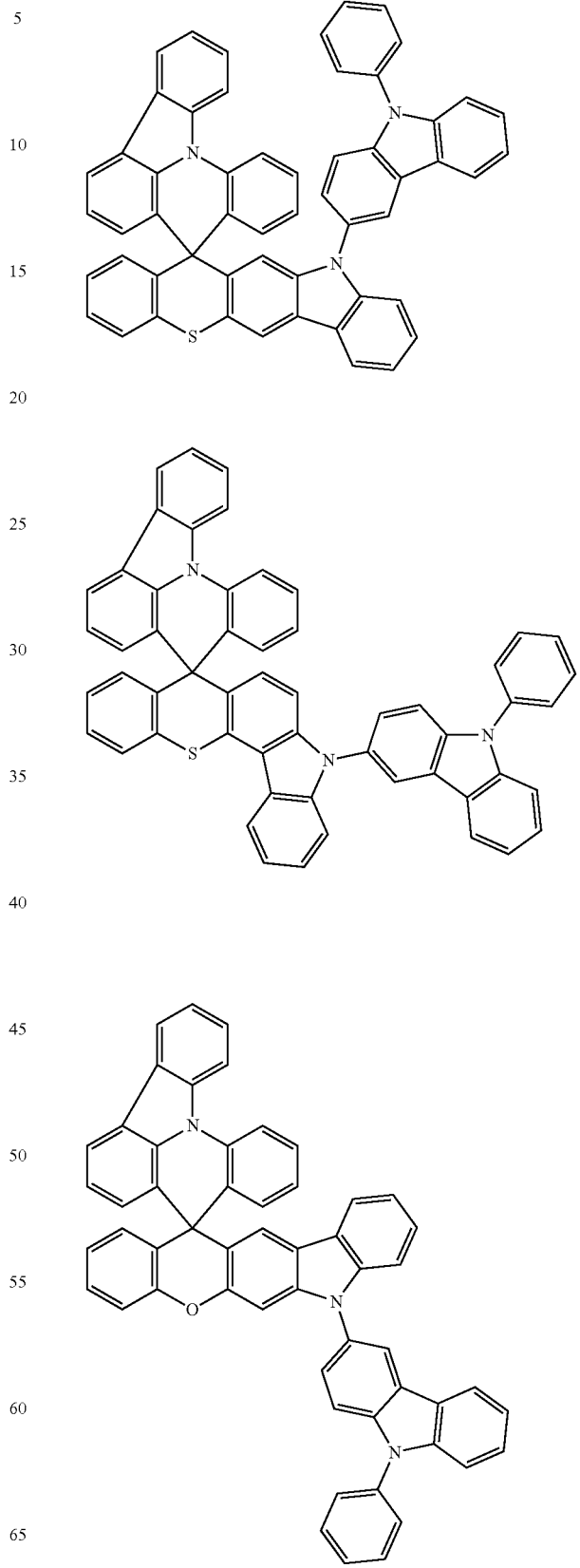

369
-continued
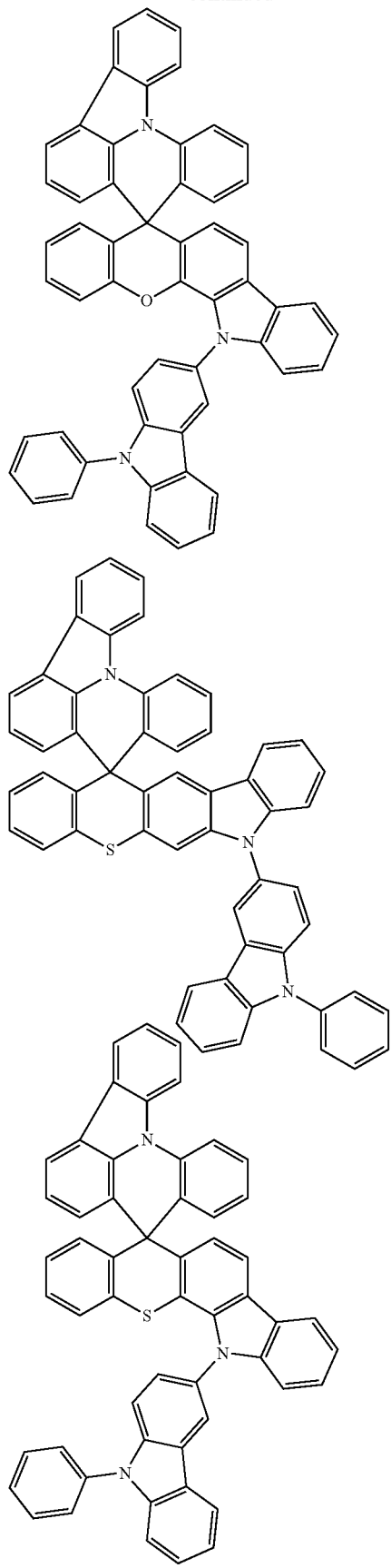
370
-continued
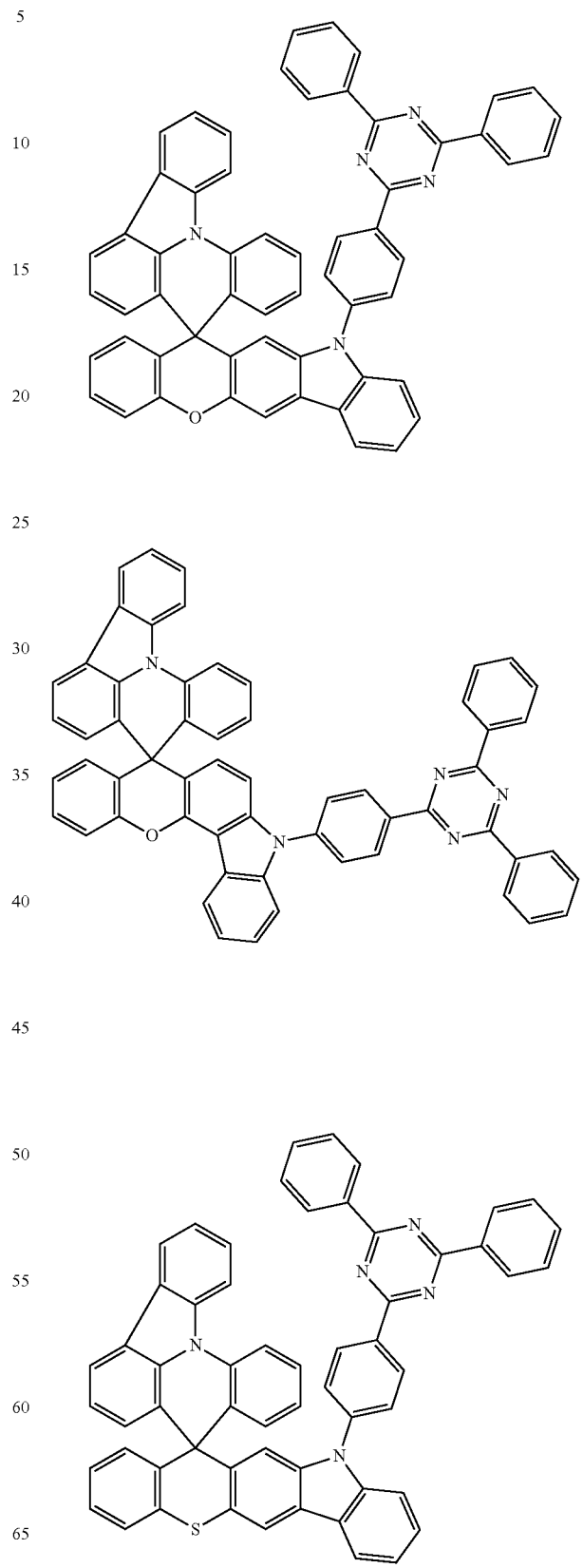

371
-continued
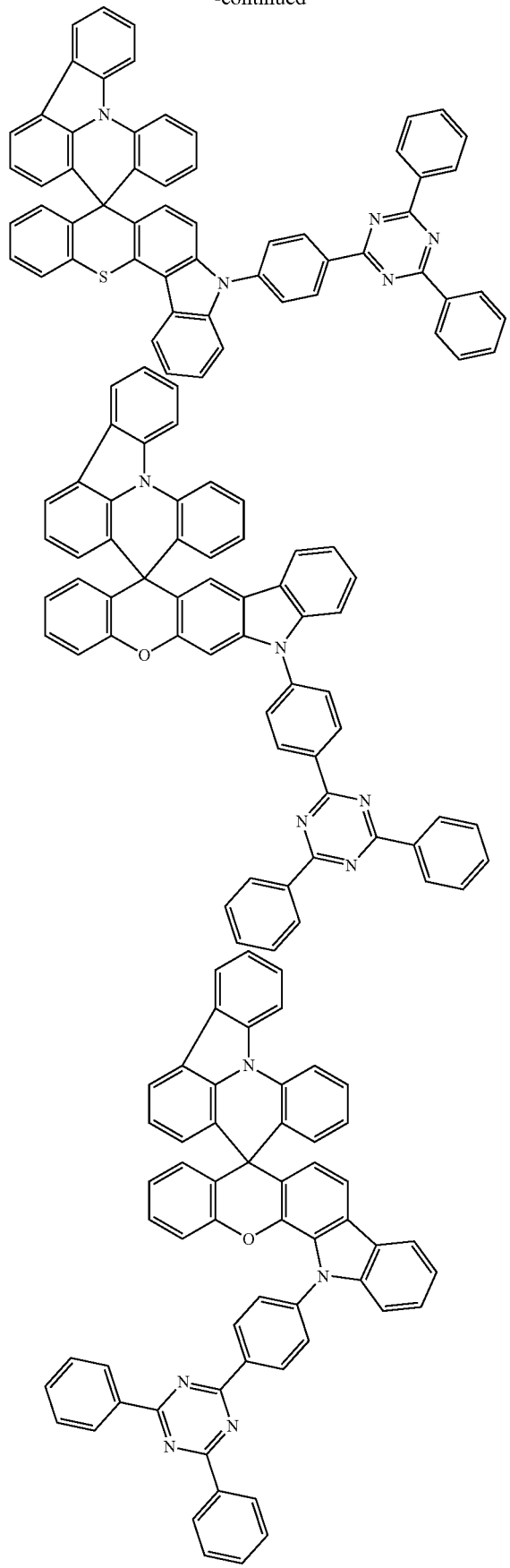
372
-continued
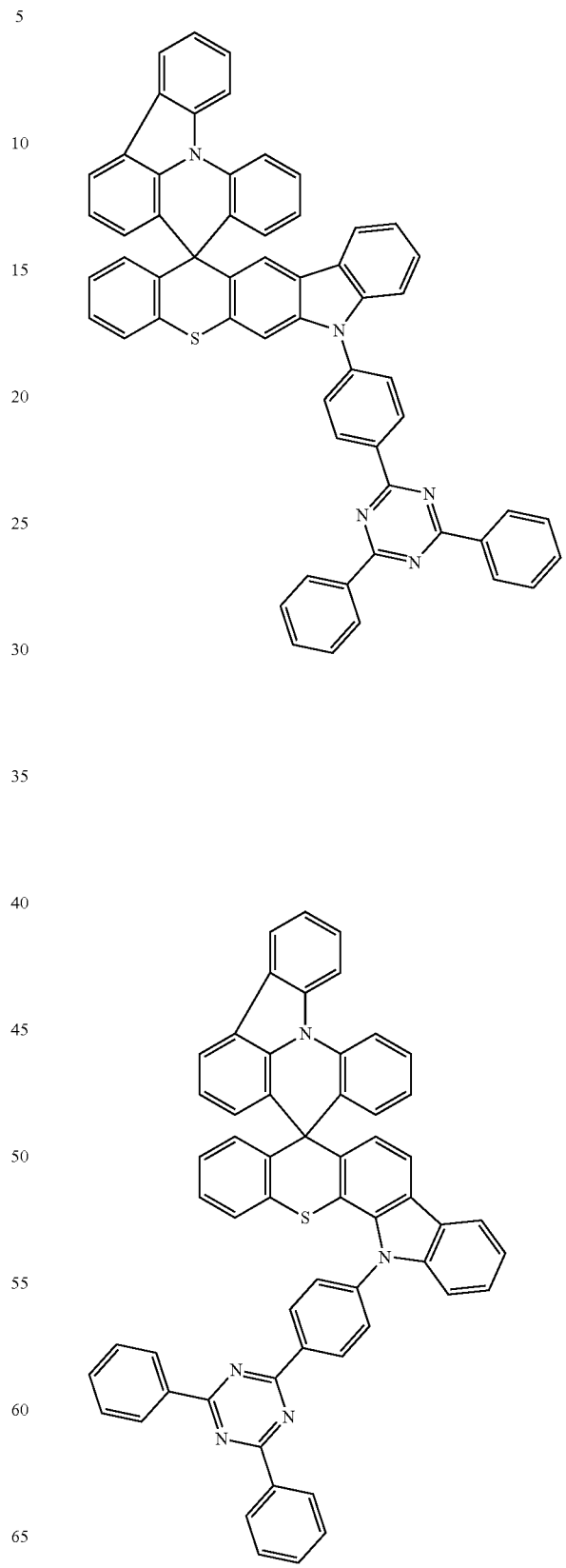

373
-continued
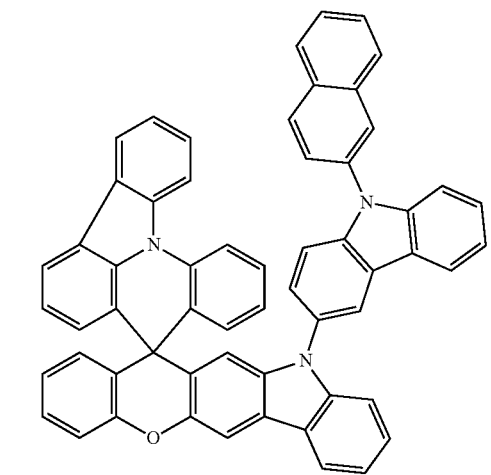
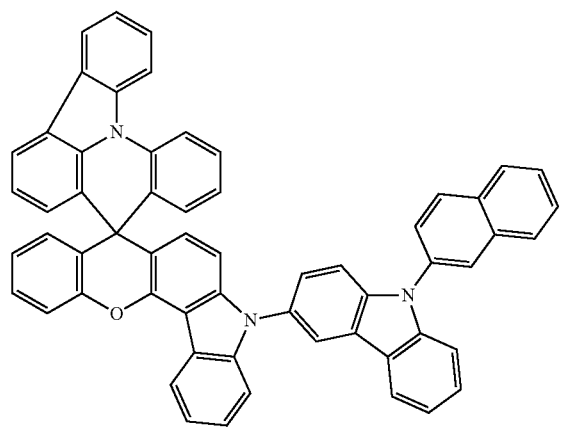
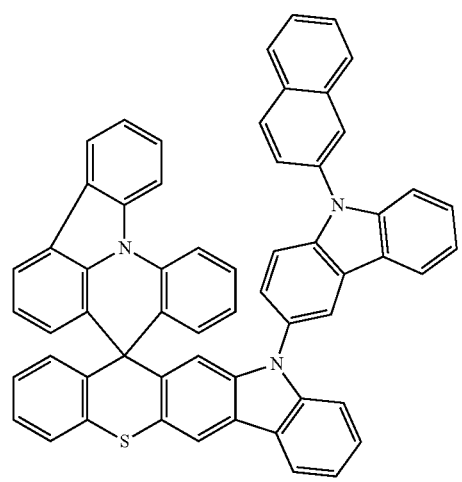
374
-continued
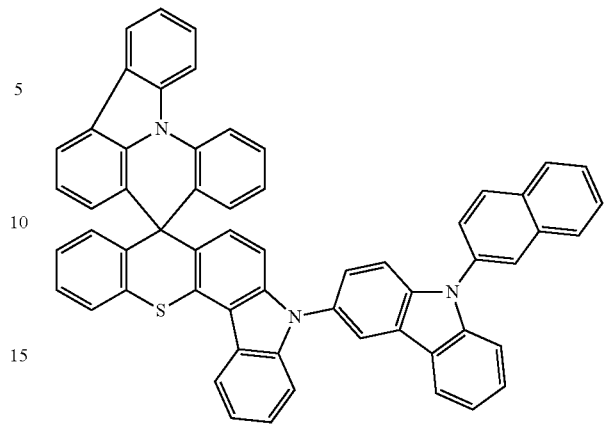
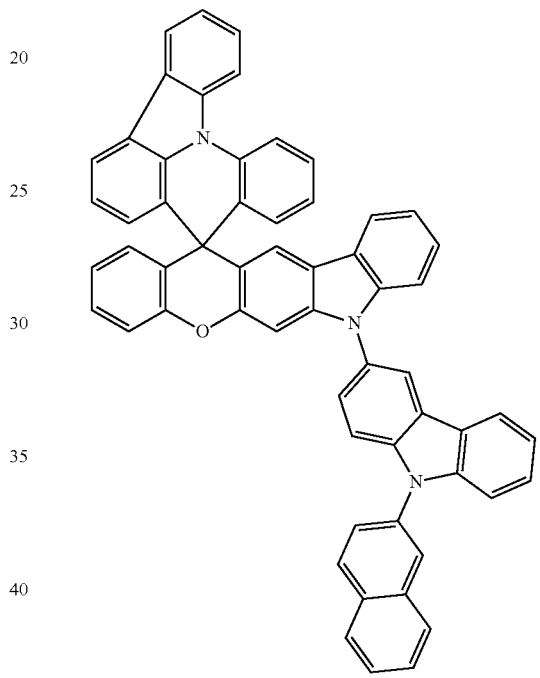
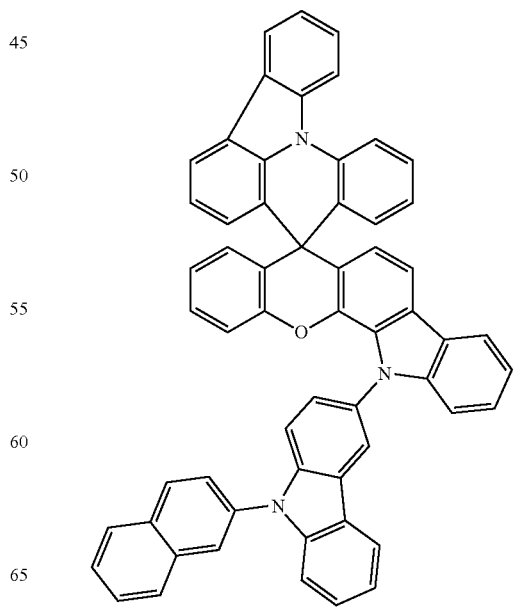

375
-continued
376
-continued
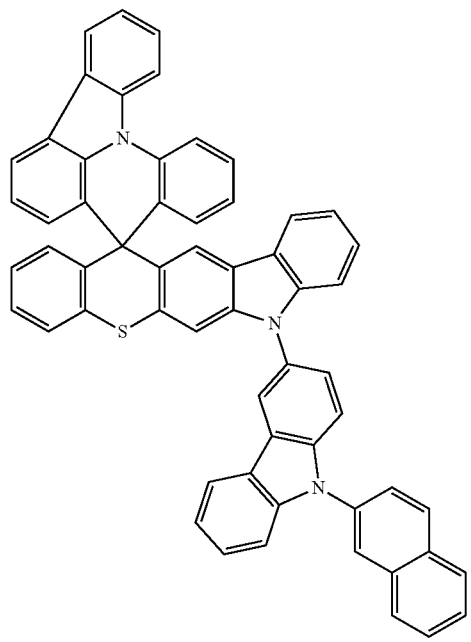
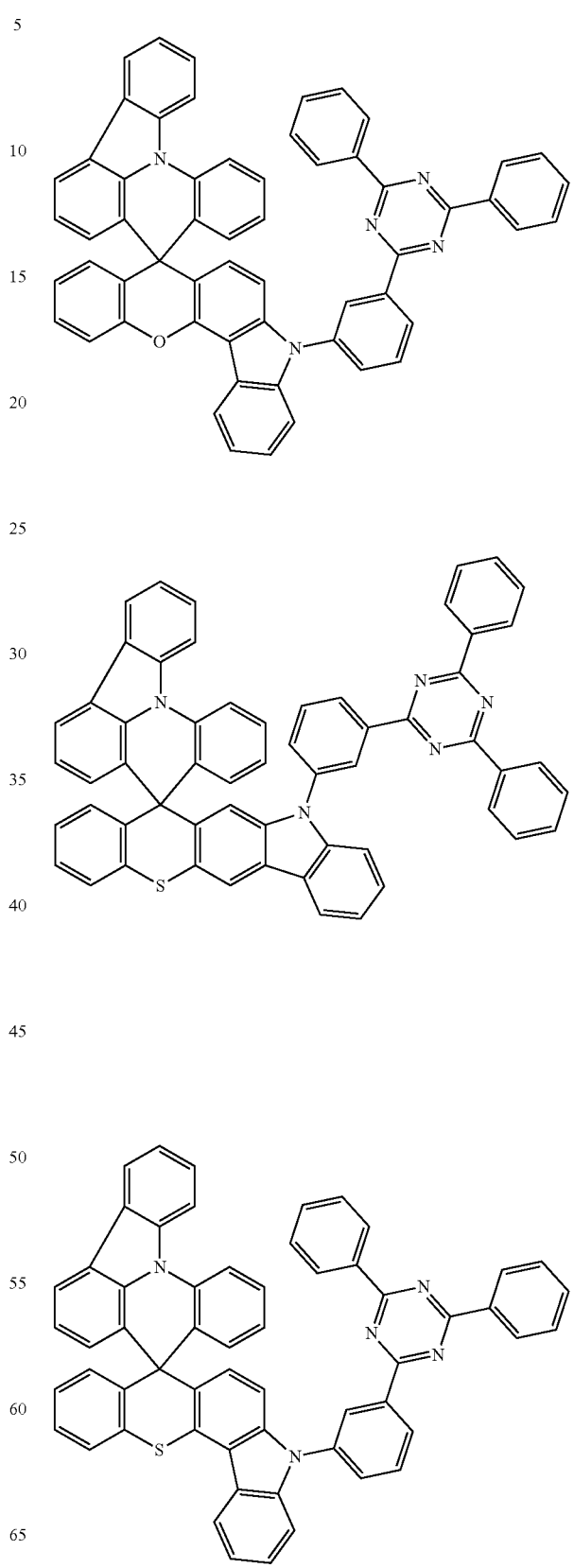

377
-continued
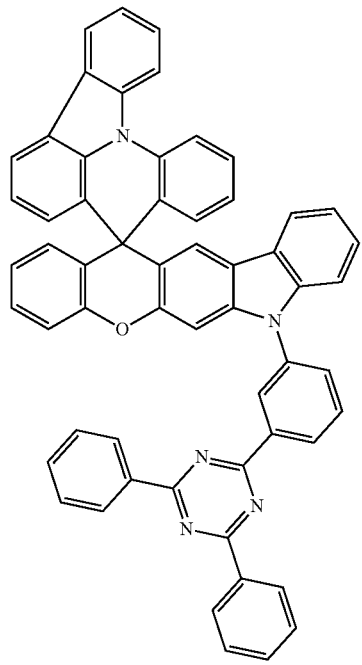
378
-continued
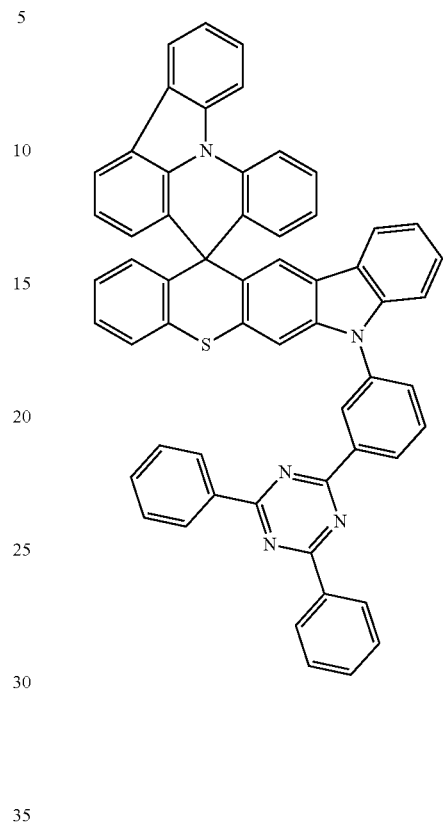
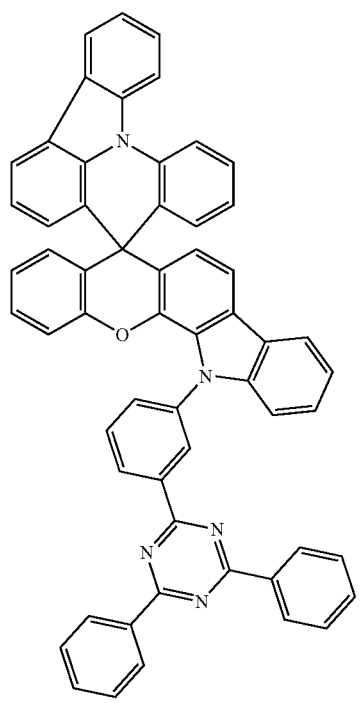
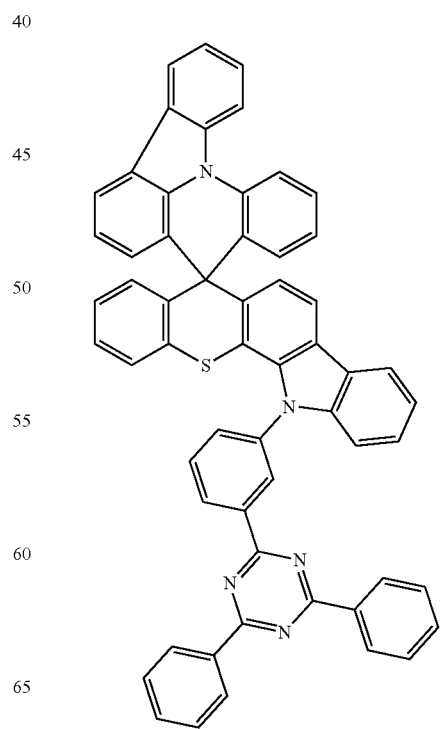

379
-continued
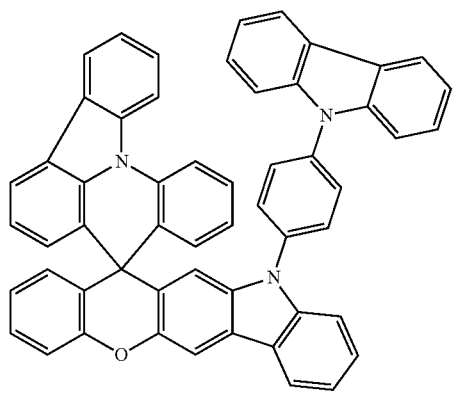
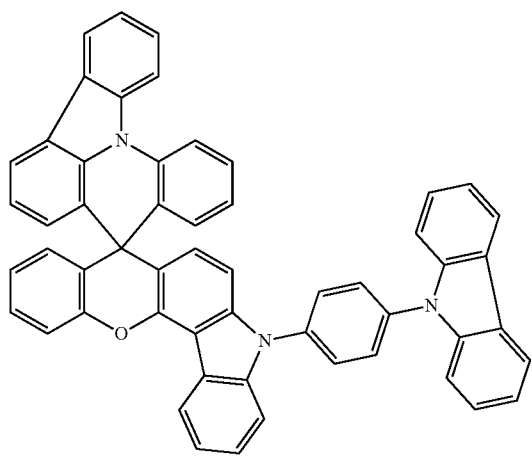
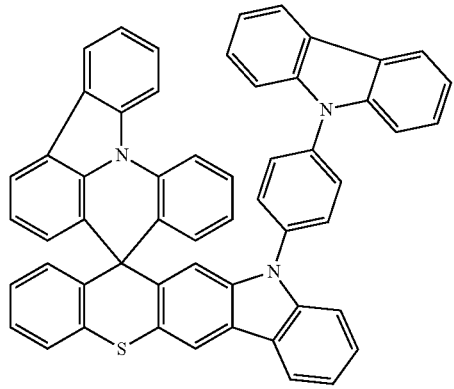
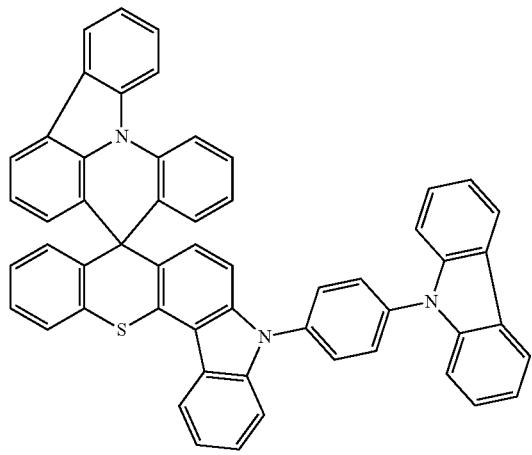
380
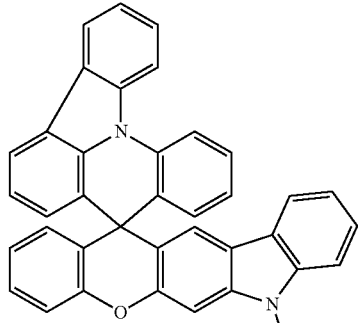
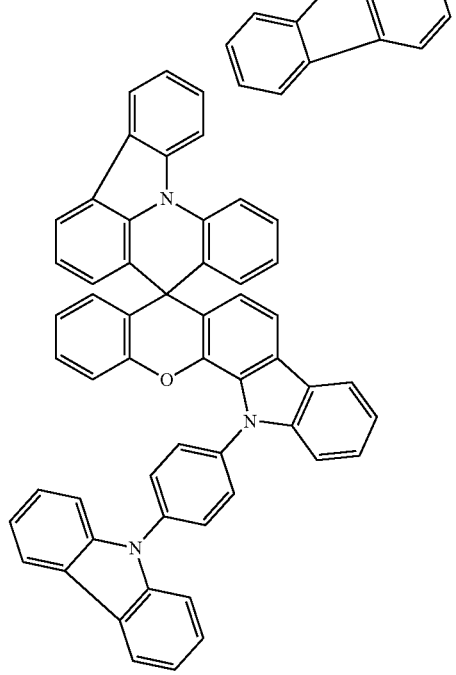
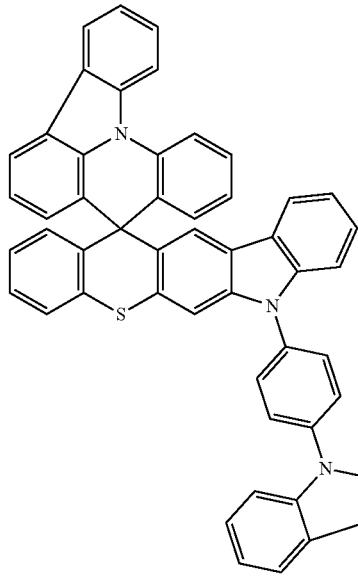

381
-continued
382
-continued
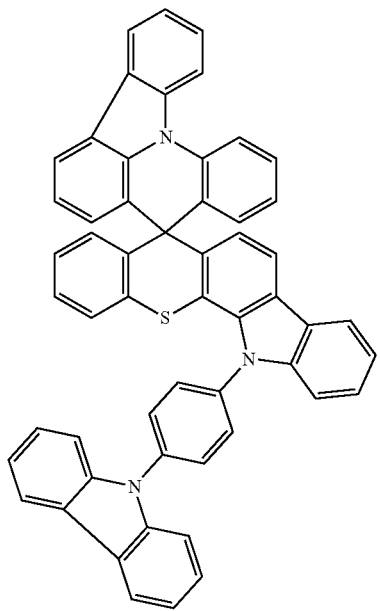
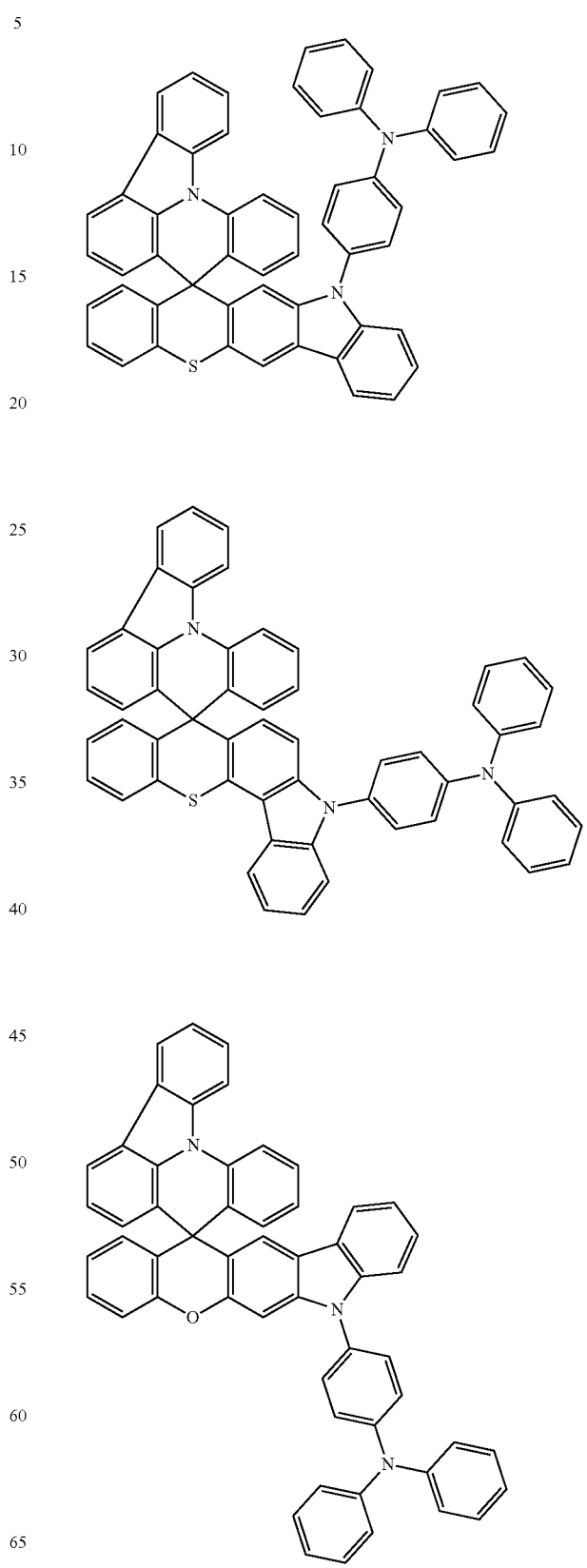

383
-continued
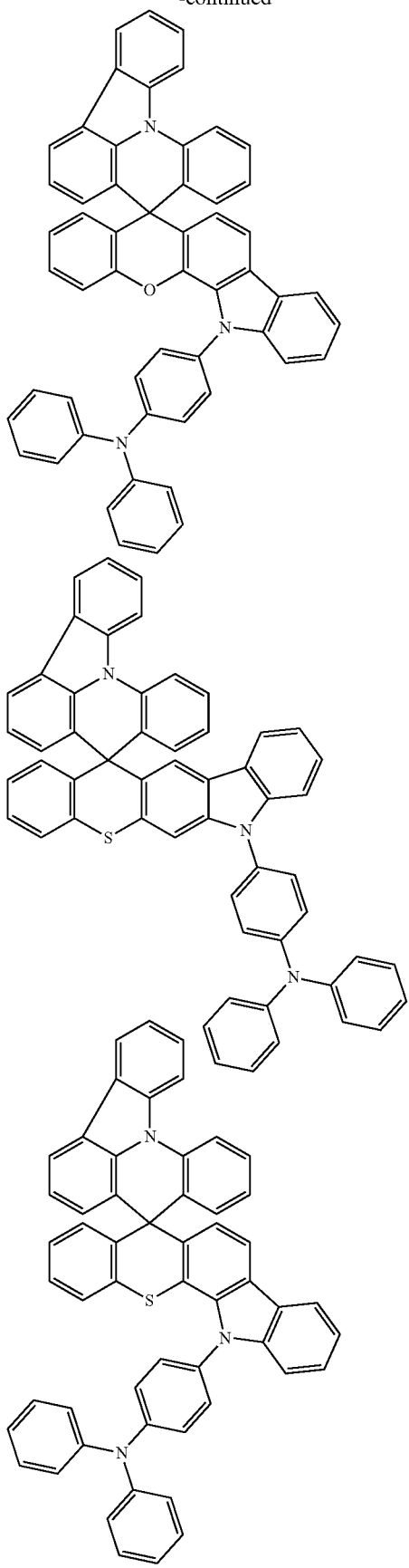
384
-continued
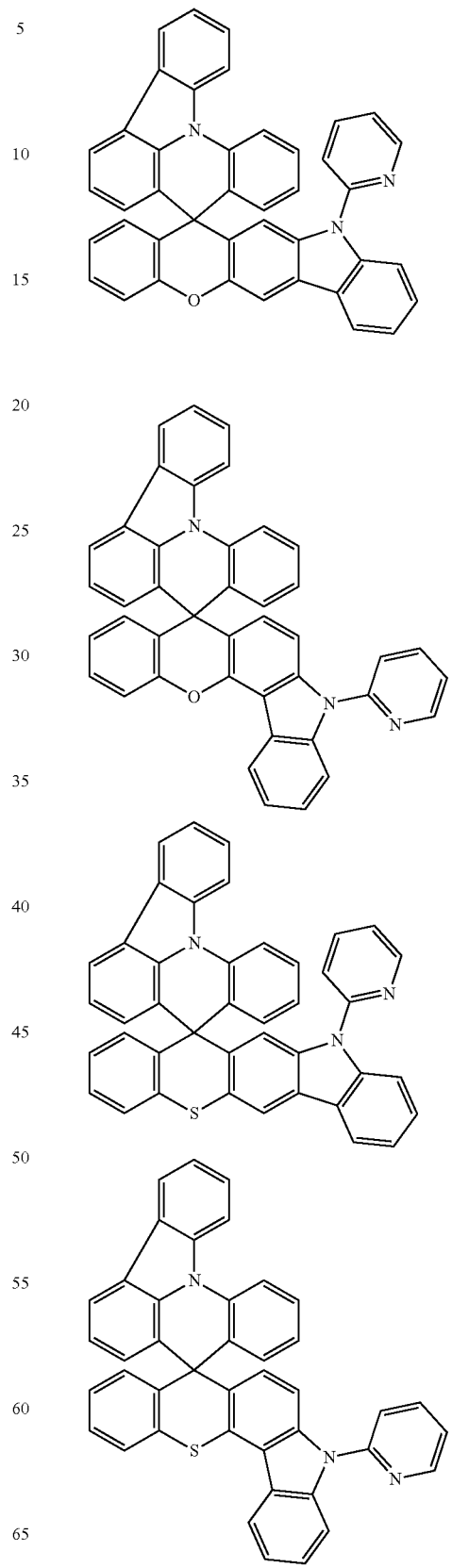

385
-continued
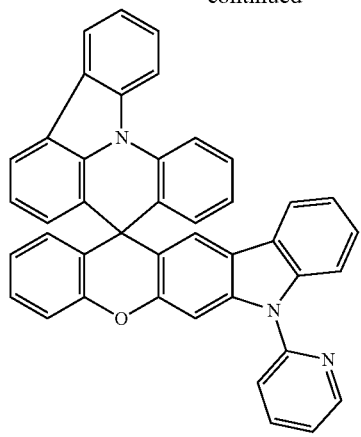
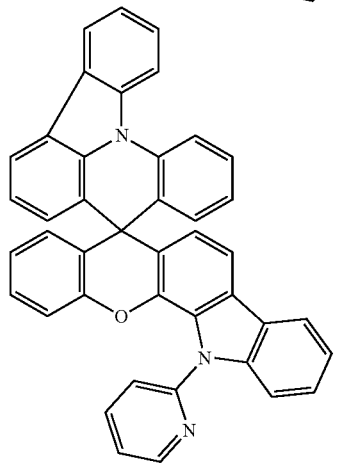
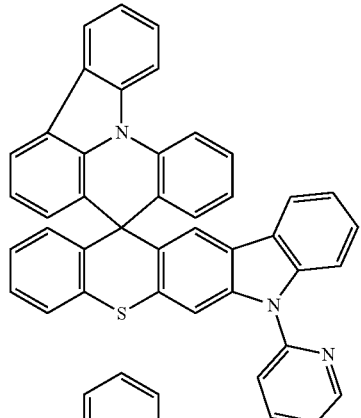
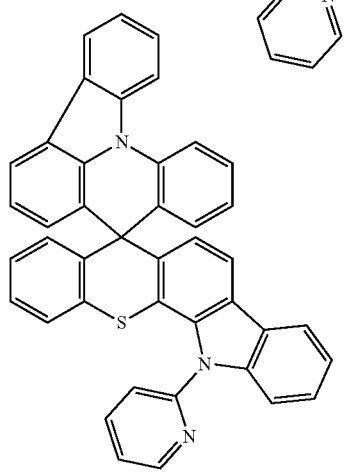
386
-continued
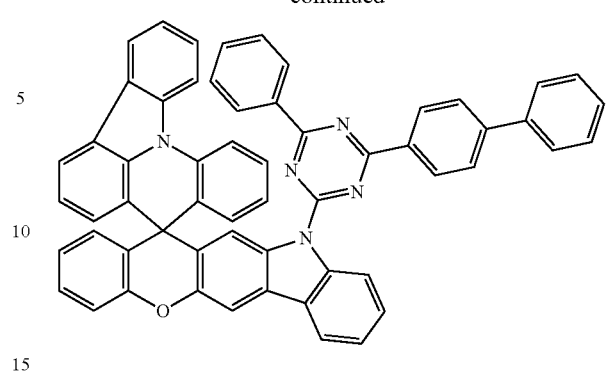
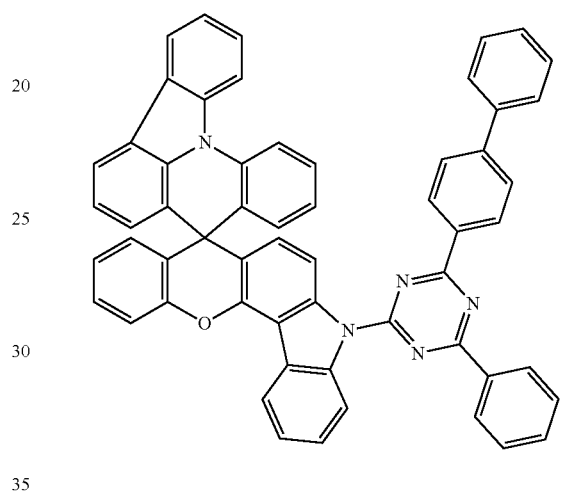
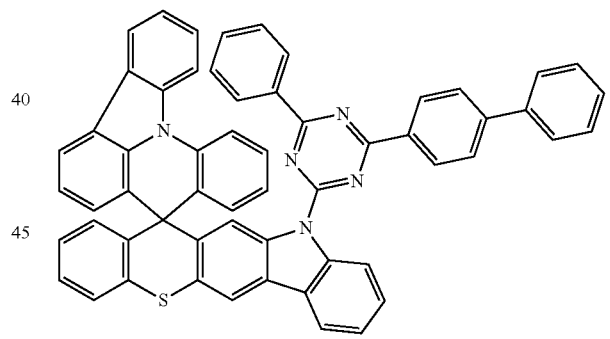
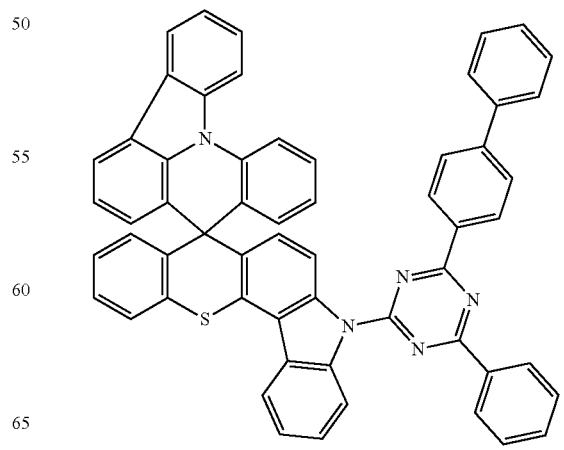

387
-continued
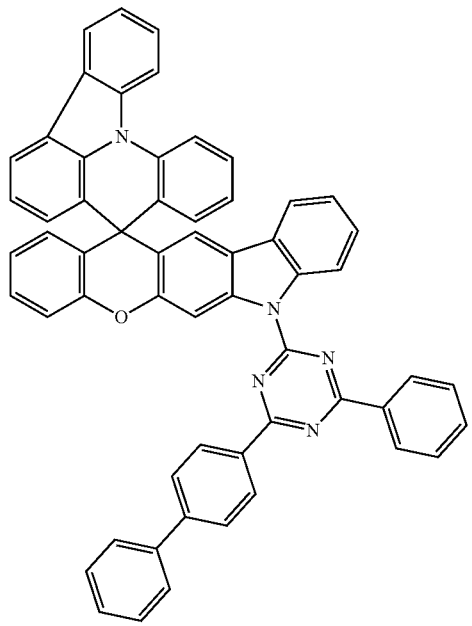
388
-continued
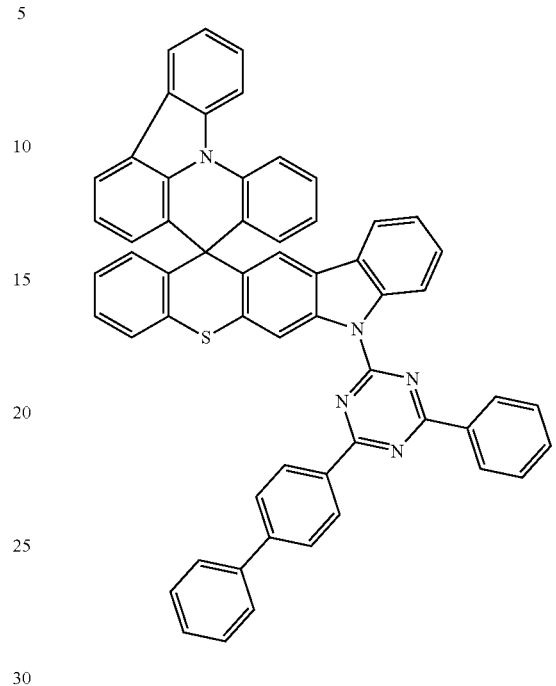
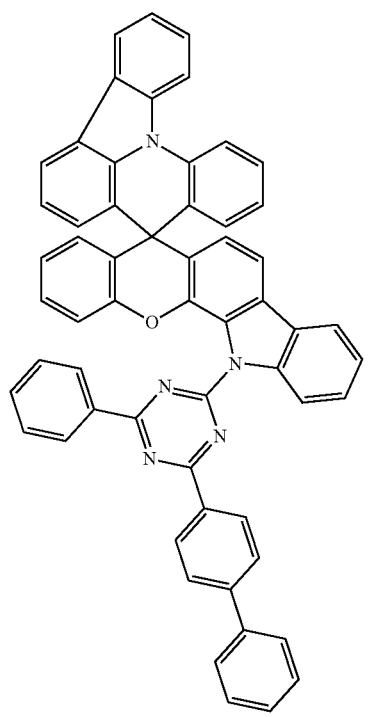

389
-continued
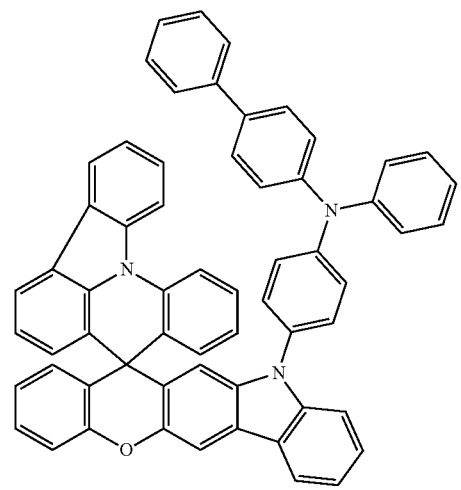
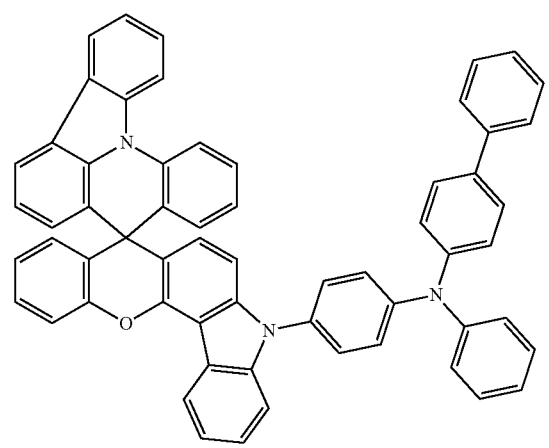
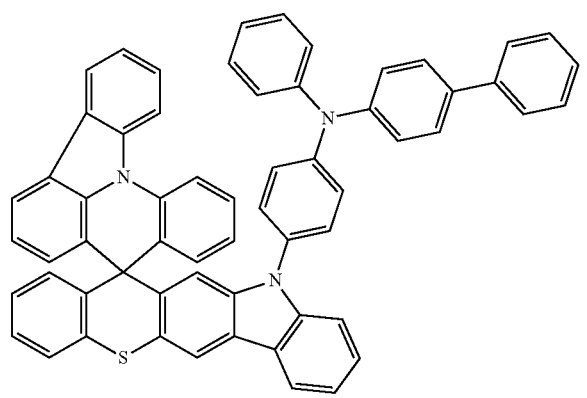
390
-continued
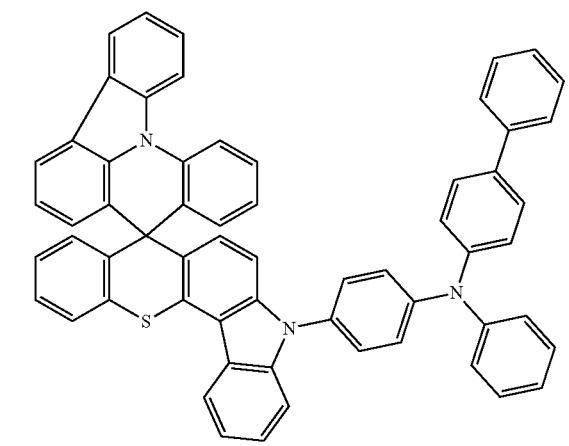
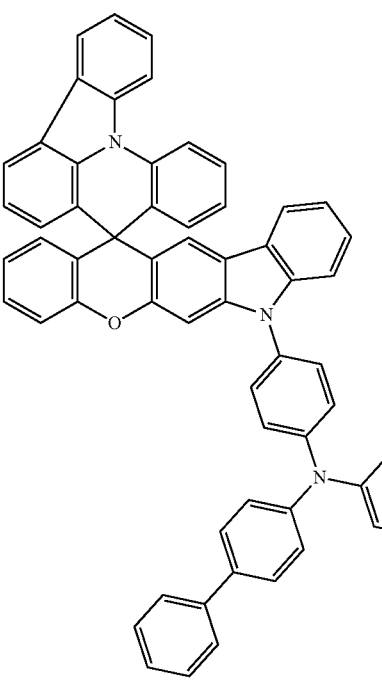

391
-continued
392
-continued
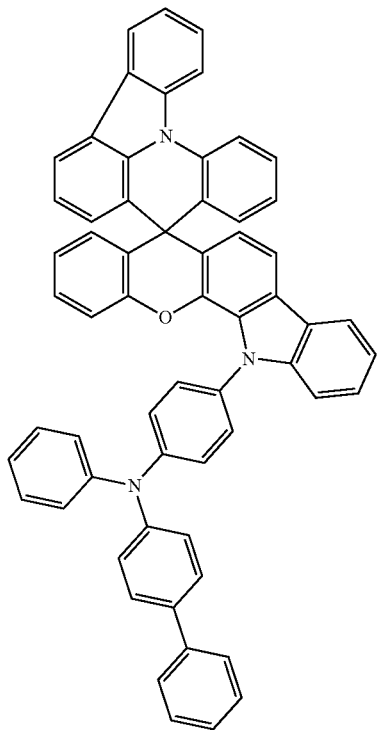
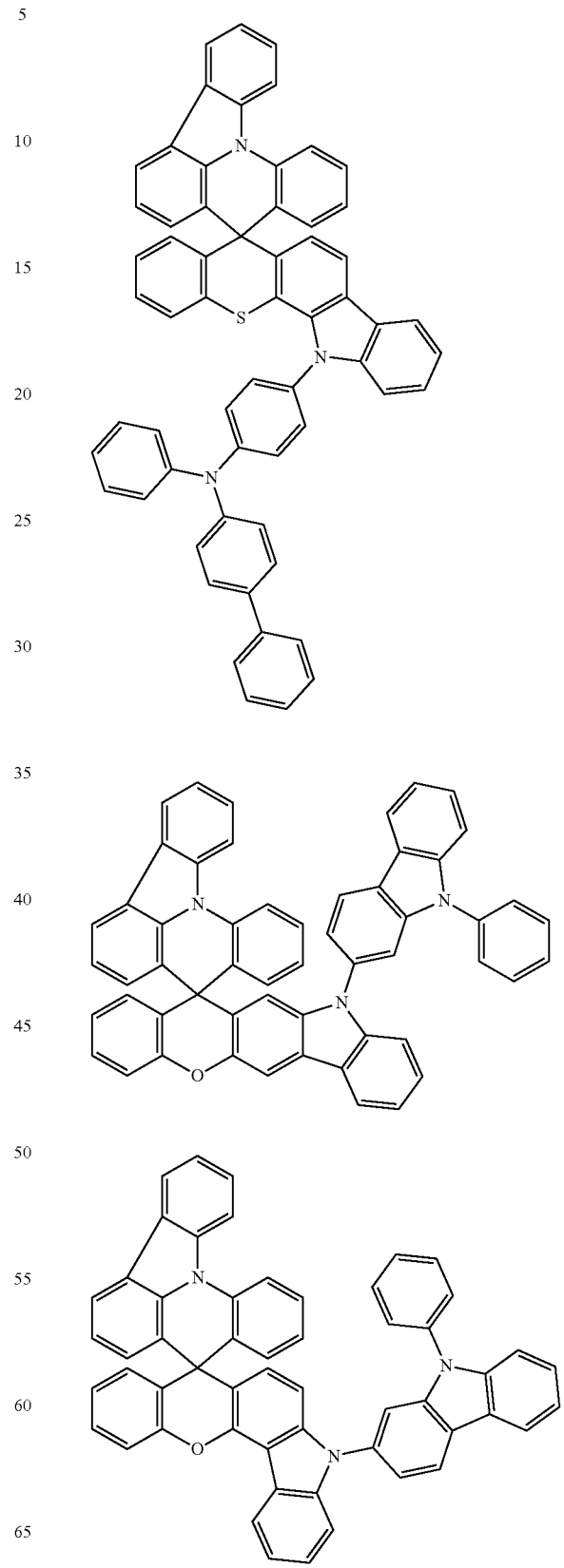

393
-continued
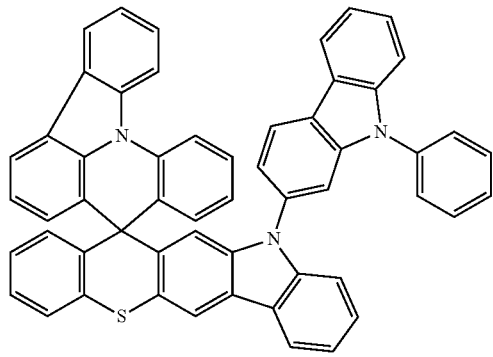
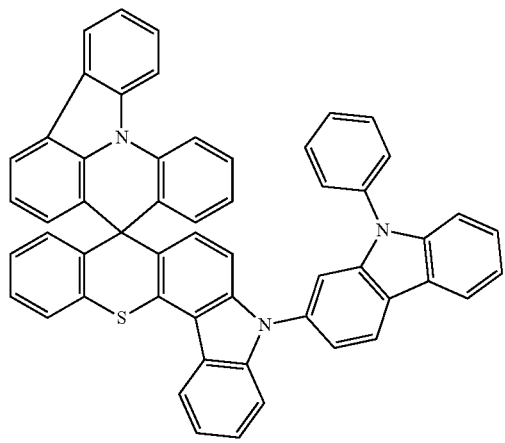
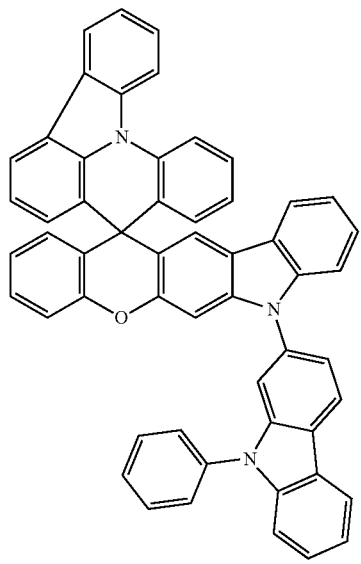
394
-continued
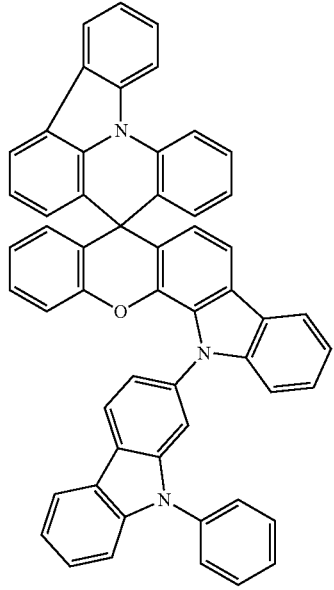
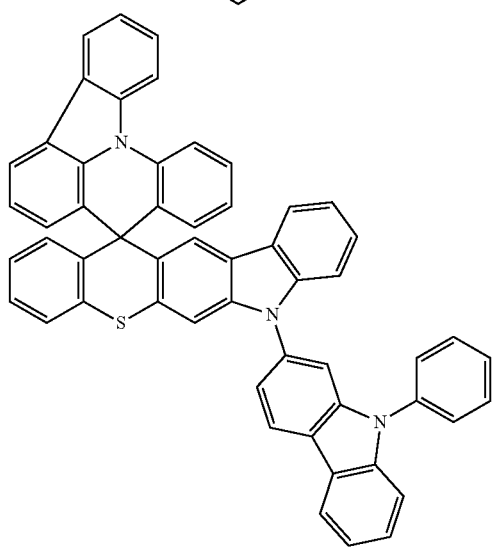
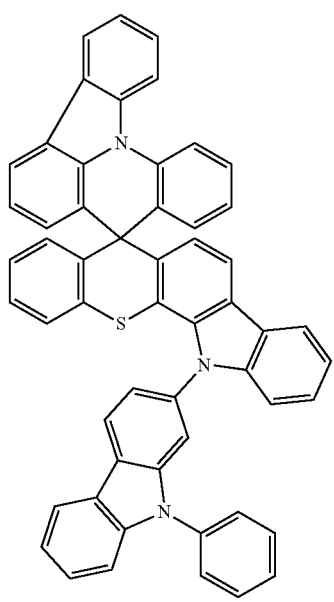

395
-continued
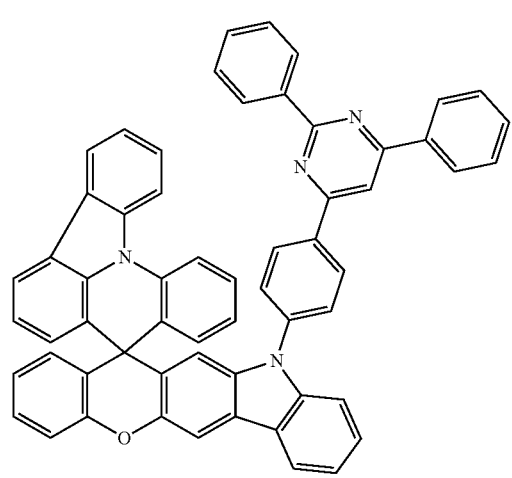
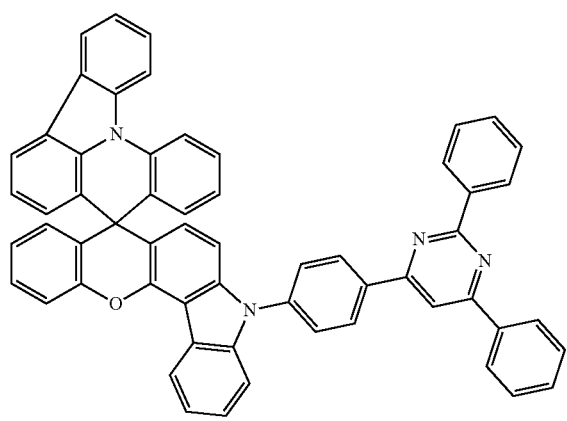
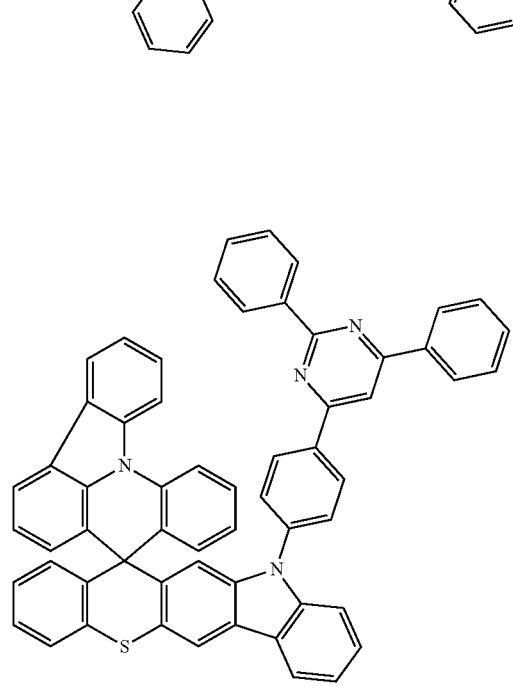
396
-continued
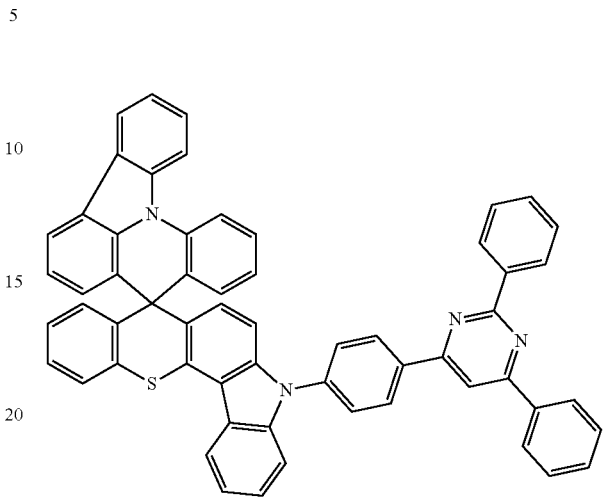
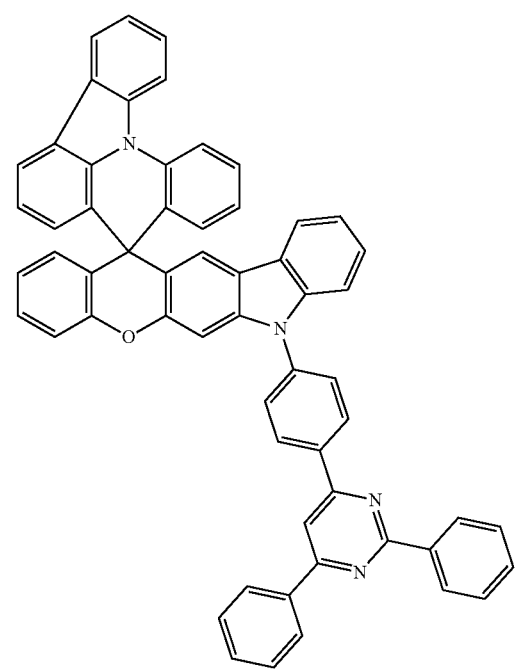

397
-continued
398
-continued
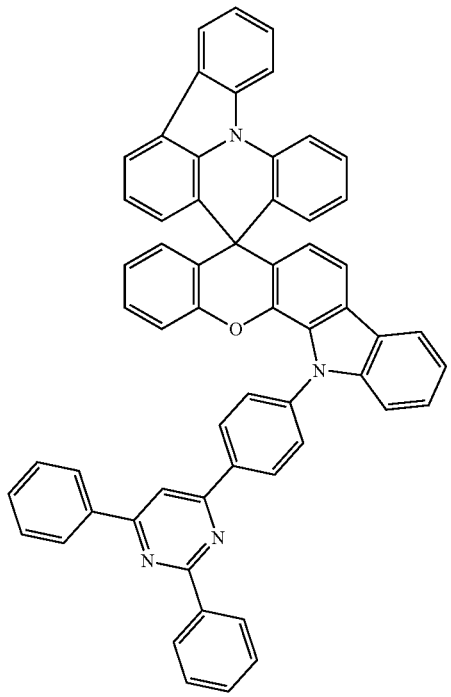
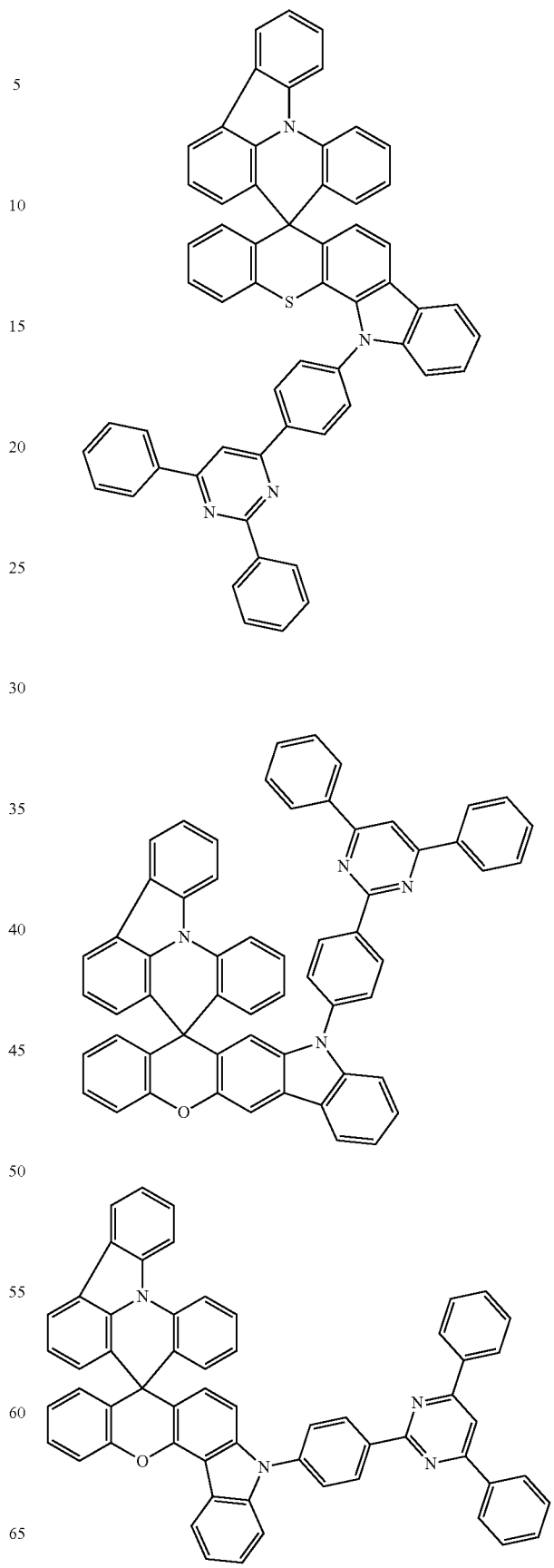

399
-continued
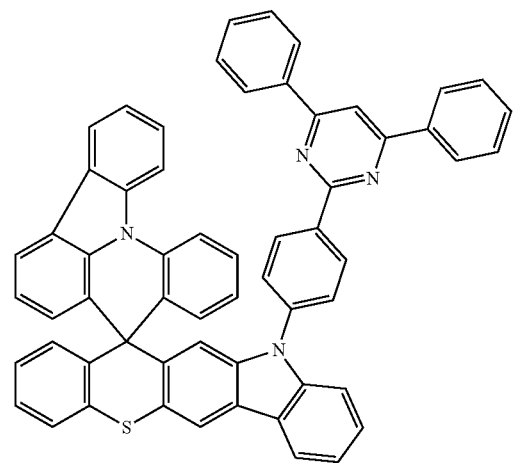
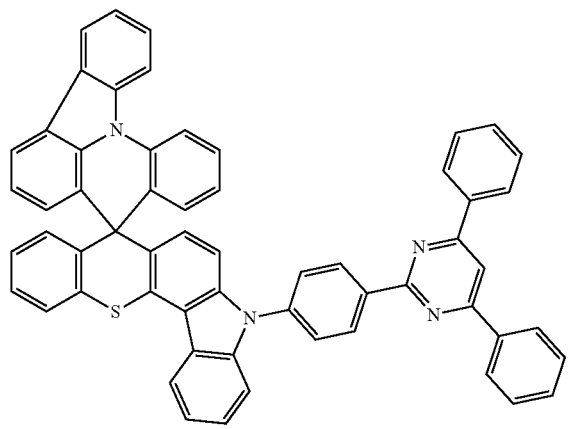
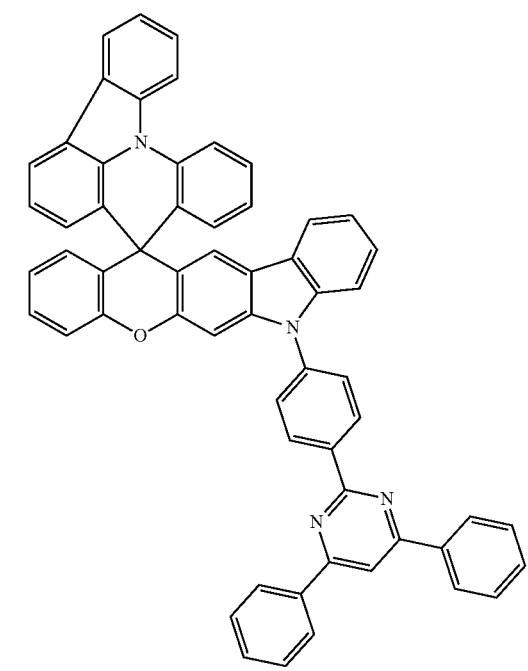
400
-continued
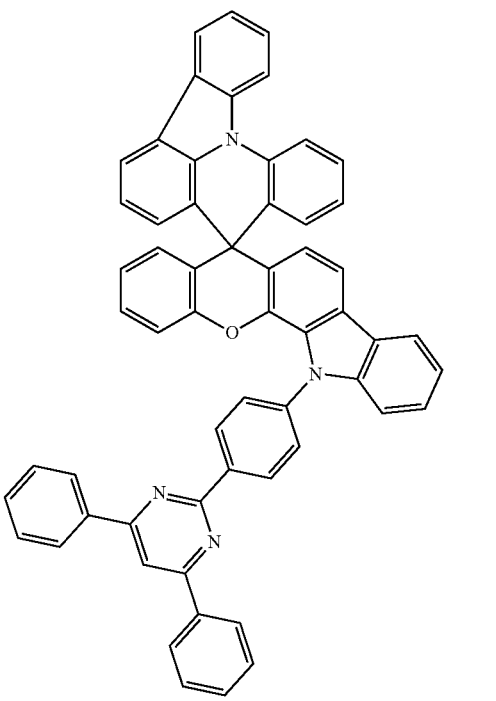
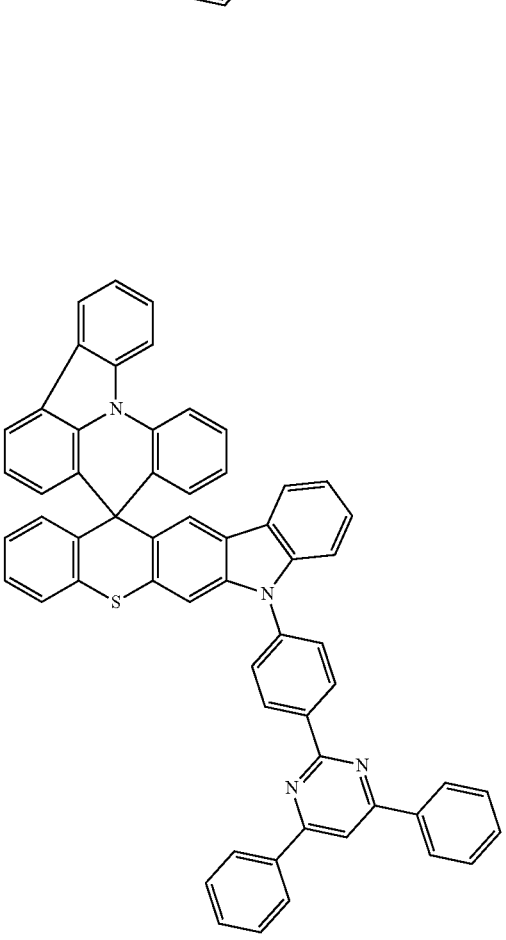

401
-continued
402
-continued
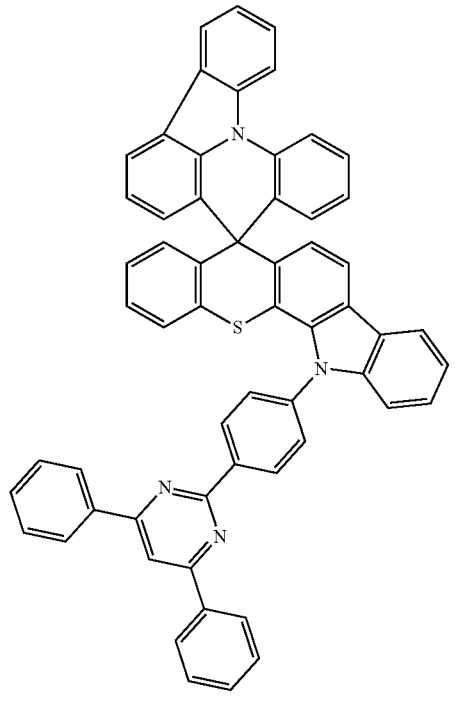
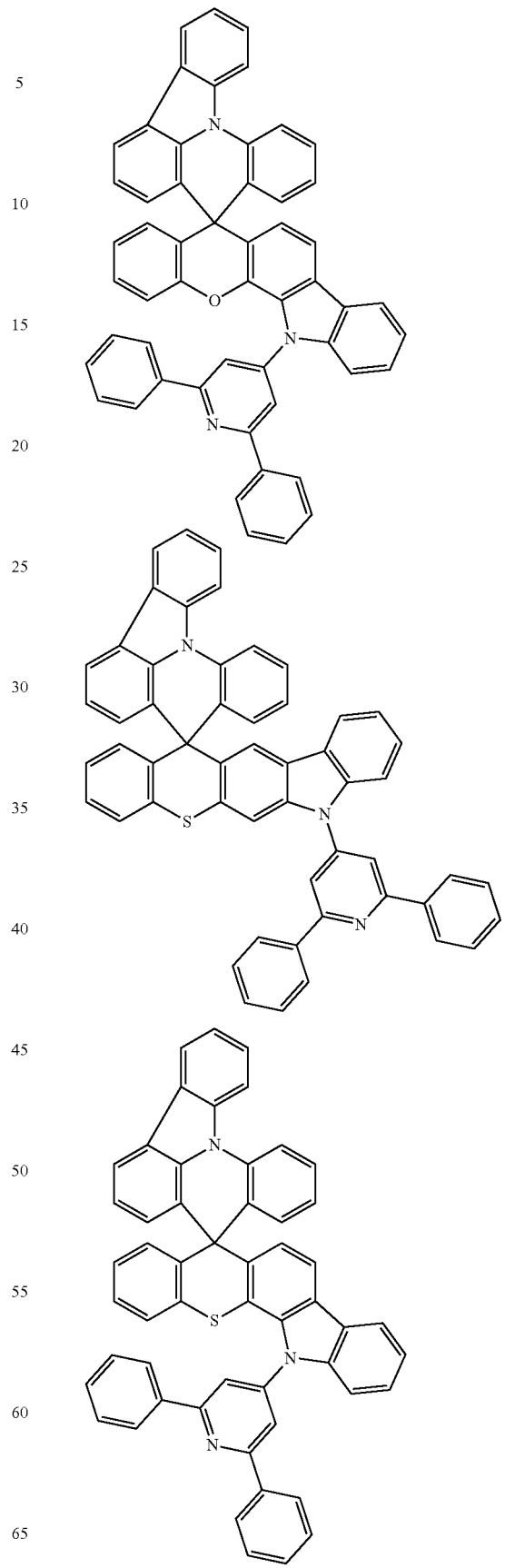

403
-continued
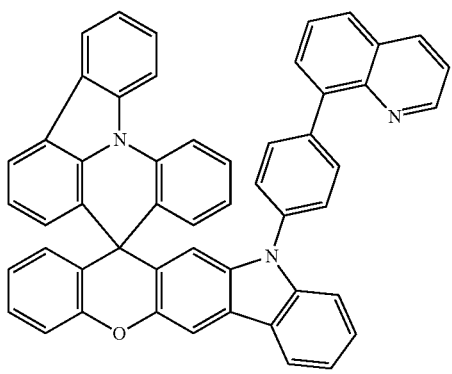
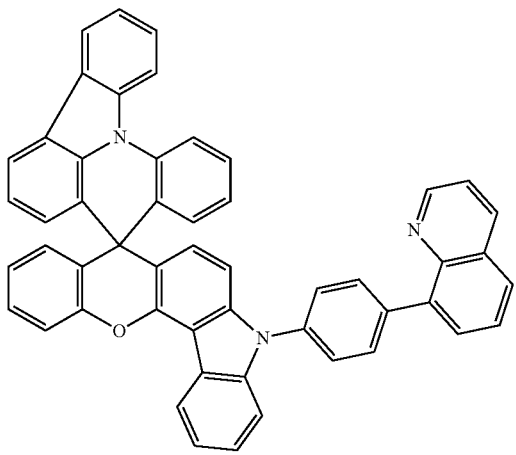
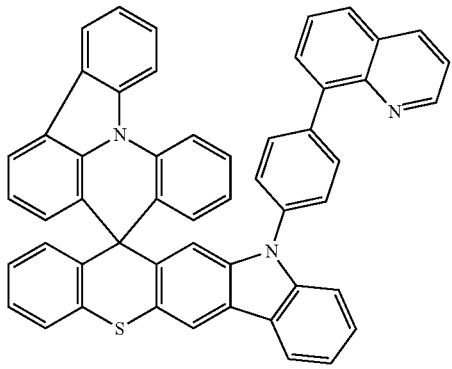
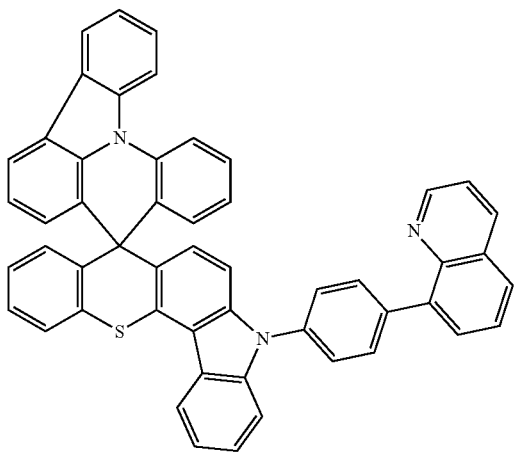
404
-continued
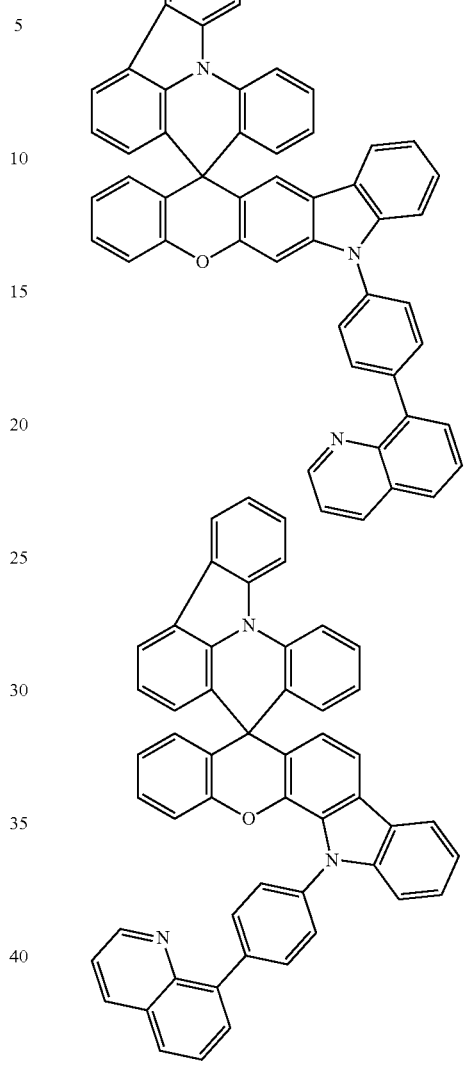
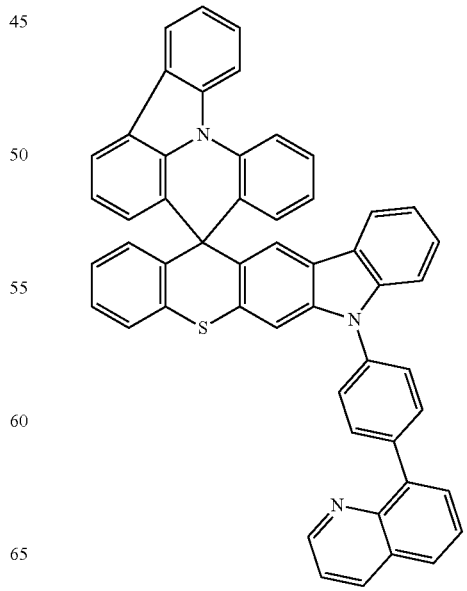

405
-continued
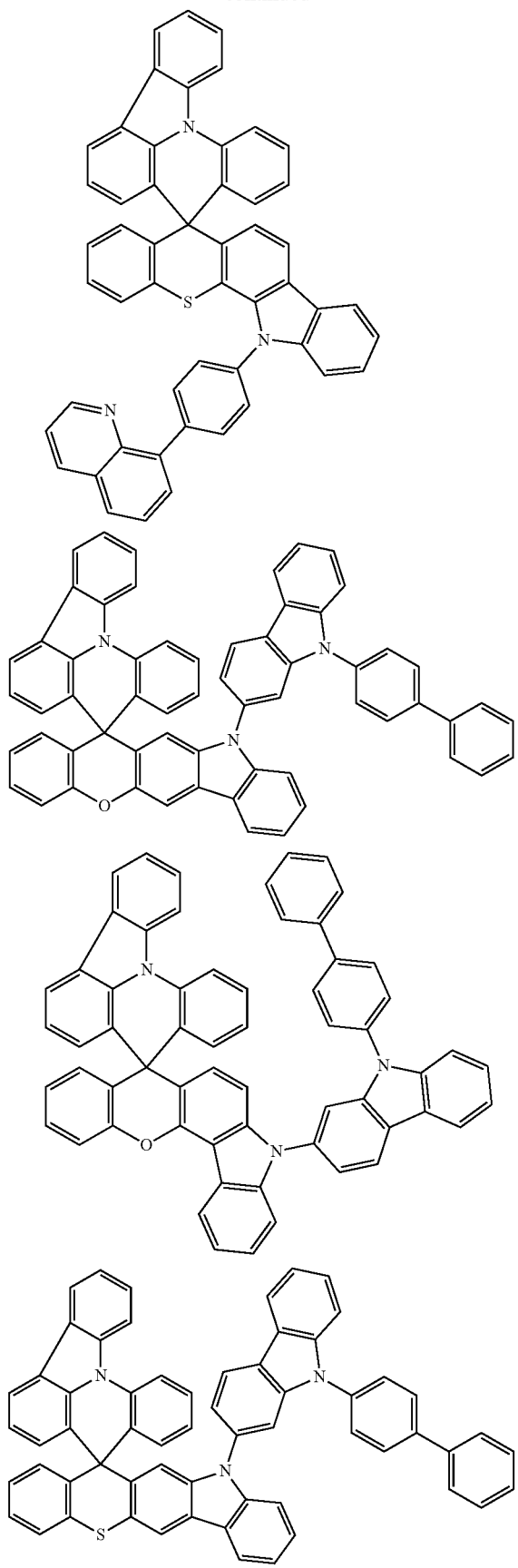
406
-continued
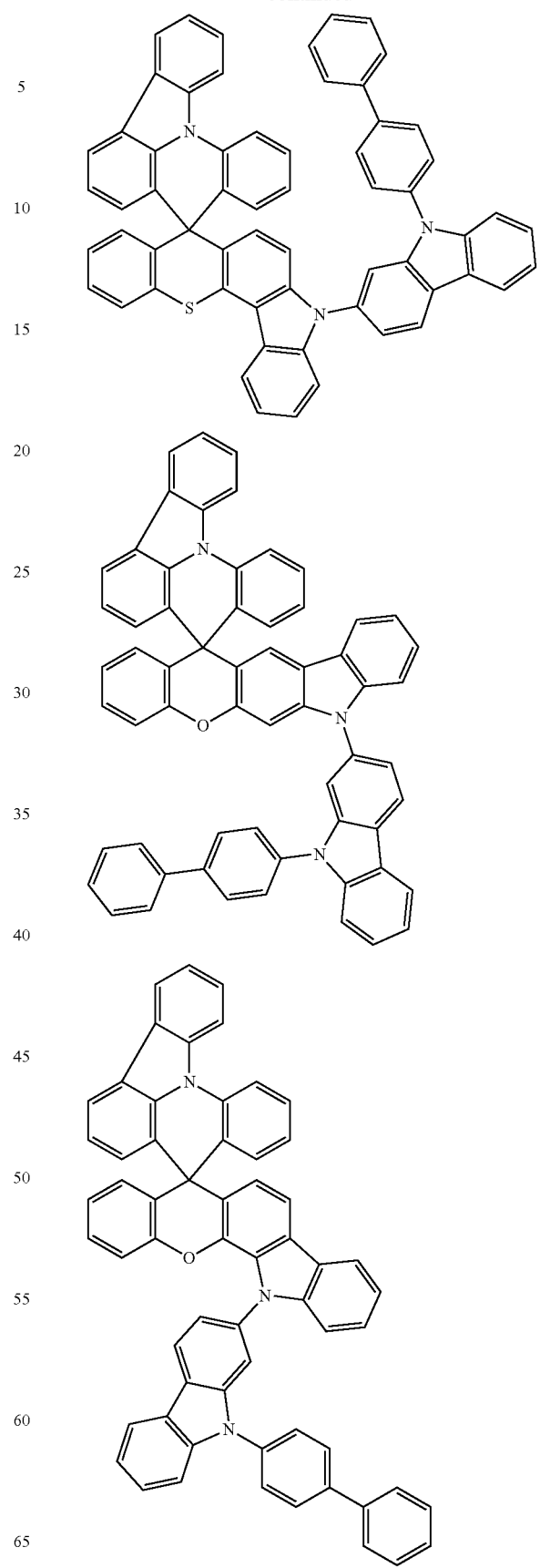

407
-continued
408
-continued
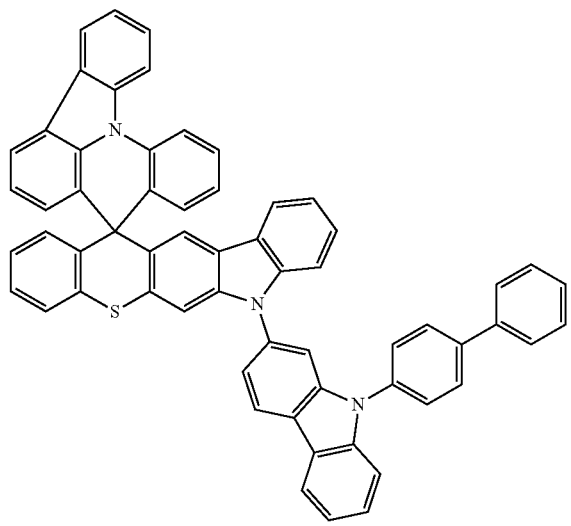
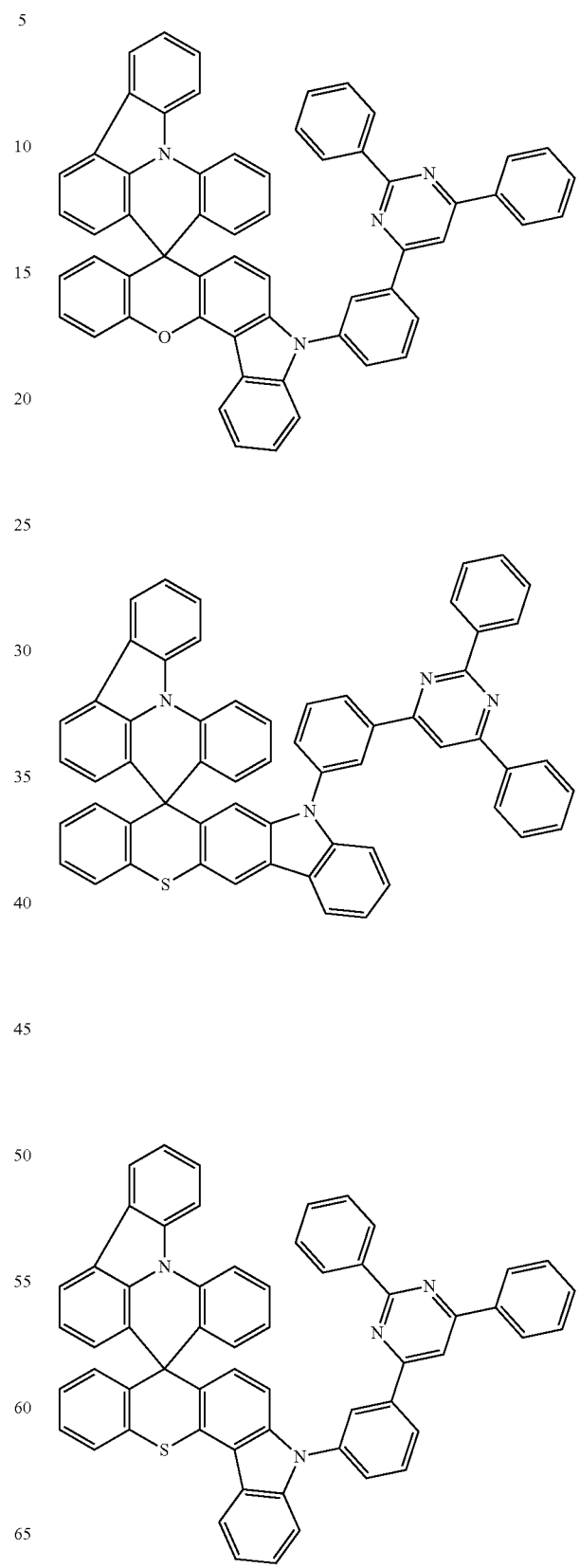

409
-continued
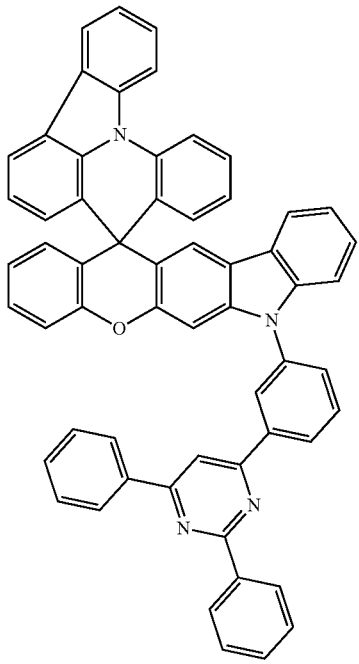
410
-continued
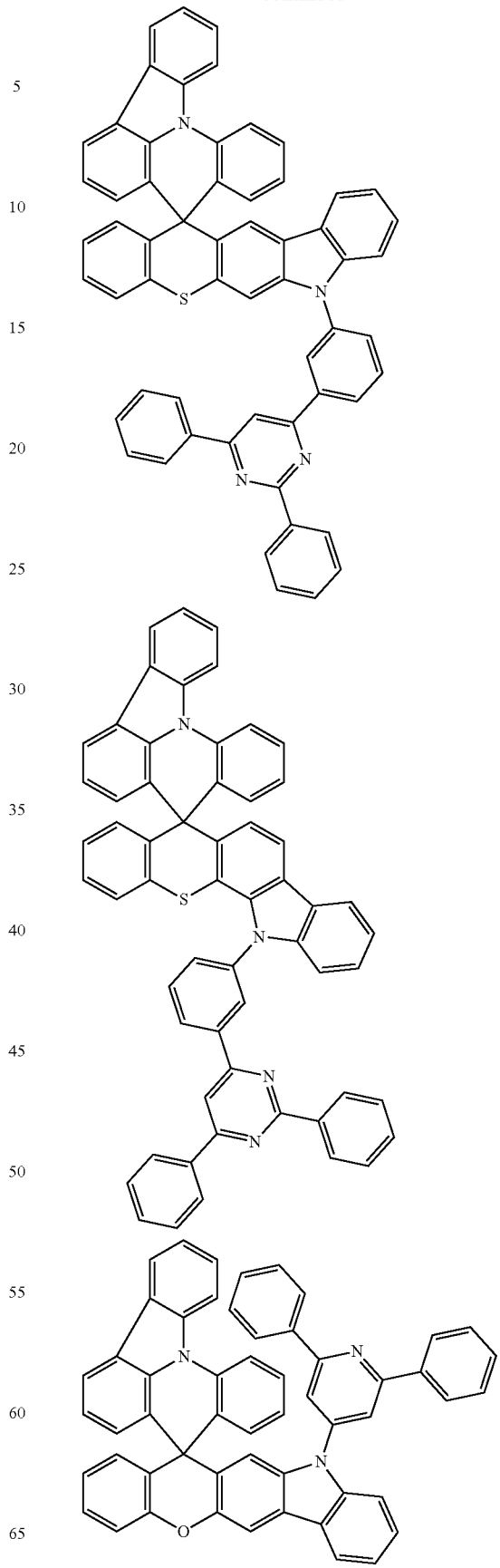

411
-continued
412
-continued
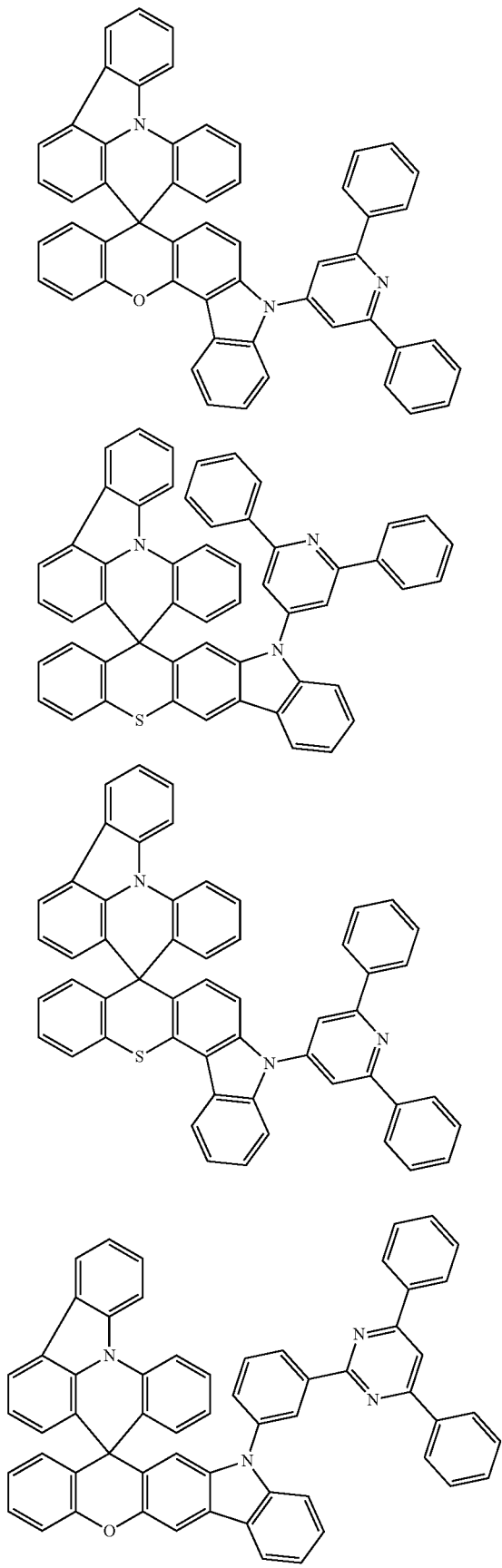
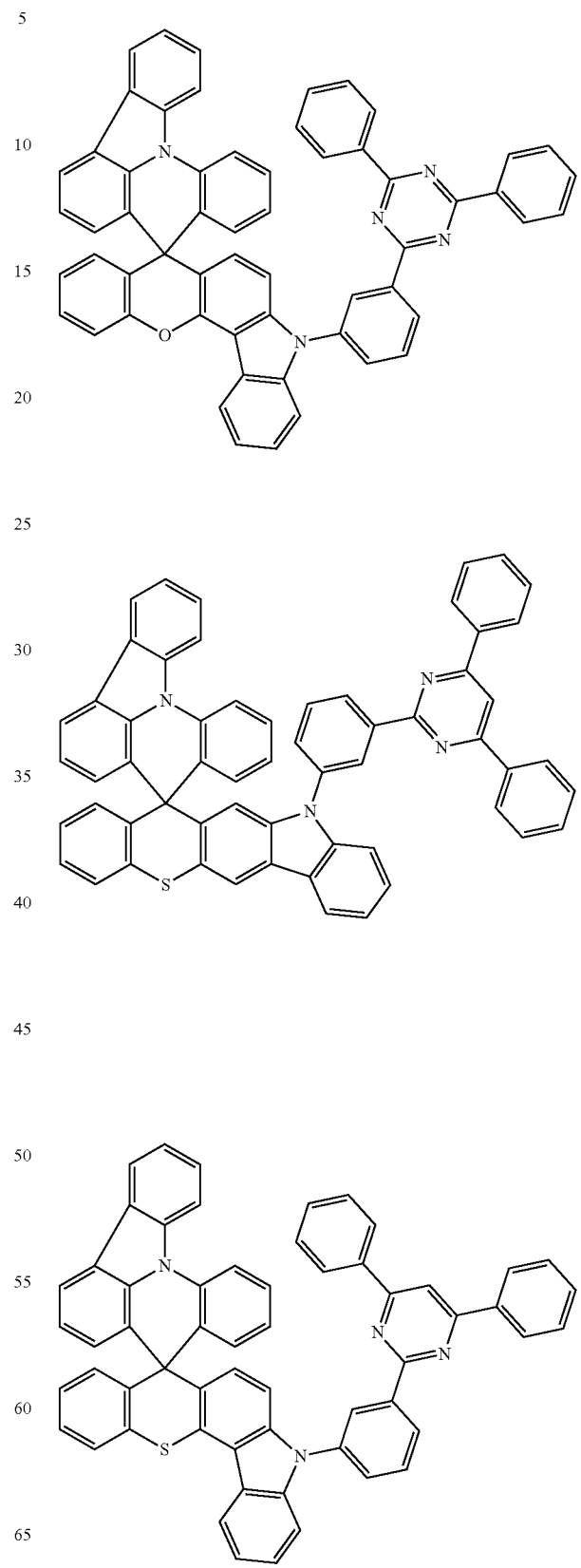

413
-continued
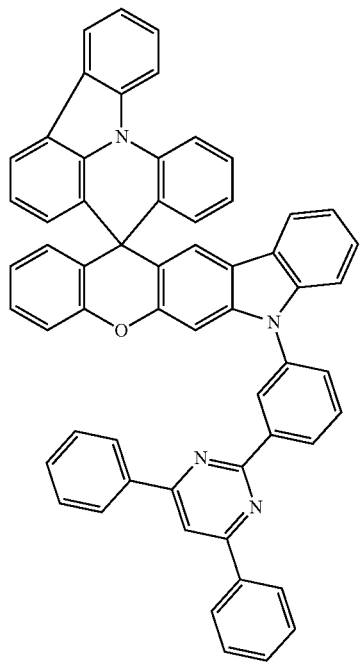
414
-continued
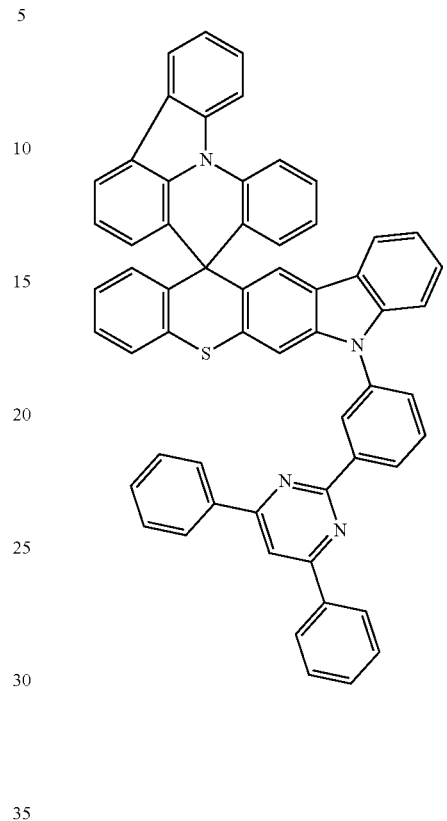
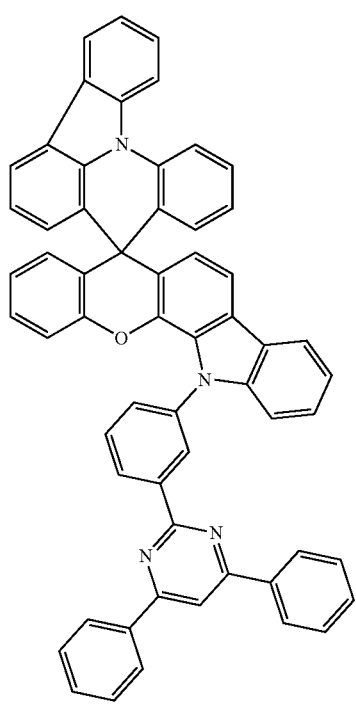
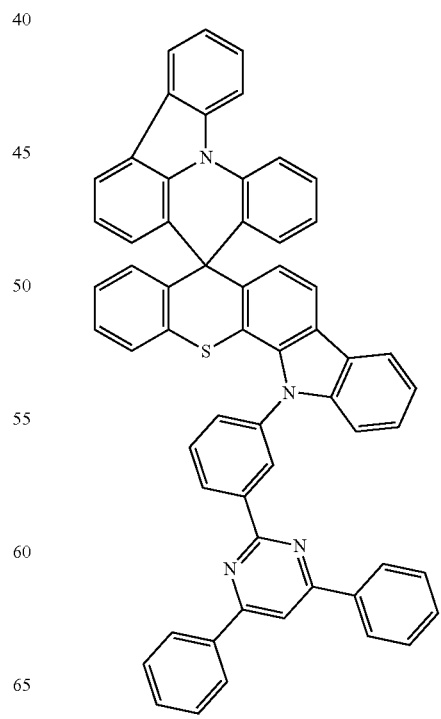

415
-continued
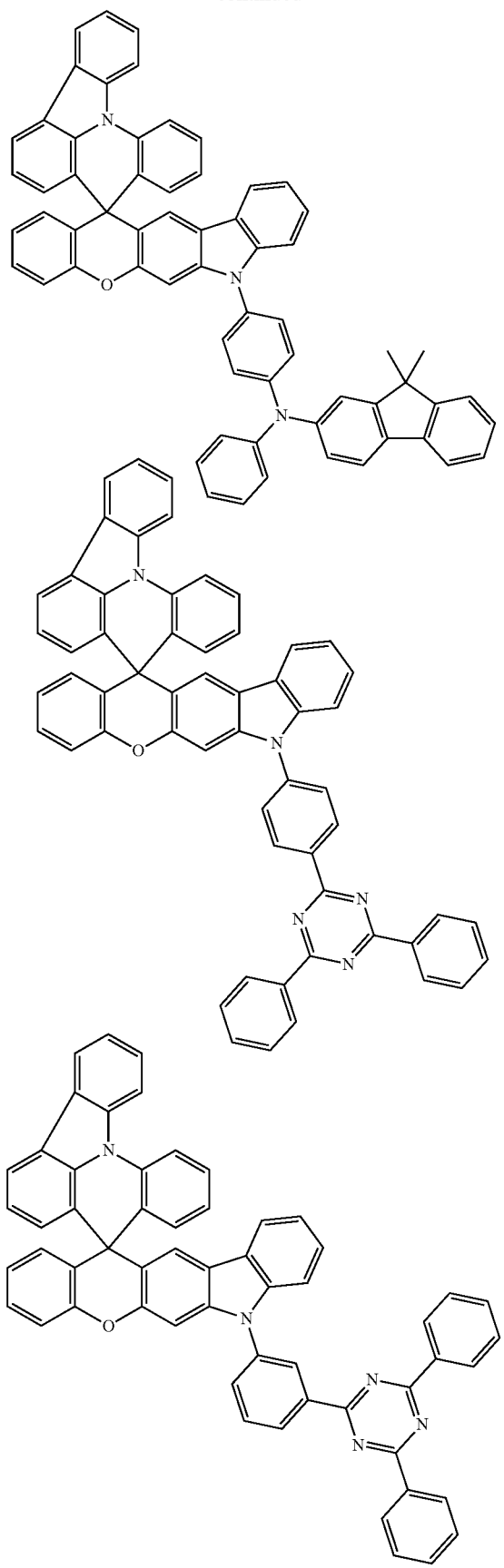
416
-continued
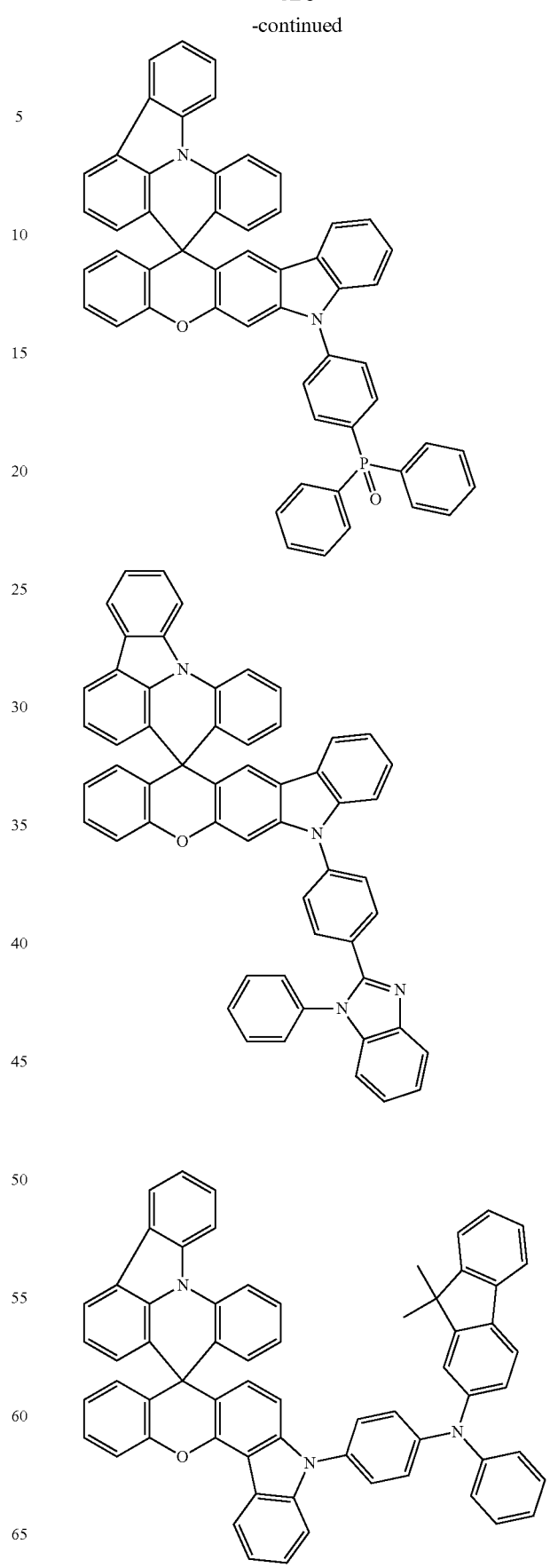

417
-continued
418
-continued
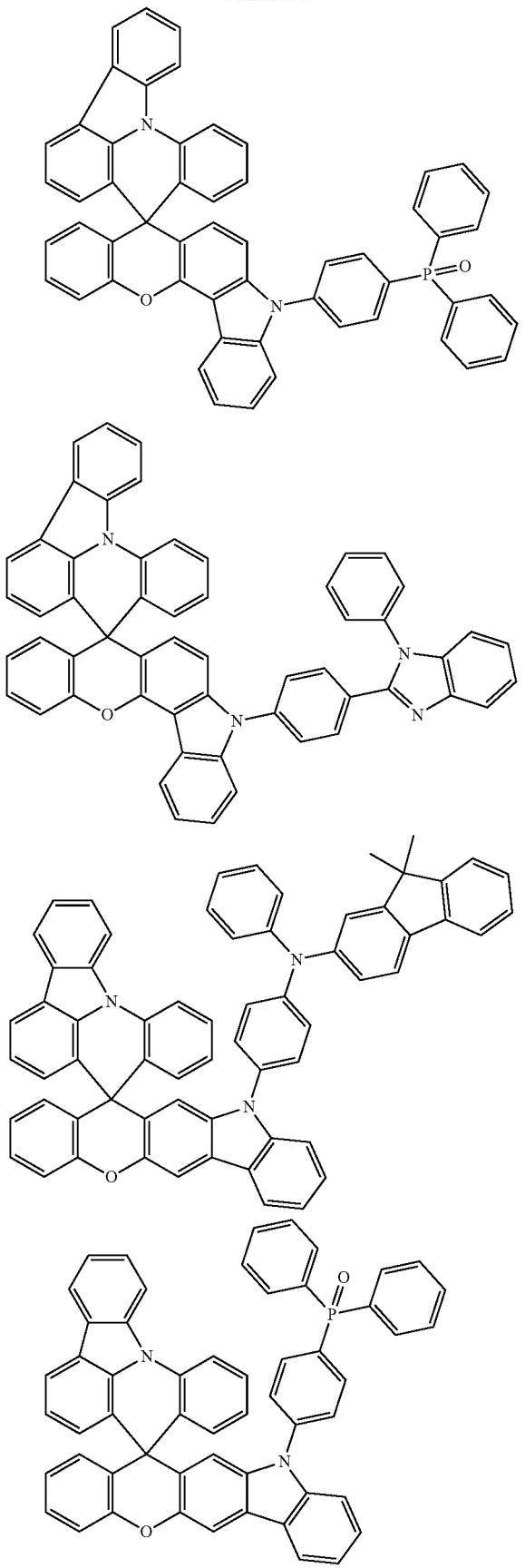
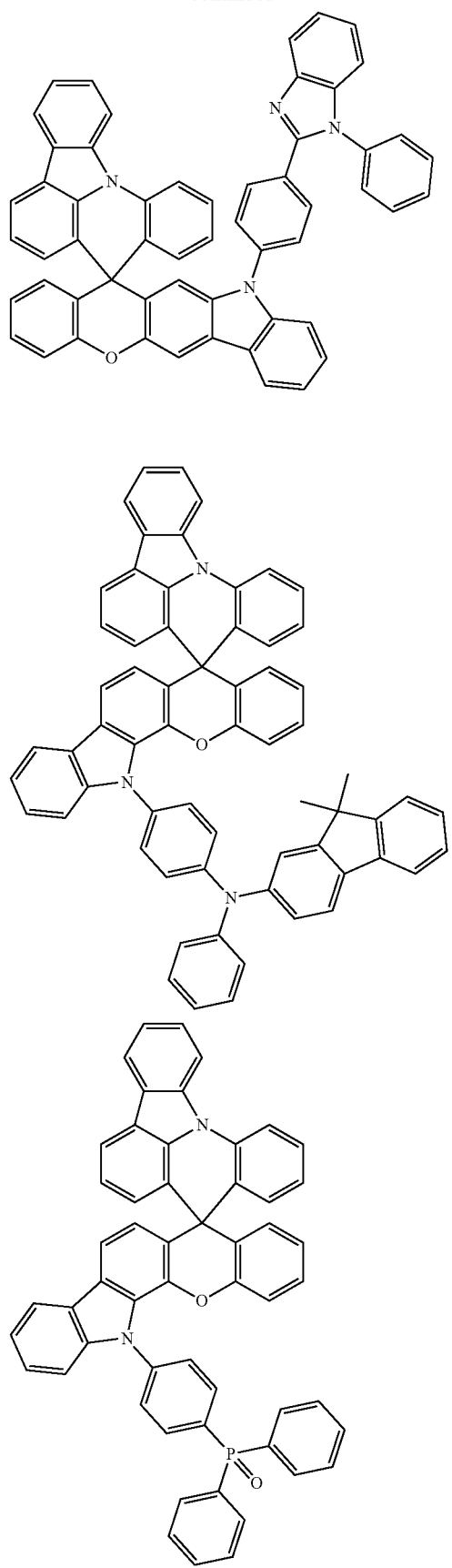

419
-continued
420
-continued
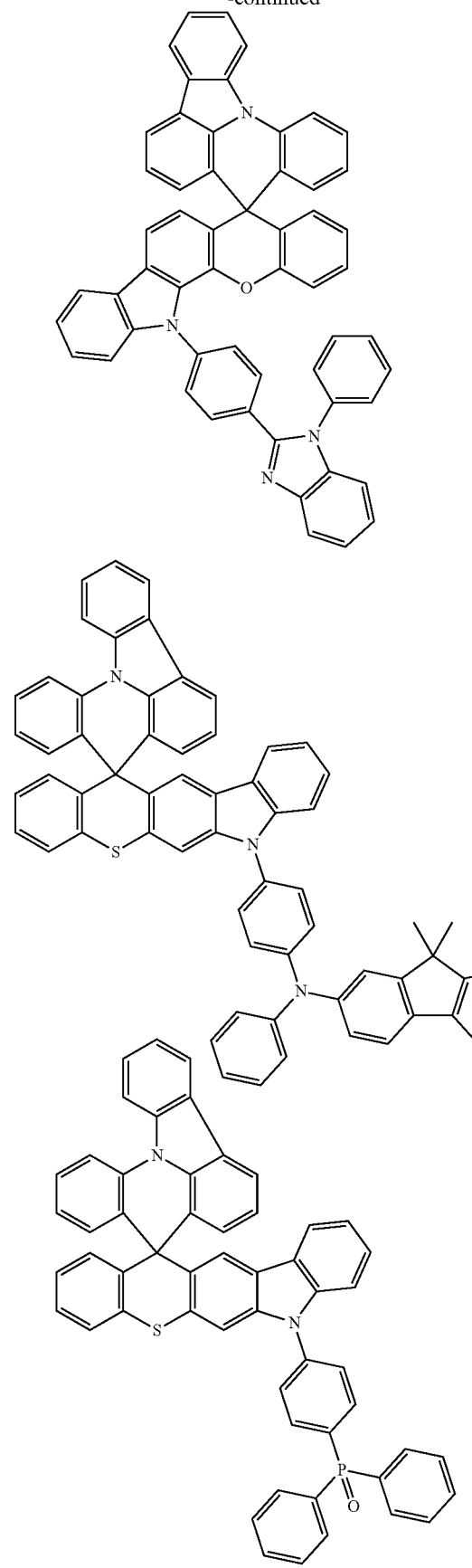
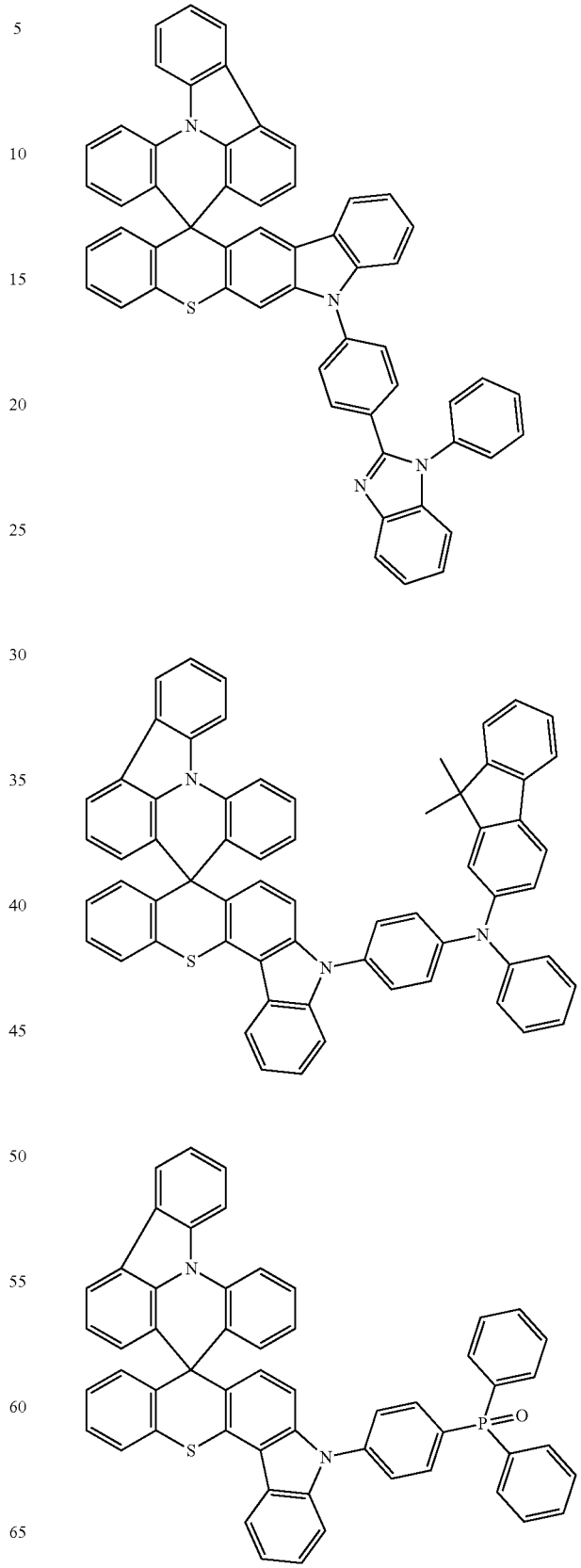

421
-continued
422
-continued
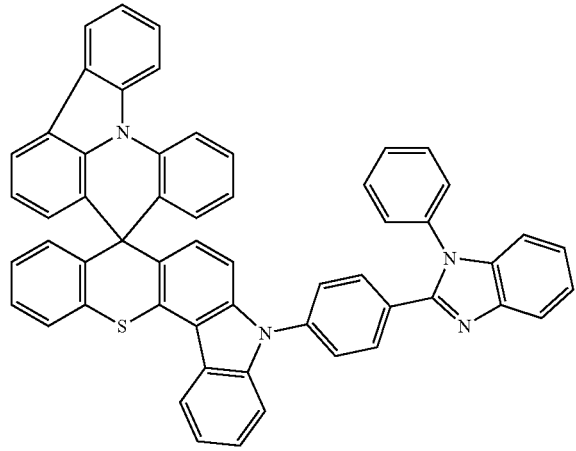
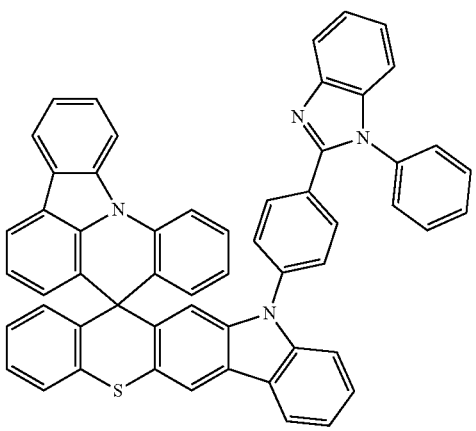
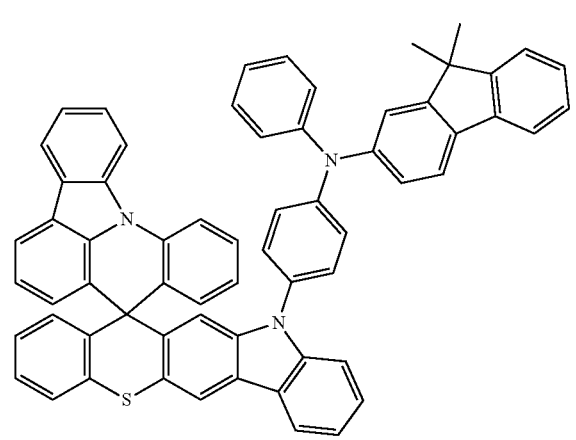
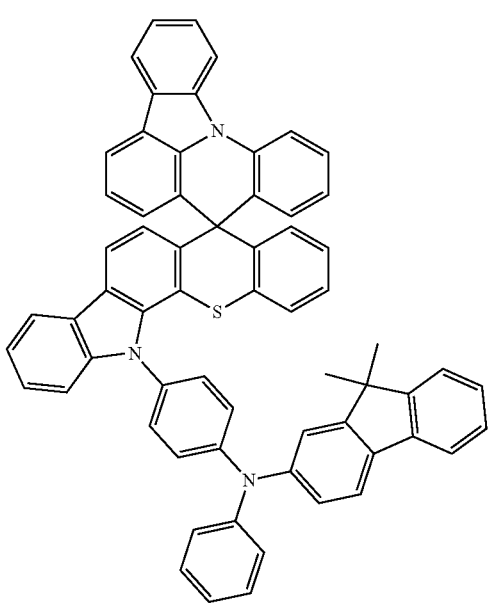
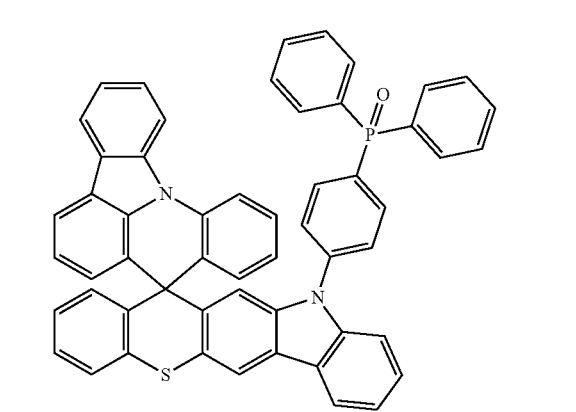
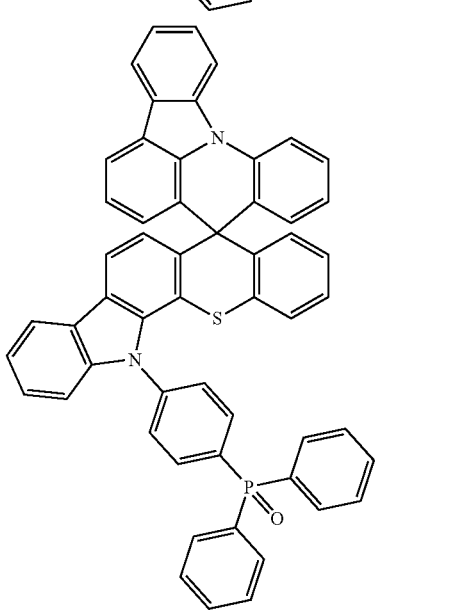

423
-continued
424
-continued
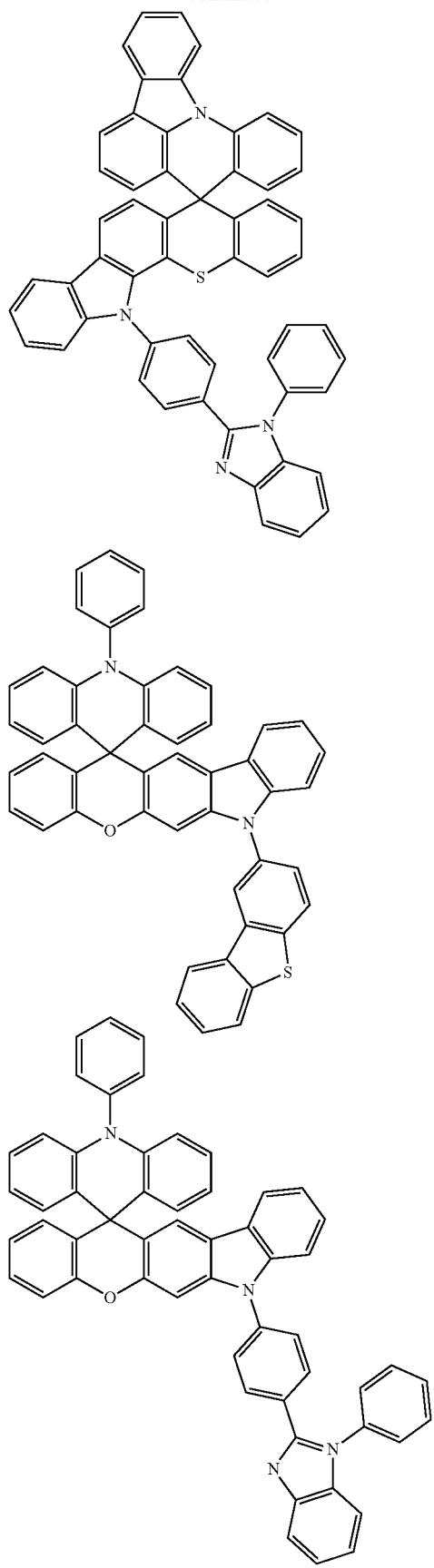
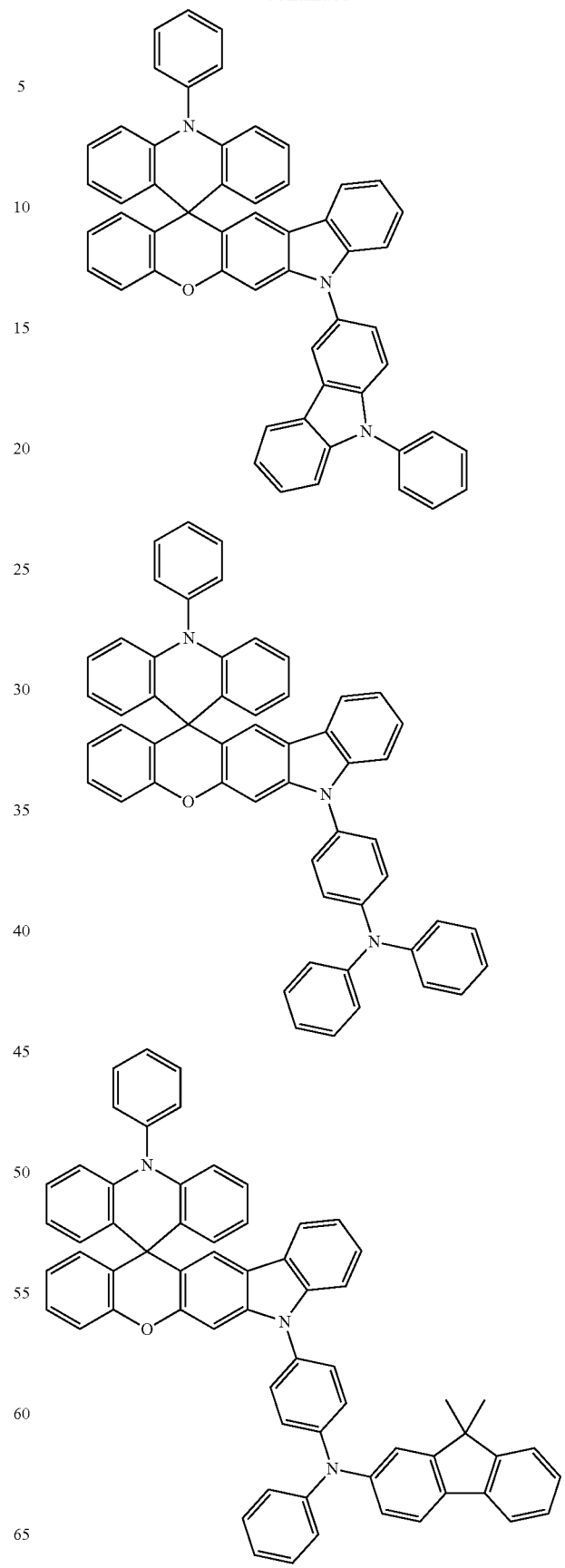

425
-continued
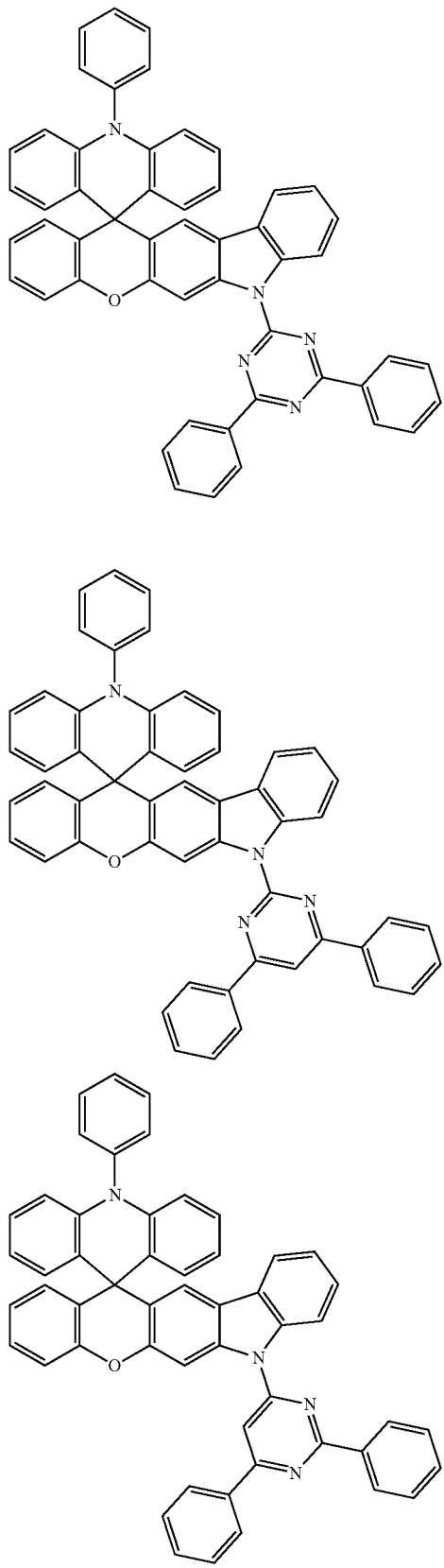
426
-continued
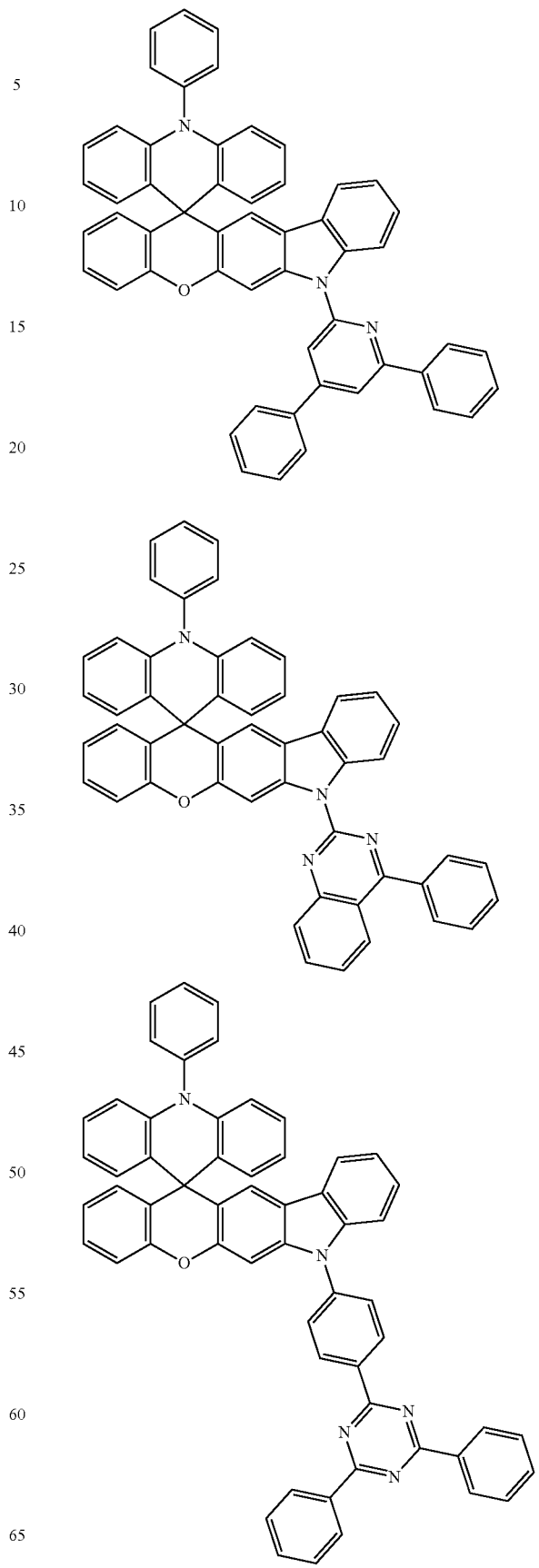

427
-continued
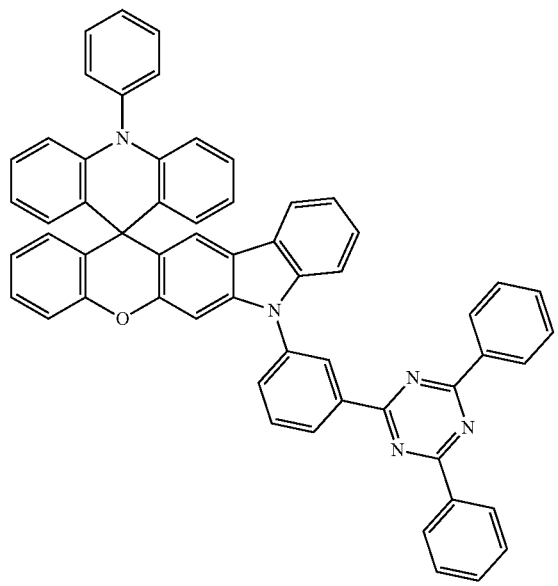
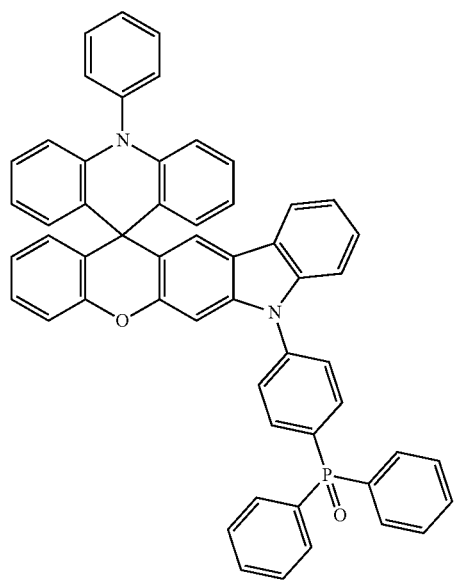
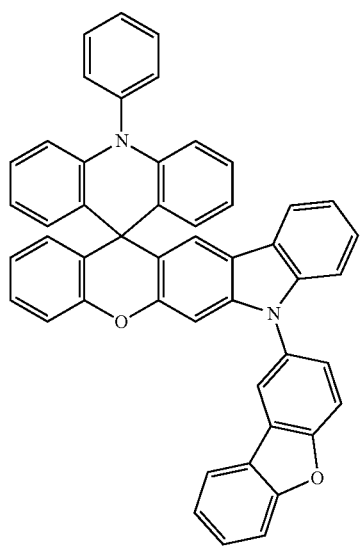
428
-continued
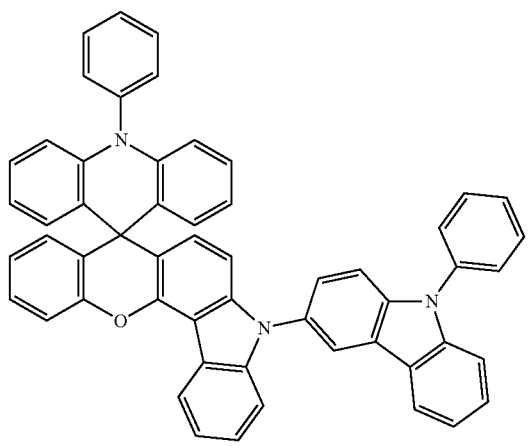
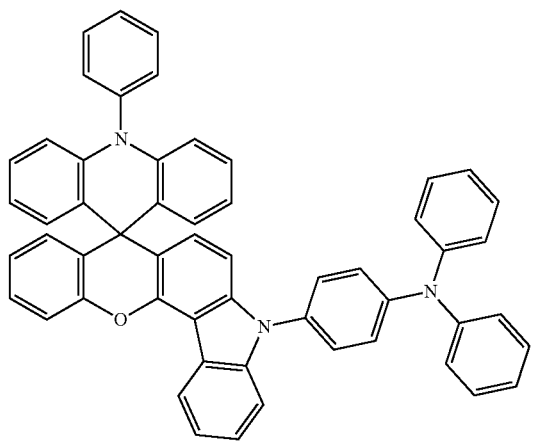
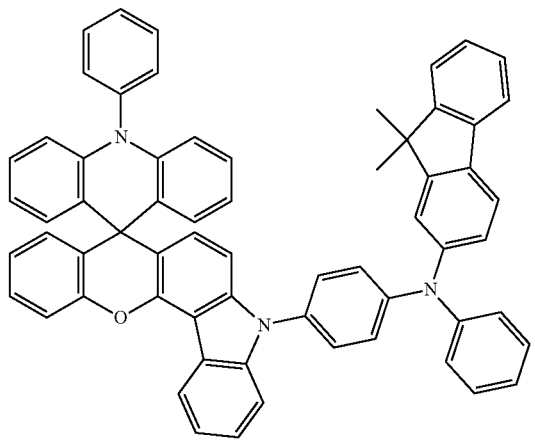

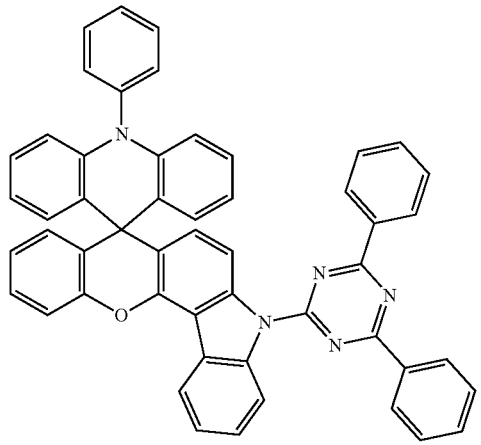
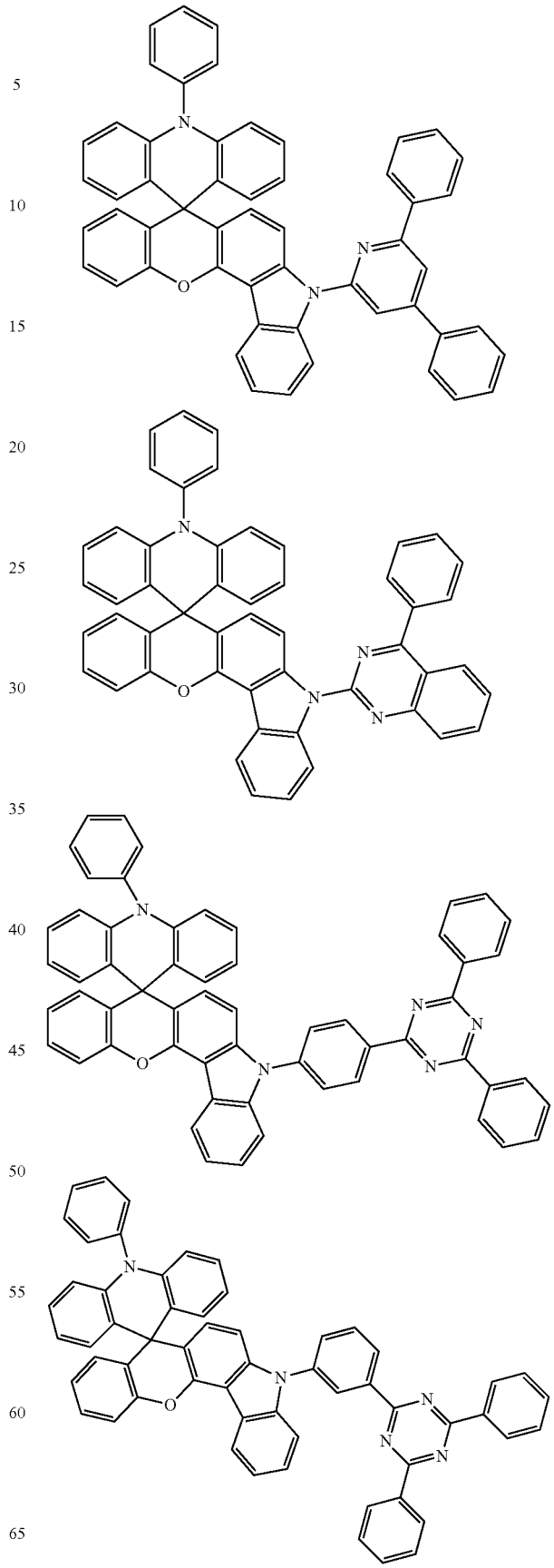

431
-continued
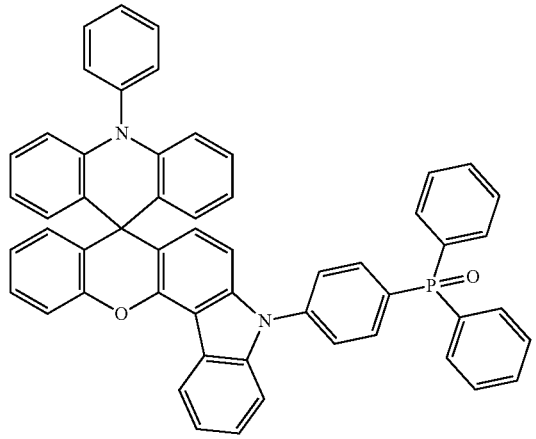
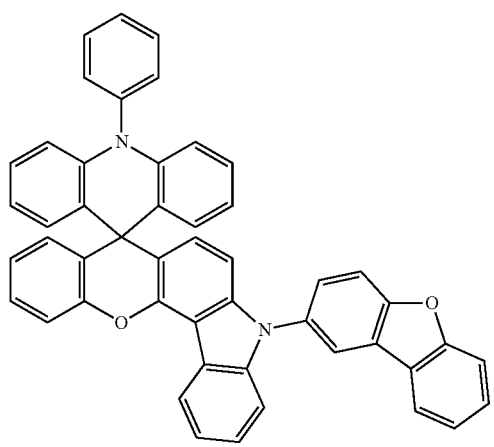
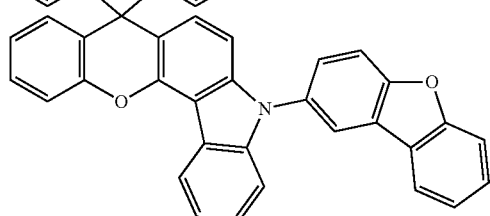
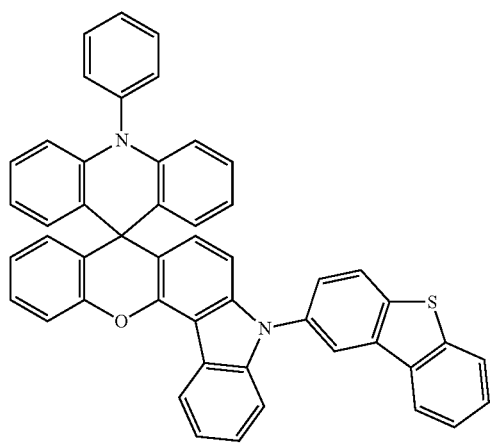
432
-continued
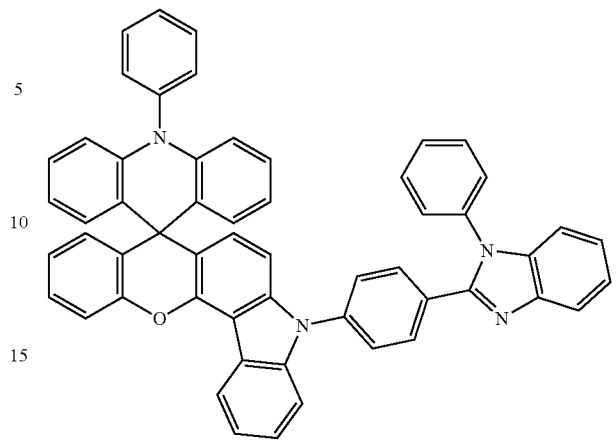
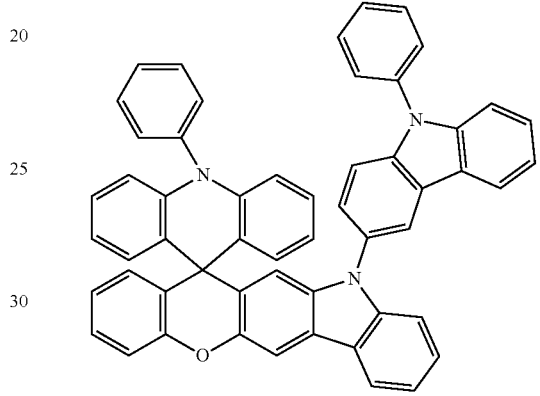
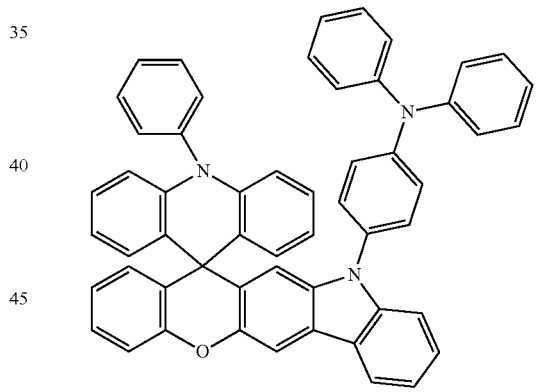
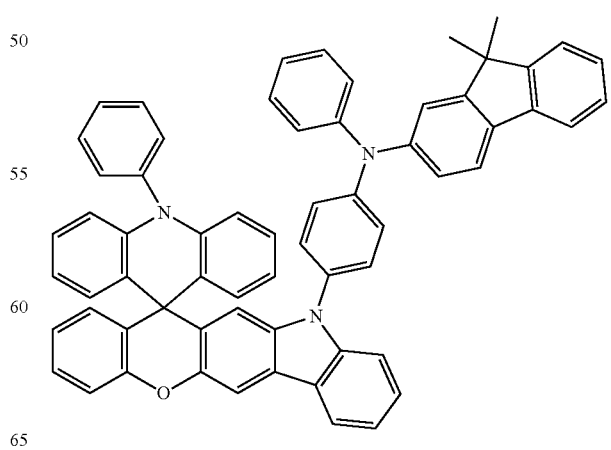

433
-continued
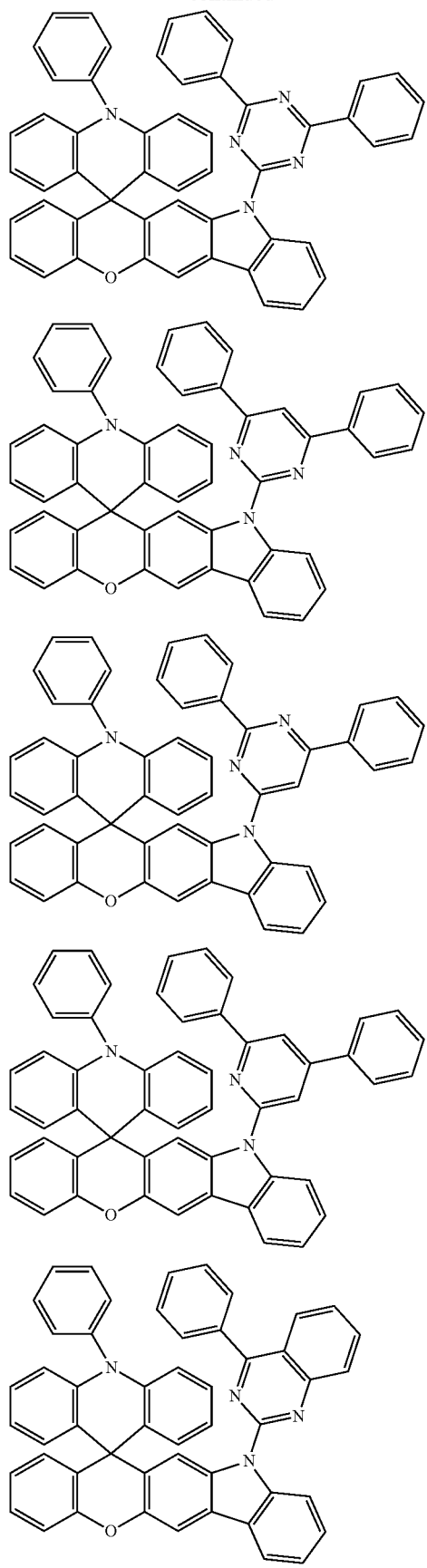
434
-continued
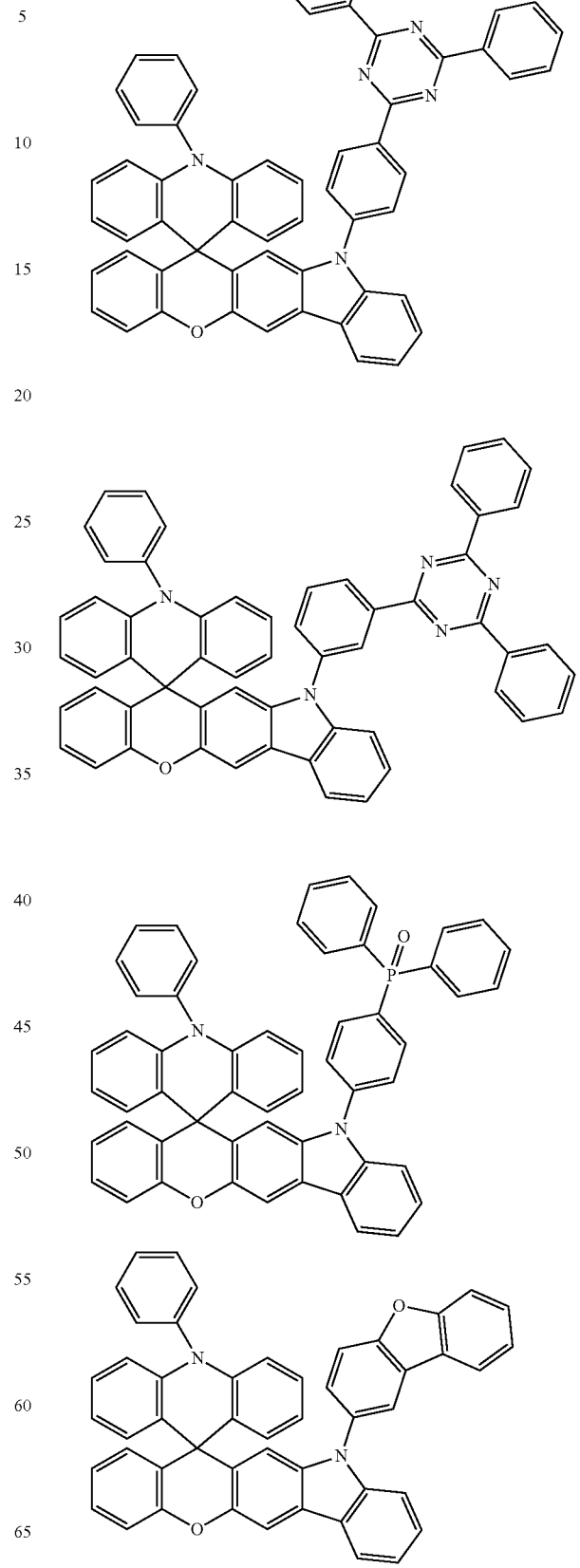

435
-continued
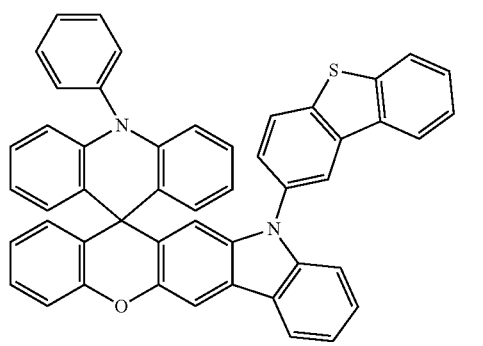
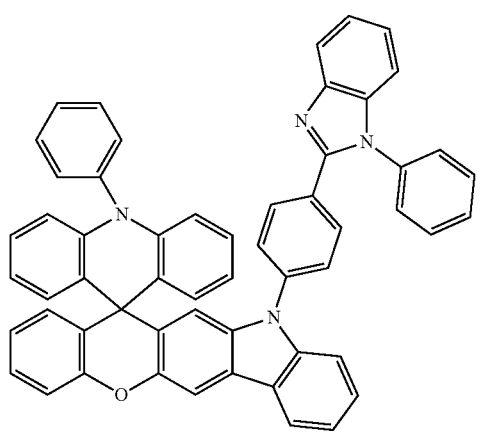
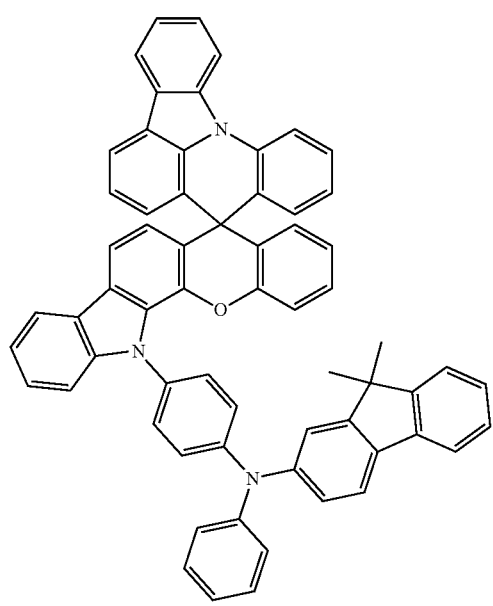
436
-continued
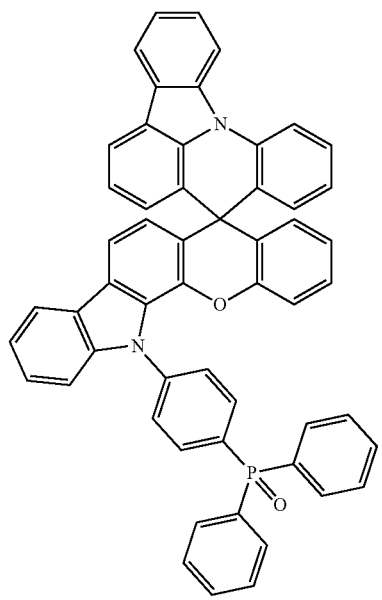
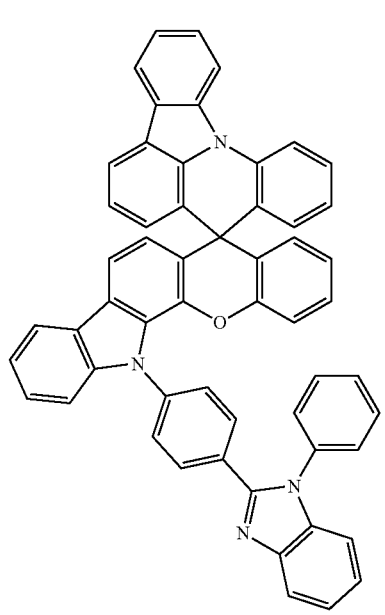

437
-continued
438
-continued
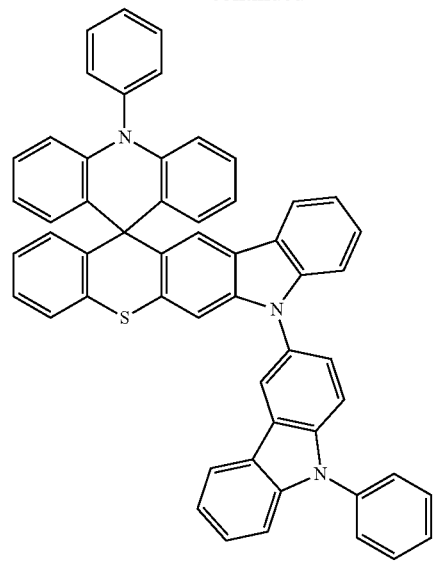
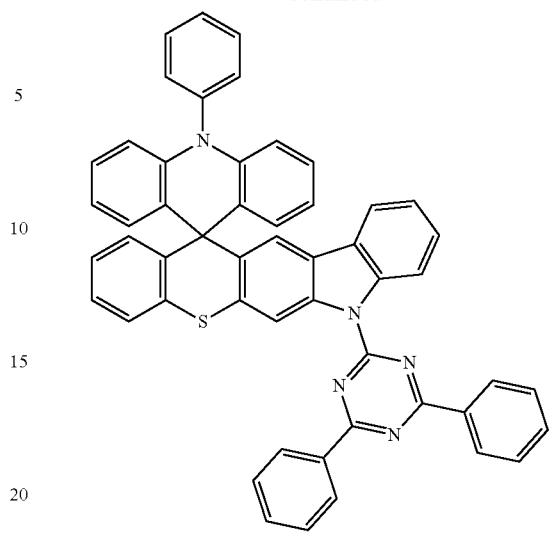
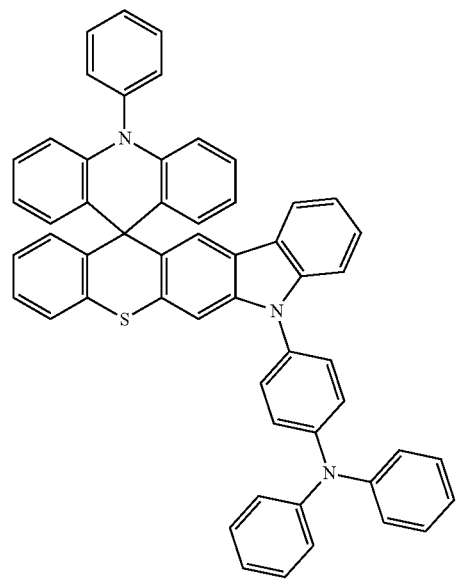
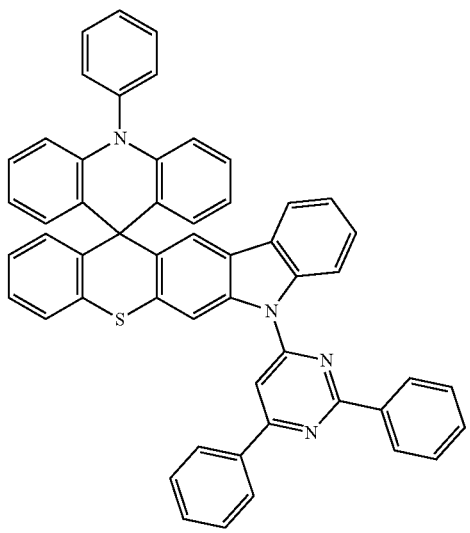
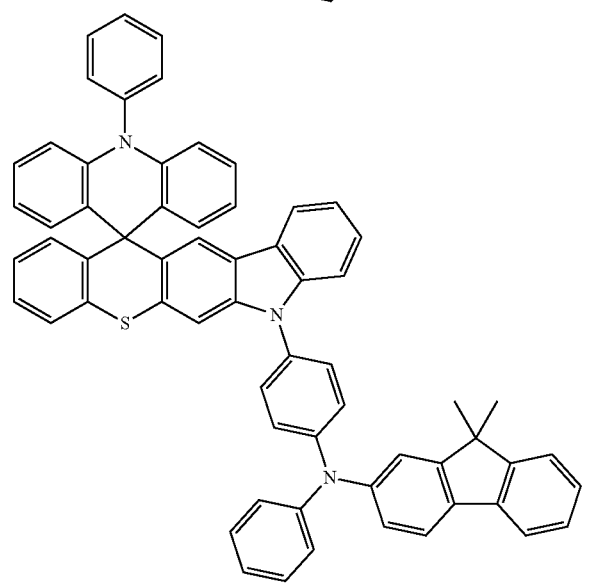

439
-continued
440
-continued
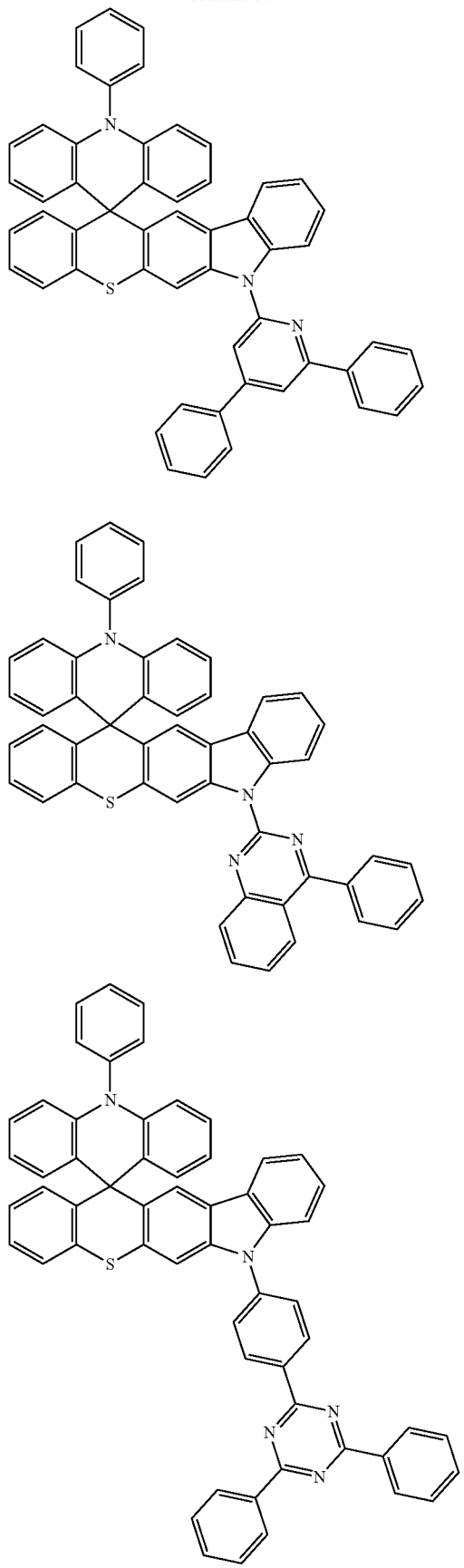 [SMILES: c1ccc(-c2cc(-c3ccccc3)nc(-n3c4ccccc4c4cc5c(cc43)Oc3ccccc3C53c4ccccc4N(c4ccccc4)c4ccccc43)c2)cc1 ; c1ccc(-c2nc(-n3c4ccccc4c4cc5c(cc43)Oc3ccccc3C53c4ccccc4N(c4ccccc4)c4ccccc43)nc3ccccc23)cc1 ; c1ccc(-c2nc(-c3ccccc3)nc(-c3ccc(-n4c5ccccc5c5cc6c(cc54)Oc4ccccc4C64c5ccccc5N(c5ccccc5)c5ccccc54)cc3)n2)cc1]
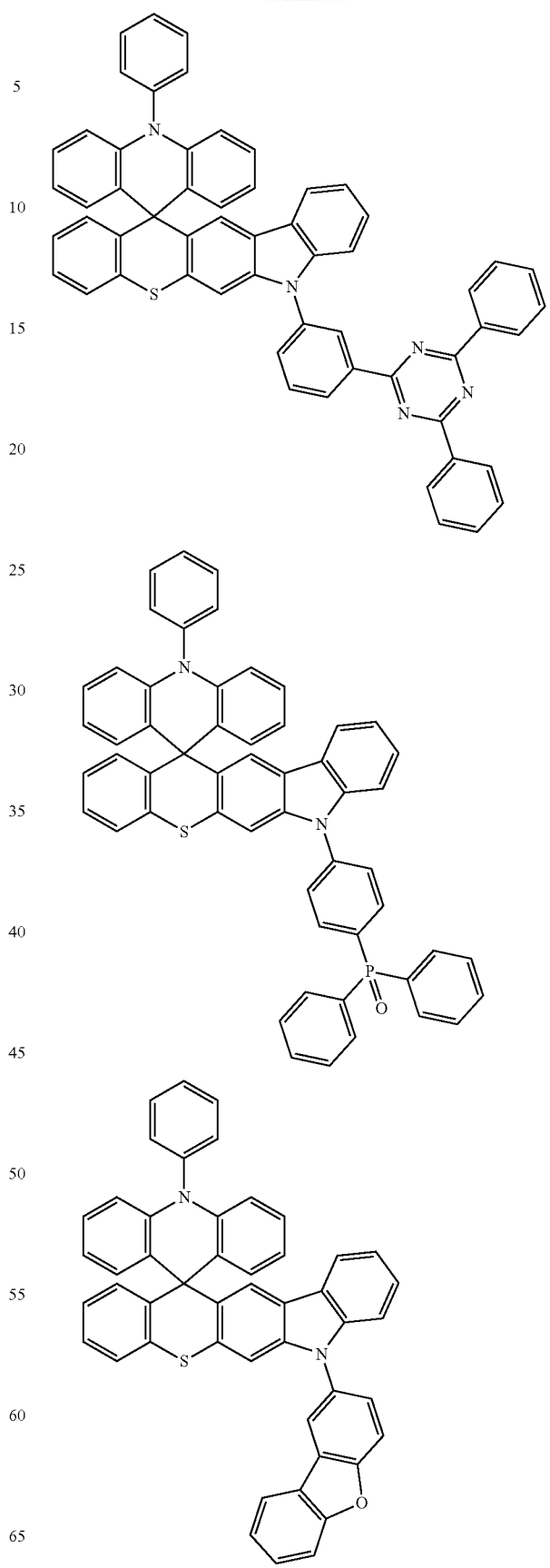

441
-continued
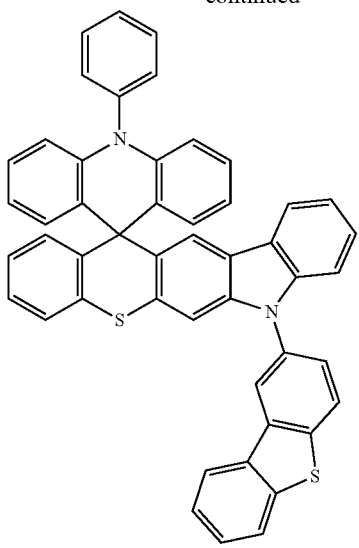
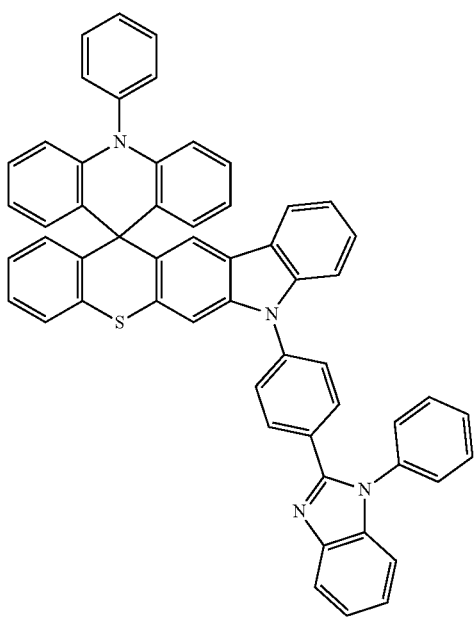
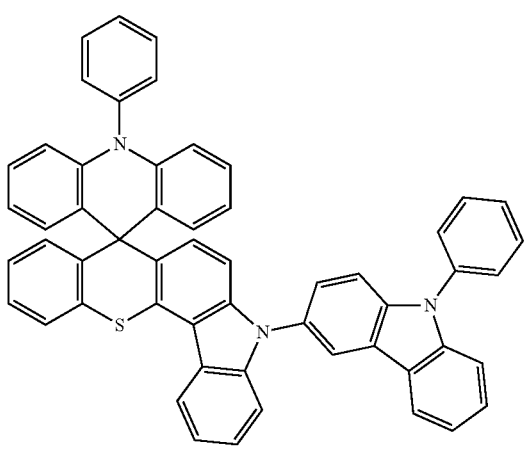
442
-continued
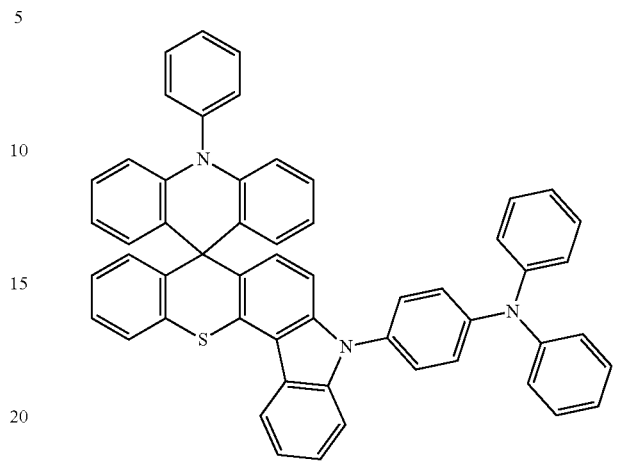
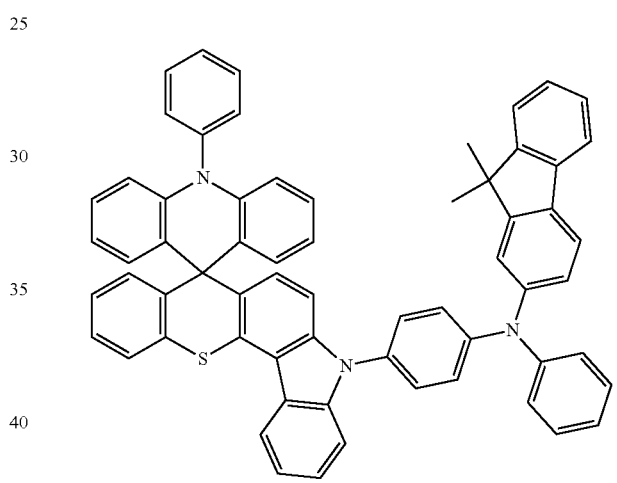
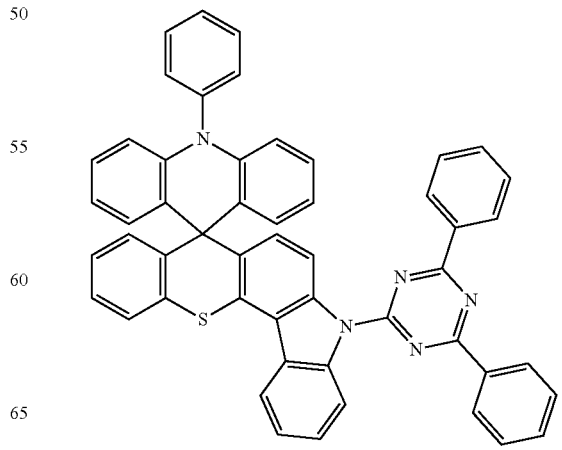

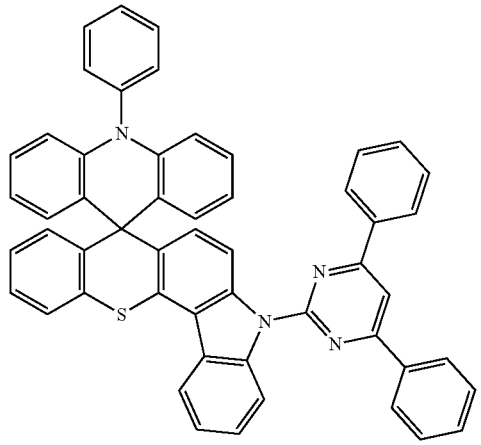
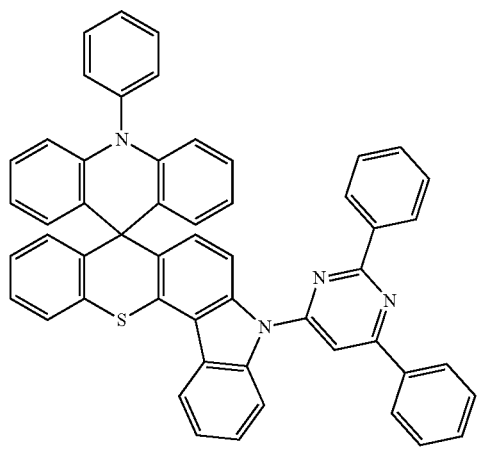
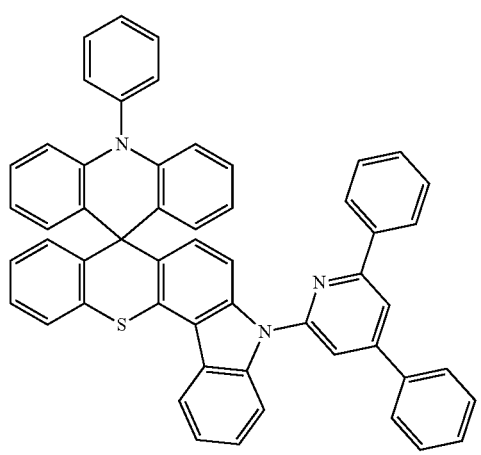
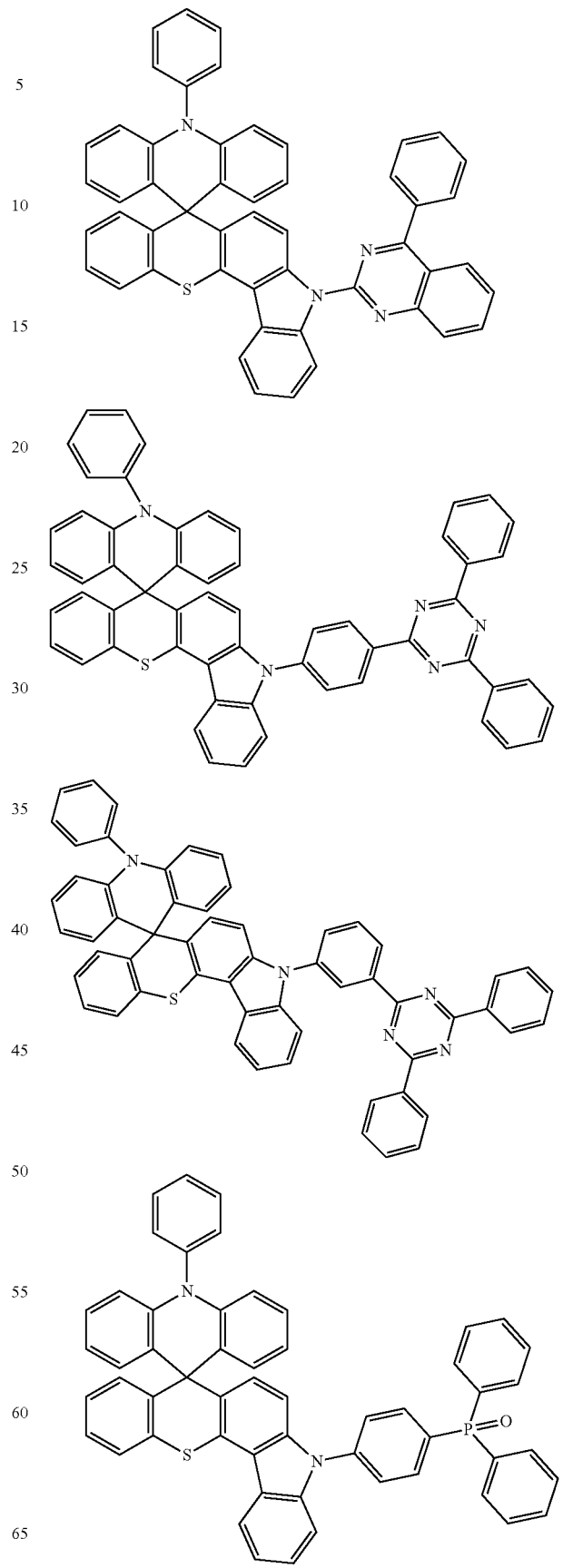

445
-continued
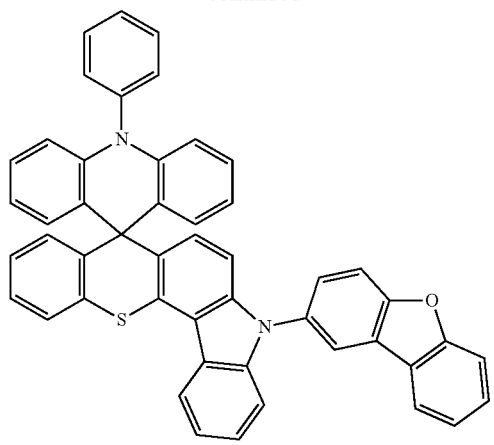
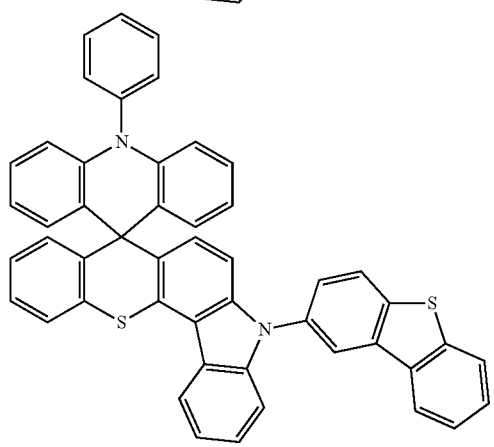
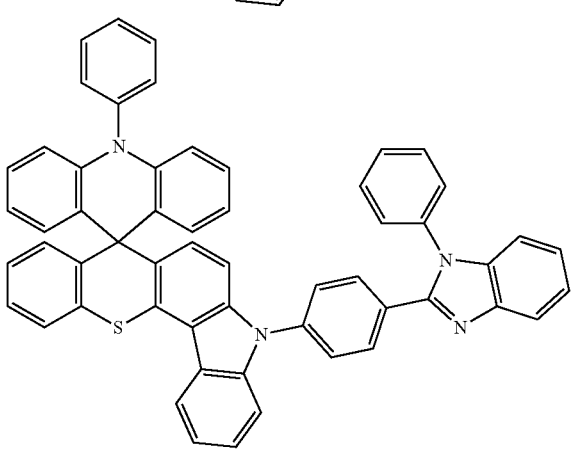
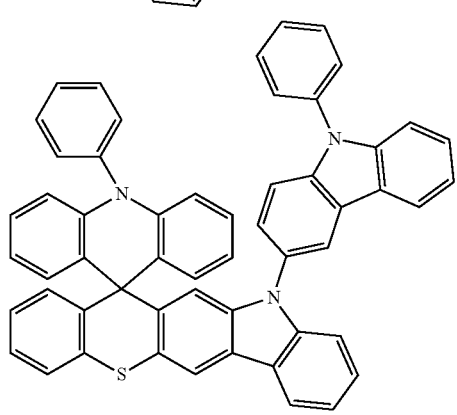
446
-continued
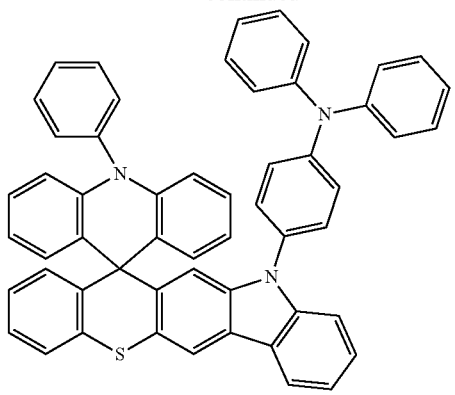
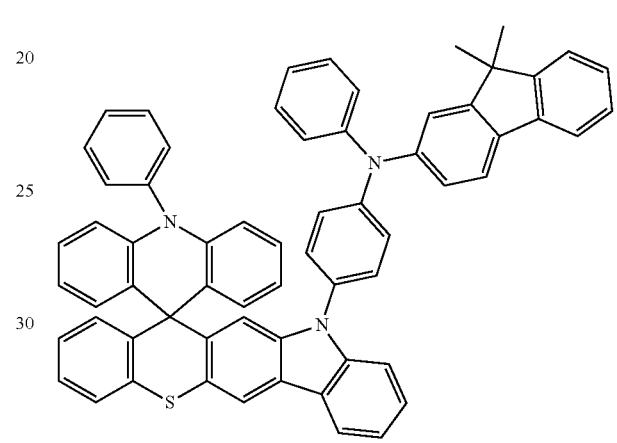
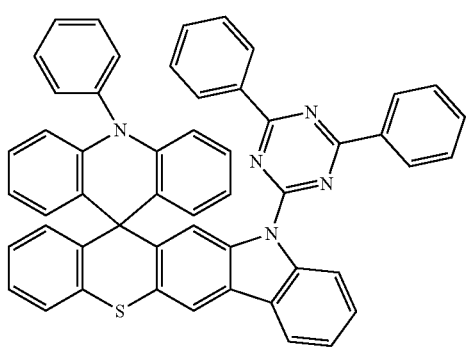
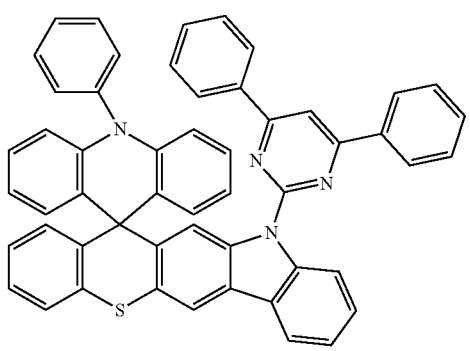

447
-continued
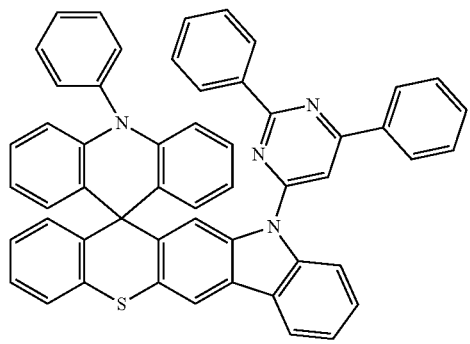
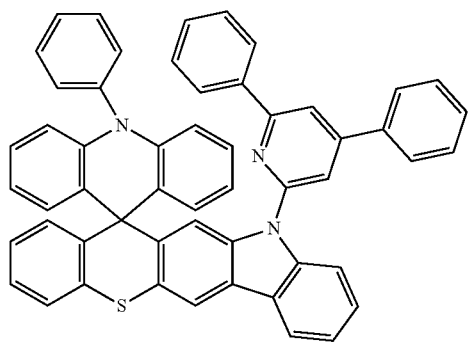
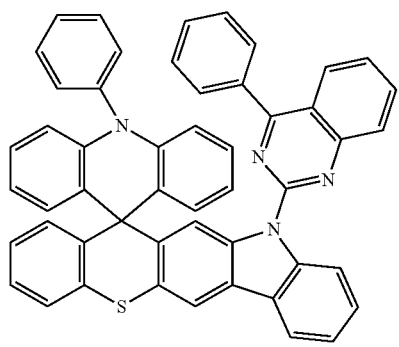
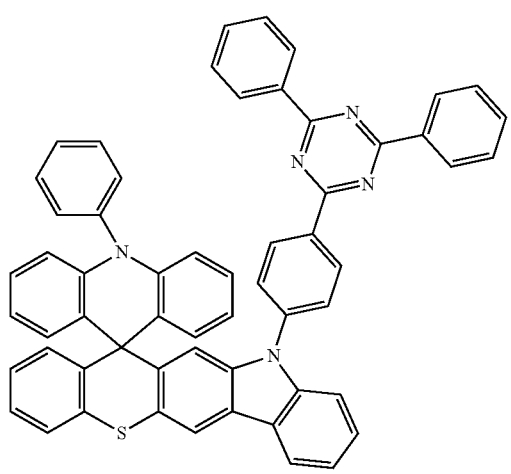
448
-continued
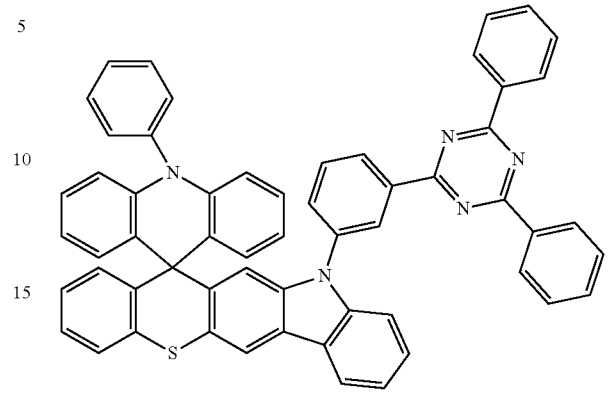
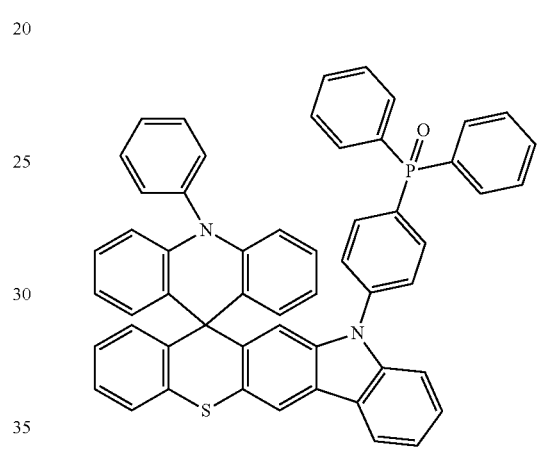
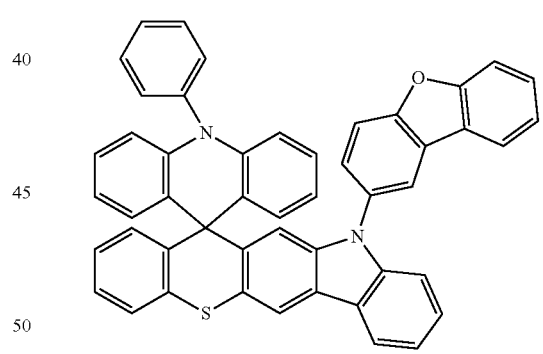
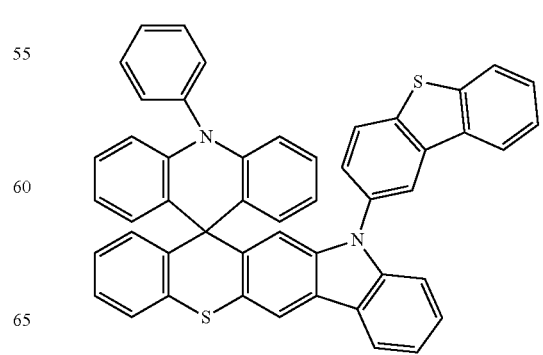

449
-continued
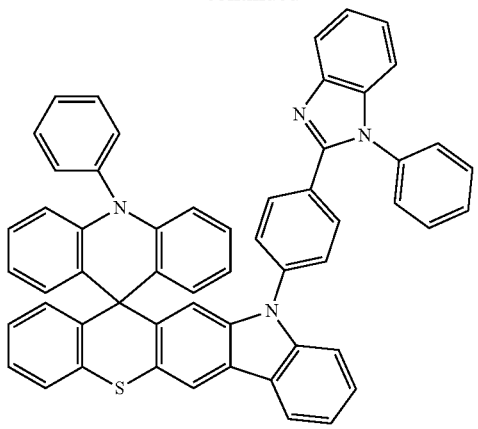
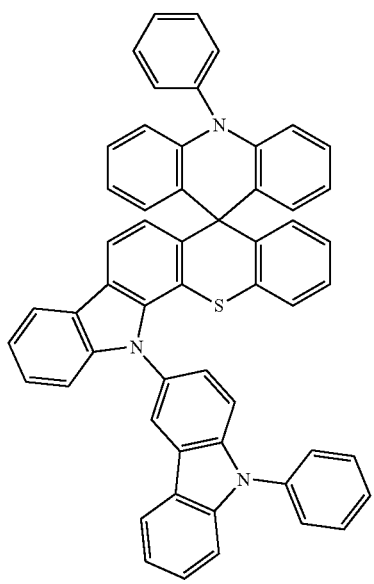
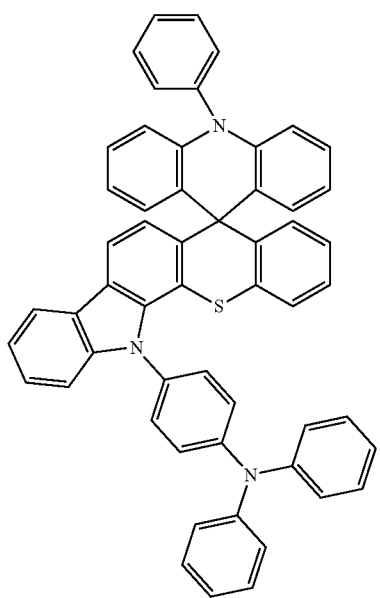
450
-continued
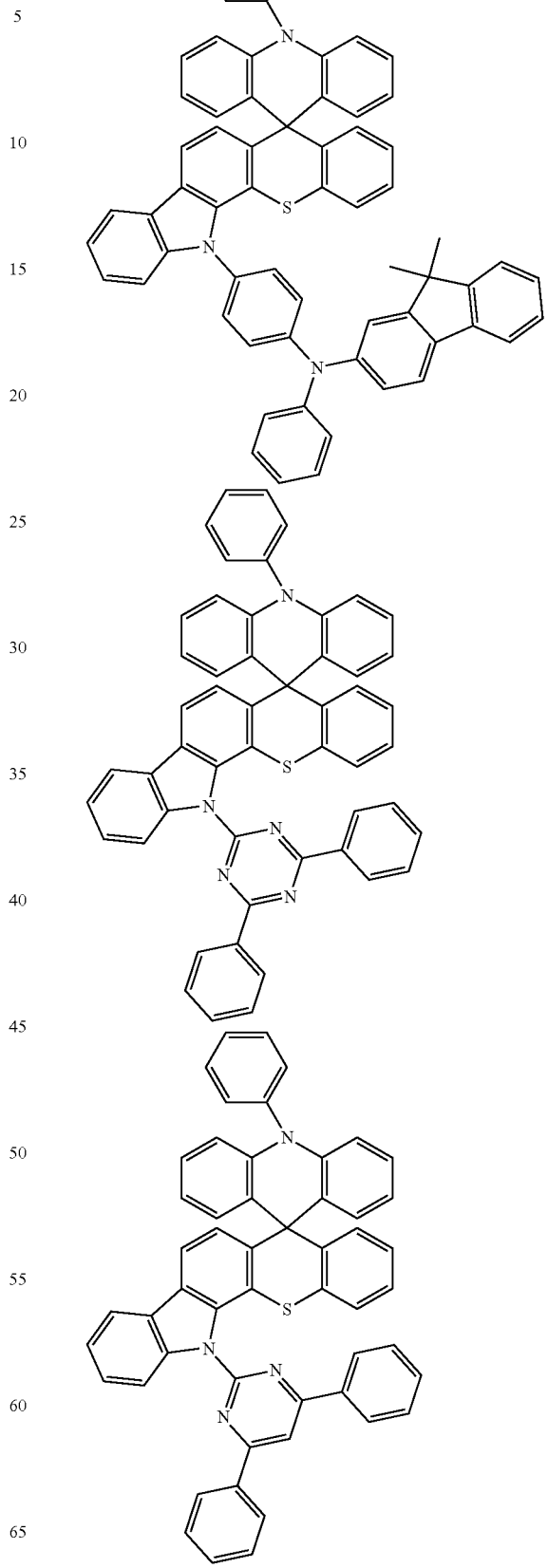

451
-continued
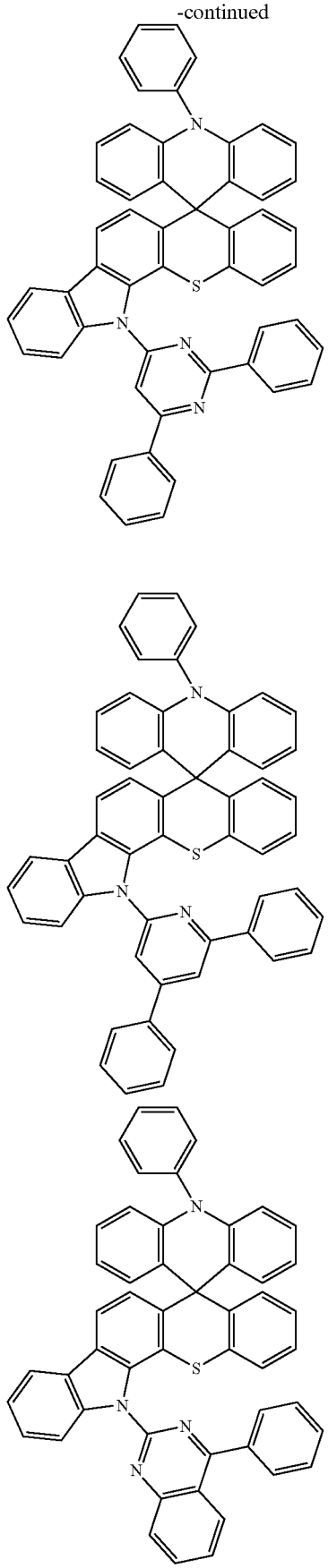
452
-continued
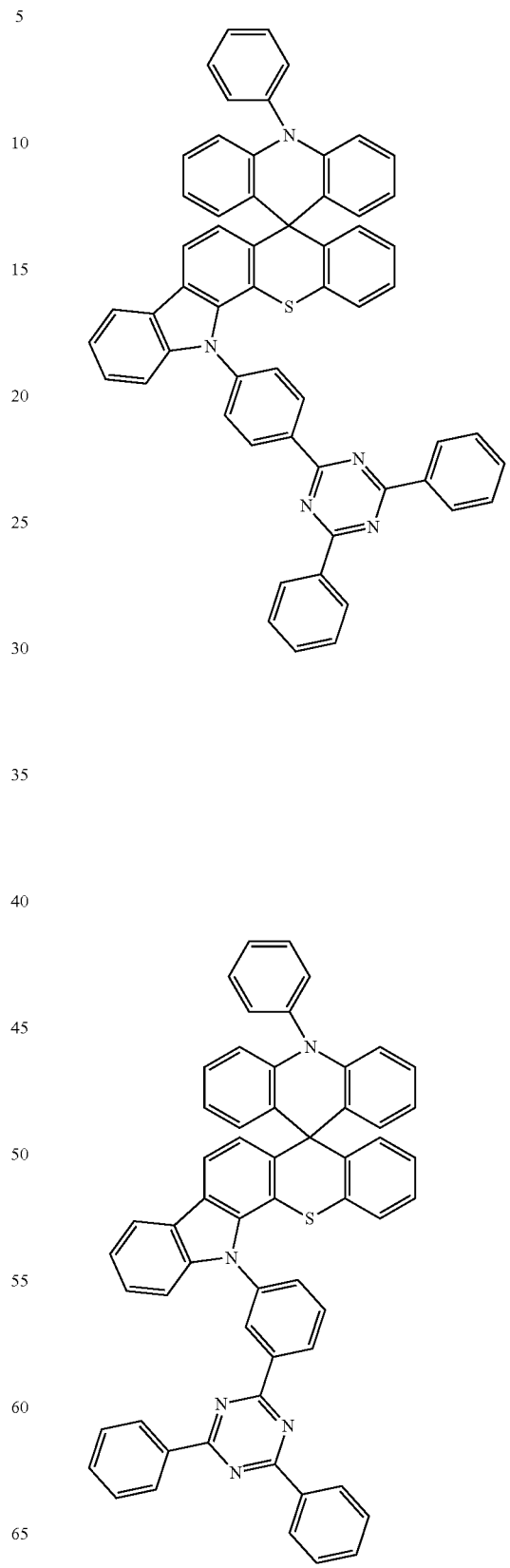

453
-continued

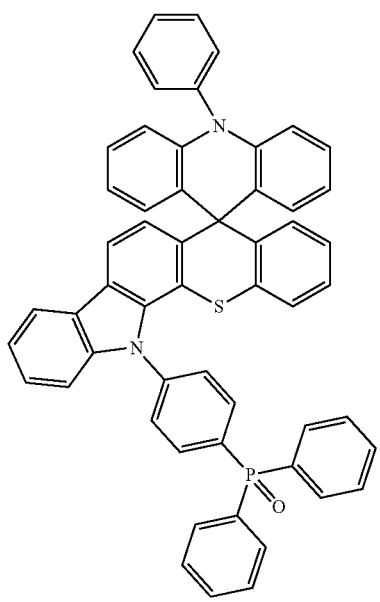

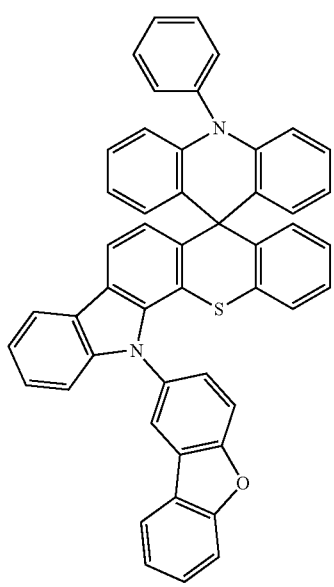

454
-continued

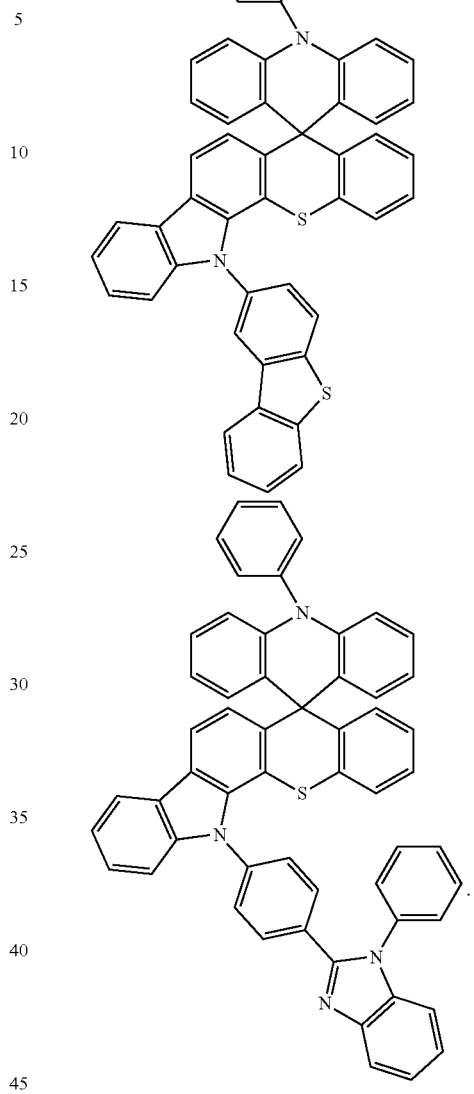

8. The organic light emitting device of claim 1, wherein the organic material layer comprises a compound represented by the following Chemical Formula 1-A:

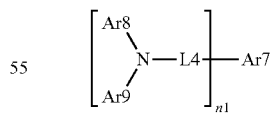

[Chemical Formula 1-A]

in Chemical Formula 1-A, n1 is an integer of 1 or more,

Ar7 is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, L4 is a direct bond; a substituted or unsubstituted arylene group; or a substituted or unsubstituted heteroarylene group, Ar8 and Ar9 are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or are optionally bonded to each other to form a substituted or unsubstituted ring, and when n1 is 2 or more, each of

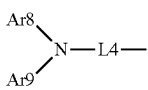

is the same as or different from each other.

9. The organic light emitting device of claim 8, wherein L4 is a direct bond, Ar7 is a divalent pyrene group, Ar8 and Ar9 are the same as or different from each other, and are each independently an aryl group having 6 to 30 carbon atoms, which is unsubstituted or substituted with an alkyl group having 1 to 30 carbon atoms, or a substituted or unsubstituted heteroaryl group having 2 to 30 carbon atoms, and n1 is 2.

10. The organic light emitting device of claim 1, wherein the organic material layer comprises a compound represented by the following Chemical Formula 2-A:

[Chemical Formula 2-A]

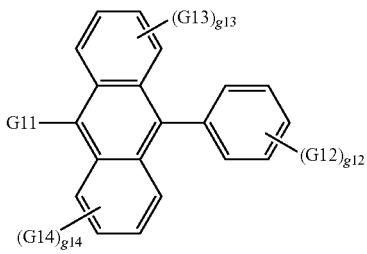

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

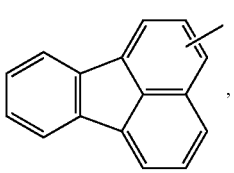

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, each of G12 to G14 is the same as or different from each other.

11. The organic light emitting device of claim 10, wherein G11 is a 1-naphthyl group, and G12 is a 2-naphthyl group.

12. The organic light emitting device of claim 8, wherein the organic material layer comprises a compound represented by the following Chemical Formula 2-A:

[Chemical Formula 2-A]

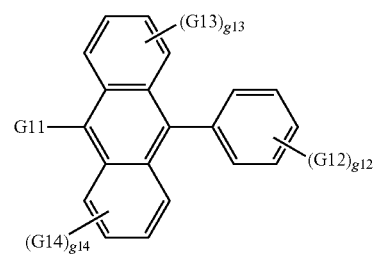

in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

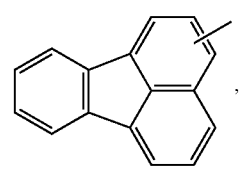

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenyl group, a 4"-t-butyl-p-terphenyl-4-yl group, or a 3-fluoranthenyl group, G13 and G14 are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g12 is an integer from 1 to 5, g13 and g14 are each an integer from 1 to 4, and when g12 to g14 are each 2 or more, each of G12 to G14 is the same as or different from each other.

* * * * *